US006861256B2

(12) United States Patent
Ruvkun et al.

(10) Patent No.: US 6,861,256 B2
(45) Date of Patent: *Mar. 1, 2005

(54) THERAPEUTIC AND DIAGNOSTIC TOOLS FOR IMPAIRED GLUCOSE TOLERANCE CONDITIONS

(75) Inventors: Gary Ruvkun, Newton, MA (US); Scott Ogg, Newton, MA (US)

(73) Assignee: The General Hospital Corporation, Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 351 days.

(21) Appl. No.: 09/205,658

(22) Filed: Dec. 3, 1998

(65) Prior Publication Data

US 2001/0029617 A1 Oct. 11, 2001

Related U.S. Application Data

(63) Continuation-in-part of application No. PCT/US98/10080, filed on May 15, 1998, which is a continuation-in-part of application No. 08/888,534, filed on Jul. 7, 1997, now abandoned, and application No. 08/857,076, filed on May 15, 1997, now Pat. No. 6,225,120.

(51) Int. Cl.[7] .......................... C12N 5/00; C07H 21/04; A61K 40/00; A01K 67/00; G01N 33/00

(52) U.S. Cl. ................... 435/375; 435/69.1; 435/320.1; 435/325; 435/455; 800/3; 800/8; 800/9; 536/23.1; 536/23.5; 424/9.2

(58) Field of Search ............................. 435/69.1, 320.1, 435/325, 375, 455; 536/23.1, 23.5; 800/3, 8, 9, 13, 18; 424/9.2, 9.1

(56) References Cited

U.S. PATENT DOCUMENTS 5,196,333 A    3/1993  Chalfie et al. .............. 435/369

FOREIGN PATENT DOCUMENTS

| WO | WO 98/33907     | 8/1998  |
| WO | WO 98/51351     | 11/1998 |
| WO | WO 01/07457 A1  | 2/2001  |

OTHER PUBLICATIONS

Curt D. Sigmund, Viewpoint: Are Studies in Genetically Altered Mice Out Of Conttrol?, Jun. 20, 2000 (6): 1425–9.*
Philip A. Wood, Phenotype Assessment: Are You Missing Something?, Comp Med Feb 2000; 50 (1): 12–5.*
Catherine A. Kappel et al, regulating gene expression in transgenic animals, 1992, 3:548–553.*
V.G.Pursel et al, Expression and performance in transgenic pigs, J Reprod. Fert. Suppl, 40 (1990), 235–245.*

Scott Ogg et al, The *C. elegans* PTEN Homolog, DAF–18, Acts in the insulin Receptor–like Metabolic Signaling Pathway, Molecular Cell, vol. 2, 887–893, Dec., 1998.*
Well RJ, Theriongenology 45:57–68, 1996.*
Larsan et al, Genetics 139:1567–1583, 1995.*
Lonngvist et al Nat. Med. 1(9):950–953, 1995.*
Zeman et al, Atherosclerosis, 134(1–2):318, 1997.*
Kimura et al, Science 277: 942–946, 1997.*
Austad, Neurobiology of Ageing 16(5):851–852, 1995.*
Maehama et al., "The tumor suppressor, PTEN/MMAC1, dephosphorylates the lipid second messenger, phosphatidylinositol 3, 4, 5–triphosphate," *J. Biol. Chem.* 273:13375–13378 (1998).
Mihaylova et al., "The PTEN tumor suppressor homolog in *Caenorhabditis elegans* regulates longevity and dauer formation in an insulin receptor–like signaling pathway," *Proc. Natl. Acad. Sci. USA* 96:7427–32 (1999).
Rouault et al., "Regulation of dauer larva development in *Caenorhabditis elegans* by daf–18, a homologue of the tumour suppressor PTEN," *Current Biol.* 9:329–332 (1999).
Scheet et al., "Direct Submission: T07A9.6 protein (DAF–18 protein)," (Accession No. 044405) European Bioinformatics Institute, European Molecular Biology Laboratory (1998).
Stephens et al., "Protein kinase B kinases that mediated phosphatidylinositol 3, 4, 5—trisphosphate–dependent activation of protein kinase B," *Science* 279:710–714 (1998).
The *C. elegans* Sequencing Consortium, "Genome sequence of the nematode *C. elegans:* A platform for investigating biology," Science, 282:2012–2018 (1998).
Waterston, "Direct Submission: *Caenorhabditis elegans* cosmid TO7A9," (Accession No. AF036706) European Bioinformatics Institute, European Molecular Biology Laboratory (1997).
Parrizas et al., "Specific Inhibition of Insulin–Like Growth Factor–1 and Insulin Receptor Tyrosine Kinase Activity and Biological Function by Tyrphostins," *Endocrinology* 138:1427–1433 (1997).
Gil et al., "Regulation of the Insulin–Like Developmental Pathway of *Caenorhabditis elegans* by a Homolog of the PTEN Tumor Suppressor Gene," Proc. Natl. Acad. Sci. USA 96:2925–2930 (1999).
Arpagaus, Vertebrate insulin induces diapause termination in *Pieris brassicae* pupae, *Roux's Arch. Dev. Biol.,* 196:527–530 (1987).
Baker et al., A novel mesoderm inducer, Madr2, functions in the activin signal transduction pathway, *Genes and Development,* 10:1880–1889 (1996).

(List continued on next page.)

*Primary Examiner*—Jeffrey Fredman
*Assistant Examiner*—Sumesh Kaushal
(74) *Attorney, Agent, or Firm*—Clark & Elbing LLP

(57) ABSTRACT

Disclosed herein are novel genes and methods for the screening of therapeutics useful for treating impaired glucose tolerance conditions, as well as diagnostics and therapeutic compositions for identifying or treating such conditions.

21 Claims, 70 Drawing Sheets

OTHER PUBLICATIONS

Bargmann et al., Control of Larval Development by Chemosensory Neurons in *Caenorhabditis elegans, Science,* 251:1243–1246 (1991).

Brown–Borg et al., Dwarf mice and the ageing process, *Nature,* 384:33 (1996).

Brüning et al., Development of a Novel Polygenic Model of NIDDm in Mice Heterozygous for IR and IRS–1 Null Alleles, *Cell,* 88:561–572 (1997).

Coleman, Obesity Genes: Beneficial Effects in Heterozygous Mice, *Science,* 203:663–665 (1979).

Dorman et al., The age–1 and daf–2 Genes Function in a Common Pathway to Control the Lifespan of *Caenorhabditis elegans, Genetics,* 141:1399–1406 (1995).

Ebina et al., The Human Insulin Receptor cDNA: The Structural Basis for Hormone–Activated Transmembrane Signalling, *Cell,* 40:747–758 (1985).

Estevez et al., The daf–4 gene encodes a bone morphogenetic protein receptor controlling *C. elegans* dauer larva development, *Nature,* 365:644–649 (1993).

Ewbank et al., Structural and Functional Conservation of the *Caenorhabditis elegans* Timing Gene clk–1, *Science,* 275:980–983 (1997).

Fernandez et al. The Drosophila insulin receptor homolog: a gene essential for embryonic development encodes tow receptor isoforms with different signaling potential, *EMBO J.,* 14:3373–3384 (1995).

Galili et al., "Fusion of a fork head domain gene to PAX3 in the Solid Tumour Alveolar Rhabdomyosarcoma," Nat. Genet. 5:230–235 (1993).

Georgi et al., daf–1, a *C. elegans* Gene Controlling Dauer Larva Development, Encodes a Novel Receptor Protein Kinase, *Cell,* 61:635–645 (1990).

Golden et al., The *Caenorhabditis elegans* Dauer Larva: Developmental Effects of Pheromone, Food, and Temperature, *Developmental Biology,* 102:368–378 (1984).

Golden et al., A pheromone–induced developmental switch in *Caenorhabditis elegans*: Temperature–sensitive mutants reveal a wild–type temperature–dependent process, *Proc. Natl. Proc. Acad. Sci. U.S.A.,* 81:819–823 (1984).

Gottlieb et al., daf–2, daf–16 and daf–23: Genetically Interacting Genes Controlling Dauer Formation in *Caenorhabditis elegans, Genetics,* 137:107–120 (1994).

Graff et al., Xenopus Mad Proteins Transduce Distinct Subsets of Signals for the TGFβ Superfamily, *Cell,* 85:479–487 (1996).

Green et al., Responses of Embryonic Xenopus Cells to Activin and FGF Are Separated by Multiple Dose Thresholds and Correspond to Distinct Axes of the Mesoderm, *Cell,* 71:731–739 (1992).

Hahn et al., DPC4, A Candidate Tumor Suppressor Gene at Human Chromosome 18q21.1, *Science,* 271:350–353 (1996).

Hemmings, Akt Signaling: Linking Membrane Events to Life and Death Decisions, *Science,* 275:628–630 (1997).

Hetru et al., Isolation and structural characterization of an insulin–related molecule, a predominant neuropeptide from *locusta migratoria Eur. J. Biochem.,* 201:495–499 (1991).

Hoodless et al., MADR1 a MAD–Related Protein That Functions in BMP2 Signaling Pathways, *Cell,* 85:489–500 (1996).

Hotamisligil et al., Adipose Expression of Tumor Necrosis Factor–α: Direct Role in Obesity–Linked Insulin Resistance, *Science,* 259:87–91 (1993).

Hubbard et al., Crystal structure of the tyrosine kinase domain of the human insulin receptor, *Nature,* 372:746–754 (1994).

Jonas et al., Regulation by insulin of a unique neuronal $Ca^{2+}$ pool and of neuropeptide secretion, *Nature,* 385:343–346 (1997).

Kahn et al., Genetics of Non–Insulin–Dependent (Type–II) Diabetes Mellitus, *Annu. Rev. Med.,* 47:509–531 (1996).

Kawakami et al., Molecular Cloning of the *Bombyx mori* Prothoracicotropic Hormone, *Science,* 247:1333–1335 (1990).

Kenyon et al., A *C. elegans* mutant that lives twice as long as wild type, *Nature,* 366:461–464 (1993).

Kim et al., Detection of mutations in the insulin receptor gene in patients with insulin resistance by analysis of single–stranded conformational polymorphisms, *Diabetologia,* 35:261–266 (1992).

Kimble, Alterations in Cell Lineage following Laser Ablation of Cells in the Somatic Gonad of *Caenorhabditis elegans, Developmental Biology,* 87:286–300 (1981).

Kimura et al., "daf–2, an Insulin Receptor–Like Gene That Regulates Longevity and Diapause in *Caenorhabditis elegans*," *Science* 277:942–946 (1997).

Klass, A Method for the Isolation of Longevity Mutants in the Nematode *Caenorhabditis elegans* and Initial Results, *Mechanisms of Ageing and Dev.,* 22:279–286 (1983).

Krause, Transcription and Translation, Chapter 20, *Methods Cell Biol.,* Academic Press, San Diego, CA, 48:483–512 (1995).

Krawczak et al., The human gene mutation database, *Trends Genet* 13:121–2 (1997).

Lagna et al., Partnership between DPC4 and SMAD proteins in TGF–β signalling pathways, *Nature,* 383:832–836 (1996).

Larsen et al., Genes that Regulate Both Development and Longevity in *Caenorhabditis elegans, Genetics,* 139:1567–1583 (1995).

Lin et al., "daf–16: An HNF–3/Forkhead Family Member That Can Function to Double the Life–Span of *Caenorhabditis elegans*," *Science* 278:1319–1322 (1997).

Liu et al., A human Mad protein acting as a BMP–regulated transcriptional activator, *Nature,* 381:620–623 (1996).

Lonnqvist et al., Overexpression of the obese (ob) gene in adipose tissue of human obese subjects, *Nat. Med.,* 1:950–953 (1995).

Macias–Silva et al., MADR2 is a Substrate of the TGFβ Receptor and Its Phosphorylation Is Required for Nuclear Accumulation and Signaling, *Cell,* 87:1215–1224 (1996).

Malone et al., A Screen for Nonconditional Dauer–Constitutive Mutations in *Caenorhabditis elegans, Genetics,* 136:879–886 (1994).

Mathews et al., Regulation of insulin–like growth factor I gene expression by growth hormone, *Proc. Natl. Acad. Sci. U.S.A.,* 83:9343–9347 (1986).

McCombie et al., "*Caenorhabditis elegans* Expressed Sequence Tags Identify Gene Families and Potential Disease Gene Homologues," *Nature Genetics* 1:124–131 (1992).

Mello et al., Efficient gene transfer in *C. elegans*: extrachromosomal maintenance and integration of transforming sequences, *Embo J.,* 10:3959–3970 (1991).

Murakami et al., "A Genetic Pathway Conferring Life Extension and Resistance to UV Stress in *Caenorhabditis elegans*," *Genetics* 143:1207–1218 (1996).

Nagasawa et al., Amino–Terminal Amino Acid Sequence of the Silkworm Prothoracicotropic Hormone: Homology with Insulin, *Science,* 266:1344–1345 (1984).

Ogg et al., The Fork head transcription factor DAF–16 transduces insulin–like metabolic and longevity signals in *C. elegans, Nature,* 389:994–999 (1997).

O'Riordan et al., Intermediary Metabolism in the Dauer Larva of the Nematode *Caenorhabditis Elegans*–II. The Glyoxylate Cycle and Fatty–Acid Oxidation, *Comp. Biochem. & Physiol.,* 95B:125–130 (1990).

O'Riordan et al., Intermediary Metabolism in the Dauer Larva of the Nematode *Caenorhabditis elegans*–I. Glycolysis, Gluconeogenesis, Oxidative Phosphorylation and the Tricarboxylic Acid Cycle, *Comp. Biochem. & Physiol.,* 92B:233–238 (1989).

Popham et al., Aspects of the fine structure of the dauer larva of the nematode *Caenorhabditis elegans, Can. J. Zool.,* 57:794–800 (1979).

Reinhardt et al., Selective Coexpression of Insulin Receptor–related Receptor (IRR) and TRK in NGF–Sensitive Neurons, *J. Neurosci.,* 14:4674–4683 (1994).

Ren et al., Control of *C. elegans* Larval Development by Neuronal Expression of a TGF–β Homolog, *Science,* 274:1389–1391 (1996).

Riddle et al., Interacting genes in nematode dauer larva formation, *Nature,* 290:668–671 (1981).

Riddle, D. et al., Genetic and Environmental Regulation of Dauer Larva Development, *C. elegans II,* pp. 739–768 (1997).

Roovers et al., Characterization of a putative molluscan insulin–related peptide receptor, *Gene,* 162:181–188 (1995).

Savage et al., *Caenorhabditis elegans* genes sma–2, sma–3, and sma–4 define a conserved family of transforming growth factor β pathway components, *PNAS,* 93:790–794 (1996).

Schackwitz et al., Chemosensory neurons function in parallel to mediate a pheromone response in *C. elegans, Neuron,* 17:719–728 (1996).

Shier et al., Primary structure of a putative receptor for a ligand of the insulin family, *J. Biol. Chem.,* 264:14605–14608 (1989).

Songyang et al., SH2 domains recognize specific phosphopeptide sequences, *Cell,* 72:767–778 (1993).

Swanson et al., Critical periods in the development of the *Caenorhabditis elegans* dauer larva, *Developmental Biology,* 84:27–40 (1981).

Taylor, Lilly Lecture: Molecular mechanisms of insulin resistance, *Diabetes,* 41:1473–1490 (1992).

Thomas et al., Evidence for parallel processing of sensory information controlling dauer formation in *Caenorhabditis elegans, Genetics,* 134:1105–1117 (1993).

Ullrich et al., Human insulin receptor and its relationship to the tyrosine kinase family of oncogenes, *Nature,* 313:756–761 (1985).

Ullrich et al., Insulin–like growth factor I receptor primary structure: comparison with insulin receptor suggests structural determinants that define functional specificity, *EMBO J.,* 5:2503–2512 (1986).

Vowels et al., Genetic analysis of chemosensory control of dauer formation in *Caenorhabditis elegans, Genetics,* 130:105–123 (1992).

Wadsworth et al., Developmental regulation of energy metabolism in *Caenorhabditis elegans, Dev. Biol.,* 132:167–173 (1989).

Waterston et al., "A Survey of expressed genes in *Caenorhabditis elegans," Nature Gen* 1:114–123 (1992).

White et al., The Insulin Signaling System, *J. Biol. Chem.,* 269:1–4 (1994).

Wrana et al., MAD–related proteins in TGF–β signalling, *Trends Genet.,* 12:493–496 (1996).

Yoshimasa et al., Effects of Amino Acid Replacements within the Tetrabasic Cleavage Site on the Processing of the Human Insulin Receptor Precursor Expressed in Chinese Hamster Ovary Cells, *J. Biol. Chem.,* 265:17230–17237 (1990).

Zhang et al., Receptor–Associated Mad homologues synergize as effectors of the TGF–β response, *Nature,* 383:168–172 (1996).

Zwaal et al., "Target–Selected Gene Inactivation in *Caenorhabditis elegans* by using a Frozen Transposon Insertion Mutant Bank," *Proc. Natl. Acad. Sci. USA* 90:7431–7435 (1993).

Allander, et al., Hepatic nuclear factor 3 and high mobility group 1/4 proteins bind the insulin response element of the insulin–like growth factor–binding protein–1 promoter. *Endocrinology,* 138:4291–300 (1997).

Ahren et al., Neuropeptidergic versus cholinergic and adrenergic regulation of islet hormone secretion. *Diabetologia* 29:827–836 (1986).

Borkhardt et al., Cloning and characterization of AFX, the gene that fuses to MLL in acute leukemias with a t(X;11)(q13; q23). *Oncogene* 14, 195–202 (1997).

Boschero, et al., Oxotremorine–m potentiation of glucose–induced insulin release from rat islets involves $M_3$ muscarinic receptors. *Am. J. Physiol.* 268:E336–E342, (1995).

Hillion, et al., A novel partner of the MLL gene in t(6;11)(q21;q23), defines a forkhead transcriptional factor subfamily, *Blood,* 90:3714–9 (1997).

Hobert, et al., regulation of interneuron function in the *C. elegans* thermoregulatory pathway by the ttx–3 LIM homeobox gene. *Neuron* 19:345–357 (1997).

Lai et al., HNG–3A, a hepatocyte–enriched transcription factor of novel structure is regulated transcriptionally, *Genes Dev.* 4:1427–1436 (1990).

Latifpour et al., Effect of insulin and dietary myoinositol on muscarinic receptor alterations in diabetic rat bladder, *J. Urol.* 147:760–763 (1992).

Lewis et al., The genetics of levamisole resistance in the nematode *Caenorhabditis elegans. Genetics* 95:905–928 (1980).

Lewis et al., Levamisole–resistant mutants of the nematode *Caenorhabditis elegans* appear to lack pharmacological acetylcholine receptors. *Neuroscience* 5:967–989 (1980).

Li et al., TEP1, encoded by a candidate tumor suppressor locus, is a novel protein tyrosine phosphatase regulated by transforming growth factor beta, *Cancer Res.,* 57:2124–2129 (1997).

Li et al., PTEN, a putative protein protein tyrosine phosphatase gene mutated in human brain, breast, and prostate cancer, *Science* 275:1943–1947 (1997).

Maehama et al., The tumor suppressor, PTEN/MMAC1, dephosphorylates the lipid second messenger, phosphatidylinositol 3,4,5–triphosphate, *J. Biol. Chem.,* 273:13375–13378 (1998).

Miller, R. E., Pancreatic neuroendocrinology: peripheral neural mechanisms in the regulation of the islets of langerhans*. *Endocr. Rev.* 2:471–494 (1981).

Morris et al., A phosphatidylinositol–3–OH kinase family member regulating longevity and diapause in *Caenorhabditis elegans*. *Nature* 382:536–539 (1996).

O'Brien et al., Hepatic nuclear factor–3 and hormone–regulated expression of the phosphoenolpyruvate carboxykinase and insulin–like growth factor–binding protein 1 genes. *Mol. Cell Biol.* 15:1747–1758 (1995).

Paradis et al., *Caenorhabditis elegans* Akt/PKB transduces insulin receptor–like signals from AGE–1 PI3 kinase to the DAF–16 transcription factor. *Genes Dev.* 12:2488–2498 (1998).

Parry et al., Cloning and characterization of the t(X;11) breakpoint from a leukemic cell line identify a new member fo the forkhead gene family. *Genes Chromosomes Cancer* 11:79–84 (1994).

Patterson et al., The DAF–3 Smad protein antagonizes TGF–B–related receptor signaling in the *Caenorhabditis elegans* dauer pathway. *Genes Dev.* 11:2679–2690 (1997).

Stambolic et al., Negative regulation of PKB/Akt–dependent cell survival by the tumor suppressor PTEN. *Cell* 95:29–39 (1998).

Steck et al., Identification of a candidate number tumour suppressor gene, MMAC1; at chromosome 10q23.3 that is mutated in multiple advanced cancers. *Nat. Genet.* 15:356–362 (1997).

Unterman et al., Hepatocyte nuclear factor–3 (HNF–3) binds to the insulin response sequence in the IGF binding protein–1 (IGFBP–1) promoter and enhances promoter function. *Biochem. Biophys. Res. Commun.* 203:1835–41 (1994).

Weinkove et al., p60 is an adaptor for the Drosophila phosphoinositide 3–kinase, Dp 110. *J. Biol. Chem.* 272:14606–14610 (1997).

Yamamura et al., Muscarinic Cholinergic Binding in Rat Brain. *Proc. Natl. Acad. Sci.*, 1725–1729.

* cited by examiner

```
   1 MTSLMLLLLFAFVQPCASIVEKRCGPIDIRNRPWDIKPQWSKLGDPNEKDLAGQRMVNCT
  61 VVEGSLTISFVLKHKTKAQEEMHRSLQPRYSQDEFITFPHLREITGTLLVFETEGLVDLR
 121 KIFPNLRVIGGRSLIQHYALIIYRNPDLEIGLDKLSVIRNGGVRIIDNRKLCYTKTIDWK
 181 HLITSSINDVVVDNAAEYAVTETGLMCPRGACEEDKGESKCHYLEEKNQEQGVERVQSCW
 241 SNTTCQKSCAYDRLLPTKEIGPGCDANGDRCHDQCVGGCERVNDATACHACKNVYHKGKC
 301 IEKCDAHLYLLLQRRCVTREQCLQLNPVLSNKTVPIKATAGLCSDKCPDGYQINPDDHRE
 361 CRKCVGKCEIVCEINHVIDTFPKAQAIRLCNIIDGNLTIEIRGKQDSGMASELKDIFANI
 421 HTITGYLLVRQSSPFISLNMFRNLRRIEAKSLFRNLYAITVFENPNLKKLFDSTTDLTLD
 481 RGTVSIANNKMLCFKYIKQLMSKLNIPLDPIDQSEGTNGEKAICEDMAINVSITAVNADS
 541 VFFSWPSFNITDIDQRKFLGYELFFKEVPRIDENMTIEEDRSACVDSWQSVFKQYYETSN
 601 GEPTPDIFMDIGPRERIRPNTLYAYYVATQMVLHAGAKNGVSKIGFVRTSYYTPDPPTLA
 661 LAQVDSDAIHITWEAPLQPNGDLTHYTIMWRENEVSPYEEAEKFCTDASTPANRQRTKDP
 721 KETIVADKPVDIPSSRTVAPTLLTMMGHEDQQKTCAATPGCCSCSAIEESSEQNKKKRPD
 781 PMSAIESSAFENKLLDEVLMPRDTMRVRRSIEDANRVSEELEKAENLGKAPKTLGGKKPL
 841 IHISKKKPSSSSTTSTPAPTIASMYALTRKPTTVPGTRIRLYEIYEPLPGSWAINVSALA
 901 LDNSYVIRNLKHYTLYAISLSACQNMTVPGASCSISHRAGALKRTKHITDIDKVLNETIE
 961 WRFMNNSQQVNVTWDPPTEVNGGIFGYVVKLKSKVDGSIVMTRCVGAKRGYSTRNQGVLF
1021 QNLADGRYFVSVTATSVHGAGPEAESSDPIVVMTPGFFTVEIILGMLLVFLILMSIAGCI
1081 IYYYIQVRYGKKVKALSDFMQLNPEQCVDNKYNADDWELRQDDVVLGQQCGEGSFGKVYL
1141 GTGNNVVSLMGDRFGPCAIKINVDDPASTENLNYLMEANIMKNFKTNFIVQLYGVISTVQ
1201 PAMVVMEMMDLGNLRDYLRSKREDEVFNETDCNFFDIIPRDKFHEWAAQICDGMAYLESL
1261 KFCHRDLAARNCMINRDETVKIGDFGMARDLFQHDQYKPSGKRMMPVRWMSPESLKDGKF
1321 DSKSDVWSFGVVLYEMVTLGAQPYIGLSNDEVLNYIGMARKVIKKPECCENYWYKVMKMC
1381 WRYSPRDRPTFLQLVHLIAAEASPEFRDLSFVLTDNQMILDDSEALDLDDIDDTDMNDQV
1441 VEVAPDVENVEVQSDSERRNTDSIPLKQFKTIPPINATTSHSTISIDETPMKAKQREGSL
1501 DEEQALMNHSGGPSDAEVRTYAGDGDYVERDVRENDVPTRRNTGASTSSYTGGGPYCLTN
1561 RGGSNERGAGFGEAVRLTDGVGSGHLNDDDYVEKEISSMDTRRSTGASSSSYGVPQTNWS
1621 GNRGATYYTSKAQQAATAAAAAAALQQQQNGGRGDRLTQLPGTGHLQSTRGGQDGDQIE
1681 TEPKNYRNNGSPSRNGNSRDIFNGRSAFGENEHLIEDNEHHPLV
```

Fig. 2A

```
   1  ggtttaatta cccaagtttg agctccaaga gcacacatct gatcgtcgga
  51  ttctactgta ctccccgaaa aaccaacaaa aaacacaagt ttttgaacac
 101  ttgtaaatgc agacagaacg atgacgagaa tgaatattgt cagatgtcgg
 151  agacgacaca aaattttgga aaatttggaa gaagagaatc tcggcccgag
 201  ctgctcgtcg acgacttcaa caaccgctgc caccgaagct ctcggaacaa
 251  ccactgagga tatgaggctt aagcagcagc gaagctcgtc gcgtgccacg
 301  gagcacgata ttgtcgacgg caatcaccac gacgacgagc acatcacaat
 351  gagacggctt cgacttgtca aaaattcgcg gacgcggcgt agaacgacgc
 401  ccgattcaag tatggactgc tatgaggaaa acccgccatc acaaaaactt
 451  caataaatta ttcttggatt tctaaaaagt catcaatgac gtcattaatg
 501  cttttactgc tattcgcttt tgtacagccg tgtgcctcaa tagtcgaaaa
 551  acgatgcggc ccaatcgata ttcgaaatag gccgtgggat attaagccgc
 601  aatggtcgaa acttggtgat ccgaacgaaa aagatttggc tggtcagaga
 651  atggtcaact gcacagtggt ggaaggttcg ctgacaatct catttgtact
 701  gaaacacaag acaaaagcac aagaagaaat gcatcgaagt ctacagccaa
 751  gatattccca agacgaattt atcacttttc cgcatctacg tgaaattact
 801  ggaactctgc tcgttttga gactgaagga ttagtggatt tgcgtaaaat
 851  tttcccaaat cttcgtgtaa ttggaggccg ttcgctgatt caacactatg
 901  cgctgataat ttatcgaaat ccggatttgg agatcggtct tgacaagctt
 951  tccgtaattc gaaatggtgg tgtacggata atcgataatc gaaaactgtg
1001  ctacacgaaa acgattgatt ggaaacattt gatcacttct tccatcaacg
1051  atgttgtcgt tgataatgct gccgagtacg ctgtcactga gactggattg
1101  atgtgcccac gtggagcttg cgaagaggat aaaggcgaat caaagtgtca
1151  ttatttggag gaaaagaatc aggaacaagg tgtcgaaaga gttcagagtt
1201  gttggtcgaa caccacttgc caaaagtctt gtgcttatga tcgtcttctt
1251  ccaacgaaag aaatcggacc gggatgtgat gcgaacggcg atcgatgtca
1301  cgatcaatgc gtgggcggtt gtgagcgtgt gaatgatgcc acagcatgcc
1351  acgcgtgcaa gaatgtctat cacaagggaa agtgtatcga aagtgtgat
1401  gctcacctgt accttctcct tcaacgtcgt tgtgtgaccc gtgagcagtg
1451  tctgcagctg aatccggtgc tctcgaacaa aacagtgcct atcaaggcga
1501  cggcaggcct ttgctcggat aaatgtcccg atggttatca aatcaacccg
1551  gatgatcatc gagaatgccg aaaatgcgtt ggcaagtgtg agattgtgtg
1601  cgagatcaat cacgtcattg atacgtttcc gaaggcacag gcgatcaggc
1651  tatgcaatat tattgacgga aatctgacga tcgagattcg cggaaaacag
1701  gattcgggaa tggcgtccga gttgaaggat atatttgcga acattcacac
1751  gatcaccggc tacctgttgg tacgtcaatc gtcaccgttt atctcgttga
1801  acatgttccg gaatttacga cgtattgagg caaagtcact gttcagaaat
1851  ctatatgcta tcacagtttt tgaaaatccg aatttaaaaa agctattcga
1901  ttcaacgacg gatttgacgc ttgatcgtgg aactgtgtca attgccaata
1951  acaagatgtt atgcttcaag tatatcaagc agctaatgtc aaagttaaat
2001  ataccactcg atccgataga tcaatcagaa gggacaaatg gtgagaaggn
2051  aatctgtgag gatatggcaa tcaacgtgag catcacagcg gtcaacgcgg
2101  actcggtctt ctttagttgg ccctcattca acattaccga tatagatcag
2151  cgaaagtttc tcggctacga gctcttcttc aaagaagtcc cacgaatcga
2201  tgagaacatg acgatcgaag aggatcgaag tgcgtgtgtc gattcgtggc
2251  agagtgtctt caaacagtac tacgagacgt cgaacggtga accgaccccg
2301  gacatttta tggatattgg accgcgcgag cgaattcggc gaatacgct
2351  ctacgcgtac tatgtggcga cgcagatggt gttgcatgcc ggtgcgaaga
2401  acggtgtatc gaagattggt tttgtgagga cgagctacta tacgcctgat
2451  cctccgacgt tggcactagc gcaagtcgat tcggacgcta ttcatattac
2501  gtgggaagcg ccgctccaac cgaacggaga cctcacgcat tacacaatta
2551  tgtggcgtga gaatgaagtg agcccgtacg aggaagccga aaagttttgt
2601  acagatgcaa gcaccccgc aaatcgacaa cgcacgaaag atccgaaaga
2651  gacgattgta gccgataagc cagtcgatat tccgtcatca cgtaccgtag
2701  ctccgacact tttgactatg atgggtcacg aagatcagca gaaaacgtgc
```

Fig. 2B-1

```
2751  gctgcaacgc ccggttgttg ttcgtgttcg gctatcgaag aatcatcgga
2801  acagaacaag aagaagcgac cggatccgat gtcggcgatc gaatcatctg
2851  catttgagaa taagctgttg gatgaggttt taatgccgag agacacgatg
2901  cgagtgagac gatcaattga agacgcgaat cgagtcagtg aagagttgga
2951  aaaagctgaa aatttgggaa aagctccaaa aactctcggt ggaaagaagc
3001  cgctgatcca tatttcgaag aagaagccgt cgagcagcag caccacatcc
3051  acaccggctc caacgatcgc atcaatgtat gccttaacaa ggaaaccgac
3101  tacggtgccg ggaacaagga ttcggctcta cgagatctac gaacctttac
3151  ccggaagctg ggcgattaat gtatcagctc tggcattgga taatagttat
3201  gtgatacgaa atttgaagca ttacacactt tatgcgattt ctctatccgc
3251  gtgccaaaac atgacagtac ccggagcatc ttgctcaata tcccatcgtg
3301  cgggagcatt gaaacgaaca aaacacatca cagacattga taaagtgttg
3351  aatgaaacaa ttgaatggag atttatgaat aatagtcaac aagtcaacgt
3401  gacgtgggat ccaccgactg aagtgaatgg tggaatattc ggttatgttg
3451  taaagcttaa gtcaaaagtc gatggatcaa ttgttatgac gagatgtgtc
3501  ggtgcgaaga gaggatattc aacacggaat cagggtgtcc tattccagaa
3551  tttggccgat ggacgttatt ttgtctcagt aacggcgacc tctgtacacg
3601  gcgctggacc ggaagccgaa tcctccgacc caatcgtcgt catgacgcca
3651  ggcttcttca ctgtggaaat cattctcggc atgcttctcg tctttttgat
3701  tttaatgtca attgccggtt gtataatcta ctactacatt caagtacgct
3751  acggcaaaaa agtgaaagct ctatctgact ttatgcaatt gaatcccgaa
3801  tattgtgtgg acaataagta caatgcagac gattgggagc tacggcagga
3851  tgatgttgtg ctcggacaac agtgtggaga gggatcattc ggaaaagtgt
3901  acctaggaac tggaaataat gttgtttctc tgatgggtga tcgtttcgga
3951  ccgtgtgcta ttaagattaa tgtagatgat ccagcgtcga ctgagaatct
4001  caactatctc atggaagcta atattatgaa gaactttaag actaacttta
4051  tcgtccaact gtacggagtt atctctactg tacaaccagc gatggttgtg
4101  atggaaatga tggatcttgg aaatctccgt gactatctcc gatcgaaacg
4151  cgaagacgaa gtgttcaatg agacggactg caactttttc gacataatcc
4201  cgagggataa attccatgag tgggccgcac agatttgtga tggtatggcg
4251  tacctggagt cgctcaagtt ttgccatcga gatctcgccg cacgtaattg
4301  catgataaat cgggatgaga ctgtcaagat tggagatttc ggaatggctc
4351  gtgatctatt ctatcatgac tattataagc catcgggcaa gcgtatgatg
4401  cctgttcgat ggatgtcacc cgagtcgttg aaagacggaa agtttgactc
4451  gaaatctgat gtttggagct cggagttgt tctctatgaa atggttacac
4501  tcggtgctca gccatatatt ggtttgagta atgatgaggt gttgaattat
4551  attggaatgg cccggaaggt tatcaagaag cccgaatgtt gtgaaaacta
4601  ttggtataag gtgatgaaaa tgtgctggag atactcacct cgggatcgtc
4651  cgacgttcct ccagctcgtt catcttctag cagctgaagc ttcaccagaa
4701  ttccgagatt tatcatttgt cctaaccgat aatcaaatga tccttgacga
4751  ttcagaagca ctggatcttg atgatattga tgatactgat atgaatgatc
4801  aggttgtcga ggtggcaccg gatgttgaga acgtcgaggt tcagagtgat
4851  tcggaacgtc ggaatacgga ttcaataccg ttgaaacagt ttaagacgat
4901  ccctccgatc aatgcgacga cgagtcattc gacaatatcg attgatgaga
4951  caccgatgaa agcgaagcag cgagaaggat cgctggatga ggagtacgca
5001  ttgatgaatc atagtggagg tccgagtgat gcggaagttc ggacgtatgc
5051  tggtgatgga gattatgtgg agagagatgt tcgagagaat gatgtgccaa
5101  cgcgacgaaa tactggtgca tcaacatcaa gttacacagg tggtggtcca
5151  tattgcctaa caaatcgtgg tggttcaaat gaacgaggag ccggtttcgg
5201  tgaagcagta cgattaactg atggtgttgg aagtggacat ttaaatgatg
5251  atgattatgt tgaaaaagag atatcatcca tggatacgcg ccggagcacg
5301  ggcgcctcga gctcttccta cggtgttcca cagacgaatt ggagtggaaa
5351  tcgtggtgcc acgtattata cgagtaaagc tcaacaggca gcaactgcag
5401  cagcagcagc agcagcagct ctcaacagc  aacaaatgg tggtcgaggc
5451  gatcgattaa ctcaactacc cggaactgga catttacaat cgacacgtgg
5501  tggacaagat ggagattata ttgaaactga accgaaaaat tatagaaata
```

Fig. 2B-2

```
5551  atggatctcc atcgcgaaac ggcaacagcc gtgacatttt caacggacgt
5601  tcggctttcg gtgaaaatga gcatctaatc gaggataatg agcatcatcc
5651  acttgtctga aaccccaaa  aaatcccgcc tcttaaatta taaattatct
5701  cccacattat catatctcta cacgaatatc ggatttttt  tcagattttt
5751  tctgaaaaat tctgaataat ttacccat   ttttcaaatc tctgtatttt
5801  tttttgttat tacccc
```

Domain I

```
DAF-3   .NIDREFDQKACESLVKKLKDKKNDLQNLIDVVLSKGTKYTGCITIPRTLDG
         |   ||||||||| ||  |  ||    |      | ||  |||||
DPC4    GGESETFAKRAIESLVKKLKEKKDELDSLITAITTNGAHPSKCVTIQRTLDG
            mg125 P->L
        RLQVHGRKGFPHVVYGKLWRFNEMTKNETRHVDHCKHAFEMKSDMVCVNPYH
        ||||  |||||||||| |  |||   |||  ||  |   || | ||||||||
        RLQVAGRKGFPHVIYARLWRWPDLHKNELKHVKYCQYAFDLKCDSVCVNPYH
```

Domain II

```
DAF-3    IVYYEKNLQIGE..KKCSRGNFHVDGGFI...CSENRYSLGLEPNPIREPVAFKV
         |||   |  ||   |        |   |       |    | || |   |
DPC4     IAYFEMDVQVGETFKVPSSCPIVTVDGYVDPSGGDRFCLGQLSNVHRTEAIERA
            mg132 G->E
         RKAIVDGIRFSYKKDGSVWLQNRMKYPVFVTSGYLDEQSGGLKKDKVHKVYGCA
         |  |    |     | ||     ||| |||  |    |     | ||| |  |
         RLHIGKGVQLECKGEGDVWVRCLSDHAVFVQSYYLDREAGRAPGDAVHKIYPSA

SIKTFGFNVSKQIIRDALLSKQMA....TMYLQGKLTPMNYIYEKKTQEELRRE
         |||       |   ||       ||       |   |      |         |
         YIKVFDLRQCHRQMQQQAATAQAAAAAQAAAVAGNIPGPGSVGGIAPAISLSAA

ATRTTDSLAKYCCVRVSFCKGFGEAYPERPSIHDCPVWIELKINIAYDFMD
         |  || | | ||||||||||||||||||| ||||  |||||  |   | |
         AGIGVDDLRRLCILRMSFVKGWGPDYP.RQSIKETPCWIEIHLHRALQLLD
```

Fig. 5C

```
   1  atgaagctaa tagcaacttc tcttctagtt cccgacgagc acacaccgat
  51  gatgtcacca gtgaatacaa ctacaaagat tctacaacgg agtggtatta
 101  aaatggaaat cccgccatat ttggatccag acagtcagga tgatgacccg
 151  gaagatggtg tcaactaccc ggatccagat ttatttgaca caaaaaacac
 201  aaatatgacc gagtacgatt tggatgtgtt gaagcttgga aaaccagcag
 251  tagatgaagc acggaaaaag atcgaagttc ccgacgctag tgcgccgcca
 301  aacaaaattg tagaatattt gatgtattat agaacgttaa agaaagtga
 351  actcatacaa ctgaatgcgt atcggacaaa acgaaatcga ttatcgttga
 401  acttggtcaa aaacaatatt gatcgagagt tcgaccaaaa agcttgcgag
 451  tccctggtga aaaaattgaa ggataagaag aatgatctcc agaacctgat
 501  tgatgtggtt ctttcaaaag gtacaaaata taccggttgc attacaattc
 551  caaggacact tgatggccgg ttacaggtcc acggaagaaa aggtttccct
 601  cacgtagtct atggcaaact gtggaggttt aatgaaatga caaaaaacga
 651  aacgcgtcat gtggaccact gcaagcacgc atttgaaatg aaaagtgaca
 701  tggtatgcgt gaatccctat cactacgaaa ttgtcattgg aactatgatt
 751  gttgggcaga gggatcatga caatcgagat atgccgccgc acatcaacg
 801  ctaccacact ccaggtcggc aggatccagt tgacgatatg agtagattta
 851  taccaccagc ttccattcgt ccgcctccga tgaacatgca cacaaggcct
 901  cagcctatgc ctcaacaatt gccttcagtt ggcgcaacgt tgcccatcc
 951  tctcccacat caggcgccac ataacccagg ggtttcacat ccgtactcca
1001  ttgctccaca gacccattac ccgttgaaca tgaacccaat tccgcaaatg
1051  ccgcaaatgc cacaaatgcc accacctctc catcagggat atggaatgaa
1101  tgggccgagt tgctcttcag aaaacaacaa tccattccac caaaatcacc
1151  attataatga tattagccat ccaaatcact attcctacga ctgtggtccg
1201  aacttgtacg ggtttccaac tccttatccg gattttcacc atcctttcaa
1251  tcagcaacca caccagccgc acaactatc acaaaaccat acgtcccaac
1301  aaggcagtca tcaaccaggg caccaaggtc aggtaccgaa tgatccacca
1351  atttcaagac cagtgttaca accatcaaca gtcaccttgg acgtgttccg
1401  tcggtactgt agacagacat ttggaaatcg atttttgaa ggagaaagtg
1451  aacaatccgg cgcaataatt cggtctagta acaaattcat tgaagaattt
1501  gattcgccga tttgtggtgt gacagttgtt cgaccgcgga tgacagacgg
1551  tgaggttttg gagaacatca tgccggaaga tgcaccatat catgacattt
1601  gcaagttcat tttgaggctc acatcagaaa gtgtaacttt ctcaggagag
1651  gggccagaag ttagtgattt gaacgaaaaa tggggaacaa ttgtgtacta
1701  tgagaaaaat ttgcaaattg gcgagaaaaa atgttcgaga ggaaatttcc
1751  acgtggatgg cggattcatt tgctctgaga atcgttacag tctcggactt
1801  gagccaaatc caattagaga accagtggcg tttaaagttc gtaaagcaat
1851  agtggatgga attcgctttt cctacaaaaa agacgggagt gtttggcttc
1901  aaaaccgcat gaagtacccg gtatttgtca cttctgggta tctcgacgag
1951  caatcaggag gcctaaagaa ggataaagtg cacaaagttt acggatgtgc
2001  gtctatcaaa acgtttggct tcaacgtttc caaacaaatc atcagagacg
2051  cgcttctttc caagcaaatg gcaacaatgt acttgcaagg aaaattgact
```

Fig. 11A-1

```
2101  ccgatgaatt atatctacga gaagaagact caggaagagc tgcgaaggga
2151  agcaacacgc accactgatt cattggccaa gtactgttgt gtccgtgtct
2201  cgttctgcaa aggatttgga gaagcatacc cagaacgccc gtcaattcat
2251  gattgtccag tttggattga gttgaaaatc aacattgcct acgatttcat
2301  ggattcaatc tgccagtaca taaccaactg cttcgagccg ctaggaatgg
2351  aagattttgc aaaattggga atcaacgtca gtgatgacta aatgataact
2401  tttttcactc accctactag atactgattt agtcttattc caaatcatcc
2451  aacgatatca aacttttttcc tttgaacttt gcatactatg ttatcacaag
2501  ttccaagcag tttcaataca aacataggat atgttaacaa cttttgataa
2551  gaatcaagtt accaactgtt cattgtgagc tttgagctgt atagaaggac
2601  aatgtatccc atacctcaat ctttaatagt catcagtcac tggtcccgca
2651  ccaattttt cgattcgcat atgtcatata ttgcaccgtg gcccttttta
2701  ttgtaacttt taatatattt tcttcccaac ttgtgaatat gattgatgaa
2751  ccaccatttt gagtaataaa tgtattttttt gtgg
```

Fig. 11A-2

```
   1  gtaatcaaat tgtaaaggaa aaatattaat agtcagagta cacataaatg
  51  ggtgatcatc ataatttaac gggccttccc ggtacctcca tcccgccaca
 101  gttcaactat tctcagcccg gtaccagcac cggaggcccg ctttatggtg
 151  gaaaaccttc tcatggattg gaagatattc ctgatgtaga ggaatatgag
 201  aggaacctgc tcggggctgg agcaggtttt aatctgctca atgtaggaaa
 251  tatggctaat gttcccgacg agcacacacc gatgatgtca ccagtgaata
 301  caactacaaa gattctacaa cggagtggta ttaaaatgga aatcccgcca
 351  tatttggatc cagacagtca ggatgatgac ccggaagatg gtgtcaacta
 401  cccggatcca gatttatttg acacaaaaaa cacaaatatg accgagtacg
 451  atttggatgt gttgaagctt ggaaaaccag cagtagatga agcacggaaa
 501  aagatcgaag ttcccgacgc tagtgcgccg ccaaacaaaa ttgtagaata
 551  tttgatgtat tatagaacgt taaagaaag tgaactcata caactgaatg
 601  cgtatcggac aaaacgaaat cgattatcgt tgaacttggt caaaaacaat
 651  attgatcgag agttcgacca aaagcttgc gagtccctgg tgaaaaaatt
 701  gaaggataag aagaatgatc tccagaacct gattgatgtg gttctttcaa
 751  aaggtacaaa atataccggt tgcattacaa ttccaaggac acttgatggc
 801  cggttacagg tccacggaag aaaaggtttc cctcacgtag tctatggcaa
 851  actgtggagg tttaatgaaa tgacaaaaaa cgaaacgcgt catgtggacc
 901  actgcaagca cgcatttgaa atgaaagtg acatggtatg cgtgaatccc
 951  tatcactacg aaattgtcat tggaactatg attgttgggc agagggatca
1001  tgacaatcga gatatgccgc cgccacatca acgctaccac actccaggtc
1051  ggcaggatcc agttgacgat atgagtagat ttataccacc agcttccatt
1101  cgtccgcctc cgatgaacat gcacacaagg cctcagccta tgcctcaaca
1151  attgccttca gttggcgcaa cgtttgccca tcctctccca catcaggcgc
1201  cacataaccc aggggtttca catccgtact ccattgctcc acagacccat
1251  tacccgttga acatgaaccc aattccgcaa atgccgcaaa tgccacaaat
1301  gccaccacct ctccatcagg gatatggaat gaatgggccg agttgctctt
1351  cagaaaacaa caatccattc caccaaaatc accattataa tgatattagc
1401  catccaaatc actattccta cgactgtggt ccgaacttgt acgggtttcc
1451  aactccttat ccggattttc accatccttt caatcagcaa ccacaccagc
1501  cgccacaact atcacaaaac catacgtccc aacaaggcag tcatcaacca
1551  gggcaccaag gtcaggtacc gaatgatcca ccaatttcaa gaccagtgtt
1601  acaaccatca acagtcacct ggacgtgtt ccgtcggtac tgtagacaga
1651  catttggaaa tcgatttttt gaaggagaaa gtgaacaatc cggcgcaata
1701  attcggtcta gtaacaaatt cattgaagaa tttgattcgc cgatttgtgg
1751  tgtgacagtt gttcgaccgc ggatgacaga cggtgaggtt ttggagaaca
1801  tcatgccgga agatgcacca tatcatgaca tttgcaagtt cattttgagg
1851  ctcacatcag aaagtgtaac tttctcagga gaggggccag aagttagtga
1901  tttgaacgaa aaatggggaa caattgtgta ctatgagaaa aatttgcaaa
1951  ttggcgagaa aaaatgttcg agaggaaatt tccacgtgga tggcggattc
2001  atttgctctg agaatcgtta cagtctcgga cttgagccaa atccaattag
2051  agaaccagtg gcgtttaaag ttcgtaaagc aatagtggat ggaattcgct
```

Fig. 11B-1

```
2101  tttcctacaa aaaagacggg agtgtttggc ttcaaaaccg catgaagtac
2151  ccggtatttg tcacttctgg gtatctcgac gagcaatcag gaggcctaaa
2201  gaaggataaa gtgcacaaag tttacggatg tgcgtctatc aaaacgtttg
2251  gcttcaacgt ttccaaacaa atcatcagag acgcgcttct ttccaagcaa
2301  atggcaacaa tgtacttgca aggaaaattg actccgatga attatatcta
2351  cgagaagaag actcaggaag agctgcgaag ggaagcaaca cgcaccactg
2401  attcattggc caagtactgt tgtgtccgtg tctcgttctg caaaggattt
2451  ggagaagcat acccagaacg cccgtcaatt catgattgtc cagtttggat
2501  tgagttgaaa atcaacattg cctacgattt catggattca atctgccagt
2551  acataaccaa ctgcttcgag ccgctaggaa tggaagattt tgcaaaattg
2601  ggaatcaacg tcagtgatga ctaaatgata actttttttca ctcaccctac
2651  tagatactga tttagtctta ttccaaatca tccaacgata tcaaactttt
2701  tcctttgaac tttgcatact atgttatcac aagttccaag cagtttcaat
2751  acaaacatag gatatgttaa caacttttga taagaatcaa gttaccaact
2801  gttcattgtg agctttgagc tgtatagaag gacaatgtat cccatacctc
2851  aatctttaat agtcatcagt cactggtccc gcaccaattt tttcgattcg
2901  catatgtcat atattgcacc gtggcccttt ttattgtaac ttttaatata
2951  ttttcttccc aacttgtgaa tatgattgat gaaccaccat tttgagtaat
3001  aaatgtattt tttgtgg
```

Fig. 11B-2

```
   1  gtaatcaaat tgtaaaggaa aaatattaat agtcagagta cacataaatg
  51  ggtgatcatc ataatttaac gggccttccc ggtacctcca tcccgccaca
 101  gttcaactat tctcagcccg gtaccagcac cggaggcccg ctttatggtg
 151  gaaaaccttc tcatggattg gaagatattc ctgatgtaga ggaatatgag
 201  aggaacctgc tcggggctgg agcaggtttt aatctgctca atgtaggaaa
 251  tatggctaat gaatttaaac caataatcac attggacacg aaaccacctc
 301  gtgatgccaa caagtcattg gcattcaatg gcgggttgaa gctaatcact
 351  ccgaaaactg aagttcccga cgagcacaca ccgatgatgt caccagtgaa
 401  tacaactaca aagattctac aacggagtgg tattaaaatg gaaatcccgc
 451  catatttgga tccagacagt caggatgatg acccggaaga tggtgtcaac
 501  tacccggatc cagatttatt tgacacaaaa aacacaaata tgaccgagta
 551  cgatttggat gtgttgaagc ttggaaaacc agcagtagat gaagcacgga
 601  aaaagatcga agttcccgac gctagtgcgc cgccaaacaa aattgtagaa
 651  tatttgatgt attatagaac gttaaaagaa agtgaactca tacaactgaa
 701  tgcgtatcgg acaaaacgaa atcgattatc gttgaacttg gtcaaaaaca
 751  atattgatcg agagttcgac caaaaagctt gcgagtccct ggtgaaaaaa
 801  ttgaaggata agaagaatga tctccagaac ctgattgatg tggttctttc
 851  aaaaggtaca aaatataccg gttgcattac aattccaagg acacttgatg
 901  gccggttaca ggtccacgga agaaaaggtt tccctcacgt agtctatggc
 951  aaactgtgga ggtttaatga aatgacaaaa aacgaaacgc gtcatgtgga
1001  ccactgcaag cacgcatttg aaatgaaaag tgacatggta tgcgtgaatc
1051  cctatcacta cgaaattgtc attggaacta tgattgttgg gcagagggat
1101  catgacaatc gagatatgcc gccgccacat caacgctacc acactccagg
1151  tcggcaggat ccagttgacg atatgagtag atttatacca ccagcttcca
1201  ttcgtccgcc tccgatgaac atgcacacaa ggcctcagcc tatgcctcaa
1251  caattgcctt cagttggcgc aacgtttgcc catcctctcc cacatcaggc
1301  gccacataac ccaggggttt cacatccgta ctccattgct ccacagaccc
1351  attaccgtt gaacatgaac ccaattccgc aaatgccgca aatgccacaa
1401  atgccaccac ctctccatca gggatatgga atgaatgggc cgagttgctc
1451  ttcagaaaac aacaatccat tccaccaaaa tcaccattat aatgatatta
1501  gccatccaaa tcactattcc tacgactgtg gtccgaactt gtacgggttt
1551  ccaactcctt atccggattt tcaccatcct ttcaatcagc aaccacacca
1601  gccgccacaa ctatcacaaa accatacgtc ccaacaaggc agtcatcaac
1651  cagggcacca aggtcaggta ccgaatgatc caccaatttc aagaccagtg
1701  ttacaaccat caacagtcac cttggacgtg ttccgtcggt actgtagaca
1751  gacatttgga aatcgatttt ttgaaggaga aagtgaacaa tccggcgcaa
1801  taattcggtc tagtaacaaa ttcattgaag aatttgattc gccgatttgt
1851  ggtgtgacag ttgttcgacc gcggatgaca gacggtgagg ttttggagaa
1901  catcatgccg gaagatgcac catatcatga catttgcaag ttcattttga
1951  ggctcacatc agaaagtgta actttctcag gagaggggcc agaagttagt
2001  gatttgaacg aaaaatgggg aacaattgtg tactatgaga aaaatttgca
2051  aattggcgag aaaaaatgtt cgagaggaaa tttccacgtg gatggcggat
```

Fig. 11C-1

```
2101  tcatttgctc tgagaatcgt tacagtctcg gacttgagcc aaatccaatt
2151  agagaaccag tggcgtttaa agttcgtaaa gcaatagtgg atggaattcg
2201  cttttcctac aaaaaagacg ggagtgtttg gcttcaaaac cgcatgaagt
2251  acccggtatt tgtcacttct gggtatctcg acgagcaatc aggaggccta
2301  aagaaggata aagtgcacaa agtttacgga tgtgcgtcta tcaaaacgtt
2351  tggcttcaac gtttccaaac aaatcatcag agacgcgctt ctttccaagc
2401  aaatggcaac aatgtacttg caaggaaaat tgactccgat gaattatatc
2451  tacgagaaga agactcagga agagctgcga agggaagcaa cacgcaccac
2501  tgattcattg gccaagtact gttgtgtccg tgtctcgttc tgcaaaggat
2551  ttggagaagc atacccagaa cgccgtcaa ttcatgattg tccagtttgg
2601  attgagttga aaatcaacat tgcctacgat ttcatggatt caatctgcca
2651  gtacataacc aactgcttcg agccgctagg aatggaagat tttgcaaaat
2701  tgggaatcaa cgtcagtgat gactaaatga taactttttt cactcaccct
2751  actagatact gatttagtct tattccaaat catccaacga tatcaaactt
2801  tttcctttga actttgcata ctatgttatc acaagttcca agcagtttca
2851  atacaaacat aggatatgtt aacaactttt gataagaatc aagttaccaa
2901  ctgttcattg tgagctttga gctgtataga aggacaatgt atcccatacc
2951  tcaatcttta atagtcatca gtcactggtc ccgcaccaat tttttcgatt
3001  cgcatatgtc atatattgca ccgtggccct ttttattgta acttttaata
3051  tattttcttc ccaacttgtg aatatgattg atgaaccacc attttgagta
3101  ataaatgtat tttttgtgg
```

Fig. 11C-2

```
  1  MKLIATSLLV PDEHTPMMSP VNTTTKILQR SGIKMEIPPY LDPDSQDDDP
 51  EDGVNYPDPD LFDTKNTNMT EYDLDVLKLG KPAVDEARKK IEVPDASAPP
101  NKIVEYLMYY RTLKESELIQ LNAYRTKRNR LSLNLVKNNI DREFDQKACE
151  SLVKKLKDKK NDLQNLIDVV LSKGTKYTGC ITIPRTLDGR LQVHGRKGFP
201  HVVYGKLWRF NEMTKNETRH VDHCKHAFEM KSDMVCVNPY HYEIVIGTMI
251  VGQRDHDNRD MPPPHQRYHT PGRQDPVDDM SRFIPPASIR PPPMNMHTRP
301  QPMPQQLPSV GATFAHPLPH QAPHNPGVSH PYSIAPQTHY PLNMNPIPQM
351  PQMPQMPPPL HQGYGMNGPS CSSENNNPFH QNHHYNDISH PNHYSYDCGP
401  NLYGFPTPYP DFHHPFNQQP HQPPQLSQNH TSQQGSHQPG HQGQVPNDPP
451  ISRPVLQPST VTLDVFRRYC RQTFGNRFFE GESEQSGAII RSSNKFIEEF
501  DSPICGVTVV RPRMTDGEVL ENIMPEDAPY HDICKFILRL TSESVTFSGE
551  GPEVSDLNEK WGTIVYYEKN LQIGEKKCSR GNFHVDGGFI CSENRYSLGL
601  EPNPIREPVA FKVRKAIVDG IRFSYKKDGS VWLQNRMKYP VFVTSGYLDE
651  QSGGLKKDKV HKVYGCASIK TFGFNVSKQI IRDALLSKQM ATMYLQGKLT
701  PMNYIYEKKT QEELRREATR TTDSLAKYCC VRVSFCKGFG EAYPERPSIH
751  DCPVWIELKI NIAYDFMDSI CQYITNCFEP LGMEDFAKLG INVSDD
```

Fig. 12A

```
  1 MGDHHNLTGL PGTSIPPQFN YSQPGTSTGG PLYGGKPSHG LEDIPDVEEY
 51 ERNLLGAGAG FNLLNVGNMA NVPDEHTPMM SPVNTTTKIL QRSGIKMEIP
101 PYLDPDSQDD DPEDGVNYPD PDLFDTKNTN MTEYDLDVLK LGKPAVDEAR
151 KKIEVPDASA PPNKIVEYLM YYRTLKESEL IQLNAYRTKR NRLSLNLVKN
201 NIDREFDQKA CESLVKKLKD KKNDLQNLID VVLSKGTKYT GCITIPRTLD
251 GRLQVHGRKG FPHVVYGKLW RFNEMTKNET RHVDHCKHAF EMKSDMVCVN
301 PYHYEIVIGT MIVGQRDHDN RDMPPPHQRY HTPGRQDPVD DMSRFIPPAS
351 IRPPPMNMHT RPQPMPQQLP SVGATFAHPL PHQAPHNPGV SHPYSIAPQT
401 HYPLNMNPIP QMPQMPQMPP PLHQGYGMNG PSCSSENNNP FHQNHHYNDI
451 SHPNHYSYDC GPNLYGFPTP YPDFHHPFNQ QPHQPPQLSQ NHTSQQGSHQ
501 PGHQGQVPND PPISRPVLQP STVTLDVFRR YCRQTFGNRF FEGESEQSGA
551 IIRSSNKFIE EFDSPICGVT VVRPRMTDGE VLENIMPEDA PYHDICKFIL
601 RLTSESVTFS GEGPEVSDLN EKWGTIVYYE KNLQIGEKKC SRGNFHVDGG
651 FICSENRYSL GLEPNPIREP VAFKVRKAIV DGIRFSYKKD GSVWLQNRMK
701 YPVFVTSGYL DEQSGGLKKD KVHKVYGCAS IKTFGFNVSK QIIRDALLSK
751 QMATMYLQGK LTPMNYIYEK KTQEELRREA TRTTDSLAKY CCVRVSFCKG
801 FGEAYPERPS IHDCPVWIEL KINIAYDFMD SICQYITNCF EPLGMEDFAK
851 LGINVSDD
```

Fig. 12B

```
  1 MGDHHNLTGL PGTSIPPQFN YSQPGTSTGG PLYGGKPSHG LEDIPDVEEY
 51 ERNLLGAGAG FNLLNVGNMA NEFKPIITLD TKPPRDANKS LAFNGGLKLI
101 TPKTEVPDEH TPMMSPVNTT TKILQRSGIK MEIPPYLDPD SQDDDPEDGV
151 NYPDPDLFDT KNTNMTEYDL DVLKLGKPAV DEARKKIEVP DASAPPNKIV
201 EYLMYYRTLK ESELIQLNAY RTKRNRLSLN LVKNNIDREF DQKACESLVK
251 KLKDKKNDLQ NLIDVVLSKG TKYTGCITIP RTLDGRLQVH GRKGFPHVVY
301 GKLWRFNEMT KNETRHVDHC KHAFEMKSDM VCVNPYHYEI VIGTMIVGQR
351 DHDNRDMPPP HQRYHTPGRQ DPVDDMSRFI PPASIRPPPM NMHTRPQPMP
401 QQLPSVGATF AHPLPHQAPH NPGVSHPYSI APQTHYPLNM NPIPQMPQMP
451 QMPPPLHQGY GMNGPSCSSE NNNPFHQNHH YNDISHPNHY SYDCGPNLYG
501 FPTPYPDFHH PFNQQPHQPP QLSQNHTSQQ GSHQPGHQGQ VPNDPPISRP
551 VLQPSTVTLD VFRRYCRQTF GNRFFEGESE QSGAIIRSSN KFIEEFDSPI
601 CGVTVVRPRM TDGEVLENIM PEDAPYHDIC KFILRLTSES VTFSGEGPEV
651 SDLNEKWGTI VYYEKNLQIG EKKCSRGNFH VDGGFICSEN RYSLGLEPNP
701 IREPVAFKVR KAIVDGIRFS YKKDGSVWLQ NRMKYPVFVT SGYLDEQSGG
751 LKKDKVHKVY GCASIKTFGF NVSKQIIRDA LLSKQMATMY LQGKLTPMNY
801 IYEKKTQEEL RREATRTTDS LAKYCCVRVS FCKGFGEAYP ERPSIHDCPV
851 WIELKINIAY DFMDSICQYI TNCFEPLGME DFAKLGINVS DD
```

Fig. 12C

```
tgatctttcaagccgaagcaatcaagacctcaaagccaatcaactctactcacttttcttcagaaccttaacttttgtg
tcactttccccaaaaaccgttcaagctgctgccttcactctcatccctcctcttactccttcttctcgtccgctacta
ctgtatcttctggacatctacctgtatacacaccagtggccagtcatctgccattacaatttcatcaattgacacttctt
caacaacaaccgccgtcctcattcactcccgattcttcctcatcctcaacatcgtcgtctttggctgaaattcccgaaga
cgttatgatggagatgctggtagatcagggaactgatgcatcgtcatccgcctccacgtccacctcatctgtttcgagat
tcggagcggacacgttcatgaatacaccggatgatgtgatgatgaatgatgatatggaaccgattcctcgtgatcggtgc
aatacgtggccaatgcgtaggccgcaactcgaaccaccactcaactcgagtcccattattcatgaacaaattcctgaaga
agatgctgacctatacgggagcaatgagcaatgtggacagctcggcggagcatcttcaaacgggtcgacagcaatgcttc
atactccagatggaagcaattctcatcagacatcgtttcttcggagtttcagaatgtccgaatcgccagacgataccgta
tcgggaaaaaagacaacgaccagacggaacgcttggggaaatatgtcatatgctgaacttatcactacagccattatggc
tagtccagagaaacggttaactcttgcacaagtttacgaatggatggtccagaatgttccatacttcagggataagggag
attcgaacagttcagctggatggaagaactcgatccgtcacaatctgtctcttcattctcgtttcatgcgaattcagaat
gaaggagccggaaagagctcgtggtgggttattaatccagatgcaaagccaggaatgaatccacggcgtacacgtgaacg
atccaatactattgagacgactacaaaggctcaactcgaaaaatctcgccgcggagccaagaagaggataaaggagagag
cattgatgggctcccttcactcgacacttaatggaaattcgattgccggatcgattcaaacgatttctcacgatttgtat
gatgatgatcaatgcaaggagcatttgataacgttccatcatctttccgtccccgaactcaatcgaacctctcgattcct
ggatcgtcgtctcgtgtttctccagctattggaagtgatatctatgatgatctagaattcccatcatgggttggcgaatc
ggttccagcaattccaagtgatattgttgatagaactgatcaaatgcgtatcgatgcaactactcatagttggtggagtt
cagattaagcaggagtcgaagccgattaagacggaaccaattgctccaccaccatcataccacgagttgaacagtgtccg
tggatcgtgtgctcagaatccacttcttcgaaatccaattgtgccaagcactaacttcaagccaatgccactaccgggtg
cctatggaaactatcaaaatggtggaataactccaatcaattggctatcaacatccaactcatctccactgcctggaatt
caatcgtgtggaattgtagctgcacagcatactgtcgcttcttcatcggctcttccaattgatttggaaaatctgacact
tcccgatcagccactgatggatactatggatgttgatgcattgatcagacatgagctgagtcaagctggagggcagcata
ttcatttttgatttgtaaattctcttcatttttgtttcccctggtgttgttcgaaagagagatagcaaagcagcgaggagtg
aggtaagcagcaataaaaattttggatttttttttggttttccagaaataatcgatttctggaaaatttcaaaaaaaa
atcggaatttttagttaattatttgatgagaaaaaaaaattagaaaacataaggaaaaatgaaaagcgttttttttttc
gaaaattttagaattctcctacatttccaataagggccttagaactgcaaacaaacaaaaattggaattttcgaatcaaa
aagttccccgaataaaagtagttcgaatattaaaaagcatttaattcctcttaaaaaaattgaataatagccgaaattt
gcagatttttttctgaaaatcgaaaaaccaaaatttttgattttaaatttttttttacttccagatagtaaaat
cattagcactgaaaattatttgaaaaaaaacttcaaatacaaattttgttttcgaaaaaaaaaatttaaatatatattt
cagaaatcttccgtcttcatcttttcaaatccctacctacacacactcaacgatcatcacagccagaccatcaatattct
tccaaattttgacgtcgttaatttttttttcagttttttcaaaaactctatttttctatttctgtcgtttgttccccttc
tctcgtctaattccaacacattcatcccagtgacgtcgtgtaataataatataaaataccctcttctctctttcttcccct
aatgcgaaatatcgaaaaaccgttgattattacctctttttttcttgtttttttttttctctctctctcccgtcatccag
gttcttcactctttaaatgctacctctatcccatctttttcgctgtaaatttgtttcgcaatcaaaactgctaaaacaca
ttccccaatctgtctttttaattgaattttcaaaaaattttgatttcttgatttctcttgtaattctttaattttcctc
ttttttttccccctggtagcaaatgtctagcgattctctttcttttttgtttaactttcacatctggccgattcgaatc
ctccgtatacacacacacatagtaatctacctccaaaatttactgaaagatgtgatccctctctgtctccctctacaa
aacattatttgtctgtttgtgtatattgccaccacgtcgatttttaaattaaaaccatcgttttttcttcttttctactttt
tttctcgaaaaatttaacaacacacaaaaaaatccttcaaaaaatctcagttttaaatggtgtggcaatatatcggatcc
ccctctacaccagaacagtcttgcaatttcagagaatgattttcagattttcatatcacaggcccctttttttgcttg
ttttttctctacctctcttttcttttcattctatttctctctcttgttttctctctgttatcctgtacattttccttcca
attctttctggctatttctgattttcgagttcatattctctacgtctcactttctctcgcgccacgcccccttttttcgtc
tccctccgcccccaaatatatttgcgactgtatgatgatgatgatgatttaataaaaat
```

Fig. 13A

```
ttacacgtggccaatgcaacaatacatctatcaggaatcgtcagcaaccattccccatcaccatttaaatcaacacaaca
atccgtatcatccaatgcatcctcatcatcaattacctcatatgcaacaacttcctcaacctctattgaatcttaacatg
acgacgttaacatcttctggcagttccgtggccagttccattggaggcggagctcaatgctctccgtgcgcgtcgggctc
ctcgaccgctgcaacaaattcctctcaacagcagcagaccgttggtcaaatgcttgctgcatcggtgccttgttcttcat
ctggcatgacacttggaatgtcacttaatctgtcacaaggcggtggtccaatgccggcaaaaaagaagcgttgtcgtaag
aagccaaccgatcaattggcacagaagaaaccgaatccatggggtgaggaatcctattcggatatcattgccaaagcatt
ggaatcggcgccagacggaaggcttaaactcaatgagatttatcaatggttctctgataatattccctactttggagaac
gatctagtcccgaggaggccgccggatggaagaactcgatccgtcacaatctgtctcttcattctcgtttcatgcgaatt
cagaatgaaggagccggaaagagctcgtggtgggttattaatccagatgcaaagccaggaatgaatccacggcgtacacg
tgaacgatccaatactattgagacgactacaaaggctcaactcgaaaaatctcgccgcggagccaagaagaggataaagg
agagagcattgatgggctcccttcactcgacacttaatggaaattcgattgccggatcgattcaaacgatttctcacgat
ttgtatgatgatgattcaatgcaaggagcatttgataacgttccatcatctttccgtccccgaactcaatcgaacctctc
gattcctggatcgtcgtctcgtgtttctccagctattggaagtgatatctatgatgatctagaattcccatcatgggttg
gcgaatcggttccagcaattccaagtgatattgttgatagaactgatcaaatgcgtatcgatgcaactactcatattggt
ggagttcagattaagcaggagtcgaagccgattaagacggaaccaattgctccaccaccatcataccacgagttgaacag
tgtccgtggatcgtgtgctcagaatccacttcttcgaaatccaattgtgccaagcactaacttcaagccaatgccactac
cgggtgcctatggaaactatcaaaatggtggaataactccaatcaattggctatcaacatccaactcatctccactgcct
ggaattcaatcgtgtggaattgtagctgcacagcatactgtcgcttcttcatcggctcttccaattgatttggaaaatct
gacacttcccgatcagccactgatggatactatggatgttgatgcattgatcagacatgagctgagtcaagctggagggc
agcatattcattttgatttgtaaattctcttcatttgtttcccctggtgttgttcgaaagagagatagcaaagcagcga
ggagtgagaaatcttccgtcttcatcttttcaaatccctacctacacacactcaacgatcatcacagccagaccatcaat
attcttccaaattttgacgtcgttaattttttttcagttttttcaaaaactctattttctattttctgtcgtttgttccc
ctttctctcgtctaattccaacacattcatcccagtgacgtcgtgtaataataatataaaatacctcttctctctttctt
cccctaatgcgaaatatcgaaaaaccgttgattattacctctttttttcttgttttttttttctctctctctctcccgtca
tccaggttcttcactctttaaatgctacctctatcccatcttttttcgctgtaaatttgtttcgcaatcaaaactgctaaa
acacattccccaatctgtctttttttaattgaattttttcaaaaaatttgatttcttgatttctcttgtaattctttaattt
tcctcttttttttttcccctggtagcaaatgtctagcgattctctttcttttttttgtttaacttttcacatctggccgattc
gaatcctccgtatacacacacacatagtaatctacctccaaaattttactgaaagatgtgatcccctctctgtctccctc
tacaaaacattatttgtctgtttgtgtatattgccaccacgtcgattttaaattaaaaccatcgttttttcttcttttct
actttttttctcgaaaaatttaacaacacacaaaaaaatccttcaaaaaatctcagttttaaatggtgtggcaatatatcg
gatccccctctacaccagaacagtcttgcaatttcagagaatgattttcagattttttcatatcacaggcccccttttttt
gcttgttttttttctctacctctctcttttcttttcattctatttctctctcttgttttctctctgttatcctgtacatttttcc
ttccaattctttctggctatttctgattttcgagttcatattctctacgtctcactttctctcgcgccacgccccctttt
tcgtctccctccgcccccaaatatatttgcgactgtatgatgatgatgatgatttaataaaaat
```

Fig. 13B

MMEMLVDQGTDASSSASTSTSSVSRFGADTFMNTPDDVMMNDDMEPIPRDR
CNTWPMRRPQLEPPLNSSPIIHEQIPEEDADLYGSNEQCGQLGGASSNGST
AMLHTPDGSNSHQTSFPSDFRMSESPDDTVSGKKTTTRRNAWGNMSYAELI
TTAIMASPEKRLTLAQVYEWMVQNVPYFRDKGDSNSSAGWKNSIRHNLSLH
SRFMRIQNEGAGKSSWWVINPDAKPGMNPRRTRERSNTIETTTKAQLEKSR
RGAKKRIKERALMGSLHSTLNGNSIAGSIQTISHDLYDDDSMQGAFDNVPS
SFRPRTQSNLSIPGSSSRVSPAIGSDIYDDLEFPSWVGESVPAIPSDIVDR
TDQMRIDATTHIGGVQIKQESKPIKTEPIAPPPSYHELNSVRGSCAQNPLL
RNPIVPSTNFKPMPLPGAYGNYQNGGITPINWLSTSNSSPLPGIQSCGIVA
AQHTVASSSALPIDLENLTLPDQPLMDTMDVDALIRHELSQAGGQHIHFDL

Fig. 14A

MQQYIYQESSATIPHHHLNQHNNPYHPMHPHHQLPHMQQLPQPLLNLNMTT
LTSSGSSVASSIGGGAQCSPCASGSSTAATNSSQQQQTVGQMLAASVPCSS
SGMTLGMSLNLSQGGGPMPAKKKRCRKKPTDQLAQKKPNPWGEESYSDIIA
KALESAPDGRLKLNEIYQWFSDNIPYFGERSSPEEAAGWKNSIRHNLSLHS
RFMRIQNEGAGKSSWWVINPDAKPGMNPRRTRERSNTIETTTKAQLEKSRR
GAKKRIKERALMGSLHSTLNGNSIAGSIQTISHDLYDDDSMQGAFDNVPSS
FRPRTQSNLSIPGSSSRVSPAIGSDIYDDLEFPSWVGESVPAIPSDIVDRT
DQMRIDATTHIGGVQIKQESKPIKTEPIAPPPSYHELNSVRGSCAQNPLLR
NPIVPSTNFKPMPLPGAYGNYQNGGITPINWLSTSNSSPLPGIQSCGIVAA
QHTVASSSALPIDLENLTLPDQPLMDTMDVDALIRHELSQAGGQHIHFDL

Fig. 14B

```
   1 cggaagccat ggagctcgag atctgattgc tggacacgga cggaactccg acgtatctcg
  61 cagatgcatg ttaacatttt acatccacaa ctgcaaacga tggtcgagca gtggcaaatg
 121 cgagaacgcc catcgctgga gaccgagaat ggcaaaggat cgctgctcct ggaaaatgaa
 181 ggtgtcgcag atatcatcac tatgtgtcca ttcggagaag ttattagtgt agtatttccg
 241 tggtttcttg caaatgtgcg aacatcgcta gaaatcaagc tatcagattt caaacatcaa
 301 cttttcgaat tgattgctcc gatgaagtgg ggaacatatt ccgtaaagcc acaggattat
 361 gtgttcagac agttgaataa tttcggcgaa attgaagtta tatttaacga cgatcaaccc
 421 ctgtcgaaat tagagctcca cggcactttc ccaatgcttt ttctctacca acctgatgga
 481 ataaacaggg ataaagaatt aatgagtgat ataagtcatt gtctaggata ctcactggat
 541 aaactggaag agagcctcga tgaggaactc cgtcaatttc gtgcttctct ctgggctcgt
 601 acgaagaaaa cgtgcttgac acgtggactt gagggtacca gtcactacgc gttccccgaa
 661 gaacagtact tgtgtgttgg tgaatcgtgc ccgaaagatt tggaatcaaa agtcaaggct
 721 gccaagctga gttatcagat gttttggaga aaacgtaaag cggaaatcaa tggagtttgc
 781 gagaaaatga tgaagattca aattgaattc aatccgaacg aaactccgaa atctctgctt
 841 cacacgtttc tctacgaaat gcgaaaattg gatgtatacg ataccgatga tcctgcagat
 901 gaaggatggt ttcttcaatt ggctggacgt accacgtttg ttacaaatcc agatgtcaaa
 961 cttacgtctt atgatggtgt ccgttcggaa ctggaaagct atcgatgccc tggattcgtt
1021 gttcgccgac aatcactagt cctcaaagac tattgtcgcc caaaaccact ctacgaacca
1081 cattatgtga gagcacacga acgaaaactt gctctagacg tgctcagcgt gtctatagat
1141 agcacaccaa aacagagcaa gaacagtgac atggttatga ctgattttcg tccgacagct
1201 tcactcaaac aagtttcact ttgggacctt gacgcgaatc ttatgatacg gcctgtgaat
1261 atttctggat tcgatttccc ggccgacgtg gatatgtacg ttcgaatcga attcagtgta
1321 tatgtgggga cactgacgct ggcatcaaaa tctacaacaa aagtgaatgc tcaatttgca
1381 aaatggaata aggaaatgta cacttttgat ctatacatga aggatatgcc accatctgca
1441 gtactcagca ttcgtgtttt gtacggaaaa gtgaaattaa aaagtgaaga attcgaagtt
1501 ggttgggtaa atatgtccct aaccgattgg agagatgaac tacgacaagg acaattttta
1561 ttccatctgt gggctcctga accgactgcc aatcgtagta ggatcggaga aatggagca
1621 aggataggca ccaacgcagc ggttacaatt gaaatctcaa gttatggtgg tagagttcga
1681 atgccgagtc aaggacaata cacatatctc gtcaagcacc gaagtacttg gacggaaact
1741 ttgaatatta tgggtgatga ctatgagtcg tgtatcagag atccaggata taagaagctt
1801 cagatgcttg tcaagaagca tgaatctgga attgtattag aggaagatga acaacgtcat
1861 gtctggatgt ggaggagata cattcaaaag caggagcctg atttgctcat tgtgctctcc
1921 gaactcgcat tgtgtggac tgatcgtgag aacttttccg agctctatgt gatgcttgaa
1981 aaatggaaac cgccgagtgt ggcagccgcg ttgactttgc ttggaaaacg ttgcacggat
2041 cgtgtgattc gaaagtttgc agtggagaag ttgaatgagc agctgagccc ggtcacattc
2101 catcttttca tattgcctct catacaggcg ttgaagtacg aaccgcgtgc tcaatcggaa
2161 gttggaatga tgctcttgac tagagctctc tgcgattatc gaattggaca tcgacttttc
2221 tggctgctcc gtgcagagat tgctcgtttg agagattgtg atctgaaaag tgaagaatat
2281 cgccgtatct cacttctgat ggaagcttac ctccgtggaa atgaagagca catcaagatc
2341 atcacccgac aagttgacat ggttgatgag ctcacacgaa tcagcactct tgtcaaagga
2401 atgccaaaag atgttgctac gatgaaactg cgtgacgagc ttcgatcgat tagtcataaa
2461 atggaaaata tggattctcc actggatcct gtgtacaaac tgggtgaaat gataatcgac
2521 aaagccatcg tcctaggaag tgcaaaacgt ccgttaatgc ttcactggaa gaacaaaaat
2581 ccaaagagtg acctgcacct tccgttctgt gcaatgatct tcaagaatgg agacgatctt
2641 cgccaggaca tgcttgttct tcaagttctc gaagttatgg ataacatctg gaaggctgca
```

Fig. 15-1

```
2701 aacattgatt gctgtttgaa cccgtacgca gttcttccaa tgggagaaat gattggaatt
2761 attgaagttg tgcctaattg taaaacaata ttcgagattc aagttggaac aggattcatg
2821 aatacagcag ttcggagtat tgatccttcg tttatgaata agtggattcg gaaacaatgc
2881 ggaattgaag atgaaaagaa gaaaagcaaa aaggactcta cgaaaaatcc catcgaaaag
2941 aagattgata atactcaagc catgaagaaa tattttgaaa gtgtcgatcg attcctatac
3001 tcgtgtgttg gatattcagt tgccacgtac ataatgggaa tcaaggatcg tcacagtgat
3061 aatctgatgc tcactgaaga tggaaaatat gtccacattg atttcggtca catttggga
3121 cacggaaaga ccaaacttgg gatccagcga gatcgtcaac cgtttattct aaccgaacac
3181 tttatgacag tgattcgatc gggtaaatct gtggatggaa attcgcatga gctacaaaaa
3241 ttcaaaacgt tatgcgtcga agcctacgaa gtaatgtgga ataatcgaga tttgttcgtt
3301 tccttgttca ccttgatgct cggaatggag ttgcctgagc tgtcgacgaa agcggatttg
3361 gatcatttga agaaaaccct cttctgcaat ggagaaagca agaagaagc gagaaagttt
3421 ttcgctggaa tctacgaaga agccttcaat ggatcatggt ctaccaaaac gaattggctc
3481 ttccacgcag tcaaacacta ctga
```

Fig. 15-2

```
   1 RKPWSSRSDC WTRTELRRIS QMHVNILHPQ LQTMVEQWQM RERPSLETEN GKGSLLLENE
  61 GVADIITMCP FGEVISVVFP WFLANVRTSL EIKLSDFKHQ LFELIAPMKW GTYSVKPQDY
 121 VFRQLNNFGE IEVIFNDDQP LSKLELHGTP PMLFLYQPDG INRDKELMSD ISHCLGYSLD
 181 KLEESLDEEL RQFRASLWAR TKKTCLTRGL EGTSHYAFPE EQYLCVGESC PKDLESKVKA
 241 AKLSYQMFWR KRKAEINGVC EKMMKIQIEF NPNETPKSLL HTFLYEMRKL DVYDTDDPAD
 301 EGWFLQLAGR TTFVTNPDVK LTSYDGVRSE LESYRCPGFV VRRQSLVLKD YCRPKPLYEP
 361 HYVRAHERKL ALDVLSVSID STPKQSKNSD MVMTDFRPTA SLKQVSLWDL DANLMIRPVN
 421 ISGFDFPADV DMYVRIEFSV YVGTLTLASK STTKVNAQFA KWNKEMYTFD LYMKDMPPSA
 481 VLSIRVLYGK VKLKSEEFEV GWVNMSLTDW RDELRQGQFL FHLWAPEPTA NRSRIGENGA
 541 RIGTNAAVTI EISSYGGRVR MPSQGQYTYL VKHRSTWTET LNIMGDDYES CIRDPGYKKL
 601 QMLVKKHESG IVLEEDEQRH VWMWRRYIQK QEPDLLIVLS ELAFVWTDRE NFSELYVMLE
 661 KWKPPSVAAA LTLLGKRCTD RVIRKFAVEK LNEQLSPVTF HLFILPLIQA LKYEPRAQSE
 721 VGMMLLTRAL CDYRIGHRLF WLLRAEIARL RDCDLKSEEY RRISLLMEAY LRGNEEHIKI
 781 ITRQVDMVDE LTRISTLVKG MPKDVATMKL RDELRSISHK MENMDSPLDP VYKLGEMIID
 841 KAIVLGSAKR PLMLHWKNKN PKSDLHLPFC AMIFKNGDDL RQDMLVLQVL EVMDNIWKAA
 901 NIDCCLNPYA VLPMGEMIGI IEVVPNCKTI FEIQVGTGFM NTAVRSIDPS FMNKWIRKQC
 961 GIEDEKKKSK KDSTKNPIEK KIDNTQAMKK YFESVDRFLY SCVGYSVATY IMGIKDRHSD
1021 NLMLTEDGKY VHIDFGHILG HGKTKLGIQR DRQPFILTEH FMTVIRSGKS VDGNSHELQK
1081 FKTLCVEAYE VMWNNRDLFV SLFTLMLGME LPELSTKADL DHLKKTLFCN GESKEEARKF
1141 FAGIYEEAFN GSWSTKTNWL FHAVKHY
```

```
DAF-16a1  511  ................................................  ................SCNGYGR
DAF-16b   531  ................................................  ..................YGR
FKHR      511  ASHNKMMNPSSH.THPGHAQTSAVNGRPEPHTVSTMEHTSGMNRLTQVKTPVQVPLPHPMOMSALGGYSVSSCNGYGR
FKHRL1    523  PNQGSLVN.QNL.LHQHQTQGALGGSRAWSNSWSNM.GLSESSSEGSAKHQQQSPVSQSMQ.TLSDSLSGSSLYSTSAN
AFX       464  QDLDLDMYMENLECDMDNIISDLMDECEGLDFNFEPDP........................................

DAF-16a1  511  ................................................SEPHSVKTTTHSWWSG
DAF-16b   531  ................................................  ............SG
FKHR      590  MGLLHQEKLPSDLD.GMEIERLDCDMESLARNDLMDGDITDENFDNVLPNQ..............
FKHRL1    599  LPVMGHEKFPSDLDLDMPNGSERCDMESIERSELMDADGLDRNFDSLISTQNVVGLNVGNETGAKQASSQSWVPG
AFX       502  ................................................................

Fig. 21A-2
```

Comparison of the human AKT protein sequence to the cosmid sequence C12D8, located in the genetic interval where sup(mg144) maps. Numbering in the AKT protein sequence by amino acid residues, and in the cosmid sequence by nucleotide position.

```
           Score = 450 (207.4 bits), Expect = 5.2e-165, Sum P(7) = 5.2e-165
           Identities = 79/121 (65%), Positives = 97/121 (80%), Frame = +1

SEQ ID NO:87  Query:  319 EVLEDNDYGRAVDWWGLGVVMYEMMCGRLPFYNQDHEKLFELILMEEIRFPRTLGPEAKS 378
SEQ ID NO:325             +VL+D+DYGR VDWWG+GVVMYEMMCGRLPFY++DH KLFELI+  ++RFP L EA++
SEQ ID NO:88  Sbjct: 33685 QVLDDHDYGRCVDWWGVGVVMYEMMCGRLPFYSKDHNKLFELIMAGDLRFPSKLSQEART 33864

Query:  379 LLSGLLKKDPTQRLGGGSEDAKEIMQHRFFPANIVWQDVYEKKLSPPFKPQVTSETDTRYFD 439
                          LL+GLL KDPTQRLGGG EDA EI +  FF  + W+  Y K++ PP+KP V SETDT YFD
              Sbjct: 33865 LLTGLLVKDPTQRLGGGPEDALEICRADFPRTVDWEATYRKEIEPPYKPNVQSETDTSYFD 34047

Score = 256 (118.0 bits), Expect = 5.2e-165, Sum P(7) = 5.2e-165
           Identities = 48/66 (72%), Positives = 59/66 (89%), Frame = +1

SEQ ID NO:89  Query:  146 TMNEFEYLKLLGKGTFGKVILVKEKATGRYYAMKILKKEVIVAKDEVAHTLTENRVLQNS 205
SEQ ID NO:326             TM +F++LK+LGKGTFGKVIL KEK T + YA+KILKK+VI+A++EVAHTLTENRVLQ
SEQ ID NO:90  Sbjct: 32314 TMEDFDFLKVLGKGTFGKVILCKEKRTQKLYAIKILKKDVIIAREEVAHTLTENRVLQRC 32493

Query:  206 RHPFLT 211
                          +HPFLT
              Sbjct: 32494 KHPFLT 32511

Score = 190 (87.6 bits), Expect = 5.2e-165, Sum P(7) = 5.2e-165
           Identities = 36/45 (80%), Positives = 37/45 (82%), Frame = +2

SEQ ID NO:91  Query:  276 KLENLMLDKDGHIKITDFGLCKEGIKDGATMKTFCGTPEYLAPEV 320
SEQ ID NO:99              KLENL+LDKDGHIKI DFGLCKE I G   TFCGTPEYLAPEV
SEQ ID NO:92  Sbjct: 33509 KLENLLLDKDGHIKIADFGLCKEEISFGDKTSTFCGTPEYLAPEV 33643

Score = 188 (86.7 bits), Expect = 5.2e-165, Sum P(7) = 5.2e-165
           Identities = 37/57 (64%), Positives = 42/57 (73%), Frame = +3

SEQ ID NO:93  Query:  209 FLTALKYSFQTHDRLCFVMEYANGGELFFHLSRERVFSEDRARFYGAEIVSALDYLH 265
SEQ ID NO:100             + LKYSFQ  LCFVM++ANGGELF H+ +   FSE RARFYGAEIV AL YLH
SEQ ID NO:94  Sbjct: 32667 YFQELKYSFQEQHYLCFVMQFANGGELFTHVRKCGTFSEPRARFYGAEIVLALGYLH 32837

Score = 166 (76.5 bits), Expect = 5.2e-165, Sum P(7) = 5.2e-165
           Identities = 29/59 (49%), Positives = 42/59 (71%), Frame = +1

SEQ ID NO:95  Query:   53 NNFSVAQCQLMKTERPRPNTFIIRCLQWTTVIERTPHVETPEEREEWATAIQTVADGLK 111
SEQ ID NO:101             + F++   Q M E+PRPN F++RCLQWTTVIERTF+ E+ E R+ W AI++++   K
SEQ ID NO:96  Sbjct: 31846 STFAIFYFQTMLFEKPRPNMFMVRCLQWTTVIERTFYAESAEVRQRWIHAIESISKKYK 32022

Score = 134 (61.8 bits), Expect = 5.2e-167, Sum P(8) = 5.2e-167
           Identities = 24/33 (72%), Positives = 30/33 (90%), Frame = +3

SEQ ID NO:97  Query:  210 LTALKYSFQTHDRLCFVMEYANGGELFFHLSRE 242
SEQ ID NO:102             L  LKYSFQT+DRLCFVME+A GG+L++HL+RE
SEQ ID NO:98  Sbjct: 33156 LQELKYSFQTNDRLCFVMEFAIGGDLYYHLNRE 33254
```

Fig. 25

```
              1             15 16            30 31            45 46            60
1 ZK84.6     -MNSVFTIIFVLCAL QVAASFRQSFG---P SMSEESASMQLLREL QH--NMMESAHRPMP  54
2 ZK75.1     -MFSFFT-YFLLSAL LLSASCRQ------P SMDT-SKADRILREI E----METELENQLS  47
3 ZK1251.2   ----MPPIILVFFLV LIPASQQY------P FSLE-SLNDQIINEE VI--EYMLENSIRSS  47
4 C06E2      --MIVTLIVFLVIGL QMAHLSQVSGNNENG FLNP-FDLSQWSEEI LHRQYHHHHHHHHGN  57
5 ZK75.2     ----MNAIIFCLLFT TVTATYEVF-----G KGIEHRNEHLIINQL D---IIPVESTPTPN  48
6 ZK75.3     MKLSVVLALFIIFQL GAASLMRN------W MFDFEKELEHDYDDS E---IGFHNIHSLMA  51
7 C17C3      --------------- --------------- ---------MKLLHI F---IIFLLFQSCSN  18
8 F13B12     --------------- --------------- ----MYWFRQVYRPS FF--FGFLAILLLSS  50
9 INSULIN    --------------- --------------- ----------MA LWMRLLPLLALLALW  17
CONSENSUS    --------------- --------------- --------------- ---------------

61            75 76            90 91           105 106           120
1 ZK84.6     RARRVPAPGETRACG RKLISLVMAVCGD-L CN------------- ---------------  85
2 ZK75.1     RARRVPA-GEVRACG RRLLLFVWSTCGE-P CT------------- ---------------  77
3 ZK1251.2   RTRRVPDEKKIYRCG RRIHSYVFAVCGK-A CE------------- ---------------  78
4 C06E2      RARRTLETEKIYRCG RKLYTDVLSACNG-P CE------------- ---------------  88
5 ZK75.2     RASRVQK----RLCG RRLILFMLATCG--E CD------------- ---------------  74
6 ZK75.3     RSRRGDK---VKICG TKVLKMVMVMCGG-E CS------------- ---------------  79
7 C17C3      KMCQYSK-KKYKICG VRALKHMKVYCTR-G MT------------- ---------------  48
8 F13B12     PTPSDAS---IRLCG SRLTTTLLAVCRNQL CTGLTAFKRSADQSY APTTRDLFHIHHQQ-  80
9 INSULIN    GPDPAAAFVNQHLCG SHLVEALYLVCGERG FFYTPKTRREAEDLQ VGQVELGGGPGAGSL  77
CONSENSUS    -------------CG -----------C--- --------------- ---------------
                        B CHAIN                          C PEPTIDE 121           135 136           150 151           165 166          180
1 ZK84.6     -------PQEGKDIA TECCGNQCSDDYIRS ACCP-----   112
2 ZK75.1     -------PQEDMDIA TVCCTTQCTPSYIKQ ACCPEK---   106
3 ZK1251.2   -------SNTEVNIA SKCCREECTDDFIRK QCCP-----   105
4 C06E2      -------PGTEQDLS KLCCGNQCTFVEIRK ACCADKL--   118
5 ZK75.2     -------TDSSEDLS HICCIKQCDVQDIIR VCCPNSFRK   106
6 ZK75.3     -------S-TNENIA TECCEKMCTMEDITT KCCPSR---   107
7 C17C3      -------R-DYGKLL VTCCSKGCNAIDIQR ICL------    73
8 F13B12     --------KRGGIA TECCEKRCSFAYLKT FCCNQDDN-   109
9 INSULIN    QPLALEGSLQKRGIV EQCCTSICSLYQLEN YCN------   110
CONSENSUS    ---------------CC---C-------- --C------
                            A CHAIN
```

```
AKT-1a     MSMTSLSTKSRR--QEDVVIEGWLHKKCGEHIRNWRPRYFMIFNDGALLGERAKPKEGOPFPEPL
AKT-1b     ...............--...
AKT-2          M..ENAHLQK...I..S..........IL.R..T......S....D....L
hAkt/PKBa         MSDVAI.K.....R..Y.KT......LLK....TEI.YKER.QDVDQREA

AKT-1a     NDFMIKDAATMLFEKPRPNMEMVRCLQWTTVIERTFYAESAEVRQRWIHALESIS--KKYKGTN
AKT-1b                                                                 ...
AKT-2      N..R......VCLD.......I..........D.DF......E..QAV.SHNRL..ENA
hAkt/PKBa  N.SVAQCQL..KT.R.....T.II..........HV.TP.E.EE.TT...QTVADGL-KQE--
                                                                 mg144 T
AKT-1a     ANPQEELMETNQQPKIDEDSEFAGAAHAIMGQPSSGHGDNCSIDFRASMISIADTSEAAKRDKI
AKT-1b     .................................................
AKT-2      G.TSMQEED..GN.SGES.VNM---------DAT.TRS..----..ESTVMN.DEPE.VPRKNTV
hAkt/PKBa  ---------------E.EMD.----------R.GSPS..SGAE-------EMEV.L.KPKHRV

AKT-1a     TMEDFDFLKVLGKGTFGKVILCKEKRTQKLYAIKILKKDVIIAREEVAHTLTENRVLQRCKHPF
AKT-1b     ....
AKT-2      ..D.........Q.........R..SSD.......IR.EMVVD.S.............YA.V.
hAkt/PKBa  ..NE.EY.L......V..A.GRY..M.....E..V.KD..............NSR.

AKT-1a     LTELKYSFQEQHYLCFVMQFANGGELFTHVRK----CGTFSEPRARFYGAEIVLALGYLH.RC
AKT-1b                TNDR......E..I..D.VY.LNREVQMNKEG......C.........AN
AKT-2      ...L....A.YHI...E......LQR---K..A.T...S..I.....HR
hAkt/PKBa  ...A....THDR...EY......F.LSRE...RV..D.......S..D..SEK

AKT-1a     DIVYRDMKLENLLLDKDGHIKIADFGLCKEEISFGDKTSTFCGTPEYLAPEVLDDHDYGRCVDW
AKT-1b     S..L..............
AKT-2      N.........R...T.......KY................IE.I..D.S.
hAkt/PKBa  NV..L......M.......T......G.KD.ATMK..........E.N...A.

AKT-1a     WGVGVVMYEMMCGRLPFYSKDHNKLFELIMAGDLRFPSKLSQEARTLLTGLLVKDPTQRLGGGP
AKT-1b
AKT-2                        SA.ENG......TTC..K..NR..P...V...S....ERV.AK...A.
hAkt/PKBa            ..........NQ..E.......LMEEI...RT.GP..KS..S...K..K....S

AKT-1a     EDALFICRADFERTVDWEATYRKEIEPPYKPNVQSETDTSYFDN-EFTSQPVQLTPPSRSGALA
AKT-1b     .............................................
AKT-2      D..R.VS..E..KD......L...V...F....M......F..RVRYV.ILLKV-----.E.I
hAkt/PKBa  ...K..MQHR..AGIV.QHV.E.KLS..F..Q.T.....R...E-...A.MITI...DQDDSME

AKT-1a     TVDEQEEMQSNFTQFSFHNVMGSINRIHEASEDNEDYDMGZ
AKT-1b     ........................................
AKT-2      ........................................
hAkt/PKBa  C..---S.RRPH.P....YSASSTA
```

Fig. 34

```
cataaaaatccagtaaatggtaaaattttcaatttcagatccatctcgatggaggatctcacaccaactaacacgtcgctcgacaccacaactac
taacaatgacacgacatcggatcgtgaagcggcgccaacggtgaggaactagtttctagacgaacatcggaatgcggcttaaagttcgggtgca
ttatcaaactagacccgtttttagaccctctttcaaagcggggaactgcaatacactttttgaacctaaaacctagattttttggtgttctaaat
tcttttgtgaattggagagccaattcaaccggaaaactctttttttataggagaaacgttttgccacgtagcagataagttaaatagaaaatattt
taaaatatttttttttttgtctaggaaaaattgataaagcacctggtccaattttcagaacgttccaatttttacctacaatacaaaattggccggca
agcttatggcttctgtttgcctacttctagcttgaacattctaaggctccgtagcgaaaaaattttttaggctttttttttaaataaatgtttggg
ccggaacacttaaccgaatagcatgatgaaacgctctaaaacttgaatttgaaaatttgcagttgatgctttaatataaaagtttgaggtttca
cctgcctaagatcgttttagcataaatatgtagatgaccgagagtatacaattaaatattaattaaatatgaatttcgaaatatgaattttggtt
gacttccattatgtttttttttttcacatttttacaactattctaggcaaaaatgaaaaaaaaaaaacttgtagaataatttttcaaaatttattttc
cagacgctcaacttaacaccaacagcaagtgaatcggagaacagcttatccccagtcaccgccgaagatctcatagctaaaagcattaaagaagg
atgtccgaagagaacttccaacgacttcatgtttcttcagagtatgggcgaaggagcctacagccaggttggtgaacgaggaaattccagaaat
gtgtgcaactagtatcagagtacaaggaaaagcttggaaaatactcggaatgcctgaattagtgcttgaagtaagcttgcccatttttttcggaa
catcggtgattctttcttggcaattcaactgatagtactggtattacctagccgcaaaaaatttgcagttttgccacaaatctatcttgacaca
atatacctcactattagttaaatgctgagttttatcgattttataagctttttttacttatgtatattcaaaatgtatgtgtttttcaaatctt
tttaaaggtttagtacggtcattaaaaaaaatatttaaaaatcatcttcatggcgctaaaatgagcgactatcataagaaattagaaaatttgga
aaattggtttattttttctagtccttgaattttcaccttcccattttatgctctaactgtgtttcaaatactcatattccaacattgtaggaa
ttctagaattgctttagatttctcttgttccaatctttttactgtaagttatcatcatttggcaccgaaaggtttttttaggtaatttta
ccactgaccgtaacacttttccaatggcgtatacaatttgaatttagcaacaaaacaaaaaaaaacaaaaatcgtaccaagacggactactgtat
ttttggcggaaaaatcggccaattttgcgtcagggttacacgactgtgggaattgaactcgcactatgtaggcccattcatgttgtctcccct
gtccaatctcttttctccacaacactttaatctcatttcgcatggagaagagaaagaagaagatgcagaaaacgacgacatcgtcatagaattgt
ctacacaaacctagtgttctgcgtctcttacacaaaataagccacgcgtctagcactatcaacattcgcaaacagctatacatgtgcttgttgaa
gggaaaaacgagacgtttgtgtgtattggggagggggtaatgtaaccgtggttgttgggttcatcaaattgacagcgcacagggatttgatttga
acgtgttatcgctttgaccctgaggcatgtttcctacacctagaacaactaccgtaatgaatcttttacattgactttcggagagaagggtttgt
actctgactatgtataactcaagaagaatgtagggaatttatgtcgttggaacttccaatttggaagtacagttttttggaaattaaattttga
ttcttaaaatagtcgacttgaaataattttttcgttatttatcaatccaatgagttgaaaaagtgaatggaaatttcttgactaaatccgtggaaa
attatctagttttgttttcagataagttgtaaacactttgatagttaaaatgattgtttgtagtgatcagaagcagaaaatctgactagtttcc
gcccccccccctatacatatgatgcacacttaaaatgtccaagtggtgtttgaatagcaaatcttgaaaacgtaaaaacaataattattttcta
tatctgtaaatattttcaacgaattttcagcttccaaattttggtcgttttggatctttttacaaaaaaaatatttatcaactgacactgata
atattttctgcctcatattaaaaaatattcctctagcaaaaactgtaagttgaacgaatttacaataaaaaacacagctgcactgaccaaaaaac
aattacactggccaaaattgagcttgcactgaccgagtttagcgaccatatcttttttgtctaatttgtggtgtgtgcggcgaattcggcaaaat
tgtcgagctcggaaaacagaaaatttggcaaatttaccgcaaactcttcaactgaagccactattgcacattaactgtcaaaattctggatataa
ttagcaaaacaataagtaacatttctgaaaaattagaacctttcccgcattgtatttgtagacgcacctaaaaaatttcaaaacaccaaaaaaca
agcttccagtaaaaccctaatattccaggtattccgatgtcgcgaagtggcaacagatgcgatgttcgccgtcaaagtgctccagaagtcgtacc
tcaaccgccatcaaaaaatggacgcaatcattcgcgagaagaatatcttaacatacctgtcacaagaatgcggtggtcatccgtttgtcacacag
ctctacacacatttcacgaccaggctagaatttgtgagttttttccagcgccaaggttcttttctgaacccatcaaaatccacttgtgatcatt
ttattccaataaaaacgtcaacttaaaaaaaaaattaaacctcaattaatattcagatttcgtgatcggacttgttgaaaatggtgatcttggcg
agtcgctgtgccatttggatcattcgacatgctccacctcaaaattctttgcctcggaaatcctcaccggactgcaattcctacacgacaacaaa
attgtgcacagagacatgaagccggacaatgtgctcatccagaaagacggtcacattctcatcacagattttggaagtgcccaggcgtttggcgg
tctccaactgtcacaggagggctttacggatgcgaatcaggcaagctcgcgatcttcggattctggatcgccgccgccaactcgattctattcgg
atgaggagggtaaggttttcggaaatttgactgaaacaattttttgccagttccagaagagaacactgctcgacgtaccacatttgttggaactgc
tctctacgtgagcccggagatgctagctgacggagatgtgggaccacagtaagctccgattctttgtagaatgtcaaatttaacagttggatttc
agaaccgacatttggggattgggatgtatcctttccagtgtctagccggacagccaccattcagagccgtcaaccagtaccatcttttgaaaag
aatccaggagttggatttctcgttcccagaaggatttccagaggaagcgtcggaaattatcgcaaag
```

Fig. 35A

```
attttggtaggttgacatgaaactttaaaaactgaatacgtaattttcaacttacaggtgcgcgacccgagtacccgtatcaccagtcaagaact
tatggctcacaagttttttgaaaacgttgactgggtgaacattgcaaatatcaagccaccagtcctgcacgcctacattccagccacatttggcg
agccggagtactactctaacattgggcctgtcgagccgggacttgatgatcGTGCCTTGTTCCGTTTGATGAATTTGGGAAATGATGCTAGCGCA
TCACAGCCATCAACGTGAGTTTGAAGCATTTTTTTCTTGCATTAAAAGTTTTACCTTGCACTGACCAAAATTTATTGAAACTATTAATTATTTGA
TTCTGATTAACAATGACCAAAAGATTTGAACTGACAAAGTGCAAATTTGCACCGACCAAAAAACAGTTTGCACTGACCACCTCTTCATTTGCACT
GACCACCTCTTCATTTGCACTGACCAACTTTTCATTTGCACTGACCATCTCTTCATTTGCACTGACCAACTTTTCATTTGCAATTCTGGCAATGA
TTCTTTTGCATCTACTGATCAAAAATTGATTCAAATCAATTAATTTTCTTTGACAGTACTATGCCTTATTCAAGGAGATGCTGATCTGAAAATTC
TCAATAGTTGATAAAAATTACTAACCCCTTAGAAAGTTTCAGACCGTCTAACGTGGAACATCGCGGAGACCCATTTGTTTCGGAAATTGCACCGT
GAGTGATTTGCACCTAATTGGTTATTTTTAATAATCATTAAATTATAGACGCGCCAATTCGGAAGCCGAAAAGAACCGCGCCGCACGTGCGCAGA
AGCTCGAAGAGCAACGTGTCAAAAACCCATTCCACATCTTCACCAACAACTCGCTCATTTTGAAACAAGGATATTTGGAAAAGAAGCGAGGATTG
TTTGCCAGACGCCGAATGTTCCTGTTGACCGAAGGACCGCATCTCTTGTACATTGATGTGCCGAATCTTGTGCTCAAAGGAGAGGTACCATGGAC
GCCGTGCATGCAGGTGGAGCTAAAAAACTCGGGAACTTTCTTTATACATACGGTAGGTCAGAATAATCATAGCTGTCTATCTCATTATAGTACTC
AATGAATCTGAAAATTTCAAATTTTCAGCCCAACCGCGTCTACTACTTGTTTGATCTCGAAAAGAAAGCAGATGAGTGGTGTAAGGCTATCAATG
ATGTTCGCAAGCGGTACTCGGTGACTATCGAAAAGACTTTTAACTCTGCGATGCGTGACGGAACATTTGGCAGCATTTATGGAAAGAAAAAGTCC
AGAAAGGTATGAATTACTGGAAGGCCCCCCCTCACTGAGTTTCCAGCAAGTTCAGAGTTTTTTATTGGAATTTTTGCCAATTTTCATTAGACTTTA
GAGCCTATTGCTATTTTGTGGACAGGTTTAAACATTTTCAAAAAAAAATTGAGAAATGTCTGAAAAAATTTGGAGTGTGACAGTTTTCTGAATTT
TGAAAATTCTGTTCTCAAAATTGGATTTTTACAGAGCTTGTTTCGAGATTTCATAATCCTTCAAAAGAATATAGAATATTTGTGTTCAACTTTTC
TTGTCAAAATATTTTTTTGGACAATCTAGATTCTGAAAATTTTCAAAAAAAAGATAATCTCTAAACAAAACTAAATTCAAAATGTTCTAAAGGT
TCTTTATTTTCCATGCAACTCTAAAATCTTCCCGTATATTTTTTGGAAAGTCTTATGATGTTTAGACGGTTTAAATTTTTTGATGATTTAAATT
TTTAGGGGTGGTCTATAATTTTGGACCACCCTGTATAATTATGGACCACCATGTACACTTATAGACCACCCAGTAACAAGCATTTTTGGACCAC
CACGCAAATCTTATTATTATGGACCACCCAAACTTAGAACACCTTCAATACTTCTTTTCTGTTCAAAAAATGATCAACTTGCTGAAAAAAAATTT
TTTGTAGGAAATGATGCGTGAACAGAAGGCGCTGCGCCGCAAACAAGAAAAGGAGGAGAAAAAGGCGCTAAAAGCCGAGCAAGTGAGCAAGAAGC
TTTCAATGCAAATGGACAAGAAGTCGCCTTGAAGGCTCACCTCCCTTCTACTCCCCACAAAATCACCATCAAACAAATCACACTTTTGTATCATT
TTGCGTCC
```

Fig. 35B

MEDLTPTNTSLDTTTTNNDTTSDREAAPTTLNLTPTASESENSLSPVTAEDLIAKSIKEGCPKRTSNDFMFLQSMGEG
AYSQVFRCREVATDAMFAVKVLQKSYLNRHQKMDAIIREKNILTYLSQECGGHPFVTQLYTHFHDQARIYFVIGLV
ENGDLGESLCHFGSFDMLTSKFFASEILTGLQFLHDNKIVHRDMKPDNVLIQKDGHILITDFGSAQAFGGLQLSQEGFT
DANQASSRSSDSGSPPPTRFYSDEEEENTARRTTFVGTALYVSPEMLADGDVGPQTDIWGLGCILFQCLAGQPPFRAV
NQYHLLKRIQELDFSFPEGFPEEASEIIAKILVRDPSTRITSQELMAHKFFENVDWVNIANIKPPVLHAYIPATFGEP
EYYSNIGPVEPGLDDRALFRLMNLGNDASASQPSTPSNVEHRGDPFVSEIAPRANSEAEKNRAARAQKLEEQRVK
NPFHIFTNNSLILKQGYLEKKRGLFARRRMFLLTEGPHLLYIDVPNLVLKGEVPWTPCMQVELKNSGTFFIHTPNR
VYYLFDLEKKADEWCKAINDVRKRYSVTIEKTFNSAMRDGTFGSIYGKKKSRKEMMREQKALRRKQEKEEKKAL
KAEQVSKKLSMQMDKKSP

Fig. 36

MEDLTPTNTSLDTTTTNNDTTSDREAAPTTLNLTPTASESENSLSPVTAEDLIAKSIKEGCPKRTSNDFMFLQSMGEG
AYSQVFRCREVATDAMFAVKVLQKSYLNRHQKMDAIIREKNILTYLSQECGGHPFVTQLYTHFHDQARIYFVIGLV
ENGDLGESLCHFGSFDMLTSKFFASEILTGLQFLHDNKIVHRDMKPDNVLIQKDGHILITDFGSAQAFGGLQLSQEGFT
DANQASSRSSDSGSPPPTRFYSDEEVPEENTARRTTFVGTALYVSPEMLADGDVGPQTDIWGLGCILFQCLAGQPPFR
AVNQYHLLKRIQELDFSFPEGFPEEASEIIAKILVRDPSTRITSQELMAHKFFENVDWVNIANIKPPVLHAYIPATF
GEPEYYSNIGPVEPGLDDRALFRLMNLGNDASASQPSTFRPSNVEHRGDPFVSEIAPRANSEAEKNRAARAQKLEE
QRVKNPFHIFTNNSLILKQGYLEKKRGLFARRRMFLLTEGPHLLYIDVPNLVLKGEVPWTPCMQVELKNSGTFFIH
TPNRVYYLFDLEKKADEWCKAINDVRKRYSVTIEKTFNSAMRDGTFGSIYGKKKSRKEMMREQKALRRKQEKEE
KKALKAEQVSKKLSMQMDKKSP

Fig. 37

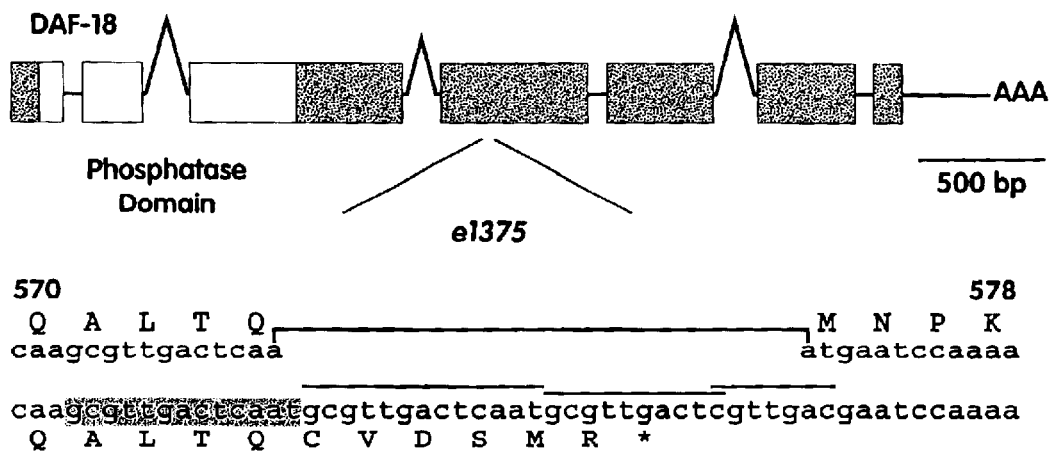

Fig. 39A

```
DAF-18    48  FFRTAVSSNR  CRTEYQNIDL DCAVITDRLI AIGYPAIGIE  ANFRNSKVQT
PTEN       4  TIKEIVSRNK  RRYQEDGFDL DLTYIYPNII AMGFPAERLE  GVYRNNIDDV

DAF-18    98  QQELTRRHGK  GNVKVFNLRG GYYDADNED GNVICFDMTD HHPPSLELMA
PTEN      54  VRFLDSKH.K  NHYKIYNLCA ERHYDTAKFN CRVAQYPFED HNPPQLELIK

DAF-18   148  PFCREAKEWL  EADDKHVIAV HCKAGKGRTG VMICALLIYI  NFYPSPRQIL
PTEN     103  PFCEDLDQWL  SEDDNHVAAI HCKAGKGRTG VMICAYLLHR  GKFLKAQEAL

DAF-18   198  DYYSIIRTKN  NKGVTIPSQR RYIYYYHKER ERELNVLDLR  MQLIGVYVER
PTEN     153  DFYGEVRTRD  KKGVTIPSQR RYVYYAYSYLL KNHLDYRPVA  LLFHKMMFET

DAF-18   248  PPKTWGGGSK  IKVEVGNGST ILFKPD..PL IISKSNHQRE  RATWENNCDT
PTEN     203  IPMFSGGTCN  PQFVWCQLKV KIYSSNSGPT RREDKFMYFE  FPQPLPVCGD
```

Fig. 39B

DAF-18 Protein

MVTPPPDVPSTSTRSMARDLQENPNRQPGEPRVSEPYHNSIVERIRHIFRTAVSSNRCRTEYQNIDLDCAYITDRIIAIG
YPATGIEANFRNSKVQTQQFLTRRHGKGNVKVFNLRGGYYYDADNFDGNVICFDMTDHHPPSLELMAPFCREAKEWLEAD
DKHVIAVHCKAGKGRTGVMICALLIYINFYPSPRQILDYYSIIRTKNNKGVTIPSQRRYIYYYHKLRERELNYLPLRMQL
IGVYVERPPKTWGGGSKIKVEVGNGSTILFKPDPLIISKSNHQRERATWLNNCDTPNEFDTGEQKYHGFVSKRAYCFMVP
EDAPVFVEGDVRIDIREIGFLKKFSDGKIGHVWFNTMFACDGGLNGGHFEYVDKTQPYIGDDTSIGRKNGMRRNETPMRK
IDPETGNEFESPWQIVNPPGLEKHITEEQAMENYTNYGMIPPRYTISKILHEKHEKGIVKDDYNDRKLPMGDKSYTESGK
SGDIRGVGGPFEIPYKAEEHVLTFPVYEMDRALKSKDLNNGMKLHVVLRCVDTRDSKMMEKSEVFGNLAFHNESTRRLQA
LTQMNPKWRPEPCAFGSKGAEMHYPPSVRYSSNDGKYNGACSENLVSDFFEHRNIAVLNRYCRYFYKQRSTSRSRYPRKF
RYCPLIKKHFYIPADTDDVDENGQPFFHSPEHYIKEQEKIDAEKAAKGIENTGPSTSGSSAPGTIKKTEASQSDKVKPAT
EDELPPARLPDNVRRFPVVGVDFENPEEESCEHKTVESIAGFEPLEHLFHESYHPNTAGNMLRQDYHTDSEVKIAEQEAK
AFVDQLLNGQGVLQEFMKQFKVPSDNSFADYVTGQAEVFKAQIALLEQSEDFQRVQANAEEVDLEHTLGEAFERFGHVVE
ESNGSSKNPKALKTREQMVKETGKDTQKTRNHVLLHLEANHRVQIERRETCPELHPEDKIPRIAHFSENSFSDSNFDQAI
YL

Fig. 40A

```
   1 ttccaggtac atctactaac cccaatggt tactcctct ccagatgtgc caagcacatc
  61 gaccaggtcg atggctcgtg accttcaaga gaatccaaac cgacaacctg gtgaaccacg
 121 tgtgtctgaa ccgtatcaca attcaatcgt cgagcggatt cgcctatttt ttcggacggc
 181 tgtatcttcc aatcgttgtc cgacggagta ccaaaatatc gacctagatt gtgcatatat
 241 cacagaccga atcatagcta tcggttatcc agcaacagga gacctagaga atttccgtaa
 301 ctcaaaagtt caaactcaac aatttctgac caggcggcac ggaaaggca acgtgaaggt
 361 gtttaacctg cgcggtggat actactacga tcggataaac ttcgatggaa atgttatttg
 421 cttcgatatg actgatcatc atccgccgag tgcggaatta atggctccgt tttgcagaga
 481 ggctaaggaa tggcttgaag cagacgataa acatgtaata gctgtacact tctatccgag
 541 aaaaggccgt cccgagtga tgatatgtgc cagatatgtgc tcttctcatc tacatcaact
 601 cccacgaaca attctcgact actacta aattcaacta aaaaacaaca aaggtgtcac
 661 aattccatca caacgacgt acatttacta ctaccataag cttcgtgaac gtgagctcac
 721 ctatttacca ttgagaatgc agtgatttgg tgtctacgtg gacggcctc caaagacatg
 781 ggggtggtggt tcaaagataa aagtggaggt tggaaatggc tcgacaattt tatttaagcc
 841 ggatcctctc ataatctcca tcaaatca tcagcgagag gacgaaatgc tttcttccaa
 901 ctgtgatacg cgtgacaccg g gagcag  aga tgctctcaa aaggtttcg gacggagga gagatgtttcg
 961 gagagcatac cgtggttat gg tgtcagaaga tgctctcaa aaggtttcg gacgtcatgt
1021 tatagacatt cgcgaaatcg gattctcaa  aggactcaac aggtggacatt ttgtcacga
1081 ttggttcaat acaatgttcg catgtgacga tcggataaatc tacatcaatc caattcaga
1141 agacaaaact cagcgtaca tcggagaaag aaaacaaat ggacggaaaa atggaatgcg
1201 aagaaatgaa acgcgatgc gaaaattga tccagaaact tccagaaact ttgagtctcc
1261 gtgcaaata gtgaatccct ctggactgga acatatatt acggagaac aagcaatgga
1321 aaattatacc aattatgca tgattctcc tgataacg tcagagaga ttcttcacga
1381 aagcatgaa acggaatcg aaggtatcg aggaaatgtt cta ataacg cgtaacac aaggtggtta caatatattgaa cacatttcca gtccatttga
1441 caatcatac aaagctgagg gaaaaagtg gcacatcga ggagaaga gcataggga gcataggga tcataggga agaaaacgg aagcttcaca
1501 gataccatat aaagatcta aaatggaat agatgccca gaaactttcc tcctgagc tggagaacgg aagcttcaca
1561 attgaagagt aaaaatga tggaaaagag cgaaatggc tcaaatgaa gcaaatggc ccggaagag taccggataa
1621 tactcgtgat cggagctc aaccgttga aagcgttca tgaatgaat gaatctgg gttttcttc aatcggtga
1681 tgaatcgaca cggagcttc gcttgaatg gtgctgaat gtgaatccct gccaaatggc gacctgaacc ttccggaaac
1741 gtgtgcgttg ggatcaaag gagcctgcag agctcgaat cggtaat gaaatgatg ttttcgagca gataacaag
1801 caatgatgga agtataatg gcgttatct atcagata aattcagaa cc gagatcatc attctacat atttcgagaa
1861 cagaaatatt gccgttctta tatccaagaa ttgatgaaa aatcagga cctgtcctg gcagtaca ttgaaaatac
1921 tgaagccgt tatccaagaa tatccaagaa ttgatgaaa aaatcagga caagtgctcc atttcaaatac
1981 tccagctgat acccgatatg accttcagg agagacgc aggaactatc ttcttcact ttgaaatac
2041 ttacattaaa gaacaggaaa aaaaatgaag aaataagcgc aaggaacggc aagaaaacgg taccggaataa
2101 tggacccagt acttcaggat acttcgaaga gaactttcct ctggagagc cggagaagg aatcgtgtga
2161 atccgacaag gtgaagcgg tcggaagttga tcggtttt tgaacatctg gaacatctat tccatgaat
2221 tgtgcaaga tttcgaagg tagatacgtca tagctgtt tgaactctg gcgtcagg gcttacactg ttgcttatg gacaaggttg
2281 acacaacacc gtagagtcaa aatacggccg gtaacatgct cgttgaccag cgtcagcct ttcacactg
2341 ataccatcca aataagatt aacaagagg caaaagtca cttcaaagt accatcggac attcacctg
2401 gaaatagct gaacaaaga gaacaagagg caaagtca catcaaaagt caggctgag gacaggtgt
2461 attacaagag tttatgaagc aattgaagc tttatgaagc aattcaaagt aattcctttg ctgattaggt
```

Fig. 40B-1

```
2521  aaccggacag  gccgaagttt  ttaaagcaca  gattgcgtta  ctggagcagt  cggaggattt
2581  tcaacgagtt  caagcgaatg  cagaggaagt  cgatcttgaa  cacactcttg  gtgaagcgtt
2641  tgagcgattc  gggcacgttg  tagaagaatc  gaatggttct  tctaaaaatc  caaaagccct
2701  gaaaactcga  gaacaaaatgg  tgcaaagaac  actcagaaga  cccgcaatca
2761  tgtgcttcta  catttggaag  ctaatcatcg  gagcgtcgtg  aaacgtgccc
2821  ggagctacat  ccagaggata  aaatcccaag  aattgctcat  ttttccgaaa  acagcttctc
2881  ggattcgaat  tttgatcaag  ctatttattt  gtaaacctaa  aacaaaactt  ttagaagatt
2941  ttcttcttac  tgaccctcca  atttcagat  aatttcaatg  tttttaagttt  tctcttcaaa
3001  gtatcattca  ctttctgtat  agtgttttgt  ttttaacaa  actattgttc  gattattttg
3061  tatattcata  ttatagctct  caacttcccg  attttccacg  tatatatgta  tatttgccg
3121  ggtgaaaaat  agcaattccc  tatgaatgta  tcccctccaa  tctgttttct  tactcagaaa
3181  ttgtaattca  cattgcgggt  catcactaat  cctatgggct  ttaacacaat  tctcccataa
3241  attaattgta  cttaccaatt  tttgtttaa  ttatttagat  ttgtaacatt  gaaattggtg
3301  ataa
```

| | | | | | | | | | | | | | | | | |
|---|---|---|---|---|---|---|---|---|---|---|---|---|---|---|---|---|
| aag K | cag Q | ttt F | ctt L | gat D | aac N | ttt F | gag E | cta L | ctg L | gag E | cat H | tgt C | gga G | tac Y | tcg S | gaa E | aat N |
| att I | ccg P | caa Q | cta L | gaa E | gat D | atc I | tgc C | aag K | ttt F | aaa K | gca A | aaa K | act T | gga G | ttc F | cgt R | gtt V |
| cca P | gtc V | gcc A | gga G | tac Y | tta L | tca S | gct A | cgt R | ttc F | ttg L | gca A | ggt G | ctt L | gca A | tat Y | cgt R | gtc V |
| ttc F | tgc C | act T | caa Q | tac Y | gtt V | cgc R | cat H | gct A | gat D | cca P | ttt F | tac Y | act T | cca P | gaa E | cca P | gac D |
| gtt V | cac H | gag E | ctc L | atg M | ggt G | cac H | atg M | cat H | ttc F | cac H | gat D | cca P | ttt F | gct A | gct A | cag Q | ttt F |
| caa Q | gag E | att I | gga G | tta L | ggt G | tct S | ctt L | atg M | tca S | tct S | gaa E | gat D | ttg L | act T | aag K | ctt L | gca A |
| ctc L | tac Y | ttc F | att I | tcc S | gct A | gaa E | cct L | ctc L | tcg S | gaa E | gat D | gac D | gct A | ttt F | gat D | cag Q | cca P |
| aaa K | aat N | aat N | ttc F | tca S | cat H | cat H | gtt V | ttt F | aaa K | aag K | tac Y | gga G | aag K | gat D | ctt L | cca P | agc S |
| gct A | gag E | gga G | cat H | cat H | aat N | gga G | cat H | gaa E | agt S | cat H | acc T | aat N | gcc A | gga G | ctg L | agc S | ccg P |
| cgt R | gag E | ttg L | cat H | gaa E | cat H | ttt F | gat D | att I | act T | act T | cag Q | gcg A | gcc A | cgt R | ctg L | act T | gat D |
| aat N | gag E | ggt G | caa Q | cag Q | gaa E | gaa E | cat H | gcc A | atg M | aga R | acc T | acc T | tat Y | tat Y | tat Y | ccc P | aga R |
| att I | ttt F | gag E | tac Y | cca P | cag Q | cag Q | gat D | tgt C | gtc V | agc S | gcc A | cag Q | atg M | aaa K | ttc F | tcc S | ttc F |
| atg M | tta L | gag E | tac Y | aca T | g attaccaagtttgaggtagcattgctctcttcaatcat

| | | | | | | | | | | | | | | | | | | |
|---|---|---|---|---|---|---|---|---|---|---|---|---|---|---|---|---|---|---|---|
| atg | gat | tcg | ttg | ttt | cag | atg | gca | tcc | gca | atg | aag | ttt | caa | tac | tcg | aag | aaa | gct | |
| M | D | S | L | F | Q | M | A | S | A | M | K | F | Q | Y | S | K | K | A | |
| gct | gga | aag | aca | atg | tct | aat | agt | gtc | aaa | aac | tgg | att | ccg | tgt | tcg | ccc | agt | cgc | cgg |
| A | G | K | T | M | S | N | S | V | K | N | W | I | P | C | S | P | S | R | R |
| ata | ctt | atc | agc | tcg | tga | ttt | ctt | ggc | agg | tct | ata | tgc | tct | ctt | tgt | ctt | ctg | cac | tca |
| I | L | I | S | S | * | | | | | | | | | | | | | | |
| ata | cgt | tcg | cca | tca | tgc | cga | tcc | att | tta | cac | tcc | aga | cac | cgt | tca | cga | gct | | |
| cat | ggg | tca | cat | ggc | tct | att | cgc | tga | tcc | aga | ttt | tgc | tca | gtt | tca | aga | gat | tgg | |
| att | agc | ttc | tct | tgg | agc | atc | aga | gga | aga | ttt | gaa | gaa | gct | tgc | aac | act | cta | ctt | ctt |
| ttc | cat | tga | att | tgg | tct | ctc | gtc | tga | cgc | tgc | cga | ttc | tcc | gag | cag | tgc | tgg | aaa | tgg |
| atc | aaa | tga | tca | aag | att | taa | agt | cgg | agc | agg | act | tct | tga | tcg | ttt | gga | tgc | tgg | cga | gtt |
| gca | aca | tgc | cgt | tga | ggg | tag | tgc | aac | cat | tat | tcg | ttt | cta | ttt | tag | aaa | ttt | tga | aga |
| gca | aga | atg | tct | cat | tac | tga | act | cag | aat | gtt | cac | caa | caa | acg | tcc | ctt | cat | tgt | tcg | tta |
| ggc | cca | gca | gaa | act | cag | aag | cgt | cga | agt | tct | caa | ctc | ccg | ttc | cat | tat | gtt | ggc | agt |
| caa | ccc | ata | cac | aga | aag | cgt | cga | agt | tct | caa | cct | gct | cgc | cgg | agc | cgg | agt | gta | g |
| gaa | ctc | tct | ccg | ctc | aga | cat | caa | cct | gct | cgc | cgg | agc | cgg | agt | gta | g | | | |

Fig. 43

ATTCGGCATGAGCATGGAGCTTCGAGTCCTAGAGAACACAAAACGTTCCCGGCGGAACCTGGGtCTGGACTGCGAC
GAGACTCAAGCGAGTCCCGCTGATATCCCCCACAGTGGACTTTGAGGCTTTCGGCTGGGACTGGATCAT
CGCACCTAAGCGCTACAAGGCCAACTACTGCTCCGGCCAGTGGGAGTACATGTTCATGCAAAAATATCGCATACC
CATTTGGTGCAGCAGGCCAATCCAGCAGATTATCTACGGCAAGATTATCTACGGCAAGATGTCCCCAATcAACA
TgcTctACTTCAATGACAAGCAGCAGATTATCTACGGCAAGATCCCTGGCATGGTGGATCGCTGTGGCTGCTC
TTAAGGTGGGGATAGAGGATGCCTCCCCACAGACCGTACCCCAAGACCCATAGCCCTGCCCAATCCACCGCCTG
ATCCAAACAT

Fig. 47A

IRHEHGASSPREHKTFPAEPGSGLRRDSSESRCCRYPLTVDFEAFGWDWIIAPKRYKANYCSGQWEYMFMQKYPHT
HLVQQANPRGYAGPCCTPTKMSPINMLYFNDKQQIIYGKIPLAMVVDRCGCS

Fig. 47B

SEQUENCE LISTING

<160> NUMBER OF SEQ ID NOS: 331

<210> SEQ ID NO 1
<211> LENGTH: 20
<212> TYPE: DNA
<213> ORGANISM: Artificial Sequence

```
-continued

<220> FEATURE:
<223> OTHER INFORMATION: Primer/probe derived from C. elegans

<400> SEQUENCE: 1
cgctacggca aaaaagtgaa                                              20

<210> SEQ ID NO 2
<211> LENGTH: 18
<212> TYPE: DNA
<213> ORGANISM: Artificial Sequence
<220> FEATURE:
<223> OTHER INFORMATION: Primer/probe derived from C. elegans

<400> SEQUENCE: 2
cgatgatgaa gatacccc                                                18

<210> SEQ ID NO 3
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 3
tgatgcgaac ggcgatcgat                                              20

<210> SEQ ID NO 4
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 4
acgctggatc atctacatta                                              20

<210> SEQ ID NO 5
<211> LENGTH: 22
<212> TYPE: DNA
<213> ORGANISM: Artificial Sequence
<220> FEATURE:
<223> OTHER INFORMATION: Primer/probe derived from C. elegans

<400> SEQUENCE: 5
ggtttaatta cccaagtttg ag                                           22

<210> SEQ ID NO 6
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 6
gctcacgggt cacacaacga                                              20

<210> SEQ ID NO 7
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 7
tgatgcgaac ggcgatcgat                                              20
```

<210> SEQ ID NO 8
<211> LENGTH: 21
<212> TYPE: DNA
<213> ORGANISM: Artificial Sequence
<220> FEATURE:
<223> OTHER INFORMATION: Primer/probe derived from C. elegans

<400> SEQUENCE: 8
tgagggccaa ctaaagaaga c                                    21

<210> SEQ ID NO 9
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 9
cgctacggca aaaaagtgaa                                      20

<210> SEQ ID NO 10
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 10
gacgatcccg aggtgagtat                                      20

<210> SEQ ID NO 11
<211> LENGTH: 5816
<212> TYPE: DNA
<213> ORGANISM: Caenorhabditis elegans
<220> FEATURE:
<221> NAME/KEY: misc_feature
<222> LOCATION: (1)...(5816)
<223> OTHER INFORMATION: n = A,T,C or G

<400> SEQUENCE: 11
ggtttaatta cccaagtttg agctccaaga gcacacatct gatcgtcgga ttctactgta    60
ctccccgaaa accaacaaa aaacacaagt ttttgaacac ttgtaaatgc agacagaacg    120
atgacgagaa tgaatattgt cagatgtcgg agacgacaca aaattttgga aaatttggaa   180
gaagagaatc tcggcccgag ctgctcgtcg acgacttcaa caaccgctgc caccgaagct   240
ctcggaacaa ccactgagga tatgaggctt aagcagcagc gaagctcgtc gcgtgccacg   300
gagcacgata ttgtcgacgg caatcaccac gacgacgagc acatcacaat gagacggctt   360
cgacttgtca aaaattcgcg gacgcggcgt agaacgacgc ccgattcaag tatggactgc   420
tatgaggaaa acccgccatc acaaaaactt caataaatta ttcttggatt tctaaaaagt   480
catcaatgac gtcattaatg cttttactgc tattcgcttt tgtacagccg tgtgcctcaa   540
tagtcgaaaa acgatgcggc ccaatcgata ttcgaaatag gccgtgggat attaagccgc   600
aatggtcgaa acttggtgat ccgaacgaaa aagatttggc tggtcagaga atggtcaact   660
gcacagtggt ggaaggttcg ctgacaatct catttgtact gaaacacaag acaaaagcac   720
aagaagaaat gcatcgaagt ctacagccaa gatattccca agacgaattt atcacttttc   780
cgcatctacg tgaaattact ggaactctgc tcgtttttga gactgaagga ttagtggatt   840
tgcgtaaaat tttcccaaat cttcgtgtaa ttggaggccg ttcgctgatt caacactatg   900
cgctgataat ttatcgaaat ccggatttgg agatcggtct tgacaagctt tccgtaattc   960

```
gaaatggtgg tgtacggata atcgataatc gaaaactgtg ctacacgaaa acgattgatt    1020
ggaaacattt gatcacttct tccatcaacg atgttgtcgt tgataatgct gccgagtacg    1080
ctgtcactga gactggattg atgtgcccac gtggagcttg cgaagaggat aaaggcgaat    1140
caaagtgtca ttatttggag gaaaagaatc aggaacaagg tgtcgaaaga gttcagagtt    1200
gttggtcgaa caccacttgc caaaagtctt gtgcttatga tcgtcttctt ccaacgaaag    1260
aaatcggacc gggatgtgat gcgaacggcg atcgatgtca cgatcaatgc gtgggcggtt    1320
gtgagcgtgt gaatgatgcc acagcatgcc acgcgtgcaa gaatgtctat cacaagggaa    1380
agtgtatcga aaagtgtgat gctcacctgt accttctcct tcaacgtcgt tgtgtgaccc    1440
gtgagcagtg tctgcagctg aatccggtgc tctcgaacaa acagtgcct atcaaggcga     1500 cggcaggcct ttgctcggat aaatgtcccg atggttatca aatcaacccg atgatcatc     1560 gagaatgccg aaaatgcgtt ggcaagtgtg agattgtgtg cgagatcaat cacgtcattg    1620
atacgtttcc gaaggcacag gcgatcaggc tatgcaatat tattgacgga aatctgacga    1680
tcgagattcg cggaaaacag gattcggaa tggcgtccga gttgaaggat atatttgcga    1740
acattcacac gatcaccggc tacctgttgg tacgtcaatc gtcaccgttt atctcgttga    1800
acatgttccg gaatttacga cgtattgagg caaagtcact gttcagaaat ctatatgcta    1860
tcacagtttt tgaaaatccg aatttaaaaa agctattcga ttcaacgacg gatttgacgc    1920
ttgatcgtgg aactgtgtca attgccaata acaagatgtt atgcttcaag tatatcaagc    1980
agctaatgtc aaagttaaat ataccactcg atccgataga tcaatcagaa gggacaaatg    2040
gtgagaaggn aatctgtgag gatatggcaa tcaacgtgag catcacagcg gtcaacgcgg    2100
actcggtctt ctttagttgg ccctcattca acattaccga tatagatcag cgaaagtttc    2160
tcggctacga gctcttcttc aaagaagtcc cacgaatcga tgagaacatg acgatcgaag    2220
aggatcgaag tgcgtgtgtc gattcgtggc agagtgtctt caaacagtac tacgagacgt    2280
cgaacggtga accgaccccg gacatttta tggatattgg accgcgcgag cgaattcggc     2340
cgaatacgct ctacgcgtac tatgtggcga cgcagatggt gttgcatgcc ggtgcgaaga    2400
acggtgtatc gaagattggt tttgtgagga cgagctacta tacgcctgat cctccgacgt    2460
tggcactagc gcaagtcgat tcggacgcta ttcatattac gtgggaagcg ccgctccaac    2520
cgaacggaga cctcacgcat tacacaatta tgtggcgtga gaatgaagtg agcccgtacg    2580
aggaagccga aaagttttgt acagatgcaa gcacccccgc aaatcgacaa cgcacgaaag    2640
atccgaaaga gacgattgta gccgataagc cagtcgatat tccgtcatca cgtaccgtag    2700
ctccgacact tttgactatg atgggtcacg aagatcagca gaaaacgtgc gctgcaacgc    2760
ccggttgttg ttcgtgttcg gctatcgaag aatcatcgga acagaacaag aagaagcgac    2820
cggatccgat gtcggcgatc gaatcatctg catttgagaa taagctgttg gatgaggttt    2880
taatgccgag agacacgatg cgagtgagac gatcaattga agacgcgaat cgagtcagtg    2940
aagagttgga aaaagctgaa aatttgggaa agctccaaa aactctcggt ggaaagaagc     3000
cgctgatcca tatttcgaag aagaagccgt cgagcagcag caccacatcc acaccggctc    3060
caacgatcgc atcaatgtat gccttaacaa ggaaaccgac tacggtgccg ggaacaagga    3120
ttcggctcta cgagatctac gaacctttac ccggaagctg ggcgattaat gtatcagctc    3180
tggcattgga taatagttat gtgatacgaa atttgaagca ttacacactt tatgcgattt    3240
ctctatccgc gtgccaaaac atgacagtac ccggagcatc ttgctcaata tcccatcgtg    3300
```

-continued

```
cgggagcatt gaaacgaaca aaacacatca cagacattga taaagtgttg aatgaaacaa      3360
ttgaatggag atttatgaat aatagtcaac aagtcaacgt gacgtgggat ccaccgactg      3420
aagtgaatgg tggaatattc ggttatgttg taaagcttaa gtcaaaagtc gatggatcaa      3480
ttgttatgac gagatgtgtc ggtgcgaaga gaggatattc aacacggaat cagggtgtcc      3540
tattccagaa tttggccgat ggacgttatt ttgtctcagt aacggcgacc tctgtacacg      3600
gcgctggacc ggaagccgaa tcctccgacc caatcgtcgt catgacgcca ggcttcttca      3660
ctgtggaaat cattctcggc atgcttctcg tcttttgat tttaatgtca attgccggtt       3720
gtataatcta ctactacatt caagtacgct acggcaaaaa agtgaaagct ctatctgact      3780
ttatgcaatt gaatcccgaa tattgtgtgg acaataagta caatgcagac gattgggagc      3840 tacgcagga tgatgttgtg ctcggacaac agtgtggaga gggatcattc ggaaaagtgt       3900
acctaggaac tggaaataat gttgtttctc tgatgggtga tcgtttcgga ccgtgtgcta      3960
ttaagattaa tgtagatgat ccagcgtcga ctgagaatct caactatctc atggaagcta     4020
atattatgaa gaactttaag actaacttta tcgtccaact gtacggagtt atctctactg     4080
tacaaccagc gatggttgtg atggaaatga tggatcttgg aaatctccgt gactatctcc     4140
gatcgaaacg cgaagacgaa gtgttcaatg agacggactg caacttttc gacataatcc       4200 cgagggataa attccatgag tgggccgcac agatttgtga tggtatggcg tacctggagt     4260
cgctcaagtt ttgccatcga gatctcgccg cacgtaattg catgataaat cgggatgaga     4320
ctgtcaagat tggagatttc ggaatggctc gtgatctatt ctatcatgac tattataagc     4380
catcgggcaa gcgtatgatg cctgttcgat ggatgtcacc cgagtcgttg aaagacggaa     4440
agtttgactc gaaatctgat gtttggagct tcggagttgt tctctatgaa atggttacac     4500
tcggtgctca gccatatatt ggtttgagta atgatgaggt gttgaattat attggaatgg     4560
cccggaaggt tatcaagaag cccgaatgtt gtgaaaacta ttggtataag gtgatgaaaa      4620
tgtgctggag atactcacct cgggatcgtc cgacgttcct ccagctcgtt catcttctag     4680
cagctgaagc ttcaccagaa ttccgagatt tatcatttgt cctaaccgat aatcaaatga     4740
tccttgacga ttcagaagca ctggatcttg atgatattga tgatactgat atgaatgatc     4800
aggttgtcga ggtggcaccg gatgttgaga acgtcgaggt tcagagtgat tcggaacgtc     4860
ggaatacgga ttcaatccg ttgaaacagt ttaagacgat ccctccgatc aatgcgacga      4920
cgagtcattc gacaatatcg attgatgaga caccgatgaa agcgaagcag cgagaaggat     4980
cgctggatga ggagtacgca ttgatgaatc atagtggagg tccgagtgat gcggaagttc     5040
ggacgtatgc tggtgatgga gattatgtgg agagagatgt tcgagagaat gatgtgccaa     5100
cgcgacgaaa tactggtgca tcaacatcaa gttacacagg tggtggtcca tattgcctaa     5160
caaatcgtgg tggttcaaat gaacgaggag ccggtttcgg tgaagcagta cgattaactg     5220
atggtgttgg aagtggacat ttaaatgatg atgattatgt tgaaaagag atatcatcca      5280 tggatacgcg ccggagcacg ggcgcctcga gctcttccta cggtgttcca cagacgaatt     5340
ggagtggaaa tcgtggtgcc acgtattata cgagtaaagc tcaacaggca gcaactgcag     5400
cagcagcagc agcagcagct ctccaacagc aacaaaatgg tggtcgaggc gatcgattaa      5460
ctcaactacc cggaactgga catttacaat cgacacgtgg tggacaagat ggagattata     5520
ttgaaactga accgaaaaat tatagaaata atggatctcc atcgcgaaac ggcaacagcc     5580
gtgacatttt caacgacgt tcggctttcg gtgaaaatga gcatctaatc gaggataatg      5640
agcatcatcc acttgtctga aaccccaaa aaatcccgcc tcttaaatta taattatct       5700
```

```
cccacattat catatctcta cacgaatatc ggattttttt tcagatttt    tctgaaaaat    5760 tctgaataat tttaccccat ttttcaaatc tctgtatttt tttttgttat taccc          5816
```

<210> SEQ ID NO 12
<211> LENGTH: 1724
<212> TYPE: PRT
<213> ORGANISM: Caenorhabditis elegans

<400> SEQUENCE: 12

```
Met Thr Ser Leu Met Leu Leu Leu Phe Ala Phe Val Gln Pro Cys
 1               5                  10                  15

Ala Ser Ile Val Glu Lys Arg Cys Gly Pro Ile Asp Ile Arg Asn Arg
                20                  25                  30

Pro Trp Asp Ile Lys Pro Gln Trp Ser Lys Leu Gly Asp Pro Asn Glu
            35                  40                  45

Lys Asp Leu Ala Gly Gln Arg Met Val Asn Cys Thr Val Glu Gly
50                  55                  60

Ser Leu Thr Ile Ser Phe Val Leu Lys His Lys Thr Lys Ala Gln Glu
65                  70                  75                  80

Glu Met His Arg Ser Leu Gln Pro Arg Tyr Ser Gln Asp Glu Phe Ile
                85                  90                  95

Thr Phe Pro His Leu Arg Glu Ile Thr Gly Thr Leu Leu Val Phe Glu
            100                 105                 110

Thr Glu Gly Leu Val Asp Leu Arg Lys Ile Phe Pro Asn Leu Arg Val
        115                 120                 125

Ile Gly Gly Arg Ser Leu Ile Gln His Tyr Ala Leu Ile Ile Tyr Arg
130                 135                 140

Asn Pro Asp Leu Glu Ile Gly Leu Asp Lys Leu Ser Val Ile Arg Asn
145                 150                 155                 160

Gly Gly Val Arg Ile Ile Asp Asn Arg Lys Leu Cys Tyr Thr Lys Thr
                165                 170                 175

Ile Asp Trp Lys His Leu Ile Thr Ser Ser Ile Asn Asp Val Val Val
            180                 185                 190

Asp Asn Ala Ala Glu Tyr Ala Val Thr Glu Thr Gly Leu Met Cys Pro
        195                 200                 205

Arg Gly Ala Cys Glu Glu Asp Lys Gly Glu Ser Lys Cys His Tyr Leu
    210                 215                 220

Glu Glu Lys Asn Gln Glu Gln Gly Val Glu Arg Val Gln Ser Cys Trp
225                 230                 235                 240

Ser Asn Thr Thr Cys Gln Lys Ser Cys Ala Tyr Asp Arg Leu Leu Pro
                245                 250                 255

Thr Lys Glu Ile Gly Pro Gly Cys Asp Ala Asn Gly Asp Arg Cys His
            260                 265                 270

Asp Gln Cys Val Gly Gly Cys Glu Arg Val Asn Asp Ala Thr Ala Cys
        275                 280                 285

His Ala Cys Lys Asn Val Tyr His Lys Gly Lys Cys Ile Glu Lys Cys
    290                 295                 300

Asp Ala His Leu Tyr Leu Leu Gln Arg Arg Cys Val Thr Arg Glu
305                 310                 315                 320

Gln Cys Leu Gln Leu Asn Pro Val Leu Ser Asn Lys Thr Val Pro Ile
                325                 330                 335

Lys Ala Thr Ala Gly Leu Cys Ser Asp Lys Cys Pro Asp Gly Tyr Gln
            340                 345                 350
```

-continued

```
Ile Asn Pro Asp Asp His Arg Glu Cys Arg Lys Cys Val Gly Lys Cys
        355                 360                 365

Glu Ile Val Cys Glu Ile Asn His Val Ile Asp Thr Phe Pro Lys Ala
        370                 375                 380

Gln Ala Ile Arg Leu Cys Asn Ile Ile Asp Gly Asn Leu Thr Ile Glu
385                 390                 395                 400

Ile Arg Gly Lys Gln Asp Ser Gly Met Ala Ser Glu Leu Lys Asp Ile
                405                 410                 415

Phe Ala Asn Ile His Thr Ile Thr Gly Tyr Leu Leu Val Arg Gln Ser
                420                 425                 430

Ser Pro Phe Ile Ser Leu Asn Met Phe Arg Asn Leu Arg Arg Ile Glu
                435                 440                 445

Ala Lys Ser Leu Phe Arg Asn Leu Tyr Ala Ile Thr Val Phe Glu Asn
450                 455                 460

Pro Asn Leu Lys Lys Leu Phe Asp Ser Thr Thr Asp Leu Thr Leu Asp
465                 470                 475                 480

Arg Gly Thr Val Ser Ile Ala Asn Asn Lys Met Leu Cys Phe Lys Tyr
                485                 490                 495

Ile Lys Gln Leu Met Ser Lys Leu Asn Ile Pro Leu Asp Pro Ile Asp
                500                 505                 510

Gln Ser Glu Gly Thr Asn Gly Glu Lys Ala Ile Cys Glu Asp Met Ala
                515                 520                 525

Ile Asn Val Ser Ile Thr Ala Val Asn Ala Asp Ser Val Phe Phe Ser
                530                 535                 540

Trp Pro Ser Phe Asn Ile Thr Asp Ile Asp Gln Arg Lys Phe Leu Gly
545                 550                 555                 560

Tyr Glu Leu Phe Phe Lys Glu Val Pro Arg Ile Asp Glu Asn Met Thr
                565                 570                 575

Ile Glu Glu Asp Arg Ser Ala Cys Val Asp Ser Trp Gln Ser Val Phe
                580                 585                 590

Lys Gln Tyr Tyr Glu Thr Ser Asn Gly Glu Pro Thr Pro Asp Ile Phe
                595                 600                 605

Met Asp Ile Gly Pro Arg Glu Arg Ile Arg Pro Asn Thr Leu Tyr Ala
        610                 615                 620

Tyr Tyr Val Ala Thr Gln Met Val Leu His Ala Gly Ala Lys Asn Gly
625                 630                 635                 640

Val Ser Lys Ile Gly Phe Val Arg Thr Ser Tyr Tyr Thr Pro Asp Pro
                645                 650                 655

Pro Thr Leu Ala Leu Ala Gln Val Asp Ser Asp Ala Ile His Ile Thr
                660                 665                 670

Trp Glu Ala Pro Leu Gln Pro Asn Gly Asp Leu Thr His Tyr Thr Ile
                675                 680                 685

Met Trp Arg Glu Asn Glu Val Ser Pro Tyr Glu Glu Ala Glu Lys Phe
        690                 695                 700

Cys Thr Asp Ala Ser Thr Pro Ala Asn Arg Gln Arg Thr Lys Asp Pro
705                 710                 715                 720

Lys Glu Thr Ile Val Ala Asp Lys Pro Val Asp Ile Pro Ser Ser Arg
                725                 730                 735

Thr Val Ala Pro Thr Leu Leu Thr Met Met Gly His Glu Asp Gln Gln
                740                 745                 750

Lys Thr Cys Ala Ala Thr Pro Gly Cys Cys Ser Cys Ser Ala Ile Glu
                755                 760                 765

Glu Ser Ser Glu Gln Asn Lys Lys Lys Arg Pro Asp Pro Met Ser Ala
```

-continued

```
            770             775             780
Ile Glu Ser Ser Ala Phe Glu Asn Lys Leu Leu Asp Glu Val Leu Met
785                 790                 795                 800

Pro Arg Asp Thr Met Arg Val Arg Arg Ser Ile Glu Asp Ala Asn Arg
                805                 810                 815

Val Ser Glu Glu Leu Glu Lys Ala Glu Asn Leu Gly Lys Ala Pro Lys
            820                 825                 830

Thr Leu Gly Gly Lys Lys Pro Leu Ile His Ile Ser Lys Lys Lys Pro
        835                 840                 845

Ser Ser Ser Ser Thr Thr Ser Thr Pro Ala Pro Thr Ile Ala Ser Met
850                 855                 860

Tyr Ala Leu Thr Arg Lys Pro Thr Thr Val Pro Gly Thr Arg Ile Arg
865                 870                 875                 880

Leu Tyr Glu Ile Tyr Glu Pro Leu Pro Gly Ser Trp Ala Ile Asn Val
                885                 890                 895

Ser Ala Leu Ala Leu Asp Asn Ser Tyr Val Ile Arg Asn Leu Lys His
            900                 905                 910

Tyr Thr Leu Tyr Ala Ile Ser Leu Ser Ala Cys Gln Asn Met Thr Val
        915                 920                 925

Pro Gly Ala Ser Cys Ser Ile Ser His Arg Ala Gly Ala Leu Lys Arg
    930                 935                 940

Thr Lys His Ile Thr Asp Ile Asp Lys Val Leu Asn Glu Thr Ile Glu
945                 950                 955                 960

Trp Arg Phe Met Asn Asn Ser Gln Gln Val Asn Val Thr Trp Asp Pro
                965                 970                 975

Pro Thr Glu Val Asn Gly Gly Ile Phe Gly Tyr Val Val Lys Leu Lys
            980                 985                 990

Ser Lys Val Asp Gly Ser Ile Val Met Thr Arg Cys Val Gly Ala Lys
        995                 1000                1005

Arg Gly Tyr Ser Thr Arg Asn Gln Gly Val Leu Phe Gln Asn Leu Ala
    1010                1015                1020

Asp Gly Arg Tyr Phe Val Ser Val Thr Ala Thr Ser Val His Gly Ala
1025                1030                1035                1040

Gly Pro Glu Ala Glu Ser Ser Asp Pro Ile Val Val Met Thr Pro Gly
                1045                1050                1055

Phe Phe Thr Val Glu Ile Ile Leu Gly Met Leu Leu Val Phe Leu Ile
            1060                1065                1070

Leu Met Ser Ile Ala Gly Cys Ile Ile Tyr Tyr Ile Gln Val Arg
        1075                1080                1085

Tyr Gly Lys Lys Val Lys Ala Leu Ser Asp Phe Met Gln Leu Asn Pro
    1090                1095                1100

Glu Tyr Cys Val Asp Asn Lys Tyr Asn Ala Asp Asp Trp Glu Leu Arg
1105                1110                1115                1120

Gln Asp Asp Val Val Leu Gly Gln Gln Cys Gly Glu Gly Ser Phe Gly
                1125                1130                1135

Lys Val Tyr Leu Gly Thr Gly Asn Asn Val Val Ser Leu Met Gly Asp
            1140                1145                1150

Arg Phe Gly Pro Cys Ala Ile Lys Ile Asn Val Asp Asp Pro Ala Ser
        1155                1160                1165

Thr Glu Asn Leu Asn Tyr Leu Met Glu Ala Asn Ile Met Lys Asn Phe
    1170                1175                1180

Lys Thr Asn Phe Ile Val Gln Leu Tyr Gly Val Ile Ser Thr Val Gln
1185                1190                1195                1200
```

```
Pro Ala Met Val Val Met Glu Met Met Asp Leu Gly Asn Leu Arg Asp
            1205                1210                1215

Tyr Leu Arg Ser Lys Arg Glu Asp Glu Val Phe Asn Glu Thr Asp Cys
            1220                1225                1230

Asn Phe Phe Asp Ile Ile Pro Arg Asp Lys Phe His Glu Trp Ala Ala
            1235                1240                1245

Gln Ile Cys Asp Gly Met Ala Tyr Leu Glu Ser Leu Lys Phe Cys His
        1250                1255                1260

Arg Asp Leu Ala Ala Arg Asn Cys Met Ile Asn Arg Asp Glu Thr Val
1265                1270                1275                1280

Lys Ile Gly Asp Phe Gly Met Ala Arg Asp Leu Phe Tyr His Asp Tyr
            1285                1290                1295

Tyr Lys Pro Ser Gly Lys Arg Met Met Pro Val Arg Trp Met Ser Pro
            1300                1305                1310

Glu Ser Leu Lys Asp Gly Lys Phe Asp Ser Lys Ser Asp Val Trp Ser
            1315                1320                1325

Phe Gly Val Val Leu Tyr Glu Met Val Thr Leu Gly Ala Gln Pro Tyr
            1330                1335                1340

Ile Gly Leu Ser Asn Asp Glu Val Leu Asn Tyr Ile Gly Met Ala Arg
1345                1350                1355                1360

Lys Val Ile Lys Lys Pro Glu Cys Cys Glu Asn Tyr Trp Tyr Lys Val
            1365                1370                1375

Met Lys Met Cys Trp Arg Tyr Ser Pro Arg Asp Arg Pro Thr Phe Leu
            1380                1385                1390
```

```
Gln Leu Val His Leu Leu Ala Ala Glu Ala Ser Pro Glu Phe Arg Asp
        1395                1400                1405

Leu Ser Phe Val Leu Thr Asp Asn Gln Met Ile Leu Asp Asp Ser Glu
    1410                1415                1420

Ala Leu Asp Leu Asp Asp Ile Asp Asp Thr Asp Met Asn Asp Gln Val
1425                1430                1435                1440

Val Glu Val Ala Pro Asp Val Glu Asn Val Glu Val Gln Ser Asp Ser
                1445                1450                1455

Glu Arg Arg Asn Thr Asp Ser Ile Pro Leu Lys Gln Phe Lys Thr Ile
            1460                1465                1470

Pro Pro Ile Asn Ala Thr Thr Ser His Ser Thr Ile Ser Ile Asp Glu
        1475                1480                1485

Thr Pro Met Lys Ala Lys Gln Arg Glu Gly Ser Leu Asp Glu Glu Tyr
    1490                1495                1500

Ala Leu Met Asn His Ser Gly Gly Pro Ser Asp Ala Glu Val Arg Thr
1505                1510                1515                1520

Tyr Ala Gly Asp Gly Asp Tyr Val Glu Arg Asp Val Arg Glu Asn Asp
                1525                1530                1535

Val Pro Thr Arg Arg Asn Thr Gly Ala Ser Thr Ser Ser Tyr Thr Gly
            1540                1545                1550

Gly Gly Pro Tyr Cys Leu Thr Asn Arg Gly Gly Ser Asn Glu Arg Gly
        1555                1560                1565

Ala Gly Phe Gly Glu Ala Val Arg Leu Thr Asp Gly Val Gly Ser Gly
    1570                1575                1580

His Leu Asn Asp Asp Asp Tyr Val Glu Lys Glu Ile Ser Ser Met Asp
1585                1590                1595                1600

Thr Arg Arg Ser Thr Gly Ala Ser Ser Ser Ser Tyr Gly Val Pro Gln
                1605                1610                1615

Thr Asn Trp Ser Gly Asn Arg Gly Ala Thr Tyr Tyr Thr Ser Lys Ala
            1620                1625                1630

Gln Gln Ala Ala Thr Ala Ala Ala Ala Ala Ala Ala Ala Leu Gln Gln
        1635                1640                1645

Gln Gln Asn Gly Gly Arg Gly Asp Arg Leu Thr Gln Leu Pro Gly Thr
    1650                1655                1660

Gly His Leu Gln Ser Thr Arg Gly Gly Gln Asp Gly Asp Tyr Ile Glu
1665                1670                1675                1680

Thr Glu Pro Lys Asn Tyr Arg Asn Asn Gly Ser Pro Ser Arg Asn Gly
                1685                1690                1695

Asn Ser Arg Asp Ile Phe Asn Gly Arg Ser Ala Phe Gly Glu Asn Glu
            1700                1705                1710

His Leu Ile Glu Asp Asn Glu His His Pro Leu Val
        1715                1720

<210> SEQ ID NO 13
<211> LENGTH: 139
<212> TYPE: PRT
<213> ORGANISM: Caenorhabditis elegans

<400> SEQUENCE: 13

Thr Ser Gly Ser Gly Met Gly Pro Thr Thr Leu His Lys Leu Thr Ile
  1               5                  10                  15

Gly Gly Gln Ile Arg Leu Thr Gly Arg Val Ser Gly Arg Phe Gly
            20                  25                  30

Asn Val Ser Arg Gly Asp Tyr Arg Gly Glu Ala Val Ala Val Lys Val
```

```
                35                  40                  45
Phe Asn Ala Leu Asp Glu Pro Ala Phe His Lys Glu Thr Glu Ile Phe
 50                  55                  60

Glu Thr Arg Met Leu Arg His Pro Asn Val Leu Arg Tyr Ile Gly Ser
65                  70                  75                  80

Asp Arg Val Asp Thr Gly Phe Val Thr Glu Leu Trp Leu Val Thr Glu
                85                  90                  95

Tyr His Pro Ser Gly Ser Leu His Asp Phe Leu Leu Glu Asn Thr Val
                100                 105                 110

Asn Ile Glu Thr Tyr Tyr Asn Leu Met Arg Ser Thr Ala Ser Gly Leu
            115                 120                 125

Ala Phe Leu His Asn Gln Ile Gly Gly Ser Lys
        130                 135

<210> SEQ ID NO 14
<211> LENGTH: 62
<212> TYPE: PRT
<213> ORGANISM: Caenorhabditis elegans

<400> SEQUENCE: 14

Glu Asp Ala Ala Ser Asp Ile Ile Ala Asn Glu Asn Tyr Lys Cys Gly
 1               5                  10                  15

Thr Val Arg Tyr Leu Ala Pro Glu Ile Leu Asn Ser Thr Met Gln Phe
                20                  25                  30

Thr Val Phe Glu Ser Tyr Gln Cys Ala Asp Val Tyr Ser Phe Ser Leu
            35                  40                  45

Val Met Trp Glu Thr Leu Cys Arg Cys Glu Asp Gly Asp Val
 50                  55                  60

<210> SEQ ID NO 15
<211> LENGTH: 31
<212> TYPE: PRT
<213> ORGANISM: Caenorhabditis elegans

<400> SEQUENCE: 15

Lys Pro Ala Met Ala His Arg Asp Ile Lys Ser Lys Asn Ile Met Val
 1               5                  10                  15

Lys Asn Asp Leu Thr Cys Ala Ile Gly Asp Leu Gly Leu Ser Leu
                20                  25                  30

<210> SEQ ID NO 16
<211> LENGTH: 72
<212> TYPE: PRT
<213> ORGANISM: Caenorhabditis elegans

<400> SEQUENCE: 16

Ile Pro Tyr Ile Glu Trp Thr Asp Arg Asp Pro Gln Asp Ala Gln Met
 1               5                  10                  15

Phe Asp Val Val Cys Thr Arg Arg Leu Arg Pro Thr Glu Asn Pro Leu
                20                  25                  30

Trp Lys Asp His Pro Glu Met Lys His Ile Met Glu Ile Ile Lys Thr
            35                  40                  45

Cys Trp Asn Gly Asn Pro Ser Ala Arg Phe Thr Ser Tyr Ile Cys Arg
 50                  55                  60

Lys Arg Met Asp Glu Arg Gln Gln
65                  70

<210> SEQ ID NO 17
```

```
<211> LENGTH: 150
<212> TYPE: PRT
<213> ORGANISM: Caenorhabditis elegans

<400> SEQUENCE: 17

Tyr Phe Glu Ser Val Asp Arg Phe Leu Tyr Ser Cys Val Gly Tyr Ser
1               5                   10                  15

Val Ala Thr Tyr Ile Met Gly Ile Lys Asp Arg His Ser Asp Asn Leu
            20                  25                  30

Met Leu Thr Glu Asp Gly Lys Tyr Val His Ile Asp Phe Gly His Ile
        35                  40                  45

Leu Gly His Gly Lys Thr Lys Leu Gly Ile Gln Arg Asp Arg Gln Pro
    50                  55                  60

Phe Ile Leu Thr Glu His Phe Met Thr Val Ile Arg Ser Gly Lys Ser
65                  70                  75                  80

Val Asp Gly Asn Ser His Glu Leu Gln Lys Phe Lys Thr Leu Cys Val
                85                  90                  95

Glu Ala Tyr Glu Val Met Trp Asn Asn Arg Asp Leu Phe Val Ser Leu
            100                 105                 110

Phe Thr Leu Met Leu Gly Met Glu Leu Pro Glu Leu Ser Thr Lys Ala
        115                 120                 125

Asp Leu Asp His Leu Lys Lys Thr Leu Phe Cys Asn Gly Glu Ser Lys
    130                 135                 140

Glu Glu Ala Arg Lys Phe
145                 150

<210> SEQ ID NO 18
<211> LENGTH: 113
<212> TYPE: PRT
<213> ORGANISM: Caenorhabditis elegans

<400> SEQUENCE: 18

Ser Pro Leu Asp Pro Val Tyr Lys Leu Gly Glu Met Ile Ile Asp Lys
1               5                   10                  15

Ala Ile Val Leu Gly Ser Ala Lys Arg Pro Leu Met Leu His Trp Lys
            20                  25                  30

Asn Lys Asn Pro Lys Ser Asp Leu His Leu Pro Phe Cys Ala Met Ile
        35                  40                  45

Phe Lys Asn Gly Asp Asp Leu Arg Gln Asp Met Leu Val Leu Gln Val
    50                  55                  60

Leu Glu Val Met Asp Asn Ile Trp Lys Ala Ala Asn Ile Asp Cys Cys
65                  70                  75                  80

Leu Asn Pro Tyr Ala Val Leu Pro Met Gly Glu Met Ile Gly Ile Ile
                85                  90                  95

Glu Val Val Pro Asn Cys Lys Thr Ile Phe Glu Ile Gln Val Gly Thr
            100                 105                 110

Gly

<210> SEQ ID NO 19
<211> LENGTH: 106
<212> TYPE: PRT
<213> ORGANISM: Caenorhabditis elegans

<400> SEQUENCE: 19

Leu Ala Phe Val Trp Thr Asp Arg Glu Asn Phe Ser Glu Leu Tyr Val
1               5                   10                  15

Met Leu Glu Lys Trp Lys Pro Pro Ser Val Ala Ala Ala Leu Thr Leu
```

```
                20                  25                  30
Leu Gly Lys Arg Cys Thr Asp Arg Val Ile Arg Lys Phe Ala Val Glu
            35                  40                  45

Lys Leu Asn Glu Gln Leu Ser Pro Val Thr Phe His Leu Phe Ile Leu
 50                  55                  60

Pro Leu Ile Gln Ala Leu Lys Tyr Glu Pro Arg Ala Gln Ser Glu Val
 65                  70                  75                  80

Gly Met Met Leu Leu Thr Arg Ala Leu Cys Asp Tyr Arg Ile Gly His
                85                  90                  95

Arg Leu Phe Trp Leu Leu Arg Ala Glu Ile
            100                 105

<210> SEQ ID NO 20
<211> LENGTH: 139
<212> TYPE: PRT
<213> ORGANISM: Caenorhabditis elegans

<400> SEQUENCE: 20

Glu Tyr Trp Ile Val Thr Glu Phe His Glu Arg Leu Ser Leu Tyr Glu
  1               5                  10                  15

Leu Leu Lys Asn Asn Val Ile Ser Ile Thr Ser Ala Asn Arg Ile Ile
                20                  25                  30

Met Ser Met Ile Asp Gly Leu Gln Phe Leu His Asp Asp Arg Pro Tyr
            35                  40                  45

Phe Phe Gly His Pro Lys Lys Pro Ile Ile His Arg Asp Ile Lys Ser
         50                  55                  60

Lys Asn Ile Leu Val Lys Ser Asp Met Thr Thr Cys Ile Ala Asp Phe
 65                  70                  75                  80

Gly Leu Ala Arg Ile Tyr Ser Tyr Asp Ile Glu Gln Ser Asp Leu Leu
                85                  90                  95

Gly Gln Val Gly Thr Lys Arg Tyr Met Ser Pro Glu Met Leu Glu Gly
            100                 105                 110

Ala Thr Glu Phe Thr Pro Thr Ala Phe Lys Ala Met Asp Val Tyr Ser
        115                 120                 125

Met Gly Leu Val Met Trp Glu Val Ile Ser Arg
        130                 135

<210> SEQ ID NO 21
<211> LENGTH: 61
<212> TYPE: PRT
<213> ORGANISM: Caenorhabditis elegans

<400> SEQUENCE: 21

Ile Gly Phe Asp Pro Thr Ile Gly Arg Met Arg Asn Tyr Val Val Ser
  1               5                  10                  15

Lys Lys Glu Arg Pro Gln Trp Arg Asp Glu Ile Ile Lys His Glu Tyr
                20                  25                  30

Met Ser Leu Leu Lys Lys Val Thr Glu Glu Met Trp Asp Pro Glu Ala
            35                  40                  45

Cys Ala Arg Ile Thr Ala Gly Cys Ala Phe Ala Arg Val
         50                  55                  60

<210> SEQ ID NO 22
<211> LENGTH: 20
<212> TYPE: PRT
<213> ORGANISM: Caenorhabditis elegans

<400> SEQUENCE: 22
```

Pro Ile Thr Asp Phe Gln Leu Ile Ser Lys Gly Arg Phe Gly Lys Val
1               5                   10                  15

Phe Lys Ala Gln
            20

<210> SEQ ID NO 23
<211> LENGTH: 163
<212> TYPE: PRT
<213> ORGANISM: Caenorhabditis elegans

<400> SEQUENCE: 23

Thr Asp Ser Glu Thr Arg Ser Arg Phe Ser Leu Gly Trp Tyr Asn Asn
1               5                   10                  15

Pro Asn Arg Ser Pro Gln Thr Ala Glu Val Arg Gly Leu Ile Gly Lys
            20                  25                  30

Gly Val Arg Phe Tyr Leu Leu Ala Gly Glu Val Tyr Val Glu Asn Leu
        35                  40                  45

Cys Asn Ile Pro Val Phe Val Gln Ser Ile Gly Ala Asn Met Lys Asn
    50                  55                  60

Gly Phe Gln Leu Asn Thr Val Ser Lys Leu Pro Pro Thr Gly Thr Met
65                  70                  75                  80

Lys Val Phe Asp Met Arg Leu Phe Ser Lys Gln Leu Arg Thr Ala Ala
                85                  90                  95

Glu Lys Thr Tyr Gln Asp Val Tyr Cys Leu Ser Arg Met Cys Thr Val
            100                 105                 110

Arg Val Ser Phe Cys Lys Gly Trp Gly Glu His Tyr Arg Arg Ser Thr
        115                 120                 125

Val Leu Arg Ser Pro Val Trp Phe Gln Ala His Leu Asn Asn Pro Met
    130                 135                 140

His Trp Val Asp Ser Val Leu Thr Cys Met Gly Ala Pro Pro Arg Ile
145                 150                 155                 160

Cys Ser Ser

<210> SEQ ID NO 24
<211> LENGTH: 44
<212> TYPE: PRT
<213> ORGANISM: Caenorhabditis elegans

<400> SEQUENCE: 24

Arg Ala Phe Arg Phe Pro Val Ile Arg Tyr Glu Ser Gln Val Lys Ser
1               5                   10                  15

Ile Leu Thr Cys Arg His Ala Phe Asn Ser His Ser Arg Asn Val Cys
            20                  25                  30

Leu Asn Pro Tyr His Tyr Arg Trp Val Glu Leu Pro
        35                  40

<210> SEQ ID NO 25
<211> LENGTH: 38
<212> TYPE: PRT
<213> ORGANISM: Caenorhabditis elegans

<400> SEQUENCE: 25

Val Glu Tyr Glu Glu Ser Pro Ser Trp Leu Lys Leu Ile Tyr Tyr Glu
1               5                   10                  15

Glu Gly Thr Met Ile Gly Glu Lys Ala Asp Val Glu Gly His His Cys
            20                  25                  30

Leu Ile Asp Gly Phe Thr

<210> SEQ ID NO 26
<211> LENGTH: 60
<212> TYPE: PRT
<213> ORGANISM: Caenorhabditis elegans

<400> SEQUENCE: 26

Asn Leu Ala Glu Thr Gly His Ser Lys Ile Met Arg Ala Ala His Lys
1               5                   10                  15

Val Ser Asn Pro Glu Ile Gly Tyr Cys Cys His Pro Thr Glu Tyr Asp
            20                  25                  30

Tyr Ile Lys Leu Ile Tyr Val Asn Arg Asp Gly Arg Val Ser Ile Ala
        35                  40                  45

Asn Val Asn Gly Met Ile Ala Lys Lys Cys Gly Cys
    50                  55                  60

<210> SEQ ID NO 27
<211> LENGTH: 20
<212> TYPE: PRT
<213> ORGANISM: Caenorhabditis elegans

<400> SEQUENCE: 27

Asp Trp Ile Val Ala Pro Pro Arg Tyr Asn Ala Tyr Met Cys Arg Gly
1               5                   10                  15

Asp Cys His Tyr
            20

<210> SEQ ID NO 28
<211> LENGTH: 43
<212> TYPE: PRT
<213> ORGANISM: Caenorhabditis elegans

<400> SEQUENCE: 28

Val Cys Asn Ala Glu Ala Gln Ser Lys Gly Cys Cys Leu Tyr Asp Leu
1               5                   10                  15

Glu Ile Glu Phe Glu Lys Ile Gly Trp Asp Trp Ile Val Ala Pro Pro
            20                  25                  30

Arg Tyr Asn Ala Tyr Met Cys Arg Gly Asp Cys
        35                  40

<210> SEQ ID NO 29
<211> LENGTH: 70
<212> TYPE: PRT
<213> ORGANISM: Caenorhabditis elegans

<400> SEQUENCE: 29

Asp Cys His Tyr Asn Ala His His Phe Asn Leu Ala Glu Thr Gly His
1               5                   10                  15

Ser Lys Ile Met Arg Ala Ala His Lys Val Ser Asn Pro Glu Ile Gly
            20                  25                  30

Tyr Cys Cys His Pro Thr Glu Tyr Asp Tyr Ile Lys Leu Ile Tyr Val
        35                  40                  45

Asn Arg Asp Gly Arg Val Ser Ile Ala Asn Val Asn Gly Met Ile Ala
    50                  55                  60

Lys Lys Cys Gly Cys Ser
65                  70

<210> SEQ ID NO 30
<211> LENGTH: 35

```
<212> TYPE: PRT
<213> ORGANISM: Caenorhabditis elegans

<400> SEQUENCE: 30

Cys Cys Leu Tyr Asp Leu Glu Ile Glu Phe Glu Lys Ile Gly Trp Asp
 1               5                  10                  15

Trp Ile Val Ala Pro Pro Arg Tyr Asn Ala Tyr Met Cys Arg Gly Asp
            20                  25                  30

Cys His Tyr
        35

<210> SEQ ID NO 31
<211> LENGTH: 23
<212> TYPE: DNA
<213> ORGANISM: Artificial Sequence
<220> FEATURE:
<223> OTHER INFORMATION: Degenerate probe
<220> FEATURE:
<221> NAME/KEY: misc_feature
<222> LOCATION: (1)...(23)
<223> OTHER INFORMATION: n = A,T,C or G

<400> SEQUENCE: 31
ggntgggayt rnrtnrtngc ncc                                          23

<210> SEQ ID NO 32
<211> LENGTH: 18
<212> TYPE: DNA
<213> ORGANISM: Artificial Sequence
<220> FEATURE:
<223> OTHER INFORMATION: Degenerate probe
<220> FEATURE:
<221> NAME/KEY: misc_feature
<222> LOCATION: (1)...(18)
<223> OTHER INFORMATION: n = A,T,C or G

<400> SEQUENCE: 32
tgytgynnnc cnacngar                                                18

<210> SEQ ID NO 33
<211> LENGTH: 127
<212> TYPE: PRT
<213> ORGANISM: Caenorhabditis elegans

<400> SEQUENCE: 33

Lys Phe His Glu Trp Ala Ala Gln Ile Cys Asp Gly Met Ala Tyr Leu
 1               5                  10                  15

Glu Ser Leu Lys Phe Cys His Arg Asp Leu Ala Ala Arg Asn Cys Met
            20                  25                  30

Ile Asn Arg Asp Glu Thr Val Lys Ile Gly Asp Phe Gly Met Ala Arg
        35                  40                  45

Asp Leu Phe Tyr His Asp Tyr Tyr Lys Pro Ser Gly Lys Arg Met Met
     50                  55                  60

Pro Val Arg Trp Met Ser Pro Glu Ser Leu Lys Asp Gly Lys Phe Asp
65                  70                  75                  80

Ser Lys Ser Asp Val Trp Ser Phe Gly Val Leu Tyr Glu Met Val
            85                  90                  95

Thr Leu Gly Ala Gln Pro Tyr Ile Gly Leu Ser Asn Asp Glu Val Leu
               100                 105                 110

Asn Tyr Ile Gly Met Ala Arg Lys Val Ile Lys Pro Glu Cys
           115                 120                 125
```

```
<210> SEQ ID NO 34
<211> LENGTH: 131
<212> TYPE: PRT
<213> ORGANISM: Caenorhabditis elegans

<400> SEQUENCE: 34

Asn Thr Thr Cys Gln Lys Ser Cys Ala Tyr Asp Arg Leu Leu Pro Thr
  1               5                  10                  15

Lys Glu Ile Gly Pro Gly Cys Asp Ala Asn Gly Asp Arg Cys His Asp
             20                  25                  30

Gln Cys Val Gly Gly Cys Glu Arg Val Asn Asp Ala Thr Ala Cys His
         35                  40                  45

Ala Cys Lys Asn Val Tyr His Lys Gly Lys Cys Ile Glu Lys Cys Asp
 50                  55                  60

Ala His Leu Tyr Leu Leu Gln Arg Arg Cys Val Thr Arg Glu Gln
 65                  70                  75                  80

Cys Leu Gln Leu Asn Pro Val Leu Ser Asn Lys Thr Val Pro Ile Lys
                 85                  90                  95

Ala Thr Ala Gly Leu Cys Ser Asp Lys Cys Pro Asp Gly Tyr Gln Ile
            100                 105                 110

Asn Pro Asp Asp His Arg Glu Cys Arg Lys Cys Val Gly Lys Cys Glu
            115                 120                 125

Ile Val Cys
       130

<210> SEQ ID NO 35
<211> LENGTH: 103
<212> TYPE: PRT
<213> ORGANISM: Caenorhabditis elegans

<400> SEQUENCE: 35

Phe Asp Gln Lys Ala Cys Glu Ser Leu Val Lys Lys Leu Lys Asp Lys
  1               5                  10                  15

Lys Asn Asp Leu Gln Asn Leu Ile Asp Val Leu Ser Lys Gly Thr
             20                  25                  30

Lys Tyr Thr Gly Cys Ile Thr Ile Pro Arg Thr Leu Asp Gly Arg Leu
         35                  40                  45

Gln Val His Gly Arg Lys Gly Phe Pro His Val Tyr Gly Lys Leu
 50                  55                  60

Trp Arg Phe Asn Glu Met Thr Lys Asn Glu Thr Arg His Val Asp His
 65                  70                  75                  80

Cys Lys His Ala Phe Glu Met Lys Ser Asp Met Val Cys Val Asn Pro
                 85                  90                  95

Tyr His Tyr Glu Ile Val Ile
            100

<210> SEQ ID NO 36
<211> LENGTH: 79
<212> TYPE: PRT
<213> ORGANISM: Caenorhabditis elegans

<400> SEQUENCE: 36

Asn Arg Tyr Ser Leu Gly Leu Glu Pro Asn Pro Ile Arg Glu Pro Val
  1               5                  10                  15

Ala Phe Lys Val Arg Lys Ala Ile Val Asp Gly Ile Arg Phe Ser Tyr
             20                  25                  30

Lys Lys Asp Gly Ser Val Trp Leu Gln Asn Arg Met Lys Tyr Pro Val
         35                  40                  45
```

Phe Val Thr Ser Gly Tyr Leu Asp Glu Gln Ser Gly Gly Leu Lys Lys
    50                  55                  60

Asp Lys Val His Lys Val Tyr Gly Cys Ala Ser Ile Lys Thr Phe
65                  70                  75

<210> SEQ ID NO 37
<211> LENGTH: 106
<212> TYPE: PRT
<213> ORGANISM: Caenorhabditis elegans

<400> SEQUENCE: 37

Lys Lys Thr Thr Thr Arg Arg Asn Ala Trp Gly Asn Met Ser Tyr Ala
1               5                   10                  15

Glu Leu Ile Thr Thr Ala Ile Met Ala Ser Pro Glu Lys Arg Leu Thr
            20                  25                  30

Leu Ala Gln Val Tyr Glu Trp Met Val Gln Asn Val Pro Tyr Phe Arg
        35                  40                  45

Asp Lys Gly Asp Ser Asn Ser Ser Ala Gly Trp Lys Asn Ser Ile Arg
    50                  55                  60

His Asn Leu Ser Leu His Ser Arg Phe Met Arg Ile Gln Asn Glu Gly
65                  70                  75                  80

Ala Gly Lys Ser Ser Trp Trp Val Ile Asn Pro Asp Ala Lys Pro Gly
                85                  90                  95

Met Asn Pro Arg Arg Thr Arg Glu Arg Ser
            100                 105

<210> SEQ ID NO 38
<211> LENGTH: 60
<212> TYPE: PRT
<213> ORGANISM: Caenorhabditis elegans

<400> SEQUENCE: 38

Glu Ile Lys Leu Ser Asp Phe Lys His Gln Leu Phe Glu Leu Ile Ala
1               5                   10                  15

Pro Met Lys Trp Gly Thr Tyr Ser Val Lys Pro Gln Asp Tyr Val Phe
            20                  25                  30

Arg Gln Leu Asn Asn Phe Gly Glu Ile Glu Val Ile Phe Asn Asp Asp
        35                  40                  45

Gln Pro Leu Ser Lys Leu Glu Leu His Gly Thr Phe
    50                  55                  60

<210> SEQ ID NO 39
<211> LENGTH: 2784
<212> TYPE: DNA
<213> ORGANISM: Caenorhabditis elegans

<400> SEQUENCE: 39
atgaagctaa tagcaacttc tcttctagtt cccgacgagc acacaccgat gatgtcacca      60
gtgaatacaa ctacaaagat tctacaacgg agtggtatta aatggaaat cccgccatat     120 ttggatccag acagtcagga tgatgacccg gaagatggtg tcaactaccc ggatccagat    180
ttatttgaca caaaaaacac aaatatgacc gagtacgatt tggatgtgtt gaagcttgga    240
aaaccagcag tagatgaagc acggaaaaag atcgaagttc ccgacgctag tgcgccgcca    300
aacaaaattg tagaatattt gatgtattat agaacgttaa agaaagtga actcatacaa    360 ctgaatgcgt atcggacaaa acgaaatcga ttatcgttga acttggtcaa aacaatatt    420 gatcgagagt cgaccaaaa agcttgcgag tccctggtga aaaaattgaa ggataagaag    480

-continued

```
aatgatctcc agaacctgat tgatgtggtt ctttcaaaag gtacaaaata taccggttgc    540
attacaattc caaggacact tgatggccgg ttacaggtcc acggaagaaa aggtttccct    600
cacgtagtct atggcaaact gtggaggttt aatgaaatga caaaaaacga aacgcgtcat    660
gtggaccact gcaagcacgc atttgaaatg aaaagtgaca tggtatgcgt gaatccctat    720
cactacgaaa ttgtcattgg aactatgatt gttgggcaga gggatcatga caatcgagat    780
atgccgccgc cacatcaacg ctaccacact ccaggtcggc aggatccagt tgacgatatg    840
agtagattta taccaccagc ttccattcgt ccgcctccga tgaacatgca cacaaggcct    900
cagcctatgc ctcaacaatt gccttcagtt ggcgcaacgt ttgcccatcc tctcccacat    960
caggcgccac ataacccagg ggtttcacat ccgtactcca ttgctccaca gacccattac   1020
ccgttgaaca tgaacccaat tccgcaaatg ccgcaaatgc cacaaatgcc accacctctc   1080
catcagggat atggaatgaa tgggccgagt tgctcttcag aaaacaacaa tccattccac   1140
caaaatcacc attataatga tattagccat ccaaatcact attcctacga ctgtggtccg   1200
aacttgtacg ggtttccaac tccttatccg gattttcacc atcctttcaa tcagcaacca   1260
caccagccgc cacaactatc acaaaaccat acgtcccaac aaggcagtca tcaaccaggg   1320
caccaaggtc aggtaccgaa tgatccacca atttcaagac cagtgttaca accatcaaca   1380
gtcaccttgg acgtgttccg tcggtactgt agacagacat ttggaaatcg atttttttgaa   1440 ggagaaagtg aacaatccgg cgcaataatt cggtctagta acaaattcat gaagaatttt   1500
gattcgccga tttgtggtgt gacagttgtt cgaccgcgga tgcagacggg tgaggttttg   1560
gagaacatca tgccggaaga tgcaccatat catgacattt gcaagttcat tttgaggctc   1620
acatcagaaa gtgtaacttt ctcaggagag gggccagaag ttagtgattt gaacgaaaaa   1680
tggggaacaa ttgtgtacta tgagaaaaat ttgcaaattg gcgagaaaaa atgttcgaga   1740
ggaaatttcc acgtggatgg cggattcatt tgctctgaga atcgttacag tctcggactt   1800
gagccaaatc caattagaga accagtggcg tttaaagttc gtaaagcaat agtggatgga   1860
attcgctttt cctacaaaaa agacgggagt gttttggctt caaaaccgcat gaagtacccg   1920 gtatttgtca cttctgggta tctcgacgag caatcaggag gcctaaagaa ggataaagtg   1980
cacaaagttt acgatgtgc gtctatcaaa acgtttggct tcaacgtttc caaacaaatc   2040
atcagagacg cgcttctttc caagcaaatg gcaacaatgt acttgcaagg aaaattgact   2100
ccgatgaatt atatctacga gaagaagact caggaagagc tgcgaaggga agcaacacgc   2160
accactgatt cattggccaa gtactgttgt gtccgtgtct cgttctgcaa aggatttgga   2220
gaagcatacc cagaacgccc gtcaattcat gattgtccag tttggattga gttgaaaatc   2280
aacattgcct acgatttcat ggattcaatc tgccagtaca taaccaactg cttcgagccg   2340
ctaggaatgg aagattttgc aaaattggga atcaacgtca gtgatgacta aatgataact   2400 ttttttcactc accctactag atactgattt agtcttattc caaatcatcc aacgatatca   2460
aactttttcc tttgaacttt gcatactatg ttatcacaag ttccaagcag tttcaataca   2520
aacataggat atgttaacaa cttttgataa gaatcaagtt accaactgtt cattgtgagc   2580
tttgagctgt atagaaggac aatgtatccc ataccctcaat cttttaatagt catcagtcac   2640 tggtcccgca ccaatttttt cgattcgcat atgtcatata ttgcaccgtg gcccttttta   2700
ttgtaacttt taatatattt tcttcccaac ttgtgaatat gattgatgaa ccaccatttt   2760
gagtaataaa tgtattttttt gtgg                                          2784
```

<210> SEQ ID NO 40
<211> LENGTH: 796
<212> TYPE: PRT
<213> ORGANISM: Caenorhabditis elegans

<400> SEQUENCE: 40

```
Met Lys Leu Ile Ala Thr Ser Leu Leu Val Pro Asp Glu His Thr Pro
1               5                   10                  15

Met Met Ser Pro Val Asn Thr Thr Lys Ile Leu Gln Arg Ser Gly
            20                  25                  30

Ile Lys Met Glu Ile Pro Pro Tyr Leu Asp Pro Asp Ser Gln Asp Asp
        35                  40                  45

Asp Pro Glu Asp Gly Val Asn Tyr Pro Asp Pro Asp Leu Phe Asp Thr
    50                  55                  60

Lys Asn Thr Asn Met Thr Glu Tyr Asp Leu Asp Val Leu Lys Leu Gly
65                  70                  75                  80

Lys Pro Ala Val Asp Glu Ala Arg Lys Lys Ile Glu Val Pro Asp Ala
                85                  90                  95

Ser Ala Pro Pro Asn Lys Ile Val Glu Tyr Leu Met Tyr Tyr Arg Thr
            100                 105                 110

Leu Lys Glu Ser Glu Leu Ile Gln Leu Asn Ala Tyr Arg Thr Lys Arg
        115                 120                 125

Asn Arg Leu Ser Leu Asn Leu Val Lys Asn Asn Ile Asp Arg Glu Phe
    130                 135                 140

Asp Gln Lys Ala Cys Glu Ser Leu Val Lys Lys Leu Lys Asp Lys Lys
145                 150                 155                 160

Asn Asp Leu Gln Asn Leu Ile Asp Val Val Leu Ser Lys Gly Thr Lys
                165                 170                 175

Tyr Thr Gly Cys Ile Thr Ile Pro Arg Thr Leu Asp Gly Arg Leu Gln
            180                 185                 190

Val His Gly Arg Lys Gly Phe Pro His Val Val Tyr Gly Lys Leu Trp
        195                 200                 205

Arg Phe Asn Glu Met Thr Lys Asn Glu Thr Arg His Val Asp His Cys
    210                 215                 220

Lys His Ala Phe Glu Met Lys Ser Asp Met Val Cys Val Asn Pro Tyr
225                 230                 235                 240

His Tyr Glu Ile Val Ile Gly Thr Met Ile Val Gly Gln Arg Asp His
                245                 250                 255

Asp Asn Arg Asp Met Pro Pro His Gln Arg Tyr His Thr Pro Gly
            260                 265                 270

Arg Gln Asp Pro Val Asp Asp Met Ser Arg Phe Ile Pro Pro Ala Ser
        275                 280                 285

Ile Arg Pro Pro Met Asn Met His Thr Arg Pro Gln Pro Met Pro
    290                 295                 300

Gln Gln Leu Pro Ser Val Gly Ala Thr Phe Ala His Pro Leu Pro His
305                 310                 315                 320

Gln Ala Pro His Asn Pro Gly Val Ser His Pro Tyr Ser Ile Ala Pro
                325                 330                 335

Gln Thr His Tyr Pro Leu Asn Met Asn Pro Ile Pro Gln Met Pro Gln
            340                 345                 350

Met Pro Gln Met Pro Pro Leu His Gln Gly Tyr Gly Met Asn Gly
        355                 360                 365

Pro Ser Cys Ser Ser Glu Asn Asn Asn Pro Phe His Gln Asn His His
    370                 375                 380
```

```
Tyr Asn Asp Ile Ser His Pro Asn His Tyr Ser Tyr Asp Cys Gly Pro
385                 390                 395                 400

Asn Leu Tyr Gly Phe Pro Thr Pro Tyr Pro Asp Phe His His Pro Phe
            405                 410                 415

Asn Gln Gln Pro His Gln Pro Pro Gln Leu Ser Gln Asn His Thr Ser
            420                 425                 430

Gln Gln Gly Ser His Gln Pro Gly His Gln Gly Gln Val Pro Asn Asp
            435                 440                 445

Pro Pro Ile Ser Arg Pro Val Leu Gln Pro Ser Thr Val Thr Leu Asp
            450                 455                 460

Val Phe Arg Arg Tyr Cys Arg Gln Thr Phe Gly Asn Arg Phe Phe Glu
465                 470                 475                 480

Gly Glu Ser Glu Gln Ser Gly Ala Ile Ile Arg Ser Ser Asn Lys Phe
            485                 490                 495

Ile Glu Glu Phe Asp Ser Pro Ile Cys Gly Val Thr Val Arg Pro
            500                 505                 510

Arg Met Thr Asp Gly Glu Val Leu Glu Asn Ile Met Pro Glu Asp Ala
            515                 520                 525

Pro Tyr His Asp Ile Cys Lys Phe Ile Leu Arg Leu Thr Ser Glu Ser
            530                 535                 540

Val Thr Phe Ser Gly Glu Gly Pro Glu Val Ser Asp Leu Asn Glu Lys
545                 550                 555                 560

Trp Gly Thr Ile Val Tyr Tyr Glu Lys Asn Leu Gln Ile Gly Glu Lys
            565                 570                 575

Lys Cys Ser Arg Gly Asn Phe His Val Asp Gly Gly Phe Ile Cys Ser
            580                 585                 590

Glu Asn Arg Tyr Ser Leu Gly Leu Glu Pro Asn Pro Ile Arg Glu Pro
            595                 600                 605

Val Ala Phe Lys Val Arg Lys Ala Ile Val Asp Gly Ile Arg Phe Ser
610                 615                 620

Tyr Lys Lys Asp Gly Ser Val Trp Leu Gln Asn Arg Met Lys Tyr Pro
625                 630                 635                 640

Val Phe Val Thr Ser Gly Tyr Leu Asp Glu Gln Ser Gly Gly Leu Lys
            645                 650                 655

Lys Asp Lys Val His Lys Val Tyr Gly Cys Ala Ser Ile Lys Thr Phe
            660                 665                 670

Gly Phe Asn Val Ser Lys Gln Ile Ile Arg Asp Ala Leu Leu Ser Lys
            675                 680                 685

Gln Met Ala Thr Met Tyr Leu Gln Gly Lys Leu Thr Pro Met Asn Tyr
690                 695                 700

Ile Tyr Glu Lys Lys Thr Gln Glu Glu Leu Arg Arg Glu Ala Thr Arg
705                 710                 715                 720

Thr Thr Asp Ser Leu Ala Lys Tyr Cys Cys Val Arg Val Ser Phe Cys
            725                 730                 735

Lys Gly Phe Gly Glu Ala Tyr Pro Glu Arg Pro Ser Ile His Asp Cys
            740                 745                 750

Pro Val Trp Ile Glu Leu Lys Ile Asn Ile Ala Tyr Asp Phe Met Asp
            755                 760                 765

Ser Ile Cys Gln Tyr Ile Thr Asn Cys Phe Glu Pro Leu Gly Met Glu
            770                 775                 780

Asp Phe Ala Lys Leu Gly Ile Asn Val Ser Asp Asp
785                 790                 795
```

```
<210> SEQ ID NO 41
<211> LENGTH: 858
<212> TYPE: PRT
<213> ORGANISM: Caenorhabditis elegans

<400> SEQUENCE: 41

Met Gly Asp His His Asn Leu Thr Gly Leu Pro Gly Thr Ser Ile Pro
1               5                   10                  15

Pro Gln Phe Asn Tyr Ser Gln Pro Gly Thr Ser Thr Gly Gly Pro Leu
            20                  25                  30

Tyr Gly Gly Lys Pro Ser His Gly Leu Glu Asp Ile Pro Asp Val Glu
        35                  40                  45

Glu Tyr Glu Arg Asn Leu Leu Gly Ala Gly Ala Gly Phe Asn Leu Leu
    50                  55                  60

Asn Val Gly Asn Met Ala Asn Val Pro Asp Glu His Thr Pro Met Met
65                  70                  75                  80

Ser Pro Val Asn Thr Thr Thr Lys Ile Leu Gln Arg Ser Gly Ile Lys
                85                  90                  95

Met Glu Ile Pro Pro Tyr Leu Asp Pro Asp Ser Gln Asp Asp Asp Pro
            100                 105                 110

Glu Asp Gly Val Asn Tyr Pro Asp Pro Asp Leu Phe Asp Thr Lys Asn
        115                 120                 125

Thr Asn Met Thr Glu Tyr Asp Leu Asp Val Leu Lys Leu Gly Lys Pro
130                 135                 140

Ala Val Asp Glu Ala Arg Lys Lys Ile Glu Val Pro Asp Ala Ser Ala
145                 150                 155                 160

Pro Pro Asn Lys Ile Val Glu Tyr Leu Met Tyr Tyr Arg Thr Leu Lys
                165                 170                 175

Glu Ser Glu Leu Ile Gln Leu Asn Ala Tyr Arg Thr Lys Arg Asn Arg
            180                 185                 190

Leu Ser Leu Asn Leu Val Lys Asn Asn Ile Asp Arg Glu Phe Asp Gln
        195                 200                 205

Lys Ala Cys Glu Ser Leu Val Lys Lys Leu Lys Asp Lys Lys Asn Asp
    210                 215                 220

Leu Gln Asn Leu Ile Asp Val Val Leu Ser Lys Gly Thr Lys Tyr Thr
225                 230                 235                 240

Gly Cys Ile Thr Ile Pro Arg Thr Leu Asp Gly Arg Leu Gln Val His
                245                 250                 255

Gly Arg Lys Gly Phe Pro His Val Val Tyr Gly Lys Leu Trp Arg Phe
            260                 265                 270

Asn Glu Met Thr Lys Asn Glu Thr Arg His Val Asp His Cys Lys His
        275                 280                 285

Ala Phe Glu Met Lys Ser Asp Met Val Cys Val Asn Pro Tyr His Tyr
    290                 295                 300

Glu Ile Val Ile Gly Thr Met Ile Val Gly Gln Arg Asp His Asp Asn
305                 310                 315                 320

Arg Asp Met Pro Pro His Gln Arg Tyr His Thr Pro Gly Arg Gln
                325                 330                 335

Asp Pro Val Asp Asp Met Ser Arg Phe Ile Pro Pro Ala Ser Ile Arg
            340                 345                 350

Pro Pro Pro Met Asn Met His Thr Arg Pro Gln Pro Met Pro Gln Gln
        355                 360                 365

Leu Pro Ser Val Gly Ala Thr Phe Ala His Pro Leu Pro His Gln Ala
    370                 375                 380
```

```
Pro His Asn Pro Gly Val Ser His Pro Tyr Ser Ile Ala Pro Gln Thr
385                 390                 395                 400

His Tyr Pro Leu Asn Met Asn Pro Ile Pro Gln Met Pro Gln Met Pro
                405                 410                 415

Gln Met Pro Pro Pro Leu His Gln Gly Tyr Gly Met Asn Gly Pro Ser
            420                 425                 430

Cys Ser Ser Glu Asn Asn Asn Pro Phe His Gln Asn His His Tyr Asn
            435                 440                 445

Asp Ile Ser His Pro Asn His Tyr Ser Tyr Asp Cys Gly Pro Asn Leu
        450                 455                 460

Tyr Gly Phe Pro Thr Pro Tyr Pro Asp Phe His His Pro Phe Asn Gln
465                 470                 475                 480

Gln Pro His Gln Pro Pro Gln Leu Ser Gln Asn His Thr Ser Gln Gln
                485                 490                 495

Gly Ser His Gln Pro Gly His Gln Gly Gln Val Pro Asn Asp Pro Pro
            500                 505                 510

Ile Ser Arg Pro Val Leu Gln Pro Ser Thr Val Thr Leu Asp Val Phe
        515                 520                 525

Arg Arg Tyr Cys Arg Gln Thr Phe Gly Asn Arg Phe Phe Glu Gly Glu
530                 535                 540

Ser Glu Gln Ser Gly Ala Ile Ile Arg Ser Ser Asn Lys Phe Ile Glu
545                 550                 555                 560

Glu Phe Asp Ser Pro Ile Cys Gly Val Thr Val Arg Pro Arg Met
                565                 570                 575

Thr Asp Gly Glu Val Leu Glu Asn Ile Met Pro Glu Asp Ala Pro Tyr
            580                 585                 590

His Asp Ile Cys Lys Phe Ile Leu Arg Leu Thr Ser Glu Ser Val Thr
            595                 600                 605

Phe Ser Gly Glu Gly Pro Glu Val Ser Asp Leu Asn Glu Lys Trp Gly
        610                 615                 620

Thr Ile Val Tyr Tyr Glu Lys Asn Leu Gln Ile Gly Glu Lys Lys Cys
625                 630                 635                 640

Ser Arg Gly Asn Phe His Val Asp Gly Gly Phe Ile Cys Ser Glu Asn
                645                 650                 655

Arg Tyr Ser Leu Gly Leu Glu Pro Asn Pro Ile Arg Glu Pro Val Ala
            660                 665                 670

Phe Lys Val Arg Lys Ala Ile Val Asp Gly Ile Arg Phe Ser Tyr Lys
        675                 680                 685

Lys Asp Gly Ser Val Trp Leu Gln Asn Arg Met Lys Tyr Pro Val Phe
690                 695                 700

Val Thr Ser Gly Tyr Leu Asp Glu Gln Ser Gly Gly Leu Lys Lys Asp
705                 710                 715                 720

Lys Val His Lys Val Tyr Gly Cys Ala Ser Ile Lys Thr Phe Gly Phe
                725                 730                 735

Asn Val Ser Lys Gln Ile Ile Arg Asp Ala Leu Leu Ser Lys Gln Met
            740                 745                 750

Ala Thr Met Tyr Leu Gln Gly Lys Leu Thr Pro Met Asn Tyr Ile Tyr
        755                 760                 765

Glu Lys Lys Thr Gln Glu Leu Arg Arg Glu Ala Thr Arg Thr Thr
770                 775                 780

Asp Ser Leu Ala Lys Tyr Cys Cys Val Arg Val Ser Phe Cys Lys Gly
785                 790                 795                 800
```

```
Phe Gly Glu Ala Tyr Pro Glu Arg Pro Ser Ile His Asp Cys Pro Val
            805                 810                 815

Trp Ile Glu Leu Lys Ile Asn Ile Ala Tyr Asp Phe Met Asp Ser Ile
            820                 825                 830

Cys Gln Tyr Ile Thr Asn Cys Phe Glu Pro Leu Gly Met Glu Asp Phe
            835                 840                 845

Ala Lys Leu Gly Ile Asn Val Ser Asp Asp
    850                 855

<210> SEQ ID NO 42
<211> LENGTH: 892
<212> TYPE: PRT
<213> ORGANISM: Caenorhabditis elegans

<400> SEQUENCE: 42

Met Gly Asp His His Asn Leu Thr Gly Leu Pro Gly Thr Ser Ile Pro
 1               5                  10                  15

Pro Gln Phe Asn Tyr Ser Gln Pro Gly Thr Ser Thr Gly Gly Pro Leu
            20                  25                  30

Tyr Gly Gly Lys Pro Ser His Gly Leu Glu Asp Ile Pro Asp Val Glu
        35                  40                  45

Glu Tyr Glu Arg Asn Leu Leu Gly Ala Gly Ala Gly Phe Asn Leu Leu
    50                  55                  60

Asn Val Gly Asn Met Ala Asn Glu Phe Lys Pro Ile Ile Thr Leu Asp
65                  70                  75                  80

Thr Lys Pro Pro Arg Asp Ala Asn Lys Ser Leu Ala Phe Asn Gly Gly
                85                  90                  95

Leu Lys Leu Ile Thr Pro Lys Thr Glu Val Pro Asp Glu His Thr Pro
            100                 105                 110

Met Met Ser Pro Val Asn Thr Thr Lys Ile Leu Gln Arg Ser Gly
        115                 120                 125

Ile Lys Met Glu Ile Pro Pro Tyr Leu Asp Pro Ser Gln Asp Asp
    130                 135                 140

Asp Pro Glu Asp Gly Val Asn Tyr Pro Asp Pro Asp Leu Phe Asp Thr
145                 150                 155                 160

Lys Asn Thr Asn Met Thr Glu Tyr Asp Leu Asp Val Leu Lys Leu Gly
                165                 170                 175

Lys Pro Ala Val Asp Glu Ala Arg Lys Lys Ile Glu Val Pro Asp Ala
            180                 185                 190

Ser Ala Pro Pro Asn Lys Ile Val Glu Tyr Leu Met Tyr Tyr Arg Thr
        195                 200                 205

Leu Lys Glu Ser Glu Leu Ile Gln Leu Asn Ala Tyr Arg Thr Lys Arg
    210                 215                 220

Asn Arg Leu Ser Leu Asn Leu Val Lys Asn Asn Ile Asp Arg Glu Phe
225                 230                 235                 240

Asp Gln Lys Ala Cys Glu Ser Leu Val Lys Leu Lys Asp Lys Lys
                245                 250                 255

Asn Asp Leu Gln Asn Leu Ile Asp Val Val Leu Ser Lys Gly Thr Lys
            260                 265                 270

Tyr Thr Gly Cys Ile Thr Ile Pro Arg Thr Leu Asp Gly Arg Leu Gln
        275                 280                 285

Val His Gly Arg Lys Gly Phe Pro His Val Val Tyr Gly Lys Leu Trp
    290                 295                 300

Arg Phe Asn Glu Met Thr Lys Asn Glu Thr Arg His Val Asp His Cys
305                 310                 315                 320
```

```
Lys His Ala Phe Glu Met Lys Ser Asp Met Val Cys Val Asn Pro Tyr
                325                 330                 335
His Tyr Glu Ile Val Ile Gly Thr Met Ile Val Gly Gln Arg Asp His
            340                 345                 350
Asp Asn Arg Asp Met Pro Pro His Gln Arg Tyr His Thr Pro Gly
        355                 360                 365
Arg Gln Asp Pro Val Asp Asp Met Ser Arg Phe Ile Pro Pro Ala Ser
    370                 375                 380
Ile Arg Pro Pro Met Asn Met His Thr Arg Pro Gln Pro Met Pro
385                 390                 395                 400
Gln Gln Leu Pro Ser Val Gly Ala Thr Phe Ala His Pro Leu Pro His
            405                 410                 415
Gln Ala Pro His Asn Pro Gly Val Ser His Pro Tyr Ser Ile Ala Pro
        420                 425                 430
Gln Thr His Tyr Pro Leu Asn Met Asn Pro Ile Pro Gln Met Pro Gln
    435                 440                 445
Met Pro Gln Met Pro Pro Leu His Gln Gly Tyr Gly Met Asn Gly
450                 455                 460
Pro Ser Cys Ser Ser Glu Asn Asn Asn Pro Phe His Gln Asn His His
465                 470                 475                 480
Tyr Asn Asp Ile Ser His Pro Asn His Tyr Ser Tyr Asp Cys Gly Pro
            485                 490                 495
Asn Leu Tyr Gly Phe Pro Thr Pro Tyr Pro Asp Phe His His Pro Phe
        500                 505                 510
Asn Gln Gln Pro His Gln Pro Pro Gln Leu Ser Gln Asn His Thr Ser
    515                 520                 525
Gln Gln Gly Ser His Gln Pro Gly His Gln Gly Gln Val Pro Asn Asp
    530                 535                 540
Pro Pro Ile Ser Arg Pro Val Leu Gln Pro Ser Thr Val Thr Leu Asp
545                 550                 555                 560
Val Phe Arg Arg Tyr Cys Arg Gln Thr Phe Gly Asn Arg Phe Glu
            565                 570                 575
Gly Glu Ser Glu Gln Ser Gly Ala Ile Ile Arg Ser Ser Asn Lys Phe
        580                 585                 590
Ile Glu Glu Phe Asp Ser Pro Ile Cys Gly Val Thr Val Val Arg Pro
    595                 600                 605
Arg Met Thr Asp Gly Glu Val Leu Glu Asn Ile Met Pro Glu Asp Ala
    610                 615                 620
Pro Tyr His Asp Ile Cys Lys Phe Ile Leu Arg Leu Thr Ser Glu Ser
625                 630                 635                 640
Val Thr Phe Ser Gly Glu Gly Pro Glu Val Ser Asp Leu Asn Glu Lys
            645                 650                 655
Trp Gly Thr Ile Val Tyr Tyr Glu Lys Asn Leu Gln Ile Gly Glu Lys
        660                 665                 670
Lys Cys Ser Arg Gly Asn Phe His Val Asp Gly Phe Ile Cys Ser
    675                 680                 685
Glu Asn Arg Tyr Ser Leu Gly Leu Glu Pro Asn Pro Ile Arg Glu Pro
    690                 695                 700
Val Ala Phe Lys Val Arg Lys Ala Ile Val Asp Gly Ile Arg Phe Ser
705                 710                 715                 720
Tyr Lys Lys Asp Gly Ser Val Trp Leu Gln Asn Arg Met Lys Tyr Pro
            725                 730                 735
```

-continued

```
Val Phe Val Thr Ser Gly Tyr Leu Asp Glu Gln Ser Gly Gly Leu Lys
        740                 745                 750
Lys Asp Lys Val His Lys Val Tyr Gly Cys Ala Ser Ile Lys Thr Phe
            755                 760                 765
Gly Phe Asn Val Ser Lys Gln Ile Ile Arg Asp Ala Leu Leu Ser Lys
        770                 775                 780
Gln Met Ala Thr Met Tyr Leu Gln Gly Lys Leu Thr Pro Met Asn Tyr
785                 790                 795                 800
Ile Tyr Glu Lys Lys Thr Gln Glu Glu Leu Arg Arg Glu Ala Thr Arg
                805                 810                 815
Thr Thr Asp Ser Leu Ala Lys Tyr Cys Cys Val Arg Val Ser Phe Cys
            820                 825                 830
Lys Gly Phe Gly Glu Ala Tyr Pro Glu Arg Pro Ser Ile His Asp Cys
        835                 840                 845
Pro Val Trp Ile Glu Leu Lys Ile Asn Ile Ala Tyr Asp Phe Met Asp
    850                 855                 860
Ser Ile Cys Gln Tyr Ile Thr Asn Cys Phe Glu Pro Leu Gly Met Glu
865                 870                 875                 880
Asp Phe Ala Lys Leu Gly Ile Asn Val Ser Asp Asp
            885                 890
```

<210> SEQ ID NO 43
<211> LENGTH: 3499
<212> TYPE: DNA
<213> ORGANISM: Caenorhabditis elegans

<400> SEQUENCE: 43

| | | | | | |
|---|---|---|---|---|---|
| tgatctttca | agccgaagca | atcaagacct | caaagccaat | caactctact | cacttttctt | 60 |
| cagaacctta | acttttttgtg | tcactttccc | caaaaaccgt | tcaagctgct | gccttcactc | 120 |
| tcatcccctc | ctcttactcc | ttctttctcg | tccgctacta | ctgtatcttc | tggacatcta | 180 |
| cctgtataca | caccagtggc | cagtcatctg | ccattacaat | ttcatcaatt | gacacttctt | 240 |
| caacaacaac | cgccgtcctc | attcactccc | gattcttcct | catcctcaac | atcgtcgtct | 300 |
| ttggctgaaa | ttcccgaaga | cgttatgatg | gagatgctgg | tagatcaggg | aactgatgca | 360 |
| tcgtcatccg | cctccacgtc | cacctcatct | gtttcgagat | tcggagcgga | cacgttcatg | 420 |
| aatacaccgg | atgatgtgat | gatgaatgat | gatatggaac | cgattcctcg | tgatcggtgc | 480 |
| aatacgtggc | caatgcgtag | gccgcaactc | gaaccaccac | tcaactcgag | tcccattatt | 540 |
| catgaacaaa | ttcctgaaga | agatgctgac | ctatacggga | gcaatgagca | atgtggacag | 600 |
| ctcggcggag | catcttcaaa | cgggtcgaca | gcaatgcttc | atactccaga | tggaagcaat | 660 |
| tctcatcaga | atcgtttcct | tcggagtttc | agaatgtccg | aatcgccaga | cgataccgta | 720 |
| tcgggaaaaa | agacaacgac | cagacggaac | gcttggggaa | atatgtcata | tgctgaactt | 780 |
| atcactacag | ccattatggc | tagtccagag | aaacggttaa | ctcttgcaca | agtttacgaa | 840 |
| tggatggtcc | agaatgttcc | atacttcagg | gataagggag | attcgaacag | ttcagctgga | 900 |
| tggaagaact | cgatccgtca | caatctgtct | cttcattctc | gtttcatgcg | aattcagaat | 960 |
| gaaggagccg | gaaagagctc | gtggtgggtt | attaatccag | atgcaaagcc | aggaatgaat | 1020 |
| ccacggcgta | cacgtgaacg | atccaatact | attgagacga | ctacaaaggc | tcaactcgaa | 1080 |
| aaatctcgcc | gcggagccaa | gaagaggata | aaggagagag | cattgatggg | ctcccttcac | 1140 |
| tcgacactta | atgaaattc | gattgccgga | tcgattcaaa | cgattctca | cgatttgtat | 1200 |
| gatgatgatc | aatgcaagga | gcatttgata | acgttccatc | atctttccgt | ccccgaactc | 1260 |

```
aatcgaacct ctcgattcct ggatcgtcgt ctcgtgtttc tccagctatt ggaagtgata      1320
tctatgatga tctagaattc ccatcatggg ttggcgaatc ggttccagca attccaagtg      1380
atattgttga tagaactgat caaatgcgta tcgatgcaac tactcatagt tggtggagtt      1440
cagattaagc aggagtcgaa gccgattaag acggaaccaa ttgctccacc accatcatac      1500
cacgagttga acagtgtccg tggatcgtgt gctcagaatc cacttcttcg aaatccaatt      1560
gtgccaagca ctaacttcaa gccaatgcca ctaccgggtg cctatggaaa ctatcaaaat      1620
ggtggaataa ctccaatcaa ttggctatca acatccaact catctccact gcctggaatt      1680
caatcgtgtg gaattgtagc tgcacagcat actgtcgctt cttcatcggc tcttccaatt      1740
gatttggaaa atctgacact tcccgatcag ccactgatgg atactatgga tgttgatgca      1800
ttgatcagac atgagctgag tcaagctgga gggcagcata ttcattttga tttgtaaatt      1860
ctcttcattt tgtttcccct ggtgttgttc gaaagagaga tagcaaagca gcgaggagtg      1920
aggtaagcag caataaaaat tttggatttt tttttggttt ttccagaaat aatcgatttt      1980
ctggaaaatt tcaaaaaaaa atcgaatttt ttagttaatt atttgatgag aaaaaaaaat      2040
tagaaaacat aaggaaaaat gaaaagcgtt ttttttttc gaaaattta gaattctcct      2100
acatttccaa taagggcctt agaactgcaa acaaacaaaa attggaattt tcgaatcaaa      2160
aagttcccga ataaaagtag ttcgaatatt aaaaagcatt taatttcctc tttaaaaaaa      2220
ttgaataata gccgaaattt gcagattttt tttctgaaaa tcgaaaaacc aaaattttt      2280
gattttttaa atttttttt tactttccag atagtaaaat cattagcact gaaattatt      2340
tgaaaaaaaa cttcaaatac aaattttgtt ttcgaaaaaa aaaatttaaa tatatatttt      2400
cagaaatctt ccgtcttcat cttttcaaat ccctacctac acacactcaa cgatcatcac      2460
agccagacca tcaatattct tccaaatttt gacgtcgtta atttttttc agttttttca      2520
aaaactctat tttctatttt ctgtcgtttg ttccccttc tctcgtctaa ttccaacaca      2580
ttcatcccag tgacgtcgtg taataataat ataaaatacc tcttctctct ttcttcccct      2640
aatgcgaaat atcgaaaaac cgttgattat tacctctttt ttcttgtttt ttttttctct      2700
ctctctctcc cgtcatccag gttcttcact ctttaaatgc tacctctatc ccatcttttt      2760
cgctgtaaat ttgtttcgca atcaaaactg ctaaaacaca ttccccaatc tgtcttttt      2820
aattgaattt ttcaaaaaat ttgatttctt gatttctctt gtaattcttt aattttcctc      2880
tttttttcc ccctggtagc aaatgtctag cgattctctt tcttttttg tttaactttc      2940
acatctggcc gattcgaatc ctccgtatac acacacacat agtaatctac ctccaaaatt      3000
ttactgaaag atgtgatccc ctctctgtct ccctctacaa aacattattt gtctgtttgt      3060
gtatattgcc accacgtcga ttttaaatta aaaccatcgt ttttcttct tttctacttt      3120
tttctcgaaa aatttaacaa cacacaaaaa aatccttcaa aaaatctcag ttttaaatgg      3180
tgtggcaata tatcggatcc ccctctacac cagaacagtc ttgcaatttc agagaatgat      3240
tttcagattt ttcatatcac aggcccccctt ttttgcttg ttttttttctc tacctctctt      3300
tcttttcatt ctatttctct ctcttgtttt ctctctgtta tcctgtacat tttccttcca      3360
attctttctg gctatttctg attttcgagt tcatattctc tacgtctcac tttctctcgc      3420
gccacgcccc cttttcgtc tccctccgcc cccaaatata tttgcgactg tatgatgatg      3480
atgatgattt aataaaaat                                                  3499
```

<210> SEQ ID NO 44

<211> LENGTH: 2704
<212> TYPE: DNA
<213> ORGANISM: Caenorhabditis elegans

<400> SEQUENCE: 44

| | | | | | |
|---|---|---|---|---|---|
| ttacacgtgg | ccaatgcaac | aatacatcta | tcaggaatcg | tcagcaacca | ttccccatca | 60 |
| ccatttaaat | caacacaaca | atccgtatca | tccaatgcat | cctcatcatc | aattacctca | 120 |
| tatgcaacaa | cttcctcaac | ctctattgaa | tcttaacatg | acgacgttaa | catcttctgg | 180 |
| cagttccgtg | gccagttcca | ttggaggcgg | agctcaatgc | tctccgtgcg | cgtcgggctc | 240 |
| ctcgaccgct | gcaacaaatt | cctctcaaca | gcagcagacc | gttggtcaaa | tgcttgctgc | 300 |
| atcggtgcct | tgttcttcat | ctggcatgac | acttggaatg | tcacttaatc | tgtcacaagg | 360 |
| cggtggtcca | atgccggcaa | aaagaagcg | ttgtcgtaag | aagccaaccg | atcaattggc | 420 |
| acagaagaaa | ccgaatccat | ggggtgagga | atcctattcg | gatatcattg | ccaaagcatt | 480 |
| ggaatcggcg | ccagacggaa | ggcttaaact | caatgagatt | tatcaatggt | tctctgataa | 540 |
| tattccctac | tttggagaac | gatctagtcc | cgaggaggcc | gccggatgga | agaactcgat | 600 |
| ccgtcacaat | ctgtctcttc | attctcgttt | catgcgaatt | cagaatgaag | gagccggaaa | 660 |
| gagctcgtgg | tgggttatta | atccagatgc | aaagccagga | atgaatccac | ggcgtacacg | 720 |
| tgaacgatcc | aatactattg | agacgactac | aaaggctcaa | ctcgaaaaat | ctcgccgcgg | 780 |
| agccaagaag | aggataaagg | agagagcatt | gatgggctcc | cttcactcga | cacttaatgg | 840 |
| aaattcgatt | gccggatcga | ttcaaacgat | ttctcacgat | ttgtatgatg | atgattcaat | 900 |
| gcaaggagca | tttgataacg | ttccatcatc | tttccgtccc | cgaactcaat | cgaacctctc | 960 |
| gattcctgga | tcgtcgtctc | gtgtttctcc | agctattgga | agtgatatct | atgatgatct | 1020 |
| agaattccca | tcatgggttg | gcgaatcggt | tccagcaatt | ccaagtgata | ttgttgatag | 1080 |
| aactgatcaa | atgcgtatcg | atgcaactac | tcatattggt | ggagttcaga | ttaagcagga | 1140 |
| gtcgaagccg | attaagacgg | aaccaattgc | tccaccacca | tcataccacg | agttgaacag | 1200 |
| tgtccgtgga | tcgtgtgctc | agaatccact | tcttcgaaat | ccaattgtgc | caagcactaa | 1260 |
| cttcaagcca | atgccactac | cgggtgccta | tggaaactat | caaaatggtg | gaataactcc | 1320 |
| aatcaattgg | ctatcaacat | ccaactcatc | tccactgcct | ggaattcaat | cgtgtggaat | 1380 |
| tgtagctgca | cagcatactg | tcgcttcttc | atcggctctt | ccaattgatt | tggaaaatct | 1440 |
| gacacttccc | gatcagccac | tgatggatac | tatggatgtt | gatgcattga | tcagacatga | 1500 |
| gctgagtcaa | gctggagggc | agcatattca | ttttgatttg | taaattctct | tcattttgtt | 1560 |
| tccctggtg | ttgttcgaaa | gagagatagc | aaagcagcga | ggagtgagaa | atcttccgtc | 1620 |
| ttcatctttt | caaatcccta | cctacacaca | ctcaacgatc | atcacagcca | gaccatcaat | 1680 |
| attcttccaa | attttgacgt | cgttaatttt | ttttcagttt | tttcaaaaac | tctatttttct | 1740 |
| atttttctgtc | gtttgttccc | ctttctctcg | tctaattcca | acacattcat | cccagtgacg | 1800 |
| tcgtgtaata | ataatataaa | atacctcttc | tctctttctt | ccctaatgc | gaaatatcga | 1860 |
| aaaaccgttg | attattacct | cttttttctt | gttttttttt | tctctctctc | tctcccgtca | 1920 |
| tccaggttct | tcactctttta | aatgctacct | ctatcccatc | tttttcgctg | taaatttgtt | 1980 |
| tcgcaatcaa | aactgctaaa | acacattccc | caatctgtct | tttttaattg | aatttttcaa | 2040 |
| aaaatttgat | tcttgatttt | ctcttgtaat | tcttttaattt | tcctctttttt | tttcccccctg | 2100 |
| gtagcaaatg | tctagcgatt | ctctttctttt | ttttgtttaa | ctttcacatc | tggccgattc | 2160 |
| gaatcctccg | tatacacaca | cacatagtaa | tctacctcca | aaattttact | gaaagatgtg | 2220 |

-continued

```
atcccctctc tgtctccctc tacaaaacat tatttgtctg tttgtgtata ttgccaccac     2280
gtcgatttta aattaaaacc atcgtttttt cttcttttct acttttttct cgaaaaattt     2340
aacaacacac aaaaaaatcc ttcaaaaaat ctcagtttta aatggtgtgg caatatatcg     2400 gatcccctc tacaccagaa cagtcttgca atttcagaga atgattttca gattttcat      2460 atcacaggcc cccttttttt gcttgttttt ttctctacct ctctttcttt tcattctatt    2520
tctctctctt gttttctctc tgttatcctg tacattttcc ttccaattct ttctggctat   2580
ttctgatttt cgagttcata ttctctacgt ctcactttct ctcgcgccac gccccctttt  2640
tcgtctccct ccgcccccaa atatatttgc gactgtatga tgatgatgat gatttaataa 2700
aaat                                                                 2704
```

<210> SEQ ID NO 45
<211> LENGTH: 510
<212> TYPE: PRT
<213> ORGANISM: Caenorhabditis elegans

<400> SEQUENCE: 45

```
Met Met Glu Met Leu Val Asp Gln Gly Thr Asp Ala Ser Ser Ser Ala
 1               5                  10                  15

Ser Thr Ser Thr Ser Ser Val Ser Arg Phe Gly Ala Asp Thr Phe Met
             20                  25                  30

Asn Thr Pro Asp Asp Val Met Met Asn Asp Asp Met Glu Pro Ile Pro
         35                  40                  45

Arg Asp Arg Cys Asn Thr Trp Pro Met Arg Arg Pro Gln Leu Glu Pro
     50                  55                  60

Pro Leu Asn Ser Ser Pro Ile Ile His Glu Gln Ile Pro Glu Glu Asp
 65                  70                  75                  80

Ala Asp Leu Tyr Gly Ser Asn Glu Gln Cys Gly Gln Leu Gly Gly Ala
                 85                  90                  95

Ser Ser Asn Gly Ser Thr Ala Met Leu His Thr Pro Asp Gly Ser Asn
            100                 105                 110

Ser His Gln Thr Ser Phe Pro Ser Asp Phe Arg Met Ser Glu Ser Pro
        115                 120                 125

Asp Asp Thr Val Ser Gly Lys Lys Thr Thr Thr Arg Arg Asn Ala Trp
    130                 135                 140

Gly Asn Met Ser Tyr Ala Glu Leu Ile Thr Thr Ala Ile Met Ala Ser
145                 150                 155                 160

Pro Glu Lys Arg Leu Thr Leu Ala Gln Val Tyr Glu Trp Met Val Gln
                165                 170                 175

Asn Val Pro Tyr Phe Arg Asp Lys Gly Asp Ser Asn Ser Ser Ala Gly
            180                 185                 190

Trp Lys Asn Ser Ile Arg His Asn Leu Ser Leu His Ser Arg Phe Met
        195                 200                 205

Arg Ile Gln Asn Glu Gly Ala Gly Lys Ser Ser Trp Trp Val Ile Asn
    210                 215                 220

Pro Asp Ala Lys Pro Gly Met Asn Pro Arg Thr Arg Glu Arg Ser
225                 230                 235                 240

Asn Thr Ile Glu Thr Thr Thr Lys Ala Gln Leu Glu Lys Ser Arg Arg
                245                 250                 255

Gly Ala Lys Lys Arg Ile Lys Glu Arg Ala Leu Met Gly Ser Leu His
            260                 265                 270

Ser Thr Leu Asn Gly Asn Ser Ile Ala Gly Ser Ile Gln Thr Ile Ser
```

```
                275                 280                 285
His Asp Leu Tyr Asp Asp Asp Ser Met Gln Gly Ala Phe Asp Asn Val
        290                 295                 300
Pro Ser Ser Phe Arg Pro Arg Thr Gln Ser Asn Leu Ser Ile Pro Gly
305                 310                 315                 320
Ser Ser Ser Arg Val Ser Pro Ala Ile Gly Ser Asp Ile Tyr Asp Asp
                325                 330                 335
Leu Glu Phe Pro Ser Trp Val Gly Glu Ser Val Pro Ala Ile Pro Ser
                340                 345                 350
Asp Ile Val Asp Arg Thr Asp Gln Met Arg Ile Asp Ala Thr Thr His
                355                 360                 365
Ile Gly Gly Val Gln Ile Lys Gln Glu Ser Lys Pro Ile Lys Thr Glu
        370                 375                 380
Pro Ile Ala Pro Pro Ser Tyr His Glu Leu Asn Ser Val Arg Gly
385                 390                 395                 400
Ser Cys Ala Gln Asn Pro Leu Leu Arg Asn Pro Ile Val Pro Ser Thr
                405                 410                 415
Asn Phe Lys Pro Met Pro Leu Pro Gly Ala Tyr Gly Asn Tyr Gln Asn
        420                 425                 430
Gly Gly Ile Thr Pro Ile Asn Trp Leu Ser Thr Ser Asn Ser Ser Pro
        435                 440                 445
Leu Pro Gly Ile Gln Ser Cys Gly Ile Val Ala Ala Gln His Thr Val
    450                 455                 460
Ala Ser Ser Ser Ala Leu Pro Ile Asp Leu Glu Asn Leu Thr Leu Pro
465                 470                 475                 480
Asp Gln Pro Leu Met Asp Thr Met Asp Val Asp Ala Leu Ile Arg His
                485                 490                 495
Glu Leu Ser Gln Ala Gly Gly Gln His Ile His Phe Asp Leu
                500                 505                 510

<210> SEQ ID NO 46
<211> LENGTH: 509
<212> TYPE: PRT
<213> ORGANISM: Caenorhabditis elegans

<400> SEQUENCE: 46

Met Gln Gln Tyr Ile Tyr Gln Glu Ser Ser Ala Thr Ile Pro His His
1               5                   10                  15
His Leu Asn Gln His Asn Asn Pro Tyr His Pro Met His Pro His His
            20                  25                  30
Gln Leu Pro His Met Gln Gln Leu Pro Gln Pro Leu Leu Asn Leu Asn
        35                  40                  45
Met Thr Thr Leu Thr Ser Ser Gly Ser Ser Val Ala Ser Ser Ile Gly
 50                 55                  60
Gly Gly Ala Gln Cys Ser Pro Cys Ala Ser Gly Ser Ser Thr Ala Ala
65                  70                  75                  80
Thr Asn Ser Ser Gln Gln Gln Thr Val Gly Gln Met Leu Ala Ala
            85                  90                  95
Ser Val Pro Cys Ser Ser Ser Gly Met Thr Leu Gly Met Ser Leu Asn
                100                 105                 110
Leu Ser Gln Gly Gly Gly Pro Met Pro Ala Lys Lys Arg Cys Arg
            115                 120                 125
Lys Lys Pro Thr Asp Gln Leu Ala Gln Lys Lys Pro Asn Pro Trp Gly
    130                 135                 140
```

```
Glu Glu Ser Tyr Ser Asp Ile Ile Ala Lys Ala Leu Glu Ser Ala Pro
145                 150                 155                 160

Asp Gly Arg Leu Lys Leu Asn Glu Ile Tyr Gln Trp Phe Ser Asp Asn
            165                 170                 175

Ile Pro Tyr Phe Gly Glu Arg Ser Ser Pro Glu Glu Ala Ala Gly Trp
        180                 185                 190

Lys Asn Ser Ile Arg His Asn Leu Ser Leu His Ser Arg Phe Met Arg
    195                 200                 205

Ile Gln Asn Glu Gly Ala Gly Lys Ser Ser Trp Trp Val Ile Asn Pro
210                 215                 220

Asp Ala Lys Pro Gly Met Asn Pro Arg Arg Thr Arg Glu Arg Ser Asn
225             230                 235                 240

Thr Ile Glu Thr Thr Thr Lys Ala Gln Leu Glu Lys Ser Arg Arg Gly
                245                 250                 255

Ala Lys Lys Arg Ile Lys Glu Arg Ala Leu Met Gly Ser Leu His Ser
            260                 265                 270

Thr Leu Asn Gly Asn Ser Ile Ala Gly Ser Ile Gln Thr Ile Ser His
        275                 280                 285

Asp Leu Tyr Asp Asp Ser Met Gln Gly Ala Phe Asp Asn Val Pro
290                 295                 300

Ser Ser Phe Arg Pro Arg Thr Gln Ser Asn Leu Ser Ile Pro Gly Ser
305             310                 315                 320

Ser Ser Arg Val Ser Pro Ala Ile Gly Ser Asp Ile Tyr Asp Asp Leu
            325                 330                 335

Glu Phe Pro Ser Trp Val Gly Glu Ser Val Pro Ala Ile Pro Ser Asp
                340                 345                 350

Ile Val Asp Arg Thr Asp Gln Met Arg Ile Asp Ala Thr Thr His Ile
            355                 360                 365

Gly Gly Val Gln Ile Lys Gln Glu Ser Lys Pro Ile Lys Thr Glu Pro
370                 375                 380

Ile Ala Pro Pro Ser Tyr His Glu Leu Asn Ser Val Arg Gly Ser
385             390                 395                 400

Cys Ala Gln Asn Pro Leu Leu Arg Asn Pro Ile Val Pro Ser Thr Asn
            405                 410                 415

Phe Lys Pro Met Pro Leu Pro Gly Ala Tyr Gly Asn Tyr Gln Asn Gly
        420                 425                 430

Gly Ile Thr Pro Ile Asn Trp Leu Ser Thr Ser Asn Ser Pro Leu
            435                 440                 445

Pro Gly Ile Gln Ser Cys Gly Ile Val Ala Ala Gln His Thr Val Ala
    450                 455                 460

Ser Ser Ser Ala Leu Pro Ile Asp Leu Glu Asn Leu Thr Leu Pro Asp
465                 470                 475                 480

Gln Pro Leu Met Asp Thr Met Asp Val Asp Ala Leu Ile Arg His Glu
                485                 490                 495

Leu Ser Gln Ala Gly Gly Gln His Ile His Phe Asp Leu
            500                 505

<210> SEQ ID NO 47
<211> LENGTH: 3504
<212> TYPE: DNA
<213> ORGANISM: Caenorhabditis elegans

<400> SEQUENCE: 47
cggaagccat ggagctcgag atctgattgc tggacacgga cggaactccg acgtatctcg    60
```

-continued

| | |
|---|---|
| cagatgcatg ttaacatttt acatccacaa ctgcaaacga tggtcgagca gtggcaaatg | 120 |
| cgagaacgcc catcgctgga gaccgagaat ggcaaaggat cgctgctcct ggaaaatgaa | 180 |
| ggtgtcgcag atatcatcac tatgtgtcca ttcggagaag ttattagtgt agtatttccg | 240 |
| tggtttcttg caaatgtgcg aacatcgcta gaaatcaagc tatcagattt caaacatcaa | 300 |
| cttttcgaat tgattgctcc gatgaagtgg ggaacatatt ccgtaaagcc acaggattat | 360 |
| gtgttcagac agttgaataa tttcggcgaa attgaagtta tatttaacga cgatcaaccc | 420 |
| ctgtcgaaat tagagctcca cggcactttc ccaatgcttt ttctctacca acctgatgga | 480 |
| ataaacaggg ataaagaatt aatgagtgat ataagtcatt gtctaggata ctcactggat | 540 |
| aaactggaag agagcctcga tgaggaactc cgtcaatttc gtgcttctct ctgggctcgt | 600 |
| acgaagaaaa cgtgcttgac acgtggactt gagggtacca gtcactacgc gttccccgaa | 660 |
| gaacagtact tgtgtgttgg tgaatcgtgc ccgaaagatt tggaatcaaa agtcaaggct | 720 |
| gccaagctga gttatcagat gttttggaga aaacgtaaag cggaaatcaa tggagtttgc | 780 |
| gagaaaatga tgaagattca aattgaattc aatccgaacg aaactccgaa atctctgctt | 840 |
| cacacgtttc tctacgaaat gcgaaaattg gatgtatacg ataccgatga tcctgcagat | 900 |
| gaaggatggt ttcttcaatt ggctggacgt accacgtttg ttacaaatcc agatgtcaaa | 960 |
| cttacgtctt atgatggtgt ccgttcggaa ctggaaagct atcgatgccc tggattcgtt | 1020 |
| gttcgccgac aatcactagt cctcaaagac tattgtcgcc caaaccact ctacgaacca | 1080 |
| cattatgtga gagcacacga acgaaaactt gctctagacg tgctcagcgt gtctatagat | 1140 |
| agcacaccaa aacagagcaa gaacagtgac atggttatga ctgattttcg tccgacagct | 1200 |
| tcactcaaac aagtttcact ttgggacctt gacgcgaatc ttatgatacg gcctgtgaat | 1260 |
| atttctggat tcgatttccc ggccgacgtg gatatgtacg ttcgaatcga attcagtgta | 1320 |
| tatgtgggga cactgacgct ggcatcaaaa tctacaacaa aagtgaatgc tcaatttgca | 1380 |
| aaatggaata aggaaatgta cactttttgat ctatacatga aggatatgcc accatctgca | 1440 |
| gtactcagca ttcgtgtttt gtacggaaaa gtgaaattaa aagtgaaga attcgaagtt | 1500 |
| ggttgggtaa atatgtccct aaccgattgg agagatgaac tacgacaagg acaatttta | 1560 |
| ttccatctgt gggctcctga accgactgcc aatcgtagta ggatcggaga aaatggagca | 1620 |
| aggataggca ccaacgcagc ggttacaatt gaaatctcaa gttatggtgg tagagttcga | 1680 |
| atgccgagtc aaggacaata cacatatctc gtcaagcacc gaagtacttg gacggaaact | 1740 |
| ttgaatatta tgggtgatga ctatgagtcg tgtatcagag atccaggata taagaagctt | 1800 |
| cagatgcttg tcaagaagca tgaatctgga attgtattag aggaagatga acaacgtcat | 1860 |
| gtctggatgt ggaggagata cattcaaaag caggagcctg atttgctcat tgtgctctcc | 1920 |
| gaactcgcat ttgtgtggac tgatcgtgag aacttttccg agctctatgt gatgcttgaa | 1980 |
| aaatggaaac cgccgagtgt ggcagccgcg ttgactttgc ttggaaaacg ttgcacggat | 2040 |
| cgtgtgattc gaaagtttgc agtggagaag ttgaatgagc agctgagccc ggtcacattc | 2100 |
| catcttttca tattgcctct catacaggcg ttgaagtacg aaccgcgtgc tcaatcggaa | 2160 |
| gttggaatga tgctcttgac tagagctctc tgcgattatc gaattggaca tcgacttttc | 2220 |
| tggctgctcc gtgcagagat tgctcgtttg agagattgtg atctgaaaag tgaagaatat | 2280 |
| cgccgtatct cacttctgat ggaagcttac ctccgtggaa atgaagagca catcaagatc | 2340 |
| atcacccgac aagttgacat ggttgatgag ctcacacgaa tcagcactct tgtcaaagga | 2400 |
| atgccaaaag atgttgctac gatgaaactg cgtgacgagc ttcgatcgat tagtcataaa | 2460 |

-continued

```
atggaaaata tggattctcc actggatcct gtgtacaaac tgggtgaaat gataatcgac    2520
aaagccatcg tcctaggaag tgcaaaacgt ccgttaatgc ttcactggaa gaacaaaaat    2580
ccaaagagtg acctgcacct tccgttctgt gcaatgatct tcaagaatgg agacgatctt    2640
cgccaggaca tgcttgttct tcaagttctc gaagttatgg ataacatctg gaaggctgca    2700
aacattgatt gctgtttgaa cccgtacgca gttcttccaa tgggagaaat gattggaatt    2760
attgaagttg tgcctaattg taaaacaata ttcgagattc aagttggaac aggattcatg    2820
aatacagcag ttcggagtat tgatccttcg tttatgaata agtggattcg gaaacaatgc    2880
ggaattgaag atgaaagaa gaaagcaaa aaggactcta cgaaaatcc catcgaaaag     2940 aagattgata atactcaagc catgaagaaa tattttgaaa gtgtcgatcg attcctatac    3000
tcgtgtgttg gatattcagt tgccacgtac ataatgggaa tcaaggatcg tcacagtgat    3060
aatctgatgc tcactgaaga tggaaaatat gtccacattg atttcggtca cattttggga    3120
cacggaaaga ccaaacttgg gatccagcga gatcgtcaac cgtttattct aaccgaacac    3180
tttatgacag tgattcgatc gggtaaatct gtggatggaa attcgcatga gctacaaaaa    3240
ttcaaaacgt tatgcgtcga agcctacgaa gtaatgtgga ataatcgaga tttgttcgtt    3300
tccttgttca ccttgatgct cggaatggag ttgcctgagc tgtcgacgaa agcggatttg    3360
gatcatttga agaaaaccct cttctgcaat ggagaaagca aagaagaagc gagaaagttt    3420
ttcgctggaa tctacgaaga agccttcaat ggatcatggt ctaccaaaac gaattggctc    3480
ttccacgcag tcaaacacta ctga    3504
```

<210> SEQ ID NO 48
<211> LENGTH: 1167
<212> TYPE: PRT
<213> ORGANISM: Caenorhabditis elegans

<400> SEQUENCE: 48

```
Arg Lys Pro Trp Ser Ser Arg Ser Asp Cys Trp Thr Arg Thr Glu Leu
  1               5                  10                  15

Arg Arg Ile Ser Gln Met His Val Asn Ile Leu His Pro Gln Leu Gln
             20                  25                  30

Thr Met Val Glu Gln Trp Gln Met Arg Glu Arg Pro Ser Leu Glu Thr
         35                  40                  45

Glu Asn Gly Lys Gly Ser Leu Leu Glu Asn Glu Gly Val Ala Asp
     50                  55                  60

Ile Ile Thr Met Cys Pro Phe Gly Glu Val Ile Ser Val Val Phe Pro
 65                  70                  75                  80

Trp Phe Leu Ala Asn Val Arg Thr Ser Leu Glu Ile Lys Leu Ser Asp
                 85                  90                  95

Phe Lys His Gln Leu Phe Glu Leu Ile Ala Pro Met Lys Trp Gly Thr
            100                 105                 110

Tyr Ser Val Lys Pro Gln Asp Tyr Val Phe Arg Gln Leu Asn Asn Phe
        115                 120                 125

Gly Glu Ile Glu Val Ile Phe Asn Asp Asp Gln Pro Leu Ser Lys Leu
    130                 135                 140

Glu Leu His Gly Thr Phe Pro Met Leu Phe Leu Tyr Gln Pro Asp Gly
145                 150                 155                 160

Ile Asn Arg Asp Lys Glu Leu Met Ser Asp Ile Ser His Cys Leu Gly
                165                 170                 175

Tyr Ser Leu Asp Lys Leu Glu Glu Ser Leu Asp Glu Glu Leu Arg Gln
```

```
                    180                 185                 190
Phe Arg Ala Ser Leu Trp Ala Arg Thr Lys Lys Thr Cys Leu Thr Arg
            195                 200                 205
Gly Leu Glu Gly Thr Ser His Tyr Ala Phe Pro Glu Glu Gln Tyr Leu
            210                 215                 220
Cys Val Gly Glu Ser Cys Pro Lys Asp Leu Glu Ser Lys Val Lys Ala
225                 230                 235                 240
Ala Lys Leu Ser Tyr Gln Met Phe Trp Arg Lys Arg Ala Glu Ile
                245                 250                 255
Asn Gly Val Cys Glu Lys Met Met Lys Ile Gln Ile Glu Phe Asn Pro
            260                 265                 270
Asn Glu Thr Pro Lys Ser Leu Leu His Thr Phe Leu Tyr Glu Met Arg
            275                 280                 285
Lys Leu Asp Val Tyr Asp Thr Asp Pro Ala Asp Glu Gly Trp Phe
290                 295                 300
Leu Gln Leu Ala Gly Arg Thr Thr Phe Val Thr Asn Pro Asp Val Lys
305                 310                 315                 320
Leu Thr Ser Tyr Asp Gly Val Arg Ser Glu Leu Glu Ser Tyr Arg Cys
                325                 330                 335
Pro Gly Phe Val Val Arg Arg Gln Ser Leu Val Leu Lys Asp Tyr Cys
            340                 345                 350
Arg Pro Lys Pro Leu Tyr Glu Pro His Tyr Val Arg Ala His Glu Arg
            355                 360                 365
Lys Leu Ala Leu Asp Val Leu Ser Val Ser Ile Asp Ser Thr Pro Lys
            370                 375                 380
Gln Ser Lys Asn Ser Asp Met Val Met Thr Asp Phe Arg Pro Thr Ala
385                 390                 395                 400
Ser Leu Lys Gln Val Ser Leu Trp Asp Leu Asp Ala Asn Leu Met Ile
                405                 410                 415
Arg Pro Val Asn Ile Ser Gly Phe Asp Phe Pro Ala Asp Val Asp Met
            420                 425                 430
Tyr Val Arg Ile Glu Phe Ser Val Tyr Val Gly Thr Leu Thr Leu Ala
            435                 440                 445
Ser Lys Ser Thr Thr Lys Val Asn Ala Gln Phe Ala Lys Trp Asn Lys
450                 455                 460
Glu Met Tyr Thr Phe Asp Leu Tyr Met Lys Asp Met Pro Pro Ser Ala
465                 470                 475                 480
Val Leu Ser Ile Arg Val Leu Tyr Gly Lys Val Lys Leu Lys Ser Glu
                485                 490                 495
Glu Phe Glu Val Gly Trp Val Asn Met Ser Leu Thr Asp Trp Arg Asp
            500                 505                 510
Glu Leu Arg Gln Gly Gln Phe Leu Phe His Leu Trp Ala Pro Glu Pro
            515                 520                 525
Thr Ala Asn Arg Ser Arg Ile Gly Glu Asn Gly Ala Arg Ile Gly Thr
            530                 535                 540
Asn Ala Ala Val Thr Ile Glu Ile Ser Ser Tyr Gly Gly Arg Val Arg
545                 550                 555                 560
Met Pro Ser Gln Gly Gln Tyr Thr Tyr Leu Val Lys His Arg Ser Thr
                565                 570                 575
Trp Thr Glu Thr Leu Asn Ile Met Gly Asp Asp Tyr Glu Ser Cys Ile
            580                 585                 590
Arg Asp Pro Gly Tyr Lys Lys Leu Gln Met Leu Val Lys Lys His Glu
            595                 600                 605
```

```
Ser Gly Ile Val Leu Glu Glu Asp Glu Gln Arg His Val Trp Met Trp
    610                 615                 620
Arg Arg Tyr Ile Gln Lys Gln Glu Pro Asp Leu Leu Ile Val Leu Ser
625                 630                 635                 640
Glu Leu Ala Phe Val Trp Thr Asp Arg Glu Asn Phe Ser Glu Leu Tyr
                645                 650                 655
Val Met Leu Glu Lys Trp Lys Pro Pro Ser Val Ala Ala Ala Leu Thr
                660                 665                 670
Leu Leu Gly Lys Arg Cys Thr Asp Arg Val Ile Arg Lys Phe Ala Val
            675                 680                 685
Glu Lys Leu Asn Glu Gln Leu Ser Pro Val Thr Phe His Leu Phe Ile
690                 695                 700
Leu Pro Leu Ile Gln Ala Leu Lys Tyr Glu Pro Arg Ala Gln Ser Glu
705                 710                 715                 720
Val Gly Met Met Leu Leu Thr Arg Ala Leu Cys Asp Tyr Arg Ile Gly
                725                 730                 735
His Arg Leu Phe Trp Leu Leu Arg Ala Glu Ile Ala Arg Leu Arg Asp
                740                 745                 750
Cys Asp Leu Lys Ser Glu Glu Tyr Arg Arg Ile Ser Leu Leu Met Glu
            755                 760                 765
Ala Tyr Leu Arg Gly Asn Glu Glu His Ile Lys Ile Ile Thr Arg Gln
            770                 775                 780
Val Asp Met Val Asp Glu Leu Thr Arg Ile Ser Thr Leu Val Lys Gly
785                 790                 795                 800
Met Pro Lys Asp Val Ala Thr Met Lys Leu Arg Asp Glu Leu Arg Ser
                805                 810                 815
Ile Ser His Lys Met Glu Asn Met Asp Ser Pro Leu Asp Pro Val Tyr
                820                 825                 830
Lys Leu Gly Glu Met Ile Ile Asp Lys Ala Ile Val Leu Gly Ser Ala
            835                 840                 845
Lys Arg Pro Leu Met Leu His Trp Lys Asn Lys Asn Pro Lys Ser Asp
850                 855                 860
Leu His Leu Pro Phe Cys Ala Met Ile Phe Lys Asn Gly Asp Asp Leu
865                 870                 875                 880
Arg Gln Asp Met Leu Val Leu Gln Val Leu Glu Val Met Asp Asn Ile
                885                 890                 895
Trp Lys Ala Ala Asn Ile Asp Cys Cys Leu Asn Pro Tyr Ala Val Leu
                900                 905                 910
Pro Met Gly Glu Met Ile Gly Ile Ile Glu Val Val Pro Asn Cys Lys
            915                 920                 925
Thr Ile Phe Glu Ile Gln Val Gly Thr Gly Phe Met Asn Thr Ala Val
            930                 935                 940
Arg Ser Ile Asp Pro Ser Phe Met Asn Lys Trp Ile Arg Lys Gln Cys
945                 950                 955                 960
Gly Ile Glu Asp Glu Lys Lys Lys Ser Lys Lys Asp Ser Thr Lys Asn
                965                 970                 975
Pro Ile Glu Lys Lys Ile Asp Asn Thr Gln Ala Met Lys Lys Tyr Phe
            980                 985                 990
Glu Ser Val Asp Arg Phe Leu Tyr Ser Cys Val Gly Tyr Ser Val Ala
            995                 1000                1005
Thr Tyr Ile Met Gly Ile Lys Asp Arg His Ser Asp Asn Leu Met Leu
    1010                1015                1020
```

-continued

```
Thr Glu Asp Gly Lys Tyr Val His Ile Asp Phe Gly His Ile Leu Gly
1025                1030                1035                1040

His Gly Lys Thr Lys Leu Gly Ile Gln Arg Asp Arg Gln Pro Phe Ile
            1045                1050                1055

Leu Thr Glu His Phe Met Thr Val Ile Arg Ser Gly Lys Ser Val Asp
        1060                1065                1070

Gly Asn Ser His Glu Leu Gln Lys Phe Lys Thr Leu Cys Val Glu Ala
    1075                1080                1085

Tyr Glu Val Met Trp Asn Asn Arg Asp Leu Phe Val Ser Leu Phe Thr
1090                1095                1100

Leu Met Leu Gly Met Glu Leu Pro Glu Leu Ser Thr Lys Ala Asp Leu
1105                1110                1115                1120

Asp His Leu Lys Lys Thr Leu Phe Cys Asn Gly Glu Ser Lys Glu Glu
            1125                1130                1135

Ala Arg Lys Phe Phe Ala Gly Ile Tyr Glu Glu Ala Phe Asn Gly Ser
            1140                1145                1150

Trp Ser Thr Lys Thr Asn Trp Leu Phe His Ala Val Lys His Tyr
        1155                1160                1165
```

<210> SEQ ID NO 49
<211> LENGTH: 23
<212> TYPE: DNA
<213> ORGANISM: Artificial Sequence
<220> FEATURE:
<223> OTHER INFORMATION: Probe/primer derived from C. elegans

<400> SEQUENCE: 49
ggaaatattt taggccagat gcg                                             23

<210> SEQ ID NO 50
<211> LENGTH: 20
<212> TYPE: DNA
<213> ORGANISM: Artificial Sequence
<220> FEATURE:
<223> OTHER INFORMATION: Probe/primer derived from C. elegans

<400> SEQUENCE: 50
cggacagtcc tgaatacacc                                                 20

<210> SEQ ID NO 51
<211> LENGTH: 28
<212> TYPE: DNA
<213> ORGANISM: Artificial Sequence
<220> FEATURE:
<223> OTHER INFORMATION: Probe/primer derived from C. elegans

<400> SEQUENCE: 51
tctcgttgtt tgccgtcgga tgtctgcc                                        28

<210> SEQ ID NO 52
<211> LENGTH: 3017
<212> TYPE: DNA
<213> ORGANISM: Caenorhabditis elegans

<400> SEQUENCE: 52
gtaatcaaat tgtaaaggaa aaatattaat agtcagagta cacataaatg ggtgatcatc      60
ataatttaac gggccttccc ggtacctcca tcccgccaca gttcaactat tctcagcccg     120
gtaccagcac cggaggcccg ctttatggtg gaaaaccttc tcatggattg gaagatattc     180
ctgatgtaga ggaaatgtgag aggaacctgc tcggggctgg agcaggtttt aatctgctca     240

-continued

```
atgtaggaaa tatggctaat gttcccgacg agcacacacc gatgatgtca ccagtgaata      300
caactacaaa gattctacaa cggagtggta ttaaaatgga aatcccgcca tatttggatc      360
cagacagtca ggatgatgac ccggaagatg tgtcaacta cccggatcca gatttatttg      420
acacaaaaaa cacaaatatg accgagtacg atttggatgt gttgaagctt ggaaaaccag      480
cagtagatga agcacggaaa aagatcgaag ttcccgacgc tagtgcgccg ccaaacaaaa      540
ttgtagaata tttgatgtat tatagaacgt taaaagaaag tgaactcata caactgaatg      600
cgtatcggac aaaacgaaat cgattatcgt tgaacttggt caaaaacaat attgatcgag      660
agttcgacca aaaagcttgc gagtccctgg tgaaaaaatt gaaggataag aagaatgatc      720
tccagaacct gattgatgtg gttctttcaa aaggtacaaa atataccggt tgcattacaa      780
ttccaaggac acttgatggc cggttacagg tccacgaag aaaaggtttc cctcacgtag       840
tctatggcaa actgtggagg tttaatgaaa tgacaaaaaa cgaaacgcgt catgtggacc      900
actgcaagca cgcatttgaa atgaaaagtg acatggtatg cgtgaatccc tatcactacg      960
aaattgtcat tggaactatg attgttgggc agagggatca tgacaatcga gatatgccgc     1020
cgccacatca acgctaccac actccaggtc ggcaggatcc agttgacgat atgagtagat     1080
ttataccacc agcttccatt cgtccgcctc cgatgaacat gcacacaagg cctcagccta     1140
tgcctcaaca attgccttca gttggcgcaa cgtttgccca tcctctccca catcaggcgc     1200
cacataaccc aggggtttca catccgtact ccattgctcc acagacccat tacccgttga     1260
acatgaaccc aattccgcaa atgccgcaaa tgccacaaat gccaccacct ctccatcagg     1320
gatatggaat gaatgggccg agttgctctt cagaaaacaa caatccattc caccaaaatc     1380
accattataa tgatattagc catccaaatc actattccta cgactgtggt ccgaacttgt     1440
acgggtttcc aactccttat ccggattttc accatccttt caatcagcaa ccacaccagc     1500
cgccacaact atcacaaaac catacgtccc aacaaggcag tcatcaacca gggcaccaag     1560
gtcaggtacc gaatgatcca ccaatttcaa gaccagtgtt acaaccatca acagtcacct     1620
tggacgtgtt ccgtcggtac tgtagacaga catttggaaa tcgattttt gaaggagaaa     1680 gtgaacaatc cggcgcaata attcggtcta gtaacaaatt cattgaagaa tttgattcgc     1740
cgatttgtgg tgtgacagtt gttcgaccgc ggatgacaga cggtgaggtt ttggagaaca     1800
tcatgccgga agatgcacca tatcatgaca tttgcaagtt cattttgagg ctcacatcag     1860
aaagtgtaac tttctcagga gaggggccag aagttagtga tttgaacgaa aaatggggaa     1920
caattgtgta ctatgagaaa aatttgcaaa ttggcgagaa aaaatgttcg agaggaaatt     1980
tccacgtgga tggcggattc atttgctctg agaatcgtta cagtctcgga cttgagccaa     2040
atccaattag agaaccagtg gcgtttaaag ttcgtaaagc aatagtggat ggaattcgct     2100
tttcctacaa aaaagacggg agtgtttggc ttcaaaaccg catgaagtac ccggtatttg     2160
tcacttctgg gtatctcgac gagcaatcag gaggcctaaa aaggataaa gtgcacaaag     2220 tttacggatg tgcgtctatc aaaacgtttg gcttcaacgt ttccaaacaa atcatcagag     2280
acgcgcttct ttccaagcaa atggcaacaa tgtacttgca aggaaaattg actccgatga     2340
attatatcta cgagaagaag actcaggaag agctgcgaag ggaagcaaca cgcaccactg     2400
attcattggc caagtactgt tgtgtccgtg tctcgttctg caaaggatttt ggagaagcat     2460 acccagaacg cccgtcaatt catgattgtc cagtttggat tgagttgaaa atcaacattg     2520
cctacgattt catggattca atctgccagt acataaccaa ctgcttcgag ccgctaggaa     2580
tggaagattt tgcaaaattg ggaatcaacg tcagtgatga ctaaatgata actttttttca     2640
```

```
ctcaccctac tagatactga tttagtctta ttccaaatca tccaacgata tcaaacttttt      2700 tcctttgaac tttgcatact atgttatcac aagttccaag cagtttcaat acaaacatag      2760
gatatgttaa caacttttga taagaatcaa gttaccaact gttcattgtg agctttgagc      2820
tgtatagaag gacaatgtat cccataccct aatctttaat agtcatcagt cactggtccc      2880
gcaccaattt tttcgattcg catatgtcat atattgcacc gtggcccttt ttattgtaac      2940
ttttaatata ttttcttccc aacttgtgaa tatgattgat gaaccaccat tttgagtaat      3000
aaatgtattt tttgtgg                                                    3017

<210> SEQ ID NO 53
<211> LENGTH: 3119
<212> TYPE: DNA
<213> ORGANISM: Caenorhabditis elegans

<400> SEQUENCE: 53
gtaatcaaat tgtaaaggaa aaatattaat agtcagagta cacataaatg ggtgatcatc        60
ataatttaac gggccttccc ggtacctcca tcccgccaca gttcaactat tctcagcccg       120
gtaccagcac cggaggcccg ctttatggtg aaaaccttc tcatggattg aagatattc         180 ctgatgtaga ggaatatgag aggaacctgc tcggggctgg agcaggtttt aatctgctca       240
atgtaggaaa tatggctaat gaatttaaac caataatcac attggacacg aaaccacctc       300
gtgatgccaa caagtcattg gcattcaatg gcgggttgaa gctaatcact ccgaaaactg       360
aagttcccga cgagcacaca ccgatgatgt caccagtgaa tacaactaca aagattctac       420
aacggagtgg tattaaaatg gaaatcccgc catatttgga tccagacagt caggatgatg       480
acccggaaga tggtgtcaac tacccggatc cagatttatt tgacacaaaa aacacaaata       540
tgaccgagta cgatttggat gtgttgaagc ttggaaaacc agcagtagat gaagcacgga       600
aaaagatcga agttcccgac gctagtgcgc cgccaaacaa aattgtagaa tatttgatgt       660
attatagaac gttaaaagaa agtgaactca tacaactgaa tgcgtatcgg acaaaacgaa       720
atcgattatc gttgaacttg gtcaaaaaca atattgatcg agagttcgac caaaaagctt       780
gcgagtccct ggtgaaaaaa ttgaaggata agaagaatga tctccagaac ctgattgatg       840
tggttctttc aaaaggtaca aaatataccg gttgcattac aattccaagg acacttgatg       900
gccggttaca ggtccacgga agaaaaggtt tccctcacgt agtctatggc aaactgtgga       960
ggtttaatga aatgacaaaa aacgaaacgc gtcatgtgga ccactgcaag cacgcatttg      1020
aaatgaaaag tgacatggta tgcgtgaatc cctatcacta cgaaattgtc attggaacta      1080
tgattgttgg gcagagggat catgacaatc gagatatgcc gccgccacat caacgctacc      1140
acactccagg tcggcaggat ccagttgacg atatgagtag atttataccca ccagcttcca      1200 ttcgtccgcc tccgatgaac atgcacacaa ggcctcagcc tatgcctcaa caattgcctt      1260
cagttggcgc aacgtttgcc catcctctcc cacatcaggc gccacataac ccagggttt       1320 cacatccgta ctccattgct ccacagaccc attacccgtt gaacatgaac ccaattccgc      1380
aaatgccgca aatgccacaa atgccaccac ctctccatca gggatatgga atgaatgggc      1440
cgagttgctc ttcagaaaac aacaatccat tccaccaaaa tcaccattat aatgatatta      1500
gccatccaaa tcactattcc tacgactgtg gtccgaactt gtacgggttt ccaactcctt      1560
atccggattt tcaccatcct ttcaatcagc aaccacacca gccgccacaa ctatcacaaa      1620
accatacgtc ccaacaaggc agtcatcaac cagggcacca aggtcaggta ccgaatgatc      1680
```

-continued

```
caccaatttc aagaccagtg ttacaaccat caacagtcac cttggacgtg ttccgtcggt      1740
actgtagaca gacatttgga aatcgatttt ttgaaggaga aagtgaacaa tccggcgcaa      1800
taattcggtc tagtaacaaa ttcattgaag aatttgattc gccgatttgt ggtgtgacag      1860
ttgttcgacc gcggatgaca gacggtgagg ttttggagaa catcatgccg gaagatgcac      1920
catatcatga catttgcaag ttcattttga ggctcacatc agaaagtgta actttctcag      1980 gagagggcc  agaagttagt gatttgaacg aaaaatgggg aacaattgtg tactatgaga      2040
aaaatttgca aattggcgag aaaaaatgtt cgagaggaaa tttccacgtg gatggcggat      2100
tcatttgctc tgagaatcgt tacagtctcg gacttgagcc aaatccaatt agagaaccag      2160
tggcgtttaa agttcgtaaa gcaatagtgg atggaattcg cttttcctac aaaaaagacg      2220
ggagtgtttg gcttcaaaac cgcatgaagt acccggtatt tgtcacttct gggtatctcg      2280
acgagcaatc aggaggccta agaaggata  aagtgcacaa agtttacgga tgtgcgtcta      2340
tcaaaacgtt tggcttcaac gtttccaaac aaatcatcag agacgcgctt ctttccaagc      2400
aaatggcaac aatgtacttg caaggaaaat tgactccgat gaattatatc tacgagaaga      2460
agactcagga gagctgcga  agggaagcaa cacgcaccac tgattcattg gccaagtact      2520
gttgtgtccg tgtctcgttc tgcaaaggat ttggagaagc atacccagaa cgcccgtcaa      2580
ttcatgattg tccagtttgg attgagttga aaatcaacat tgcctacgat tcatggatt       2640 caatctgcca gtacataacc aactgcttcg agccgctagg aatggaagat tttgcaaaat      2700
tgggaatcaa cgtcagtgat gactaaatga taactttttt cactcaccct actagatact      2760
gatttagtct tattccaaat catccaacga tatcaaactt tttcctttga actttgcata      2820
ctatgttatc acaagttcca agcagtttca atacaaacat aggatatgtt aacaacttt       2880 gataagaatc aagttaccaa ctgttcattg tgagctttga gctgtataga aggacaatgt      2940
atcccatacc tcaatcttta atagtcatca gtcactggtc ccgcaccaat ttttcgatt       3000 cgcatatgtc atatattgca ccgtggccct ttttattgta actttttaata tattttcttc     3060 ccaacttgtg aatatgattg atgaaccacc attttgagta ataaatgtat ttttgtgg        3119
```

<210> SEQ ID NO 54
<211> LENGTH: 103
<212> TYPE: PRT
<213> ORGANISM: Caenorhabditis elegans

<400> SEQUENCE: 54

```
Lys Lys Thr Thr Thr Arg Arg Asn Ala Trp Gly Asn Met Ser Tyr Ala
  1               5                  10                  15

Glu Leu Ile Thr Thr Ala Ile Met Ala Ser Pro Glu Lys Arg Leu Thr
             20                  25                  30

Leu Ala Gln Val Tyr Glu Trp Met Val Gln Asn Val Pro Tyr Phe Arg
         35                  40                  45

Asp Lys Gly Asp Ser Asn Ser Ser Ala Gly Trp Lys Asn Ser Ile Arg
     50                  55                  60

His Asn Leu Ser Leu His Ser Arg Phe Met Arg Ile Gln Asn Glu Gly
 65                  70                  75                  80

Ala Gly Lys Ser Ser Trp Trp Val Ile Asn Pro Asp Ala Lys Pro Gly
                 85                  90                  95

Met Asn Pro Arg Arg Thr Arg
            100
```

<210> SEQ ID NO 55

```
<211> LENGTH: 41
<212> TYPE: PRT
<213> ORGANISM: Caenorhabditis elegans

<400> SEQUENCE: 55

Thr Phe Met Asn Thr Pro Asp Asp Val Met Met Asn Asp Asp Met Glu
 1               5                  10                  15

Pro Ile Pro Arg Asp Arg Cys Asn Thr Trp Pro Met Arg Arg Pro Gln
            20                  25                  30

Leu Glu Pro Pro Leu Asn Ser Ser Pro
        35                  40

<210> SEQ ID NO 56
<211> LENGTH: 109
<212> TYPE: PRT
<213> ORGANISM: Caenorhabditis elegans

<400> SEQUENCE: 56

Asp Asp Thr Val Ser Gly Lys Lys Thr Thr Arg Arg Asn Ala Trp
 1               5                  10                  15

Gly Asn Met Ser Tyr Ala Glu Leu Ile Thr Thr Ala Ile Met Ala Ser
            20                  25                  30

Pro Glu Lys Arg Leu Thr Leu Ala Gln Val Tyr Glu Trp Met Val Gln
        35                  40                  45

Asn Val Pro Tyr Phe Arg Asp Lys Gly Asp Ser Asn Ser Ser Ala Gly
    50                  55                  60

Trp Lys Asn Ser Ile Arg His Asn Leu Ser Leu His Ser Arg Phe Met
65                  70                  75                  80

Arg Ile Gln Asn Glu Gly Ala Gly Lys Ser Ser Trp Trp Val Ile Asn
                85                  90                  95

Pro Asp Ala Lys Pro Gly Met Asn Pro Arg Arg Thr Arg
            100                 105

<210> SEQ ID NO 57
<211> LENGTH: 655
<212> TYPE: PRT
<213> ORGANISM: Homo sapiens

<400> SEQUENCE: 57

Met Ala Glu Ala Pro Gln Val Val Glu Ile Asp Pro Asp Phe Glu Pro
 1               5                  10                  15

Leu Pro Arg Pro Arg Ser Cys Thr Trp Pro Leu Pro Arg Pro Glu Phe
            20                  25                  30

Ser Gln Ser Asn Ser Ala Thr Ser Ser Pro Ala Pro Ser Gly Ser Ala
        35                  40                  45

Ala Ala Asn Pro Asp Ala Ala Ala Gly Leu Pro Ser Ala Ser Ala Ala
    50                  55                  60

Ala Val Ser Ala Asp Phe Met Ser Asn Leu Ser Leu Leu Glu Glu Ser
65                  70                  75                  80

Glu Asp Phe Pro Gln Ala Pro Gly Ser Val Ala Ala Val Ala Ala
                85                  90                  95

Ala Ala Ala Ala Ala Thr Gly Gly Leu Cys Gly Asp Phe Gln Gly
            100                 105                 110

Pro Glu Ala Gly Cys Leu His Pro Ala Pro Pro Gln Pro Pro Pro
        115                 120                 125

Gly Pro Val Ser Gln His Pro Pro Val Pro Pro Ala Ala Ala Gly Pro
    130                 135                 140
```

-continued

```
Leu Ala Gly Gln Pro Arg Lys Ser Ser Ser Arg Asn Ala Trp
145                 150                 155                 160

Gly Asn Leu Ser Tyr Ala Asp Leu Ile Thr Lys Ala Ile Glu Ser Ser
            165                 170                 175

Ala Glu Lys Arg Leu Thr Leu Ser Gln Ile Tyr Glu Trp Met Val Lys
            180                 185                 190

Ser Val Pro Tyr Phe Lys Asp Lys Gly Asp Ser Asn Ser Ser Ala Gly
            195                 200                 205

Trp Lys Asn Ser Ile Arg His Asn Leu Ser Leu His Ser Lys Phe Ile
            210                 215                 220

Arg Val Gln Asn Glu Gly Thr Gly Lys Ser Ser Trp Trp Met Leu Asn
225                 230                 235                 240

Pro Glu Gly Gly Lys Ser Gly Lys Ser Pro Arg Arg Ala Ala Ser
                245                 250                 255

Met Asp Asn Asn Ser Lys Phe Ala Lys Ser Arg Ser Arg Ala Ala Lys
                260                 265                 270

Lys Lys Ala Ser Leu Gln Ser Gly Gln Glu Gly Ala Gly Asp Ser Pro
            275                 280                 285

Gly Ser Gln Phe Ser Lys Trp Pro Ala Ser Pro Gly Ser His Ser Asn
            290                 295                 300

Asp Asp Phe Asp Asn Trp Ser Thr Phe Arg Pro Arg Thr Ser Ser Asn
305                 310                 315                 320

Ala Ser Thr Ile Ser Gly Arg Leu Ser Pro Ile Met Thr Glu Gln Asp
                325                 330                 335

Asp Leu Gly Glu Gly Asp Val His Ser Met Val Tyr Pro Pro Ser Ala
            340                 345                 350

Ala Lys Met Ala Ser Thr Leu Pro Ser Leu Ser Glu Ile Ser Asn Pro
            355                 360                 365

Glu Asn Met Glu Asn Leu Leu Asp Asn Leu Asn Leu Leu Ser Ser Pro
            370                 375                 380

Thr Ser Leu Thr Val Ser Thr Gln Ser Ser Pro Gly Thr Met Met Gln
385                 390                 395                 400

Gln Thr Pro Cys Tyr Ser Phe Ala Pro Pro Asn Thr Ser Leu Asn Ser
                405                 410                 415

Pro Ser Pro Asn Tyr Gln Lys Tyr Thr Tyr Gly Gln Ser Ser Met Ser
                420                 425                 430

Pro Leu Pro Gln Met Pro Ile Gln Thr Leu Gln Asp Asn Lys Ser Ser
            435                 440                 445

Tyr Gly Gly Met Ser Gln Tyr Asn Cys Ala Pro Gly Leu Leu Lys Glu
            450                 455                 460

Leu Leu Thr Ser Asp Ser Pro Pro His Asn Asp Ile Met Thr Pro Val
465                 470                 475                 480

Asp Pro Gly Val Ala Gln Pro Asn Ser Arg Val Leu Gly Gln Asn Val
                485                 490                 495

Met Met Gly Pro Asn Ser Val Met Ser Thr Tyr Gly Ser Gln Ala Ser
                500                 505                 510

His Asn Lys Met Met Asn Pro Ser Ser His Thr His Pro Gly His Ala
            515                 520                 525

Gln Gln Thr Ser Ala Val Asn Gly Arg Pro Leu Pro His Thr Val Ser
            530                 535                 540

Thr Met Pro His Thr Ser Gly Met Asn Arg Leu Thr Gln Val Lys Thr
545                 550                 555                 560

Pro Val Gln Val Pro Leu Pro His Pro Met Gln Met Ser Ala Leu Gly
```

```
                    565                 570                 575
Gly Tyr Ser Ser Val Ser Ser Cys Asn Gly Tyr Gly Arg Met Gly Leu
            580                 585                 590

Leu His Gln Glu Lys Leu Pro Ser Asp Leu Asp Gly Met Phe Ile Glu
        595                 600                 605

Arg Leu Asp Cys Asp Met Glu Ser Ile Ile Arg Asn Asp Leu Met Asp
    610                 615                 620

Gly Asp Thr Leu Asp Phe Asn Phe Asp Asn Val Leu Pro Asn Gln Ser
625                 630                 635                 640

Phe Pro His Ser Val Lys Thr Thr Thr His Ser Trp Val Ser Gly
                645                 650                 655

<210> SEQ ID NO 58
<211> LENGTH: 98
<212> TYPE: PRT
<213> ORGANISM: Caenorhabditis elegans

<400> SEQUENCE: 58

Lys Pro Asn Pro Trp Gly Glu Ser Tyr Ser Asp Ile Ile Ala Lys
1               5                   10                  15

Ala Leu Glu Ser Ala Pro Asp Gly Arg Leu Lys Leu Asn Glu Ile Tyr
            20                  25                  30

Gln Trp Phe Ser Asp Asn Ile Pro Tyr Phe Gly Glu Arg Ser Ser Pro
        35                  40                  45

Glu Glu Ala Ala Gly Trp Lys Asn Ser Ile Arg His Asn Leu Ser Leu
    50                  55                  60

His Ser Arg Phe Met Arg Ile Gln Asn Glu Gly Ala Gly Lys Ser Ser
65                  70                  75                  80

Trp Trp Val Ile Asn Pro Asp Ala Lys Pro Gly Met Asn Pro Arg Arg
                85                  90                  95

Thr Arg

<210> SEQ ID NO 59
<211> LENGTH: 7
<212> TYPE: PRT
<213> ORGANISM: Caenorhabditis elegans

<400> SEQUENCE: 59

Trp Lys Asn Ser Ile Arg His
1               5

<210> SEQ ID NO 60
<211> LENGTH: 121
<212> TYPE: PRT
<213> ORGANISM: Caenorhabditis elegans

<400> SEQUENCE: 60

Gln Val Leu Asp Asp His Asp Tyr Gly Arg Cys Val Asp Trp Trp Gly
1               5                   10                  15

Val Gly Val Val Met Tyr Glu Met Met Cys Gly Arg Leu Pro Phe Tyr
            20                  25                  30

Ser Lys Asp His Asn Lys Leu Phe Glu Leu Ile Met Ala Gly Asp Leu
        35                  40                  45

Arg Phe Pro Ser Lys Leu Ser Gln Glu Ala Arg Thr Leu Leu Thr Gly
    50                  55                  60

Leu Leu Val Lys Asp Pro Thr Gln Arg Leu Gly Gly Gly Pro Glu Asp
65                  70                  75                  80
```

```
Ala Leu Glu Ile Cys Arg Ala Asp Phe Phe Arg Thr Val Asp Trp Glu
                85                  90                  95

Ala Thr Tyr Arg Lys Glu Ile Glu Pro Pro Tyr Lys Pro Asn Val Gln
            100                 105                 110

Ser Glu Thr Asp Thr Ser Tyr Phe Asp
        115                 120

<210> SEQ ID NO 61
<211> LENGTH: 66
<212> TYPE: PRT
<213> ORGANISM: Caenorhabditis elegans

<400> SEQUENCE: 61

Thr Met Glu Asp Phe Asp Phe Leu Lys Val Leu Gly Lys Gly Thr Phe
1               5                   10                  15

Gly Lys Val Ile Leu Cys Lys Glu Lys Arg Thr Gln Lys Leu Tyr Ala
            20                  25                  30

Ile Lys Ile Leu Lys Lys Asp Val Ile Ala Arg Glu Glu Val Ala
            35                  40                  45

His Thr Leu Thr Glu Asn Arg Val Leu Gln Arg Cys Lys His Pro Phe
        50                  55                  60

Leu Thr
65

<210> SEQ ID NO 62
<211> LENGTH: 45
<212> TYPE: PRT
<213> ORGANISM: Caenorhabditis elegans

<400> SEQUENCE: 62

Lys Leu Glu Asn Leu Leu Asp Lys Asp Gly His Ile Lys Ile Ala
1               5                   10                  15

Asp Phe Gly Leu Cys Lys Glu Glu Ile Ser Phe Gly Asp Lys Thr Ser
            20                  25                  30

Thr Phe Cys Gly Thr Pro Glu Tyr Leu Ala Pro Glu Val
            35                  40                  45

<210> SEQ ID NO 63
<211> LENGTH: 57
<212> TYPE: PRT
<213> ORGANISM: Caenorhabditis elegans

<400> SEQUENCE: 63

Tyr Phe Gln Glu Leu Lys Tyr Ser Phe Gln Glu Gln His Tyr Leu Cys
1               5                   10                  15

Phe Val Met Gln Phe Ala Asn Gly Gly Glu Leu Phe Thr His Val Arg
            20                  25                  30

Lys Cys Gly Thr Phe Ser Glu Pro Arg Ala Arg Phe Tyr Gly Ala Glu
            35                  40                  45

Ile Val Leu Ala Leu Gly Tyr Leu His
        50                  55

<210> SEQ ID NO 64
<211> LENGTH: 59
<212> TYPE: PRT
<213> ORGANISM: Caenorhabditis elegans

<400> SEQUENCE: 64

Ser Thr Phe Ala Ile Phe Tyr Phe Gln Thr Met Leu Phe Glu Lys Pro
1               5                   10                  15
```

```
Arg Pro Asn Met Phe Met Val Arg Cys Leu Gln Trp Thr Thr Val Ile
            20                  25                  30

Glu Arg Thr Phe Tyr Ala Glu Ser Ala Glu Val Arg Gln Arg Trp Ile
        35                  40                  45

His Ala Ile Glu Ser Ile Ser Lys Lys Tyr Lys
    50                  55
```

```
<210> SEQ ID NO 65
<211> LENGTH: 33
<212> TYPE: PRT
<213> ORGANISM: Caenorhabditis elegans

<400> SEQUENCE: 65

Leu Gln Glu Leu Lys Tyr Ser Phe Gln Thr Asn Asp Arg Leu Cys Phe
1               5                   10                  15

Val Met Glu Phe Ala Ile Gly Gly Asp Leu Tyr Tyr His Leu Asn Arg
            20                  25                  30

Glu
```

```
<210> SEQ ID NO 66
<211> LENGTH: 21
<212> TYPE: PRT
<213> ORGANISM: Caenorhabditis elegans

<400> SEQUENCE: 66

Val Val Ile Glu Gly Trp Leu His Lys Lys Gly Glu His Ile Arg Asn
1               5                   10                  15

Trp Arg Pro Arg Phe
            20
```

```
<210> SEQ ID NO 67
<211> LENGTH: 26
<212> TYPE: PRT
<213> ORGANISM: Caenorhabditis elegans

<400> SEQUENCE: 67

Phe Ser Glu Pro Arg Ala Arg Phe Tyr Gly Ser Glu Ile Val Leu Ala
1               5                   10                  15

Leu Gly Tyr Leu His Ala Asn Ser Ile Val
            20                  25
```

```
<210> SEQ ID NO 68
<211> LENGTH: 39
<212> TYPE: PRT
<213> ORGANISM: Caenorhabditis elegans

<400> SEQUENCE: 68

Ile Arg Val Ser Phe Cys Lys Gly Phe Gly Glu Thr Tyr Ser Arg Leu
1               5                   10                  15

Lys Val Val Asn Leu Pro Cys Trp Ile Glu Ile Ile Leu His Glu Pro
            20                  25                  30

Ala Asp Glu Tyr Asp Thr Val
        35
```

```
<210> SEQ ID NO 69
<211> LENGTH: 45
<212> TYPE: PRT
<213> ORGANISM: Caenorhabditis elegans

<400> SEQUENCE: 69
```

```
Ser Arg Asn Ser Lys Ser Ser Gln Ile Arg Asn Thr Val Gly Ala Gly
 1               5                   10                  15

Ile Gln Leu Ala Tyr Glu Asn Gly Glu Leu Trp Leu Thr Val Leu Thr
             20                  25                  30

Asp Gln Ile Val Phe Val Gln Cys Pro Phe Leu Asn Gln
         35                  40                  45

<210> SEQ ID NO 70
<211> LENGTH: 29
<212> TYPE: PRT
<213> ORGANISM: Caenorhabditis elegans

<400> SEQUENCE: 70

Asn Glu Met Leu Asp Pro Glu Pro Lys Tyr Pro Lys Glu Glu Lys Pro
 1               5                   10                  15

Trp Cys Thr Ile Phe Tyr Tyr Glu Leu Thr Val Arg Val
             20                  25

<210> SEQ ID NO 71
<211> LENGTH: 29
<212> TYPE: PRT
<213> ORGANISM: Caenorhabditis elegans

<400> SEQUENCE: 71

Gln Leu Gly Lys Ala Phe Glu Ala Lys Val Pro Thr Ile Thr Ile Asp
 1               5                   10                  15

Gly Ala Thr Gly Ala Ser Asp Glu Cys Arg Met Ser Leu
             20                  25

<210> SEQ ID NO 72
<211> LENGTH: 105
<212> TYPE: PRT
<213> ORGANISM: Caenorhabditis elegans

<400> SEQUENCE: 72

Ser Pro Asp Asp Gly Leu Leu Asp Ser Ser Glu Glu Ser Arg Arg Arg
 1               5                   10                  15

Gln Lys Thr Cys Arg Val Cys Gly Asp His Ala Thr Gly Tyr Asn Phe
             20                  25                  30

Asn Val Ile Thr Cys Glu Ser Cys Lys Ala Phe Phe Arg Arg Asn Ala
         35                  40                  45

Leu Arg Pro Lys Glu Phe Lys Cys Pro Tyr Ser Glu Asp Cys Glu Ile
     50                  55                  60

Asn Ser Val Ser Arg Arg Phe Cys Gln Lys Cys Arg Leu Arg Lys Cys
 65                  70                  75                  80

Phe Thr Val Gly Met Lys Lys Glu Trp Ile Leu Asn Glu Glu Gln Leu
                 85                  90                  95

Arg Arg Arg Lys Asn Ser Arg Leu Asn
                100                 105

<210> SEQ ID NO 73
<211> LENGTH: 89
<212> TYPE: PRT
<213> ORGANISM: Caenorhabditis elegans

<400> SEQUENCE: 73

Leu Asp Ser Ser Glu Glu Ser Arg Arg Arg Gln Lys Thr Cys Arg Val
 1               5                   10                  15

Cys Gly Asp His Ala Thr Gly Tyr Asn Phe Asn Val Ile Thr Cys Glu
             20                  25                  30
```

```
Ser Cys Lys Ala Phe Phe Arg Arg Asn Ala Leu Arg Pro Lys Glu Phe
        35                  40                  45

Lys Cys Pro Tyr Ser Glu Asp Cys Glu Ile Asn Ser Val Ser Arg Arg
 50                  55                  60

Phe Cys Gln Lys Cys Arg Leu Arg Lys Cys Phe Thr Val Gly Met Lys
 65                  70                  75                  80

Lys Glu Trp Ile Leu Asn Glu Glu Gln
                 85

<210> SEQ ID NO 74
<211> LENGTH: 73
<212> TYPE: PRT
<213> ORGANISM: Caenorhabditis elegans

<400> SEQUENCE: 74

Asp Ile Met Asn Ile Met Asp Val Thr Met Arg Arg Phe Val Lys Val
 1               5                  10                  15

Ala Lys Gly Val Pro Ala Phe Arg Glu Val Ser Gln Glu Gly Lys Phe
                20                  25                  30

Ser Leu Leu Lys Gly Gly Met Ile Glu Met Leu Thr Val Arg Gly Val
        35                  40                  45

Thr Arg Tyr Asp Ala Ser Thr Asn Ser Phe Lys Thr Pro Thr Ile Lys
 50                  55                  60

Gly Gln Asn Val Ser Val Asn Val Asp
 65                  70

<210> SEQ ID NO 75
<211> LENGTH: 112
<212> TYPE: PRT
<213> ORGANISM: Caenorhabditis elegans

<400> SEQUENCE: 75

Ser Gly Ser Leu Val Asp Leu Met Ile Lys Asn Leu Thr Ala Tyr Thr
 1               5                  10                  15

Gln Gly Leu Asn Glu Thr Val Lys Asn Arg Thr Ala Glu Leu Glu Lys
                20                  25                  30

Glu Gln Glu Lys Gly Asp Gln Leu Leu Met Glu Leu Leu Pro Lys Ser
        35                  40                  45

Val Ala Asn Asp Leu Lys Asn Gly Ile Ala Val Asp Pro Lys Val Tyr
 50                  55                  60

Glu Asn Ala Thr Ile Leu Tyr Ser Asp Ile Val Gly Phe Thr Ser Leu
 65                  70                  75                  80

Cys Ser Gln Ser Gln Pro Met Glu Val Val Thr Leu Leu Ser Gly Met
                85                  90                  95

Tyr Gln Arg Phe Asp Leu Ile Ser Gln Gln Gly Gly Tyr Lys Val
                100                 105                 110

<210> SEQ ID NO 76
<211> LENGTH: 107
<212> TYPE: PRT
<213> ORGANISM: Caenorhabditis elegans

<400> SEQUENCE: 76

Met Glu Thr Ile Gly Asp Ala Tyr Cys Val Ala Ala Gly Leu Pro Val
 1               5                  10                  15

Val Met Glu Lys Asp His Val Lys Ser Ile Cys Met Ile Ala Leu Leu
                20                  25                  30
```

-continued

Gln Arg Asp Cys Leu His His Phe Glu Ile Pro His Arg Pro Gly Thr
         35                  40                  45

Phe Leu Asn Cys Arg Trp Gly Phe Asn Ser Gly Pro Val Phe Ala Gly
 50                  55                  60

Val Ile Gly Gln Lys Ala Pro Arg Tyr Ala Cys Phe Gly Glu Ala Val
 65                  70                  75                  80

Ile Leu Ala Ser Lys Met Glu Ser Ser Gly Val Glu Asp Arg Ile Gln
             85                  90                  95

Met Thr Leu Ala Ser Gln Gln Leu Leu Glu Glu
            100                 105

<210> SEQ ID NO 77
<211> LENGTH: 43
<212> TYPE: PRT
<213> ORGANISM: Caenorhabditis elegans

<400> SEQUENCE: 77

Asp Ile Leu Lys Gly Leu Glu Tyr Ile His Ala Ser Ala Ile Asp Phe
 1               5                  10                  15

His Gly Asn Leu Thr Leu His Asn Cys Met Leu Asp Ser His Trp Ile
             20                  25                  30

Val Lys Leu Ser Gly Phe Gly Val Asn Arg Leu
         35                  40

<210> SEQ ID NO 78
<211> LENGTH: 15
<212> TYPE: PRT
<213> ORGANISM: Caenorhabditis elegans

<400> SEQUENCE: 78

Asp Met Tyr Ser Phe Gly Val Ile Leu His Glu Ile Ile Leu Lys
 1               5                  10                  15

<210> SEQ ID NO 79
<211> LENGTH: 67
<212> TYPE: PRT
<213> ORGANISM: Caenorhabditis elegans

<400> SEQUENCE: 79

Ala Ile Lys Ile Asn Val Asp Asp Pro Ala Ser Thr Glu Asn Leu Asn
 1               5                  10                  15

Tyr Leu Met Glu Ala Asn Ile Met Lys Asn Phe Lys Thr Asn Phe Ile
             20                  25                  30

Val Gln Leu Tyr Gly Val Ile Ser Thr Val Gln Pro Ala Met Val Val
         35                  40                  45

Met Glu Met Met Asp Leu Gly Asn Leu Arg Asp Tyr Leu Arg Ser Lys
     50                  55                  60

Arg Glu Asp
 65

<210> SEQ ID NO 80
<211> LENGTH: 54
<212> TYPE: PRT
<213> ORGANISM: Caenorhabditis elegans

<400> SEQUENCE: 80

Val Ile Lys Lys Pro Glu Cys Cys Glu Asn Tyr Trp Tyr Lys Val Met
 1               5                  10                  15

Lys Met Cys Trp Arg Tyr Ser Pro Arg Asp Arg Pro Thr Phe Leu Gln
             20                  25                  30

```
Leu Val His Leu Ala Ala Glu Ala Ser Pro Glu Phe Arg Asp Leu
        35                  40                  45
Ser Phe Val Leu Thr Asp
        50

<210> SEQ ID NO 81
<211> LENGTH: 69
<212> TYPE: PRT
<213> ORGANISM: Caenorhabditis elegans

<400> SEQUENCE: 81

Lys Gln Asp Ser Gly Met Ala Ser Glu Leu Lys Asp Ile Phe Ala Asn
  1               5                  10                  15

Ile His Thr Ile Thr Gly Tyr Leu Leu Val Arg Gln Ser Ser Pro Phe
                20                  25                  30

Ile Ser Leu Asn Met Phe Arg Asn Leu Arg Arg Ile Glu Ala Lys Ser
            35                  40                  45

Leu Phe Arg Asn Leu Tyr Ala Ile Thr Val Phe Glu Asn Pro Asn Leu
    50                  55                  60

Lys Lys Leu Phe Asp
 65

<210> SEQ ID NO 82
<211> LENGTH: 52
<212> TYPE: PRT
<213> ORGANISM: Caenorhabditis elegans

<400> SEQUENCE: 82

Phe Pro His Leu Arg Glu Ile Thr Gly Thr Leu Leu Val Phe Glu Thr
  1               5                  10                  15

Glu Gly Leu Val Asp Leu Arg Lys Ile Phe Pro Asn Leu Arg Val Ile
                20                  25                  30

Gly Gly Arg Ser Leu Ile Gln His Tyr Ala Leu Ile Ile Tyr Arg Asn
            35                  40                  45

Pro Asp Leu Glu
    50

<210> SEQ ID NO 83
<211> LENGTH: 46
<212> TYPE: PRT
<213> ORGANISM: Caenorhabditis elegans

<400> SEQUENCE: 83

Glu Ile Gly Leu Asp Lys Leu Ser Val Ile Arg Asn Gly Gly Val Arg
  1               5                  10                  15

Ile Ile Asp Asn Arg Lys Leu Cys Tyr Thr Lys Thr Ile Asp Trp Lys
                20                  25                  30

His Leu Ile Thr Ser Ser Ile Asn Asp Val Val Val Asp Asn
            35                  40                  45

<210> SEQ ID NO 84
<211> LENGTH: 36
<212> TYPE: PRT
<213> ORGANISM: Caenorhabditis elegans

<400> SEQUENCE: 84

Tyr Asn Ala Asp Asp Trp Glu Leu Arg Gln Asp Asp Val Val Leu Gly
  1               5                  10                  15

Gln Gln Cys Gly Glu Gly Ser Phe Gly Lys Val Tyr Leu Gly Thr Gly
```

```
                   20                  25                  30

Asn Asn Val Val
         35

<210> SEQ ID NO 85
<211> LENGTH: 24
<212> TYPE: PRT
<213> ORGANISM: Caenorhabditis elegans

<400> SEQUENCE: 85

Asp Ser Leu Ala Lys Tyr Cys Cys Val Arg Val Ser Phe Cys Lys Gly
1               5                   10                  15

Phe Gly Glu Ala Tyr Pro Glu Arg
            20

<210> SEQ ID NO 86
<211> LENGTH: 13
<212> TYPE: PRT
<213> ORGANISM: Caenorhabditis elegans

<400> SEQUENCE: 86

Gly Trp Asp Trp Ile Val Ala Pro Pro Arg Tyr Asn Ala
1               5                   10

<210> SEQ ID NO 87
<211> LENGTH: 121
<212> TYPE: PRT
<213> ORGANISM: Homo sapiens

<400> SEQUENCE: 87

Glu Val Leu Glu Asp Asn Asp Tyr Gly Arg Ala Val Asp Trp Trp Gly
1               5                   10                  15

Leu Gly Val Val Met Tyr Glu Met Met Cys Gly Arg Leu Pro Phe Tyr
                20                  25                  30

Asn Gln Asp His Glu Lys Leu Phe Glu Leu Ile Leu Met Glu Glu Ile
            35                  40                  45

Arg Phe Pro Arg Thr Leu Gly Pro Glu Ala Lys Ser Leu Leu Ser Gly
        50                  55                  60

Leu Leu Lys Lys Asp Pro Thr Gln Arg Leu Gly Gly Gly Ser Glu Asp
65                  70                  75                  80

Ala Lys Glu Ile Met Gln His Arg Phe Phe Ala Asn Ile Val Trp Gln
                85                  90                  95

Asp Val Tyr Glu Lys Lys Leu Ser Pro Pro Phe Lys Pro Gln Val Thr
            100                 105                 110

Ser Glu Thr Asp Thr Arg Tyr Phe Asp
        115                 120

<210> SEQ ID NO 88
<211> LENGTH: 121
<212> TYPE: PRT
<213> ORGANISM: Caenorhabditis elegans

<400> SEQUENCE: 88

Gln Val Leu Asp Asp His Asp Tyr Gly Arg Cys Val Asp Trp Trp Gly
1               5                   10                  15

Val Gly Val Val Met Tyr Glu Met Met Cys Gly Arg Leu Pro Phe Tyr
                20                  25                  30

Ser Lys Asp His Asn Lys Leu Phe Glu Leu Ile Met Ala Gly Asp Leu
            35                  40                  45
```

```
Arg Phe Pro Ser Lys Leu Ser Gln Glu Ala Arg Thr Leu Leu Thr Gly
    50                  55                  60

Leu Leu Val Lys Asp Pro Thr Gln Arg Leu Gly Gly Pro Glu Asp
65                  70                  75                  80

Ala Leu Glu Ile Cys Arg Ala Asp Phe Phe Arg Thr Val Asp Trp Glu
                85                  90                  95

Ala Thr Tyr Arg Lys Glu Ile Glu Pro Pro Tyr Lys Pro Asn Val Gln
            100                 105                 110

Ser Glu Thr Asp Thr Ser Tyr Phe Asp
            115                 120

<210> SEQ ID NO 89
<211> LENGTH: 66
<212> TYPE: PRT
<213> ORGANISM: Homo sapiens

<400> SEQUENCE: 89

Thr Met Asn Glu Phe Glu Tyr Leu Lys Leu Leu Gly Lys Gly Thr Phe
1               5                   10                  15

Gly Lys Val Ile Leu Val Lys Glu Lys Ala Thr Gly Arg Tyr Tyr Ala
            20                  25                  30

Met Lys Ile Leu Lys Lys Glu Val Ile Val Ala Lys Asp Glu Val Ala
            35                  40                  45

His Thr Leu Thr Glu Asn Arg Val Leu Gln Asn Ser Arg His Pro Phe
    50                  55                  60

Leu Thr
65

<210> SEQ ID NO 90
<211> LENGTH: 66
<212> TYPE: PRT
<213> ORGANISM: Caenorhabditis elegans

<400> SEQUENCE: 90

Thr Met Glu Asp Phe Asp Phe Leu Lys Val Leu Gly Lys Gly Thr Phe
1               5                   10                  15

Gly Lys Val Ile Leu Cys Lys Glu Lys Arg Thr Gln Lys Leu Tyr Ala
            20                  25                  30

Ile Lys Ile Leu Lys Lys Asp Val Ile Ile Ala Arg Glu Glu Val Ala
            35                  40                  45

His Thr Leu Thr Glu Asn Arg Val Leu Gln Arg Cys Lys His Pro Phe
    50                  55                  60

Leu Thr
65

<210> SEQ ID NO 91
<211> LENGTH: 45
<212> TYPE: PRT
<213> ORGANISM: Homo sapiens

<400> SEQUENCE: 91

Lys Leu Glu Asn Leu Met Leu Asp Lys Asp Gly His Ile Lys Ile Thr
1               5                   10                  15

Asp Phe Gly Leu Cys Lys Glu Gly Ile Lys Asp Gly Ala Thr Met Lys
            20                  25                  30

Thr Phe Cys Gly Thr Pro Glu Tyr Leu Ala Pro Glu Val
            35                  40                  45
```

-continued

<210> SEQ ID NO 92
<211> LENGTH: 45
<212> TYPE: PRT
<213> ORGANISM: Caenorhabditis elegans

<400> SEQUENCE: 92

Lys Leu Glu Asn Leu Leu Asp Lys Asp Gly His Ile Lys Ile Ala
1               5                   10                  15

Asp Phe Gly Leu Cys Lys Glu Glu Ile Ser Phe Gly Asp Lys Thr Ser
            20                  25                  30

Thr Phe Cys Gly Thr Pro Glu Tyr Leu Ala Pro Glu Val
        35                  40                  45

<210> SEQ ID NO 93
<211> LENGTH: 57
<212> TYPE: PRT
<213> ORGANISM: Homo sapiens

<400> SEQUENCE: 93

Phe Leu Thr Ala Leu Lys Tyr Ser Phe Gln Thr His Asp Arg Leu Cys
1               5                   10                  15

Phe Val Met Glu Tyr Ala Asn Gly Gly Glu Leu Phe Phe His Leu Ser
            20                  25                  30

Arg Glu Arg Val Phe Ser Glu Asp Arg Ala Arg Phe Tyr Gly Ala Glu
        35                  40                  45

Ile Val Ser Ala Leu Asp Tyr Leu His
    50                  55

<210> SEQ ID NO 94
<211> LENGTH: 57
<212> TYPE: PRT
<213> ORGANISM: Caenorhabditis elegans

<400> SEQUENCE: 94

Tyr Phe Gln Glu Leu Lys Tyr Ser Phe Gln Glu Gln His Tyr Leu Cys
1               5                   10                  15

Phe Val Met Gln Phe Ala Asn Gly Gly Glu Leu Phe Thr His Val Arg
            20                  25                  30

Lys Cys Gly Thr Phe Ser Glu Pro Arg Ala Arg Phe Tyr Gly Ala Glu
        35                  40                  45

Ile Val Leu Ala Leu Gly Tyr Leu His
    50                  55

<210> SEQ ID NO 95
<211> LENGTH: 59
<212> TYPE: PRT
<213> ORGANISM: Homo sapiens

<400> SEQUENCE: 95

Asn Asn Phe Ser Val Ala Gln Cys Gln Leu Met Lys Thr Glu Arg Pro
1               5                   10                  15

Arg Pro Asn Thr Phe Ile Ile Arg Cys Leu Gln Trp Thr Thr Val Ile
            20                  25                  30

Glu Arg Thr Phe His Val Glu Thr Pro Glu Glu Arg Glu Glu Trp Ala
        35                  40                  45

Thr Ala Ile Gln Thr Val Ala Asp Gly Leu Lys
    50                  55

<210> SEQ ID NO 96
<211> LENGTH: 59

```
<212> TYPE: PRT
<213> ORGANISM: Caenorhabditis elegans

<400> SEQUENCE: 96

Ser Thr Phe Ala Ile Phe Tyr Phe Gln Thr Met Leu Phe Glu Lys Pro
  1               5                  10                  15

Arg Pro Asn Met Phe Met Val Arg Cys Leu Gln Trp Thr Thr Val Ile
             20                  25                  30

Glu Arg Thr Phe Tyr Ala Glu Ser Ala Glu Val Arg Gln Arg Trp Ile
         35                  40                  45

His Ala Ile Glu Ser Ile Ser Lys Lys Tyr Lys
     50                  55

<210> SEQ ID NO 97
<211> LENGTH: 33
<212> TYPE: PRT
<213> ORGANISM: Homo sapiens

<400> SEQUENCE: 97

Leu Thr Ala Leu Lys Tyr Ser Phe Gln Thr His Asp Arg Leu Cys Phe
  1               5                  10                  15

Val Met Glu Tyr Ala Asn Gly Gly Glu Leu Phe Phe His Leu Ser Arg
             20                  25                  30

Glu

<210> SEQ ID NO 98
<211> LENGTH: 33
<212> TYPE: PRT
<213> ORGANISM: Caenorhabditis elegans

<400> SEQUENCE: 98

Leu Gln Glu Leu Lys Tyr Ser Phe Gln Thr Asn Asp Arg Leu Cys Phe
  1               5                  10                  15

Val Met Glu Phe Ala Ile Gly Gly Asp Leu Tyr Tyr His Leu Asn Arg
             20                  25                  30

Glu

<210> SEQ ID NO 99
<211> LENGTH: 36
<212> TYPE: PRT
<213> ORGANISM: Homo sapiens or Caenorhabditis elegans

<400> SEQUENCE: 99

Lys Leu Glu Asn Leu Leu Asp Lys Asp Gly His Ile Lys Ile Asp Phe
  1               5                  10                  15

Gly Leu Cys Lys Glu Ile Gly Thr Phe Cys Gly Thr Pro Glu Tyr Leu
             20                  25                  30

Ala Pro Glu Val
         35

<210> SEQ ID NO 100
<211> LENGTH: 37
<212> TYPE: PRT
<213> ORGANISM: Homo sapiens or Caenorhabditis elegans

<400> SEQUENCE: 100

Leu Lys Tyr Ser Phe Gln Leu Cys Phe Val Met Ala Asn Gly Gly Glu
  1               5                  10                  15

Leu Phe His Phe Ser Glu Arg Ala Arg Phe Tyr Gly Ala Glu Ile Val
             20                  25                  30
```

```
Ala Leu Tyr Leu His
        35

<210> SEQ ID NO 101
<211> LENGTH: 29
<212> TYPE: PRT
<213> ORGANISM: Homo sapiens or Caenorhabditis elegans

<400> SEQUENCE: 101

Phe Gln Met Glu Pro Arg Pro Asn Phe Arg Cys Leu Gln Trp Thr Thr
1               5                   10                  15

Val Ile Glu Arg Thr Phe Glu Arg Trp Ala Ile Lys
            20                  25

<210> SEQ ID NO 102
<211> LENGTH: 24
<212> TYPE: PRT
<213> ORGANISM: Homo sapiens or Caenorhabditis elegans

<400> SEQUENCE: 102

Leu Leu Lys Tyr Ser Phe Gln Thr Asp Arg Leu Cys Phe Val Met Glu
1               5                   10                  15

Ala Gly Gly Leu His Leu Arg Glu
            20

<210> SEQ ID NO 103
<211> LENGTH: 366
<212> TYPE: PRT
<213> ORGANISM: Homo sapiens

<400> SEQUENCE: 103

Arg Gly Ala Ile Arg Ile Glu Lys Asn Ala Asp Leu Cys Tyr Leu Ser
1               5                   10                  15

Thr Val Asp Trp Ser Leu Ile Leu Asp Ala Val Ser Asn Asn Tyr Ile
            20                  25                  30

Val Gly Asn Lys Pro Pro Lys Glu Cys Gly Asp Leu Cys Pro Gly Thr
        35                  40                  45

Met Glu Glu Lys Pro Met Cys Glu Lys Thr Thr Ile Asn Asn Glu Tyr
    50                  55                  60

Asn Tyr Arg Cys Trp Thr Thr Asn Arg Cys Gln Lys Met Cys Pro Ser
65                  70                  75                  80

Thr Cys Gly Lys Arg Ala Cys Thr Glu Asn Asn Glu Cys Cys His Pro
                85                  90                  95

Glu Cys Leu Gly Ser Cys Ser Ala Pro Asp Asn Asp Thr Ala Cys Val
            100                 105                 110

Ala Cys Arg His Tyr Tyr Tyr Ala Gly Val Cys Val Pro Ala Cys Pro
        115                 120                 125

Pro Asn Thr Tyr Arg Phe Glu Gly Trp Arg Cys Val Asp Arg Asp Phe
    130                 135                 140

Cys Ala Asn Ile Leu Ser Ala Glu Ser Ser Asp Ser Glu Gly Phe Val
145                 150                 155                 160

Ile His Asp Gly Glu Cys Met Gln Glu Cys Pro Ser Gly Phe Ile Arg
                165                 170                 175

Asn Gly Ser Gln Ser Met Tyr Cys Ile Pro Cys Glu Gly Pro Cys Pro
            180                 185                 190

Lys Val Cys Glu Glu Glu Lys Lys Thr Lys Thr Ile Asp Ser Val Thr
        195                 200                 205
```

Ser Ala Gln Met Leu Gln Gly Cys Thr Ile Phe Lys Gly Asn Leu Leu
    210                 215                 220

Ile Asn Ile Arg Arg Gly Asn Asn Ile Ala Ser Glu Leu Glu Asn Phe
225                 230                 235                 240

Met Gly Leu Ile Glu Val Val Thr Gly Tyr Val Lys Ile Arg His Ser
                245                 250                 255

His Ala Leu Val Ser Leu Ser Phe Leu Lys Asn Leu Arg Leu Ile Leu
            260                 265                 270

Gly Glu Glu Gln Leu Glu Gly Asn Tyr Ser Phe Tyr Val Leu Asp Asn
        275                 280                 285

Gln Asn Leu Gln Gln Leu Trp Asp Trp Asp His Arg Asn Leu Thr Ile
    290                 295                 300

Lys Ala Gly Lys Met Tyr Phe Ala Phe Asn Pro Lys Leu Cys Val Ser
305                 310                 315                 320

Glu Ile Tyr Arg Met Glu Glu Val Thr Gly Thr Lys Gly Arg Gln Ser
                325                 330                 335

Lys Gly Asp Ile Asn Thr Arg Asn Asn Gly Glu Arg Ala Ser Cys Glu
            340                 345                 350

Ser Asp Val Leu His Phe Thr Ser Thr Thr Thr Ser Lys Asn
        355                 360                 365

<210> SEQ ID NO 104
<211> LENGTH: 370
<212> TYPE: PRT
<213> ORGANISM: Homo sapiens

<400> SEQUENCE: 104

Arg Gly Ser Val Arg Ile Glu Lys Asn Asn Glu Leu Cys Tyr Leu Ala
1               5                   10                  15

Thr Ile Asp Trp Ser Arg Ile Leu Asp Ser Val Glu Asp Asn Tyr Ile
                20                  25                  30

Val Leu Asn Lys Asp Asp Asn Glu Cys Gly Asp Ile Cys Pro Gly
            35                  40                  45

Thr Ala Lys Gly Lys Thr Asn Cys Pro Ala Thr Val Ile Asn Gly Gln
    50                  55                  60

Phe Val Glu Arg Cys Trp Thr His Ser His Cys Gln Lys Val Cys Pro
65                  70                  75                  80

Thr Ile Cys Lys Ser His Gly Cys Thr Ala Glu Gly Leu Cys Cys His
                85                  90                  95

Ser Glu Cys Leu Gly Asn Cys Ser Gln Pro Asp Asp Pro Thr Lys Cys
            100                 105                 110

Val Ala Cys Arg Asn Phe Tyr Leu Asp Gly Arg Cys Val Glu Thr Cys
        115                 120                 125

Pro Pro Pro Tyr Tyr His Phe Gln Asp Trp Arg Cys Val Asn Phe Ser
    130                 135                 140

Phe Cys Gln Asp Leu His His Lys Cys Lys Asn Ser Arg Arg Gln Gly
145                 150                 155                 160

Cys His Gln Tyr Val Ile His Asn Asn Lys Cys Ile Pro Glu Cys Pro
                165                 170                 175

Ser Gly Tyr Thr Met Asn Ser Ser Asn Leu Leu Cys Thr Pro Cys Leu
            180                 185                 190

Gly Pro Cys Pro Lys Val Cys His Leu Leu Glu Gly Glu Lys Thr Ile
        195                 200                 205

Asp Ser Val Thr Ser Ala Gln Glu Leu Arg Gly Cys Thr Val Ile Asn
    210                 215                 220

-continued

```
Gly Ser Leu Ile Ile Asn Ile Arg Gly Gly Asn Asn Leu Ala Ala Glu
225                 230                 235                 240

Leu Glu Ala Asn Leu Gly Leu Ile Glu Glu Ile Ser Gly Tyr Leu Lys
            245                 250                 255

Ile Arg Arg Ser Tyr Ala Leu Val Ser Leu Ser Phe Phe Arg Lys Leu
                260                 265                 270

Arg Leu Ile Arg Gly Glu Thr Leu Glu Ile Gly Asn Tyr Ser Phe Tyr
            275                 280                 285

Ala Leu Asp Asn Gln Asn Leu Arg Gln Leu Trp Asp Trp Ser Lys His
        290                 295                 300

Asn Leu Thr Ile Thr Gln Gly Lys Leu Phe Phe His Tyr Asn Pro Lys
305                 310                 315                 320

Leu Cys Leu Ser Glu Ile His Lys Met Glu Glu Val Ser Gly Thr Lys
                325                 330                 335

Gly Arg Gln Glu Arg Asn Asp Ile Ala Leu Lys Thr Asn Gly Asp Gln
            340                 345                 350

Ala Ser Cys Glu Asn Glu Leu Leu Lys Phe Ser Tyr Ile Arg Thr Ser
        355                 360                 365

Phe Asp
    370

<210> SEQ ID NO 105
<211> LENGTH: 383
<212> TYPE: PRT
<213> ORGANISM: Drosophila melanogaster

<400> SEQUENCE: 105

Arg Gly Gly Val Arg Ile Glu Lys Asn His Lys Leu Cys Tyr Asp Arg
1               5                   10                  15

Thr Ile Asp Trp Leu Glu Ile Leu Ala Glu Asn Glu Ser Gln Leu Val
            20                  25                  30

Val Leu Thr Glu Asn Gly Lys Glu Lys Glu Cys Ser Leu Ser Lys Cys
        35                  40                  45

Pro Gly Glu Ile Arg Ile Glu Glu Gly His Asp Asn Thr Ala Ile Glu
    50                  55                  60

Gly Glu Leu Asn Ala Ser Cys Gln Leu His Asn Asn Arg Arg Leu Cys
65                  70                  75                  80

Trp Asn Ser Lys Leu Cys Gln Thr Lys Cys Pro Glu Lys Cys Arg Asn
                85                  90                  95

Asn Cys Ile Asp Glu His Thr Cys Cys Ser Gln Asp Cys Leu Gly Gly
            100                 105                 110

Cys Val Ile Asp Lys Asn Gly Asn Glu Ser Cys Ile Ser Cys Arg Asn
        115                 120                 125

Val Ser Phe Asn Asn Ile Cys Met Asp Ser Cys Pro Lys Gly Tyr Tyr
    130                 135                 140

Gln Phe Asp Ser Arg Cys Val Thr Ala Asn Glu Cys Ile Thr Leu Thr
145                 150                 155                 160

Lys Phe Glu Thr Asn Ser Val Tyr Ser Gly Ile Pro Tyr Asn Gly Gln
                165                 170                 175

Cys Ile Thr His Cys Pro Thr Gly Tyr Gln Lys Ser Glu Asn Lys Arg
            180                 185                 190

Met Cys Glu Pro Cys Pro Gly Gly Lys Cys Asp Lys Glu Cys Ser Ser
        195                 200                 205

Gly Leu Ile Asp Ser Leu Glu Arg Ala Arg Glu Phe His Gly Cys Thr
```

```
            210                 215                 220
Ile Ile Thr Gly Thr Glu Pro Leu Thr Ile Ser Ile Lys Arg Glu Ser
225                 230                 235                 240

Gly Ala His Val Met Asp Glu Leu Lys Tyr Gly Leu Ala Ala Val His
                245                 250                 255

Lys Ile Gln Ser Ser Leu Met Val His Leu Thr Tyr Gly Leu Lys Ser
                260                 265                 270

Leu Lys Phe Phe Gln Ser Leu Thr Glu Ile Ser Gly Asp Pro Pro Met
                275                 280                 285

Asp Ala Asp Lys Tyr Ala Leu Tyr Val Leu Asp Asn Arg Asp Leu Asp
        290                 295                 300

Glu Leu Trp Gly Pro Asn Gln Thr Val Phe Ile Arg Lys Gly Gly Val
305                 310                 315                 320

Phe Phe His Phe Asn Pro Lys Leu Cys Val Ser Thr Ile Asn Gln Leu
                325                 330                 335

Leu Pro Met Leu Ala Ser Lys Pro Lys Phe Phe Glu Lys Ser Asp Glu
                340                 345                 350

Gly Ala Asp Ser Asn Gly Asn Arg Gly Ser Cys Gly Thr Ala Val Leu
                355                 360                 365

Asn Val Thr Leu Gln Ser Val Gly Ala Asn Ser Ala Ser Leu Asn
        370                 375                 380

<210> SEQ ID NO 106
<211> LENGTH: 381
<212> TYPE: PRT
<213> ORGANISM: Caenorhabditis elegans

<400> SEQUENCE: 106

Asn Gly Gly Val Arg Ile Ile Asp Asn Arg Lys Leu Cys Tyr Thr Lys
1               5                   10                  15

Thr Ile Asp Trp Lys His Leu Ile Thr Ser Ser Ile Asn Asp Val Val
                20                  25                  30

Val Asp Asn Ala Ala Glu Tyr Ala Val Thr Glu Thr Gly Leu Met Cys
            35                  40                  45

Pro Arg Gly Ala Cys Glu Glu Asp Lys Gly Glu Ser Lys Cys His Tyr
    50                  55                  60

Leu Glu Glu Lys Asn Gln Glu Gln Gly Val Glu Arg Val Gln Ser Cys
65                  70                  75                  80

Trp Ser Asn Thr Thr Cys Gln Lys Ser Cys Ala Tyr Asp Arg Leu Leu
                85                  90                  95

Pro Thr Lys Glu Ile Gly Pro Gly Cys Asp Ala Asn Gly Asp Arg Cys
                100                 105                 110

His Asp Gln Cys Val Gly Gly Cys Glu Arg Val Asn Asp Ala Thr Ala
            115                 120                 125

Cys His Ala Cys Lys Asn Val Tyr His Lys Gly Lys Cys Ile Glu Lys
        130                 135                 140

Cys Asp Ala His Leu Tyr Leu Leu Gln Arg Arg Cys Val Thr Arg
145                 150                 155                 160

Glu Gln Cys Leu Gln Leu Asn Pro Val Leu Ser Asn Lys Thr Val Pro
                165                 170                 175

Ile Lys Ala Thr Ala Gly Leu Cys Ser Asp Lys Cys Pro Asp Gly Tyr
                180                 185                 190

Gln Ile Asn Pro Asp Asp His Arg Glu Cys Arg Lys Cys Val Gly Lys
        195                 200                 205
```

```
Cys Glu Ile Val Cys Glu Ile Asn His Val Ile Asp Thr Phe Pro Lys
210                 215                 220

Ala Gln Ala Ile Arg Leu Cys Asn Ile Ile Asp Gly Asn Leu Thr Ile
225                 230                 235                 240

Glu Ile Arg Gly Lys Gln Asp Ser Gly Met Ala Ser Glu Leu Lys Asp
                245                 250                 255

Ile Phe Ala Asn Ile His Thr Ile Thr Gly Tyr Leu Leu Val Arg Gln
                260                 265                 270

Ser Ser Pro Phe Ile Ser Leu Asn Met Phe Arg Asn Leu Arg Arg Ile
                275                 280                 285

Glu Ala Lys Ser Leu Phe Arg Asn Leu Tyr Ala Ile Thr Val Phe Glu
290                 295                 300

Asn Pro Asn Leu Lys Lys Leu Phe Asp Ser Thr Thr Asp Leu Thr Leu
305                 310                 315                 320

Asp Arg Gly Thr Val Ser Ile Ala Asn Asn Lys Met Leu Cys Phe Lys
                325                 330                 335

Tyr Ile Lys Gln Leu Met Ser Lys Leu Asn Ile Pro Leu Asp Pro Ile
                340                 345                 350

Asp Gln Ser Glu Gly Thr Asn Gly Glu Lys Ala Ile Cys Glu Asp Met
                355                 360                 365

Ala Ile Asn Val Ser Ile Thr Ala Val Asn Ala Asp Ser
370                 375                 380

<210> SEQ ID NO 107
<211> LENGTH: 370
<212> TYPE: PRT
<213> ORGANISM: Homo sapiens

<400> SEQUENCE: 107

Ala Leu Pro Val Ala Val Leu Leu Ile Val Gly Gly Leu Val Ile Met
1               5                   10                  15

Leu Tyr Val Phe His Arg Lys Arg Asn Asn Ser Arg Leu Gly Asn Gly
                20                  25                  30

Val Leu Tyr Ala Ser Val Asn Pro Glu Tyr Phe Ser Ala Ala Asp Val
                35                  40                  45

Tyr Val Pro Asp Glu Trp Glu Val Ala Arg Glu Lys Ile Thr Met Ser
50                  55                  60

Arg Glu Leu Gly Gln Gly Ser Phe Gly Met Val Tyr Glu Gly Val Ala
65                  70                  75                  80

Lys Gly Val Val Lys Asp Glu Pro Glu Thr Arg Val Ala Ile Lys Thr
                85                  90                  95

Val Asn Glu Ala Ala Ser Met Arg Glu Arg Ile Glu Phe Leu Asn Glu
                100                 105                 110

Ala Ser Val Met Lys Glu Phe Asn Cys His His Val Val Arg Leu Leu
                115                 120                 125

Gly Val Val Ser Gln Gly Gln Pro Thr Leu Val Ile Met Glu Leu Met
                130                 135                 140

Thr Arg Gly Asp Leu Lys Ser Tyr Leu Arg Ser Leu Arg Pro Glu Met
145                 150                 155                 160

Glu Asn Asn Pro Val Leu Ala Pro Pro Ser Leu Ser Lys Met Ile Gln
                165                 170                 175

Met Ala Gly Glu Ile Ala Asp Gly Met Ala Tyr Leu Asn Ala Asn Lys
                180                 185                 190

Phe Val His Arg Asp Leu Ala Ala Arg Asn Cys Met Val Ala Glu Asp
                195                 200                 205
```

```
Phe Thr Val Lys Ile Gly Asp Phe Gly Met Thr Arg Asp Ile Tyr Glu
    210                 215                 220

Thr Asp Tyr Tyr Arg Lys Gly Lys Gly Leu Leu Pro Val Arg Trp
225                 230                 235                 240

Met Ser Pro Glu Ser Leu Lys Asp Gly Val Phe Thr Thr Tyr Ser Asp
                245                 250                 255

Val Trp Ser Phe Gly Val Val Leu Trp Glu Ile Ala Thr Leu Ala Glu
                260                 265                 270

Gln Pro Tyr Gln Gly Leu Ser Asn Glu Gln Val Leu Arg Phe Val Met
                275                 280                 285

Glu Gly Gly Leu Leu Asp Lys Pro Asp Asn Cys Pro Asp Met Leu Phe
    290                 295                 300

Glu Leu Met Arg Met Cys Trp Gln Tyr Asn Pro Lys Met Arg Pro Ser
305                 310                 315                 320

Phe Leu Glu Ile Ile Ser Ser Ile Lys Glu Glu Met Glu Pro Gly Phe
                325                 330                 335

Arg Glu Val Ser Phe Tyr Tyr Ser Glu Glu Asn Lys Leu Pro Glu Pro
                340                 345                 350

Glu Glu Leu Asp Leu Glu Pro Glu Asn Met Glu Ser Val Pro Leu Asp
    355                 360                 365

Pro Ser
    370

<210> SEQ ID NO 108
<211> LENGTH: 374
<212> TYPE: PRT
<213> ORGANISM: Homo sapiens

<400> SEQUENCE: 108

Ile Gly Pro Leu Ile Phe Val Phe Leu Phe Ser Val Val Ile Gly Ser
1               5                   10                  15

Ile Tyr Leu Phe Leu Arg Lys Arg Gln Pro Asp Gly Pro Leu Gly Pro
            20                  25                  30

Leu Tyr Ala Ser Ser Asn Pro Glu Tyr Leu Ser Ala Ser Asp Val Phe
        35                  40                  45

Pro Cys Ser Val Tyr Val Pro Asp Glu Trp Glu Val Ser Arg Glu Lys
    50                  55                  60

Ile Thr Leu Leu Arg Glu Leu Gly Gln Gly Ser Phe Gly Met Val Tyr
65                  70                  75                  80

Glu Gly Asn Ala Arg Asp Ile Ile Lys Gly Glu Ala Glu Thr Arg Val
                85                  90                  95

Ala Val Lys Thr Val Asn Glu Ser Ala Ser Leu Arg Glu Arg Ile Glu
            100                 105                 110

Phe Leu Asn Glu Ala Ser Val Met Lys Gly Phe Thr Cys His His Val
        115                 120                 125

Val Arg Leu Leu Gly Val Val Ser Lys Gly Gln Pro Thr Leu Val Val
    130                 135                 140

Met Glu Leu Met Ala His Gly Asp Leu Lys Ser Tyr Leu Arg Ser Leu
145                 150                 155                 160

Arg Pro Glu Ala Glu Asn Asn Pro Gly Arg Pro Pro Pro Thr Leu Gln
                165                 170                 175

Glu Met Ile Gln Met Ala Ala Glu Ile Ala Asp Gly Met Ala Tyr Leu
            180                 185                 190

Asn Ala Lys Lys Phe Val His Arg Asp Leu Ala Ala Arg Asn Cys Met
```

-continued

```
                195                 200                 205
Val Ala His Asp Phe Thr Val Lys Ile Gly Asp Phe Gly Met Thr Arg
    210                 215                 220
Asp Ile Tyr Glu Thr Asp Tyr Tyr Arg Lys Gly Gly Lys Gly Leu Leu
225                 230                 235                 240
Pro Val Arg Trp Met Ala Pro Glu Ser Leu Lys Asp Gly Val Phe Thr
                245                 250                 255
Thr Ser Ser Asp Met Trp Ser Phe Gly Val Val Leu Trp Glu Ile Thr
                260                 265                 270
Ser Leu Ala Glu Gln Pro Tyr Gln Gly Leu Ser Asn Glu Gln Val Leu
                275                 280                 285
Lys Phe Val Met Asp Gly Gly Tyr Leu Asp Gln Pro Asp Asn Cys Pro
    290                 295                 300
Glu Arg Val Thr Asp Leu Met Arg Met Cys Trp Gln Phe Asn Pro Lys
305                 310                 315                 320
Met Arg Pro Thr Phe Leu Glu Ile Val Asn Leu Leu Lys Asp Asp Leu
                325                 330                 335
His Pro Ser Phe Pro Glu Val Ser Phe Phe His Ser Glu Glu Asn Lys
                340                 345                 350
Ala Pro Glu Ser Glu Glu Leu Glu Met Glu Phe Glu Asp Met Glu Asn
                355                 360                 365
Val Pro Leu Asp Arg Ser
    370

<210> SEQ ID NO 109
<211> LENGTH: 384
<212> TYPE: PRT
<213> ORGANISM: Drosophila melanogaster

<400> SEQUENCE: 109

Gly Ile Gly Leu Ala Phe Leu Ile Val Ser Leu Phe Gly Tyr Val Cys
  1               5                  10                  15
Tyr Leu His Lys Arg Lys Val Pro Ser Asn Asp Leu His Met Asn Thr
                 20                  25                  30
Glu Val Asn Pro Phe Tyr Ala Ser Met Gln Tyr Ile Pro Asp Asp Trp
             35                  40                  45
Glu Val Leu Arg Glu Asn Ile Ile Gln Leu Ala Pro Leu Gly Gln Gly
         50                  55                  60
Ser Phe Gly Met Val Tyr Glu Gly Ile Leu Lys Ser Phe Pro Pro Asn
 65                  70                  75                  80
Gly Val Asp Arg Glu Cys Ala Ile Lys Thr Val Asn Glu Asn Ala Thr
                 85                  90                  95
Asp Arg Glu Arg Thr Asn Phe Leu Ser Glu Ala Ser Val Met Lys Glu
                100                 105                 110
Phe Asp Thr Tyr His Val Val Arg Leu Leu Gly Val Cys Ser Arg Gly
            115                 120                 125
Gln Pro Ala Leu Val Val Met Glu Leu Met Lys Lys Gly Asp Leu Lys
        130                 135                 140
Ser Tyr Leu Arg Ala His Arg Pro Glu Glu Arg Asp Glu Ala Met Met
145                 150                 155                 160
Thr Tyr Leu Asn Arg Ile Gly Val Thr Gly Asn Val Gln Pro Pro Thr
                165                 170                 175
Tyr Gly Arg Ile Tyr Gln Met Ala Ile Glu Ile Ala Asp Gly Met Ala
            180                 185                 190
```

```
Tyr Leu Ala Ala Lys Lys Phe Val His Arg Asp Leu Ala Ala Arg Asn
            195                 200                 205

Cys Met Val Ala Asp Asp Leu Thr Val Lys Ile Gly Asp Phe Gly Met
    210                 215                 220

Thr Arg Asp Ile Tyr Glu Thr Asp Tyr Tyr Arg Lys Gly Thr Lys Gly
225                 230                 235                 240

Leu Leu Pro Val Arg Trp Met Pro Pro Glu Ser Leu Arg Asp Gly Val
                245                 250                 255

Tyr Ser Ser Ala Ser Asp Val Phe Ser Phe Gly Val Val Leu Trp Glu
            260                 265                 270

Met Ala Thr Leu Ala Ala Gln Pro Tyr Gln Gly Leu Ser Asn Glu Gln
        275                 280                 285

Val Leu Arg Tyr Val Ile Asp Gly Gly Val Met Glu Arg Pro Glu Asn
    290                 295                 300

Cys Pro Asp Phe Leu His Lys Leu Met Gln Arg Cys Trp His His Arg
305                 310                 315                 320

Ser Ser Ala Arg Pro Ser Phe Leu Asp Ile Ile Ala Tyr Leu Glu Pro
                325                 330                 335

Gln Cys Pro Asn Ser Gln Phe Lys Glu Val Ser Phe Tyr His Ser Glu
            340                 345                 350

Ala Gly Leu Gln His Arg Glu Lys Glu Arg Lys Glu Arg Asn Gln Leu
        355                 360                 365

Asp Ala Phe Ala Ala Val Pro Leu Asp Gln Asp Leu Gln Asp Arg Glu
    370                 375                 380

<210> SEQ ID NO 110
<211> LENGTH: 380
<212> TYPE: PRT
<213> ORGANISM: Caenorhabditis elegans

<400> SEQUENCE: 110

Gly Met Leu Leu Val Phe Leu Ile Leu Met Ser Ile Ala Gly Cys Ile
1               5                   10                  15

Ile Tyr Tyr Tyr Ile Gln Val Arg Tyr Gly Lys Lys Val Lys Ala Leu
            20                  25                  30

Ser Asp Phe Met Gln Leu Asn Pro Glu Tyr Cys Val Asp Asn Lys Tyr
        35                  40                  45

Asn Ala Asp Asp Trp Glu Leu Arg Gln Asp Val Val Leu Gly Gln
50                  55                  60

Gln Cys Gly Glu Gly Ser Phe Gly Lys Val Tyr Leu Gly Thr Gly Asn
65                  70                  75                  80

Asn Val Val Ser Leu Met Gly Asp Arg Phe Gly Pro Cys Ala Ile Lys
            85                  90                  95

Ile Asn Val Asp Asp Pro Ala Ser Thr Glu Asn Leu Asn Tyr Leu Met
        100                 105                 110

Glu Ala Asn Ile Met Lys Asn Phe Lys Thr Asn Phe Ile Val Gln Leu
    115                 120                 125

Tyr Gly Val Ile Ser Thr Val Gln Pro Ala Met Val Val Met Glu Met
130                 135                 140

Met Asp Leu Gly Asn Leu Arg Asp Tyr Leu Arg Ser Lys Arg Glu Asp
145                 150                 155                 160

Glu Val Phe Asn Glu Thr Asp Cys Asn Phe Phe Asp Ile Ile Pro Arg
                165                 170                 175

Asp Lys Phe His Glu Trp Ala Ala Gln Ile Cys Asp Gly Met Ala Tyr
            180                 185                 190
```

```
Leu Glu Ser Leu Lys Phe Cys His Arg Asp Leu Ala Ala Arg Asn Cys
            195                 200                 205

Met Ile Asn Arg Asp Glu Thr Val Lys Ile Gly Asp Phe Gly Met Ala
            210                 215                 220

Arg Asp Leu Phe Tyr His Asp Tyr Tyr Lys Pro Ser Gly Lys Arg Met
225                 230                 235                 240

Met Pro Val Arg Trp Met Ser Pro Glu Ser Leu Lys Asp Gly Lys Phe
            245                 250                 255

Asp Ser Lys Ser Asp Val Trp Ser Phe Gly Val Val Leu Tyr Glu Met
            260                 265                 270

Val Thr Leu Gly Ala Gln Pro Tyr Ile Gly Leu Ser Asn Asp Glu Val
            275                 280                 285

Leu Asn Tyr Ile Gly Met Ala Arg Lys Val Ile Lys Pro Glu Cys
            290                 295                 300

Cys Glu Asn Tyr Trp Tyr Lys Val Met Lys Met Cys Trp Arg Tyr Ser
305                 310                 315                 320

Pro Arg Asp Arg Pro Thr Phe Leu Gln Leu Val His Leu Leu Ala Ala
            325                 330                 335

Glu Ala Ser Pro Glu Phe Arg Asp Leu Ser Phe Val Leu Thr Asp Asn
            340                 345                 350

Gln Met Ile Leu Asp Asp Ser Glu Ala Leu Asp Leu Asp Asp Ile Asp
            355                 360                 365

Asp Thr Asp Met Asn Asp Gln Val Val Glu Val Ala
            370                 375                 380

<210> SEQ ID NO 111
<211> LENGTH: 103
<212> TYPE: PRT
<213> ORGANISM: Caenorhabditis elegans

<400> SEQUENCE: 111

Asn Ile Asp Arg Glu Phe Asp Gln Lys Ala Cys Glu Ser Leu Val Lys
1               5                   10                  15

Lys Leu Lys Asp Lys Asn Asp Leu Gln Asn Leu Ile Asp Val Val
            20                  25                  30

Leu Ser Lys Gly Thr Lys Tyr Thr Gly Cys Ile Thr Ile Pro Arg Thr
        35                  40                  45

Leu Asp Gly Arg Leu Gln Val His Gly Arg Lys Gly Phe Pro His Val
    50                  55                  60

Val Tyr Gly Lys Leu Trp Arg Phe Asn Glu Met Thr Lys Asn Glu Thr
65                  70                  75                  80

Arg His Val Asp His Cys Lys His Ala Phe Glu Met Lys Ser Asp Met
                85                  90                  95

Val Cys Val Asn Pro Tyr His
            100

<210> SEQ ID NO 112
<211> LENGTH: 104
<212> TYPE: PRT
<213> ORGANISM: Homo sapiens

<400> SEQUENCE: 112

Gly Gly Glu Ser Glu Thr Phe Ala Lys Arg Ala Ile Glu Ser Leu Val
1               5                   10                  15

Lys Lys Leu Lys Glu Lys Lys Asp Glu Leu Asp Ser Leu Ile Thr Ala
            20                  25                  30
```

```
Ile Thr Thr Asn Gly Ala His Pro Ser Lys Cys Val Thr Ile Gln Arg
            35                  40                  45

Thr Leu Asp Gly Arg Leu Gln Val Ala Gly Arg Lys Gly Phe Pro His
    50                  55                  60

Val Ile Tyr Ala Arg Leu Trp Arg Trp Pro Asp Leu His Lys Asn Glu
65                  70                  75                  80

Leu Lys His Val Lys Tyr Cys Gln Tyr Ala Phe Asp Leu Lys Cys Asp
                85                  90                  95

Ser Val Cys Val Asn Pro Tyr His
                100
```

<210> SEQ ID NO 113
<211> LENGTH: 205
<212> TYPE: PRT
<213> ORGANISM: Caenorhabditis elegans

<400> SEQUENCE: 113

```
Ile Val Tyr Tyr Glu Lys Asn Leu Gln Ile Gly Glu Lys Lys Cys Ser
1               5                   10                  15

Arg Gly Asn Phe His Val Asp Gly Gly Phe Ile Cys Ser Glu Asn Arg
            20                  25                  30

Tyr Ser Leu Gly Leu Glu Pro Asn Pro Ile Arg Glu Pro Val Ala Phe
            35                  40                  45

Lys Val Arg Lys Ala Ile Val Asp Gly Ile Arg Phe Ser Tyr Lys Lys
            50                  55                  60

Asp Gly Ser Val Trp Leu Gln Asn Arg Met Lys Tyr Pro Val Phe Val
65                  70                  75                  80

Thr Ser Gly Tyr Leu Asp Glu Gln Ser Gly Gly Leu Lys Lys Asp Lys
                85                  90                  95

Val His Lys Val Tyr Gly Cys Ala Ser Ile Lys Thr Phe Gly Phe Asn
                100                 105                 110

Val Ser Lys Gln Ile Ile Arg Asp Ala Leu Leu Ser Lys Gln Met Ala
            115                 120                 125

Thr Met Tyr Leu Gln Gly Lys Leu Thr Pro Met Asn Tyr Ile Tyr Glu
    130                 135                 140

Lys Lys Thr Gln Glu Glu Leu Arg Arg Glu Ala Thr Arg Thr Thr Asp
145                 150                 155                 160

Ser Leu Ala Lys Tyr Cys Cys Val Arg Val Ser Phe Cys Lys Gly Phe
                165                 170                 175

Gly Glu Ala Tyr Pro Glu Arg Pro Ser Ile His Asp Cys Pro Val Trp
            180                 185                 190

Ile Glu Leu Lys Ile Asn Ile Ala Tyr Asp Phe Met Asp
            195                 200                 205
```

<210> SEQ ID NO 114
<211> LENGTH: 212
<212> TYPE: PRT
<213> ORGANISM: Homo sapiens

<400> SEQUENCE: 114

```
Ile Ala Tyr Phe Glu Met Asp Val Gln Val Gly Glu Thr Phe Lys Val
1               5                   10                  15

Pro Ser Ser Cys Pro Ile Val Thr Val Asp Gly Tyr Val Asp Pro Ser
            20                  25                  30

Gly Gly Asp Arg Phe Cys Leu Gly Gln Leu Ser Asn Val His Arg Thr
            35                  40                  45
```

```
Glu Ala Ile Glu Arg Ala Arg Leu His Ile Gly Lys Gly Val Gln Leu
 50                  55                  60

Glu Cys Lys Gly Glu Gly Asp Val Trp Val Arg Cys Leu Ser Asp His
 65                  70                  75                  80

Ala Val Phe Val Gln Ser Tyr Tyr Leu Asp Arg Glu Ala Gly Arg Ala
                 85                  90                  95

Pro Gly Asp Ala Val His Lys Ile Tyr Pro Ser Ala Tyr Ile Lys Val
            100                 105                 110

Phe Asp Leu Arg Gln Cys His Arg Gln Met Gln Gln Ala Ala Thr
            115                 120                 125

Ala Gln Ala Ala Ala Ala Gln Ala Ala Val Ala Gly Asn Ile
130                 135                 140

Pro Gly Pro Gly Ser Val Gly Gly Ile Ala Pro Ala Ile Ser Leu Ser
145                 150                 155                 160

Ala Ala Ala Gly Ile Gly Val Asp Asp Leu Arg Arg Leu Cys Ile Leu
                165                 170                 175

Arg Met Ser Phe Val Lys Gly Trp Gly Pro Asp Tyr Pro Arg Gln Ser
            180                 185                 190

Ile Lys Glu Thr Pro Cys Trp Ile Glu Ile His Leu His Arg Ala Leu
            195                 200                 205

Gln Leu Leu Asp
        210

<210> SEQ ID NO 115
<211> LENGTH: 50
<212> TYPE: PRT
<213> ORGANISM: Caenorhabditis elegans
<220> FEATURE:
<221> NAME/KEY: VARIANT
<222> LOCATION: (1)...(50)
<223> OTHER INFORMATION: Xaa = Any Amino Acid

<400> SEQUENCE: 115

Leu Cys Gly Xaa Xaa Leu Val Glu Ala Leu Xaa Xaa Val Cys Gly Xaa
 1                5                  10                  15

Arg Gly Phe Phe Tyr Thr Pro Lys Thr Arg Arg Lys Arg Gly Ile Val
                20                  25                  30

Glu Gln Cys Cys Xaa Xaa Xaa Cys Xaa Xaa Xaa Gln Leu Glu Xaa Tyr
            35                  40                  45

Cys Asn
    50

<210> SEQ ID NO 116
<211> LENGTH: 39
<212> TYPE: PRT
<213> ORGANISM: Caenorhabditis elegans

<400> SEQUENCE: 116

Leu Cys Gly Arg His Leu Ala Asp Ala Leu Tyr Phe Val Cys Gly Asn
 1                5                  10                  15

Arg Gly Phe Gly Ile Val Glu Cys Cys His Asn Pro Cys Thr Leu
                20                  25                  30

Tyr Gln Leu Glu Asn Tyr Cys
        35

<210> SEQ ID NO 117
<211> LENGTH: 112
<212> TYPE: PRT
```

```
<213> ORGANISM: Caenorhabditis elegans

<400> SEQUENCE: 117

Met Asn Ser Val Phe Thr Ile Ile Phe Val Leu Cys Ala Leu Gln Val
1               5                   10                  15

Ala Ala Ser Phe Arg Gln Ser Phe Gly Pro Ser Met Ser Glu Glu Ser
            20                  25                  30

Ala Ser Met Gln Leu Leu Arg Glu Leu Gln His Asn Met Met Glu Ser
        35                  40                  45

Ala His Arg Pro Met Pro Arg Ala Arg Arg Val Pro Ala Pro Gly Glu
    50                  55                  60

Thr Arg Ala Cys Gly Arg Lys Leu Ile Ser Leu Val Met Ala Val Cys
65                  70                  75                  80

Gly Asp Leu Cys Asn Pro Gln Gly Gly Lys Asp Ile Ala Thr Glu Cys
                85                  90                  95

Cys Gly Asn Gln Cys Ser Asp Asp Tyr Ile Arg Ser Ala Cys Cys Pro
            100                 105                 110

<210> SEQ ID NO 118
<211> LENGTH: 106
<212> TYPE: PRT
<213> ORGANISM: Caenorhabditis elegans

<400> SEQUENCE: 118

Met Phe Ser Phe Phe Thr Tyr Phe Leu Leu Ser Ala Leu Leu Leu Ser
1               5                   10                  15

Ala Ser Cys Arg Gln Pro Ser Met Asp Thr Ser Lys Ala Asp Arg Ile
            20                  25                  30

Leu Arg Glu Ile Glu Met Glu Thr Glu Leu Glu Asn Gln Leu Ser Arg
        35                  40                  45

Ala Arg Arg Val Pro Ala Gly Glu Val Arg Ala Cys Gly Arg Arg Leu
    50                  55                  60

Leu Leu Phe Val Trp Ser Thr Cys Gly Glu Pro Cys Thr Pro Gln Glu
65                  70                  75                  80

Asp Met Asp Ile Ala Thr Val Cys Cys Thr Thr Gln Cys Thr Pro Ser
                85                  90                  95

Tyr Ile Lys Gln Ala Cys Cys Pro Glu Lys
            100                 105

<210> SEQ ID NO 119
<211> LENGTH: 105
<212> TYPE: PRT
<213> ORGANISM: Caenorhabditis elegans

<400> SEQUENCE: 119

Met Pro Pro Ile Ile Leu Val Phe Phe Leu Val Leu Ile Pro Ala Ser
1               5                   10                  15

Gln Gln Tyr Pro Phe Ser Leu Glu Ser Leu Asn Asp Gln Ile Ile Asn
            20                  25                  30

Glu Glu Val Ile Glu Tyr Met Leu Glu Asn Ser Ile Arg Ser Ser Arg
        35                  40                  45

Thr Arg Arg Val Pro Asp Glu Lys Lys Ile Tyr Arg Cys Gly Arg Arg
    50                  55                  60

Ile His Ser Tyr Val Phe Ala Val Cys Gly Lys Ala Cys Glu Ser Asn
65                  70                  75                  80

Thr Glu Val Asn Ile Ala Ser Lys Cys Cys Arg Glu Glu Cys Thr Asp
                85                  90                  95
```

-continued

```
Asp Phe Ile Arg Lys Gln Cys Cys Pro
            100             105

<210> SEQ ID NO 120
<211> LENGTH: 118
<212> TYPE: PRT
<213> ORGANISM: Caenorhabditis elegans

<400> SEQUENCE: 120

Met Ile Val Thr Leu Ile Val Phe Leu Val Ile Gly Leu Gln Met Ala
1               5                   10                  15

His Leu Ser Gln Val Ser Gly Asn Glu Asn Gly Phe Leu Asn Pro
            20                  25                  30

Phe Asp Leu Ser Gln Trp Ser Glu Glu Ile Leu His Arg Gln Tyr His
        35                  40                  45

His His His His His His Gly Asn Arg Ala Arg Arg Thr Leu Glu
    50                  55                  60

Thr Glu Lys Ile Tyr Arg Cys Gly Arg Lys Leu Tyr Thr Asp Val Leu
65                  70                  75                  80

Ser Ala Cys Asn Gly Pro Cys Glu Pro Gly Thr Glu Gln Asp Leu Ser
                85                  90                  95

Lys Leu Cys Cys Gly Asn Gln Cys Thr Phe Val Glu Ile Arg Lys Ala
            100                 105                 110

Cys Cys Ala Asp Lys Leu
        115

<210> SEQ ID NO 121
<211> LENGTH: 106
<212> TYPE: PRT
<213> ORGANISM: Caenorhabditis elegans

<400> SEQUENCE: 121

Met Asn Ala Ile Ile Phe Cys Leu Leu Phe Thr Thr Val Thr Ala Thr
1               5                   10                  15

Tyr Glu Val Phe Gly Lys Gly Ile Glu His Arg Asn Glu His Leu Ile
            20                  25                  30

Ile Asn Gln Leu Asp Ile Ile Pro Val Glu Ser Thr Pro Thr Pro Asn
        35                  40                  45

Arg Ala Ser Arg Val Gln Lys Arg Leu Cys Gly Arg Arg Leu Ile Leu
    50                  55                  60

Phe Met Leu Ala Thr Cys Gly Glu Cys Asp Thr Asp Ser Ser Glu Asp
65                  70                  75                  80

Leu Ser His Ile Cys Cys Ile Lys Gln Cys Asp Val Gln Asp Ile Ile
                85                  90                  95

Arg Val Cys Cys Pro Asn Ser Phe Arg Lys
            100                 105

<210> SEQ ID NO 122
<211> LENGTH: 107
<212> TYPE: PRT
<213> ORGANISM: Caenorhabditis elegans

<400> SEQUENCE: 122

Met Lys Leu Ser Val Val Leu Ala Leu Phe Ile Ile Phe Gln Leu Gly
1               5                   10                  15

Ala Ala Ser Leu Met Arg Asn Trp Met Phe Asp Phe Glu Lys Glu Leu
            20                  25                  30
```

Glu His Asp Tyr Asp Asp Ser Glu Ile Gly Phe His Asn Ile His Ser
                35                  40                  45

Leu Met Ala Arg Ser Arg Arg Gly Asp Lys Val Lys Ile Cys Gly Thr
    50                  55                  60

Lys Val Leu Lys Met Val Met Val Met Cys Gly Gly Glu Cys Ser Ser
65                  70                  75                  80

Thr Asn Glu Asn Ile Ala Thr Glu Cys Cys Glu Lys Met Cys Thr Met
                85                  90                  95

Glu Asp Ile Thr Thr Lys Cys Cys Pro Ser Arg
            100                 105

<210> SEQ ID NO 123
<211> LENGTH: 73
<212> TYPE: PRT
<213> ORGANISM: Caenorhabditis elegans

<400> SEQUENCE: 123

Met Lys Leu Leu His Ile Phe Ile Ile Phe Leu Leu Phe Gln Ser Cys
1               5                   10                  15

Ser Asn Lys Met Cys Gln Tyr Ser Lys Lys Lys Tyr Lys Ile Cys Gly
                20                  25                  30

Val Arg Ala Leu Lys His Met Lys Val Tyr Cys Thr Arg Gly Met Thr
            35                  40                  45

Arg Asp Tyr Gly Lys Leu Leu Val Thr Cys Cys Ser Lys Gly Cys Asn
    50                  55                  60

Ala Ile Asp Ile Gln Arg Ile Cys Leu
65                  70

<210> SEQ ID NO 124
<211> LENGTH: 109
<212> TYPE: PRT
<213> ORGANISM: Caenorhabditis elegans

<400> SEQUENCE: 124

Met Tyr Trp Phe Arg Gln Val Tyr Arg Pro Ser Phe Phe Gly Phe
1               5                   10                  15

Leu Ala Ile Leu Leu Leu Ser Ser Pro Thr Pro Ser Asp Ala Ser Ile
                20                  25                  30

Arg Leu Cys Gly Ser Arg Leu Thr Thr Thr Leu Leu Ala Val Cys Arg
            35                  40                  45

Asn Gln Leu Cys Thr Gly Leu Thr Ala Phe Lys Arg Ser Ala Asp Gln
    50                  55                  60

Ser Tyr Ala Pro Thr Thr Arg Asp Leu Phe His Ile His His Gln Gln
65                  70                  75                  80

Lys Arg Gly Gly Ile Ala Thr Glu Cys Cys Glu Lys Arg Cys Ser Phe
                85                  90                  95

Ala Tyr Leu Lys Thr Phe Cys Cys Asn Gln Asp Asp Asn
            100                 105

<210> SEQ ID NO 125
<211> LENGTH: 110
<212> TYPE: PRT
<213> ORGANISM: Homo sapiens

<400> SEQUENCE: 125

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly

```
                    20                  25                  30
Ser His Leu Val Glu Ala Leu Tyr Leu Val Cys Gly Glu Arg Gly Phe
             35                  40                  45

Phe Tyr Thr Pro Lys Thr Arg Arg Glu Ala Glu Asp Leu Gln Val Gly
         50                  55                  60

Gln Val Glu Leu Gly Gly Pro Gly Ala Gly Ser Leu Gln Pro Leu
 65                  70                  75                  80

Ala Leu Glu Gly Ser Leu Gln Lys Arg Gly Ile Val Glu Gln Cys Cys
                 85                  90                  95

Thr Ser Ile Cys Ser Leu Tyr Gln Leu Glu Asn Tyr Cys Asn
            100                 105                 110

<210> SEQ ID NO 126
<211> LENGTH: 46
<212> TYPE: PRT
<213> ORGANISM: Caenorhabditis elegans
<220> FEATURE:
<221> NAME/KEY: VARIANT
<222> LOCATION: (1)...(46)
<223> OTHER INFORMATION: Xaa = Any Amino Acid

<400> SEQUENCE: 126

Ala Cys Gly Arg Arg Leu Leu Leu Phe Val Trp Ser Thr Cys Gly Glu
 1               5                  10                  15

Pro Cys Thr Xaa Xaa Xaa Gln Glu Asp Met Asp Ile Ala Thr Val Cys
                 20                  25                  30

Cys Thr Thr Gln Cys Thr Pro Ser Tyr Ile Lys Gln Ala Cys
             35                  40                  45

<210> SEQ ID NO 127
<211> LENGTH: 46
<212> TYPE: PRT
<213> ORGANISM: Caenorhabditis elegans
<220> FEATURE:
<221> NAME/KEY: VARIANT
<222> LOCATION: (1)...(46)
<223> OTHER INFORMATION: Xaa = Any Amino Acid

<400> SEQUENCE: 127

Ala Cys Gly Arg Lys Leu Ile Ser Leu Val Met Ala Val Cys Gly Asp
 1               5                  10                  15

Leu Cys Asn Xaa Xaa Xaa Gln Glu Gly Lys Asp Ile Ala Thr Glu Cys
                 20                  25                  30

Cys Gly Asn Gln Cys Ser Asp Asp Tyr Ile Arg Ser Ala Cys
             35                  40                  45

<210> SEQ ID NO 128
<211> LENGTH: 46
<212> TYPE: PRT
<213> ORGANISM: Caenorhabditis elegans
<220> FEATURE:
<221> NAME/KEY: VARIANT
<222> LOCATION: (1)...(46)
<223> OTHER INFORMATION: Xaa = Any Amino Acid

<400> SEQUENCE: 128

Arg Cys Gly Arg Arg Ile His Ser Tyr Val Phe Ala Val Cys Gly Lys
 1               5                  10                  15

Ala Cys Glu Xaa Xaa Xaa Ser Thr Glu Val Asn Ile Ala Ser Lys Cys
                 20                  25                  30

Cys Arg Glu Glu Cys Thr Asp Asp Phe Ile Arg Lys Gln Cys
             35                  40                  45
```

```
<210> SEQ ID NO 129
<211> LENGTH: 46
<212> TYPE: PRT
<213> ORGANISM: Caenorhabditis elegans
<220> FEATURE:
<221> NAME/KEY: VARIANT
<222> LOCATION: (1)...(46)
<223> OTHER INFORMATION: Xaa = Any Amino Acid

<400> SEQUENCE: 129

Arg Cys Gly Arg Lys Leu Tyr Thr Asp Val Leu Ser Ala Cys Asn Gly
 1               5                  10                  15

Pro Cys Glu Xaa Xaa Xaa Gly Thr Glu Gln Asp Leu Ser Lys Leu Cys
             20                  25                  30

Cys Gly Asn Gln Cys Thr Phe Asx Glu Ile Arg Lys Ala Cys
         35                  40                  45

<210> SEQ ID NO 130
<211> LENGTH: 46
<212> TYPE: PRT
<213> ORGANISM: Caenorhabditis elegans
<220> FEATURE:
<221> NAME/KEY: VARIANT
<222> LOCATION: (1)...(46)
<223> OTHER INFORMATION: Xaa = Any Amino Acid

<400> SEQUENCE: 130

Ile Cys Gly Thr Lys Asx Leu Lys Met Val Met Val Met Cys Gly Gly
 1               5                  10                  15

Glu Cys Ser Xaa Xaa Xaa Ser Thr Asn Glu Asn Ile Ala Thr Glu Cys
             20                  25                  30

Cys Glu Lys Met Cys Thr Met Glu Asp Ile Thr Thr Lys Cys
         35                  40                  45

<210> SEQ ID NO 131
<211> LENGTH: 46
<212> TYPE: PRT
<213> ORGANISM: Caenorhabditis elegans
<220> FEATURE:
<221> NAME/KEY: VARIANT
<222> LOCATION: (1)...(46)
<223> OTHER INFORMATION: Xaa = Any Amino Acid

<400> SEQUENCE: 131

Leu Cys Gly Arg Arg Leu Ile Leu Phe Met Leu Ala Thr Cys Gly Glu
 1               5                  10                  15

Cys Asp Thr Xaa Xaa Xaa Asp Ser Ser Glu Asp Leu Ser His Ile Cys
             20                  25                  30

Cys Ile Lys Gln Cys Asp Val Gln Asp Ile Ile Arg Val Cys
         35                  40                  45

<210> SEQ ID NO 132
<211> LENGTH: 46
<212> TYPE: PRT
<213> ORGANISM: Caenorhabditis elegans
<220> FEATURE:
<221> NAME/KEY: VARIANT
<222> LOCATION: (1)...(46)
<223> OTHER INFORMATION: Xaa = Any Amino Acid

<400> SEQUENCE: 132

Leu Cys Gly Ser His Leu Val Glu Ala Leu Tyr Leu Val Cys Gly Glu
 1               5                  10                  15
```

```
Arg Gly Phe Xaa Xaa Xaa Leu Gln Lys Arg Gly Ile Val Glu Gln Cys
            20              25                  30

Cys Thr Ser Ile Cys Ser Leu Tyr Gln Leu Glu Asn Tyr Cys
            35              40              45
```

<210> SEQ ID NO 133
<211> LENGTH: 46
<212> TYPE: PRT
<213> ORGANISM: Rabbit
<220> FEATURE:
<221> NAME/KEY: VARIANT
<222> LOCATION: (1)...(46)
<223> OTHER INFORMATION: Xaa = Any Amino Acid

<400> SEQUENCE: 133

```
Leu Cys Gly Ser His Leu Val Glu Ala Leu Tyr Leu Val Cys Gly Glu
 1               5                  10                  15

Arg Gly Phe Xaa Xaa Xaa Thr Pro Lys Ser Gly Ile Val Glu Gln Cys
            20              25                  30

Cys Thr Ser Ile Cys Ser Leu Tyr Gln Leu Glu Asn Tyr Cys
            35              40              45
```

<210> SEQ ID NO 134
<211> LENGTH: 46
<212> TYPE: PRT
<213> ORGANISM: Xenopus laevis
<220> FEATURE:
<221> NAME/KEY: VARIANT
<222> LOCATION: (1)...(46)
<223> OTHER INFORMATION: Xaa = Any Amino Acid

<400> SEQUENCE: 134

```
Leu Cys Gly Ser His Leu Val Glu Ala Leu Tyr Leu Val Cys Gly Asp
 1               5                  10                  15

Arg Gly Phe Xaa Xaa Xaa Lys Met Lys Arg Gly Ile Val Glu Gln Cys
            20              25                  30

Cys His Ser Thr Cys Ser Leu Phe Gln Leu Glu Ser Tyr Cys
            35              40              45
```

<210> SEQ ID NO 135
<211> LENGTH: 46
<212> TYPE: PRT
<213> ORGANISM: Xenopus laevis
<220> FEATURE:
<221> NAME/KEY: VARIANT
<222> LOCATION: (1)...(46)
<223> OTHER INFORMATION: Xaa = Any Amino Acid

<400> SEQUENCE: 135

```
Leu Cys Gly Ser His Leu Val Glu Ala Leu Tyr Leu Val Cys Gly Asp
 1               5                  10                  15

Arg Gly Phe Xaa Xaa Xaa Lys Met Lys Arg Gly Ile Val Glu Gln Cys
            20              25                  30

Cys His Ser Thr Cys Ser Leu Phe Gln Leu Glu Asn Tyr Cys
            35              40              45
```

<210> SEQ ID NO 136
<211> LENGTH: 46
<212> TYPE: PRT
<213> ORGANISM: Alligator
<220> FEATURE:
<221> NAME/KEY: VARIANT
<222> LOCATION: (1)...(46)
<223> OTHER INFORMATION: Xaa = Any Amino Acid -continued

```
<400> SEQUENCE: 136

Leu Cys Gly Ser His Leu Val Asp Ala Leu Tyr Leu Val Cys Gly Glu
1               5                   10                  15

Arg Gly Phe Xaa Xaa Xaa Ser Pro Lys Gly Gly Ile Val Glu Gln Cys
            20                  25                  30

Cys His Asn Thr Cys Ser Leu Tyr Gln Leu Glu Asn Tyr Cys
        35                  40                  45

<210> SEQ ID NO 137
<211> LENGTH: 46
<212> TYPE: PRT
<213> ORGANISM: Elephant fish
<220> FEATURE:
<221> NAME/KEY: VARIANT
<222> LOCATION: (1)...(46)
<223> OTHER INFORMATION: Xaa = Any Amino Acid

<400> SEQUENCE: 137

Leu Cys Gly Ser His Leu Val Asp Ala Leu Tyr Phe Val Cys Gly Glu
1               5                   10                  15

Arg Gly Phe Xaa Xaa Xaa Pro Lys Gln Ile Gly Ile Val Glu Gln Cys
            20                  25                  30

Cys His Asn Thr Cys Ser Leu Val Asn Leu Glu Gly Tyr Cys
        35                  40                  45

<210> SEQ ID NO 138
<211> LENGTH: 46
<212> TYPE: PRT
<213> ORGANISM: Bos taurus
<220> FEATURE:
<221> NAME/KEY: VARIANT
<222> LOCATION: (1)...(46)
<223> OTHER INFORMATION: Xaa = Any Amino Acid

<400> SEQUENCE: 138

Leu Cys Gly Ala Glu Leu Val Asp Ala Leu Gln Phe Val Cys Gly Asp
1               5                   10                  15

Arg Gly Phe Xaa Xaa Xaa Ala Pro Gln Thr Gly Ile Val Asp Glu Cys
            20                  25                  30

Cys Phe Arg Ser Cys Asp Leu Arg Arg Leu Glu Met Tyr Cys
        35                  40                  45

<210> SEQ ID NO 139
<211> LENGTH: 46
<212> TYPE: PRT
<213> ORGANISM: Canis
<220> FEATURE:
<221> NAME/KEY: VARIANT
<222> LOCATION: (1)...(46)
<223> OTHER INFORMATION: Xaa = Any Amino Acid

<400> SEQUENCE: 139

Leu Cys Gly Ala Glu Leu Val Asp Ala Leu Gln Phe Val Cys Gly Asp
1               5                   10                  15

Arg Gly Phe Xaa Xaa Xaa Ala Pro Gln Thr Gly Ile Val Asp Glu Cys
            20                  25                  30

Cys Phe Arg Ser Cys Asp Leu Arg Arg Leu Glu Met Tyr Cys
        35                  40                  45

<210> SEQ ID NO 140
<211> LENGTH: 46
<212> TYPE: PRT
<213> ORGANISM: Horse
```

```
<220> FEATURE:
<221> NAME/KEY: VARIANT
<222> LOCATION: (1)...(46)
<223> OTHER INFORMATION: Xaa = Any Amino Acid

<400> SEQUENCE: 140

Leu Cys Gly Gly Glu Leu Val Asp Thr Leu Gln Phe Val Cys Gly Asp
1               5                   10                  15

Arg Gly Phe Xaa Xaa Xaa Arg Arg Ser Arg Gly Ile Val Glu Glu Cys
            20                  25                  30

Cys Phe Arg Ser Cys Asp Leu Ala Leu Leu Glu Thr Tyr Cys
        35                  40                  45

<210> SEQ ID NO 141
<211> LENGTH: 46
<212> TYPE: PRT
<213> ORGANISM: Homo sapiens
<220> FEATURE:
<221> NAME/KEY: VARIANT
<222> LOCATION: (1)...(46)
<223> OTHER INFORMATION: Xaa = Any Amino Acid

<400> SEQUENCE: 141

Leu Cys Gly Gly Glu Leu Val Asp Thr Leu Gln Phe Val Cys Gly Asp
1               5                   10                  15

Arg Gly Phe Xaa Xaa Xaa Arg Arg Ser Arg Gly Ile Val Glu Glu Cys
            20                  25                  30

Cys Phe Arg Ser Cys Asp Leu Ala Leu Leu Glu Thr Tyr Cys
        35                  40                  45

<210> SEQ ID NO 142
<211> LENGTH: 46
<212> TYPE: PRT
<213> ORGANISM: Amphioxus
<220> FEATURE:
<221> NAME/KEY: VARIANT
<222> LOCATION: (1)...(46)
<223> OTHER INFORMATION: Xaa = Any Amino Acid

<400> SEQUENCE: 142

Leu Cys Gly Ser Thr Leu Ala Asp Val Leu Ser Phe Val Cys Gly Asn
1               5                   10                  15

Arg Gly Tyr Xaa Xaa Xaa Arg Arg Arg Gly Leu Val Glu Glu Cys
            20                  25                  30

Cys Tyr Asn Val Cys Asp Tyr Ser Gln Leu Glu Ser Tyr Cys
        35                  40                  45

<210> SEQ ID NO 143
<211> LENGTH: 46
<212> TYPE: PRT
<213> ORGANISM: Locust
<220> FEATURE:
<221> NAME/KEY: VARIANT
<222> LOCATION: (1)...(46)
<223> OTHER INFORMATION: Xaa = Any Amino Acid

<400> SEQUENCE: 143

Tyr Cys Gly Glu Lys Leu Ser Asn Ala Leu Lys Leu Val Cys Arg Gly
1               5                   10                  15

Asn Tyr Asn Xaa Xaa Xaa Arg Arg Thr Arg Gly Val Phe Asp Glu Cys
            20                  25                  30

Cys Arg Lys Ser Cys Ser Ile Ser Glu Leu Gln Thr Tyr Cys
        35                  40                  45
```

```
<210> SEQ ID NO 144
<211> LENGTH: 46
<212> TYPE: PRT
<213> ORGANISM: Bommo
<220> FEATURE:
<221> NAME/KEY: VARIANT
<222> LOCATION: (1)...(46)
<223> OTHER INFORMATION: Xaa = Any Amino Acid

<400> SEQUENCE: 144

Tyr Cys Gly Arg His Leu Ala Arg Thr Leu Ala Asp Leu Cys Trp Glu
 1               5                  10                  15

Ala Gly Val Xaa Xaa Xaa Arg Gly Lys Arg Gly Ile Val Asp Glu Cys
            20                  25                  30

Cys Leu Arg Pro Cys Ser Val Asp Val Leu Leu Ser Tyr Cys
        35                  40                  45

<210> SEQ ID NO 145
<211> LENGTH: 46
<212> TYPE: PRT
<213> ORGANISM: Bommo
<220> FEATURE:
<221> NAME/KEY: VARIANT
<222> LOCATION: (1)...(46)
<223> OTHER INFORMATION: Xaa = Any Amino Acid

<400> SEQUENCE: 145

Tyr Cys Gly Arg His Leu Ala Asp Thr Leu Ala Asp Leu Cys Phe Gly
 1               5                  10                  15

Val Glu Lys Xaa Xaa Xaa Arg Gly Lys Arg Gly Val Val Asp Glu Cys
            20                  25                  30

Cys Phe Arg Pro Cys Thr Leu Asp Val Leu Leu Ser Tyr Cys
        35                  40                  45

<210> SEQ ID NO 146
<211> LENGTH: 46
<212> TYPE: PRT
<213> ORGANISM: Horn worm
<220> FEATURE:
<221> NAME/KEY: VARIANT
<222> LOCATION: (1)...(46)
<223> OTHER INFORMATION: Xaa = Any Amino Acid

<400> SEQUENCE: 146

Ile Cys Gly Arg His Leu Ala Arg Thr Leu Ala Asp Leu Cys Pro Asn
 1               5                  10                  15

Val Glu Tyr Xaa Xaa Xaa Gly Lys Arg Ala Gly Val Ala Asp Asp Cys
            20                  25                  30

Cys Asx Asn Ser Cys Thr Met Asp Val Leu Leu Ser Tyr Cys
        35                  40                  45

<210> SEQ ID NO 147
<211> LENGTH: 46
<212> TYPE: PRT
<213> ORGANISM: Bombyx mori
<220> FEATURE:
<221> NAME/KEY: VARIANT
<222> LOCATION: (1)...(46)
<223> OTHER INFORMATION: Xaa = Any Amino Acid

<400> SEQUENCE: 147

Tyr Cys Gly Arg Arg Leu Ala Thr Met Leu Ser Phe Val Cys Asp Asn
 1               5                  10                  15

Gln Tyr Gln Xaa Xaa Xaa Gly Lys Arg Gln Gly Ile Ala Glu Glu Cys
```

```
                    20                  25                  30

Cys Asn Lys Pro Cys Thr Glu Asn Glu Leu Leu Gly Tyr Cys
            35                  40                  45

<210> SEQ ID NO 148
<211> LENGTH: 46
<212> TYPE: PRT
<213> ORGANISM: Bombyx mori
<220> FEATURE:
<221> NAME/KEY: VARIANT
<222> LOCATION: (1)...(46)
<223> OTHER INFORMATION: Xaa = Any Amino Acid

<400> SEQUENCE: 148

Tyr Cys Gly Arg Arg Leu Ala Thr Met Leu Leu Tyr Val Cys Asp Asn
 1               5                  10                  15

Gln Tyr Gln Xaa Xaa Xaa Gly Lys Arg Gln Gly Ile Val Glu Glu Cys
            20                  25                  30

Cys Asn Lys Pro Cys Thr Glu Asn Glu Leu Leu Gly Tyr Cys
            35                  40                  45

<210> SEQ ID NO 149
<211> LENGTH: 46
<212> TYPE: PRT
<213> ORGANISM: Bombys mori
<220> FEATURE:
<221> NAME/KEY: VARIANT
<222> LOCATION: (1)...(46)
<223> OTHER INFORMATION: Xaa = Any Amino Acid

<400> SEQUENCE: 149

Tyr Cys Gly Arg Arg Leu Ala Ile Met Leu Ser Tyr Leu Cys Asp Asn
 1               5                  10                  15

Gln Tyr Leu Xaa Xaa Xaa Gly Lys Arg Gln Gly Ile Ala Glu Glu Cys
            20                  25                  30

Cys Asn Lys Pro Cys Thr Glu Asp Glu Leu Leu Gly Tyr Cys
            35                  40                  45

<210> SEQ ID NO 150
<211> LENGTH: 46
<212> TYPE: PRT
<213> ORGANISM: Caenorhabditis elegans
<220> FEATURE:
<221> NAME/KEY: VARIANT
<222> LOCATION: (1)...(46)
<223> OTHER INFORMATION: Xaa = Any Amino Acid

<400> SEQUENCE: 150

Leu Cys Gly Ser Arg Leu Thr Thr Thr Leu Leu Ala Val Cys Arg Asn
 1               5                  10                  15

Gln Leu Cys Xaa Xaa Xaa Gln Lys Arg Gly Gly Ile Ala Thr Glu Cys
            20                  25                  30

Cys Glu Lys Arg Cys Ser Phe Ala Tyr Leu Lys Thr Phe Cys
            35                  40                  45

<210> SEQ ID NO 151
<211> LENGTH: 46
<212> TYPE: PRT
<213> ORGANISM: Moi 3
<220> FEATURE:
<221> NAME/KEY: VARIANT
<222> LOCATION: (1)...(46)
<223> OTHER INFORMATION: Xaa = Any Amino Acid

<400> SEQUENCE: 151
```

```
Leu Cys Gly Ser Thr Leu Ala Asn Met Val Gln Trp Leu Cys Ser Thr
  1               5                  10                  15

Tyr Thr Thr Xaa Xaa Xaa Glu Ser Arg Pro Ser Ile Val Cys Glu Cys
                20                  25                  30

Cys Phe Asn Gln Cys Thr Val Gln Glu Leu Leu Ala Tyr Cys
            35                  40                  45
```

<210> SEQ ID NO 152
<211> LENGTH: 46
<212> TYPE: PRT
<213> ORGANISM: Homo sapiens
<220> FEATURE:
<221> NAME/KEY: VARIANT
<222> LOCATION: (1)...(46)
<223> OTHER INFORMATION: Xaa = Any Amino Acid

<400> SEQUENCE: 152

```
Leu Cys Gly Arg Glu Leu Val Arg Ala Gln Ile Ala Ile Cys Gly Met
  1               5                  10                  15

Ser Thr Trp Xaa Xaa Xaa Arg Pro Tyr Val Ala Leu Phe Glu Lys Cys
                20                  25                  30

Cys Leu Ile Gly Cys Thr Lys Arg Ser Leu Ala Lys Tyr Cys
            35                  40                  45
```

<210> SEQ ID NO 153
<211> LENGTH: 46
<212> TYPE: PRT
<213> ORGANISM: Homo sapiens
<220> FEATURE:
<221> NAME/KEY: VARIANT
<222> LOCATION: (1)...(46)
<223> OTHER INFORMATION: Xaa = Any Amino Acid

<400> SEQUENCE: 153

```
Leu Cys Gly His His Phe Val Arg Ala Leu Val Arg Val Cys Gly Gly
  1               5                  10                  15

Pro Arg Trp Xaa Xaa Xaa Ala Ala Ala Thr Asn Pro Ala Arg Tyr Cys
                20                  25                  30

Cys Leu Ser Gly Cys Thr Gln Gln Asp Leu Leu Thr Leu Cys
            35                  40                  45
```

<210> SEQ ID NO 154
<211> LENGTH: 541
<212> TYPE: PRT
<213> ORGANISM: Caenorhabditis elegans

<400> SEQUENCE: 154

```
Met Ser Met Thr Ser Leu Ser Thr Lys Ser Arg Arg Gln Glu Asp Val
  1               5                  10                  15

Val Ile Glu Gly Trp Leu His Lys Lys Gly Glu His Ile Arg Asn Trp
                20                  25                  30

Arg Pro Arg Tyr Phe Met Ile Phe Asn Asp Gly Ala Leu Leu Gly Phe
                35                  40                  45

Arg Ala Lys Pro Lys Glu Gly Gln Pro Phe Pro Glu Pro Leu Asn Asp
     50                  55                  60

Phe Met Ile Lys Asp Ala Ala Thr Met Leu Phe Glu Lys Pro Arg Pro
 65                  70                  75                  80

Asn Met Phe Met Val Arg Cys Leu Gln Trp Thr Thr Val Ile Glu Arg
                85                  90                  95

Thr Phe Tyr Ala Glu Ser Ala Glu Val Arg Gln Arg Trp Ile His Ala
```

|       |       |       |       | 100   |       |       |       |       | 105   |       |       |       |       | 110   |       |
|-------|-------|-------|-------|-------|-------|-------|-------|-------|-------|-------|-------|-------|-------|-------|-------|

Ile Glu Ser Ile Ser Lys Lys Tyr Lys Gly Thr Asn Ala Asn Pro Gln
                115                 120                 125

Glu Glu Leu Met Glu Thr Asn Gln Gln Pro Lys Ile Asp Glu Asp Ser
        130                 135                 140

Glu Phe Ala Gly Ala Ala His Ala Ile Met Gly Gln Pro Ser Ser Gly
145                 150                 155                 160

His Gly Asp Asn Cys Ser Ile Asp Phe Arg Ala Ser Met Ile Ser Ile
                165                 170                 175

Ala Asp Thr Ser Glu Ala Ala Lys Arg Asp Lys Ile Thr Met Glu Asp
        180                 185                 190

Phe Asp Phe Leu Lys Val Leu Gly Lys Gly Thr Phe Gly Lys Val Ile
        195                 200                 205

Leu Cys Lys Glu Lys Arg Thr Gln Lys Leu Tyr Ala Ile Lys Ile Leu
210                 215                 220

Lys Lys Asp Val Ile Ile Ala Arg Glu Glu Val Ala His Thr Leu Thr
225                 230                 235                 240

Glu Asn Arg Val Leu Gln Arg Cys Lys His Pro Phe Leu Thr Glu Leu
                245                 250                 255

Lys Tyr Ser Phe Gln Glu Gln His Tyr Leu Cys Phe Val Met Gln Phe
                260                 265                 270

Ala Asn Gly Gly Glu Leu Phe Thr His Val Arg Lys Cys Gly Thr Phe
        275                 280                 285

Ser Glu Pro Arg Ala Arg Phe Tyr Gly Ala Glu Ile Val Leu Ala Leu
        290                 295                 300

Gly Tyr Leu His Arg Cys Asp Ile Val Tyr Arg Asp Met Lys Leu Glu
305                 310                 315                 320

Asn Leu Leu Leu Asp Lys Asp Gly His Ile Lys Ile Ala Asp Phe Gly
                325                 330                 335

Leu Cys Lys Glu Glu Ile Ser Phe Gly Asp Lys Thr Ser Thr Phe Cys
                340                 345                 350

Gly Thr Pro Glu Tyr Leu Ala Pro Glu Val Leu Asp Asp His Asp Tyr
        355                 360                 365

Gly Arg Cys Val Asp Trp Trp Gly Val Gly Val Val Met Tyr Glu Met
        370                 375                 380

Met Cys Gly Arg Leu Pro Phe Tyr Ser Lys Asp His Asn Lys Leu Phe
385                 390                 395                 400

Glu Leu Ile Met Ala Gly Asp Leu Arg Phe Pro Ser Lys Leu Ser Gln
                405                 410                 415

Glu Ala Arg Thr Leu Leu Thr Gly Leu Leu Val Lys Asp Pro Thr Gln
                420                 425                 430

Arg Leu Gly Gly Gly Pro Glu Asp Ala Leu Glu Ile Cys Arg Ala Asp
        435                 440                 445

Phe Phe Arg Thr Val Asp Trp Glu Ala Thr Tyr Arg Lys Glu Ile Glu
        450                 455                 460

Pro Pro Tyr Lys Pro Asn Val Gln Ser Glu Thr Asp Thr Ser Tyr Phe
465                 470                 475                 480

Asp Asn Glu Phe Thr Ser Gln Pro Val Gln Leu Thr Pro Pro Ser Arg
                485                 490                 495

Ser Gly Ala Leu Ala Thr Val Asp Glu Gln Glu Met Gln Ser Asn
                500                 505                 510

Phe Thr Gln Phe Ser Phe His Asn Val Met Gly Ser Ile Asn Arg Ile
        515                 520                 525

His Glu Ala Ser Glu Asp Asn Glu Asp Tyr Asp Met Gly
                530                 535                 540

<210> SEQ ID NO 155
<211> LENGTH: 546
<212> TYPE: PRT
<213> ORGANISM: Caenorhabditis elegans

<400> SEQUENCE: 155

Met Ser Met Thr Ser Leu Ser Thr Lys Ser Arg Arg Gln Glu Asp Val
1               5                   10                  15

Val Ile Glu Gly Trp Leu His Lys Lys Gly Glu His Ile Arg Asn Trp
            20                  25                  30

Arg Pro Arg Tyr Phe Met Ile Phe Asn Asp Gly Ala Leu Leu Gly Phe
        35                  40                  45

Arg Ala Lys Pro Lys Glu Gly Gln Pro Phe Pro Glu Pro Leu Asn Asp
    50                  55                  60

Phe Met Ile Lys Asp Ala Ala Thr Met Leu Phe Glu Lys Pro Arg Pro
65                  70                  75                  80

Asn Met Phe Met Val Arg Cys Leu Gln Trp Thr Thr Val Ile Glu Arg
                85                  90                  95

Thr Phe Tyr Ala Glu Ser Ala Glu Val Arg Gln Arg Trp Ile His Ala
            100                 105                 110

Ile Glu Ser Ile Ser Lys Lys Tyr Lys Gly Thr Asn Ala Asn Pro Gln
        115                 120                 125

Glu Glu Leu Met Glu Thr Asn Gln Gln Pro Lys Ile Asp Glu Asp Ser
    130                 135                 140

Glu Phe Ala Gly Ala Ala His Ala Ile Met Gly Gln Pro Ser Ser Gly
145                 150                 155                 160

His Gly Asp Asn Cys Ser Ile Asp Phe Arg Ala Ser Met Ile Ser Ile
                165                 170                 175

Ala Asp Thr Ser Glu Ala Ala Lys Arg Asp Lys Ile Thr Met Glu Asp
            180                 185                 190

Phe Asp Phe Leu Lys Val Leu Gly Lys Gly Thr Phe Gly Lys Val Ile
        195                 200                 205

Leu Cys Lys Glu Lys Arg Thr Gln Lys Leu Tyr Ala Ile Lys Ile Leu
    210                 215                 220

Lys Lys Asp Val Ile Ile Ala Arg Glu Glu Val Ala His Thr Leu Thr
225                 230                 235                 240

Glu Asn Arg Val Leu Gln Arg Cys Lys His Pro Phe Leu Thr Glu Leu
                245                 250                 255

Lys Tyr Ser Phe Gln Thr Asn Asp Arg Leu Cys Phe Val Met Glu Phe
            260                 265                 270

Ala Ile Gly Gly Asp Leu Tyr Tyr His Leu Asn Arg Glu Val Gln Met
        275                 280                 285

Asn Lys Glu Gly Phe Ser Glu Pro Arg Ala Arg Phe Tyr Gly Ser Glu
    290                 295                 300

Ile Val Leu Ala Leu Gly Tyr Leu His Ala Asn Ser Ile Val Tyr Arg
305                 310                 315                 320

Asp Leu Lys Leu Glu Asn Leu Leu Asp Lys Asp Gly His Ile Lys
                325                 330                 335

Ile Ala Asp Phe Gly Leu Cys Lys Glu Glu Ile Ser Phe Gly Asp Lys
            340                 345                 350

Thr Ser Thr Phe Cys Gly Thr Pro Glu Tyr Leu Ala Pro Glu Val Leu

```
                    355                 360                 365
Asp Asp His Asp Tyr Gly Arg Cys Val Asp Trp Trp Gly Val Gly Val
    370                 375                 380

Val Met Tyr Glu Met Met Cys Gly Arg Leu Pro Phe Tyr Ser Lys Asp
385                 390                 395                 400

His Asn Lys Leu Phe Glu Leu Ile Met Ala Gly Asp Leu Arg Phe Pro
                405                 410                 415

Ser Lys Leu Ser Gln Glu Ala Arg Thr Leu Leu Thr Gly Leu Leu Val
                420                 425                 430

Lys Asp Pro Thr Gln Arg Leu Gly Gly Pro Glu Asp Ala Leu Glu
            435                 440                 445

Ile Cys Arg Ala Asp Phe Phe Arg Thr Val Asp Trp Glu Ala Thr Tyr
    450                 455                 460

Arg Lys Glu Ile Glu Pro Pro Tyr Lys Pro Asn Val Gln Ser Glu Thr
465                 470                 475                 480

Asp Thr Ser Tyr Phe Asp Asn Glu Phe Thr Ser Gln Pro Val Gln Leu
                485                 490                 495

Thr Pro Pro Ser Arg Ser Gly Ala Leu Ala Thr Val Asp Glu Gln Glu
            500                 505                 510

Glu Met Gln Ser Asn Phe Thr Gln Phe Ser Phe His Asn Val Met Gly
            515                 520                 525

Ser Ile Asn Arg Ile His Glu Ala Ser Glu Asp Asn Glu Asp Tyr Asp
        530                 535                 540

Met Gly
545

<210> SEQ ID NO 156
<211> LENGTH: 483
<212> TYPE: PRT
<213> ORGANISM: Caenorhabditis elegans

<400> SEQUENCE: 156

Met Ser Thr Glu Asn Ala His Leu Gln Lys Glu Asp Ile Val Ile Glu
1               5                   10                  15

Ser Trp Leu His Lys Lys Gly Glu His Ile Arg Asn Trp Arg Pro Arg
            20                  25                  30

Tyr Phe Ile Leu Phe Arg Asp Gly Thr Leu Leu Gly Phe Arg Ser Lys
        35                  40                  45

Pro Lys Glu Asp Gln Pro Leu Pro Glu Pro Leu Asn Asn Phe Met Ile
    50                  55                  60

Arg Asp Ala Ala Thr Val Cys Leu Asp Lys Pro Arg Pro Asn Met Phe
65                  70                  75                  80

Ile Val Arg Cys Leu Gln Trp Thr Thr Val Ile Glu Arg Thr Phe Tyr
                85                  90                  95

Ala Asp Ser Ala Asp Phe Arg Gln Met Trp Ile Glu Ala Ile Gln Ala
            100                 105                 110

Val Ser Ser His Asn Arg Leu Lys Glu Asn Ala Gly Asn Thr Ser Met
        115                 120                 125

Gln Glu Glu Asp Thr Asn Gly Asn Pro Ser Gly Glu Ser Asp Val Asn
    130                 135                 140

Met Asp Ala Thr Ser Thr Arg Ser Asp Asn Asp Phe Glu Ser Thr Val
145                 150                 155                 160

Met Asn Ile Asp Glu Pro Glu Glu Val Pro Arg Lys Asn Thr Val Thr
                165                 170                 175
```

```
Met Asp Asp Phe Asp Phe Leu Lys Val Leu Gly Gln Gly Thr Phe Gly
            180                 185                 190

Lys Val Ile Leu Cys Arg Glu Lys Ser Ser Asp Lys Leu Tyr Ala Ile
            195                 200                 205

Lys Ile Ile Arg Lys Glu Met Val Val Asp Arg Ser Glu Val Ala His
            210                 215                 220

Thr Leu Thr Glu Asn Arg Val Leu Tyr Ala Cys Val His Pro Phe Leu
225                 230                 235                 240

Thr Leu Leu Lys Tyr Ser Phe Gln Ala Gln Tyr His Ile Cys Phe Val
                245                 250                 255

Met Glu Phe Ala Asn Gly Gly Glu Leu Phe Thr His Leu Gln Arg Cys
            260                 265                 270

Lys Thr Phe Ser Glu Ala Arg Thr Arg Phe Tyr Gly Ser Glu Ile Ile
            275                 280                 285

Leu Ala Leu Gly Tyr Leu His His Arg Asn Ile Val Tyr Arg Asp Met
            290                 295                 300

Lys Leu Glu Asn Leu Leu Leu Asp Arg Asp Gly His Ile Lys Ile Thr
305                 310                 315                 320

Asp Phe Gly Leu Cys Lys Glu Glu Ile Lys Tyr Gly Asp Lys Thr Ser
                325                 330                 335

Thr Phe Cys Gly Thr Pro Glu Tyr Leu Ala Pro Glu Val Ile Glu Asp
            340                 345                 350

Ile Asp Tyr Asp Arg Ser Val Asp Trp Trp Gly Val Gly Val Val Met
            355                 360                 365

Tyr Glu Met Met Cys Gly Arg Leu Pro Phe Ser Ala Lys Glu Asn Gly
            370                 375                 380

Lys Leu Phe Glu Leu Ile Thr Thr Cys Asp Leu Lys Phe Pro Asn Arg
385                 390                 395                 400

Leu Ser Pro Glu Ala Val Thr Leu Leu Ser Gly Leu Leu Glu Arg Val
                405                 410                 415

Pro Ala Lys Arg Leu Gly Ala Gly Pro Asp Asp Ala Arg Glu Val Ser
            420                 425                 430

Arg Ala Glu Phe Phe Lys Asp Val Asp Trp Glu Ala Thr Leu Arg Lys
            435                 440                 445

Glu Val Glu Pro Pro Phe Lys Pro Asn Val Met Ser Glu Thr Asp Thr
            450                 455                 460

Ser Phe Phe Asp Arg Val Arg Tyr Val Ser Ile Leu Leu Lys Val Ser
465                 470                 475                 480

Glu Ala Ile

<210> SEQ ID NO 157
<211> LENGTH: 480
<212> TYPE: PRT
<213> ORGANISM: Homo sapiens

<400> SEQUENCE: 157

Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Val Asp Val Gln Arg
        35                  40                  45

Glu Ala Pro Leu Asn Asn Phe Ser Val Ala Gln Cys Gln Leu Met Lys
    50                  55                  60
```

-continued

```
Thr Glu Arg Pro Arg Pro Asn Thr Phe Ile Ile Arg Cys Leu Gln Trp
 65                  70                  75                  80

Thr Thr Val Ile Glu Arg Thr Phe His Val Glu Thr Pro Glu Glu Arg
                 85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Phe Ala Phe Arg Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415

Tyr Glu Lys Lys Leu Ser Pro Pro Phe Lys Pro Gln Val Thr Ser Glu
            420                 425                 430

Thr Asp Thr Arg Tyr Phe Asp Glu Phe Thr Ala Gln Met Ile Thr
        435                 440                 445

Ile Thr Pro Pro Asp Gln Asp Asp Ser Met Glu Cys Val Asp Ser Glu
    450                 455                 460

Arg Arg Pro His Phe Pro Gln Phe Ser Tyr Ser Ala Ser Ser Thr Ala
465                 470                 475                 480
```

<210> SEQ ID NO 158
<211> LENGTH: 6250
<212> TYPE: DNA
<213> ORGANISM: Caenorhabditis elegans

<400> SEQUENCE: 158

| | | | | | |
|---|---|---|---|---|---|
| cataaaaatc | cagtaaatgg | taaaattttc | aatttcagat | ccatctcgat | ggaggatctc | 60 |
| acaccaacta | acacgtcgct | cgacaccaca | actactaaca | atgacacgac | atcggatcgt | 120 |
| gaagcggcgc | caacggtgag | gaactagttt | ctagacgaac | atcggaatgc | ggcttaaagt | 180 |
| tcgggtgcac | ttatcaaact | agaccegttt | tttagaccct | cttcaaagc | ggggaactgc | 240 |
| aatacacttt | ttgaacctaa | aacctagatt | tttggtgttc | taaattcttt | tgtgaattgg | 300 |
| agagccaatt | caaccggaaa | actcttttt | atagggaaaa | cgttttgcca | cgtagcagat | 360 |
| aagttaaata | gaaatatttt | taaatatttt | tttttgtct | aggaaaaatt | gataaagcac | 420 |
| ctggtccaat | tttcagaacg | ttccaatttt | acctacaata | caaaattggc | cggcaagctt | 480 |
| atggcttctg | tttgcctact | tctagcttga | acattctaag | gctccgtagc | gaaaaaaatt | 540 |
| ttttaggctt | tttttaaata | aatgtttggg | ccggaacact | taaccgaata | gcatgatgaa | 600 |
| acgctctaaa | acttgaattt | gaaaatttgc | agttgatgct | ttaatataaa | agttttgagg | 660 |
| tttcacctgc | ctaagatcgt | tttagcataa | atatgtagat | gaccgagagt | atacaattaa | 720 |
| atattaatta | aatatgaatt | tcgaaatatg | aattttggtt | gacttccatt | atgttttttt | 780 |
| tttcacattt | tacaactatt | ctaggcaaaa | atgaaaaaaa | aaaacttgta | gaataatttt | 840 |
| caaaatttta | ttttccagac | gctcaactta | acaccaacag | caagtgaatc | ggagaacagc | 900 |
| ttatccccag | tcaccgccga | agatctcata | gctaaaagca | ttaagaaggg | atgtccgaag | 960 |
| agaacttcca | acgacttcat | gtttcttcag | agtatgggcg | aaggagccta | cagccaggtt | 1020 |
| ggtgaacgag | gaaatttcca | gaaatgtgtg | caactagtat | cagagtacaa | ggaaaagctt | 1080 |
| ggaaaatact | cggaatgcct | gaattagtgc | ttgaagtaag | cttgcccatt | tttttcggaa | 1140 |
| catcggtgat | tctttcttgg | caattcaact | gatagtactg | gtattaccta | gccgcaaaaa | 1200 |
| atttgcagtt | tttgccacaa | atctatcttg | acacaatata | cctcactatt | agttaaatgc | 1260 |
| tgagttttta | tcgatttta | tagctttttt | tacttatgta | tattcaaaat | gtatgtgttt | 1320 |
| ttcaaatctt | tttaaaggtt | tagtacggtc | attaaaaaaa | atatttaaaa | atcatcttca | 1380 |
| tggcgctaaa | atgagcgact | atcataagaa | attagaaaat | ttggaaaatt | ggtttatttt | 1440 |
| tttctagtcc | ttgaatttc | accttcccat | ttttatgctc | taactgtgtt | tcaaatactc | 1500 |
| atattccaac | attgtaggaa | ttctagaatt | gctttagatt | tctctttgtt | ttccaatctt | 1560 |
| ttttactgta | agttatcatc | attttggcac | cgaaaggttt | ttttaggtaa | ttttaccact | 1620 |
| gaccgtaaca | cttttccaat | ggcgtataca | atttgaattt | agcaacaaaa | caaaaaaaaa | 1680 |
| caaaaatcgt | accaagacgg | actactgtat | tttttggcgg | aaaaatcggc | caattttgcg | 1740 |
| tcagggttac | acgactgtgg | gaattgaact | cgcactatgt | aggcccattc | atgttgtctc | 1800 |
| cccctgtcca | atctcttttc | tccacaacac | tttaatctca | tttcgcatgg | agaagagaaa | 1860 |
| gaagaagatg | cagaaaacga | cgacatcgtc | atagaattgt | ctacacaaac | ctagtgttct | 1920 |
| gcgtctctta | cacaaaataa | gccacgcgtc | tagcactatc | aacattcgca | aacagctata | 1980 |
| catgtgcttg | ttgaagggaa | aaacgagacg | tttgtgtgta | ttggggaggg | gtaatgtaac | 2040 |
| cgtggttgtt | gggttcatca | aattgacagc | gcacagggat | ttgattttga | acgtgttatc | 2100 |
| gctttggacc | ctgaggcatg | tttcctacac | ctagaacaac | taccgtaatg | aatctttaca | 2160 |

-continued

```
ttgactttcg gagagaaggg tttgtactct gactatgtat aactcaagaa gaatgtaggg    2220
aatttatgtc gttggaactt ccaatttgga agtacagttt tttggaaatt aaattttga     2280 ttcttaaaat agtcgacttg aaataatttt tcgttattta tcaatccaat gagttgaaaa    2340
agtgaatgga aatttcttga ctaaatccgt ggaaaattat ctagttttgt ttttcagata    2400
agttgtaaac actttgatag ttaaaatgat tgtttgtagt gatcagaagc agaaaatctg    2460 actagttttcc gcccccccccc cctatacata tgatgcacac ttaaaatgtc caagtggtgt   2520
ttgaatagca aatcttgaaa acgtaaaaac aataattatt ttctatatct gtaaatattt    2580
tcaacgaatt ttcagcttcc aaattttggt cgtttttgga tcttttttaca aaaaaaatat   2640 tttatcaact gacactgata atattttctg cctcatatta aaaatattc ctctagcaaa     2700 aactgtaagt tgaacgaatt tacaataaaa acacagctg cactgaccaa aaaacaatta     2760
cactggccaa aattgagctt gcactgaccg agtttagcga ccatatcttt tttgtctaat    2820
ttgtggtgtg tgcggcgaat tcggcaaaat tgtcgagctc ggaaaacaga aaatttggca    2880
aatttaccgc aaactcttca actgaagcca ctattgcaca ttaactgtca aaattctgga    2940
tataattagc aaaacaataa gtaacatttc tgaaaaatta gaaccttttcc cgcattgtat   3000 ttgtagacgc acctaaaaaa tttcaaaaca ccaaaaaaca agcttccagt aaaaccctaa    3060
tattccaggt attccgatgt cgcgaagtgg caacagatgc gatgttcgcc gtcaaagtgc    3120
tccagaagtc gtacctcaac cgccatcaaa aaatggacgc aatcattcgc gagaagaata    3180
tcttaacata cctgtcacaa gaatgcggtg gtcatccgtt tgtcacacag ctctacacac    3240
attttcacga ccaggctaga atttgtgagt tttttccagc gccaaggttc ttttctgaac    3300
ccatcaaaat ccacttgtga tcattttatt ccaataaaaa cgtcaactta aaaaaaaat    3360 taaacctcaa ttaatattca gatttcgtga tcggacttgt tgaaaatggt gatcttggcg    3420
agtcgctgtg ccatttttgga tcattcgaca tgctcacctc aaaattcttt gcctcggaaa   3480
tcctcaccgg actgcaattc ctacacgaca acaaaattgt gcacagagac atgaagccgg    3540
acaatgtgct catccagaaa gacggtcaca ttctcatcac agattttgga agtgcccagg    3600
cgtttggcgg tctccaactg tcacaggagg gctttacgga tgcgaatcag gcaagctcgc    3660
gatcttcgga ttctggatcg ccgccgccaa ctcgattcta ttcggatgag gagggtaagg    3720
ttttcggaaa tttgactgaa acaattttg ccagttccag aagagaacac tgctcgacgt     3780
accacatttg ttggaactgc tctctacgtg agcccggaga tgctagctga cggagatgtg    3840
ggaccacagt aagctccgat tctttgtaga atgtcaaatt taacagttgg atttcagaac    3900
cgacatttgg ggattgggat gtatcctttt ccagtgtcta gccggacagc caccattcag    3960
agccgtcaac cagtaccatc ttttgaaaag aatccaggag ttggatttct cgttcccaga    4020
aggatttcca gaggaagcgt cggaaattat cgcaaagatt ttggtaggtt gacatgaaac    4080
tttaaaaact gaatacgtaa ttttcaactt acaggtgcgc gacccgagta cccgtatcac    4140
cagtcaagaa cttatggctc acaagttttt tgaaaacgtt gactgggtga acattgcaaa    4200
tatcaagcca ccagtcctgc acgcctacat tccagccaca tttggcgagc ggagtacta    4260 ctctaacatt gggcctgtcg agccgggact tgatgatcgt gccttgttcc gtttgatgaa    4320
tttgggaaat gatgctagcg catcacagcc atcaacgtga gtttgaagca ttttttctt    4380 gcattaaaag ttttaccttg cactgaccaa aatttattga aactattaat tatttgattc    4440
tgattaacaa tgaccaaaag atttgaactg acaaagtgca aatttgcacc gaccaaaaaa    4500
cagtttgcac tgaccacctc ttcatttgca ctgaccacct cttcatttgc actgaccaac    4560
```

```
tttcatttg cactgaccat ctcttcattt gcactgacca actttcatt tgcaattctg    4620 gcaatgattc tttgcatct actgatcaaa aattgattca atcaattaa ttttctttga    4680 cagtactatg ccttattcaa ggagatgctg atctgaaaat tctcaatagt tgataaaaat    4740
tactaacccc ttagaaagtt tcagaccgtc taacgtggaa catcgcggag acccatttgt    4800
ttcggaaatt gcaccgtgag tgatttgcac ctaattggtt atttttaata atcattaaat    4860
tatagacgcg ccaattcgga agccgaaaag aaccgcgccg cacgtgcgca gaagctcgaa    4920
gagcaacgtg tcaaaaaccc attccacatc ttcaccaaca actcgctcat tttgaaacaa    4980
ggatatttgg aaaagaagcg aggattgttt gccagacgcc gaatgttcct gttgaccgaa    5040
ggaccgcatc tcttgtacat tgatgtgccg aatcttgtgc tcaaaggaga ggtaccatgg    5100
acgccgtgca tgcaggtgga gctaaaaaac tcgggaactt tctttataca tacggtaggt    5160
cagaataatc atagctgtct atctcattat agtactcaat gaatctgaaa atttcaaatt    5220
ttcagcccaa ccgcgtctac tacttgtttg atctcgaaaa gaaagcagat gagtggtgta    5280
aggctatcaa tgatgttcgc aagcggtact cggtgactat cgaaaagact tttaactctg    5340
cgatgcgtga cggaacattt ggcagcattt atggaaagaa aaagtccaga aaggtatgaa    5400
ttactggaag gcccccctca ctgagtttcc agcaagttca gagtttttta ttggaatttt    5460
tgccaatttt cattagactt tagagcctat tgctattttg tggacaggtt taaacatttt    5520
caaaaaaaaa ttgagaaatg tctgaaaaaa tttggagtgt gacagttttc tgaattttga    5580
aaattctgtt ctcaaaattg gatttttaca gagcttgttt cgagatttca taatccttca    5640
aaagaatata gaatatttgt gttcaacttt tcttgtcaaa atattttttt tggacaatct    5700
agattctgga aaattttcaa aaaagataaa tctctaaaca aaactaaatt caaatgttc    5760 taaaggttct ttattttcca tgcaactcta aaatcttccc gtatattttt ttggaaagtc    5820
ttatgatgtt tagacggttt aaatttttg atgatttaaa ttttttaggg gtggtctata    5880
attttggacc accctgtata attatggacc accatgtaca cttatagacc acccagtaac    5940
aagcattttt ggaccaccac gcaaatctta ttattatgga ccacccaaac ttagaacacc    6000
ttcaatactt ctttttctgtt caaaaaatga tcaacttgct gaaaaaaaat ttttgtagg    6060 aaatgatgcg tgaacagaag gcgctgcgcc gcaaacaaga aaggaggag aaaaaggcgc    6120 taaaagccga gcaagtgagc aagaagcttt caatgcaaat ggacaagaag tcgccttgaa    6180
ggctcacctc ccttctactc cccacaaaat caccatcaaa caaatcacac ttttgtatca    6240
ttttgcgtcc                                                          6250
```

<210> SEQ ID NO 159
<211> LENGTH: 632
<212> TYPE: PRT
<213> ORGANISM: Caenorhabditis elegans

<400> SEQUENCE: 159

Met Glu Asp Leu Thr Pro Thr Asn Thr Ser Leu Asp Thr Thr Thr Thr
1               5                   10                  15

Asn Asn Asp Thr Thr Ser Asp Arg Glu Ala Ala Pro Thr Thr Leu Asn
            20                  25                  30

Leu Thr Pro Thr Ala Ser Glu Ser Glu Asn Ser Leu Ser Pro Val Thr
        35                  40                  45

Ala Glu Asp Leu Ile Ala Lys Ser Ile Lys Glu Gly Cys Pro Lys Arg
    50                  55                  60

-continued

```
Thr Ser Asn Asp Phe Met Phe Leu Gln Ser Met Gly Glu Gly Ala Tyr
 65                  70                  75                  80

Ser Gln Val Phe Arg Cys Arg Glu Val Ala Thr Asp Ala Met Phe Ala
                 85                  90                  95

Val Lys Val Leu Gln Lys Ser Tyr Leu Asn Arg His Gln Lys Met Asp
            100                 105                 110

Ala Ile Ile Arg Glu Lys Asn Ile Leu Thr Tyr Leu Ser Gln Glu Cys
            115                 120                 125

Gly Gly His Pro Phe Val Thr Gln Leu Tyr Thr His Phe His Asp Gln
            130                 135                 140

Ala Arg Ile Tyr Phe Val Ile Gly Leu Val Glu Asn Gly Asp Leu Gly
145                 150                 155                 160

Glu Ser Leu Cys His Phe Gly Ser Phe Asp Met Leu Thr Ser Lys Phe
                165                 170                 175

Phe Ala Ser Glu Ile Leu Thr Gly Leu Gln Phe Leu His Asp Asn Lys
                180                 185                 190

Ile Val His Arg Asp Met Lys Pro Asp Asn Val Leu Ile Gln Lys Asp
            195                 200                 205

Gly His Ile Leu Ile Thr Asp Phe Gly Ser Ala Gln Ala Phe Gly Gly
            210                 215                 220

Leu Gln Leu Ser Gln Glu Gly Phe Thr Asp Ala Asn Gln Ala Ser Ser
225                 230                 235                 240

Arg Ser Ser Asp Ser Gly Ser Pro Pro Thr Arg Phe Tyr Ser Asp
                245                 250                 255

Glu Glu Glu Glu Asn Thr Ala Arg Arg Thr Thr Phe Val Gly Thr Ala
                260                 265                 270

Leu Tyr Val Ser Pro Glu Met Leu Ala Asp Gly Asp Val Gly Pro Gln
            275                 280                 285

Thr Asp Ile Trp Gly Leu Gly Cys Ile Leu Phe Gln Cys Leu Ala Gly
290                 295                 300

Gln Pro Pro Phe Arg Ala Val Asn Gln Tyr His Leu Leu Lys Arg Ile
305                 310                 315                 320

Gln Glu Leu Asp Phe Ser Phe Pro Glu Gly Phe Pro Glu Glu Ala Ser
                325                 330                 335

Glu Ile Ile Ala Lys Ile Leu Val Arg Asp Pro Ser Thr Arg Ile Thr
            340                 345                 350

Ser Gln Glu Leu Met Ala His Lys Phe Phe Glu Asn Val Asp Trp Val
            355                 360                 365

Asn Ile Ala Asn Ile Lys Pro Pro Val Leu His Ala Tyr Ile Pro Ala
370                 375                 380

Thr Phe Gly Glu Pro Glu Tyr Tyr Ser Asn Ile Gly Pro Val Glu Pro
385                 390                 395                 400

Gly Leu Asp Asp Arg Ala Leu Phe Arg Leu Met Asn Leu Gly Asn Asp
                405                 410                 415

Ala Ser Ala Ser Gln Pro Ser Thr Pro Ser Asn Val Glu His Arg Gly
            420                 425                 430

Asp Pro Phe Val Ser Glu Ile Ala Pro Arg Ala Asn Ser Glu Ala Glu
            435                 440                 445

Lys Asn Arg Ala Ala Arg Ala Gln Lys Leu Glu Glu Gln Arg Val Lys
450                 455                 460

Asn Pro Phe His Ile Phe Thr Asn Asn Ser Leu Ile Leu Lys Gln Gly
465                 470                 475                 480

Tyr Leu Glu Lys Lys Arg Gly Leu Phe Ala Arg Arg Arg Met Phe Leu
```

```
                    485                 490                 495
Leu Thr Glu Gly Pro His Leu Leu Tyr Ile Asp Val Pro Asn Leu Val
            500                 505                 510
Leu Lys Gly Glu Val Pro Trp Thr Pro Cys Met Gln Val Glu Leu Lys
            515                 520                 525
Asn Ser Gly Thr Phe Phe Ile His Thr Pro Asn Arg Val Tyr Tyr Leu
            530                 535                 540
Phe Asp Leu Glu Lys Lys Ala Asp Glu Trp Cys Lys Ala Ile Asn Asp
545                 550                 555                 560
Val Arg Lys Arg Tyr Ser Val Thr Ile Glu Lys Thr Phe Asn Ser Ala
                565                 570                 575
Met Arg Asp Gly Thr Phe Gly Ser Ile Tyr Gly Lys Lys Ser Arg
                580                 585                 590
Lys Glu Met Met Arg Glu Gln Lys Ala Leu Arg Arg Lys Gln Glu Lys
                595                 600                 605
Glu Glu Lys Lys Ala Leu Lys Ala Glu Gln Val Ser Lys Lys Leu Ser
            610                 615                 620
Met Gln Met Asp Lys Lys Ser Pro
625                 630

<210> SEQ ID NO 160
<211> LENGTH: 636
<212> TYPE: PRT
<213> ORGANISM: Caenorhabditis elegans

<400> SEQUENCE: 160

Met Glu Asp Leu Thr Pro Thr Asn Thr Ser Leu Asp Thr Thr Thr Thr
1                5                  10                  15
Asn Asn Asp Thr Thr Ser Asp Arg Glu Ala Ala Pro Thr Thr Leu Asn
                20                  25                  30
Leu Thr Pro Thr Ala Ser Glu Ser Glu Asn Ser Leu Ser Pro Val Thr
            35                  40                  45
Ala Glu Asp Leu Ile Ala Lys Ser Ile Lys Glu Gly Cys Pro Lys Arg
        50                  55                  60
Thr Ser Asn Asp Phe Met Phe Leu Gln Ser Met Gly Glu Gly Ala Tyr
65                  70                  75                  80
Ser Gln Val Phe Arg Cys Arg Glu Val Ala Thr Asp Ala Met Phe Ala
                85                  90                  95
Val Lys Val Leu Gln Lys Ser Tyr Leu Asn Arg His Gln Lys Met Asp
                100                 105                 110
Ala Ile Ile Arg Glu Lys Asn Ile Leu Thr Tyr Leu Ser Gln Glu Cys
            115                 120                 125
Gly Gly His Pro Phe Val Thr Gln Leu Tyr Thr His Phe His Asp Gln
        130                 135                 140
Ala Arg Ile Tyr Phe Val Ile Gly Leu Val Glu Asn Gly Asp Leu Gly
145                 150                 155                 160
Glu Ser Leu Cys His Phe Gly Ser Phe Asp Met Leu Thr Ser Lys Phe
                165                 170                 175
Phe Ala Ser Glu Ile Leu Thr Gly Leu Gln Phe Leu His Asp Asn Lys
            180                 185                 190
Ile Val His Arg Asp Met Lys Pro Asp Asn Val Leu Ile Gln Lys Asp
        195                 200                 205
Gly His Ile Leu Ile Thr Asp Phe Gly Ser Ala Gln Ala Phe Gly Gly
    210                 215                 220
```

```
Leu Gln Leu Ser Gln Glu Gly Phe Thr Asp Ala Asn Gln Ala Ser Ser
225                 230                 235                 240

Arg Ser Ser Asp Ser Gly Ser Pro Pro Thr Arg Phe Tyr Ser Asp
            245                 250                 255

Glu Glu Val Pro Glu Asn Thr Ala Arg Arg Thr Thr Phe Val Gly
            260                 265                 270

Thr Ala Leu Tyr Val Ser Pro Glu Met Leu Ala Asp Gly Asp Val Gly
            275                 280                 285

Pro Gln Thr Asp Ile Trp Gly Leu Gly Cys Ile Leu Phe Gln Cys Leu
            290                 295                 300

Ala Gly Gln Pro Pro Phe Arg Ala Val Asn Gln Tyr His Leu Leu Lys
305                 310                 315                 320

Arg Ile Gln Glu Leu Asp Phe Ser Phe Pro Glu Gly Phe Pro Glu Glu
                325                 330                 335

Ala Ser Glu Ile Ile Ala Lys Ile Leu Val Arg Asp Pro Ser Thr Arg
            340                 345                 350

Ile Thr Ser Gln Glu Leu Met Ala His Lys Phe Phe Glu Asn Val Asp
            355                 360                 365

Trp Val Asn Ile Ala Asn Ile Lys Pro Pro Val Leu His Ala Tyr Ile
    370                 375                 380

Pro Ala Thr Phe Gly Glu Pro Glu Tyr Tyr Ser Asn Ile Gly Pro Val
385                 390                 395                 400

Glu Pro Gly Leu Asp Asp Arg Ala Leu Phe Arg Leu Met Asn Leu Gly
            405                 410                 415

Asn Asp Ala Ser Ala Ser Gln Pro Ser Thr Phe Arg Pro Ser Asn Val
            420                 425                 430

Glu His Arg Gly Asp Pro Phe Val Ser Glu Ile Ala Pro Arg Ala Asn
        435                 440                 445

Ser Glu Ala Glu Lys Asn Arg Ala Ala Arg Ala Gln Lys Leu Glu Glu
    450                 455                 460

Gln Arg Val Lys Asn Pro Phe His Ile Phe Thr Asn Asn Ser Leu Ile
465                 470                 475                 480

Leu Lys Gln Gly Tyr Leu Glu Lys Lys Arg Gly Leu Phe Ala Arg Arg
                485                 490                 495

Arg Met Phe Leu Leu Thr Glu Gly Pro His Leu Leu Tyr Ile Asp Val
            500                 505                 510

Pro Asn Leu Val Leu Lys Gly Glu Val Pro Trp Thr Pro Cys Met Gln
            515                 520                 525

Val Glu Leu Lys Asn Ser Gly Thr Phe Phe Ile His Thr Pro Asn Arg
530                 535                 540

Val Tyr Tyr Leu Phe Asp Leu Glu Lys Lys Ala Asp Glu Trp Cys Lys
545                 550                 555                 560

Ala Ile Asn Asp Val Arg Lys Arg Tyr Ser Val Thr Ile Glu Lys Thr
            565                 570                 575

Phe Asn Ser Ala Met Arg Asp Gly Thr Phe Gly Ser Ile Tyr Gly Lys
            580                 585                 590

Lys Lys Ser Arg Lys Glu Met Met Arg Glu Gln Lys Ala Leu Arg Arg
        595                 600                 605

Lys Gln Glu Lys Glu Glu Lys Ala Leu Lys Ala Glu Gln Val Ser
    610                 615                 620

Lys Lys Leu Ser Met Gln Met Asp Lys Lys Ser Pro
625                 630                 635
```

```
<210> SEQ ID NO 161
<211> LENGTH: 54
<212> TYPE: PRT
<213> ORGANISM: Homo sapiens

<400> SEQUENCE: 161

Ser Pro Val Gly His Phe Ala Lys Trp Ser Gly Ser Pro Cys Ser Arg
1               5                   10                  15

Asn Arg Glu Glu Ala Asp Met Trp Thr Thr Phe Arg Pro Arg Ser Ser
            20                  25                  30

Ser Asn Ala Ser Ser Val Ser Thr Arg Leu Ser Pro Leu Arg Pro Glu
        35                  40                  45

Ser Glu Val Leu Ala Glu
    50

<210> SEQ ID NO 162
<211> LENGTH: 28
<212> TYPE: PRT
<213> ORGANISM: Homo sapiens

<400> SEQUENCE: 162

Ser Pro Phe Lys Trp Ser Pro Ser Asp Trp Thr Phe Arg Pro Arg Ser
1               5                   10                  15

Ser Asn Ala Ser Ser Arg Leu Ser Pro Glu Leu Glu
            20                  25

<210> SEQ ID NO 163
<211> LENGTH: 54
<212> TYPE: PRT
<213> ORGANISM: Homo sapiens

<400> SEQUENCE: 163

Ser Pro Gly Ser Gln Phe Ser Lys Trp Pro Ala Ser Pro Gly Ser His
1               5                   10                  15

Ser Asn Asp Asp Phe Asp Asn Trp Ser Thr Phe Arg Pro Arg Thr Ser
            20                  25                  30

Ser Asn Ala Ser Thr Ile Ser Gly Arg Leu Ser Pro Ile Met Thr Glu
        35                  40                  45

Gln Asp Asp Leu Gly Glu
    50

<210> SEQ ID NO 164
<211> LENGTH: 17
<212> TYPE: PRT
<213> ORGANISM: Caenorhabditis elegans

<400> SEQUENCE: 164

Ser Phe Arg Pro Arg Thr Gln Ser Asn Leu Ser Ile Pro Gly Ser Ser
1               5                   10                  15

Ser

<210> SEQ ID NO 165
<211> LENGTH: 42
<212> TYPE: PRT
<213> ORGANISM: Homo sapiens

<400> SEQUENCE: 165

Lys Ala Ala Ala Ile Ile Asp Leu Asp Pro Asp Phe Glu Pro Gln Ser
1               5                   10                  15

Arg Pro Arg Ser Cys Thr Trp Pro Leu Pro Arg Pro Glu Ile Ala Asn
            20                  25                  30
```

Gln Pro Ser Glu Pro Pro Glu Val Glu Pro
        35                  40

<210> SEQ ID NO 166
<211> LENGTH: 22
<212> TYPE: PRT
<213> ORGANISM: Homo sapiens

<400> SEQUENCE: 166

Ala Asp Pro Asp Phe Glu Pro Arg Pro Arg Ser Cys Thr Trp Pro Leu
1               5                   10                  15

Pro Arg Pro Glu Ser Pro
            20

<210> SEQ ID NO 167
<211> LENGTH: 42
<212> TYPE: PRT
<213> ORGANISM: Homo sapiens

<400> SEQUENCE: 167

Glu Ala Pro Gln Val Val Glu Ile Asp Pro Asp Phe Glu Pro Leu Pro
1               5                   10                  15

Arg Pro Arg Ser Cys Thr Trp Pro Leu Pro Arg Pro Glu Phe Ser Gln
            20                  25                  30

Ser Asn Ser Ala Thr Ser Ser Pro Ala Pro
        35                  40

<210> SEQ ID NO 168
<211> LENGTH: 41
<212> TYPE: PRT
<213> ORGANISM: Caenorhabditis elegans

<400> SEQUENCE: 168

Thr Phe Met Asn Thr Pro Asp Asp Val Met Met Asn Asp Asp Met Glu
1               5                   10                  15

Pro Ile Pro Arg Asp Arg Cys Asn Thr Trp Pro Met Arg Arg Pro Gln
            20                  25                  30

Leu Glu Pro Pro Leu Asn Ser Ser Pro
        35                  40

<210> SEQ ID NO 169
<211> LENGTH: 14
<212> TYPE: PRT
<213> ORGANISM: Caenorhabditis elegans or Homo sapiens

<400> SEQUENCE: 169

Thr Pro Val Asp Glu Pro Pro Arg Arg Thr Trp Pro Arg Pro
1               5                   10

<210> SEQ ID NO 170
<211> LENGTH: 80
<212> TYPE: PRT
<213> ORGANISM: Mus musculus or Homo sapiens

<400> SEQUENCE: 170

Leu Glu Lys Gln Ala Gly Gly Asn Pro Trp His Gln Phe Val Glu Asn
1               5                   10                  15

Asn Leu Ile Leu Lys Met Gly Pro Val Asp Lys Arg Lys Gly Leu Phe
            20                  25                  30

Ala Arg Arg Arg Gln Leu Leu Leu Thr Glu Gly Pro His Leu Tyr Tyr
        35                  40                  45

-continued

Val Asp Pro Val Asn Lys Val Leu Lys Gly Glu Ile Pro Trp Ser Gln
    50                      55                      60

Glu Leu Arg Pro Glu Ala Lys Asn Phe Lys Thr Phe Val His Thr
65                      70                      75                      80

<210> SEQ ID NO 171
<211> LENGTH: 47
<212> TYPE: PRT
<213> ORGANISM: Mus musculus or Homo sapiens or C elegans

<400> SEQUENCE: 171

Leu Glu Gln Asn Pro His Phe Asn Leu Ile Leu Lys Gly Lys Gly Leu
1                  5                      10                  15

Phe Ala Arg Arg Arg Leu Leu Thr Glu Gly Pro His Leu Tyr Asp Asn
                20                      25                      30

Val Leu Lys Gly Glu Pro Trp Glu Lys Asn Thr Phe Phe His Thr
                35                      40                      45

<210> SEQ ID NO 172
<211> LENGTH: 80
<212> TYPE: PRT
<213> ORGANISM: Caenorhabditis elegans

<400> SEQUENCE: 172

Leu Glu Glu Gln Arg Val Lys Asn Pro Phe His Ile Phe Thr Asn Asn
1                  5                      10                  15

Ser Leu Ile Leu Lys Gln Gly Tyr Leu Glu Lys Lys Arg Gly Leu Phe
                20                      25                      30

Ala Arg Arg Arg Met Phe Leu Leu Thr Glu Gly Pro His Leu Leu Tyr
                35                      40                      45

Ile Asp Val Pro Asn Leu Val Leu Lys Gly Glu Val Pro Trp Thr Pro
              50                      55                      60

Cys Met Gln Val Glu Leu Lys Asn Ser Gly Thr Phe Phe Ile His Thr
65                      70                      75                      80

<210> SEQ ID NO 173
<211> LENGTH: 113
<212> TYPE: PRT
<213> ORGANISM: Mus musculus or Homo sapiens

<400> SEQUENCE: 173

Ser Asp Leu Trp Ala Leu Gly Cys Ile Ile Tyr Gln Leu Val Ala Gly
1                  5                      10                  15

Leu Pro Pro Phe Arg Ala Gly Asn Glu Tyr Leu Ile Phe Gln Lys Ile
                20                      25                      30

Ile Lys Leu Glu Tyr Asp Phe Pro Glu Lys Phe Phe Pro Lys Ala Arg
                35                      40                      45

Asp Leu Val Glu Lys Leu Leu Val Leu Asp Ala Thr Lys Arg Leu Gly
              50                      55                      60

Cys Glu Glu Met Glu Gly Tyr Gly Pro Leu Lys Ala His Pro Phe Phe
65                      70                      75                      80

Glu Ser Val Thr Trp Glu Asn Leu His Gln Gln Thr Pro Pro Lys Leu
                85                      90                      95

Thr Ala Tyr Leu Pro Ala Met Ser Glu Asp Asp Glu Asp Cys Tyr Gly
                100                    105                   110

Asn

```
<210> SEQ ID NO 174
<211> LENGTH: 48
<212> TYPE: PRT
<213> ORGANISM: Mus musculus or Homo sapiens or C elegans

<400> SEQUENCE: 174

Asp Trp Leu Gly Cys Ile Gln Ala Gly Pro Pro Phe Arg Ala Asn Tyr
1               5                   10                  15

Ile Leu Phe Pro Glu Phe Ala Lys Leu Val Leu Glu Pro Leu Ala His
            20                  25                  30

Phe Phe Glu Val Trp Asn Pro Pro Leu Ala Tyr Pro Ala Glu Tyr Asn
        35                  40                  45

<210> SEQ ID NO 175
<211> LENGTH: 122
<212> TYPE: PRT
<213> ORGANISM: Caenorhabditis elegans

<400> SEQUENCE: 175

Thr Asp Ile Trp Gly Leu Gly Cys Ile Leu Phe Gln Cys Leu Ala Gly
1               5                   10                  15

Gln Pro Pro Phe Arg Ala Val Asn Gln Tyr His Leu Leu Lys Arg Ile
            20                  25                  30

Gln Glu Leu Asp Phe Ser Phe Pro Glu Gly Phe Pro Glu Glu Ala Ser
        35                  40                  45

Glu Ile Ile Ala Lys Ile Leu Val Gly His Glu Thr Leu Lys Thr Glu
    50                  55                  60

Tyr Val Ile Phe Asn Leu Gln Val Arg Asp Pro Ser Thr Arg Ile Thr
65                  70                  75                  80

Ser Gln Glu Leu Met Ala His Lys Phe Phe Glu Asn Val Asp Trp Val
                85                  90                  95

Asn Ile Ala Asn Ile Lys Pro Pro Val Leu His Ala Tyr Ile Pro Ala
            100                 105                 110

Thr Phe Gly Glu Pro Glu Tyr Tyr Ser Asn
        115                 120

<210> SEQ ID NO 176
<211> LENGTH: 72
<212> TYPE: PRT
<213> ORGANISM: Mus musculus or Homo sapiens

<400> SEQUENCE: 176

Phe Gly Leu Ser Tyr Ala Lys Asn Gly Glu Leu Leu Lys Tyr Ile Arg
1               5                   10                  15

Lys Ile Gly Ser Phe Asp Glu Thr Cys Thr Arg Phe Tyr Thr Ala Glu
            20                  25                  30

Ile Val Ser Ala Leu Glu Tyr Leu His Gly Lys Gly Ile Ile His Arg
        35                  40                  45

Asp Leu Lys Pro Glu Asn Ile Leu Leu Asn Glu Asp Met His Ile Gln
    50                  55                  60

Ile Thr Asp Phe Gly Thr Ala Lys
65                  70

<210> SEQ ID NO 177
<211> LENGTH: 31
<212> TYPE: PRT
<213> ORGANISM: Mus musculus or Homo sapiens or C elegans

<400> SEQUENCE: 177
```

```
Phe Asn Gly Leu Gly Ser Phe Asp Phe Glu Ile Leu Leu His Ile His
 1               5                  10                  15

Arg Asp Lys Pro Asn Leu Asp His Ile Ile Thr Asp Phe Gly Ala
            20                  25                  30
```

<210> SEQ ID NO 178
<211> LENGTH: 72
<212> TYPE: PRT
<213> ORGANISM: Caenorhabditis elegans

<400> SEQUENCE: 178

```
Phe Val Ile Gly Leu Val Glu Asn Gly Asp Leu Gly Glu Ser Leu Cys
 1               5                  10                  15

His Phe Gly Ser Phe Asp Met Leu Thr Ser Lys Phe Phe Ala Ser Glu
            20                  25                  30

Ile Leu Thr Gly Leu Gln Phe Leu His Asp Asn Lys Ile Val His Arg
        35                  40                  45

Asp Met Lys Pro Asp Asn Val Leu Ile Gln Lys Asp Gly His Ile Leu
    50                  55                  60

Ile Thr Asp Phe Gly Ser Ala Gln
65                  70
```

<210> SEQ ID NO 179
<211> LENGTH: 48
<212> TYPE: PRT
<213> ORGANISM: Mus musculus or Homo sapiens

<400> SEQUENCE: 179

```
Tyr Ala Ile Lys Ile Leu Glu Lys Arg His Ile Ile Lys Glu Asn Lys
 1               5                  10                  15

Val Pro Tyr Val Thr Arg Glu Arg Asp Val Met Ser Arg Leu Asp His
            20                  25                  30

Pro Phe Phe Val Lys Leu Tyr Phe Thr Phe Gln Asp Asp Glu Lys Leu
        35                  40                  45
```

<210> SEQ ID NO 180
<211> LENGTH: 15
<212> TYPE: PRT
<213> ORGANISM: Mus musculus or Homo sapiens or C elegans

<400> SEQUENCE: 180

```
Ala Lys Leu Lys Lys Arg Glu Leu His Pro Phe Leu Tyr Phe Asp
 1               5                  10                  15
```

<210> SEQ ID NO 181
<211> LENGTH: 53
<212> TYPE: PRT
<213> ORGANISM: Caenorhabditis elegans

<400> SEQUENCE: 181

```
Phe Ala Val Lys Val Leu Gln Lys Ser Tyr Leu Asn Arg His Gln Lys
 1               5                  10                  15

Met Asp Ala Ile Ile Arg Glu Lys Asn Ile Leu Thr Tyr Leu Ser Gln
            20                  25                  30

Glu Cys Gly Gly His Pro Phe Val Thr Gln Leu Tyr Thr His Phe His
        35                  40                  45

Asp Gln Ala Arg Ile
    50
```

<210> SEQ ID NO 182

```
<211> LENGTH: 29
<212> TYPE: PRT
<213> ORGANISM: Mus musculus or Homo sapiens

<400> SEQUENCE: 182

Pro Asn Arg Thr Tyr Tyr Leu Met Asp Pro Ser Gly Asn Ala His Lys
1               5                   10                  15

Trp Cys Arg Lys Ile Gln Glu Val Trp Arg Gln Arg Tyr
            20                  25

<210> SEQ ID NO 183
<211> LENGTH: 15
<212> TYPE: PRT
<213> ORGANISM: Mus musculus or Homo sapiens or C elegans

<400> SEQUENCE: 183

Pro Asn Arg Tyr Tyr Leu Asp Ala Trp Cys Ile Val Arg Arg Tyr
1               5                   10                  15

<210> SEQ ID NO 184
<211> LENGTH: 28
<212> TYPE: PRT
<213> ORGANISM: Caenorhabditis elegans

<400> SEQUENCE: 184

Pro Asn Arg Val Tyr Tyr Leu Phe Asp Leu Glu Lys Lys Ala Asp Glu
1               5                   10                  15

Trp Cys Lys Ala Ile Asn Asp Val Arg Lys Arg Tyr
            20                  25

<210> SEQ ID NO 185
<211> LENGTH: 25
<212> TYPE: PRT
<213> ORGANISM: Mus musculus or Homo sapiens

<400> SEQUENCE: 185

Pro Glu Ser Lys Gln Ala Arg Ala Asn Ser Phe Val Gly Thr Ala Gln
1               5                   10                  15

Tyr Val Ser Pro Glu Leu Leu Thr Glu
            20                  25

<210> SEQ ID NO 186
<211> LENGTH: 15
<212> TYPE: PRT
<213> ORGANISM: Mus musculus or Homo sapiens or C elegans

<400> SEQUENCE: 186

Pro Glu Ala Arg Phe Val Gly Thr Ala Tyr Val Ser Pro Glu Leu
1               5                   10                  15

<210> SEQ ID NO 187
<211> LENGTH: 25
<212> TYPE: PRT
<213> ORGANISM: Caenorhabditis elegans

<400> SEQUENCE: 187

Pro Glu Glu Asn Thr Ala Arg Arg Thr Thr Phe Val Gly Thr Ala Leu
1               5                   10                  15

Tyr Val Ser Pro Glu Met Leu Ala Asp
            20                  25

<210> SEQ ID NO 188
<211> LENGTH: 62
```

```
<212> TYPE: PRT
<213> ORGANISM: Caenorhabditis elegans

<400> SEQUENCE: 188

Lys Arg Thr Ser Asn Asp Phe Met Phe Leu Gln Ser Met Gly Glu Gly
  1               5                  10                  15

Ala Tyr Ser Gln Val Phe Arg Cys Arg Glu Val Ala Thr Asp Ala Met
             20                  25                  30

Phe Ala Val Lys Val Leu Gln Lys Ser Tyr Leu Asn Arg His Gln Lys
         35                  40                  45

Met Asp Ala Ile Ile Arg Glu Lys Asn Ile Leu Thr Tyr Leu
     50                  55                  60

<210> SEQ ID NO 189
<211> LENGTH: 21
<212> TYPE: PRT
<213> ORGANISM: Caenorhabditis elegans or Homo sapiens

<400> SEQUENCE: 189

Lys Asp Phe Phe Gly Glu Gly Ser Val Arg Glu Ala Thr Ala Lys Leu
  1               5                  10                  15

Lys Lys Arg Glu Leu
             20

<210> SEQ ID NO 190
<211> LENGTH: 62
<212> TYPE: PRT
<213> ORGANISM: Homo sapiens

<400> SEQUENCE: 190

Lys Lys Arg Pro Glu Asp Phe Lys Phe Gly Lys Ile Leu Gly Glu Gly
  1               5                  10                  15

Ser Phe Ser Thr Val Val Leu Ala Arg Glu Leu Ala Thr Ser Arg Glu
             20                  25                  30

Tyr Ala Ile Lys Ile Leu Glu Lys Arg His Ile Ile Lys Glu Asn Lys
         35                  40                  45

Val Pro Tyr Val Thr Arg Glu Arg Asp Val Met Ser Arg Leu
     50                  55                  60

<210> SEQ ID NO 191
<211> LENGTH: 90
<212> TYPE: PRT
<213> ORGANISM: Caenorhabditis elegans

<400> SEQUENCE: 191

His Pro Phe Val Thr Gln Leu Tyr Thr His Phe His Asp Gln Ala Arg
  1               5                  10                  15

Ile Tyr Phe Val Ile Gly Leu Val Glu Asn Gly Asp Leu Gly Glu Ser
             20                  25                  30

Leu Cys His Phe Gly Ser Phe Asp Met Leu Thr Ser Lys Phe Phe Ala
         35                  40                  45

Ser Glu Ile Leu Thr Gly Leu Gln Phe Leu His Asp Asn Lys Ile Val
     50                  55                  60

His Arg Asp Met Lys Pro Asp Asn Val Leu Ile Gln Lys Asp Gly His
 65                  70                  75                  80

Ile Leu Ile Thr Asp Phe Gly Ser Ala Gln
                 85                  90

<210> SEQ ID NO 192
```

-continued

```
<211> LENGTH: 39
<212> TYPE: PRT
<213> ORGANISM: Caenorhabditis elegans

<400> SEQUENCE: 192

His Pro Phe Leu Tyr Phe Asp Tyr Phe Asn Gly Leu Gly Ser Phe Asp
1               5                   10                  15

Phe Glu Ile Leu Leu His Ile His Arg Asp Lys Pro Asn Leu Asp His
            20                  25                  30

Ile Ile Thr Asp Phe Gly Ala
        35

<210> SEQ ID NO 193
<211> LENGTH: 90
<212> TYPE: PRT
<213> ORGANISM: Homo sapiens

<400> SEQUENCE: 193

His Pro Phe Phe Val Lys Leu Tyr Phe Thr Phe Gln Asp Asp Glu Lys
1               5                   10                  15

Leu Tyr Phe Gly Leu Ser Tyr Ala Lys Asn Gly Glu Leu Leu Lys Tyr
            20                  25                  30

Ile Arg Lys Ile Gly Ser Phe Asp Glu Thr Cys Thr Arg Phe Tyr Thr
        35                  40                  45

Ala Glu Ile Val Ser Ala Leu Glu Tyr Leu His Gly Lys Gly Ile Ile
    50                  55                  60

His Arg Asp Leu Lys Pro Glu Asn Ile Leu Leu Asn Glu Asp Met His
65                  70                  75                  80

Ile Gln Ile Thr Asp Phe Gly Thr Ala Lys
                85                  90

<210> SEQ ID NO 194
<211> LENGTH: 98
<212> TYPE: PRT
<213> ORGANISM: Caenorhabditis elegans

<400> SEQUENCE: 194

Glu Glu Asn Thr Ala Arg Arg Thr Thr Phe Val Gly Thr Ala Leu Tyr
1               5                   10                  15

Val Ser Pro Glu Met Leu Ala Asp Gly Asp Val Gly Pro Gln Thr Asp
            20                  25                  30

Ile Trp Gly Leu Gly Cys Ile Leu Phe Gln Cys Leu Ala Gly Gln Pro
        35                  40                  45

Pro Phe Arg Ala Val Asn Gln Tyr His Leu Leu Lys Arg Ile Gln Glu
    50                  55                  60

Leu Asp Phe Ser Phe Pro Glu Gly Phe Pro Glu Ala Ser Glu Ile
65                  70                  75                  80

Ile Ala Lys Ile Leu Val Arg Asp Pro Ser Thr Arg Ile Thr Ser Gln
                85                  90                  95

Glu Leu

<210> SEQ ID NO 195
<211> LENGTH: 43
<212> TYPE: PRT
<213> ORGANISM: Caenorhabditis elegans or Homo sapiens

<400> SEQUENCE: 195

Glu Ala Arg Phe Val Gly Thr Ala Tyr Val Ser Pro Glu Leu Asp Trp
1               5                   10                  15
```

```
Leu Gly Cys Ile Gln Ala Gly Pro Pro Phe Arg Ala Asn Tyr Ile Leu
            20                  25                  30

Phe Pro Glu Phe Ala Lys Leu Val Asp Arg Glu
        35                  40
```

<210> SEQ ID NO 196
<211> LENGTH: 98
<212> TYPE: PRT
<213> ORGANISM: Homo sapiens

<400> SEQUENCE: 196

```
Glu Ser Lys Gln Ala Arg Ala Asn Ser Phe Val Gly Thr Ala Gln Tyr
 1               5                  10                  15

Val Ser Pro Glu Leu Leu Thr Glu Lys Ser Ala Cys Lys Ser Ser Asp
            20                  25                  30

Leu Trp Ala Leu Gly Cys Ile Ile Tyr Gln Leu Val Ala Gly Leu Pro
        35                  40                  45

Pro Phe Arg Ala Gly Asn Glu Tyr Leu Ile Phe Gln Lys Ile Ile Lys
    50                  55                  60

Leu Glu Tyr Asp Phe Pro Glu Lys Phe Phe Pro Lys Ala Arg Asp Leu
65                  70                  75                  80

Val Glu Lys Leu Leu Val Leu Asp Ala Thr Lys Arg Leu Gly Cys Glu
                85                  90                  95

Glu Met
```

<210> SEQ ID NO 197
<211> LENGTH: 35
<212> TYPE: PRT
<213> ORGANISM: Caenorhabditis elegans

<400> SEQUENCE: 197

```
Leu Met Ala His Lys Phe Phe Glu Asn Val Asp Trp Val Asn Ile Ala
 1               5                  10                  15

Asn Ile Lys Pro Pro Val Leu His Ala Tyr Ile Pro Ala Thr Phe Gly
            20                  25                  30

Glu Pro Glu
        35
```

<210> SEQ ID NO 198
<211> LENGTH: 17
<212> TYPE: PRT
<213> ORGANISM: Caenorhabditis elegans or Homo sapiens

<400> SEQUENCE: 198

```
Leu Ala His Phe Phe Glu Val Trp Asn Pro Pro Leu Ala Tyr Pro Ala
 1               5                  10                  15

Glu
```

<210> SEQ ID NO 199
<211> LENGTH: 35
<212> TYPE: PRT
<213> ORGANISM: Homo sapiens

<400> SEQUENCE: 199

```
Leu Lys Ala His Pro Phe Phe Glu Ser Val Thr Trp Glu Asn Leu His
 1               5                  10                  15

Gln Gln Thr Pro Pro Lys Leu Thr Ala Tyr Leu Pro Ala Met Ser Glu
            20                  25                  30
```

Asp Asp Glu
        35

<210> SEQ ID NO 200
<211> LENGTH: 104
<212> TYPE: PRT
<213> ORGANISM: Caenorhabditis elegans

<400> SEQUENCE: 200

Leu Glu Glu Gln Arg Val Lys Asn Pro Phe His Ile Phe Thr Asn Asn
1               5                   10                  15

Ser Leu Ile Leu Lys Gln Gly Tyr Leu Glu Lys Arg Gly Leu Phe
            20                  25                  30

Ala Arg Arg Met Phe Leu Leu Thr Glu Gly Pro His Leu Leu Tyr
        35                  40                  45

Ile Asp Val Pro Asn Leu Val Leu Lys Gly Glu Val Pro Trp Thr Pro
    50                  55                  60

Cys Met Gln Val Glu Leu Lys Asn Ser Gly Thr Phe Phe Ile His Thr
65                  70                  75                  80

Pro Asn Arg Val Tyr Tyr Leu Phe Asp Leu Glu Lys Lys Ala Asp Glu
                85                  90                  95

Trp Cys Lys Ala Ile Asn Asp Val
            100

<210> SEQ ID NO 201
<211> LENGTH: 59
<212> TYPE: PRT
<213> ORGANISM: Caenorhabditis elegans or Homo sapiens

<400> SEQUENCE: 201

Leu Glu Gln Asn Pro His Phe Asn Leu Ile Leu Lys Gly Lys Gly Leu
1               5                   10                  15

Phe Ala Arg Arg Arg Leu Leu Thr Glu Gly Pro His Leu Tyr Asp Asn
            20                  25                  30

Val Leu Lys Gly Glu Pro Trp Glu Lys Asn Thr Phe Phe His Thr Pro
            35                  40                  45

Asn Arg Tyr Tyr Leu Asp Ala Trp Cys Ile Val
    50                  55

<210> SEQ ID NO 202
<211> LENGTH: 104
<212> TYPE: PRT
<213> ORGANISM: Homo sapiens

<400> SEQUENCE: 202

Leu Glu Lys Gln Ala Gly Gly Asn Pro Trp His Gln Phe Val Glu Asn
1               5                   10                  15

Asn Leu Ile Leu Lys Met Gly Pro Val Asp Lys Arg Lys Gly Leu Phe
            20                  25                  30

Ala Arg Arg Arg Gln Leu Leu Leu Thr Glu Gly Pro His Leu Tyr Tyr
        35                  40                  45

Val Asp Pro Val Asn Lys Val Leu Lys Gly Glu Ile Pro Trp Ser Gln
    50                  55                  60

Glu Leu Arg Pro Glu Ala Lys Asn Phe Lys Thr Phe Phe Val His Thr
65                  70                  75                  80

Pro Asn Arg Thr Tyr Tyr Leu Met Asp Pro Ser Gly Asn Ala His Lys
                85                  90                  95

Trp Cys Arg Lys Ile Gln Glu Val

-continued

100

<210> SEQ ID NO 203
<211> LENGTH: 45
<212> TYPE: PRT
<213> ORGANISM: Homo sapiens

<400> SEQUENCE: 203

```
Lys Leu Glu Asn Leu Met Leu Asp Lys Asp Gly His Ile Lys Ile Thr
 1               5                  10                  15
Asp Phe Gly Leu Cys Lys Glu Gly Ile Lys Asp Gly Ala Thr Met Lys
                20                  25                  30
Thr Phe Cys Gly Thr Pro Glu Tyr Leu Ala Pro Glu Val
            35                  40                  45
```

<210> SEQ ID NO 204
<211> LENGTH: 36
<212> TYPE: PRT
<213> ORGANISM: Homo sapiens or Caenorhabditis elegans

<400> SEQUENCE: 204

```
Lys Leu Glu Asn Leu Leu Asp Lys Asp Gly His Ile Lys Ile Asp Phe
 1               5                  10                  15
Gly Leu Cys Lys Glu Ile Gly Thr Phe Cys Gly Thr Pro Glu Tyr Leu
                20                  25                  30
Ala Pro Glu Val
            35
```

<210> SEQ ID NO 205
<211> LENGTH: 45
<212> TYPE: PRT
<213> ORGANISM: Caenorhabditis elegans

<400> SEQUENCE: 205

```
Lys Leu Glu Asn Leu Leu Asp Lys Asp Gly His Ile Lys Ile Ala
 1               5                  10                  15
Asp Phe Gly Leu Cys Lys Glu Glu Ile Ser Phe Gly Asp Lys Thr Ser
                20                  25                  30
Thr Phe Cys Gly Thr Pro Glu Tyr Leu Ala Pro Glu Val
            35                  40                  45
```

<210> SEQ ID NO 206
<211> LENGTH: 62
<212> TYPE: PRT
<213> ORGANISM: Caenorhabditis elegans

<400> SEQUENCE: 206

```
Leu Cys Lys Glu Glu Ile Lys Tyr Gly Asp Lys Thr Ser Thr Phe Cys
 1               5                  10                  15
Gly Thr Pro Glu Tyr Leu Ala Pro Glu Val Ile Glu Asp Ile Asp Tyr
                20                  25                  30
Asp Arg Ser Val Asp Trp Trp Gly Val Gly Val Val Met Tyr Glu Met
            35                  40                  45
Met Cys Gly Arg Leu Pro Phe Ser Ala Lys Glu Asn Gly Lys
        50                  55                  60
```

<210> SEQ ID NO 207
<211> LENGTH: 43
<212> TYPE: PRT
<213> ORGANISM: Caenorhabditis elegans or Mus musculus

```
<400> SEQUENCE: 207

Leu Cys Lys Glu Ile Gly Thr Phe Cys Gly Thr Pro Glu Tyr Leu Ala
 1               5                  10                  15

Pro Glu Val Glu Asp Asp Tyr Arg Val Asp Trp Trp Gly Gly Val Val
            20                  25                  30

Met Tyr Glu Met Met Cys Gly Arg Leu Pro Phe
        35                  40

<210> SEQ ID NO 208
<211> LENGTH: 492
<212> TYPE: PRT
<213> ORGANISM: Caenorhabditis elegans

<400> SEQUENCE: 208

Met Gly Val Asn Asp His Asp Val Ser Val Pro Leu Gln Glu Val Gln
 1               5                  10                  15

Ser Arg Thr Val Glu Gly Lys Leu Thr Lys Cys Leu Ala Phe Ser Ala
            20                  25                  30

Phe Val Ile Thr Leu Ala Ser Phe Gln Phe Gly Tyr His Ile Gly Cys
        35                  40                  45

Val Asn Ala Pro Gly Gly Leu Ile Thr Glu Trp Ile Ile Gly Ser His
    50                  55                  60

Lys Asp Leu Phe Asp Lys Glu Leu Ser Arg Glu Asn Ala Asp Leu Ala
65                  70                  75                  80

Trp Ser Val Ala Val Ser Val Phe Ala Val Gly Gly Met Ile Gly Gly
                85                  90                  95

Leu Ser Ser Gly Trp Leu Ala Asp Lys Val Gly Arg Arg Gly Ala Leu
            100                 105                 110

Phe Tyr Asn Asn Leu Leu Ala Leu Ala Ala Ala Leu Met Gly Leu
        115                 120                 125

Ala Lys Ser Val Gly Ala Tyr Pro Met Val Ile Leu Gly Arg Leu Ile
    130                 135                 140

Ile Gly Leu Asn Cys Gly Phe Ser Ser Ala Leu Val Pro Met Phe Leu
145                 150                 155                 160

Thr Glu Ile Ser Pro Asn Asn Leu Arg Gly Met Leu Gly Ser Leu His
                165                 170                 175

Gln Leu Leu Val Thr Ile Ala Ile Leu Val Ser Gln Ile Phe Gly Leu
            180                 185                 190

Pro His Leu Leu Gly Thr Gly Asp Arg Trp Pro Leu Ile Phe Ala Phe
        195                 200                 205

Thr Val Val Pro Ala Val Leu Gln Leu Ala Leu Leu Met Leu Cys Pro
    210                 215                 220

Glu Ser Pro Lys Tyr Thr Met Ala Val Arg Gly Gln Arg Asn Glu Ala
225                 230                 235                 240

Glu Ser Ala Leu Lys Lys Leu Arg Asp Thr Glu Asp Val Ser Thr Glu
                245                 250                 255

Ile Glu Ala Met Gln Glu Ala Thr Ala Ala Gly Val Gln Glu Lys
            260                 265                 270

Pro Lys Met Gly Asp Met Phe Lys Gly Ala Leu Leu Trp Pro Met Ser
        275                 280                 285

Ile Ala Ile Met Met Met Leu Ala Gln Gln Leu Ser Gly Ile Asn Val
    290                 295                 300

Ala Met Phe Tyr Ser Thr Val Ile Phe Arg Gly Ala Gly Leu Thr Gly
305                 310                 315                 320
```

-continued

Asn Glu Pro Phe Tyr Ala Thr Ile Gly Met Gly Ala Val Asn Val Ile
                325                 330                 335

Met Thr Leu Ile Ser Val Trp Leu Val Asp His Pro Lys Phe Gly Arg
            340                 345                 350

Arg Ser Leu Leu Leu Ala Gly Leu Thr Gly Met Phe Val Ser Thr Leu
        355                 360                 365

Leu Leu Val Gly Ala Leu Thr Ile Gln Asn Ser Gly Gly Asp Lys Trp
    370                 375                 380

Ala Ser Tyr Ser Ala Ile Gly Phe Val Leu Phe Val Ile Ser Phe
385                 390                 395                 400

Ala Thr Gly Pro Gly Ala Ile Pro Trp Phe Val Ser Glu Ile Phe
                405                 410                 415

Asp Ser Ser Ala Arg Gly Asn Ala Asn Ser Ile Ala Val Met Val Asn
                420                 425                 430

Trp Ala Ala Asn Leu Leu Val Gly Leu Thr Phe Leu Pro Ile Asn Asn
            435                 440                 445

Leu Met Gln Gln Tyr Ser Phe Phe Ile Phe Ser Gly Phe Leu Ala Phe
        450                 455                 460

Phe Ile Phe Tyr Thr Trp Lys Phe Val Pro Glu Thr Lys Gly Lys Ser
465                 470                 475                 480

Ile Glu Gln Ile Gln Ala Glu Phe Glu Lys Arg Lys
                485                 490

<210> SEQ ID NO 209
<211> LENGTH: 22
<212> TYPE: PRT
<213> ORGANISM: Caenorhabditis elegans

<400> SEQUENCE: 209

Arg Asn Glu Ala Glu Ser Ala Leu Lys Lys Leu Arg Asp Thr Glu Asp
1               5                   10                  15

Val Ser Thr Glu Ile Glu
            20

<210> SEQ ID NO 210
<211> LENGTH: 28
<212> TYPE: DNA
<213> ORGANISM: Caenorhabditis elegans

<400> SEQUENCE: 210
tctcgttgtt tgccgtcgga tgtctgcc                                          28

<210> SEQ ID NO 211
<211> LENGTH: 223
<212> TYPE: PRT
<213> ORGANISM: Ascoris suum

<400> SEQUENCE: 211

Ala Lys Asn Asn Gly Glu Phe Val Arg Cys Val His Ser Val Gly Gln
1               5                   10                  15

Pro Lys Pro Val Ala Thr Lys Val Ile Asn His Trp Pro Cys Asn Pro
            20                  25                  30

Glu Lys Thr Ile Ile Ala His Arg Pro Ala Glu Arg Glu Ile Trp Ser
        35                  40                  45

Phe Gly Ser Gly Tyr Gly Gly Asn Ser Leu Leu Gly Lys Lys Cys Phe
    50                  55                  60

Ala Leu Arg Ile Ala Met Asn Ile Gly Tyr Asp Glu Gly Trp Met Ala
65                  70                  75                  80

```
Glu His Met Leu Ile Met Gly Val Thr Ser Pro Lys Gly Glu Arg
                85                  90                  95

Phe Val Ala Ala Ala Phe Pro Ser Ala Cys Gly Lys Thr Asn Leu Ala
            100                 105                 110

Met Leu Glu Pro Thr Ile Pro Gly Trp Lys Val Arg Val Ile Gly Asp
        115                 120                 125

Asp Ile Ala Trp Met Lys Phe Gly Ala Asp Gly Arg Leu Tyr Ala Ile
    130                 135                 140

Asn Pro Glu Tyr Gly Phe Phe Gly Val Ala Pro Gly Thr Ser His Lys
145                 150                 155                 160

Thr Asn Pro Met Ala Met Ala Ser Phe Gln Glu Asn Thr Ile Phe Thr
                165                 170                 175

Asn Val Ala Glu Thr Ala Asp Gly Glu Tyr Phe Trp Glu Gly Leu Glu
            180                 185                 190

His Glu Val Lys Asn Pro Lys Val Asp Met Ile Asn Trp Leu Gly Glu
        195                 200                 205

Pro Trp His Ile Gly Asp Glu Ser Lys Ala Ala His Pro Asn Ser
    210                 215                 220

<210> SEQ ID NO 212
<211> LENGTH: 176
<212> TYPE: PRT
<213> ORGANISM: Caenorhabditis elegans or Ascoris suum

<400> SEQUENCE: 212

Ala Asn Phe Val Arg Cys His Ser Val Gly Pro Val Val Ile Asn
1               5                   10                  15

His Trp Pro Cys Asn Pro Glu Ile Ala His Arg Pro Glu Arg Glu Ile
            20                  25                  30

Trp Ser Phe Gly Ser Gly Tyr Gly Gly Asn Ser Leu Leu Gly Lys Lys
        35                  40                  45

Cys Phe Ala Leu Arg Ile Ala Asn Ile Asp Glu Gly Trp Met Ala Glu
    50                  55                  60

His Met Leu Ile Met Gly Val Thr Pro Gly Glu Phe Ala Ala Ala Phe
65                  70                  75                  80

Pro Ser Ala Cys Gly Lys Thr Asn Leu Ala Met Leu Glu Pro Thr Pro
                85                  90                  95

Gly Trp Lys Val Arg Gly Asp Ile Ala Trp Met Lys Phe Gly Asp
            100                 105                 110

Gly Arg Leu Tyr Ala Ile Asn Pro Glu Gly Phe Phe Gly Val Ala Pro
        115                 120                 125

Gly Thr Ser Lys Thr Asn Pro Met Ala Ala Phe Gln Asn Ile Phe Thr
    130                 135                 140

Asn Val Ala Glu Thr Ala Gly Glu Tyr Phe Trp Glu Gly Leu Glu Glu
145                 150                 155                 160

Val Asp Trp Leu Gly Glu Trp His Ile Gly Ala Ala His Pro Asn Ser
                165                 170                 175

<210> SEQ ID NO 213
<211> LENGTH: 223
<212> TYPE: PRT
<213> ORGANISM: Caenorhabditis elegans

<400> SEQUENCE: 213

Ala Leu Gly Asn Gln Asp Phe Val Arg Cys Ile His Ser Val Gly Leu
1               5                   10                  15
```

```
Pro Arg Pro Val Lys Gln Arg Val Ile Asn His Trp Pro Cys Asn Pro
            20                  25                  30

Glu Arg Val Leu Ile Ala His Arg Pro Pro Glu Arg Glu Ile Trp Ser
            35                  40                  45

Phe Gly Ser Gly Tyr Gly Gly Asn Ser Leu Leu Gly Lys Lys Cys Phe
        50                  55                  60

Ala Leu Arg Ile Ala Ser Asn Ile Ala Lys Asp Glu Gly Trp Met Ala
 65                  70                  75                  80

Glu His Met Leu Ile Met Gly Val Thr Arg Pro Cys Gly Arg Glu His
                85                  90                  95

Phe Ile Ala Ala Ala Phe Pro Ser Ala Cys Gly Lys Thr Asn Leu Ala
            100                 105                 110

Met Leu Glu Pro Thr Leu Pro Gly Trp Lys Val Arg Cys Val Gly Asp
            115                 120                 125

Asp Ile Ala Trp Met Lys Phe Gly Glu Asp Gly Arg Leu Tyr Ala Ile
        130                 135                 140

Asn Pro Glu Ala Gly Phe Phe Gly Val Ala Pro Gly Thr Ser Asn Lys
145                 150                 155                 160

Thr Asn Pro Met Ala Val Ala Thr Phe Gln Lys Asn Ser Ile Phe Thr
                165                 170                 175

Asn Val Ala Glu Thr Ala Asn Gly Glu Tyr Phe Trp Glu Gly Leu Glu
            180                 185                 190

Asp Glu Ile Ala Asp Lys Asn Val Asp Ile Thr Thr Trp Leu Gly Glu
            195                 200                 205

Lys Trp His Ile Gly Glu Pro Gly Val Ala Ala His Pro Asn Ser
        210                 215                 220

<210> SEQ ID NO 214
<211> LENGTH: 173
<212> TYPE: PRT
<213> ORGANISM: Ascoris suum

<400> SEQUENCE: 214

Lys Gly Asp Phe Val Ser Leu Pro Lys His Val Gln Arg Phe Val Ala
 1               5                  10                  15

Glu Lys Ala Glu Leu Met Lys Pro Ser Ala Ile Phe Ile Cys Asp Gly
            20                  25                  30

Ser Gln Asn Glu Ala Asp Glu Leu Ile Ala Arg Cys Val Glu Arg Gly
            35                  40                  45

Val Leu Val Pro Leu Lys Ala Tyr Lys Asn Asn Tyr Leu Cys Arg Thr
        50                  55                  60

Asp Pro Arg Asp Val Ala Arg Val Glu Ser Lys Thr Trp Met Ile Thr
 65                  70                  75                  80

Pro Glu Lys Tyr Asp Ser Val Cys His Thr Pro Glu Gly Val Lys Pro
                85                  90                  95

Met Met Gly Gln Trp Met Ser Pro Asp Glu Phe Gly Lys Glu Leu Asp
            100                 105                 110

Asp Arg Phe Pro Gly Cys Met Ala Gly Arg Thr Met Tyr Val Ile Pro
        115                 120                 125

Tyr Ser Met Gly Pro Val Gly Pro Leu Ser Lys Ile Gly Ile Glu
        130                 135                 140

Leu Thr Asp Ser Asp Tyr Val Val Leu Cys Met Arg Ile Met Thr Arg
145                 150                 155                 160

Met Gly Glu Pro Val Leu Lys Ala Leu Ala Lys Asn Asn
```

-continued

```
                  165                 170

<210> SEQ ID NO 215
<211> LENGTH: 120
<212> TYPE: PRT
<213> ORGANISM: Caenorhabditis elegans or Ascoris suum

<400> SEQUENCE: 215

Gly Asp Phe Leu Pro Val Gln Arg Phe Ala Glu Lys Ala Glu Leu Met
1               5                  10                  15

Pro Ile Phe Ile Cys Asp Gly Ser Gln Glu Ala Asp Glu Leu Ile Glu
            20                  25                  30

Arg Gly Leu Leu Ala Tyr Asn Asn Tyr Cys Arg Thr Asp Pro Asp Val
        35                  40                  45

Ala Arg Val Glu Ser Lys Thr Trp Met Thr Lys Tyr Asp Val His Thr
    50                  55                  60

Glu Gly Val Pro Met Gly Trp Pro Glu Leu Asp Arg Phe Pro Gly Cys
65                  70                  75                  80

Met Ala Gly Arg Met Tyr Val Ile Pro Ser Met Gly Pro Val Gly Gly
                85                  90                  95

Pro Leu Ser Lys Ile Gly Ile Leu Thr Asp Ser Tyr Val Val Leu Met
            100                 105                 110

Arg Ile Met Thr Arg Val Ala Leu
        115                 120

<210> SEQ ID NO 216
<211> LENGTH: 173
<212> TYPE: PRT
<213> ORGANISM: Caenorhabditis elegans

<400> SEQUENCE: 216

Gln Gly Asp Phe His Leu Leu Pro Ala Lys Val Gln Arg Phe Ile Ala
1               5                  10                  15

Glu Lys Ala Glu Leu Met Arg Pro Arg Gly Ile Phe Ile Cys Asp Gly
            20                  25                  30

Ser Gln His Glu Ala Asp Glu Leu Ile Asp Lys Leu Ile Glu Arg Gly
        35                  40                  45

Met Leu Ser Lys Leu Glu Ala Tyr Glu Asn Asn Tyr Ile Cys Arg Thr
    50                  55                  60

Asp Pro Lys Asp Val Ala Arg Val Glu Ser Lys Thr Trp Met Val Thr
65                  70                  75                  80

Lys Asn Lys Tyr Asp Thr Val Thr His Thr Lys Glu Gly Val Glu Pro
                85                  90                  95

Ile Met Gly His Trp Leu Ala Pro Glu Asp Leu Ala Thr Glu Leu Asp
            100                 105                 110

Ser Arg Phe Pro Gly Cys Met Ala Gly Arg Ile Met Tyr Val Ile Pro
        115                 120                 125

Phe Ser Met Gly Pro Val Gly Gly Pro Leu Ser Lys Ile Gly Ile Gln
    130                 135                 140

Leu Thr Asp Ser Asn Tyr Val Val Leu Ser Met Arg Ile Met Thr Arg
145                 150                 155                 160

Val Asn Asn Asp Val Trp Asp Ala Leu Gly Asn Gln Asp
                165                 170

<210> SEQ ID NO 217
<211> LENGTH: 107
<212> TYPE: PRT
```

<213> ORGANISM: Ascoris suum

<400> SEQUENCE: 217

Arg Phe Thr Ala Pro Ala Gly Gln Cys Pro Ile Ile His Pro Asp Trp
1               5                   10                  15

Glu Lys Pro Glu Gly Val Pro Ile Asp Ala Ile Ile Phe Gly Gly Arg
            20                  25                  30

Arg Pro Glu Gly Val Pro Leu Val Phe Glu Ser Arg Ser Trp Val His
        35                  40                  45

Gly Ile Phe Val Gly Ala Cys Val Lys Ser Glu Ala Thr Ala Ala Ala
    50                  55                  60

Glu His Thr Gly Lys Gln Val Met His Asp Pro Met Ala Met Arg Pro
65                  70                  75                  80

Phe Met Gly Tyr Asn Phe Gly Arg Tyr Met Arg His Trp Met Lys Leu
                85                  90                  95

Gly Gln Pro Pro His Lys Val Pro Lys Ile Phe
            100                 105

<210> SEQ ID NO 218
<211> LENGTH: 77
<212> TYPE: PRT
<213> ORGANISM: Caenorhabditis elegans or Ascoris suum

<400> SEQUENCE: 218

Arg Phe Ala Pro Ala Gln Cys Pro Ile Ile His Pro Asp Trp Glu Pro
1               5                   10                  15

Gly Val Pro Ile Ala Ile Ile Phe Gly Gly Arg Arg Pro Gly Val Pro
            20                  25                  30

Leu Glu Ser Trp His Gly Phe Gly Cys Lys Ser Glu Ala Thr Ala Ala
        35                  40                  45

Ala Glu Thr Gly Lys Val Met His Asp Pro Met Ala Met Arg Pro Phe
    50                  55                  60

Met Gly Tyr Asn Phe Gly Tyr His Trp Leu Lys Val Phe
65                  70                  75

<210> SEQ ID NO 219
<211> LENGTH: 107
<212> TYPE: PRT
<213> ORGANISM: Caenorhabditis elegans

<400> SEQUENCE: 219

Arg Phe Ala Ala Pro Ala Asn Gln Cys Pro Ile Ile His Pro Asp Trp
1               5                   10                  15

Glu Ser Pro Gln Gly Val Pro Ile Glu Ala Ile Ile Phe Gly Gly Arg
            20                  25                  30

Arg Pro Gln Gly Val Pro Leu Ile Tyr Glu Thr Asn Ser Trp Glu His
        35                  40                  45

Gly Val Phe Thr Gly Ser Cys Leu Lys Ser Glu Ala Thr Ala Ala Ala
    50                  55                  60

Glu Phe Thr Gly Lys Thr Val Met His Asp Pro Met Ala Met Arg Pro
65                  70                  75                  80

Phe Met Gly Tyr Asn Phe Gly Lys Tyr Leu Gln His Trp Leu Asp Leu
                85                  90                  95

Lys Thr Asp Ser Arg Lys Val Ile Asp Phe Phe
            100                 105

<210> SEQ ID NO 220

```
<211> LENGTH: 116
<212> TYPE: PRT
<213> ORGANISM: Ascoris suum

<400> SEQUENCE: 220

Val Pro Lys Ile Phe His Val Asn Trp Phe Arg Gln Ser Ala Asp His
1               5                   10                  15

Lys Phe Leu Trp Pro Gly Tyr Gly Asp Asn Ile Arg Val Ile Asp Trp
            20                  25                  30

Ile Leu Arg Arg Cys Ser Gly Asp Ala Thr Ile Ala Glu Glu Thr Pro
        35                  40                  45

Ile Gly Phe Ile Pro Lys Lys Gly Thr Ile Asn Leu Glu Gly Leu Pro
    50                  55                  60

Asn Val Asn Trp Asp Glu Leu Met Ser Ile Pro Lys Ser Tyr Trp Leu
65                  70                  75                  80

Glu Asp Met Val Glu Thr Lys Thr Phe Phe Glu Asn Gln Val Gly Ser
                85                  90                  95

Asp Leu Pro Pro Glu Ile Ala Lys Glu Leu Glu Ala Gln Thr Glu Arg
            100                 105                 110

Ile Lys Ala Leu
        115

<210> SEQ ID NO 221
<211> LENGTH: 68
<212> TYPE: PRT
<213> ORGANISM: Caenorhabditis elegans or Ascoris suum

<400> SEQUENCE: 221

Pro Lys Ile His Val Asn Trp Phe Arg Lys Phe Leu Trp Pro Gly Gly
1               5                   10                  15

Asp Asn Ile Arg Val Ile Asp Trp Ile Arg Arg Gly Ile Glu Thr Pro
            20                  25                  30

Ile Gly Pro Lys Gly Ile Asn Leu Glu Gly Leu Val Asn Trp Asp Glu
        35                  40                  45

Leu Met Ser Pro Tyr Trp Asp Glu Phe Gln Val Gly Asp Leu Pro Glu
    50                  55                  60

Ala Gln Arg Leu
65

<210> SEQ ID NO 222
<211> LENGTH: 116
<212> TYPE: PRT
<213> ORGANISM: Caenorhabditis elegans

<400> SEQUENCE: 222

Met Pro Lys Ile Tyr His Val Asn Trp Phe Arg Lys Asp Ser Asn Asn
1               5                   10                  15

Lys Phe Leu Trp Pro Gly Phe Gly Asp Asn Ile Arg Val Ile Asp Trp
            20                  25                  30

Ile Ile Arg Arg Leu Asp Gly Glu Gln Glu Ile Gly Val Glu Thr Pro
        35                  40                  45

Ile Gly Thr Val Pro Ala Lys Gly Ser Ile Asn Leu Glu Gly Leu Gly
    50                  55                  60

Glu Val Asn Trp Asp Glu Leu Met Ser Val Pro Ala Asp Tyr Trp Lys
65                  70                  75                  80

Gln Asp Ala Gln Glu Ile Arg Lys Phe Leu Asp Glu Gln Val Gly Glu
                85                  90                  95
```

```
Asp Leu Pro Glu Pro Val Arg Ala Glu Met Asp Ala Gln Glu Lys Arg
            100                 105                 110

Val Gln Thr Leu
        115

<210> SEQ ID NO 223
<211> LENGTH: 36
<212> TYPE: PRT
<213> ORGANISM: Ascoris suum

<400> SEQUENCE: 223

Ser Leu Ser His Phe Lys Asp Asp Phe Ala Val Val Ser Glu Val
  1               5                  10                  15

Val Thr His Lys Gln Asn His Ile Pro Val Ile Lys Gly Asp Phe Val
             20                  25                  30

Ser Leu Pro Lys
        35

<210> SEQ ID NO 224
<211> LENGTH: 15
<212> TYPE: PRT
<213> ORGANISM: Caenorhabditis elegans or Ascoris suum

<400> SEQUENCE: 224

Ser Leu Asp Phe Val Val Glu Val Val His Pro Lys Phe Ser Lys
  1               5                  10                  15

<210> SEQ ID NO 225
<211> LENGTH: 36
<212> TYPE: PRT
<213> ORGANISM: Caenorhabditis elegans

<400> SEQUENCE: 225

Ser Leu Arg Gln Ile Ser Glu Asp Ala Phe Tyr Val Val Asn Glu Val
  1               5                  10                  15

Val Met Lys Arg Leu Gly His Val Pro Ile Leu Lys Val Ile Phe Glu
             20                  25                  30

Ser Ser Glu Lys
        35

<210> SEQ ID NO 226
<211> LENGTH: 25
<212> TYPE: PRT
<213> ORGANISM: Ascoris suum

<400> SEQUENCE: 226

Gly Cys Met Ala Gly Arg Thr Met Tyr Val Ile Pro Tyr Ser Met Gly
  1               5                  10                  15

Pro Val Gly Gly Pro Leu Ser Lys Ile
             20                  25

<210> SEQ ID NO 227
<211> LENGTH: 9
<212> TYPE: PRT
<213> ORGANISM: Caenorhabditis elegans or Ascoris suum

<400> SEQUENCE: 227

Gly Cys Arg Val Pro Ser Pro Leu Lys
  1               5

<210> SEQ ID NO 228
<211> LENGTH: 25
```

```
<212> TYPE: PRT
<213> ORGANISM: Caenorhabditis elegans

<400> SEQUENCE: 228

Gly Cys Ser Gly Arg Arg Val Leu Cys Val Cys Pro Cys Ser His Ser
  1               5                  10                  15

Ser Ser Ala Leu Pro Leu Gln Lys Val
             20                  25

<210> SEQ ID NO 229
<211> LENGTH: 16
<212> TYPE: PRT
<213> ORGANISM: Ascoris suum

<400> SEQUENCE: 229

Leu Pro Asn Val Asn Trp Asp Glu Leu Met Ser Ile Pro Lys Ser Tyr
  1               5                  10                  15

<210> SEQ ID NO 230
<211> LENGTH: 7
<212> TYPE: PRT
<213> ORGANISM: Caenorhabditis elegans or Ascoris suum

<400> SEQUENCE: 230

Leu Asn Trp Ser Pro Ser Tyr
  1               5

<210> SEQ ID NO 231
<211> LENGTH: 16
<212> TYPE: PRT
<213> ORGANISM: Caenorhabditis elegans

<400> SEQUENCE: 231

Leu Glu Ser Phe Asn Trp Phe Ser Phe Val Ser Cys Pro Asp Ser Tyr
  1               5                  10                  15

<210> SEQ ID NO 232
<211> LENGTH: 14
<212> TYPE: PRT
<213> ORGANISM: Ascoris suum

<400> SEQUENCE: 232

Ser Val Cys His Thr Pro Glu Gly Val Lys Pro Met Met Gly
  1               5                  10

<210> SEQ ID NO 233
<211> LENGTH: 6
<212> TYPE: PRT
<213> ORGANISM: Caenorhabditis elegans or Ascoris suum

<400> SEQUENCE: 233

Val His Pro Pro Met Gly
  1               5

<210> SEQ ID NO 234
<211> LENGTH: 14
<212> TYPE: PRT
<213> ORGANISM: Caenorhabditis elegans

<400> SEQUENCE: 234

Thr Val Met His Asp Pro Met Ala Met Arg Pro Phe Met Gly
  1               5                  10

<210> SEQ ID NO 235
```

```
<211> LENGTH: 197
<212> TYPE: PRT
<213> ORGANISM: Homo sapiens

<400> SEQUENCE: 235

Ser Gly Phe Phe Asp Tyr Gly Ser Phe Ser Glu Ile Met Gln Pro Trp
 1               5                  10                  15

Ala Gln Thr Val Val Gly Arg Ala Arg Leu Gly Gly Ile Pro Val
             20                  25                  30

Gly Val Val Ala Val Glu Thr Arg Thr Val Glu Leu Ser Val Pro Ala
         35                  40                  45

Asp Pro Ala Asn Leu Asp Ser Glu Ala Lys Ile Ile Gln Gln Ala Gly
 50                  55                  60

Gln Val Trp Phe Pro Asp Ser Ala Phe Lys Thr Tyr Gln Ala Ile Lys
65                  70                  75                  80

Asp Phe Asn Arg Glu Gly Leu Pro Leu Met Val Phe Ala Asn Trp Arg
                 85                  90                  95

Gly Phe Ser Gly Gly Met Lys Asp Met Tyr Asp Gln Val Leu Lys Phe
                100                 105                 110

Gly Ala Tyr Ile Val Asp Gly Leu Arg Glu Cys Ser Gln Pro Val Met
            115                 120                 125

Val Tyr Ile Pro Pro Gln Ala Glu Leu Arg Gly Gly Ser Trp Val Val
130                 135                 140

Ile Asp Pro Thr Ile Asn Pro Arg His Met Glu Met Tyr Ala Asp Arg
145                 150                 155                 160

Glu Ser Arg Gly Ser Val Leu Glu Pro Glu Gly Thr Val Glu Ile Lys
                165                 170                 175

Phe Arg Lys Lys Asp Leu Val Lys Thr Met Arg Arg Val Asp Pro Val
                180                 185                 190

Tyr Ile Arg Leu Ala
            195

<210> SEQ ID NO 236
<211> LENGTH: 109
<212> TYPE: PRT
<213> ORGANISM: Caenorhabditis elegans or Homo sapiens

<400> SEQUENCE: 236

Gly Asp Ser Phe Glu Ile Trp Ala Val Gly Arg Ala Arg Leu Gly Ile
 1               5                  10                  15

Pro Gly Val Val Glu Arg Val Pro Ala Asp Pro Ala Ser Gln Ala Gly
             20                  25                  30

Gln Val Trp Pro Asp Ser Ala Phe Lys Thr Ala Ile Asp Asn Glu Leu
             35                  40                  45

Pro Leu Met Ala Arg Gly Phe Ser Gly Gly Lys Asp Met Tyr Asp Val
 50                  55                  60

Leu Lys Phe Gly Ala Ile Val Asp Leu Pro Val Val Tyr Ile Pro Glu
65                  70                  75                  80

Leu Arg Gly Gly Trp Val Asp Ile Pro Ala Asp Ser Arg Gly Leu Glu
                 85                  90                  95

Pro Val Ile Lys Phe Arg Lys Met Arg Asp Pro Tyr Leu
                100                 105

<210> SEQ ID NO 237
<211> LENGTH: 197
<212> TYPE: PRT
<213> ORGANISM: Caenorhabditis elegans
```

```
<400> SEQUENCE: 237

Thr Gly Ile Cys Asp Thr Met Ser Phe Asp Glu Ile Cys Gly Asp Trp
1               5                  10                  15

Ala Lys Ser Ile Val Ala Gly Arg Ala Arg Leu Cys Gly Ile Pro Ile
            20                  25                  30

Gly Val Val Ser Ser Glu Phe Arg Asn Phe Ser Thr Ile Val Pro Ala
        35                  40                  45

Asp Pro Ala Ile Asp Gly Ser Gln Val Gln Asn Thr Gln Arg Ala Gly
    50                  55                  60

Gln Val Trp Tyr Pro Asp Ser Ala Phe Lys Thr Ala Glu Ala Ile Asn
65                  70                  75                  80

Asp Leu Asn Lys Glu Asn Leu Pro Leu Met Ile Ile Ala Ser Leu Arg
                85                  90                  95

Gly Phe Ser Gly Gly Gln Lys Asp Met Tyr Asp Met Val Leu Lys Phe
            100                 105                 110

Gly Ala Gln Ile Val Asp Ala Leu Ala Val Tyr Asn Arg Pro Val Ile
        115                 120                 125

Val Tyr Ile Pro Glu Ala Gly Glu Leu Arg Gly Gly Ala Trp Ala Val
    130                 135                 140

Leu Asp Ser Lys Ile Arg Pro Glu Phe Ile His Leu Val Ala Asp Glu
145                 150                 155                 160

Lys Ser Arg Gly Gly Ile Leu Glu Pro Asn Ala Val Val Gly Ile Lys
                165                 170                 175

Phe Arg Lys Pro Met Met Met Glu Met Met Lys Arg Ser Asp Pro Thr
            180                 185                 190

Tyr Ser Lys Leu Ser
        195

<210> SEQ ID NO 238
<211> LENGTH: 124
<212> TYPE: PRT
<213> ORGANISM: Homo sapiens
<220> FEATURE:
<221> NAME/KEY: VARIANT
<222> LOCATION: (1)...(124)
<223> OTHER INFORMATION: Xaa = Any Amino Acid

<400> SEQUENCE: 238

Val Gly Tyr Pro Val Met Ile Lys Ala Ser Glu Gly Gly Gly Gly Lys
1               5                  10                  15

Gly Ile Arg Lys Val Asn Asn Ala Asp Asp Phe Pro Asn Leu Phe Arg
            20                  25                  30

Gln Val Gln Ala Glu Val Pro Gly Ser Pro Ile Phe Val Met Arg Leu
        35                  40                  45

Ala Lys Gln Ser Arg His Leu Glu Val Gln Ile Leu Ala Asp Gln Tyr
    50                  55                  60

Gly Asn Ala Ile Ser Leu Phe Gly Arg Asp Cys Ser Val Gln Arg Arg
65                  70                  75                  80

His Gln Lys Xaa Xaa Xaa Xaa Xaa Xaa Xaa Xaa Xaa Xaa Xaa Xaa Xaa
                85                  90                  95

Val Phe Glu His Met Glu Gln Cys Ala Val Lys Leu Ala Lys Met Val
            100                 105                 110

Gly Tyr Val Ser Ala Gly Thr Val Glu Tyr Leu Tyr
        115                 120
```

```
<210> SEQ ID NO 239
<211> LENGTH: 68
<212> TYPE: PRT
<213> ORGANISM: Homo sapiens or Caenorhabditis elegans

<400> SEQUENCE: 239

Gly Pro Met Ile Lys Ala Ser Glu Gly Gly Gly Lys Gly Ile Arg
1               5                   10                  15

Lys Asp Phe Val Glu Val Gly Ser Pro Ile Phe Met Arg His Glu
                20                  25                  30

Val Gln Leu Ala Asp Tyr Asn Ile Ser Arg Asp Cys Ser Gln Arg Arg
            35                  40                  45

Gln Lys Met Ala Val Leu Ala Lys Val Gly Tyr Ser Ala Gly Thr Val
        50                  55                  60

Glu Tyr Leu Tyr
65

<210> SEQ ID NO 240
<211> LENGTH: 124
<212> TYPE: PRT
<213> ORGANISM: Caenorhabditis elegans

<400> SEQUENCE: 240

Ile Gly Phe Pro Leu Met Ile Lys Ala Ser Glu Gly Gly Gly Lys
1               5                   10                  15

Gly Ile Arg Lys Cys Thr Lys Val Glu Asp Phe Lys Ser Met Phe Glu
                20                  25                  30

Glu Val Ala Gln Glu Val Gln Gly Ser Pro Ile Phe Leu Met Lys Cys
            35                  40                  45

Val Asp Gly Ala Arg His Ile Glu Val Gln Leu Ala Asp Arg Tyr
        50                  55                  60

Glu Asn Val Ile Ser Val Tyr Thr Arg Asp Cys Ser Ile Gln Arg Arg
65                  70                  75                  80

Cys Gln Lys Ile Ile Glu Glu Ala Pro Ala Ile Ile Ala Ser Ser His
                85                  90                  95

Ile Arg Lys Ser Met Gln Glu Asp Ala Val Arg Leu Ala Lys Tyr Val
            100                 105                 110

Gly Tyr Glu Ser Ala Gly Thr Val Glu Tyr Leu Tyr
        115                 120

<210> SEQ ID NO 241
<211> LENGTH: 116
<212> TYPE: PRT
<213> ORGANISM: Rat

<400> SEQUENCE: 241

Lys Glu Glu Gly Leu Gly Ala Glu Asn Leu Arg Gly Ser Gly Met Ile
1               5                   10                  15

Ala Gly Glu Ser Ser Leu Ala Tyr Asp Glu Ile Ile Thr Ile Ser Leu
                20                  25                  30

Val Thr Cys Arg Ala Ile Gly Ile Gly Ala Tyr Leu Val Arg Leu Gly
            35                  40                  45

Gln Arg Thr Ile Gln Val Glu Asn Ser His Leu Ile Leu Thr Gly Ala
        50                  55                  60

Gly Ala Leu Asn Lys Val Leu Gly Arg Glu Val Tyr Thr Ser Asn Asn
65                  70                  75                  80

Gln Leu Gly Gly Ile Gln Ile Met His Asn Asn Gly Val Thr His Cys
                85                  90                  95
```

Thr Val Cys Asp Asp Phe Glu Gly Val Phe Thr Val Leu His Trp Leu
                100                 105                 110

Ser Tyr Met Pro
        115

<210> SEQ ID NO 242
<211> LENGTH: 65
<212> TYPE: PRT
<213> ORGANISM: Caenorhabditis elegans or Rat

<400> SEQUENCE: 242

Lys Glu Gly Glu Asn Leu Gly Ser Gly Ile Ala Gly Glu Ala Tyr Glu
 1               5                  10                  15

Thr Val Thr Arg Gly Ile Gly Ala Tyr Arg Leu Arg Gln Ser His Leu
            20                  25                  30

Ile Leu Thr Gly Ala Leu Asn Leu Gly Val Tyr Thr Ser Asn Asn Gln
        35                  40                  45

Leu Gly Gly Met Asn Gly Val Thr His Val Asp Glu Gly Val Trp Ser
    50                  55                  60

Pro
65

<210> SEQ ID NO 243
<211> LENGTH: 116
<212> TYPE: PRT
<213> ORGANISM: Caenorhabditis elegans

<400> SEQUENCE: 243

Lys Asn Glu Lys Ile Gly Val Glu Asn Leu Gln Gly Ser Gly Leu Ile
 1               5                  10                  15

Ala Gly Glu Thr Ala Arg Ala Tyr Ala Glu Val Pro Thr Tyr Cys Tyr
            20                  25                  30

Val Thr Gly Arg Ser Val Gly Ile Gly Ala Tyr Thr Ala Arg Leu Ala
        35                  40                  45

His Arg Ile Val Gln His Lys Gln Ser His Leu Ile Leu Thr Gly Tyr
    50                  55                  60

Glu Ala Leu Asn Thr Leu Leu Gly Lys Lys Val Tyr Thr Ser Asn Asn
65                  70                  75                  80

Gln Leu Gly Gly Pro Glu Val Met Phe Arg Asn Gly Val Thr His Ala
                85                  90                  95

Val Val Asp Asn Asp Leu Glu Gly Ile Ala Lys Val Ile Arg Trp Met
                100                 105                 110

Ser Phe Leu Pro
        115

<210> SEQ ID NO 244
<211> LENGTH: 119
<212> TYPE: PRT
<213> ORGANISM: Homo sapiens

<400> SEQUENCE: 244

His Val Ile Ala Ala Arg Ile Thr Ser Glu Asn Pro Asp Glu Gly Phe
 1               5                  10                  15

Lys Pro Ser Ser Gly Thr Val Gln Glu Leu Asn Phe Arg Ser Asn Lys
            20                  25                  30

Asn Val Trp Gly Tyr Phe Ser Val Ala Ala Ala Gly Gly Leu His Glu
        35                  40                  45

```
Phe Ala Asp Ser Gln Phe Gly His Cys Phe Ser Trp Gly Asn Arg
    50                  55                  60
Glu Glu Ala Ile Ser Asn Met Val Val Ala Leu Lys Glu Leu Ser Ile
65                  70                  75                  80
Arg Gly Asp Phe Arg Thr Thr Val Glu Tyr Leu Ile Lys Leu Leu Glu
                85                  90                  95
Thr Glu Ser Phe Gln Leu Asn Arg Ile Asp Thr Gly Trp Leu Asp Arg
                100                 105                 110
Leu Ile Ala Glu Lys Val Gln
        115

<210> SEQ ID NO 245
<211> LENGTH: 59
<212> TYPE: PRT
<213> ORGANISM: Caenorhabditis elegans or Homo sapiens

<400> SEQUENCE: 245

His Ile Ala Ala Arg Ile Thr Glu Asn Pro Asp Phe Pro Ser Gly Val
1               5                   10                  15
Glu Asn Phe Ser Trp Tyr Phe Ser Val His Phe Ala Asp Ser Gln Phe
                20                  25                  30
Gly His Phe Gly Arg Glu Ala Met Leu Lys Ile Arg Phe Thr Val Tyr
            35                  40                  45
Leu Leu Phe Asn Thr Trp Leu Asp Ile Ala Lys
        50                  55

<210> SEQ ID NO 246
<211> LENGTH: 119
<212> TYPE: PRT
<213> ORGANISM: Caenorhabditis elegans

<400> SEQUENCE: 246

His Ala Ile Ala Ala Arg Ile Thr Cys Glu Asn Pro Asp Ser Phe
1               5                   10                  15
Arg Pro Ser Thr Gly Lys Val Tyr Glu Ile Asn Phe Pro Ser Ser Gln
                20                  25                  30
Asp Ala Trp Ala Tyr Phe Ser Val Gly Arg Gly Ser Ser Val His Gln
            35                  40                  45
Phe Ala Asp Ser Gln Phe Gly His Ile Phe Thr Arg Gly Thr Ser Arg
    50                  55                  60
Thr Glu Ala Met Asn Thr Met Cys Ser Thr Leu Lys His Met Thr Ile
65                  70                  75                  80
Arg Ser Ser Phe Pro Thr Gln Val Asn Tyr Leu Val Asp Leu Met His
                85                  90                  95
Asp Ala Asp Phe Ile Asn Asn Ala Phe Asn Thr Gln Trp Leu Asp Lys
                100                 105                 110
Arg Ile Ala Met Lys Ile Lys
        115

<210> SEQ ID NO 247
<211> LENGTH: 90
<212> TYPE: PRT
<213> ORGANISM: Rat

<400> SEQUENCE: 247

Pro Gly Gly Ala Asn Asn Asn Tyr Ala Asn Val Glu Leu Ile Leu
1               5                   10                  15
Asp Ile Ala Lys Arg Ile Pro Val Gln Ala Val Trp Ala Gly Trp Gly
```

-continued

```
                         20                  25                  30

His Ala Ser Glu Asn Pro Lys Leu Pro Glu Leu Leu Leu Lys Asn Gly
            35                  40                  45

Ile Ala Phe Met Gly Pro Pro Ser Gln Ala Met Trp Ala Leu Gly Asp
 50                  55                  60

Lys Ile Ala Ser Ser Ile Val Ala Gln Thr Ala Gly Ile Pro Thr Leu
 65                  70                  75                  80

Pro Trp Ser Gly Ser Gly Leu Arg Val Asp
                85                  90

<210> SEQ ID NO 248
<211> LENGTH: 55
<212> TYPE: PRT
<213> ORGANISM: Caenorhabditis elegans or Rat

<400> SEQUENCE: 248

Pro Gly Asn Asn Asn Ala Asn Val Ile Leu Ala Val Ala Val Trp Ala
 1               5                  10                  15

Gly Trp Gly His Ala Ser Glu Asn Pro Leu Pro Leu Ile Ala Phe Gly
                20                  25                  30

Pro Pro Ala Met Leu Gly Asp Lys Ile Ala Ser Ile Ala Gln Thr Gly
            35                  40                  45

Pro Thr Trp Ser Gly Ser Gly
 50                  55

<210> SEQ ID NO 249
<211> LENGTH: 90
<212> TYPE: PRT
<213> ORGANISM: Caenorhabditis elegans

<400> SEQUENCE: 249

Pro Ser Gly Thr Asn Lys Asn Asn Phe Ala Asn Val Asp Glu Ile Leu
 1               5                  10                  15

Lys His Ala Ile Lys Tyr Glu Val Asp Ala Val Trp Ala Gly Trp Gly
                20                  25                  30

His Ala Ser Glu Asn Pro Asp Leu Pro Arg Arg Leu Asn Asp His Asn
            35                  40                  45

Ile Ala Phe Ile Gly Pro Pro Ala Ser Ala Met Phe Ser Leu Gly Asp
 50                  55                  60

Lys Ile Ala Ser Thr Ile Ile Ala Gln Thr Val Gly Val Pro Thr Val
 65                  70                  75                  80

Ala Trp Ser Gly Ser Gly Ile Thr Met Glu
                85                  90

<210> SEQ ID NO 250
<211> LENGTH: 67
<212> TYPE: PRT
<213> ORGANISM: Caenorhabditis elegans

<400> SEQUENCE: 250

Val Ile Lys Asn Leu Gly Tyr Met Val Asp Asn His Gly Phe Val Pro
 1               5                  10                  15

Asn Gly Gly Arg Val Tyr Tyr Leu Thr Arg Ser Gln Pro Pro Leu Leu
                20                  25                  30

Thr Pro Met Val Tyr Glu Tyr Met Ser Thr Gly Asp Leu Asp Phe
            35                  40                  45

Val Met Glu Ile Leu Pro Thr Leu Asp Lys Glu Tyr Glu Phe Trp Ile
 50                  55                  60
```

Lys Asn Arg
65

<210> SEQ ID NO 251
<211> LENGTH: 36
<212> TYPE: PRT
<213> ORGANISM: Caenorhabditis elegans

<400> SEQUENCE: 251

Ile Asn Gly Phe Val Pro Asn Gly Gly Arg Val Tyr Tyr Leu Arg Ser
1               5                   10                  15

Gln Pro Pro Pro Met Val Tyr Glu Tyr Tyr Thr Asp Val Pro Lys Glu
            20                  25                  30

Tyr Phe Trp Arg
        35

<210> SEQ ID NO 252
<211> LENGTH: 67
<212> TYPE: PRT
<213> ORGANISM: Caenorhabditis elegans

<400> SEQUENCE: 252

Met Ile Leu Asn Phe Ala His Ile Ile Glu Thr Tyr Gly Phe Val Pro
1               5                   10                  15

Asn Gly Gly Arg Val Tyr Tyr Leu Arg Arg Ser Gln Pro Pro Phe Phe
            20                  25                  30

Ala Pro Met Val Tyr Glu Tyr Tyr Leu Ala Thr Gln Asp Ile Gln Leu
        35                  40                  45

Val Ala Asp Leu Ile Pro Val Ile Glu Lys Glu Tyr Thr Phe Trp Ser
    50                  55                  60

Glu Arg Arg
65

<210> SEQ ID NO 253
<211> LENGTH: 92
<212> TYPE: PRT
<213> ORGANISM: Caenorhabditis elegans

<400> SEQUENCE: 253

Met Asp Ser Ile Arg Thr Trp Ser Ile Ile Pro Ala Asp Leu Asn Ala
1               5                   10                  15

Phe Met Cys Ala Asn Ala Arg Ile Leu Ala Ser Leu Tyr Glu Ile Ala
            20                  25                  30

Gly Asp Phe Lys Lys Val Lys Val Phe Glu Gln Arg Tyr Thr Trp Ala
        35                  40                  45

Lys Arg Glu Met Arg Glu Leu His Trp Asn Glu Thr Asp Gly Ile Trp
    50                  55                  60

Tyr Asp Tyr Asp Ile Glu Leu Lys Thr His Ser Asn Gln Tyr Tyr Val
65                  70                  75                  80

Ser Asn Ala Val Pro Leu Tyr Ala Lys Cys Tyr Asp
            85                  90

<210> SEQ ID NO 254
<211> LENGTH: 32
<212> TYPE: PRT
<213> ORGANISM: Caenorhabditis elegans

<400> SEQUENCE: 254

Ile Thr Ile Pro Asp Leu Asn Ala Phe Cys Asn Ile Tyr Gly Lys Arg

```
                              1               5                  10                 15
       Thr Trp Tyr Asp Tyr Thr His Ser Asn Ala Val Pro Leu Cys Tyr Asp
                      20                  25                 30

<210> SEQ ID NO 255
<211> LENGTH: 92
<212> TYPE: PRT
<213> ORGANISM: Caenorhabditis elegans

<400> SEQUENCE: 255

Ile Ser Thr Ile Glu Thr Thr Asn Ile Val Pro Val Asp Leu Asn Ala
       1               5                  10                 15

Phe Leu Cys Tyr Asn Met Asn Ile Met Gln Leu Phe Tyr Lys Leu Thr
                      20                  25                 30

Gly Asn Pro Leu Lys His Leu Glu Trp Ser Ser Arg Phe Thr Asn Phe
                      35                  40                  45

Arg Glu Ala Phe Thr Lys Val Phe Tyr Val Pro Ala Arg Lys Gly Trp
                      50                  55                  60

Tyr Asp Tyr Asn Leu Arg Thr Leu Thr His Asn Thr Asp Phe Phe Ala
       65                  70                  75                  80

Ser Asn Ala Val Pro Leu Phe Ser Gln Cys Tyr Asp
                      85                  90

<210> SEQ ID NO 256
<211> LENGTH: 102
<212> TYPE: PRT
<213> ORGANISM: Caenorhabditis elegans

<400> SEQUENCE: 256

Val His Asp Tyr Leu Glu Arg Gln Gly Leu Leu Lys Tyr Thr Lys Gly
       1               5                  10                 15

Leu Pro Thr Ser Leu Ala Met Ser Ser Thr Gln Gln Trp Asp Lys Glu
                      20                  25                 30

Asn Ala Trp Pro Pro Met Ile His Met Val Ile Glu Gly Phe Arg Thr
                      35                  40                  45

Thr Gly Asp Ile Lys Leu Met Lys Val Ala Glu Lys Met Ala Thr Ser
                      50                  55                  60

Trp Leu Thr Gly Thr Tyr Gln Ser Phe Ile Arg Thr His Ala Met Phe
       65                  70                  75                  80

Glu Lys Tyr Asn Val Thr Pro His Thr Glu Glu Thr Ser Gly Gly Gly
                      85                  90                  95

Gly Gly Glu Tyr Glu Val
                      100

<210> SEQ ID NO 257
<211> LENGTH: 37
<212> TYPE: PRT
<213> ORGANISM: Caenorhabditis elegans

<400> SEQUENCE: 257

Val Gly Gly Pro Thr Ser Gln Gln Trp Asp Asn Trp Pro Met His Met
       1               5                  10                 15

Ile Glu Gly Arg Leu Ala Ala Trp Leu Gln Phe Met Glu Lys Tyr Asn
                      20                  25                 30

Val Gly Gly Glu Val
                      35

<210> SEQ ID NO 258
```

<211> LENGTH: 102
<212> TYPE: PRT
<213> ORGANISM: Caenorhabditis elegans

<400> SEQUENCE: 258

Val Tyr Asn Glu Met Gln Asn Ser Gly Ala Phe Ser Ile Pro Gly Gly
1               5                   10                  15

Ile Pro Thr Ser Met Asn Glu Glu Thr Asn Gln Gln Trp Asp Phe Pro
            20                  25                  30

Asn Gly Trp Ser Pro Met Asn His Met Ile Ile Glu Gly Leu Arg Lys
        35                  40                  45

Ser Asn Asn Pro Ile Leu Gln Gln Lys Ala Phe Thr Leu Ala Glu Lys
    50                  55                  60

Trp Leu Glu Thr Asn Met Gln Thr Phe Asn Val Ser Asp Glu Met Trp
65                  70                  75                  80

Glu Lys Tyr Asn Val Lys Glu Pro Leu Gly Lys Leu Ala Thr Gly Gly
                85                  90                  95

Glu Tyr Glu Val Gln Val
            100

<210> SEQ ID NO 259
<211> LENGTH: 58
<212> TYPE: PRT
<213> ORGANISM: Caenorhabditis elegans

<400> SEQUENCE: 259

Tyr Gln Tyr Lys Ala Lys Leu Lys Val Pro Arg Pro Glu Ser Tyr Arg
1               5                   10                  15

Glu Asp Ser Glu Leu Ala Glu His Leu Gln Thr Glu Ala Glu Lys Ile
            20                  25                  30

Gln Met Trp Ser Glu Ile Ala Ser Ala Glu Thr Gly Trp Asp Phe
        35                  40                  45

Ser Thr Arg Trp Phe Ser Gln Asn Gly Asp
    50                  55

<210> SEQ ID NO 260
<211> LENGTH: 29
<212> TYPE: PRT
<213> ORGANISM: Caenorhabditis elegans

<400> SEQUENCE: 260

Gln Tyr Pro Arg Pro Glu Ser Arg Glu Asp Ala Glu His Thr Lys Gln
1               5                   10                  15

Ser Ala Glu Gly Trp Asp Phe Ser Arg Trp Phe Asp
            20                  25

<210> SEQ ID NO 261
<211> LENGTH: 58
<212> TYPE: PRT
<213> ORGANISM: Caenorhabditis elegans

<400> SEQUENCE: 261

Phe Gln Tyr Arg Thr Glu Ala Glu Thr Pro Arg Pro Glu Ser Phe Arg
1               5                   10                  15

Glu Asp Val Leu Ser Ala Glu His Phe Thr Thr Lys Asp Arg Lys Lys
            20                  25                  30

Gln Phe Phe Lys Asp Leu Gly Ser Ala Ala Glu Ser Gly Trp Asp Phe
        35                  40                  45

Ser Ser Arg Trp Phe Lys Asn His Lys Asp

```
<210> SEQ ID NO 262
<211> LENGTH: 21
<212> TYPE: PRT
<213> ORGANISM: Caenorhabditis elegans

<400> SEQUENCE: 262

Gln Thr Gly Phe Gly Trp Thr Asn Gly Val Ile Leu Asp Leu Leu Asp
 1               5                  10                  15

Lys Tyr Gly Asp Gln
            20

<210> SEQ ID NO 263
<211> LENGTH: 13
<212> TYPE: PRT
<213> ORGANISM: Caenorhabditis elegans

<400> SEQUENCE: 263

Gln Gly Phe Gly Trp Thr Asn Gly Leu Asp Leu Tyr Asp
 1               5                  10

<210> SEQ ID NO 264
<211> LENGTH: 21
<212> TYPE: PRT
<213> ORGANISM: Caenorhabditis elegans

<400> SEQUENCE: 264

Gln Ala Gly Phe Gly Trp Thr Asn Gly Ala Ala Leu Asp Leu Ile Phe
 1               5                  10                  15

Thr Tyr Ser Asp Arg
            20

<210> SEQ ID NO 265
<211> LENGTH: 24
<212> TYPE: PRT
<213> ORGANISM: Caenorhabditis elegans

<400> SEQUENCE: 265

Ser Ser Ser Thr Ala Ser Lys Phe Ser Phe Ser Leu Ser Asn Ile Thr
 1               5                  10                  15

Phe Val Val Phe Ile Leu Tyr Ile
            20

<210> SEQ ID NO 266
<211> LENGTH: 10
<212> TYPE: PRT
<213> ORGANISM: Caenorhabditis elegans

<400> SEQUENCE: 266

Ser Ser Ser Phe Ser Val Phe Leu Tyr Ile
 1               5                  10

<210> SEQ ID NO 267
<211> LENGTH: 24
<212> TYPE: PRT
<213> ORGANISM: Caenorhabditis elegans

<400> SEQUENCE: 267

Thr Ser Ser Ser Ser Ser Thr Phe Gly Tyr Ser Asn Ile Leu Thr Leu
 1               5                  10                  15

Ile Thr Val Phe Val Leu Tyr Ile
            20
```

<210> SEQ ID NO 268
<211> LENGTH: 7
<212> TYPE: PRT
<213> ORGANISM: Caenorhabditis elegans

<400> SEQUENCE: 268

Gly Gly Glu Tyr Glu Val Gln
1               5

<210> SEQ ID NO 269
<211> LENGTH: 7
<212> TYPE: PRT
<213> ORGANISM: Caenorhabditis elegans

<400> SEQUENCE: 269

Gly Gly Glu Tyr Glu Val Gln
1               5

<210> SEQ ID NO 270
<211> LENGTH: 7
<212> TYPE: PRT
<213> ORGANISM: Caenorhabditis elegans

<400> SEQUENCE: 270

Gly Gly Glu Tyr Glu Val Gln
1               5

<210> SEQ ID NO 271
<211> LENGTH: 18
<212> TYPE: PRT
<213> ORGANISM: Caenorhabditis elegans

<400> SEQUENCE: 271

Lys Thr His Ser Asn Gln Tyr Tyr Val Ser Asn Ala Val Pro Leu Tyr
1               5                   10                  15

Ala Lys

<210> SEQ ID NO 272
<211> LENGTH: 8
<212> TYPE: PRT
<213> ORGANISM: Caenorhabditis elegans

<400> SEQUENCE: 272

Lys Tyr Tyr Val Ser Pro Tyr Lys
1               5

<210> SEQ ID NO 273
<211> LENGTH: 18
<212> TYPE: PRT
<213> ORGANISM: Caenorhabditis elegans

<400> SEQUENCE: 273

Lys Phe Thr Ala His Pro Tyr Tyr Val Ser Arg Thr Pro Pro Arg Tyr
1               5                   10                  15

His Lys

<210> SEQ ID NO 274
<211> LENGTH: 67
<212> TYPE: PRT
<213> ORGANISM: Caenorhabditis elegans

<400> SEQUENCE: 274

```
Val Ile Lys Asn Leu Gly Tyr Met Val Asp Asn His Gly Phe Val Pro
 1               5                  10                  15

Asn Gly Gly Arg Val Tyr Tyr Leu Thr Arg Ser Gln Pro Pro Leu Leu
                20                  25                  30

Thr Pro Met Val Tyr Glu Tyr Tyr Met Ser Thr Gly Asp Leu Asp Phe
            35                  40                  45

Val Met Glu Ile Leu Pro Thr Leu Asp Lys Glu Tyr Glu Phe Trp Ile
 50                  55                  60

Lys Asn Arg
 65

<210> SEQ ID NO 275
<211> LENGTH: 43
<212> TYPE: PRT
<213> ORGANISM: Caenorhabditis elegans

<400> SEQUENCE: 275

Ile Asn Leu Met Val Asp Gly Phe Val Pro Asn Gly Gly Arg Val Tyr
 1               5                  10                  15

Tyr Leu Arg Ser Gln Pro Pro Leu Met Val Tyr Glu Tyr Thr Asp Phe
                20                  25                  30

Val Glu Leu Pro Thr Leu Lys Glu Phe Trp Arg
            35                  40

<210> SEQ ID NO 276
<211> LENGTH: 67
<212> TYPE: PRT
<213> ORGANISM: Caenorhabditis elegans

<400> SEQUENCE: 276

Met Ile Arg Asn Leu Ala Ser Met Val Asp Lys Tyr Gly Phe Val Pro
 1               5                  10                  15

Asn Gly Gly Arg Val Tyr Tyr Leu Gln Arg Ser Gln Pro Pro Phe Leu
                20                  25                  30

Ala Ala Met Val Tyr Glu Leu Tyr Glu Ala Thr Asn Asp Lys Ala Phe
            35                  40                  45

Val Ala Glu Leu Leu Pro Thr Leu Leu Lys Glu Leu Asn Phe Trp Asn
 50                  55                  60

Glu Lys Arg
 65

<210> SEQ ID NO 277
<211> LENGTH: 84
<212> TYPE: PRT
<213> ORGANISM: Caenorhabditis elegans

<400> SEQUENCE: 277

Ile Ile Pro Ala Asp Leu Asn Ala Phe Met Cys Ala Asn Ala Arg Ile
 1               5                  10                  15

Leu Ala Ser Leu Tyr Glu Ile Ala Gly Asp Phe Lys Lys Val Lys Val
                20                  25                  30

Phe Glu Gln Arg Tyr Thr Trp Ala Lys Arg Glu Met Arg Glu Leu His
            35                  40                  45

Trp Asn Glu Thr Asp Gly Ile Trp Tyr Asp Tyr Asp Ile Glu Leu Lys
 50                  55                  60

Thr His Ser Asn Gln Tyr Tyr Val Ser Asn Ala Val Pro Leu Tyr Ala
 65                  70                  75                  80

Lys Cys Tyr Asp
```

<210> SEQ ID NO 278
<211> LENGTH: 31
<212> TYPE: PRT
<213> ORGANISM: Caenorhabditis elegans

<400> SEQUENCE: 278

Pro Asp Leu Asn Cys Asn Ile Leu Tyr Glu Gly Asp Lys Phe Asn Thr
1               5                   10                  15

Asp Gly Trp Tyr Asp Tyr His Tyr Ser Ala Val Pro Leu Cys Tyr
            20                  25                  30

<210> SEQ ID NO 279
<211> LENGTH: 84
<212> TYPE: PRT
<213> ORGANISM: Caenorhabditis elegans

<400> SEQUENCE: 279

Val Leu Pro Val Asp Leu Asn Gly Leu Leu Cys Trp Asn Met Asp Ile
1               5                   10                  15

Met Glu Tyr Leu Tyr Glu Gln Ile Gly Asp Thr Lys Asn Ser Gln Ile
            20                  25                  30

Phe Arg Asn Lys Arg Ala Asp Phe Arg Asp Thr Val Gln Asn Val Phe
        35                  40                  45

Tyr Asn Arg Thr Asp Gly Thr Trp Tyr Asp Tyr Asn Leu Arg Thr Gln
    50                  55                  60

Ser His Asn Pro Arg Phe Tyr Thr Ser Thr Ala Val Pro Leu Phe Thr
65                  70                  75                  80

Asn Cys Tyr Asn

<210> SEQ ID NO 280
<211> LENGTH: 48
<212> TYPE: PRT
<213> ORGANISM: Caenorhabditis elegans

<400> SEQUENCE: 280

Tyr Leu Glu Arg Gln Gly Leu Leu Lys Tyr Thr Lys Gly Leu Pro Thr
1               5                   10                  15

Ser Leu Ala Met Ser Ser Thr Gln Gln Trp Asp Lys Glu Asn Ala Trp
            20                  25                  30

Pro Pro Met Ile His Met Val Ile Glu Gly Phe Arg Thr Thr Gly Asp
        35                  40                  45

<210> SEQ ID NO 281
<211> LENGTH: 20
<212> TYPE: PRT
<213> ORGANISM: Caenorhabditis elegans

<400> SEQUENCE: 281

Gly Tyr Gly Pro Thr Ser Ser Gln Gln Trp Asp Asn Trp Pro His Met
1               5                   10                  15

Ile Glu Gly Arg
            20

<210> SEQ ID NO 282
<211> LENGTH: 48
<212> TYPE: PRT
<213> ORGANISM: Caenorhabditis elegans

<400> SEQUENCE: 282

-continued

```
Phe Phe Gln Lys Met Gly Val Phe Thr Tyr Pro Gly Ile Pro Thr
 1               5                  10                  15

Ser Met Ser Gln Glu Ser Asp Gln Gln Trp Asp Phe Pro Asn Gly Trp
                20                  25                  30

Ser Pro Asn Asn His Met Ile Ile Glu Gly Leu Arg Lys Ser Ala Asn
                35                  40                  45
```

<210> SEQ ID NO 283
<211> LENGTH: 18
<212> TYPE: PRT
<213> ORGANISM: Caenorhabditis elegans

<400> SEQUENCE: 283

```
Glu Ile Ala Ser Ala Ala Glu Thr Gly Trp Asp Phe Ser Thr Arg Trp
 1               5                  10                  15

Phe Ser
```

<210> SEQ ID NO 284
<211> LENGTH: 15
<212> TYPE: PRT
<213> ORGANISM: Caenorhabditis elegans

<400> SEQUENCE: 284

```
Ala Ser Ala Ala Glu Gly Trp Asp Phe Ser Thr Arg Trp Phe Ser
 1               5                  10                  15
```

<210> SEQ ID NO 285
<211> LENGTH: 18
<212> TYPE: PRT
<213> ORGANISM: Caenorhabditis elegans

<400> SEQUENCE: 285

```
Asp Leu Ala Ser Ala Ala Glu Ser Gly Trp Asp Phe Ser Thr Arg Trp
 1               5                  10                  15

Phe Ser
```

<210> SEQ ID NO 286
<211> LENGTH: 40
<212> TYPE: PRT
<213> ORGANISM: Caenorhabditis elegans

<400> SEQUENCE: 286

```
Lys Gln Phe Pro Tyr Tyr Gln Tyr Lys Ala Lys Leu Lys Val Pro Arg
 1               5                  10                  15

Pro Glu Ser Tyr Arg Glu Asp Ser Glu Leu Ala Glu His Leu Gln Thr
                20                  25                  30

Glu Ala Glu Lys Ile Gln Met Trp
                35                  40
```

<210> SEQ ID NO 287
<211> LENGTH: 18
<212> TYPE: PRT
<213> ORGANISM: Caenorhabditis elegans

<400> SEQUENCE: 287

```
Lys Phe Tyr Gln Tyr Lys Val Pro Arg Pro Glu Ser Tyr Arg Asp Leu
 1               5                  10                  15

Ala Gln
```

<210> SEQ ID NO 288
<211> LENGTH: 40

```
<212> TYPE: PRT
<213> ORGANISM: Caenorhabditis elegans

<400> SEQUENCE: 288

Lys Ser Phe Lys Val Tyr Gln Tyr Lys Thr Ala Ser Asn Val Pro Arg
 1               5                  10                  15

Pro Glu Ser Tyr Arg Val Asp Thr Gln Asn Ser Ala Lys Leu Ala Asn
            20                  25                  30

Gly Ala Asp Gln Gln Gln Phe Tyr
        35                  40

<210> SEQ ID NO 289
<211> LENGTH: 21
<212> TYPE: PRT
<213> ORGANISM: Caenorhabditis elegans

<400> SEQUENCE: 289

Gln Thr Gly Phe Gly Trp Thr Asn Gly Val Ile Leu Asp Leu Leu Asp
 1               5                  10                  15

Lys Tyr Gly Asp Gln
            20

<210> SEQ ID NO 290
<211> LENGTH: 14
<212> TYPE: PRT
<213> ORGANISM: Caenorhabditis elegans

<400> SEQUENCE: 290

Gln Gly Phe Gly Trp Asn Gly Ile Leu Asp Leu Leu Tyr Asp
 1               5                  10

<210> SEQ ID NO 291
<211> LENGTH: 21
<212> TYPE: PRT
<213> ORGANISM: Caenorhabditis elegans

<400> SEQUENCE: 291

Gln Asp Gly Phe Gly Trp Ser Asn Gly Ala Ile Leu Asp Leu Leu Leu
 1               5                  10                  15

Thr Tyr Asn Asp Arg
            20

<210> SEQ ID NO 292
<211> LENGTH: 27
<212> TYPE: PRT
<213> ORGANISM: Caenorhabditis elegans

<400> SEQUENCE: 292

Tyr Gly Asp Gln Phe Ala Ser Ser Ser Thr Ala Ser Lys Phe Ser Phe
 1               5                  10                  15

Ser Leu Ser Asn Ile Thr Phe Val Val Phe Ile
            20                  25

<210> SEQ ID NO 293
<211> LENGTH: 11
<212> TYPE: PRT
<213> ORGANISM: Caenorhabditis elegans

<400> SEQUENCE: 293

Tyr Phe Ala Ser Ser Ser Ala Ser Phe Ser Phe
 1               5                  10
```

```
<210> SEQ ID NO 294
<211> LENGTH: 26
<212> TYPE: PRT
<213> ORGANISM: Caenorhabditis elegans

<400> SEQUENCE: 294

Tyr Asn Pro Phe Ala Ser Ser Ser Asp Ala Ser Ser Cys Pro Phe Ser
1               5                   10                  15

Thr Asn Ser Val Ile Phe Ser Ile Leu Val
            20                  25

<210> SEQ ID NO 295
<211> LENGTH: 9
<212> TYPE: PRT
<213> ORGANISM: Caenorhabditis elegans

<400> SEQUENCE: 295

Gly Gly Gly Gly Glu Tyr Glu Val Gln
1               5

<210> SEQ ID NO 296
<211> LENGTH: 7
<212> TYPE: PRT
<213> ORGANISM: Caenorhabditis elegans

<400> SEQUENCE: 296

Gly Gly Gly Glu Tyr Val Gln
1               5

<210> SEQ ID NO 297
<211> LENGTH: 9
<212> TYPE: PRT
<213> ORGANISM: Caenorhabditis elegans

<400> SEQUENCE: 297

Gly Ser Gly Gly Glu Tyr Asp Val Gln
1               5

<210> SEQ ID NO 298
<211> LENGTH: 14
<212> TYPE: PRT
<213> ORGANISM: Caenorhabditis elegans

<400> SEQUENCE: 298

Asn Gln Tyr Tyr Val Ser Asn Ala Val Pro Leu Tyr Ala Lys
1               5                   10

<210> SEQ ID NO 299
<211> LENGTH: 7
<212> TYPE: PRT
<213> ORGANISM: Caenorhabditis elegans

<400> SEQUENCE: 299

Asn Tyr Tyr Val Leu Tyr Lys
1               5

<210> SEQ ID NO 300
<211> LENGTH: 14
<212> TYPE: PRT
<213> ORGANISM: Caenorhabditis elegans

<400> SEQUENCE: 300

Asn His Tyr Tyr Ile Ile Gln Met Val Ser Leu Tyr Thr Lys
1               5                   10
```

-continued

```
<210> SEQ ID NO 301
<211> LENGTH: 30
<212> TYPE: PRT
<213> ORGANISM: Caenorhabditis elegans

<400> SEQUENCE: 301

Asp Gln Phe Ala Ser Ser Ser Thr Ala Ser Lys Phe Ser Phe Ser Leu
1               5                   10                  15

Ser Asn Ile Thr Phe Val Val Phe Ile Leu Tyr Ile Phe Ser
            20                  25                  30

<210> SEQ ID NO 302
<211> LENGTH: 11
<212> TYPE: PRT
<213> ORGANISM: Caenorhabditis elegans

<400> SEQUENCE: 302

Asp Gln Phe Ser Ser Lys Phe Ser Phe Phe Ser
1               5                   10

<210> SEQ ID NO 303
<211> LENGTH: 30
<212> TYPE: PRT
<213> ORGANISM: Caenorhabditis elegans

<400> SEQUENCE: 303

Asp Gln Phe Val Ile Ser Phe Ile Cys Ser Lys Phe Ser Lys Asn
1               5                   10                  15

Lys Lys Leu Tyr Phe Cys Pro Ser His Phe Ser Leu Phe Ser
            20                  25                  30

<210> SEQ ID NO 304
<211> LENGTH: 9
<212> TYPE: PRT
<213> ORGANISM: Caenorhabditis elegans
<220> FEATURE:
<221> NAME/KEY: VARIANT
<222> LOCATION: (1)...(9)
<223> OTHER INFORMATION: Xaa = Any Amino Acid

<400> SEQUENCE: 304

Gly Trp Asp Xaa Xaa Ile Ala Pro Lys
1               5

<210> SEQ ID NO 305
<211> LENGTH: 62
<212> TYPE: PRT
<213> ORGANISM: Mus musculus

<400> SEQUENCE: 305

Leu Cys Lys Glu Gly Ile Ser Asp Gly Ala Thr Met Lys Thr Phe Cys
1               5                   10                  15

Gly Thr Pro Glu Tyr Leu Ala Pro Glu Val Leu Glu Asp Asn Asp Tyr
            20                  25                  30

Gly Arg Ala Val Asp Trp Trp Gly Leu Gly Val Val Met Tyr Glu Met
        35                  40                  45

Met Cys Gly Arg Leu Pro Phe Tyr Asn Gln Asp His Glu Arg
    50                  55                  60

<210> SEQ ID NO 306
<211> LENGTH: 9
<212> TYPE: PRT
<213> ORGANISM: Caenorhabditis elegans
```

-continued

```
<400> SEQUENCE: 306

Gln Ala Leu Thr Gln Met Asn Pro Lys
1               5

<210> SEQ ID NO 307
<211> LENGTH: 11
<212> TYPE: PRT
<213> ORGANISM: Caenorhabditis elegans

<400> SEQUENCE: 307

Gln Ala Leu Thr Gln Cys Val Asp Ser Met Arg
1               5                   10

<210> SEQ ID NO 308
<211> LENGTH: 248
<212> TYPE: PRT
<213> ORGANISM: Caenorhabditis elegans

<400> SEQUENCE: 308

Ile Phe Arg Thr Ala Val Ser Ser Asn Arg Cys Arg Thr Glu Tyr Gln
1               5                   10                  15

Asn Ile Asp Leu Asp Cys Ala Tyr Ile Thr Asp Arg Ile Ile Ala Ile
            20                  25                  30

Gly Tyr Pro Ala Thr Gly Ile Glu Ala Asn Phe Arg Asn Ser Lys Val
        35                  40                  45

Gln Thr Gln Gln Phe Leu Thr Arg Arg His Gly Lys Gly Asn Val Lys
    50                  55                  60

Val Phe Asn Leu Arg Gly Gly Tyr Tyr Asp Ala Asp Asn Phe Asp
65                  70                  75                  80

Gly Asn Val Ile Cys Phe Asp Met Thr Asp His His Pro Pro Ser Leu
                85                  90                  95

Glu Leu Met Ala Pro Phe Cys Arg Glu Ala Lys Glu Trp Leu Glu Ala
            100                 105                 110

Asp Asp Lys His Val Ile Ala Val His Cys Lys Ala Gly Lys Gly Arg
        115                 120                 125

Thr Gly Val Met Ile Cys Ala Leu Leu Ile Tyr Ile Asn Phe Tyr Pro
    130                 135                 140

Ser Pro Arg Gln Ile Leu Asp Tyr Tyr Ser Ile Ile Thr Arg Lys Asn
145                 150                 155                 160

Asn Lys Gly Val Thr Ile Pro Ser Gln Arg Arg Tyr Ile Tyr Tyr Tyr
                165                 170                 175

His Lys Leu Arg Glu Arg Glu Leu Asn Tyr Leu Pro Leu Arg Met Gln
            180                 185                 190

Leu Ile Gly Val Tyr Val Glu Arg Pro Pro Lys Thr Trp Gly Gly Gly
        195                 200                 205

Ser Lys Ile Lys Val Glu Val Gly Asn Gly Ser Thr Ile Leu Phe Lys
    210                 215                 220

Pro Asp Pro Leu Ile Ile Ser Lys Ser Asn His Gln Arg Glu Arg Ala
225                 230                 235                 240

Thr Trp Leu Asn Asn Cys Asp Thr
                245

<210> SEQ ID NO 309
<211> LENGTH: 249
<212> TYPE: PRT
<213> ORGANISM: Homo sapiens
```

```
<400> SEQUENCE: 309

Ile Ile Lys Glu Ile Ser Arg Asn Lys Arg Tyr Gln Glu Asp
 1               5                  10                  15

Gly Phe Asp Leu Asp Leu Thr Tyr Ile Tyr Pro Asn Ile Ile Ala Met
                 20                  25                  30

Gly Phe Pro Ala Glu Arg Leu Glu Gly Val Tyr Arg Asn Asn Ile Asp
                 35                  40                  45

Asp Val Val Arg Phe Leu Asp Ser Lys His Lys Asn His Tyr Lys Ile
             50                  55                  60

Tyr Asn Leu Cys Ala Glu Arg His Tyr Asp Thr Ala Lys Phe Asn Cys
 65                  70                  75                  80

Arg Val Ala Gln Tyr Pro Phe Glu Asp His Asn Pro Pro Gln Leu Glu
                 85                  90                  95

Leu Ile Lys Pro Phe Cys Glu Asp Leu Asp Gln Trp Leu Ser Glu Asp
                100                 105                 110

Asp Asn His Val Ala Ala Ile His Cys Lys Ala Gly Lys Gly Arg Thr
            115                 120                 125

Gly Val Met Ile Cys Ala Tyr Leu Leu His Arg Gly Lys Phe Leu Lys
    130                 135                 140

Ala Gln Glu Ala Leu Asp Phe Tyr Gly Glu Val Arg Thr Arg Asp Lys
145                 150                 155                 160

Lys Gly Val Thr Ile Pro Ser Gln Arg Arg Tyr Val Tyr Tyr Tyr Ser
                165                 170                 175

Tyr Leu Leu Lys Asn His Leu Asp Tyr Arg Pro Val Ala Leu Leu Phe
                180                 185                 190

His Lys Met Met Phe Glu Thr Ile Pro Met Phe Ser Gly Gly Thr Cys
                195                 200                 205

Asn Pro Gln Phe Val Val Cys Gln Leu Lys Val Lys Ile Tyr Ser Ser
    210                 215                 220

Asn Ser Gly Pro Thr Arg Arg Glu Asp Lys Phe Asn Tyr Phe Glu Phe
225                 230                 235                 240

Pro Gln Pro Leu Pro Val Cys Gly Asp
                245

<210> SEQ ID NO 310
<211> LENGTH: 962
<212> TYPE: PRT
<213> ORGANISM: Caenorhabditis elegans

<400> SEQUENCE: 310

Met Val Thr Pro Pro Asp Val Pro Ser Thr Ser Thr Arg Ser Met
 1               5                  10                  15

Ala Arg Asp Leu Gln Glu Asn Pro Asn Arg Gln Pro Gly Glu Pro Arg
                 20                  25                  30

Val Ser Glu Pro Tyr His Asn Ser Ile Val Glu Arg Ile Arg His Ile
                 35                  40                  45

Phe Arg Thr Ala Val Ser Ser Asn Arg Cys Arg Thr Glu Tyr Gln Asn
             50                  55                  60

Ile Asp Leu Asp Cys Ala Tyr Ile Thr Asp Arg Ile Ile Ala Ile Gly
 65                  70                  75                  80

Tyr Pro Ala Thr Gly Ile Glu Ala Asn Phe Arg Asn Ser Lys Val Gln
                 85                  90                  95

Thr Gln Gln Phe Leu Thr Arg Arg His Gly Lys Gly Asn Val Lys Val
                100                 105                 110
```

```
Phe Asn Leu Arg Gly Gly Tyr Tyr Tyr Asp Ala Asp Asn Phe Asp Gly
        115                 120                 125

Asn Val Ile Cys Phe Asp Met Thr Asp His His Pro Pro Ser Leu Glu
    130                 135                 140

Leu Met Ala Pro Phe Cys Arg Glu Ala Lys Glu Trp Leu Glu Ala Asp
145                 150                 155                 160

Asp Lys His Val Ile Ala Val His Cys Lys Ala Gly Lys Gly Arg Thr
                165                 170                 175

Gly Val Met Ile Cys Ala Leu Leu Ile Tyr Ile Asn Phe Tyr Pro Ser
            180                 185                 190

Pro Arg Gln Ile Leu Asp Tyr Ser Ile Ile Arg Thr Lys Asn Asn
        195                 200                 205

Lys Gly Val Thr Ile Pro Ser Gln Arg Arg Tyr Ile Tyr Tyr His
    210                 215                 220

Lys Leu Arg Glu Arg Glu Leu Asn Tyr Leu Pro Leu Arg Met Gln Leu
225                 230                 235                 240

Ile Gly Val Tyr Val Glu Arg Pro Pro Lys Thr Trp Gly Gly Ser
            245                 250                 255

Lys Ile Lys Val Glu Val Gly Asn Gly Ser Thr Ile Leu Phe Lys Pro
            260                 265                 270

Asp Pro Leu Ile Ile Ser Lys Ser Asn His Gln Arg Glu Arg Ala Thr
        275                 280                 285

Trp Leu Asn Asn Cys Asp Thr Pro Asn Glu Phe Asp Thr Gly Glu Gln
        290                 295                 300

Lys Tyr His Gly Phe Val Ser Lys Arg Ala Tyr Cys Phe Met Val Pro
305                 310                 315                 320

Glu Asp Ala Pro Val Phe Val Glu Gly Asp Val Arg Ile Asp Ile Arg
                325                 330                 335

Glu Ile Gly Phe Leu Lys Lys Phe Ser Asp Gly Lys Ile Gly His Val
            340                 345                 350

Trp Phe Asn Thr Met Phe Ala Cys Asp Gly Gly Leu Asn Gly Gly His
        355                 360                 365

Phe Glu Tyr Val Asp Lys Thr Gln Pro Tyr Ile Gly Asp Asp Thr Ser
370                 375                 380

Ile Gly Arg Lys Asn Gly Met Arg Arg Asn Glu Thr Pro Met Arg Lys
385                 390                 395                 400

Ile Asp Pro Glu Thr Gly Asn Glu Phe Glu Ser Pro Trp Gln Ile Val
                405                 410                 415

Asn Pro Pro Gly Leu Glu Lys His Ile Thr Glu Glu Gln Ala Met Glu
            420                 425                 430

Asn Tyr Thr Asn Tyr Gly Met Ile Pro Pro Arg Tyr Thr Ile Ser Lys
        435                 440                 445

Ile Leu His Glu Lys His Glu Lys Gly Ile Val Lys Asp Asp Tyr Asn
    450                 455                 460

Asp Arg Lys Leu Pro Met Gly Asp Lys Ser Tyr Thr Glu Ser Gly Lys
465                 470                 475                 480

Ser Gly Asp Ile Arg Gly Val Gly Gly Pro Phe Glu Ile Pro Tyr Lys
                485                 490                 495

Ala Glu Glu His Val Leu Thr Phe Pro Val Tyr Glu Met Asp Arg Ala
            500                 505                 510

Leu Lys Ser Lys Asp Leu Asn Asn Gly Met Lys Leu His Val Val Leu
        515                 520                 525

Arg Cys Val Asp Thr Arg Asp Ser Lys Met Met Glu Lys Ser Glu Val
```

-continued

```
                530             535             540
Phe Gly Asn Leu Ala Phe His Asn Glu Ser Thr Arg Arg Leu Gln Ala
545                 550                 555                 560
Leu Thr Gln Met Asn Pro Lys Trp Arg Pro Glu Pro Cys Ala Phe Gly
                565                 570                 575
Ser Lys Gly Ala Glu Met His Tyr Pro Pro Ser Val Arg Tyr Ser Ser
                580                 585                 590
Asn Asp Gly Lys Tyr Asn Gly Ala Cys Ser Glu Asn Leu Val Ser Asp
                595                 600                 605
Phe Phe Glu His Arg Asn Ile Ala Val Leu Asn Arg Tyr Cys Arg Tyr
610                 615                 620
Phe Tyr Lys Gln Arg Ser Thr Ser Arg Ser Arg Tyr Pro Arg Lys Phe
625                 630                 635                 640
Arg Tyr Cys Pro Leu Ile Lys Lys His Phe Tyr Ile Pro Ala Asp Thr
                645                 650                 655
Asp Asp Val Asp Glu Asn Gly Gln Pro Phe Phe His Ser Pro Glu His
                660                 665                 670
Tyr Ile Lys Glu Gln Glu Lys Ile Asp Ala Glu Lys Ala Ala Lys Gly
                675                 680                 685
Ile Glu Asn Thr Gly Pro Ser Thr Ser Gly Ser Ser Ala Pro Gly Thr
                690                 695                 700
Ile Lys Lys Thr Glu Ala Ser Gln Ser Asp Lys Val Lys Pro Ala Thr
705                 710                 715                 720
Glu Asp Glu Leu Pro Pro Ala Arg Leu Pro Asp Asn Val Arg Arg Phe
                725                 730                 735
Pro Val Val Gly Val Asp Phe Glu Asn Pro Glu Glu Glu Ser Cys Glu
                740                 745                 750
His Lys Thr Val Glu Ser Ile Ala Gly Phe Glu Pro Leu Glu His Leu
                755                 760                 765
Phe His Glu Ser Tyr His Pro Asn Thr Ala Gly Asn Met Leu Arg Gln
                770                 775                 780
Asp Tyr His Thr Asp Ser Glu Val Lys Ile Ala Glu Gln Glu Ala Lys
785                 790                 795                 800
Ala Phe Val Asp Gln Leu Leu Asn Gly Gln Gly Val Leu Gln Glu Phe
                805                 810                 815
Met Lys Gln Phe Lys Val Pro Ser Asp Asn Ser Phe Ala Asp Tyr Val
                820                 825                 830
Thr Gly Gln Ala Glu Val Phe Lys Ala Gln Ile Ala Leu Leu Glu Gln
                835                 840                 845
Ser Glu Asp Phe Gln Arg Val Gln Ala Asn Ala Glu Glu Val Asp Leu
850                 855                 860
Glu His Thr Leu Gly Glu Ala Phe Glu Arg Phe Gly His Val Val Glu
865                 870                 875                 880
Glu Ser Asn Gly Ser Ser Lys Asn Pro Lys Ala Leu Lys Thr Arg Glu
                885                 890                 895
Gln Met Val Lys Glu Thr Gly Lys Asp Thr Gln Lys Thr Arg Asn His
                900                 905                 910
Val Leu Leu His Leu Glu Ala Asn His Arg Val Gln Ile Glu Arg Arg
                915                 920                 925
Glu Thr Cys Pro Glu Leu His Pro Glu Asp Lys Ile Pro Arg Ile Ala
                930                 935                 940
His Phe Ser Glu Asn Ser Phe Ser Asp Ser Asn Phe Asp Gln Ala Ile
945                 950                 955                 960
```

Tyr Leu

<210> SEQ ID NO 311
<211> LENGTH: 3304
<212> TYPE: DNA
<213> ORGANISM: Caenorhabditis elegans

<400> SEQUENCE: 311

| | | | | | |
|---|---|---|---|---|---|
| ttccaggtac | atctactaac | ccccaatggt | tactcctcct | ccagatgtgc | caagcacatc | 60 |
| gaccaggtcg | atggctcgtg | accttcaaga | gaatccaaac | cgacaacctg | gtgaaccacg | 120 |
| tgtgtctgaa | ccgtatcaca | attcaatcgt | cgagcggatt | cgccatattt | ttcggacggc | 180 |
| tgtatcttcc | aatcgttgtc | gcaccgagta | ccaaaatatc | gacctagatt | gtgcatatat | 240 |
| cacagaccga | atcatagcta | tcggttatcc | agcaacagga | atcgaagcga | atttccgtaa | 300 |
| ctcaaaagtt | caaactcaac | aatttctgac | caggcggcac | ggaaagggca | acgtgaaggt | 360 |
| gtttaacctg | cgcggtggat | actactacga | tgcggataac | ttcgatggaa | atgttatttg | 420 |
| cttcgatatg | actgatcatc | atccgccgag | tctcgaatta | atggctccgt | tttgcagaga | 480 |
| ggctaaggaa | tggcttgaag | cagacgataa | acatgtaata | gctgtacact | gtaaagctgg | 540 |
| aaaaggccgt | accggagtga | tgatatgtgc | tcttctcatc | tacatcaact | tctatccgag | 600 |
| cccacgacaa | attctcgact | actactcaat | aattcgtaca | aaaaacaaca | aggtgtcac | 660 |
| aattccatca | caacgacgct | acatttacta | ctaccataag | cttcgtgaac | gtgagctcaa | 720 |
| ctatttacca | ttgagaatgc | agttgattgg | tgtctacgtg | aacggcctc | caaagacatg | 780 |
| gggtggtggt | tcaaagataa | aagtggaggt | tggaaatggc | tcgacaattt | tatttaagcc | 840 |
| ggatcctctc | ataatctcca | aatcaaatca | tcagcgagag | cgtgcgacgt | ggctgaacaa | 900 |
| ctgtgatacg | cctaacgaat | tcgacaccgg | agagcaaaaa | tatcatggat | ttgtttccaa | 960 |
| gagagcatac | tgttttatgg | tgccagaaga | tgctccagta | tttgtcgaag | gagatgttcg | 1020 |
| tatagacatt | cgcgaaatcg | gatttctcaa | aaagttttcg | gacgggaaga | ttggtcatgt | 1080 |
| ttggttcaat | acaatgttcg | catgtgatgg | aggactcaac | ggtggacatt | tcgagtacgt | 1140 |
| agacaaaact | cagccgtaca | tcggagacga | tacatcaatc | ggacggaaaa | atggaatgcg | 1200 |
| aagaaatgaa | acgccgatgc | gaaaaattga | tccagaaact | ggaaatgaat | ttgagtctcc | 1260 |
| gtggcaaata | gtgaatcctc | ctggactgga | aaaacatatt | acggaggaac | aagcaatgga | 1320 |
| aaattatacc | aattatggca | tgattcctcc | tcgatacacg | atcagcaaga | ttcttcacga | 1380 |
| aaagcatgaa | aaaggtatcg | tcaaggatga | ctataatgat | cgtaagctgc | caatgggaga | 1440 |
| caaatcatac | acggaatcag | gaaaaagtgg | agatattcga | ggagtcggtg | gtccatttga | 1500 |
| gataccatat | aaagctgagg | aacatgttct | cacatttcca | gtttatgaaa | tggatcgagc | 1560 |
| attgaagagt | aaagatctta | acaacggaat | gaaacttcac | gttgttcttc | gttgtgtaga | 1620 |
| tactcgtgat | tcaaaaatga | tggaaaagag | cgaagtgttc | ggcaatctgg | cattccataa | 1680 |
| tgaatcgaca | cggaggcttc | aagcgttgac | tcaaatgaat | ccaaaatggc | gacctgaacc | 1740 |
| gtgtgcgttc | ggatccaaag | gtgctgaaat | gcattaccct | ccgtcggttc | gatattcaag | 1800 |
| caatgatgga | agtataatg | gagcctgcag | tgagaacctt | gttagcgatt | ttttcgagca | 1860 |
| cagaaatatt | gccgttctta | atcgatattg | ccgatatttc | tacaagcaac | gcagtacatc | 1920 |
| tcgaagccgt | tatccaagaa | aattcagata | ctgtcctctg | atcaagaaac | atttctacat | 1980 |
| tccagctgat | accgatgatg | ttgatgaaaa | tgggcaaccg | ttcttccact | caccagagca | 2040 |

-continued

```
ttacattaaa gaacaggaaa aaatagacgc agagaaagca gctaaaggaa ttgaaaatac    2100
tggacccagt acttcaggat caagtgctcc cggaactatc aagaaaacgg aagcttcaca    2160
atccgacaag gtgaagccgg caactgaaga cgaacttcct cctgcgaggc taccggataa    2220
tgtgcgaaga tttccagtcg tcggcgttga tttcgaaaat ccgaagaag  aatcgtgtga    2280 acacaaaacc gtagagtcaa tagctggttt tgaaccactc gaacatctat tccatgaatc    2340
ataccatcca aatacggccg gtaacatgct gcgtcaggat tatcacactg attcggaagt    2400
gaaaatagct gaacaagagg caaaagcctt cgttgaccag ttgcttaatg gacaaggtgt    2460
attacaagag tttatgaagc aattcaaagt accatcggac aattcctttg ctgattatgt    2520
aaccggacag gccgaagttt ttaaagcaca gattgcgtta ctggagcagt cggaggattt    2580
tcaacgagtt caagcgaatg cagaggaagt cgatcttgaa cacactcttg gtgaagcgtt    2640
tgagcgattc gggcacgttg tagaagaatc gaatggttct tctaaaaatc caaaagccct    2700
gaaaactcga gaacaaatgg tgaaagaaac tggcaaagac actcagaaga cccgcaatca    2760
tgtgcttcta catttggaag ctaatcatcg tgtgcaaatc gagcgtcgtg aaacgtgccc    2820
ggagctacat ccagaggata aaatcccaag aattgctcat ttttccgaaa acagcttctc    2880
ggattcgaat tttgatcaag ctatttattt gtaaacctaa acaaaactt  ttagaagatt    2940 ttcttcttac tgaccctcca attttcagat aatttcaatg ttttaagttt tctcttcaaa    3000
gtatcattca ctttctgtat agtgttttgt tttttaacaa actattgttc gattattttg    3060
tatattcata ttatagctct caacttcccg attttccacg tatatatgta tattttgccg    3120
ggtgaaaaat agcaattccc tatgaatgta tccccttcca tctgttttct tactcagaaa    3180
ttgtaattca cattgcgggt catcactaat cctatgggct taacacaat  tctcccataa    3240 attaattgta cttaccaatt ttttgtttaa ttatttagat ttgtaacatt gaaattggtg    3300
ataa                                                                3304
```

<210> SEQ ID NO 312
<211> LENGTH: 1642
<212> TYPE: DNA
<213> ORGANISM: Caenorhabditis elegans

<400> SEQUENCE: 312

```
tttaattacc caagtttgag gtagcattgc tctcttcaat catatggatt cgttgtttca     60
gatggcatcc gcaatgaagt ttcaatacta ctcgaagaaa gctgctggaa agacaatgtc    120
taatagtgtc tccatgtcca gtgacaatcg catggaggat ttt aaacgtc gttttcgtcg    180 aagtggatcg ttaggaattc catttgtccc agaagaagat gttaaacaac tcttcacacc    240
aactcgtact gttcgtcgag aagcatctat tcgcgaaggg gatgaggaag aaggagtaca    300
aattctcaca ataattgtca agtcaagtcg tgtttcggag gatatctcaa aaatgattgc    360
aaacctccct gatcacactc gtatcaaaca tttggagact cgtgacagtc aagatggaag    420
ttccaaaact atggatgttc ttctagagat tgagctcttt cattatggaa acaagaagc     480 aatggatctt atgagactta atgggcttga tgttcatgag gtgtcatcga ctattcgtcc    540
aactgcaata aaagagcaat atacagagcc tggatctgat gatgcgacaa ccggttctga    600
atggtttcca aaaagtattt atgatttgga tatttgtgca aaaagagtga ttatgtatgg    660
agcagggctg gacgctgatc atcctggttt caaagatacc gagtatcgtc aacgtcgaat    720
gatgtttgct gaactggcgc tcaattacaa acacggtgag ccaattccgc gaaccgaata    780
tacatcatcc gaacggaaaa cttggggaat tatatataga aaattgagag aattgcacaa    840
```

-continued

```
aaagcacgca tgcaagcagt ttcttgataa ctttgagcta ctggagagac attgtggata    900
ctcggaaaat aatattccgc aactagaaga tatctgcaag tttttgaaag caaaaactgg    960
attccgtgtt cgcccagtcg ccggatactt atcagctcgt gatttcttgg caggtcttgc   1020
atatcgtgtc ttcttctgca ctcaatacgt tcgccatcat gccgatccat tttacactcc   1080
agaaccagac accgttcacg agctcatggg tcacatggct ctattcgctg atccagattt   1140
tgctcagttt tctcaagaga ttggattagc ttctcttgga gcatcagagg aagatttgaa   1200
gaagcttgca acactctact tcttttccat tgaatttggt ctctcgtctg atgacgctgc   1260
cgattctcca gtaaaagaaa atggatcaaa tcatgaaaga tttaaagtat acggagcagg   1320
acttctgagc agtgctggcg agttgcaaca tgccgttgag ggtagtgcaa ccattattcg   1380
ttttgatccg gatcgtgttg ttgagcaaga atgtctcatt actactttcc agtcagcgta   1440
tttctatact agaaattttg aagaggccca gcagaaactc agaatgttca ccaacaacat   1500
gaaacgtccc ttcattgttc gttacaaccc atacacagaa agcgtcgaag ttctcaacaa   1560
ctcccgttcc attatgttgg cagtgaactc tctccgctca gacatcaacc tgctcgccgg   1620
agctctccac tacatcctgt ag                                            1642
```

<210> SEQ ID NO 313
<211> LENGTH: 532
<212> TYPE: PRT
<213> ORGANISM: Caenorhabditis elegans

<400> SEQUENCE: 313

```
Met Asp Ser Leu Phe Gln Met Ala Ser Ala Met Lys Phe Gln Tyr Tyr
  1               5                  10                  15

Ser Lys Lys Ala Ala Gly Lys Thr Met Ser Asn Ser Val Ser Met Ser
             20                  25                  30

Ser Asp Asn Arg Met Glu Asp Phe Lys Arg Arg Phe Arg Arg Ser Gly
         35                  40                  45

Ser Leu Gly Ile Pro Phe Val Pro Glu Glu Asp Val Lys Gln Leu Phe
     50                  55                  60

Thr Pro Thr Arg Thr Val Arg Arg Glu Ala Ser Ile Arg Glu Gly Asp
 65                  70                  75                  80

Glu Glu Glu Gly Val Gln Ile Leu Thr Ile Val Lys Ser Ser Arg
                 85                  90                  95

Val Ser Glu Asp Ile Ser Lys Met Ile Ala Asn Leu Pro Asp His Thr
            100                 105                 110

Arg Ile Lys His Leu Glu Thr Arg Asp Ser Gln Asp Gly Ser Ser Lys
        115                 120                 125

Thr Met Asp Val Leu Leu Glu Ile Glu Leu Phe His Tyr Gly Lys Gln
    130                 135                 140

Glu Ala Met Asp Leu Met Arg Leu Asn Gly Leu Asp Val His Glu Val
145                 150                 155                 160

Ser Ser Thr Ile Arg Pro Thr Ala Ile Lys Glu Gln Tyr Thr Glu Pro
                165                 170                 175

Gly Ser Asp Asp Ala Thr Thr Gly Ser Glu Trp Phe Pro Lys Ser Ile
            180                 185                 190

Tyr Asp Leu Asp Ile Cys Ala Lys Arg Val Ile Met Tyr Gly Ala Gly
        195                 200                 205

Leu Asp Ala Asp His Pro Gly Phe Lys Asp Thr Glu Tyr Arg Gln Arg
    210                 215                 220
```

```
Arg Met Met Phe Ala Glu Leu Ala Leu Asn Tyr Lys His Gly Glu Pro
225                 230                 235                 240

Ile Pro Arg Thr Glu Tyr Thr Ser Ser Glu Arg Lys Thr Trp Gly Ile
            245                 250                 255

Ile Tyr Arg Lys Leu Arg Glu Leu His Lys His Ala Cys Lys Gln
                260                 265                 270

Phe Leu Asp Asn Phe Glu Leu Leu Glu Arg His Cys Gly Tyr Ser Glu
            275                 280                 285

Asn Asn Ile Pro Gln Leu Glu Asp Ile Cys Lys Phe Leu Lys Ala Lys
290                 295                 300

Thr Gly Phe Arg Val Arg Pro Val Ala Gly Tyr Leu Ser Ala Arg Asp
305                 310                 315                 320

Phe Leu Ala Gly Leu Ala Tyr Arg Val Phe Phe Cys Thr Gln Tyr Val
                325                 330                 335

Arg His His Ala Asp Pro Phe Tyr Thr Pro Glu Pro Asp Thr Val His
                340                 345                 350

Glu Leu Met Gly His Met Ala Leu Phe Ala Asp Pro Asp Phe Ala Gln
                355                 360                 365

Phe Ser Gln Glu Ile Gly Leu Ala Ser Leu Gly Ala Ser Glu Glu Asp
370                 375                 380

Leu Lys Lys Leu Ala Thr Leu Tyr Phe Phe Ser Ile Glu Phe Gly Leu
385                 390                 395                 400

Ser Ser Asp Asp Ala Ala Asp Ser Pro Val Lys Glu Asn Gly Ser Asn
                405                 410                 415

His Glu Arg Phe Lys Val Tyr Gly Ala Gly Leu Leu Ser Ser Ala Gly
                420                 425                 430

Glu Leu Gln His Ala Val Glu Gly Ser Ala Thr Ile Ile Arg Phe Asp
                435                 440                 445

Pro Asp Arg Val Val Glu Gln Glu Cys Leu Ile Thr Thr Phe Gln Ser
450                 455                 460

Ala Tyr Phe Tyr Thr Arg Asn Phe Glu Glu Ala Gln Gln Lys Leu Arg
465                 470                 475                 480

Met Phe Thr Asn Asn Met Lys Arg Pro Phe Ile Val Arg Tyr Asn Pro
                485                 490                 495

Tyr Thr Glu Ser Val Glu Val Leu Asn Asn Ser Arg Ser Ile Met Leu
            500                 505                 510

Ala Val Asn Ser Leu Arg Ser Asp Ile Asn Leu Leu Ala Gly Ala Leu
            515                 520                 525

His Tyr Ile Leu
    530

<210> SEQ ID NO 314
<211> LENGTH: 817
<212> TYPE: DNA
<213> ORGANISM: Caenorhabditis elegans

<400> SEQUENCE: 314
attacccaag tttgaggtag cattgctctc ttcaatcata tggattcgtt gtttcagatg    60
gcatccgcaa tgaagtttca atactactcg aagaaagctg ctggaaagac aatgtctaat   120
agtgtcaaaa actggattcc gtgttcgccc agtcgccgga tacttatcag ctcgtgattt   180
cttggcaggt cttgcatatc gtgtcttctt ctgcactcaa tacgttcgcc atcatgccga   240 tccatttttac actccagaac cagacaccgt tcacgagctc atgggtcaca tggctctatt   300
cgctgatcca gattttgctc agttttctca agagattgga ttagcttctc ttggagcatc   360
```

-continued

```
agaggaagat tgaagaagc ttgcaacact ctacttcttt tccattgaat ttggtctctc      420
gtctgatgac gctgccgatt ctccagtaaa agaaaatgga tcaaatcatg aaagatttaa      480
agtatacgga gcaggacttc tgagcagtgc tggcgagttg caacatgccg ttgagggtag      540
tgcaaccatt attcgttttg atccggatcg tgttgttgag caagaatgtc tcattactac      600
tttccagtca gcgtatttct atactagaaa ttttgaagag gcccagcaga aactcagaat      660
gttcaccaac aacatgaaac gtcccttcat tgttcgttac aacccataca cagaaagcgt      720
cgaagttctc aacaactccc gttccattat gttggcagtg aactctctcc gctcagacat      780
caacctgctc gccggagctc tccactacat cctgtag                               817
```

<210> SEQ ID NO 315
<211> LENGTH: 45
<212> TYPE: PRT
<213> ORGANISM: Caenorhabditis elegans

<400> SEQUENCE: 315

```
Met Asp Ser Leu Phe Gln Met Ala Ser Ala Met Lys Phe Gln Tyr Tyr
1               5                   10                  15

Ser Lys Lys Ala Ala Gly Lys Thr Met Ser Asn Ser Val Lys Asn Trp
            20                  25                  30

Ile Pro Cys Ser Pro Ser Arg Arg Ile Leu Ile Ser Ser
        35                  40                  45
```

<210> SEQ ID NO 316
<211> LENGTH: 466
<212> TYPE: DNA
<213> ORGANISM: Caenorhabditis elegans

<400> SEQUENCE: 316

```
attcggcatg agcatggagc ttcgagtcct agagaacaca aaacgttccc ggcggaacct       60
gggtctggac tgcgacgaga ctcaagcgag tcccgctgct gccgatatcc cctcacagtg      120
gactttgagg ctttcggctg ggactggatc atcgcaccta gcgctacaa ggccaactac       180 tgctccggcc agtgggagta catgttcatg caaaaatatc cgcataccca tttggtgcag      240
caggccaatc aagaggtta tgctgggccc tgttgtaccc ccaccaagat gtccccaatc       300
aacatgctct acttcaatga caagcagcag attatctacg gcaagatccc tggcatggtg      360
gtggatcgct gtggctgctc ttaaggtggg ggatagagga tgcctccccc acagaccgta      420
ccccaagacc catagccctg cccaatccac cgcctgatcc aaacat                    466
```

<210> SEQ ID NO 317
<211> LENGTH: 128
<212> TYPE: PRT
<213> ORGANISM: Caenorhabditis elegans

<400> SEQUENCE: 317

```
Ile Arg His Glu His Gly Ala Ser Ser Pro Arg Glu His Lys Thr Phe
1               5                   10                  15

Pro Ala Glu Pro Gly Ser Gly Leu Arg Arg Asp Ser Ser Glu Ser Arg
            20                  25                  30

Cys Cys Arg Tyr Pro Leu Thr Val Asp Phe Glu Ala Phe Gly Trp Asp
        35                  40                  45

Trp Ile Ile Ala Pro Lys Arg Tyr Lys Ala Asn Tyr Cys Ser Gly Gln
    50                  55                  60

Trp Glu Tyr Met Phe Met Gln Lys Tyr Pro His Thr His Leu Val Gln
```

```
                65                  70                  75                  80
            Gln Ala Asn Pro Arg Gly Tyr Ala Gly Pro Cys Cys Thr Pro Thr Lys
                            85                  90                  95
            Met Ser Pro Ile Asn Met Leu Tyr Phe Asn Asp Lys Gln Gln Ile Ile
                        100                 105                 110
            Tyr Gly Lys Ile Pro Leu Ala Met Val Val Asp Arg Cys Gly Cys Ser
                    115                 120                 125
```

<210> SEQ ID NO 318
<211> LENGTH: 8
<212> TYPE: DNA
<213> ORGANISM: Homo sapiens
<220> FEATURE:
<221> NAME/KEY: misc_feature
<222> LOCATION: 6
<223> OTHER INFORMATION: n = c or t

<400> SEQUENCE: 318 caaaanaa                                                                    8

<210> SEQ ID NO 319
<211> LENGTH: 20
<212> TYPE: DNA
<213> ORGANISM: Caenorhabditis elegans

<400> SEQUENCE: 319
ccactatggc cgagatttcc                                                      20

<210> SEQ ID NO 320
<211> LENGTH: 44
<212> TYPE: DNA
<213> ORGANISM: Caenorhabditis elegans

<400> SEQUENCE: 320
ccagtgaaaa gttcttctcc tttcttcctc ttctcgaatt cgga                           44

<210> SEQ ID NO 321
<211> LENGTH: 21
<212> TYPE: DNA
<213> ORGANISM: Caenorhabditis elegans

<400> SEQUENCE: 321
cttcctcttc tcgaattcgg c                                                    21

<210> SEQ ID NO 322
<211> LENGTH: 8
<212> TYPE: PRT
<213> ORGANISM: Caenorhabditis elegans

<400> SEQUENCE: 322

```
Gly Arg Lys Gly Phe Pro His Val
 1               5
```

<210> SEQ ID NO 323
<211> LENGTH: 7
<212> TYPE: PRT
<213> ORGANISM: Caenorhabditis elegans
<220> FEATURE:
<221> NAME/KEY: VARIANT
<222> LOCATION: (1)...(7)
<223> OTHER INFORMATION: Xaa = Any Amino Acid

<400> SEQUENCE: 323

Arg Xaa Xaa Ile Xaa Xaa Gly

<210> SEQ ID NO 324
<211> LENGTH: 7
<212> TYPE: PRT
<213> ORGANISM: Caenorhabditis elegans or Homo sapiens

<400> SEQUENCE: 324

Cys Gly Cys Cys Cys Cys Cys
1               5

<210> SEQ ID NO 325
<211> LENGTH: 79
<212> TYPE: PRT
<213> ORGANISM: Homo sapiens or Caenorhabditis elegans

<400> SEQUENCE: 325

Val Leu Asp Asp Tyr Gly Arg Val Asp Trp Trp Gly Gly Val Val Met
1               5                   10                  15

Tyr Glu Met Met Cys Gly Arg Leu Pro Phe Tyr Asp His Lys Leu Phe
            20                  25                  30

Glu Leu Ile Arg Phe Pro Leu Glu Ala Leu Leu Gly Leu Leu Lys Asp
        35                  40                  45

Pro Thr Gln Arg Leu Gly Gly Gly Glu Asp Ala Glu Ile Phe Phe Trp
    50                  55                  60

Tyr Lys Pro Pro Lys Pro Val Ser Glu Thr Asp Thr Tyr Phe Asp
65                  70                  75

<210> SEQ ID NO 326
<211> LENGTH: 48
<212> TYPE: PRT
<213> ORGANISM: Homo sapiens or Caenorhabditis elegans

<400> SEQUENCE: 326

Thr Met Phe Leu Lys Leu Gly Lys Gly Thr Phe Gly Lys Val Ile Leu
1               5                   10                  15

Lys Glu Lys Thr Tyr Ala Lys Ile Leu Lys Lys Val Ile Ala Glu Val
            20                  25                  30

Ala His Thr Leu Thr Glu Asn Arg Val Leu Gln His Pro Phe Leu Thr
        35                  40                  45

<210> SEQ ID NO 327
<211> LENGTH: 27
<212> TYPE: DNA
<213> ORGANISM: Caenorhabditis elegans

<400> SEQUENCE: 327
caagcgttga ctcaaatgaa tccaaaa                                    27

<210> SEQ ID NO 328
<211> LENGTH: 55
<212> TYPE: DNA
<213> ORGANISM: Caenorhabditis elegans

<400> SEQUENCE: 328
caagcgttga ctcaatgcgt tgactcaatg cgttgactcg ttgacgaatc caaaa     55

<210> SEQ ID NO 329
<211> LENGTH: 530
<212> TYPE: PRT
<213> ORGANISM: C. elegans

<400> SEQUENCE: 329

```
Met Asn Asp Ser Ile Asp Asp Phe Pro Pro Glu Pro Arg Gly Arg
  1               5                  10                  15

Cys Tyr Thr Trp Pro Met Gln Gln Tyr Ile Tyr Gln Glu Ser Ser Ala
             20                  25                  30

Thr Ile Pro His His His Leu Asn Gln His Asn Asn Pro Tyr His Pro
             35                  40                  45

Met His Pro His His Gln Leu Pro His Met Gln Gln Leu Pro Gln Pro
     50                  55                  60

Leu Leu Asn Leu Asn Met Thr Thr Leu Thr Ser Ser Gly Ser Ser Val
 65                  70                  75                  80

Ala Ser Ser Ile Gly Gly Gly Ala Gln Cys Ser Pro Cys Ala Ser Gly
                 85                  90                  95

Ser Ser Thr Ala Ala Thr Asn Ser Ser Gln Gln Gln Gln Thr Val Gly
             100                 105                 110

Gln Met Leu Ala Ala Ser Val Pro Cys Ser Ser Ser Gly Met Thr Leu
             115                 120                 125

Gly Met Ser Leu Asn Leu Ser Gln Gly Gly Pro Met Pro Ala Lys
 130                 135                 140

Lys Lys Arg Cys Arg Lys Lys Pro Thr Asp Gln Leu Ala Gln Lys Lys
 145                 150                 155                 160

Pro Asn Pro Trp Gly Glu Ser Tyr Ser Asp Ile Ile Ala Lys Ala
                 165                 170                 175

Leu Glu Ser Ala Pro Asp Gly Arg Leu Lys Leu Asn Glu Ile Tyr Gln
             180                 185                 190

Trp Phe Ser Asp Asn Ile Pro Tyr Phe Gly Glu Arg Ser Ser Pro Glu
             195                 200                 205

Glu Ala Ala Gly Trp Lys Asn Ser Ile Arg His Asn Leu Ser Leu His
 210                 215                 220

Ser Arg Phe Met Arg Ile Gln Asn Glu Gly Ala Gly Lys Ser Ser Trp
 225                 230                 235                 240

Trp Val Ile Asn Pro Asp Ala Lys Pro Gly Arg Asn Pro Arg Arg Thr
                 245                 250                 255

Arg Glu Arg Ser Asn Thr Ile Glu Thr Thr Lys Ala Gln Leu Glu
             260                 265                 270

Lys Ser Arg Arg Gly Ala Lys Lys Arg Ile Lys Glu Arg Ala Leu Met
 275                 280                 285

Gly Ser Leu His Ser Thr Leu Asn Gly Asn Ser Ile Ala Gly Ser Ile
 290                 295                 300

Gln Thr Ile Ser His Asp Leu Tyr Asp Asp Ser Met Gln Gly Ala
305                 310                 315                 320

Phe Asp Asn Val Pro Ser Ser Phe Arg Pro Arg Thr Gln Ser Asn Leu
             325                 330                 335

Ser Ile Pro Gly Ser Ser Ser Arg Val Ser Pro Ala Ile Gly Ser Asp
                 340                 345                 350

Ile Tyr Asp Asp Leu Glu Phe Pro Ser Trp Val Gly Glu Ser Val Pro
             355                 360                 365

Ala Ile Pro Ser Asp Ile Val Asp Arg Thr Asp Gln Met Arg Ile Asp
 370                 375                 380

Ala Thr Thr His Ile Gly Gly Val Gln Ile Lys Gln Glu Ser Lys Pro
 385                 390                 395                 400

Ile Lys Thr Glu Pro Ile Ala Pro Pro Ser Tyr His Glu Leu Asn
                 405                 410                 415
```

-continued

```
Ser Val Arg Gly Ser Cys Ala Gln Asn Pro Leu Leu Arg Asn Pro Ile
            420                 425                 430

Val Pro Ser Thr Asn Phe Lys Pro Met Pro Leu Pro Gly Ala Tyr Gly
            435                 440                 445

Asn Tyr Gln Asn Gly Gly Ile Thr Pro Ile Asn Trp Leu Ser Thr Ser
    450                 455                 460

Asn Ser Ser Pro Leu Pro Gly Ile Gln Ser Cys Gly Ile Val Ala Ala
465                 470                 475                 480

Gln His Thr Val Ala Ser Ser Ala Leu Pro Ile Asp Leu Glu Asn
            485                 490                 495

Leu Thr Leu Pro Asp Gln Pro Leu Met Asp Thr Met Asp Val Asp Ala
            500                 505                 510

Leu Ile Arg His Glu Leu Ser Gln Ala Gly Gly Gln His Ile His Phe
            515                 520                 525

Asp Leu
    530

<210> SEQ ID NO 330
<211> LENGTH: 673
<212> TYPE: PRT
<213> ORGANISM: Homo sapiens

<400> SEQUENCE: 330

Met Ala Glu Ala Pro Ala Ser Pro Ala Pro Leu Ser Pro Leu Glu Val
  1               5                  10                  15

Glu Leu Asp Pro Glu Phe Glu Pro Gln Ser Arg Pro Arg Ser Cys Thr
             20                  25                  30

Trp Pro Leu Gln Arg Pro Glu Leu Gln Ala Ser Pro Ala Lys Pro Ser
         35                  40                  45

Gly Glu Thr Ala Ala Asp Ser Met Ile Pro Glu Glu Asp Asp Glu
     50                  55                  60

Asp Asp Glu Asp Gly Gly Gly Arg Ala Gly Ser Ala Met Ala Ile Gly
 65                  70                  75                  80

Gly Gly Gly Gly Ser Gly Thr Leu Gly Ser Gly Leu Leu Leu Glu Asp
                 85                  90                  95

Ser Ala Arg Val Leu Ala Pro Gly Gly Gln Asp Pro Gly Ser Gly Pro
            100                 105                 110

Ala Thr Ala Ala Gly Gly Leu Ser Gly Gly Thr Gln Ala Leu Leu Gln
        115                 120                 125

Pro Gln Gln Pro Leu Pro Pro Pro Gln Pro Gly Ala Ala Gly Gly Ser
    130                 135                 140

Gly Gln Pro Arg Lys Cys Ser Ser Arg Arg Asn Ala Trp Gly Asn Leu
145                 150                 155                 160

Ser Tyr Ala Asp Leu Ile Thr Arg Ala Ile Glu Ser Ser Pro Asp Lys
                165                 170                 175

Arg Leu Thr Leu Ser Gln Ile Tyr Glu Trp Met Val Arg Cys Val Pro
            180                 185                 190

Tyr Phe Lys Asp Lys Gly Asp Ser Asn Ser Ser Ala Gly Trp Lys Asn
        195                 200                 205

Ser Ile Arg His Asn Leu Ser Leu His Ser Arg Phe Met Arg Val Gln
    210                 215                 220

Asn Glu Gly Thr Gly Lys Ser Ser Trp Trp Ile Ile Asn Pro Asp Gly
225                 230                 235                 240

Gly Lys Ser Gly Lys Ala Pro Arg Arg Arg Ala Val Ser Met Asp Asn
```

-continued

```
                245                 250                 255
Ser Asn Lys Tyr Thr Lys Ser Arg Gly Arg Ala Ala Lys Lys Ala
                260                 265                 270

Ala Leu Gln Thr Ala Pro Glu Ser Ala Asp Asp Ser Pro Ser Gln Leu
                275                 280                 285

Ser Lys Trp Pro Gly Ser Pro Thr Ser Arg Ser Ser Asp Glu Leu Asp
                290                 295                 300

Ala Trp Thr Asp Phe Arg Ser Arg Thr Asn Ser Asn Ala Ser Thr Val
305                 310                 315                 320

Ser Gly Arg Leu Ser Pro Ile Met Ala Ser Thr Glu Leu Asp Glu Val
                325                 330                 335

Gln Asp Asp Asp Ala Pro Leu Ser Pro Met Leu Tyr Ser Ser Ser Ala
                340                 345                 350

Ser Leu Ser Pro Ser Val Ser Lys Pro Cys Thr Val Glu Leu Pro Arg
                355                 360                 365

Leu Thr Asp Met Ala Gly Thr Met Asn Leu Asn Asp Gly Leu Thr Glu
                370                 375                 380

Asn Leu Met Asp Asp Leu Leu Asp Asn Ile Thr Leu Pro Pro Ser Gln
385                 390                 395                 400

Pro Ser Pro Thr Gly Gly Leu Met Gln Arg Ser Ser Ser Phe Pro Tyr
                405                 410                 415

Thr Thr Lys Gly Ser Gly Leu Gly Ser Pro Thr Ser Ser Phe Asn Ser
                420                 425                 430

Thr Val Phe Gly Pro Ser Ser Leu Asn Ser Leu Arg Gln Ser Pro Met
                435                 440                 445

Gln Thr Ile Gln Glu Asn Lys Pro Ala Thr Phe Ser Ser Met Ser His
                450                 455                 460

Tyr Gly Asn Gln Thr Leu Gln Asp Leu Leu Thr Ser Asp Ser Leu Ser
465                 470                 475                 480

His Ser Asp Val Met Met Thr Gln Ser Asp Pro Leu Met Ser Gln Ala
                485                 490                 495

Ser Thr Ala Val Ser Ala Gln Asn Ser Arg Arg Asn Val Met Leu Arg
                500                 505                 510

Asn Asp Pro Met Met Ser Phe Ala Ala Gln Pro Asn Gln Gly Ser Leu
                515                 520                 525

Val Asn Gln Asn Leu Leu His His Gln His Gln Thr Gln Gly Ala Leu
                530                 535                 540

Gly Gly Ser Arg Ala Leu Ser Asn Ser Val Ser Asn Met Gly Leu Ser
545                 550                 555                 560

Glu Ser Ser Ser Leu Gly Ser Ala Lys His Gln Gln Gln Ser Pro Val
                565                 570                 575

Ser Gln Ser Met Gln Thr Leu Ser Asp Ser Leu Ser Gly Ser Ser Leu
                580                 585                 590

Tyr Ser Thr Ser Ala Asn Leu Pro Val Met Gly His Glu Lys Phe Pro
                595                 600                 605

Ser Asp Leu Asp Leu Asp Met Phe Asn Gly Ser Leu Glu Cys Asp Met
                610                 615                 620

Glu Ser Ile Ile Arg Ser Glu Leu Met Asp Ala Asp Gly Leu Asp Phe
625                 630                 635                 640

Asn Phe Asp Ser Leu Ile Ser Thr Gln Asn Val Val Gly Leu Asn Val
                645                 650                 655

Gly Asn Phe Thr Gly Ala Lys Gln Ala Ser Ser Gln Ser Trp Val Pro
                660                 665                 670
```

Gly

<210> SEQ ID NO 331
<211> LENGTH: 501
<212> TYPE: PRT
<213> ORGANISM: Homo sapiens

<400> SEQUENCE: 331

```
Met Arg Ile Gln Pro Gln Lys Ala Ala Ile Ile Asp Leu Asp Pro
1               5                   10                  15

Asp Phe Glu Pro Gln Ser Arg Pro Arg Ser Cys Thr Trp Pro Leu Pro
            20                  25                  30

Arg Pro Glu Ile Ala Asn Gln Pro Ser Glu Pro Pro Glu Val Glu Pro
        35                  40                  45

Asp Leu Gly Glu Lys Val His Thr Glu Gly Arg Ser Glu Pro Ile Leu
    50                  55                  60

Leu Pro Ser Arg Leu Ser Glu Pro Ala Gly Pro Gln Pro Gly Ile
65                  70                  75                  80

Leu Gly Ala Val Thr Gly Pro Arg Lys Gly Gly Ser Arg Arg Asn Ala
                85                  90                  95

Trp Gly Asn Gln Ser Tyr Ala Glu Phe Ile Ser Gln Ala Ile Glu Ser
            100                 105                 110

Ala Pro Glu Lys Arg Leu Thr Leu Ala Gln Ile Tyr Glu Trp Met Val
        115                 120                 125

Arg Thr Val Pro Tyr Phe Lys Asp Lys Gly Asp Ser Asn Ser Ser Ala
    130                 135                 140

Gly Trp Lys Asn Ser Ile Arg His Asn Leu Ser Leu His Ser Lys Phe
145                 150                 155                 160

Ile Lys Val His Asn Glu Ala Thr Gly Lys Ser Ser Trp Trp Met Leu
                165                 170                 175

Asn Pro Glu Gly Gly Lys Ser Gly Lys Ala Pro Arg Arg Ala Ala
            180                 185                 190

Ser Met Asp Ser Ser Ser Lys Leu Leu Arg Gly Arg Ser Lys Ala Pro
        195                 200                 205

Lys Lys Lys Pro Ser Val Leu Pro Ala Pro Pro Glu Gly Ala Thr Pro
    210                 215                 220

Thr Ser Pro Val Gly His Phe Ala Lys Trp Ser Gly Ser Pro Cys Ser
225                 230                 235                 240

Arg Asn Arg Glu Glu Ala Asp Met Trp Thr Thr Phe Arg Pro Arg Ser
                245                 250                 255

Ser Ser Asn Ala Ser Ser Val Ser Thr Arg Leu Ser Pro Leu Arg Pro
            260                 265                 270

Glu Ser Glu Val Leu Ala Glu Ile Pro Ala Ser Val Ser Ser Tyr
        275                 280                 285

Ala Gly Gly Val Pro Pro Thr Leu Asn Glu Gly Leu Glu Leu Leu Asp
    290                 295                 300

Gly Leu Asn Leu Thr Ser Ser His Ser Leu Leu Ser Arg Ser Gly Leu
305                 310                 315                 320

Ser Gly Phe Ser Leu Gln His Pro Gly Val Thr Gly Pro Leu His Thr
                325                 330                 335

Tyr Ser Ser Ser Leu Phe Ser Pro Ala Glu Gly Pro Leu Ser Ala Gly
            340                 345                 350

Glu Gly Cys Phe Ser Ser Ser Gln Ala Leu Glu Ala Leu Leu Thr Ser
        355                 360                 365
```

```
Asp Thr Pro Pro Pro Pro Ala Asp Val Leu Met Thr Gln Val Asp Pro
    370             375                 380
Ile Leu Ser Gln Ala Pro Thr Leu Leu Leu Leu Gly Gly Leu Pro Ser
385                 390                 395                 400
Ser Ser Lys Leu Ala Thr Gly Val Gly Leu Cys Pro Lys Pro Leu Glu
                405                 410                 415
Ala Arg Gly Pro Ser Ser Leu Val Pro Thr Leu Ser Met Ile Ala Pro
            420                 425                 430
Pro Pro Val Met Ala Ser Ala Pro Ile Pro Lys Ala Leu Gly Thr Pro
            435                 440                 445
Val Leu Thr Pro Pro Thr Glu Ala Ala Ser Gln Asp Arg Met Pro Gln
        450                 455                 460
Asp Leu Asp Leu Asp Met Tyr Met Glu Asn Leu Glu Cys Asp Met Asp
465                 470                 475                 480
Asn Ile Ile Ser Asp Leu Met Asp Glu Gly Glu Gly Leu Asp Phe Asn
            485                 490                 495
Phe Glu Pro Asp Pro
            500
```

THERAPEUTIC AND DIAGNOSTIC TOOLS FOR IMPAIRED GLUCOSE TOLERANCE CONDITIONS

REFERENCE TO RELATED APPLICATIONS

This application is a continuation-in-part of PCT/US98/10080, filed May 15, 1998, which is a continuation-in-part of U.S. Ser. No. 08/888,534, filed Jul. 7, 1997, now abandoned and U.S. Ser. No. 08/857,076, filed May 15, 1997, issued as U.S. Pat. No. 6,225,120 on May 1, 2001.

STATEMENT AS TO FEDERALLY SPONSORED RESEARCH

This invention was made in part with support from the Federal government through NIH Grant Nos. AG05790 and AG14161. The Government has certain rights in the invention.

BACKGROUND OF THE INVENTION

This invention relates to compositions and methods useful for delaying or ameliorating human diseases associated with glucose intolerance.

Diabetes is a major disease affecting over 16 million individuals in the United States alone at an annual cost of over 92 billion dollars. Type I diabetes or insulin-dependent diabetes (IDDD) is an autoimmune disease. In the IDDM patient, the immune system attacks and destroys the insulin-producing beta cells in the pancreas. The central role of insulin in human metabolism is to aid in the transport of glucose into muscle cells and fat cells. The body's inability to produce insulin results in hyperglycemia, ketoacidosis, thirst, and weight loss. In addition, diabetics often suffer from chronic atherosclerosis and kidney and eyesight failure. A patient with IDDM requires daily injections of insulin to survive.

The most common form of diabetes is non-insulin dependent diabetes (NIDDM) or Type II diabetes. Type II diabetes is a heterogenous group of disorders in which hyperglycemia results from both impaired insulin secretory response to glucose and decreased insulin effectiveness (i.e., insulin resistance). Older people who are overweight are at particular risk for Type II diabetes. Genetic studies have suggested that, Type II diabetes is found in families and that the disease may be due to multiple genetic defects. In addition, the link between obesity and Type II diabetes is strong. Approximately 80 percent of Type II diabetics are obese. Weight loss and exercise can be effective to keep blood glucose levels normal, reducing the long-term complications of the disease.

At present there are few reliable methods for presymptomatic diagnosis of a genetic predisposition for diabetes or obesity. The search for genetic markers linked to diabetes and obesity has proven difficult, and this is especially true for Type II diabetes.

Treatments for diabetes emphasize control of blood glucose through blood glucose monitoring. The majority of patients take oral medications and/or insulin injections for appropriate control. Treatment of diabetes is generally chronic and lifelong, and treatments are generally not satisfactory over the long run. In addition, insulin treatment may become increasingly ineffective as the disease progresses. While insulin has been known for decades, and within the past decade, the receptors for insulin and aspects of its signaling pathway have been identified, the transcriptional output from these signaling pathways have not been characterized. In addition, the molecular basis of the obesity-induced insulin resistance is unknown.

SUMMARY OF THE INVENTION

We have discovered that the *C. elegans* metabolic regulatory genes daf-2 and age-1 encode homologues of the mammalian insulin receptor/PI 3-kinase signaling pathway proteins, respectively. We have also discovered that the *C. elegans* PKB kinase and AKT kinase act downstream of these genes, as their mammalian homologues act downstream of insulin signaling. These results further endorse the congruence between the *C. elegans* and mammalian insulin signaling pathways, strongly supporting the contention that new genes identified in the *C. elegans* pathway also act in mammalian insulin signaling. In addition, we have also found that the *C. elegans* PTEN lipid phosphatase homologue, DAF-18, acts upstream of AKT in this signaling pathway. Thus, our molecular genetic analysis maps mammalian PTEN action to the insulin signaling pathway.

We have also discovered that the DAF-16 forkhead protein represents the major transcriptional output of this insulin signaling pathway. For example, we have discovered that it is the dysregulation of the DAF-16 transcription factor in the absence of insulin signaling that leads to metabolic defects; inactivation of DAF-16 reverses the metabolic defects caused by lack of insulin signaling in *C. elegans*. We have found 3 human DAF-16 orthologues: FKHRL1, FKHR, and AFX. Our molecular genetic analysis strongly suggests that the activity of these transcription factors is strongly coupled to insulin signaling and that drug-induced inhibition of one or all of these transcription factors ameliorates diabetic disease. As discussed in more detail below, we have developed screening strategies to identify such drugs.

We have also found that the *C. elegans* daf-7, daf-1, daf-4, daf-8, daf-14, and daf-3 genes encode neuroendocrine/target tissue TGF-β type signal transduction molecules that genetically interact with the insulin signaling pathway. Similarly, we have shown that the metabolic defects caused by lack of neuroendocrine TGF-β signals can be reversed by inactivation of the DAF-3 transcription factor. Finally, we have found that another *C. elegans* gene, daf-18, the homologue of the mammalian PTEN lipid phosphatase gene, also functions in the DAF-2 signaling pathway.

Together, this evidence indicates that the DAF-16, DAF-3, DAF-8, and DAF-14 transcriptional outputs of these converging signaling pathways regulate metabolism. In addition, these discoveries also indicate that insulin and TGF-β-like signals are integrated in humans to regulate metabolism, and that the homologues of other DAF proteins are likely to be defective or down regulated in human diabetic pedigrees as well as obesity induced diabetes. These results therefore indicate that the *C. elegans* daf genes are excellent candidate genes and proteins for human disease associated with glucose intolerance, e.g., diabetes, obesity, and atherosclerosis. Our findings indicate that the human homologues of these daf genes and proteins mediate insulin signaling in normal people and may be defective or mis-regulated in diabetics. Moreover, our findings indicate that there are at least two classes of type II diabetics: those with defects in the TGF-β signaling genes, and those with defects in insulin signaling genes. Below we describe exemplary sequence and functional characteristics of the human homologues of the daf genes.

The discovery of converging DAF-7 and DAF-2 insulin-like signaling indicates that many cases of obesity-induced and genetically-induced diabetes (and obesity) may be treated by administration of a human DAF-7 polypeptide.

The discovery that defects in the TGF-β signaling pathway can be suppressed by decreases in DAF-3 pathway activity and that defects in the insulin pathway can be suppressed by decreases in DAF-16 activity highlight the utility of transcriptional regulatory DAF proteins in drug development; in particular, drugs that inhibit the activity of these proteins are useful for reversing the effects of obesity-induced or genetically-induced defects in DAF-7 TGF-β type or insulin signaling.

In one aspect, the invention features a substantially pure preparation of a DAF-2 polypeptide, which can be derived from an animal (for example, a mammal, such as a human, or an invertebrate, such as *C. elegans*). In preferred embodiments, the DAF-2 polypeptide has insulin receptor (InR) activity, insulin receptor related activity, insulin-like growth factor receptor (IGF-1) receptor activity, or a combination of these activities.

The invention also features isolated DNA encoding a DAF-2 polypeptide. This isolated DNA can have a nucleotide sequence that includes, for example, the nucleotide sequence of the daf-2 gene shown in FIG. 2B. This isolated DNA can also, in preferred embodiments, complement a daf-2 mutation in *C. elegans*, an InR mutation in a mouse, or an IGF-1 receptor mutation in a mouse.

The isolated DNA encoding a DAF-2 polypeptide can be included in a vector, such as a vector that is capable of directing the expression of the protein encoded by the DNA in a vector-containing cell. The isolated DNA in the vector can be operatively linked to a promoter, for example, a promoter selected from the group consisting of daf-2, age-1, daf-16, daf-1, daf-4, daf-3, and akt promoters. The isolated DNA encoding a DAF-2 polypeptide, or a vector including this DNA, can be contained in a cell, such as a bacterial, mammalian, or nematode cell.

Also included in the invention is a method of producing a recombinant DAF-2 polypeptide, and a DAF-2 polypeptide produced by this method. This method involves (a) providing a cell transformed with isolated DNA that (i) encodes a DAF-2 polypeptide, and (ii) is positioned for expression in the cell, under conditions for expressing the isolated DNA, and (b) isolating the recombinant DAF-2 polypeptide.

A substantially pure antibody, such as a monoclonal or polyclonal antibody, that specifically recognizes and binds a DAF-2 polypeptide is also included in the invention.

The invention also features a method of detecting a gene, or a portion of a gene, that is found in a human cell and has sequence identity to the daf-2 sequence of FIG. 2B. In this method, isolated DNA encoding a DAF-2 polypeptide, a portion of such DNA greater than about 12 residues in length, or a degenerate oligonucleotide corresponding to SEQ ID NOS: 33, 34, 79, 80, 81, 82, 83, or 84, is contacted with a preparation of DNA from the human cell under hybridization conditions that provide detection of DNA sequences having about 70% or greater nucleic acid sequence identity to the daf-2 sequence of FIG. 2B. This method can also include a step of testing the gene, or portion thereof, for the ability to functionally complement a *C. elegans* daf-2 mutant.

Another method included in the invention is a method of isolating a gene, or a portion of a gene, that is found in a human cell and has at least 90% nucleic acid sequence identity to a sequence encoding SEQ ID NOS: 33, 34, 79, 80, 81, 82, 83, or 84. This method involves (a) amplifying by PCR the human gene, or portion thereof, using oligonucleotide primers that (i) are each greater than about 12 residues in length, and (ii) each have regions of complementarity to opposite DNA strands in a region of the nucleotide sequence of FIG. 2B, and (b) isolating the human gene, or portion thereof. This method can also include a step of testing the gene, or portion thereof, for the ability to functionally complement a *C. elegans* daf-2 mutant.

In another aspect, the invention features a substantially pure preparation of a DAF-3 polypeptide, which can be derived from an animal (for example, a mammal, such as a human, or an invertebrate, such as *C. elegans*). In a preferred embodiment, the polypeptide is a SMAD protein. In other preferred embodiments, the polypeptide is capable of binding and interacting with a nematode DAF-1, DAF-4, DAF-8, DAF-14, or DAF-16 polypeptide.

The invention also features isolated DNA encoding a DAF-3 polypeptide. This isolated DNA can have a sequence that includes, for example, the nucleotide sequence of a daf-3 gene shown in FIGS. 11A, 11B, or 11C. This isolated DNA can also, in preferred embodiments, complement a daf-3 mutation in *C. elegans* or complement a daf-3 knock-out mouse.

The isolated DNA encoding a DAF-3 polypeptide can be included in a vector, such as a vector that is capable of directing the expression of the protein encoded by the DNA in a vector-containing cell. The isolated DNA in the vector can be operatively linked to a promoter, for example, a promoter selected from the group consisting of daf-3, daf-4, daf-16, daf-2, age-1, and akt promoters. The isolated DNA encoding a DAF-3 polypeptide, or a vector including this DNA, can be contained in a cell, such as a bacterial, mammalian, or nematode cell.

Also included in the invention is a method of producing a recombinant DAF-3 polypeptide, and a DAF-3 polypeptide produced by this method. This method involves (a) providing a cell transformed with isolated DNA that (i) encodes a DAF-3 polypeptide, and (ii) is positioned for expression in the cell, under conditions for expressing the isolated DNA, and (b) isolating the recombinant DAF-3 polypeptide.

A substantially pure antibody, such as a monoclonal or polyclonal antibody, that specifically recognizes and binds a DAF-3 polypeptide is also included in the invention.

The invention also features a method of detecting a gene, or a portion of a gene, that is found in a human cell and has sequence identity to any of the daf-3 sequences of FIGS. 11A, 11B, or 11C. In this method, isolated DNA encoding a DAF-3 polypeptide, a portion of such DNA that is greater than about 12 residues in length, or a degenerate oligonucleotide corresponding to SEQ ID NOS: 35, 36, or 85, is contacted with a preparation of DNA from the human cell under hybridization conditions that provide detection of DNA sequences having about 70% or greater nucleic acid sequence identity to any of the daf-3 sequences of FIGS. 11A, 11B, or 11C. This method can also include a step of testing the gene, or portion thereof, for the ability to functionally complement a *C. elegans* daf-3 mutant.

Another method included in the invention is a method of isolating a gene, or a portion thereof, that is found in a human cell and has at least 90% nucleic acid sequence identity to a sequence encoding SEQ ID NOS: 35, 36, or 85. This method includes (a) amplifying by PCR the human gene, or portion thereof, using oligonucleotide primers that (i) are each greater than about 12 residues in length, and (ii) each have regions of complementarity to opposite DNA strands in a region of any of the nucleotide sequences of FIGS. 11A, 11B, or 11C, and (b) isolating the human gene, or portion thereof. This method can also include a step of testing the gene, or portion thereof, for the ability to functionally complement a *C. elegans* daf-3 mutant.

In yet another aspect, the invention features a substantially pure preparation of DAF-16 polypeptide, which can be derived from an animal (for example, a mammal, such as a human, or an invertebrate, such as *C. elegans*). In a preferred embodiment, the polypeptide is a forkhead transcription factor that binds DNA. In other preferred embodiments, the polypeptide is capable of interacting with a polypeptide selected from the group consisting of DAF-3, DAF-8, and DAF-14.

The invention also features isolated DNA encoding a DAF-16 polypeptide. This isolated DNA can have a sequence that includes, for example, the sequence of the daf-16 gene shown in FIG. 13A or 13B. This isolated DNA can also, in preferred embodiments, complement a daf-16 mutation in *C. elegans*, or complement an FKHR, FKHRL1, or AFX mutation in a mouse.

The isolated DNA encoding a DAF-16 polypeptide can be included in a vector, such as a vector that is capable of directing the expression of the protein encoded by the DNA in a vector-containing cell. The isolated DNA in the vector can be operatively linked to a promoter, for example, a promoter selected from the group consisting of daf-2, age-1, daf-16, daf-3, daf-4, and akt promoters. The isolated DNA encoding a DAF-16 polypeptide, or a vector containing this DNA, can be contained in a cell, such as a bacterial, mammalian, or nematode cell.

Also included in the invention is a method for producing a recombinant DAF-16 polypeptide, and a DAF-16 polypeptide produced by this method. This method involves (a) providing a cell transformed with purified DNA that (i) encodes a DAF-16 polypeptide, and (ii) is positioned for expression in the cell, under conditions for expressing the isolated DNA, and (b) isolating the recombinant DAF-16 polypeptide.

A substantially pure antibody, such as a monoclonal or polyclonal antibody, that specifically recognizes and binds a DAF-16 polypeptide is also included in the invention.

The invention also features a method of detecting a gene, or a portion of a gene, that is found in a human cell and has sequence identity to the daf-16 sequence of FIGS. 13A or 13B. In this method, isolated DNA encoding a DAF-16 polypeptide, a portion of such DNA that is greater than about 12 residues in length, or a degenerate oligonucleotide corresponding to SEQ ID NO: 54, 55, 56, or 58, is contacted with a preparation of DNA from the human cell under hybridization conditions that provide detection of DNA sequences having about 70% or greater nucleic acid sequence identity to the daf-16 sequence of FIG. 13A or 13B. This method can also include a step of testing the gene, or portion of the gene, for the ability to functionally complement a *C. elegans* daf-16 mutant.

Another method included in the invention is a method of isolating a gene, or a portion of a gene, that is found in a human cell and has at least 90% nucleic acid sequence identity to a sequence encoding SEQ ID NO: 54, 55, 56, or 58. This method involves (a) amplifying by PCR the human gene, or portion thereof, using oligonucleotide primers that (i) are each greater than about 12 residues in length, and (ii) each have regions of complementarity to opposite DNA strands in a region of the nucleotide sequence of FIG. 13A or 13B, and (b) isolating the human gene, or portion thereof. This method can also include a step of testing the gene, or portion thereof, for the ability to functionally complement a *C. elegans* daf-16 mutant.

In another aspect, the invention features a method of determining whether a human gene is involved in an impaired glucose tolerance condition (for example, a condition involving atherosclerosis) or obesity. This method involves (a) providing a nematode having a mutation in a daf or age gene, and (b) expressing in the nematode the human gene, which is operatively linked to a nematode gene promoter. Complementation of the daf or age mutation in the nematode is indicative of a human gene that is involved in an impaired glucose tolerance condition or obesity. In preferred embodiments, the nematode gene promoter is selected from the group consisting of daf-1, daf-3, daf-4, daf-2, age-1, and akt gene promoters. In other preferred embodiments, the daf mutation is selected from the group consisting of daf-2, daf-3, daf-1, daf-4, daf-7, daf-8, daf-11, daf-12, daf-14, and daf-16 mutations. In yet another preferred embodiment, the mutation can also be found in the age-1 gene.

In further aspects, the invention features methods for diagnosing an impaired glucose tolerance condition (for example, Type II diabetes or a condition involving atherosclerosis), or a propensity for such a condition, in a patient. One such method includes analyzing the DNA of the patient to determine whether the DNA contains a mutation in a daf gene. Identification of such a mutation indicates that the patient has an impaired glucose tolerance condition or a propensity for such a condition. The analysis in this method can be carried out, for example, by nucleotide sequencing or RFLP analysis. The analysis can also include amplifying (for example, by PCR or reverse transcriptase PCR) the gene (for example, a human gene), or a fragment thereof, using primers, and analyzing the amplified gene, or a fragment thereof, for the presence of the mutation. In preferred embodiments, the daf gene analyzed in this method is, for example, a daf-1, daf-2, daf-3 daf-4, daf-7, daf-8, daf-11, daf-12, daf-14, daf-16, akt-1, akt-2, pdk-1, or daf-18(PTEN) coding sequence, or the daf gene is FKHR, FKHRL1, or AFX.

Another method for diagnosing an impaired glucose tolerance condition, such as Type II diabetes, or a propensity for such a condition, in a patient, includes analyzing the DNA of the patient to determine whether the DNA contains a mutation in an age gene. Identification of such a mutation indicates that the patient has an impaired glucose tolerance condition or a propensity for such a condition. The analysis in this method can be carried out, for example, by nucleotide sequencing or RFLP analysis. The analysis can also include amplifying (for example, by PCR or reverse transcriptase PCR) the gene (for example, a human gene), or a fragment thereof, using primers and analyzing the amplified gene, or fragment thereof, for the presence of the mutation. In a preferred embodiment, the age gene is an age-1 coding sequence.

Yet another method for diagnosing an impaired glucose tolerance condition, such as Type II diabetes or a condition that involves atherosclerosis, or a propensity for such a condition, in a patient, includes analyzing the DNA of the patient to determine whether the DNA contains a mutation in an akt gene. Identification of such a mutation indicates that the patient has an impaired glucose tolerance condition (for example, Type II diabetes) or a propensity for such a condition (for example, a pre-diabetic condition). The analysis in this method can be carried out, for example, by nucleotide sequencing or RFLP analysis. The analysis can also include amplifying (for example, by PCR or reverse transcriptase PCR) the gene (for example, a human gene), or a fragment thereof, using primers and analyzing the amplified gene, or fragment thereof, for the presence of the mutation.

The invention also includes kits for use in the diagnosis of an impaired glucose tolerance condition, or a propensity for such a condition, in a patient. One such kit includes a PCR primer complementary to a daf nucleic acid sequence and instructions for diagnosing an impaired glucose tolerance condition or a propensity for such a condition. Another kit includes a PCR primer complementary to an age nucleic acid sequence and instructions for diagnosing an impaired glucose tolerance condition or a propensity for such a condition. Yet another kit includes a PCR primer complementary to an akt nucleic acid sequence and instructions for diagnosing an impaired glucose tolerance condition or a propensity for such a condition.

In another aspect, the invention features methods for ameliorating or delaying the onset of an impaired glucose tolerance condition (for example, Type II diabetes) in a patient. In one such method a therapeutically effective amount of a DAF polypeptide (for example, the human or nematode DAF-7 polypeptide) is administered to the patient. In another method, which can be used, for example, in the case of a condition involving atherosclerosis, a therapeutically effective amount of a compound that is capable of inhibiting the activity of a DAF-16 or DAF-3 polypeptide is administered to the patient. In yet another method, a therapeutically effective amount of a compound that activates a DAF-1, DAF-4, DAF-8, DAF-11, or DAF-14 polypeptide is administered to the patient.

Another aspect of the invention provides methods for ameliorating or preventing obesity (for example, obesity associated with Type II diabetes) in a patient. One such method involves administering to the patient a therapeutically effective amount of a DAF polypeptide, such as a human or nematode DAF-7 polypeptide. Another such method involves administering to the patient a therapeutically effective amount of a compound that is capable of inhibiting the activity of a DAF-16, DAF-3, or DAF-18 (PTEN) polypeptide.

Yet another aspect of the invention features a transgenic, non-human animal, such as a mouse or a nematode, whose germ cells and somatic cells contain a transgene coding for a mutant DAF polypeptide, for example, a mutant DAF polypeptide that is derived from a human. In preferred embodiments, the mutant DAF polypeptide is a DAF-1, DAF-2, DAF-3, DAF-4, DAF-7, DAF-8, DAF-11, DAF-12, DAF-14, DAF-16, or DAF-18 (PTEN) polypeptide. In another preferred embodiment, the transgene includes a knockout mutation.

In a related aspect, the invention features a transgenic, non-human animal, such as a mouse or a nematode, whose germ cells and somatic cells contain a transgene coding for a mutant AGE polypeptide, for example, a mutant AGE polypeptide derived from a human. In a preferred embodiment, the mutant AGE polypeptide is an AGE-1 polypeptide. In another preferred embodiment, the transgene includes a knockout mutation.

In yet another aspect, the invention features a transgenic, non-human animal, such as a mouse or a nematode, whose germ cells and somatic cells contain a transgene coding for a mutant AKT polypeptide, for example, a mutant AKT polypeptide derived from a human. In a preferred embodiment, the transgene includes a knockout mutation.

In related aspects, the invention features cells (for example, cells isolated from a mammal, such as mouse, human, or nematode cells) isolated from the transgenic animals described above.

The invention also includes methods for producing transgenic, non-human animals. For example, the invention includes a method for producing a transgenic, non-human animal that lacks an endogenous daf gene and is capable of expressing a human DAF polypeptide. This method involves (a) providing a transgenic, non-human animal whose germ cells and somatic cells contain a mutation in a daf gene, and (b) introducing a transgene that (i) encodes a human DAF polypeptide, and (ii) is capable of expressing the human polypeptide, into an embryonal cell of the non-human animal.

Another method included in the invention can be used for producing a transgenic, non-human animal that lacks an endogenous age gene and is capable of expressing a human AGE polypeptide. This method involves (a) providing a transgenic, non-human animal whose germ cells and somatic cells contain a mutation in an age gene, and (b) introducing a transgene that (i) encodes a human AGE polypeptide, and (ii) is capable of expressing the human polypeptide, into an embryonal cell of the non-human animal.

Similarly, the invention includes a method for producing a transgenic, non-human animal that lacks an endogenous akt gene and is capable of expressing of expressing a human AKT polypeptide. This method involves (a) providing a transgenic, non-human animal whose germ cells and somatic cells contain a mutation in an akt gene, and (b) introducing a transgene that (i) encodes a human AKT polypeptide, and (ii) is capable of expressing the human polypeptide, into an embryonal cell of the non-human animal.

Another aspect of the invention features a method of screening for a compound that increases the activity of a DAF polypeptide. This method includes (a) exposing a non-human transgenic animal whose germ cells and somatic cells contain a transgene coding for a mutant DAF polypeptide to a candidate compound, and (b) determining the activity of the DAF polypeptide in the transgenic animal. An increase in DAF polypeptide activity, as compared to untreated controls, is indicative of a compound that is capable of increasing DAF polypeptide activity. In preferred embodiments, the compound can be used to treat an impaired glucose tolerance condition or obesity.

In a related aspect, the invention features a method of screening for a compound that decreases the activity of a DAF polypeptide. This method includes (a) exposing a non-human transgenic animal whose germ cells and somatic cells contain a transgene coding for a mutant DAF polypeptide to a candidate compound, and (b) determining the activity of the DAF polypeptide in the transgenic animal. A decrease in DAF polypeptide activity, as compared to untreated controls, is indicative of a compound that is capable of decreasing DAF polypeptide activity. In preferred embodiments, the compound can be used to treat an impaired glucose tolerance condition, obesity, or atherosclerosis. In other preferred embodiments, the compound decreases the activity of DAF-3 or DAF-16.

In another aspect, the invention features a method of screening for a compound that increases the activity of an AGE polypeptide. This method includes (a) exposing a non-human transgenic animal whose germ cells and somatic cells contain a transgene coding for a mutant AGE polypeptide to a candidate compound, and (b) determining the activity of the AGE polypeptide in the transgenic animal. An increase in AGE polypeptide activity, as compared to untreated controls, is indicative of a compound that is capable of increasing AGE polypeptide activity. In preferred embodiments, the compound can be used to treat an impaired glucose tolerance condition, obesity, or atherosclerosis.

In a related aspect, the invention features a method of screening for a compound that decreases the activity of a AGE polypeptide. This method includes (a) exposing a non-human, transgenic animal whose germ cells and somatic cells contain a transgene coding for a mutant AGE polypeptide to a candidate compound, and (b) determining the activity of the AGE polypeptide in the transgenic animal. A decrease in AGE polypeptide activity, as compared to untreated controls, is indicative of a compound that is capable of decreasing AGE polypeptide activity. In preferred embodiments, the compound can be used to treat or delay aging. In another preferred embodiment, the AGE polypeptide is AGE-1.

In another aspect, the invention features a method of screening for a compound that increases the activity of an AKT polypeptide. This method includes (a) exposing a transgenic, non-human animal whose germ cells and somatic cells contain a transgene coding for a mutant AKT polypeptide to a candidate compound, and (b) determining the activity of the AKT polypeptide in the transgenic animal. An increase in AKT polypeptide activity, as compared to untreated controls, is indicative of a compound that is capable of increasing AKT polypeptide activity. In preferred embodiments, the compound can be used to treat an impaired glucose tolerance condition, obesity, or atherosclerosis.

In a related aspect, the invention features a method of screening for a compound that decreases the activity of a AKT polypeptide. This method includes (a) exposing a transgenic, non-human animal whose germ cells and somatic cells contain a transgene coding for a mutant AKT polypeptide to a candidate compound, and (b) determining the activity of the AKT polypeptide in the transgenic animal. A decrease in AKT polypeptide activity, as compared to untreated controls, is indicative of a compound that is capable of decreasing AKT polypeptide activity. In preferred embodiments, the compound can be used to treat or delay aging.

Also included in the invention is a method of screening for a compound that is capable of ameliorating or delaying an impaired glucose tolerance condition. This method involves (a) exposing a transgenic, non-human animal whose germ cells and somatic cells contain a transgene coding for a mutant DAF, AGE, or AKT polypeptide to a candidate compound, and (b) monitoring the blood glucose level of the animal. A compound that promotes maintenance of a physiologically acceptable level of blood glucose in the animal, as compared to untreated controls, is indicative of a compound that is capable of ameliorating or delaying an impaired glucose tolerance condition. In a preferred embodiment, the compound can be used to treat Type II diabetes.

Another method of screening for a compound that is capable of ameliorating or delaying obesity is also included in the invention. This method involves (a) exposing a transgenic, non-human animal whose germ cells and somatic cells contain a transgene coding for a mutant DAF, AGE, or AKT polypeptide to a candidate compound, and (b) monitoring the adipose tissue of the animal. A compound that promotes maintenance of a physiologically acceptable level of adipose tissue in the animal, as compared to untreated controls, is indicative of a compound that is capable of ameliorating or delaying obesity.

A related method of the invention can be used for screening for a compound that is capable of ameliorating or delaying atherosclerosis. This method involves (a) exposing a transgenic, non-human animal whose germ cells and somatic cells contain a transgene coding for a mutant DAF, AGE, or AKT polypeptide to a candidate compound, and (b) monitoring the adipose tissue of the animal. A compound that promotes maintenance of a physiologically acceptable level of adipose tissue in the animal, as compared to untreated controls, is indicative of a compound that is capable of ameliorating or delaying atherosclerosis.

In another aspect, the invention includes a method for identifying a modulatory compound that is capable of decreasing the expression of a daf gene. This method involves (a) providing a cell expressing the daf gene, and (b) contacting the cell with a candidate compound. A decrease in daf expression following contact with the candidate compound identifies a modulatory compound. In preferred embodiments, the compound can be used to treat an impaired glucose tolerance condition or obesity. In other preferred embodiments, the compound is capable of decreasing the expression of DAF-3 or DAF-16. This method can be carried out in an animal, such as a nematode.

In a related aspect, the invention includes a method for the identification of a modulatory compound that is capable of increasing the expression of a daf gene. This method involves (a) providing a cell expressing the daf gene, and (b) contacting the cell with a candidate compound. An increase in daf expression following contact with the candidate compound identifies a modulatory compound. In preferred embodiments, the compound can be used to treat an impaired glucose tolerance condition or obesity. In other preferred embodiments, the compound is capable of increasing expression of DAF-1, DAF-2, DAF-4, DAF-7, DAF-8, DAF-11, or DAF-14. This method can be carried out in an animal, such as a nematode.

In another aspect, the invention includes a method for the identification of a modulatory compound that is capable of increasing the expression of an age-1 gene. This method involves (a) providing a cell expressing the age-1 gene, and (b) contacting the cell with a candidate compound. An increase in age-1 expression following contact with the candidate compound identifies a modulatory compound. In preferred embodiments, the compound is capable of treating an impaired glucose tolerance condition or obesity. This method can be carried out in an animal, such as a nematode.

In another aspect, the invention provides a method for identification of a compound that is capable of ameliorating or delaying an impaired glucose tolerance condition. This method involves (a) providing a dauer larvae including a mutation in a daf gene, and (b) contacting the dauer larvae with a compound. Release from the dauer larval state is an indication that the compound is capable of ameliorating or delaying an impaired glucose tolerance condition. In a preferred embodiment, the dauer larvae carries a daf-2 mutation. In another preferred embodiment, the dauer larvae is from *C. elegans*. In yet another embodiment, the impaired glucose tolerance condition involves obesity or atherosclerosis.

In a related aspect, the invention provides a method for identification of a compound that is capable of ameliorating or delaying an impaired glucose tolerance condition. This method involves (a) providing a dauer larvae including a mutation in an age-1 gene, and (b) contacting the dauer larvae with a compound. Release from the dauer larval state is an indication that the compound is capable of ameliorating or delaying an impaired glucose tolerance condition. In a preferred embodiment, the dauer larvae carries an age-1 mutation. In another preferred embodiment, the dauer larvae is from *C. elegans*. In yet another preferred embodiment, the impaired glucose tolerance condition involves obesity or atherosclerosis.

In another related aspect, the invention provides a method for the identification of a compound that is capable of ameliorating or delaying an impaired glucose tolerance condition. This method involves (a) providing a dauer larvae including a mutation in an akt gene, and (b) contacting the dauer larvae with a compound. Release from the dauer larval state is an indication that the compound is capable of ameliorating or delaying an impaired glucose tolerance condition. In a preferred embodiment, the dauer larvae is from *C. elegans*. In another preferred embodiment, the impaired glucose tolerance condition involves obesity or atherosclerosis.

In another aspect, the invention provides a method for the identification of a compound for ameliorating or delaying an impaired glucose tolerance condition. This method involves (a) combining PIP3 and an AKT polypeptide in the presence and absence of a compound under conditions that allow PIP3:AKT complex formation, (b) identifying a compound that is capable of decreasing the formation of the PIP3:AKT complex, and (c) determining whether the compound identified in step (b) is capable of increasing AKT activity. An increase in AKT kinase activity is taken as an indication of a compound useful for ameliorating or delaying an impaired glucose tolerance condition.

In yet another aspect, the invention provides a method for the identification of a compound for ameliorating or delaying an impaired glucose tolerance condition. This method involves (a) providing a daf-7, daf-3 mutant nematode, (b) expressing in the cells of the nematode a mammalian DAF-3 polypeptide, whereby the nematode forms a dauer larva, and (c) contacting the dauer larva with a compound. A release from the dauer larval state is an indication that the compound is capable of ameliorating or delaying the glucose intolerance condition.

In a further aspect, the invention features a method for the identification of a compound for ameliorating or delaying an impaired glucose tolerance condition. This method involves (a) providing a daf-2, daf-16 mutant nematode, (b) expressing in the cells of the nematode a mammalian DAF-16 polypeptide, whereby the nematode forms a dauer larva, and (c) contacting the dauer larva with a compound. A release from the dauer larval state is an indication that the compound is capable of ameliorating or delaying the glucose intolerance condition.

In yet another aspect, the invention features insulin-like molecules and their use as diagnostic and therapeutic reagents.

As used herein, by a "DAF" polypeptide is meant a polypeptide that functionally complements a *C. elegans* daf mutation and/or that has at least 60%, preferably 75%, and more preferably 90% amino acid sequence identity to a 100 amino acid region (and preferably a conserved domain) of a *C. elegans* DAF polypeptide. Complementation may be assayed in an organism (for example, in a nematode) or in a cell culture system. Complementation may be partial or complete, but must provide a detectable increase in function (as described herein). DAF polypeptides are encoded by "DAF" genes or nucleic acid sequences.

By an "AGE" polypeptide is meant a polypeptide that functionally complements a *C. elegans* age mutation and/or that has at least 60%, preferably 75%, and more preferably 90% amino acid sequence identity to a 100 amino acid region (and preferably a conserved domain) of a *C. elegans* AGE polypeptide. Complementation may be assayed in an organism (for example, in a nematode) or in a cell culture system. Complementation may be partial or complete, but must provide a detectable increase in a known AGE function. AGE polypeptides are encoded by "AGE" genes or nucleic acid sequences.

As used herein, by an "AKT" polypeptide is meant a polypeptide that functionally complements a *C. elegans* akt mutation and/or that possess at least 64% amino acid sequence identity to SEQ ID NO: 60, at least 71% amino acid sequence identity to SEQ ID NO: 61, at least 79% amino acid sequence identity to SEQ ID NO: 62, at least 63% amino acid sequence identity to SEQ ID NO: 63, at least 48% amino acid sequence identity to SEQ ID NO: 64, at least 70% amino acid sequence identity to SEQ ID NO: 65, at least 64% amino acid sequence identity to SEQ ID NO: 66, at least 67% amino acid sequence identity to SEQ ID NO: 67, or a combination thereof. Complementation may be assayed in an organism (for example, in a nematode) or in a cell culture system. Complementation may be partial or complete, but must provide a detectable increase in a known AKT function. AKT polypeptides are encoded by "AKT" genes or nucleic acid sequences.

By a "DAF-2 polypeptide" is meant a polypeptide that complements (as defined above) a *C. elegans* daf-2 mutation and/or that possesses at least 61% amino acid sequence identity to SEQ ID NO: 33, at least 31% amino acid sequence identity to SEQ ID NO: 34, at least 43% amino acid sequence identity to SEQ ID NO: 79, at least 35% amino acid sequence identity to SEQ ID NO: 80, at least 35% amino acid sequence identity to SEQ ID NO: 81, at least 48% amino acid sequence identity to SEQ ID NO: 82, at least 43% amino acid sequence identity to SEQ ID NO: 83, at least 40% amino acid sequence identity to SEQ ID NO: 84, or a combination thereof. Preferably, a DAF-2 polypeptide includes an aspartic acid, a proline, a proline, a serine, an alanine, an aspartic acid, a cysteine, or a proline at amino acid positions corresponding to *C. elegans* DAF-2 amino acids 1252, 1312, 1343, 347, 451, 458, 526, 279, and 348 respectively, or a combination thereof.

By a "DAF-3 polypeptide" is meant a polypeptide that complements (as defined above) a *C. elegans* daf-3 mutation and/or that possesses at least 60% amino acid sequence identity to SEQ ID NO: 35, at least 38% amino acid sequence identity to SEQ ID NO: 36, at least 47% amino acid sequence identity to SEQ ID NO: 85, or a combination thereof. Preferably, a DAF-3 polypeptide includes a proline or a glycine at amino acid positions corresponding to *C. elegans* daf-3 amino acids at positions 200 (proline) and/or 620 (glycine) in FIG. 12A, respectively, or a combination thereof. For example, the polypeptide may include a proline in the motif GRKGFPHV (SEQ ID NO: 322) or a glycine in the motif RIXXIXXG (where X is any amino acid) (SEQ ID NO: 323).

By a "DAF-16 polypeptide" is meant a polypeptide that complements (as defined above) a *C. elegans* daf-16 mutation and/or that possesses at least 71% amino acid sequence identity to SEQ ID NO: 54, at least 35% amino acid sequence identity to SEQ ID NO: 55, at least 65% amino acid sequence identity to SEQ ID NO: 56, at least 53% amino acid sequence identity to SEQ ID NO: 58, or a combination thereof. In addition, a DAF-16 polypeptide preferably includes a serine residue in the conserved motif WKNSIRH (SEQ ID NO: 59).

By a "DAF-7 polypeptide" is meant a polypeptide that complements (as defined above) a *C. elegans* daf-7 mutation and/or that possesses at least 29% amino acid sequence identity to SEQ ID NO: 26, at least 66% amino acid sequence identity to SEQ ID NO: 27, at least 45% amino acid sequence identity to SEQ ID NO: 28, at least 33% amino acid sequence identity to SEQ ID NO: 29, at least 56% amino acid sequence identity to SEQ ID NO: 30, at least 75% sequence identity to SEQ ID No: 86, or a combination thereof. Preferably, a DAF-7 polypeptide includes a proline or a glycine at amino acid positions corresponding to C. elegans daf-7 amino acids 271 and 280, respectively, or a combination thereof.

By a "DAF-8 polypeptide" is meant a polypeptide that complements (as defined above) a C. elegans daf-8 mutation and/or that possesses at least 46% amino acid sequence identity to SEQ ID NO: 23, at least 45% amino acid sequence identity to SEQ ID NO: 24, at least 36% amino acid sequence identity to SEQ ID NO: 25, or a combination thereof.

By an "AGE-1 polypeptide" is meant a polypeptide that complements (as defined above) a C. elegans age-1 mutation (previously known as a daf-23 mutation) and/or that possesses at least 40% amino acid sequence identity to SEQ ID NO: 17, at least 45% amino acid sequence identity to SEQ ID NO: 18, at least 30% amino acid sequence identity to SEQ ID NO: 19, at least 24% amino acid sequence identity to SEQ ID NO: 38, or a combination thereof. Preferably, an AGE-1 polypeptide includes an alanine at amino acid positions corresponding to C. elegans age-1 amino acids 845.

By a "DAF-1 polypeptide" is meant a polypeptide that complements (as defined above) a C. elegans daf-1 mutation and/or that possesses at least 45% amino acid sequence identity to SEQ ID NO: 13, at least 35% amino acid sequence identity to SEQ ID NO: 14, at least 65% amino acid sequence identity to SEQ ID NO: 15, at least 25% amino acid sequence identity to SEQ ID NO: 16, or a combination thereof. Preferably, a DAF-1 polypeptide includes a proline at the amino acid position corresponding to C. elegans DAF-1 amino acid 546.

By a "DAF-4 polypeptide" is meant a polypeptide that complements (as defined above) a C. elegans daf-4 mutation and/or that possesses at least 45% amino acid sequence identity to SEQ ID NO: 20, at least 40% amino acid sequence identity to SEQ ID NO: 21, at least 44% amino acid sequence identity to SEQ ID NO: 22, or a combination thereof.

By a "DAF-11 polypeptide" is meant a polypeptide that complements (as defined above) a C. elegans daf-11 mutation and/or that possesses at least 40% amino acid sequence identity to SEQ ID NO: 75, at least 43% amino acid sequence identity to SEQ ID NO: 76, at least 36% amino acid sequence identity to SEQ ID NO: 77, at least 65% amino acid sequence identity to SEQ ID NO: 78, or a combination thereof.

By a "DAF-12 polypeptide" is meant a polypeptide that complements (as defined above) a C. elegans daf-12 mutation and/or that possesses at least 42% amino acid sequence identity to SEQ ID NO: 72, at least 58% amino acid sequence identity to SEQ ID NO: 73, at least 34% amino acid sequence identity to SEQ ID NO: 74, or a combination thereof.

By a "DAF-14 polypeptide" is meant a polypeptide that complements (as defined above) a C. elegans daf-14 mutation and/or that possesses at least 48% amino acid sequence identity to SEQ ID NO: 68, at least 37% amino acid sequence identity to SEQ ID NO: 69, at least 48% amino acid sequence identity to SEQ ID NO: 70, at least 37% amino acid sequence identity to SEQ ID NO: 71, or a combination thereof.

By a "PTEN" polypeptide is meant a PTEN lipid phosphatase from any animal. Preferably, this animal is a mammal and, most preferably, a human. This polypeptide is also referred to as MMAC1 and TEP1.

By "insulin receptor activity" is meant any activity exhibited by an insulin receptor and measured by either (i) activation of insulin receptor substrate-1 (IRS-1) phosphorylation and recruitment of PI-3 kinase, (ii) activation of glucose transporter (Glut 4) fusion with a cellular membrane and concomitant glucose uptake, or (iii) activation of glycogen and/or fat synthesis and concomitant inhibition of gluconeogenesis or lipolysis or both.

By "insulin receptor related activity" is meant any activity not directly attributable to the insulin receptor but that is measured by an activation of IRS-1 phosphorylation and recruitment of PI3-kinase.

By "IGF-1 receptor activity" is meant any activity exhibited by an insulin-like growth factor-1 receptor and measured by (i) activation of IRS-1 phosphorylation and recruitment of PI-3 kinase, (ii) activation of cell division in NIH3T3 cells (e.g., as described in Gronborg et al., J. Biol. Chem. 268: 23435-23440, 1993), or (iii) activation of bone growth in, for example, the mouse model.

By "SMAD protein" is meant a protein that is capable of coupling to TGF-β type ser/thr receptors. Smad proteins typically contain a smad conserved motif as described by Derynk et al. (Cell 87: 173, 1996). Exemplary smad proteins include, without limitation, DAF-3, MADR-2, MAD, DPC-4, and Sma-2.

By "AKT activity" is meant any activity exhibited by an AKT polypeptide and measured by phosphatidylinositol-regulated increases in serine phosphorylation of GSK-3, DAF-16, AFX, FKHR, or FKHRL1, or activation of non-dauer growth in C. elegans akt mutants.

By "impaired glucose tolerance condition" is meant any condition in which blood sugar levels are inappropriately elevated or lack normal metabolic regulation. Examples of such conditions include, without limitation, Type I diabetes, Type II diabetes, and gestational diabetes, and may be associated with obesity and atherosclerosis.

By "protein" or "polypeptide" is meant any chain of amino acids, regardless of length or post-translational modification (e.g., glycosylation or phosphorylation).

By "substantially pure" is meant a preparation which is at least 60% by weight (dry weight) the compound of interest, e.g., any of the polypeptides of the invention such as the DAF-2, DAF-3, or DAF-16 polypeptides or DAF-2, DAF-3, or DAF-16-specific antibodies. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "isolated DNA" is meant DNA that is not immediately contiguous with both of the coding sequences with which it is immediately contiguous (one on the 5' end and one on the 3' end) in the naturally-occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By a "substantially identical" polypeptide sequence is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein).

Preferably, such a sequence is at least 75%, more preferably 85%, and most preferably 95% identical at the amino acid level to the sequence used for comparison.

Homology is typically measured using sequence analysis software (e.g., Sequence Analysis Software Package of the Genetics Computer Group, University of Wisconsin Biotechnology Center, 1710 University Avenue, Madison, Wis. 53705 or BLAST software available from the National Library of Medicine). Examples of useful software include the programs, Pileup and PrettyBox. Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By a "substantially identical" nucleic acid is meant a nucleic acid sequence which encodes a polypeptide differing only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein). Preferably, the encoded sequence is at least 75%, more preferably 85%, and most preferably 95% identical at the amino acid level to the sequence of comparison. If nucleic acid sequences are compared a "substantially identical" nucleic acid sequence is one which is at least 85%, more preferably 90%, and most preferably 95% identical to the sequence of comparison. The length of nucleic acid sequence comparison will generally be at least 50 nucleotides, preferably at least 60 nucleotides, more preferably at least 75 nucleotides, and most preferably 110 nucleotides. Again, homology is typically measured using sequence analysis software (e.g., Sequence Analysis Software Package of the Genetics Computer Group, University of Wisconsin Biotechnology Center, 1710 University Avenue, Madison, Wis. 53705).

By "positioned for expression" is meant that the DNA molecule is positioned adjacent to a DNA sequence which directs transcription and translation of the sequence (i.e., facilitates the production of any of the polypeptides disclosed herein including, but not limited to, DAF-2, DAF-3, and DAF-16 and any human homolog thereof).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody which recognizes and binds a polypeptide of the invention (e.g., DAF-2, DAF-3, and DAF-16) but which does not substantially recognize and bind other molecules in a sample (e.g., a biological sample) which naturally includes a polypeptide of the invention. An antibody which "specifically binds" such a polypeptide is sufficient to detect protein product in such a biological sample using one or more of the standard immunological techniques available to those in the art (for example, Western blotting or immunoprecipitation).

By "immunological methods" is meant any assay involving antibody-based detection techniques including, without limitation, Western blotting, immunoprecipitation, and direct and competitive ELISA and RIA techniques.

By "means for detecting" is meant any one or a series of components that sufficiently indicate a detection event of interest. Such means involve at least one label that may be assayed or observed, including, without limitation, radioactive, fluorescent, and chemiluminescent labels.

By "hybridization techniques" is meant any detection assay involving specific interactions (based on complementarity) between nucleic acid strands, including DNA-DNA, RNA-RNA, and DNA-RNA interactions. Such hybridization techniques may, if desired, include a PCR amplification step.

By a "modulatory compound", as used herein, is meant any compound capable of either decreasing DAF-3, DAF-16, or DAF-18 (PTEN) expression (i.e., at the level of transcription, translation, or post-translation) or decreasing DAF-3, DAF-16, or DAF-18 (PTEN) protein levels or activity. Also included are compounds capable of either increasing DAF-1, DAF-2, DAF-4, DAF-8, DAF-7, DAF-11, DAF-14, AGE-1, AKT, or PDK1 expression (i.e., at the level of transcription, translation, or post-translation) or increasing DAF-1, DAF-2, DAF-4, DAF-8, DAF-7, DAF-11, DAF-14, AGE-1, AKT, or PDK-1 protein levels or their corresponding activities.

By "complementation" is meant an improvement of a genetic defect or mutation. In one example, complementation of a genetic defect in a daf, age, or akt gene can be carried out by providing the wild-type daf, age, or akt genes, respectively. Complementation is generally accomplished by expressing the wild-type version of the protein in a host cell or animal bearing a mutant or inactive version of the gene.

Other features and advantages of the invention will be apparent from the following detailed description thereof, and from the claims.

DETAILED DESCRIPTION

The drawings will first be described.

DRAWINGS

FIG. 1 shows the genetic and physical map of C. elegans daf-2. The top panel shows the genetic map of daf-2. daf-2 maps on the left arm of chromosome III 11.4 map units to the right of dpy-1 and 1.6 map units to the left of ben-1 (ACeDB). The middle panel shows the physical map of daf-2. daf-2 maps between mgP34 and mgP44 in a region not covered by cosmid clones but covered by YAC Y53G8. Cosmids from the approximate daf-2 genetic location detect RFLPs between C. elegans strains Bristol N2 and Bergerac RC301. mgP31 on cosmid T21A6 is a HindIII RFLP: 5.3 kb in Bristol, 4.5 kb in RC301. mgP33 on cosmid T02B2 is a HindIII RFLP: 9 kb in Bristol, 8 kb in RC301. mgP34 on cosmid R10F2 is an EcoRI RFLP: 4.1 and 2.8 kb in Bristol, 3.6 kb in RC301. mgP44 on cosmid R07G11 is a complex EcoRI RFLP: 2.9 kb, 2.4 kb, 1.9 kb and 1.7 kb in Bristol; 3.6 kb, 2.5 kb and 1.6 kb in RC301. mgP35 on cosmid T10D5 is a StyI RFLP: 5.4 kb in Bristol, 5.8 kb in RC301. mgP32 on cosmid C42B8 is a StyI RFLP: 2.8 kb in Bristol; 2.9 kb in RC301. mgP48 detected with daf-2 probe (nt 1277–2126 and 3747–4650) is a HindIII RFLP: 4.3 kb and 7 kb in Bristol and 4.1 kb and 6.2 kb in RC301. Thirty-one out of thirty-three Dpy-non-Daf recombinants carry the RC301 allele of mgP34 whereas all thirty-three recombinants in this interval carry the RC301 allele of mgP44, mapping daf-2 0.69 map units to the right of mgP34 and to the left of mgP44. Fourteen out of twenty-four Ben-non-Daf recombinants carry the RC301 mgP44 allele whereas all of these recombinants carry the RC301 allele of mgP34, mapping daf-2 0.66 map units to the left of mgP44.

Y53G8 YAC DNA was isolated from CHEF gels as described in Ausubel et al. (*Current Protocols in Molecular Biology*, John Wiley & Sons, New York, N.Y., 1990), labeled, and shown to hybridize to multiple restriction fragments from cosmids bearing mgP34 and mgP44. A probe from the insulin receptor homolog on Y53G8 detects the mgP48 RFLP between N2 and RC301. All thirty-three Dpy-non-Daf and all twenty-four Ben-non-Daf recombinants described above carry the RC301 allele of mgP48, indicating that daf-2 could not be separated from this insulin receptor gene by these fifty-seven recombination events in a thirteen map unit interval.

The bottom panel shows the structure of daf-2 cDNA. The daf-2 cDNA was amplified from a cDNA library constructed according to standard methods by PCR using internal primers derived from the genomic shotgun sequences, vector sequence primers (for 3' end) and an SL1 transspliced leader PCR primer (M. Krause, In: *Methods Cell Biol.*, vol. 48, pp. 483–512, H. F. Epstein and D. C. Shakes, eds., Academic Press, San Diego, Calif., 1995). To isolate a cDNA, pooled plasmid DNA from 106 clones of a 107 clone complexity cDNA library was used as a PCR template. To obtain a daf-2 cDNA 3' end, daf-2 internal primer CGCTACG-GCAAAAAAGTGAA (SEQ ID NO: 1) in the kinase domain and a cloning vector primer CGATGATGAA-GATACCCC (SEQ ID NO: 2) were used in a nested PCR reaction with adjacent internal primers. For the cDNA fragment from the ligand-binding domain to the kinase domain, PCR was carried out with TGATGCGAACGGC-GATCGAT (SEQ ID NO: 3) and ACGCTGGATCATCTA-CATTA (SEQ ID NO: 4) primers. For the daf-2 5' end, SL1 primer GGTTTAATTACCCAAGTTTGAG (SEQ ID NO: 5) and one internal daf-2 primer GCTCACGGGTCACA-CAACGA (SEQ ID NO: 6) were used in a nested PCR reaction with adjacent internal primers. Using PCR to amplify genomic DNA from a set of 20 daf-2 mutants, we searched for daf-2 mutations in a 0.8 kb region of the ligand binding domain and in a 0.9 kb region of the kinase domain. For sequencing the ligand-binding domain PCR primers TGATGCGAACGGCGATCGAT (SEQ ID NO: 7) and TGAGGGCCAACTAAAGAAGAC (SEQ ID NO: 8) were used. In the kinase domain primers CGCTACG-GCAAAAAAGTGAA (SEQ ID NO: 9) and GACGATC-CCGAGGTGAGTAT (SEQ ID NO: 10) were used. The presence of an SL1 spliced leader sequence indicates a full length daf-2 cDNA. The predicted ORF is shown as a box; 5' and 3' UTRs are shown as thick bars. The predicted DAF-2 initiator methionine at base 486 is preceded by an in frame stop codon 63 bases upstream. The predicted DAF-2 stop codon is found at base 5658. No consensus polyadenylation signal was found in the cDNA nor in genomic shotgun sequence #00678, which extends 302 bp further downstream. The initial insulin receptor homolog shotgun sequences are shown as thin bars above the box.

Introns were detected by a combination of in silico genomic and cDNA sequence comparison, and by comparison of PCR products derived from cDNA and genomic DNA templates. The open triangles over a vertical bar indicate positions of the detected exon/intron boundaries. All the intron donor sites have GT consensus and the acceptor sites have AG consensus (Krause, 1995 supra). The triangles without a vertical bar indicate the approximate intron locations determined by comparison of PCR products using genomic DNA or cDNA as a template. Intron lengths were estimated by comparison of the PCR product size using cDNA or genomic DNA templates. Genomic regions corresponding to some of the introns could not be PCR amplified suggesting that these introns are long. The minimum daf-2 gene size based on this analysis is 33 kb.

FIG. 2A shows the predicted *C. elegans* DAF-2 (SEQ ID NO:12) amino acid sequence. The predicted cysteine-rich region (amino acids 207–372) and tyrosine kinase domain (amino acids 1124–1398) are boxed. The signal peptide (amino acids 1–20), proteolysis site (amino acids 806–809), transmembrane domain (amino acids 1062–1085), and PTB binding motif in the juxtamembrane region (NPEY, amino acids 1103–1106) are underlined. Three DAF-2 tyrosine residues, Y1293, Y1296 and Y1297, in the region corresponding to the insulin receptor kinase Y1158 to Y1163 activation loop are likely to be autophosphorylated, based on the predicted similarity between the DAF-2 and insulin receptor phosphorylation targets (FIG. 2B). Another likely target for DAF-2 autophosphorylation is the Y1106 NPEY motif located in the region corresponding to the insulin receptor juxtamembrane region NPEY motif (at Y972), that has been shown to mediate IRS-1 binding via its PTB domain to the insulin receptor (White and Kahn, *J. Biol. Chem.* 269: 1–4, 1994). While DAF-2 bears one YXXM motif implicated in coupling to PI 3-kinase, mammalian IRS-1 and *Drosophila* insulin receptor (Fernandez et al., EMBO J. 14: 3373–3384, 1995) bear multiple YXXM motifs. Although no p85-like adaptor subunit has yet been detected in the *C. elegans* database, the AGE-1 homology to mammalian p110 suggests the existence of a homologous or analogous adaptor (Morris et al., *Nature* 382: 536–539, 1996). In the DAF-2 C-terminal domain, two other tyrosine residues may be autophosphorylated and bound to particular SH2-containing proteins: Y1678 binding to a PLC-g or SHP-2 homolog, and Y1686, perhaps binding to SEM-5 (FIG. 2A) (Songyang et al., *Cell* 72: 767–778, 1993). While mutations in, for example, ras and MAP kinase have not been identified in screens for dauer constitutive or dauer defective mutations, these general signaling pathway proteins may couple to DAF-2 as they couple to insulin signaling in vertebrates (White and Kahn, *J. Biol. Chem.* 269: 1–4, 1994). The predicted phosphotyrosine residues in juxtamembrane region and the kinase domain activation loop are circled. In the extended C-terminal region, predicted phosphotyrosine residues are also circled and SH2-binding sites are underlined (see below).

FIG. 2B shows the cDNA encoding the *C. elegans* DAF-2 (SEQ ID NO:11).

FIG. 2C shows the amino acid comparison of *C. elegans* DAF-2 (SEQ ID NO:106 and 110) to the human insulin receptor (SEQ ID NOS:104 and 108) and human IGF-I receptor (SEQ ID NOS:103 and 107) (shown in parenthesis), and to the *Drosophila* insulin receptor homolog (SEQ ID NOS:105 and 109), with daf-2 and human insulin receptor mutations highlighted. Six daf-2 mutations map in the ligand-binding domain: sa187 (C347S, TGT to AGT), e1368 (S451L, TCA to TTA), e1365 (A458T, GCT to ACT), sa229 (D526N, GAT to AAT), and two mutations in mg43 (C279Y, TGT to TAT and P348L, CCC to CTC). Three daf-2 mutations substitute conserved amino acid residues in the insulin receptor kinase domain: sa219 (D1252N, GAT to AAT), e1391 (P1312L, CCC to CTC), and e1370 (P1343S, CCA to TCA). Darkened residues indicate amino acid identity. Hatched residues indicate amino acid similarity. The percentages under the domains represents the percentage of identity observed between DAF-2 and each receptor. The corresponding BLAST probabilities of DAF-2 random match to each protein is: $6.4 \times 10^{-157}$ (human insulin receptor), $2.7 \times 10^{-156}$ (human IGF-I receptor), $2.1 \times 10^{-153}$ (molluscan InR homolog), $8.3 \times 10^{-153}$ (mosquito InR homolgoue), $1.6 \times 10^{-138}$ (human insulin receptor-related receptor), $1.7 \times 10^{-122}$ (*Drosophila* InR homolog ), $2.0 \times 10^{-108}$ (Hydra InR homolog). DAF-2 is more distant from the next most closely related kinase families: $8.9 \times 10^{-58}$ (v-ros) and $3.0 \times 10^{-51}$ (trkC neurotrophin receptor).

Conserved cysteine residues in the ligand-binding domain (top) are marked with dots. In the kinase domain, active site residues that mediate insulin receptor kinase specificity are marked with stars. All of these residues are homologous in DAF-2. The mutations found in human patients are indicated at the top of the row, and daf-2 allele substitutions are indicated below with allele names. The sequence alignments were done with GCG programs, Pileup and Prettybox, and the identities were calculated with the GCG program, Gap.

FIG. 3 is a photograph showing the metabolic control by *C. elegans* daf-2 and daf-7. The top panel shows low levels of fat accumulation in a wild type L3 animal grown at 25° C. that has been stained with Sudan black. Non-starved animals were fixed in 1% paraformaldehyde in PBS, frozen at −70° C., and freeze-thawed three times. Fixed animals were washed three times in PBS, and then incubated overnight in 1× Sudan black according to standard methods. The next panel shows higher levels of fat accumulation in daf-2(e1370) grown at the non-permissive temperature of 25° C. These animals accumulate fat in both intestinal and hypodermal cells. daf-2(e1370) animals grown at 15° C., the permissive temperature, accumulate low levels of fat, like wild type (data not shown). The next panel shows high fat levels in the intestine and hypodermis of daf-7(e1372) animals grown at 25° C. The bottom panel shows high levels of fat in daf-2(e1370) animals grown at the permissive temperature until the L4 stage and then shifted to the non-permissive temperature. This shows that daf-2 regulates metabolism without entry into the dauer stage.

FIG. 4 is a schematic diagram showing a model of insulin signaling in the *C. elegans* dauer formation pathway. In the absence of dauer pheromone, an insulin-like ligand activates DAF-2, and DAF-7 TGF-β-like signal activates the DAF-1 and DAF-4 receptors. Activated DAF-2 autophosphorylates particular tyrosine residues and recruits signaling molecules, including the PI 3-kinase homolog (a heterodimer of an as yet unidentified p85 homolog and the PI 3-kinase catalytic subunit AGE-1). The AGE-1 PI 3-kinase produces PIP3 second messenger. This second messenger may regulate glucose transport (White and Kahn, 1994 supra), metabolic kinase cascades that include AKT and GSK-3 (Hemmings, *Science* 226:1344–1345, 1984; Jonas et al., *Nature*, 385:343–346, 1997), and transcription and translation of metabolic genes (White and Kahn, 1994, supra). DAF-16 acts downstream of DAF-2 and AGE-1 in this pathway and is negatively regulated by them (Vowels and Thomas, *Genetics*, 130:105–123, 1992; Gottlieb and Ruvkun, *Genetics*, 137:107–110, 1994). While both the DAF-7/TGF-β and DAF-2/insulin signaling pathways converge to control dauer formation, only the DAF-2 pathway controls reproductive phase longevity. This may be due to non-transcriptional outputs of DAF-2 suggested by precedents from insulin receptor signaling. DAF-7 signaling output is predicted to be only transcriptional as described herein.

FIG. 5A shows that *C. elegans* daf-3 was genetically mapped to a region on the X chromosome between aex-3 and unc-1. Cosmid and plasmid clones from the region were assayed for transformation rescue (Mello et al., *EMBO J* 10: 3959–3970,1991). Plasmid pRF4 (rol-6 transformation marker, 100 ng/ml), and cosmids (5–6 ng/ml) were injected into the gonad of daf-7 (e1372); daf-3 (e1376) animals. Transgenic animals were scored for dauer formation at 25° C.; a dauer (i.e., a return to the daf-7 phenotype) indicates rescue of daf-3; clones that rescue daf-3 are boxed. B0217 rescues the daf-3 phenotype; eighteen of nineteen transgenic lines were rescued (~80% dauers). Examination of sequence provided by the *C. elegans* Sequencing Consortium revealed a Smad homologous gene on B0217. A 13 kb subclone of B0217 containing just the Smad also rescues daf-3 (see FIG. 3). No rescue was seen upon injection of other cosmids from the region, B0504 (7 lines tested, <1% rescue) and C05H10 (10 lines tested, <1% rescue). mgDf90 is a deletion that removes all of daf-3.

FIG. 5B shows the structure of the *C. elegans* daf-3 coding region. The top is the exon/intron structure of daf-3; coding exons are filled boxes, non-coding regions are open boxes, and lines are introns. daf-3 cDNAs were isolated according to standard methods. Four cDNAs were sequenced completely; their N-termini are indicated by vertical lines. These three cDNAs contain ~400 bp of 3' UTR, but no poly-A tail; a *C. elegans* consensus poly-adenylation sequence is found 12 bp from the 3' end of the cDNAs. The longest of this cDNA appears full-length, as it contains a methionine codon and the genomic sequence contains no other methionine codon and no putative splice sites upstream before in-frame stop codons. To further characterize the 5' end of daf-3, PCR products from libraries or individual daf-3 cDNAs were sequenced. From DNA isolated from a cDNA library, we amplified a product with a primer to SL1 and to a region in conserved domain I (shown as primer 1). For the individual cDNAs, we amplified with a primer to the cDNA vector and primer 1. These PCR products were sequenced from primer 2 to the 5' end, and we found that there is alternative splicing at the 5' end of daf-3, upstream of the conserved domains. The two alternate splice forms are indicated, and the ends of individual cDNAs are indicated by vertical lines. Note that the second has the trans-spliced leader SL1 that is found at the 5' end of many *C. elegans* cDNAs; thus, this cDNA shows a bonafide 5' end of daf-3.

FIG. 5C shows the protein sequence alignment of *C. elegans* daf-3 DAF-3(SEQ ID NOS:111 and 113) and the closest homolog found to date, human DPC4(SEQ ID NOS:112 and 114), in the Smad conserved domains I and II. Dots indicate gaps introduced to maximize alignment. DAF-3 is 55% identical to DPC4 in domain I and 30% identical in domain II. daf-3(mg125) and daf-3(mg132) mutations are indicated by boldface and underline. The Smad mutational hotspot is underlined. In addition to mg125 and mg132, seven other daf-3 alleles were sequenced in the hotspot; none of them contains a mutation. Alleles sequenced were mg91, mg93, mg105, mg121, mg126, mg133 (isolated by A. Koweek and G. Patterson, unpublished) and sa205.

FIGS. 6A–6G is a panel of photographs showing C. elegans DAF-3 and DAF-4 expression. These photographs show GFP fluorescence, paired with DAPI fluorescence or Nomarski optics photographs, as marked. All DAF-3 photographs show animals with the second plasmid from FIG. 6A illustrates DAF-3/GFP head expression in an L1 animal. FIG. 6B illustrates DAF-3/GFP expression in the ventral nerve cord of an adult animal. L1 animals demonstrated similar expression patterns. FIG. 6C illustrates DAF-3/GFP expression in the intestine of an L1 animal. FIG. 6D illustrates DAF-3/GFP expression in the distal tip cell of an L4 animal. FIG. 6E illustrates DAF-3/GFP expression in an embryo with approximately 200 nuclei. FIG. 6F illustrates DAF-4/GFP expression in the head of an L1 animal. FIG. 6G illustrates DAF-4/GFP expression in the dorsal nerve cord and ventral nerve cord of an L4 animal.

FIG. 7 is a table that shows the rescuing ability and suppression of C. elegans daf-7 by daf-3 plasmids. The solid boxes represent the Smad conserved domains I and II of daf-3; the stippled boxes represent green fluorescent protein (GFP). For all experiments shown, daf-3 plasmids were injected at a concentration of 10 ng/ml, and the pRF4 injection marker was injected at a concentration of 90 ng/ml. To score dauer formation, transgenic adult animals were allowed to lay eggs on plates for several hours at room temperature and were then removed. The plates were scored after two days at 25° C. The rescue experiment shows the rescue of daf-7(m62); daf-3(e1376) by each of the fusion proteins. Failure to rescue results in rolling nondauers, while rescue of daf-3 results in rolling dauers (the daf-7 phenotype). The control is an array with the pRF4 transformation marker and a non-rescuing cosmid. For each construct, four or more lines were measured in two separate experiments. To measure suppression of daf-7, transgenic arrays were crossed into daf-7 (for plasmids 1 and 3), or produced by injecting directly into daf-7 (for plasmid 2). Transgenic (rolling) animals were scored for suppression of daf-7 (=nondauers) or failure to suppress daf-7 (=dauers). The controls are two array strains with the pRF4 marker and an unrelated GFP expressing transgene.

FIG. 8A is a photographs showing that DAF-3/GFP is associated with metaphase chromosomes. Fixed L1 animals were immunostained with anti-GFP antibody and anti-α-tublin antibody. DNA was visualized using DAPI staining.

FIG. 8B is a photograph showing that a truncated C. elegans daf-3/GFP protein is predominantly nuclear. Wild-type animals were injected with the truncated construct shown in FIG. 7 at a concentration of 10 ng/ml. The pRF4 transformation marker was injected at 100 ng/ml. The photograph shows a late L1 or early L2 animal, and daf-3 is predominantly nuclear. The clear spot in the center of some of the nuclei is the nucleolus, which has no daf-3/GFP. All cells in these animals have predominantly nuclear daf-3/GFP, including the ventral cord neurons, intestinal cells, and distal tip cell (all shown), as well as head and tail neurons and hypodermal cells.

FIGS. 9A and 9B show models for the role of the C. elegans daf-3/DAF-8/DAF-14 Smad proteins in dauer formation. FIG. 9A shows dauer reproductive growth induction. FIG. 9B shows reproductive dauer growth induction.

FIGS. 11A–11C show the cDNA sequences of the differentially spliced C. elegans daf-3 transcripts (SEQ ID NOS: 39, 52, and 53).

FIGS. 12A–12C show the amino acid sequences of the C. elegans DAF-3 polypeptide isoforms (SEQ ID NOS: 40–42).

FIGS. 13A and 13B show the cDNA sequence of the differentially spliced C. elegans daf-16 transcripts (SEQ ID NOS: 43 and 44).

FIGS. 14A and 14B show the amino acid sequences of the C. elegans DAF-16 polypeptide isoforms (SEQ ID NOS: 45 and 46).

FIG. 15 shows the cDNA sequence of the C. elegans age-1 gene (SEQ ID NO: 47).

FIG. 16 shows the amino acid sequence of the C. elegans AGE-1 polypeptide (SEQ ID NO: 48).

FIG. 21A is an illustration showing that human FKHR (SEQ ID NO:57), FKHRL1 (SEQ ID NO:330), and AFX (SEQ ID NO:331) are the closest relatives to DAF-16 (SEQ ID NO:45). Note that the differentially spliced DAF-15 forkhead domain (DAF-16b) (SEQ ID NO:329) is less homologous.

FIG. 25 is an illustration showing the comparison of C. elegans AKT with mammalian AKT (SEQ ID NOs: 87–102 and 327–328).

FIG. 28 is a graph illustrating the homology of C. elegans insulin-like molecules (SEQ ID NOs:117–124) with human insulin (SEQ ID NO:125) and a consensus motif (SEQ ID NO:324).

FIG. 29 is a graph illustrating a PRETTYBOX analysis of insulin superfamily members (SEQ ID NOS: 126–153).

Figure 31:
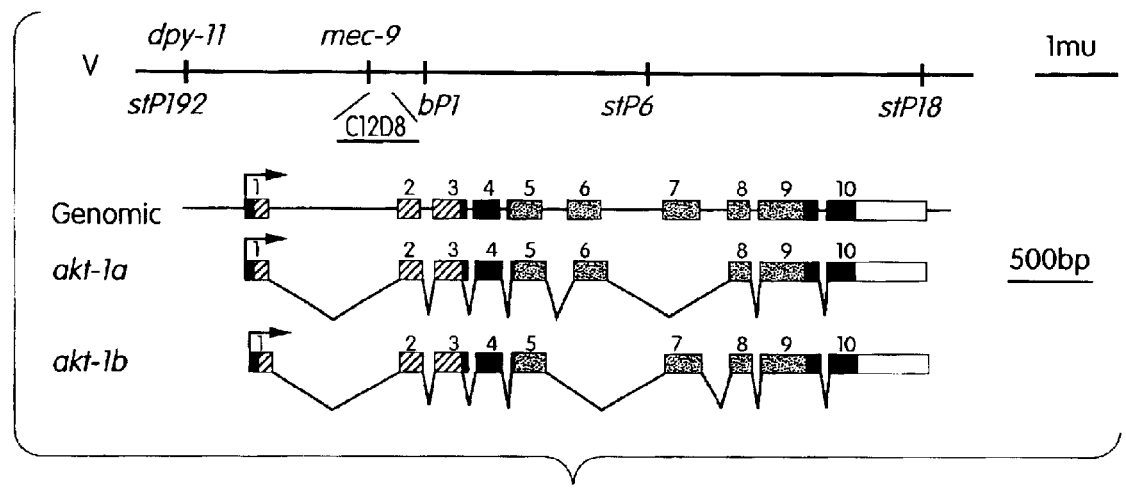

FIG. 31 is a diagram illustrating the akt-1 region. On the top is shown the genetic and physical map of akt-1. akt-1 is contained on cosmid C12D8. Shown on the bottom is the exon/intron structure of akt-1. Coding regions are filled boxes, non-coding regions are open boxes, and introns are lines. The pleckstrin homology domain is indicated by hatched boxes (Musacchio et al., Trends Biochem. Sci. 18:343–348, 1993). The kinase domain is indicated in gray (Hanks and Hunter, in The Protein Kinase Facts Book Protein-Serine Kinases, eds. Hardie, G. & Hanks, S., Academic Press, Inc., San Diego, Calif., pp. 7–47, 1995). akt-1a gene structure was confirmed by sequencing of cDNAs. akt-1b gene structure was deduced based on partial cDNA sequence that confirmed the exon 5 to exon 7 splice and 3'UTR only.

Figure 32:
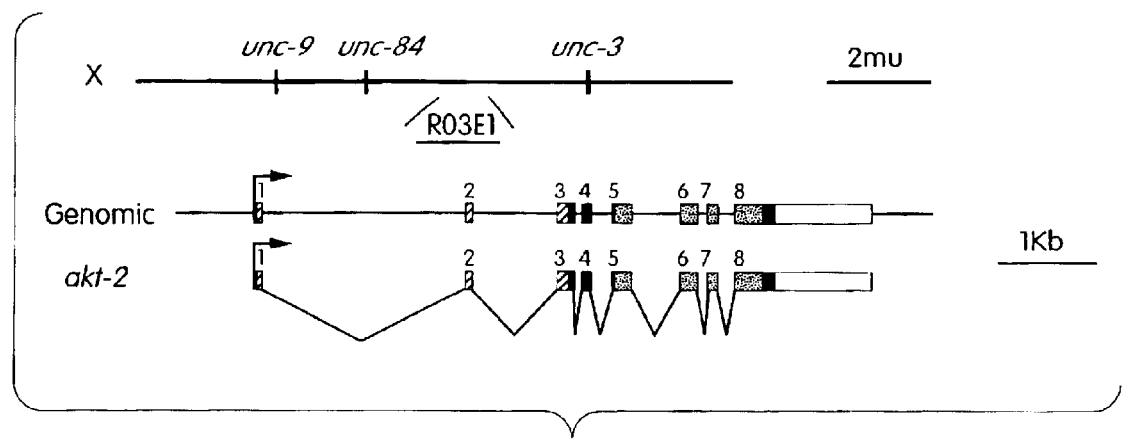

FIG. 32 is a diagram illustrating the akt-2 region. On the top is shown the genetic and physical maps of the akt-2 region. akt-2 is contained on cosmid R03E1. On the bottom is shown the exon/intron structure of akt-2. All symbols are as in FIG. 31. Gene structure was deduced by sequencing of a cDNA which confirmed exons 2–8 and the 3'UTR; Genefinder (Univ. of WA) predicts exon 1.

Figure 33:
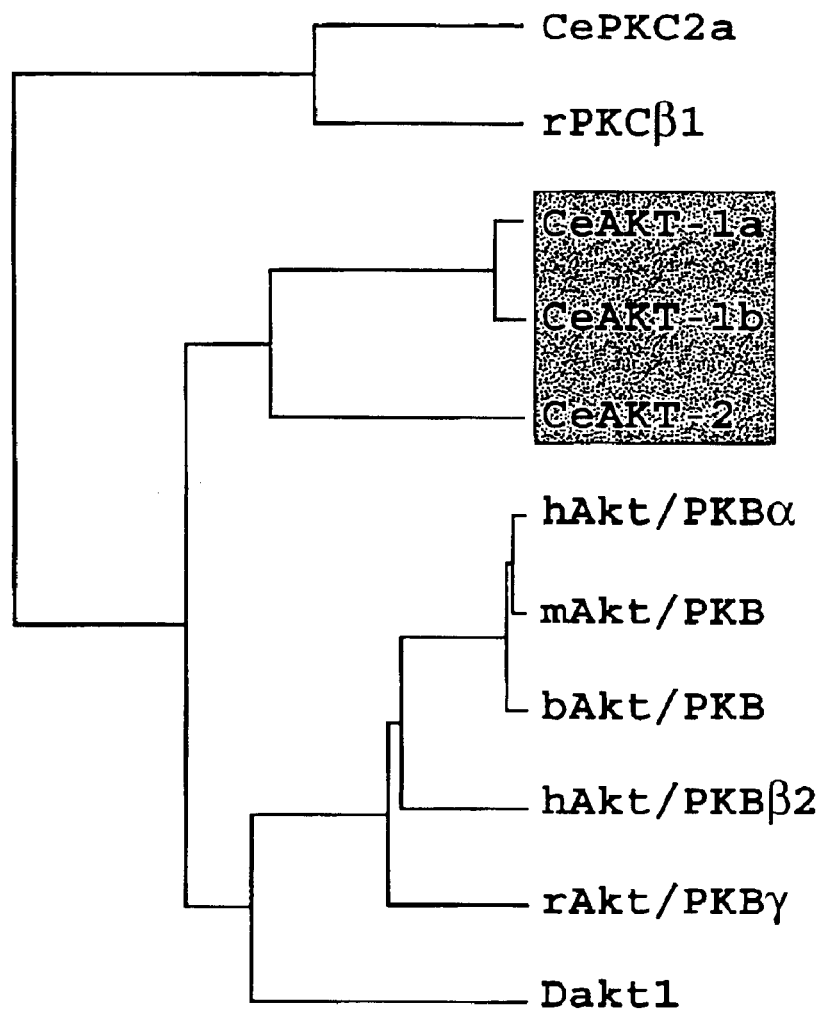

FIG. 33 is a graph illustrating a dendogram of Akt/PKB and PKC protein kinase families. Pileup (GCG) was used to align the entire coding sequences of the indicated proteins. C. elegans proteins are indicated by "Ce," rat by "r," human by "h," mouse by "m," bovine by "b," and D. melanogaster by "D." The accession numbers for the proteins used in the Pileup are contained in parentheses: CePKC2a(U82935), rPKCβ1(M19007), hAkt/PKBα(M63167), mAkt/PKB (M94335), bAkt/PKB(X61036), hAkt/PKBβ2(M95936), rAkt/PKBγ(D49836), Dakt1(Z26242). To anchor the tree, rPKCβ1 (the closest non-Akt/PKB homolog to both akt-1a and hAkt/PKBα), and CePKC2a (the closest C. elegans homolog to rPKCβ1) were included in the Pileup. The Akt/PKB homologs described in this report are indicated by the gray box.

FIG. 34 is a graph illustrating a PILEUP (GCG) analysis of AKT-1a (SEQ ID NO: 154), AKT-1b (SEQ ID NO: 155), AKT-2 (SEQ ID NO: 156), and human Akt/PKBα (M63167) (SEQ ID NO: 157). Identical residues are indicated by dots, gaps introduced in order to align the sequence are indicated by dashes. The pleckstrin homology domain (Musacchio et al., Trends Biochem. Sci. 18:343–348, 1993) is indicated by the N-terminal gray shaded areas, the kinase domain (Hanks and Hunter, in The Protein Kinase Facts Book Protein-Serine Kinases, eds. Hardie, G. & Hanks, S., Academic Press, Inc., San Diego, Calif., pp. 7–47, 1995) is indicated by the C-terminal gray shaded areas. The mg144 Ala183Thr substitution is indicated as a T above the AKT-1a sequence. The Akt-1 and AKT-2 phosphorylation sites that correspond to the hAkt/PKBα Thr308 and Ser473 phosphorylation sites (Alessi et al., EMBO J. 15:6541–6551, 1996) are indicated as dots above the amino acid residue that is phosphorylated.

FIGS. 35A and 35B show the genomic sequence of pdk-1(SEQ ID NO: 158).

FIG. 36 shows the amino acid sequence of pdk-1a (SEQ ID NO: 159).

FIG. 37 shows the amino acid sequence of pdk-1b (SEQ ID NO: 160).

Figure 38A:
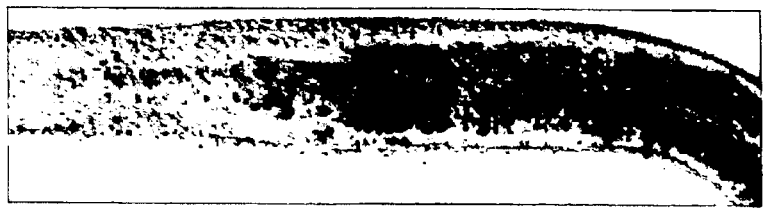
Figure 38B:
Figure 38C:
Figure 38D:
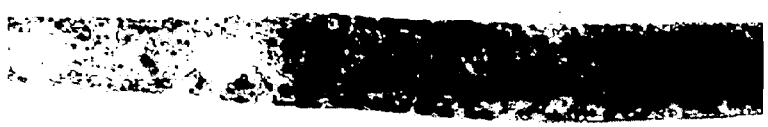
Figure 38E:
Figure 38F:

FIGS. 38A–38F show metabolic control by age-1 and daf-18. Fat accumulation was assayed by Sudan Black staining in hermaphrodites grown at 20° C. The animal in FIG. 38E is a dauer larva, whereas FIGS. 38A–D and F are comparable reproductive larval stage 4 animals. FIG. 38A shows a wild type (Bristol N2) animal. FIG. 38B shows a daf-18(e1375) animal. FIG. 38C shows an age-1(mg44)/mnC1 animal. This L4 stage larva has both maternal and zygotic contributions of age-1. FIG. 38D shows an age-1 (mg44) animal. This L4 stage larva is a homozygote from an age-1(mg44)/mnC1 parent and has a maternal, but not zygotic, contribution of age-1. This maternal contribution of age-1 is sufficient to allow reproductive development, but the animal accumulates larger amounts of fat than the wild type or the zygotically rescued age-1 mutant. FIG. 38E shows an age-1(mg44) animal. This dauer larva is a progeny of a maternally rescued age-1(mg44) animal. The lack of maternal and zygotic contribution of age-1 causes this animal to develop as a dauer and accumulate fat. FIG. 38F shows an age-1(mg44); daf-18(e1375) animal. This L4 stage larva lacks both a maternal and zygotic contribution of age-1, but does not develop into a dauer due to the suppression by the daf-18 mutation. The daf-18 mutation also suppresses the accumulation of fat phenotype of the age-1 null mutant.

FIGS. 39A and 39B illustrate that daf-19 encodes a homologue of PTEN (MMAC/TEP1). FIG. 39A shows the exon/intron structure of DAF-18, including the nucleic acid sequence (SEQ ID NO:327) that encodes amino acids, 570–578 (SEQ ID NO:306) and the nucleic acids (SEQ ID NO:328) that encode amino acids 579–589 (SEQ ID NO:327). The phosphatase domain is indicated in gray. The bottom of this figure indicates that daf-18(e1375) has a 30 base pair insertion in the fourth exon. 13 base pairs (shaded) are duplicated along with two smaller segments of the repeat (thick bars). This mutation introduces a premature stop codon (*) FIG. 39B shows an alignment of the phosphatase domains of DAF-18 and PTEN (GeneBank accession U93051) (SEQ ID NO:308 and 309) Pileup (GCG) was used to align the entire coding sequence. The phosphatase domain is shown with identical amino acids shaded. The probable active site Cys-(X)$_5$-Arg sequence is indicated with a bar.

FIGS. 40A and 40B show the amino acid and nucleic acid sequences of the C. elegans daf-18 gene (SEQ ID 310 and 311).

Figure 41:
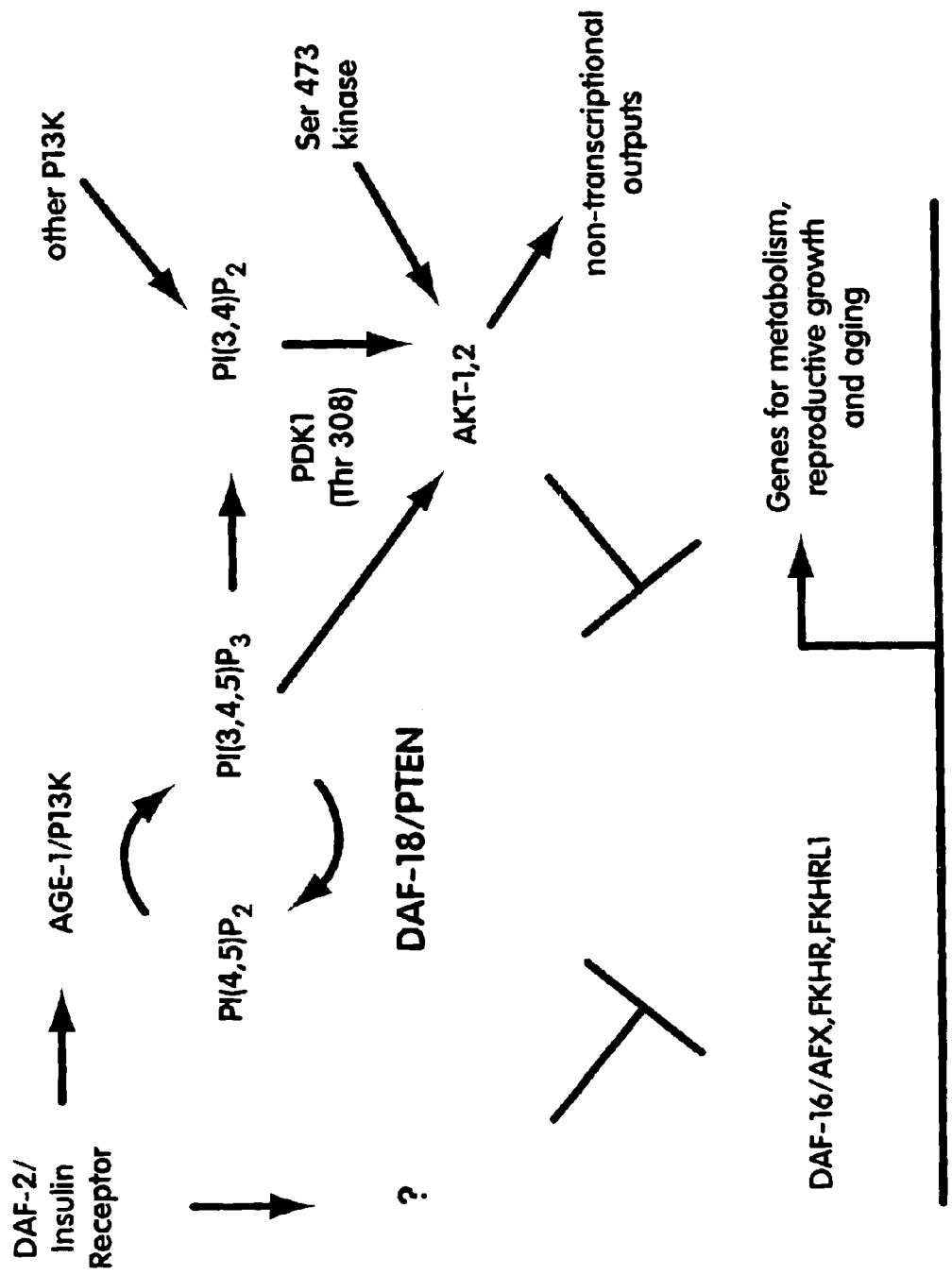

FIG. 41 illustrates a model for the regulation of metabolism and dauer arrest by insulin receptor-like signaling. DAF-2 insulin receptor-like activates AGE-1 PI3K to generate PIP$_3$ and PI(3,4)P$_2$. PIP$_3$ and PI(3,4)P$_2$ may activate AKT-1 and AKT-2 directly by binding to the PH domain and indirectly by regulating PDK1-mediated phosophorylation of the threonine 308 equivalent site. In addition, AKT-1 may be regulated by phosphorylation at the serine 473 equivalent (AKT-2 lacks this site). DAF-18 PTEN limits AGE-1 PI3K signals by dephosphorylating PIP$_3$ and/or PI(3,4)P$_2$. In the absence of AGE-1 signals, loss of DAF-18 allows an alternative source of PI(3,4)P$_2$ and PIP$_3$ to accumulate and activate AKT-1 and AKT-2. AKT-1/AKT-2 signals converge with an additional signaling pathway from the DAF-2 receptor to regulate the DAF-16 Fork head transcription factor. DAF-16 responsive genes control metabolism, reproductive growth, and lifespan.

FIG. 42 shows the C. elegans cod-5 nucleic acid and amino acid sequences (SEQ ID NOs: 312 and 313).

FIG. 43 shows the C. elegans cod-5 knockout cDNA and amino acid sequences (SEQ ID NOs:314 and 315).

Figure 44A:
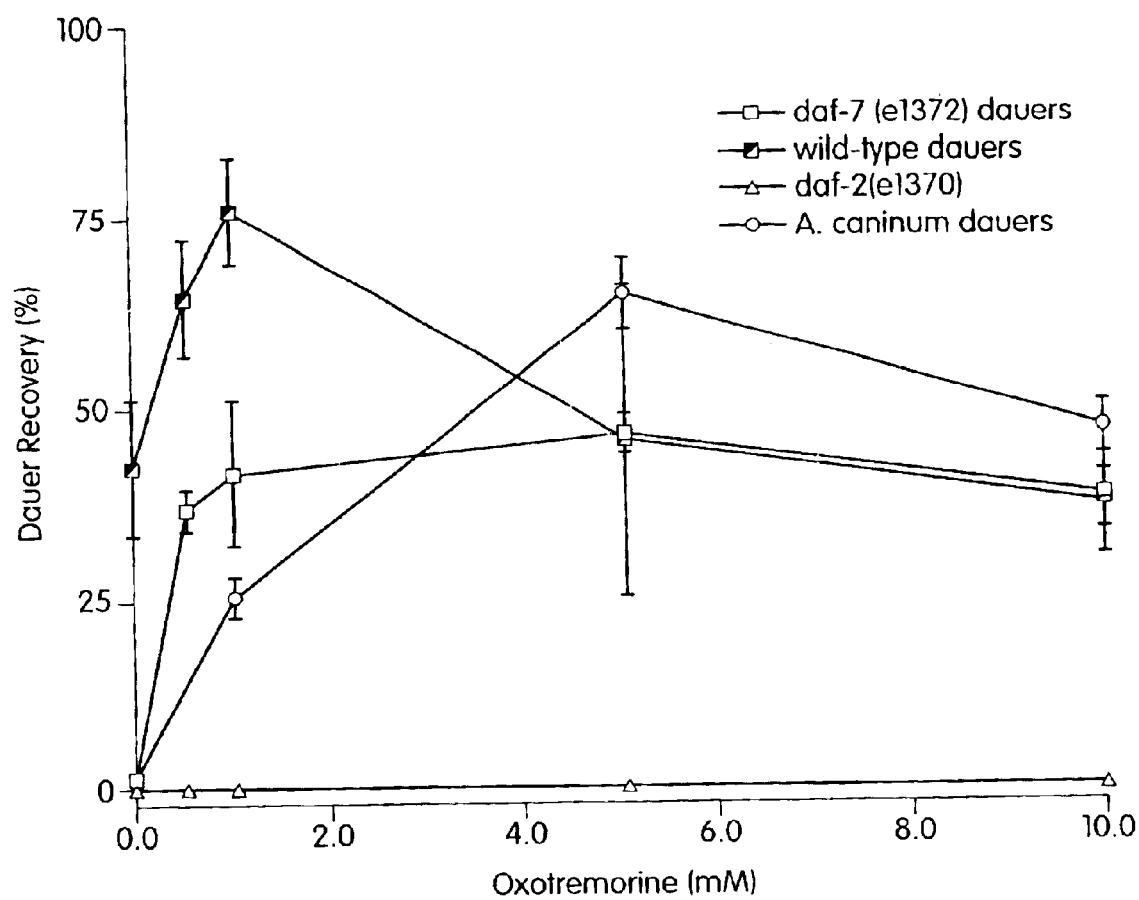
Figure 44B:
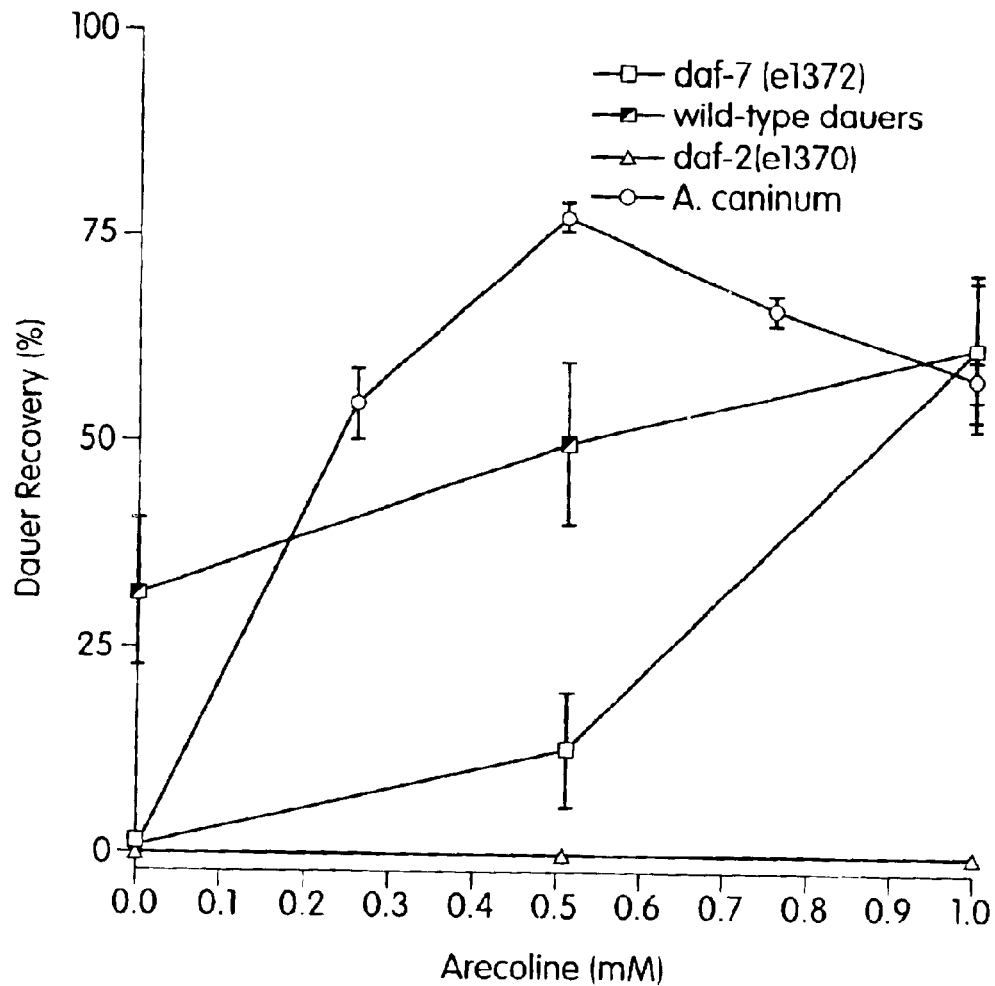
Figure 44C:
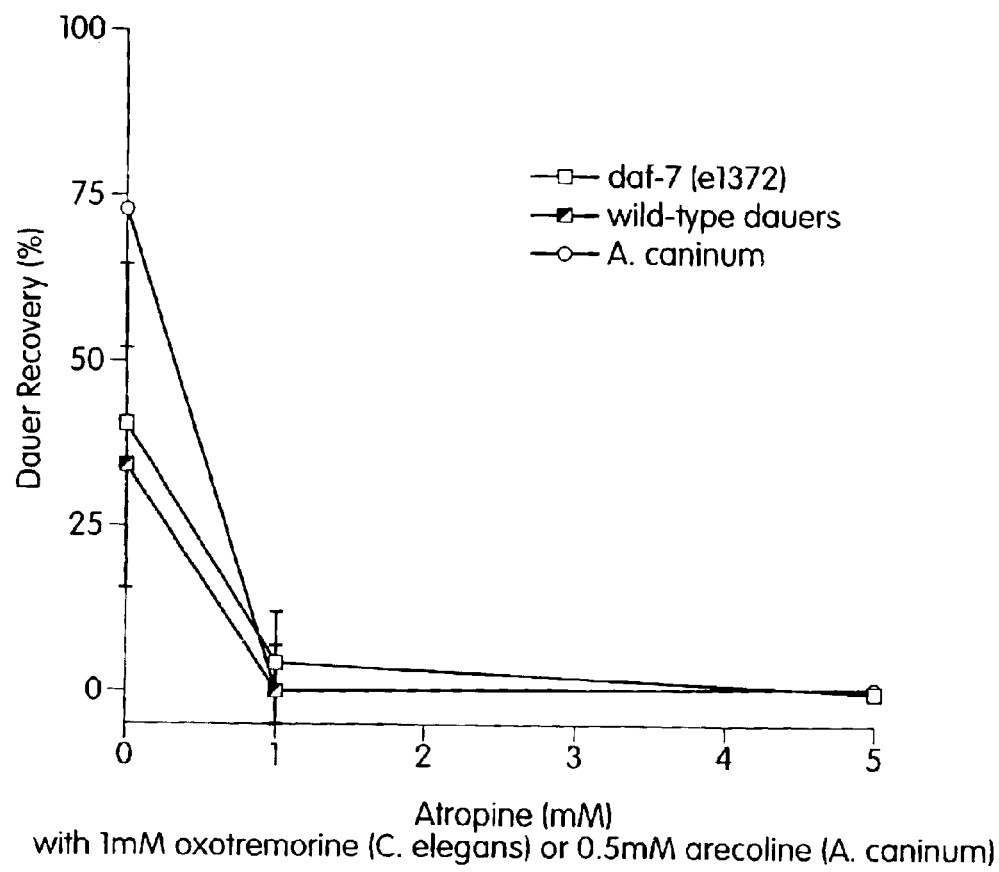

FIGS. 44A, 44B, and 44C show the effect of muscarinic agonists and an antagonist on dauer recovery in C. elegans and A. caninum. In FIG. 44A, oxotremorine, a synthetic muscarinic agonist, promotes dauer recovery in both C. elegans and A. caninum. Note that daf-2(e1370) fails to recover at all concentrations. In FIG. 44B, arecoline, a natural muscarinic agonist, promotes dauer recovery in both C. elegans and A. caninum. Note that daf-2(e1370) fails to recover at all concentrations. FIG. 44C shows that atropine can specifically inhibit the muscarinic agonist-induced response. In C. elegans, at 1 mM oxotremorine, as the concentration of atropine, a muscarinic antagonist, is increased, dauer recovery is completely inhibited. Similarly, in A. caninum larvae, arecoline and increasing amounts of atropine cause dauer recovery to be completely inhibited.

Figure 45A:
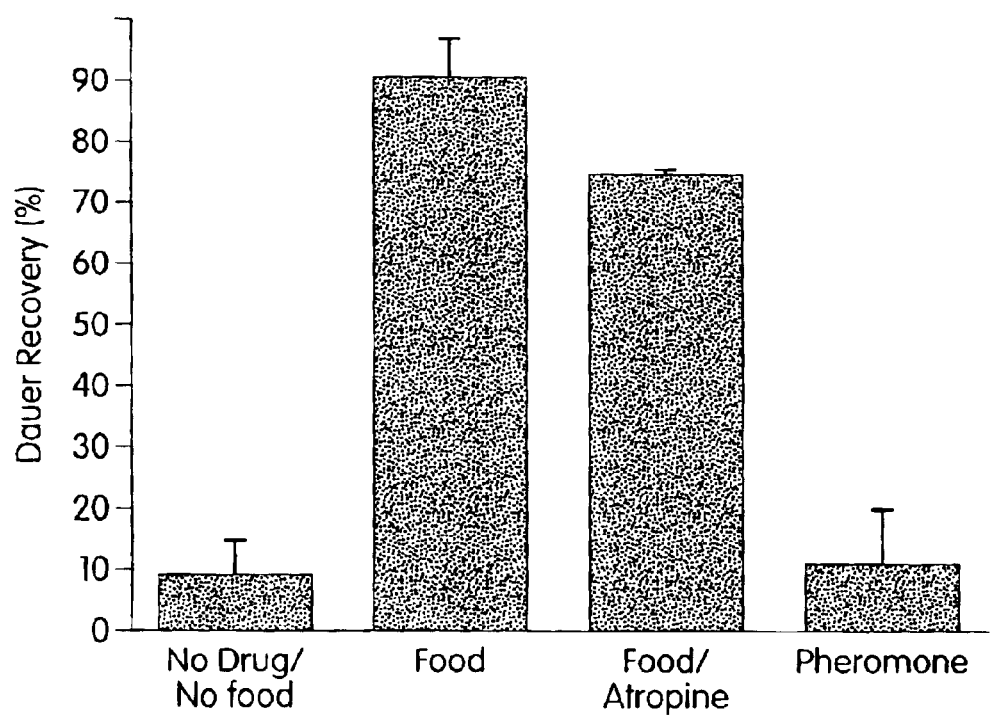
Figure 45B:
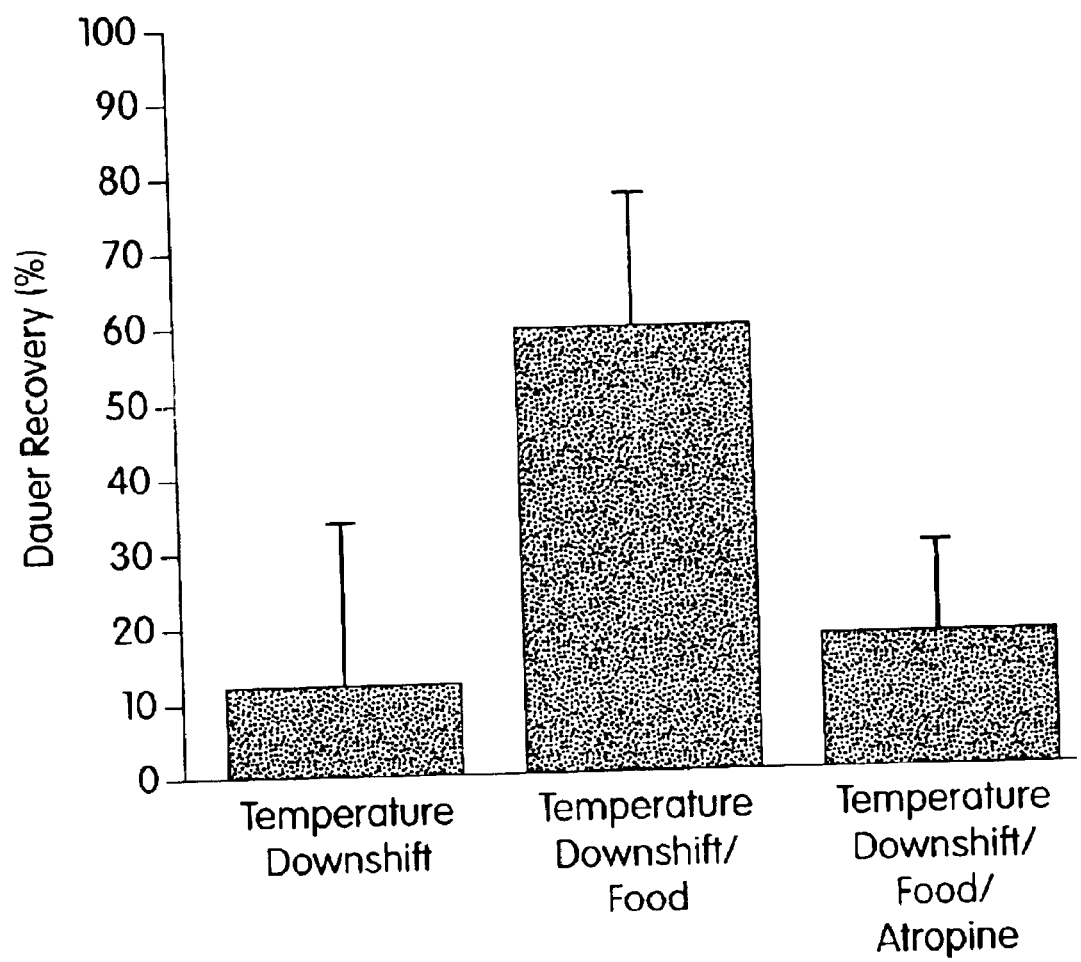

FIGS. 45A and 45B show that atropine specifically inhibits dauer recovery in C. elegans and A. caninum. In FIG.

45A, wild-type N2 dauers were placed on plates containing either bacterial food; no bacteria and no pheromone; bacteria and 1 mM atropine; or pheromone at 25 degrees. 42 hours later, the plates were scored for the presence of dauers and reproductive L4/adults. With no food and no pheromone, 100% of the animals remained arrested at the dauer stage (n>280). Addition of food caused efficient dauer recovery at 25 degrees. Dauers placed on plates with food recovered efficiently, with less than 1% remaining arrested at the dauer stage (n>1000). Addition of 1 mM atropine in the presence of food inhibited dauer recovery: 82% remained arrested at the dauer stage (n=1432). 80% of the animals maintained on plates with pheromone but no food (n=505) remained arrested at the dauer stage. The pheromone preparation contained bacterial contaminants that may have been used as a food source. In *A. caninum* incubated with 10% serum and 25 mM GSM, 9% of the infective larvae remained as dauers and did not resume feeding. Addition of atropine (0.5 mM) to the serum and GSM completely inhibited recovery of *A. caninum* L3 and no worms resumed feeding. In FIG. 45B, daf-2(e1370) and daf-7(e1372) dauers were placed onto plates at 15 degrees. Animals were scored for the presence of dauers and reproductive adults two days after food was added to the plate. Bacterial food was added after temperature downshift failed to induce dauer recovery in daf-2 (e1370) (n=140) and daf-7(e1372) (n=36). Only 21% of the daf-2(e1370) (n=509) and 21% of the daf-7(e1372) (n=112) dauer larvae on plates at the lower temperature with food remained as dauers after two days. Atropine at 1 mM completely inhibited dauer recovery on daf-2(e1370) (n=205) and daf-7(e1372) (n=166) dauers on plates at 15 degrees in the presence of food.

Figure 46:
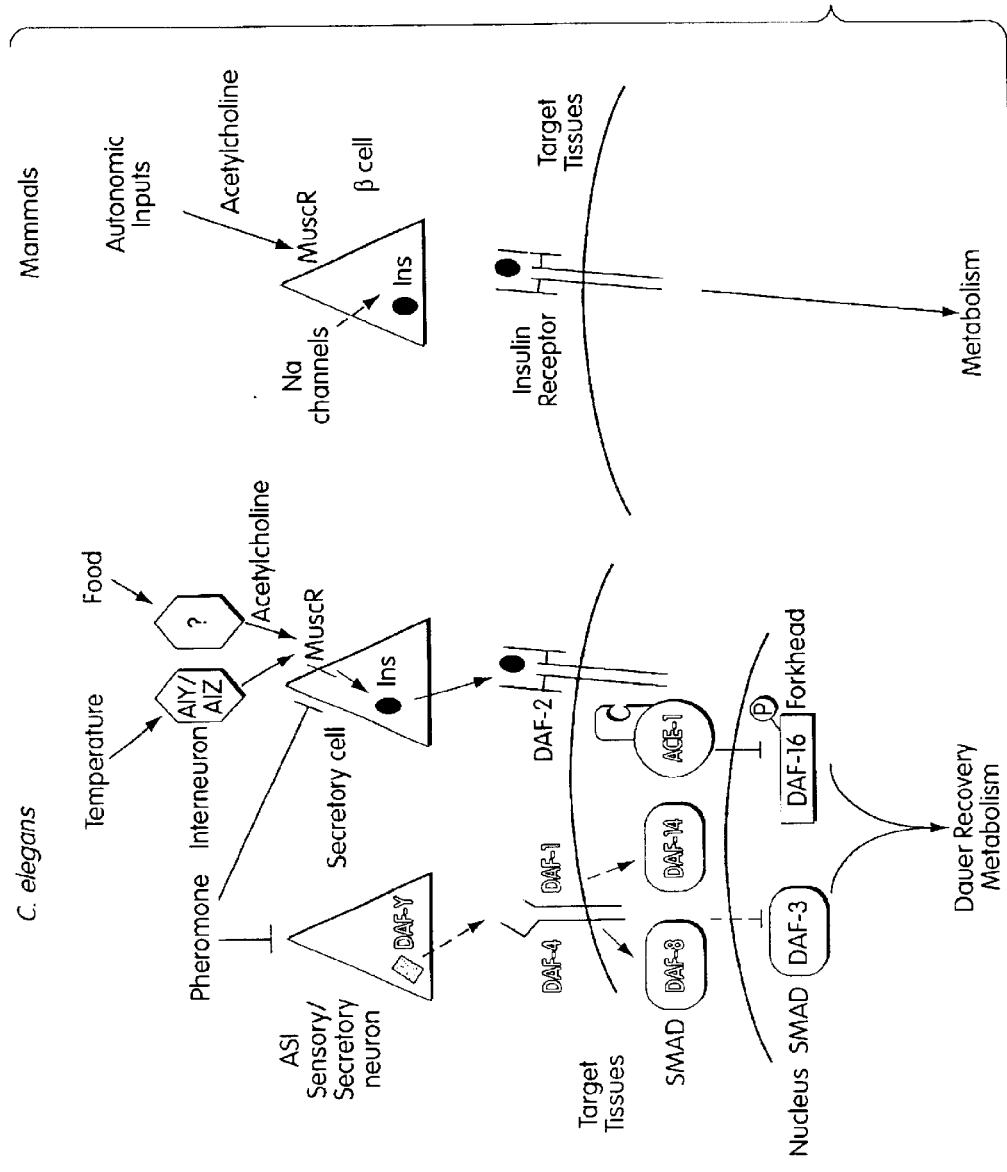

FIG. 46 shows a model for cholinergic input induction of dauer recovery. In dauer pheromone or in a daf-7 mutant, the DAF-7 TGF-β ligand is not produced by the ASI sensory/secretory neuron. Therefore, there is no activation of the DAF-1 and DAF-4 TGF-β receptors or downstream DAF-8 and DAF-14Smad proteins, and this results in high DAF-3 Smad activity in target tissues. In pheromone without muscarinic agonists, no insulin like signal is released, causing a lack of DAF-16 regulation, which in combination with unregulated DAF-3 induces dauer arrest. Under these conditions, muscarinic stimulation causes release of an insulin-like DAF-2 ligand which stimulates the DAF-2/AGE-1 signaling pathway to DAF-16 activation in target tissues. Since daf-7 mutants can recover in muscarinic agonists, the TGF-β signaling pathway is not required for dauer recovery.

Under normal conditions of dauer recovery upon release from pheromone and addition of food and low temperature, these conditions may cause release of acetylcholine, either through the temperature or food pathways, which binds to the muscarinic receptor on the insulin-like signaling cell. Binding of acetylcholine to the receptor causes an increase in insulin release. Temperature may be coupled via the interneurons AIY and AIZ to the DAF-2 insulin-like signaling pathway, rather than the TGF-β signaling pathway, because mutations in the thermoregulatory gene ttx-3 can suppress mutations in daf-7 and not mutations in daf-2.

FIGS. 47A and 47B show the nucleic acid and amino acid sequences of a human DAF-7 homologue (SEQ ID NOs: 316 and 317).

The DAF-2 Insulin Receptor Family Member Regulates Longevity and Diapause in *C. elegans*

Arrest at the *C. elegans* dauer stage is normally triggered by a dauer-inducing pheromone detected by sensory neurons which signal via a complex pathway to target tissues that are remodeled and metabolically shifted such as the germ line, intestine, and ectoderm (Riddle, In: *Caenorhabditis elegans* II, D. Riddle, T. Blumenthal, B. Meyer, J. Priess, eds., Cold Spring Harbor Laboratory, Cold Spring Harbor, N.Y., 1997, pp. 739–768. Kenyon, op cit., pp. 791–813.). Genetic epistasis analysis of daf mutants that arrest at the dauer stage or enter the reproductive life cycle independent of pheromone regulation has revealed parallel genetic pathways that regulate distinct aspects of the dauer metamorphosis (Vowels and Thomas, *Genetics* 130: 105–123, 1992; Gottlieb and Ruvkun, *Genetics* 137: 107–120, 1994). The pathway that includes daf-2 is unique in that it controls both reproductive development and normal senescence: daf-2 mutant animals arrest development at the dauer larval stage and have dramatically increased longevity (Table I) (Riddle, In: *Caenorhabditis elegans* II, D. Riddle, T. Blumenthal, B. Meyer, J. Priess, eds., Cold Spring Harbor Laboratory, Cold Spring Harbor, N.Y., 1997, pp. 739–768; Kenyon, op cit., pp. 791–813; Vowels and Thomas, Genetics 130: 105–123, 1992; Gottlieb and Ruvkun, Genetics 137: 107–120, 1994; Larsen et al., Genetics 139: 1567–1583, 1995; Kenyon et al., Nature 366: 461–464, 1993; Dorman et al., Genetics 141: 1399–1406, 1995).

Table I shows the percentage of dauer formation of daf-2 alleles and the associated mutations. Eggs from animals grown at 15° C. (day 0) were incubated at 15, 20, or 25° C. Numbers in parenthesis are animals counted. Numbers of wild-type animals and dauers were counted on day 3 (20° C. and 25° C.) or day 5 (15° C.). Most of the dauers marked with stars recovered by day 4 (sa229 at 25° C.) or by day 8 (sa229) and sa219 at 15° C., e1368 and sg219 at 20° C., and e1365 and el368 at 25° C.). mg43 was studied as follows: dpy-1(el)daf-2(mg43); SDP3 animals were grown at 20° C. until the young adult stage. Eggs from five adults were laid at 15° C. or 20° C. and grown at the same temperatures. Numbers of Dpy-Daf animal and Dpy-non-Daf animals were counted on day 3 (20° C.) or day 5 (15° C.). Sg187 and sg229 were also studied by Malone and Thomas (*Genetics* 136:879–886, 1994).

TABLE I

Percentage of dauer formation of daf-2 alleles

| Region | Allele | mutation | % dauer formation 15° C. | 20° C. | 25° C. |
|---|---|---|---|---|---|
| cys-rich | mg43 | C279Y & P348L | 100.0(215) | 100.0(245) | n.d. |
| ligand-binding | sa187 | C347S | 0.4(461) | 98.7(224) | 100(910) |
| | e1368 | S451L | 0.0(328) | 4.5*(418) | 99.7*(698) |
| | e1365 | A458T | 0.0(450) | 0.0(461) | 99.4*(814) |
| | sa229 | D526N | 3.4*(234) | n.d. | 22.1*(420) |
| | sa219 | D1252N | 10.0*(460) | 99.7*(396) | 100(514) |
| kinase | e1391 | P1312L | 3.3(332) | 100(323) | 100(322) |
| | e1370 | P1343S | 0.0(520) | 0.0(188) | 100(635) |

Figure 1:
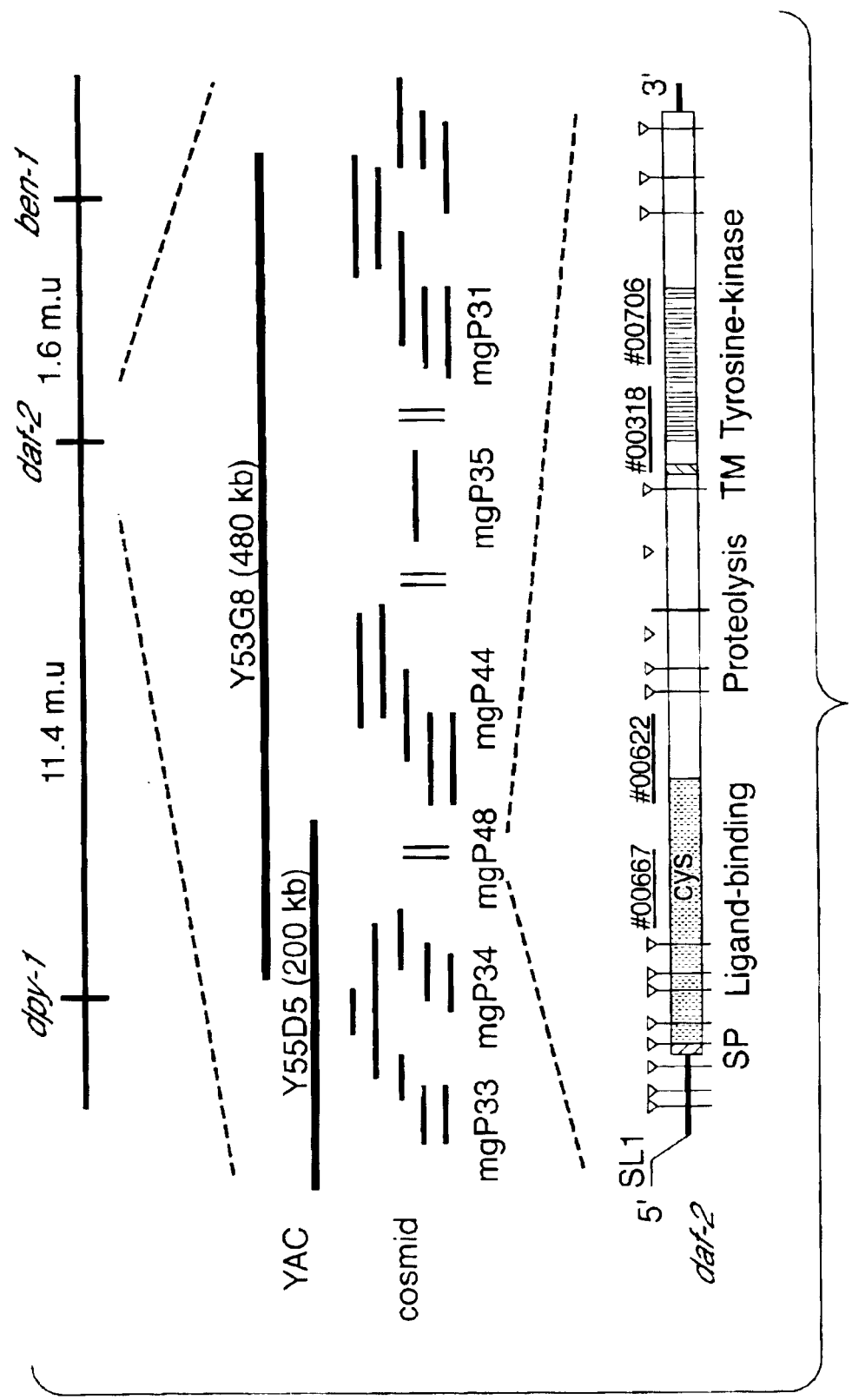

Genetic mapping using both visible genetic markers and restriction fragment length polymorphism (RFLP) markers places daf-2 between mgP34 and mgP44 (FIG. 1). While cosmid coverage of this physical genetic region is not complete, YAC Y53G8 carries the genomic region that includes mgP34 and mgP44, which flank daf-2 (FIG. 1). As a step in the *C. elegans* genome sequencing effort, random M13 subclones derived from Y53G8 were sequenced by the Genome Sequencing Center.

Figures 2, 2C:
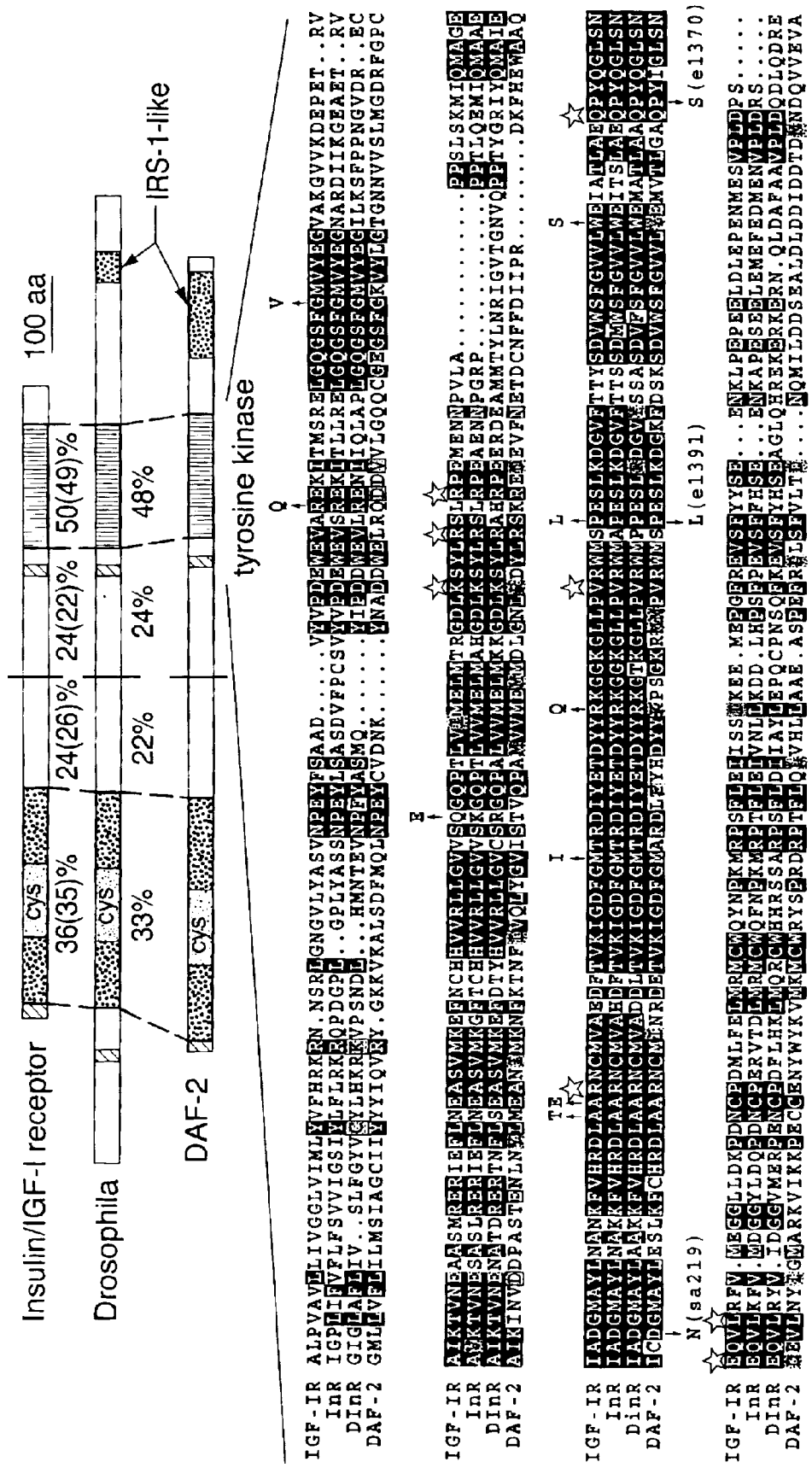

Sequence Identities Show that DAF-2 is Likely to Bind to an Insulin-like Ligand and to Phosorylate Tyrosine Residues The amino acid sequences and nucleotide sequences encoding DAF-2 are shown in FIGS. 2A and 2B, respectively. Using BLASTX to compare 570 translated Y53G8 M13 subclone sequences against the Genbank protein database, we found that four sequences are homologous to the mammalian insulin receptor family. An insulin receptor was a good daf-2 candidate gene because insulin regulates vertebrate growth and metabolism (White and Kahn, *J. Biol. Chem.* 269: 1–4, 1994), and because a phosphatidylinositol (PI) 3-kinase has been shown to act in both the insulin receptor and daf-2 pathways (White and Kahn, *J. Biol. Chem.* 269: 1–4, 1994; Morris et al., *Nature* 382: 536–539, 1996). The detection of multiple daf-2 mutations in the gene (see below), and the coincidence of the genetic location of this insulin receptor homolog with daf-2 (FIG. 2C) establish that this insulin receptor homolog corresponds to daf-2.

The daf-2 transcription unit and gene structure were determined using PCR primers derived from daf-2 genomic subclone sequences to amplify daf-2 genomic and cDNA regions. A probable full length daf-2 cDNA bears a 5172 base open reading frame, a 485 base 5' UTR and a 159 base 3' UTR (FIGS. 1, 2A). The predicted DAF-2 protein shows long regions of sequence identity to the insulin receptor family. Over the entire protein, DAF-2 is 35% identical to the human insulin receptor (Ebina et al., *Cell* 40: 747–58, 1985; Ullrich, et al., *Nature* 313: 756–61, 1985), 34% identical to the human IGF-I receptor (Ullrich, et al., *EMBO J.*: 5, 2503–12, 1986), and 33% identical to the human insulin receptor-related receptor (Shier and Watt, *J. Biol. Chem.* 264: 14605–8, 1989). DAF-2 is the only member of the insulin receptor family in the 90 Mb *C. elegans* genome sequence (about 90% complete) or in the 10 Mb *C. elegans* EST sequence database. Because it is equally distant from insulin, IGF-I, and insulin receptor-related receptors, DAF-2 is probably the homolog of the ancestor of these duplicated and diverged receptors, and thus may subserve any or all of the functions of these mammalian receptors (see below). Like these receptors, DAF-2 has a putative signal peptide, a cysteine-rich region in the putative ligand binding domain, a putative proteolysis site, a transmembrane domain, and a tyrosine kinase domain. In addition, DAF-2 has a C-terminal region that may serve a function similar to the mammalian insulin receptor substrate-1 (IRS-1) (FIG. 2; White and Kahn, *J. Biol. Chem.* 269: 1–4, 1994).

In the approximately 500 amino acid ligand-binding domain of the insulin receptor, DAF-2 is 36% identical to insulin receptor and 35% identical to the IGF-I receptor. Twenty-one of twenty-three phylogenetically conserved cysteine residues in this domain are conserved in DAF-2 (FIG. 2C). The DAF-2 cys-rich region is 34% identical to human insulin receptor and 28% identical to the IGF-I receptor. Six daf-2 mutations map in this domain (FIG. 2C, Table I). The mg43 and sa187 mutations substitute conserved residues in the cys-rich region (FIG. 2C). daf-2 (mg43) carries two mutations which substitute conserved residues, which may explain the strength of this allele (non-conditional, Table I). Other substitutions at non-conserved residues cause less severe phenotypes (Table I). Insulin resistant and diabetic patients with mutations in the ligand binding domain of the human insulin receptor gene have been identified (Taylor, *Diabetes* 41: 1473–1490, 1992) (see below). These mutations impair receptor transport to cell surface, or insulin binding affinity, or both. The DAF-2 mutations in this domain might similarly decrease receptor signaling to cause dauer arrest.

Insulin receptors are α2,β2 tetramers proteolytically processed from a single precursor protein (White and Kahn, *J. Biol. Chem.* 269: 1–4, 1994). DAF-2 bears a probable protease recognition site at a position analogous to the insulin receptor processing site (RVRR 806–809) (Yoshimasa et al., *J. Biol. Chem.* 265: 17230–17237, 1990).

The 275 amino acid DAF-2 tyrosine kinase domain is 70% similar and 50% identical to the human insulin receptor kinase domain. Upon insulin binding, the intracellular tyrosine kinase domain of the insulin receptor phosphorylates particular tyrosine residues flanked by signature amino acid residues (upstream acidic and downstream hydrophobic amino acids (Songyang and Cantley, *Trends Biochem. Sci.* 20: 470–475, 1995)) in the intracellular domain as well as on IRS-1 (White and Kahn, *J. Biol. Chem.* 269: 1–4, 1994). Multiple DAF-2 tyrosine residues in these sequence contexts are likely autophosphorylation targets, including three tyrosines in a region similar to the insulin receptor activation loop and one in the juxtamembrane region as described above (FIG. 2C). Based on the crystal structure of the insulin receptor kinase domain bound to its activation loop, eight kinase domain residues mediate target site specificity (Hubbard et al., *Nature* 372: 746–754, 1994). In DAF-2 (but not in more distantly related receptor kinases), these residues are invariant (5/8) or replaced with similar amino acids (3/8: K to R, E to D) (FIG. 2C), suggesting that DAF-2 phosphorylates the same target tyrosine motifs as the insulin receptor kinase.

Three daf-2 missense mutations substitute conserved amino acid residues in the kinase domain (FIG. 2C, Table I). All three mutations cause moderate to strong dauer constitutive phenotype, but none are as strong as the non-conditional alleles, for example, mg43 (Table I). Human insulin receptor mutations in the kinase domain exhibit decreased kinase activity and cause severe insulin resistance and associated defects (FIG. 2C; Taylor, *Diabetes* 41: 1473–1490, 1992). Remarkably, a human diabetic insulin resistant patient bears the same amino acid substitution (P1178L) as daf-2(e1391) (Kim et al., *Diabetologia* 35: 261–266, 1992). This patient was reported to be heterozygous for this substitution. daf-2(e1391) is not dominant whereas it is a highly penetrance recessive mutation (Table I).

To test for dominance of daf-2(e1391), using a genetically marked balancer chromosome, 105 dauers segregated from 485 daf-2/+ parents as expected for a recessive mutations. The genotype of 76/77 of these animals was homozygous daf-2(e1391) whereas 1/77 of the dauers was daf-2 (e1391)/+, indicating a less than 1% dominance. It is possible that in contrast to *C. elegans*, the P1178L mutation in humans is dominant, or that the patient carries a second insulin receptor mutation in trans, or carries mutations in other genes (for example, other complex type II diabetes loci) that enhance the dominance of P1178L (Bruning et al., *Cell* 88: 561–572, 1997).

AGE-1 PI 3-kinase is a Major DAF-2 Signaling Output

Like the *Drosophila* insulin receptor homolog, DAF-2 has a long C-terminal extension that may function analogously to mammalian IRS-1 (Fernandez et al., *EMBO J.* 14: 3373–3384, 1995). In mammals, IRS-1 tyrosine residues are phosphorylated by the insulin receptor kinase, and these phosphotyrosines mediate binding to a variety of signaling proteins bearing SH2 domains (White and Kahn, *J. Biol. Chem.* 269: 1–4, 1994; Songyang et al., *Cell* 72: 767–778, 1993.). Many, but not all, of the DAF-2 C-terminal extension tyrosines bear flanking sequence motifs suggestive that they are autophosphorylated (FIG. 2A; Songyang and Cantley, *Trends Biochem.* Sci. 20: 470–475, 1995). Based on precedents from IRS-1 interactions with mammalian PI 3-kinases (White and Kahn, *J. Biol Chem.* 269: 1–4, 1994), a YXXM motif at DAF-2 Y1504 is likely to mediate interaction with the AGE-1 PI 3-kinase, which acts in the same genetic pathway as daf-2 (FIG. 4) (Morris et al., *Nature* 382: 536–539, 1996).

Three DAF-2 tyrosine residues, Y1293, Y1296 and Y1297, in the region corresponding to the insulin receptor kinase Y1158 to Y1163 activation loop are likely to be autophosphorylated, based on the predicted similarity between the DAF-2 and insulin receptor phosphorylation targets (FIG. 2C). Another likely target for DAF-2 autophosphorylation is the Y1106 NPEY motif located in the region corresponding to the insulin receptor juxtamembrane region NPEY motif (at Y972), that has been shown to mediate IRS-1 binding via its PTB domain to the insulin receptor (White and Kahn, *J. Biol. Chem.* 269: 1–4, 1994). While DAF-2 bears one YXXM motif implicated in coupling to PI 3-kinase, mammalian IRS-1 and *Drosophila* insulin receptor (Fernandez et al., *EMBO J.* 14: 3373–3384, 1995) bear multiple YXXM motifs. Although no p85-like adaptor subunit has yet been detected in the *C. elegans* database, the AGE-1 homology to mammalian p110 suggests the existence of a homologous or analogous adaptor (Morris et al., *Nature* 382: 536–539, 1996). In the DAF-2 C-terminal domain, two other tyrosine residues may be autophosphorylated and bound to particular SH2-containing proteins: Y1678 binding to a PLC-γ or SHP-2 homolog, and Y1686, perhaps binding to SEM-5 (FIG. 2A) (Songyang et al., *Cell* 72: 767–778, 1993). While mutations in, for example, ras and MAP kinase have not been identified in screens for dauer constitutive or dauer defective mutations, these general signaling pathway proteins may couple to DAF-2 as they couple to insulin signaling in vertebrates (White and Kahn, *J. Biol. Chem.* 269: 1–4, 1994).

The insulin receptor also couples to other signaling pathways (White and Kahn, *J. Biol. Chem.* 269: 1–4, 1994); analogous DAF-2 phosphotyrosine residues may mediate these interactions (as described above). Thus, we suggest that tyrosines in the DAF-2 cytoplasmic domain are autophosphorylated upon ligand binding, and recruit the AGE-1 PI-3 kinase homolog (as well as other molecules) to signal reproductive development and normal senescence.

Metabolic Control by daf-2 in Control of Diapause and Aging

Insulin and its receptor families play key roles in vertebrate (and by our evidence in invertebrates) metabolic and growth control (Kahn and Weir, eds., *Joslin's Diabetes Mellitus*, Lea & Febiger, 1994). Upon insulin release—by increasing blood glucose and autonomic inputs—insulin receptor engagement directs a shift in the activities of key metabolic enzymes, as well as changes in the transcription and translation of metabolic regulators in fat, liver, and muscle cells, all of which lead to assimilation of glucose into glycogen and fat (White and Kahn, *J. Biol. Chem.* 269: 1–4, 1994). IGF-I is released from the liver in response to pituitary growth hormone, and mediates many of the growth and development responses to that endocrine signal (Mathews et al., *Proc Natl Acad Sci. U.S.A.* 83: 9343–7, 1986). Interestingly, lifespan is dramatically increased in dwarf mice with defects in growth hormone signaling, and presumably decreased IGF-I signaling as well (Brown-Borg et al., *Nature* 384: 33, 1996). No function for the insulin receptor-related receptor has yet been established, though it is expressed in conjunction with NGF receptor (Reinhardt et al., *J. Neurosci.* 14: 4674–4683, 1994).

Figure 3:
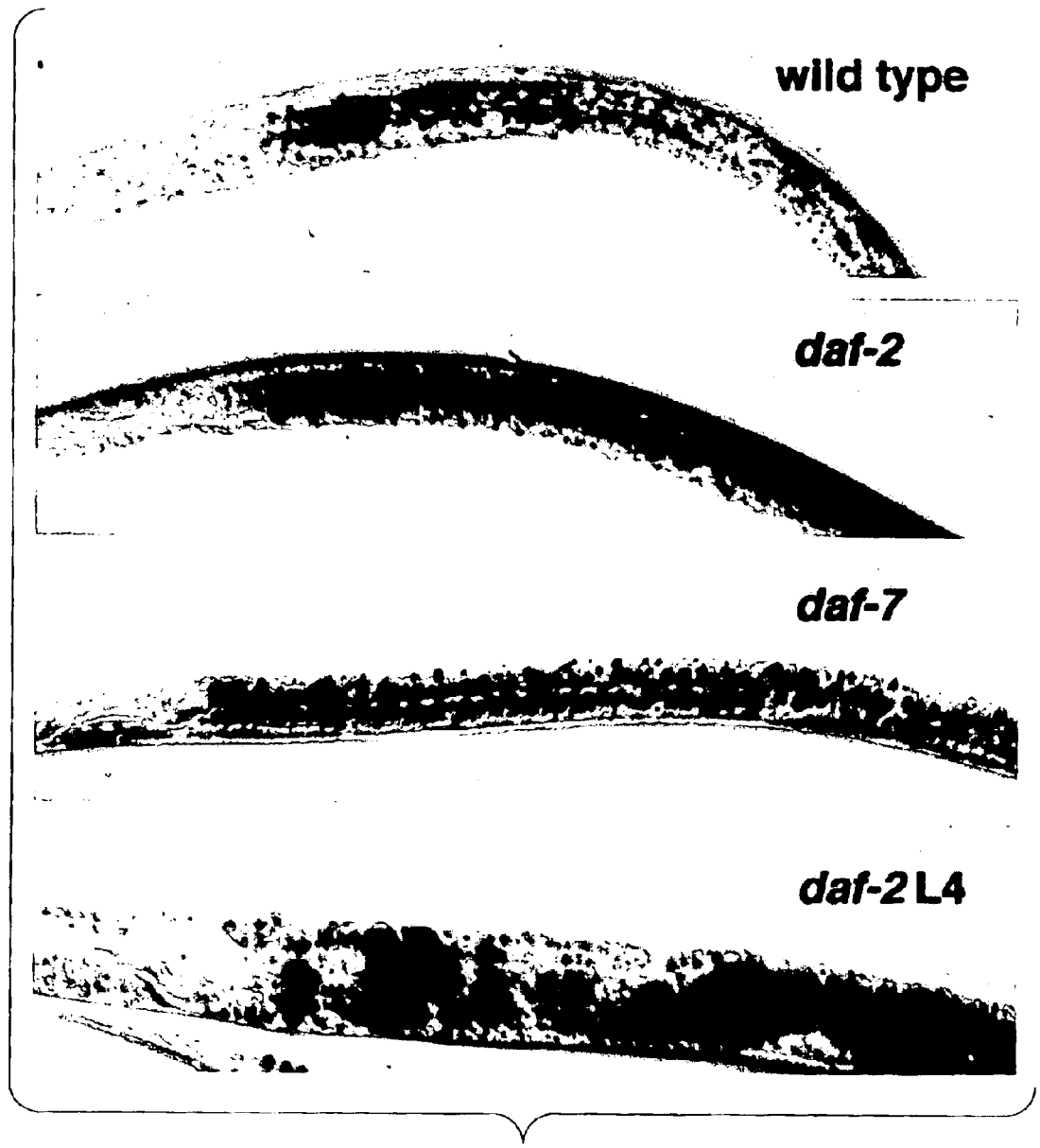

Diapause arrest in general and dauer arrest in particular are associated with major metabolic changes (Tauber et al., *Seasonal Adaptation of Insects*, Oxford University Press, New York, N.Y., 1986), consistent with a model that daf-2 acts in a metabolic regulatory pathway related to insulin signaling. In wild-type animals, DAF-2 signaling allows non-dauer reproductive growth, which is associated with utilization of food for growth in cell number and size, and small stores of fat (FIG. 3). In daf-2 mutant animals, metabolism is shifted to the production of fat (FIG. 3) and glycogen (data not shown) in intestinal and hypodermal cells. Even when a temperature-sensitive daf-2 mutant allele is shifted to the non-permissive temperature at the L4 or adult stage (after the critical period for daf-2 control of dauer formation), metabolism is shifted towards storage of fat (FIG. 3). Thus daf-2 also regulates metabolism during reproductive development. Similar metabolic shifts are seen in wild-type pheromone-induced dauers (data not shown), age-1 mutants (data not shown), and daf-7 mutants (FIG. 3). In support of this metabolic shift, in dauer larvae, enzymes that regulate glycolysis are down-regulated while those that regulate glycogen and fat synthesis are up-regulated, and there is ultrastructural evidence for increased lipid and glycogen (O'Riordan and Burnell, *Comp. Biochem. & Physiol.* 92B: 233–238, 1989; O'Riordan and Burnell, *Comp. Biochem. & Physiol.* 95B: 125–130,1990; Popham and Webster, *Can. J. Zool.* 57: 794–800, 1978; Wadsworth and Riddle, *Develop. Biol.* 132: 167–173, 1989). The dauer metabolic shift is associated with arrest of germ line proliferation, and arrest of somatic cell division and enlargement (Riddle, In: *Caenorhabditis elegans* II, D. Riddle, T. Blumenthal, B. Meyer, J. Priess, eds., Cold Spring Harbor Laboratory, Cold Spring Harbor, N.Y., 1997, pp. 739–768; Kenyon, op cit., pp.791–813).

There is precedent for insulin-like signaling in invertebrate metabolic and growth control: insulin-like growth factors have been detected in metabolism-regulating ganglia in molluscs (Roovers et al., *Gene* 162: 181–188, 1995) and regulate molting in locust (Hetru et al., *Eur. J. Biochem* 201: 495–499, 1991) and silkworm (Kawakami et al., *Science* 247: 1333–1335, 1990). Consistent with the daf-2 regulation of diapause, injection of insulin into diapausing *Pieris brassicae* (an insect) pupae induces recovery (Arpagaus, *Roux's Arch. Dev. Biol.* 196: 527–530, 1987).

Without being bound to a particular theory, we hypothesize that an insulin-like signal is up-regulated during reproductive development and stimulates DAF-2 receptor autophosphorylation and recruitment of the AGE-1 PI 3-kinase to produce the second messenger PIP3. AGE-1 is likely to be a major signaling output of DAF-2 because of the similarity of the age-1 and daf-2 mutant phenotypes and because of their similar placement in the epistasis pathway (Vowels and Thomas, *Genetics* 130: 105–123, 1992; Gottlieb and Ruvkun, *Genetics* 137: 107–120, 1994). Precedents from insulin receptor signaling suggest the following candidate targets for DAF-2/AGE-1/PIP3 regulation of metabolism: (1) membrane fusion of vesicles bearing glucose transporters (Kahn and Weir, eds., *Joslin's Diabetes Mellitus*, Lea & Febiger, 1994) (or more probably trehalose transporters (Tauber et al., *Seasonal Adaptation of Insects*, Oxford University Press, New York, N.Y., 1986)) to facilitate flux of this molecule for growth and reproductive metabolism; (2) PIP3 activates an AKT/GSK-3 kinase cascade (Hemmings, *Science* 275: 628–630, 1997) which may regulate the activities of glycogen and fat synthetic and lytic enzymes; (3) transcription and translation of metabolic genes such as PEPCK, GDH, fat synthetases, and lipases (White and Kahn, *J. Biol. Chem.* 269:1–4, 1994). Genetic epistasis analysis suggests that DAF-2/AGE-1 signaling negatively regulates daf-16 gene activity (Vowels and Thomas, *Genetics* 130: 105–123, 1992; Gottlieb and Ruvkun, *Genetics* 137: 107–120, 1994).

DAF-16 could act at any point downstream of AGE-1 in this signaling pathway. Evidence is presented herein that DAF-16 represents the major transcriptional output to DAF-2/AGE-1 PIP3 signaling.

In addition to these metabolic changes, the DAF-2 signaling cascade also controls the reproductive maturation of the germ line as well as morphogenetic aspects of the pharynx and hypodermis (Riddle, In: *Caenorhabditis elegans* II, D. Riddle, T. Blumenthal, B. Meyer, J. Priess, eds., Cold Spring Harbor Laboratory, Cold Spring Harbor, N.Y., 1997, pp. 739–768; Kenyon, op cit., pp. 791–813). The DAF-2 receptor may act, for example, in the hypodermal and intestinal target tissues where we note a change in metabolism triggered by the dauer regulatory cascade (FIG. 3). It is also possible that DAF-2 regulates the metabolism and remodeling of tissues indirectly, for example, by controlling the production of other hormones (Nagasawa et al., *Science* 226: 1344–1345, 1984; Jonas, et al., *Nature* 385: 343–346, 1997). Expression and genetic mosaic analysis of daf-2 is essential to distinguish these models.

Even though DAF-2 and the mammalian insulin receptor both regulate metabolism, the metabolic defects associated with mutations in these receptors appear to be different. Complete loss of mammalian insulin receptor activity causes growth arrest at birth (Leprechaunism in humans), and a metabolic shift to runaway lipolysis and ketoacidosis (Kahn and Weir, eds., *Joslin's Diabetes Mellitus*, Lea & Febiger, 1994), rather than the fat accumulation we observe in daf-2 mutants (FIG. 3). This distinction between insulin receptor and daf-2 mutants may reflect distinct metabolic responses to this signaling, or a difference between complete loss and declines in insulin signaling. In humans, ketoacidosis is only induced during severe starvation or pathological states when insulin levels are very low (Kahn and Weir, eds., *Joslin's Diabetes Mellitus*, Lea & Febiger, 1994). Since none of the daf-2 mutations described herein are clear null mutations, it is possible that daf-2 dauer-constitutive alleles are more analogous to non-null human insulin receptor mutations. Most daf-2 alleles are temperature sensitive, including alleles isolated in genetic screens that would allow the recovery of non-temperature sensitive mutations (Vowels and Thomas, *Genetics* 130: 105–123, 1992; Gottlieb and Ruvkun, *Genetics* 137: 107–120, 1994). Substitutions of DAF-2 amino acid residues conserved across phylogeny cause more penetrant dauer arrest at all temperatures than substitutions of non-conserved residues. daf-2 mutants that arrest development at the dauer stage independent of growth temperature are likely to have the least gene activity (for example mg43). Several daf-2 alleles also cause 5% to 10% embryonic lethality (unpublished results), suggesting that daf-2 functions during embryonic development. None of the daf-2 mutations detected so far are nonsense, frameshift, or deletion alleles. It is possible that the daf-2 null phenotype is stronger than non-conditional dauer arrest, for example embryonic lethality. However, dauer constitutive daf-2 mutant alleles are isolated from EMS mutagenesis at a very high rate (about 1/300 chromosomes), suggesting that the existing alleles are not rare viable alleles. In fact, the 14 year old patient with the same insulin receptor mutation as daf-2(e1391) was morbidly obese (Kim et al., *Diabetologia* 35: 261–266, 1992), suggesting that metabolic effects of decreased insulin signaling may be similar to daf-2 mutants.

It may be significant to human diabetes that animals carrying mutations in daf-16 can grow reproductively even if they also carry daf-2 and age-1 mutations that disable insulin-like metabolic control signals (Vowels and Thomas, *Genetics* 130: 105–123, 1992; Gottlieb and Ruvkun, *Genetics* 137: 107–120, 1994). These data suggest that it is unregulated daf-16 gene activity that causes these metabolic shifts. The analogous metabolic defects associated with both type I and type II diabetes may be caused by similar unregulated activity of the human DAF-16 homolog. Below we disclose the molecular identity of daf-16. Inhibition of its activity is expected to ameliorate the metabolic dysregulation associated with insulin signaling defects.

DAF-16 Encodes a Forkhead Transcription Factor Homolog

Figure 27:
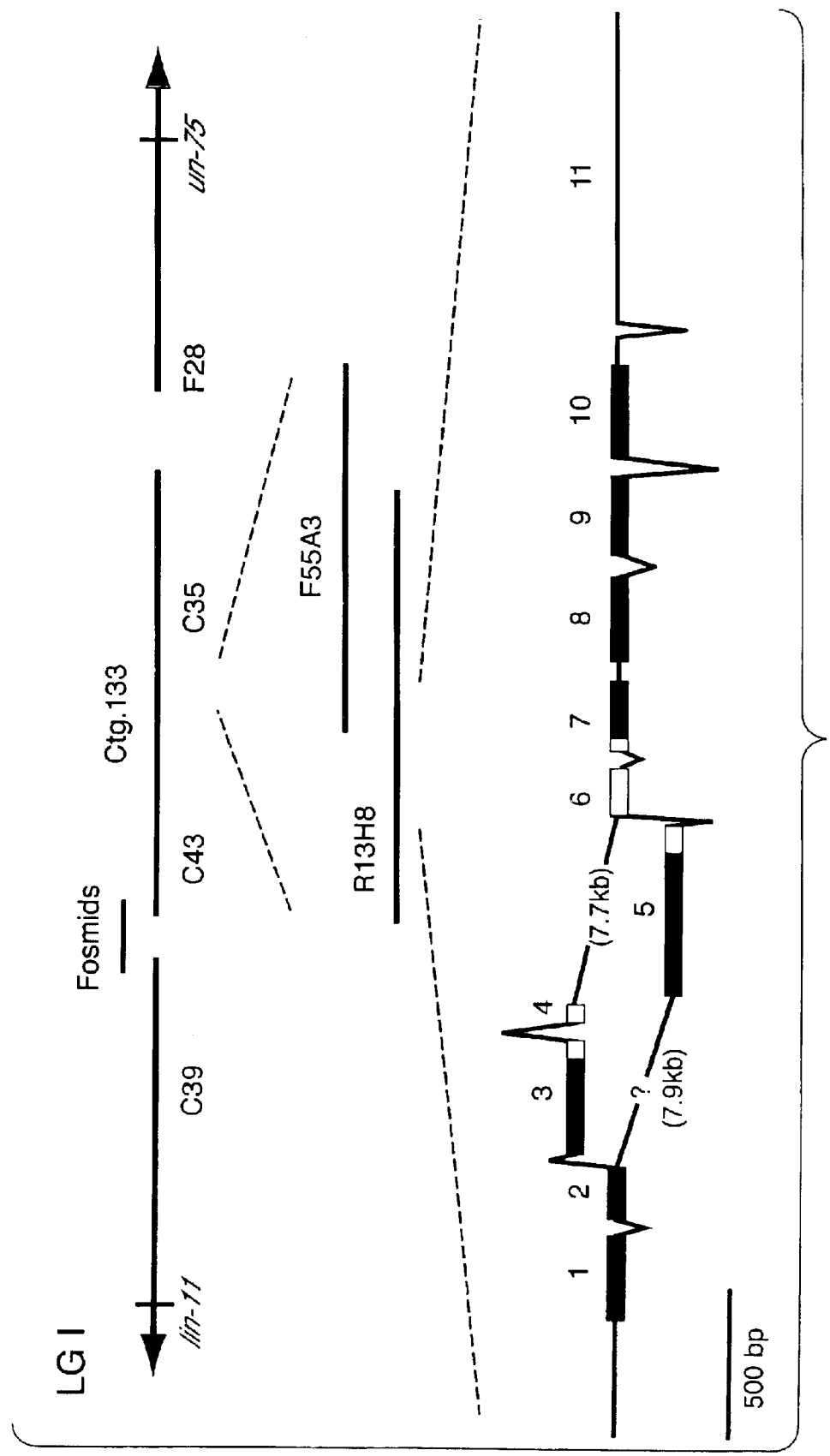

Using a combination of genetic mapping and detection of multiple daf-16 mutations in a 5 kb region, we have determined the nucleic acid sequence of daf-16. daf-16 was mapped 1 map unit to the left of lin-11 and 3.3 map units right of unc-75 on Chromosome I. This region of the genome contained a gap that was not covered by cosmids nor YACs. We used a fosmid library (Genome Sciences, Inc.) to walk into the gap. Sequence analysis of the ends of four fosmids (H27K20, H01H03, H12I08, and H35K06) revealed that the previously unmapped contig 133 lies in the lin-11 unc-75 gap. Cosmids from the approximate daf-16 genetic location were used to detect RFLPs between *C. elegans* strains Bristol N2 and Bergerac RC301: mgP45 on cosmid C39H11, mgP46 on cosmid F28D9, mgP49 on cosmid C35E7, mgP50 is on cosmid C43H8. Zero out of 30 daf non-Unc recombinants carry the RC301 alleles of mgP45 and mgP50. Two out of 30 Daf non-Unc recombinants carry the RC301 allele of mgP49. 10 out of 30 Daf non-Unc recombinants carry the RC301 allele of mgP46. 1 out of 4 non-Lin Daf recombinants carry the N2 allele of mgP45. 4 out of 4 non-Lin Daf recombinants carry the N2 allele of mgP49. These data indicate that daf-16 lies between cosmids C43H8 and C35E7. The daf-16 gene was identified by identifying deletions (mgDf50) and point mutations (mg53 and mg54) within the forkhead gene on the cosmid R13H8 (FIG. 27). There are two major daf-16 transcripts whose sequences are shown in FIG. 13A and FIG. 13B (SEQ ID NOS: 43 and 44, respectively). The amino acid sequences coding for the DAF-16 isoforms are shown in FIGS. 14A–B (SEQ ID NOS: 45–46).

We have detected three daf-16 mutations: (1) a large deletion of conserved regions in daf-16 (mg ΔF50) that proves that the daf-16 null phenotype is a suppression of daf-2 mutations; (2) a S to L substitution in exon 6 in daf-16 (mg 53) that alters a conserved WKNSIRH motif; and (3) a nonsense mutation in exon 3 in daf-16 (mg 54) that is predicted to truncate one of the daf-16 differentially spliced isoforms. Interestingly, this spliced isoform has a distinct forkhead DNA binding domain and is therefore expected to bind to distinct promoters or combinatorial partners. This mutant is a weak suppressor of daf-2, suggesting that both DAF-16 isoforms are necessary for metabolic control.

Figure 21A-1:
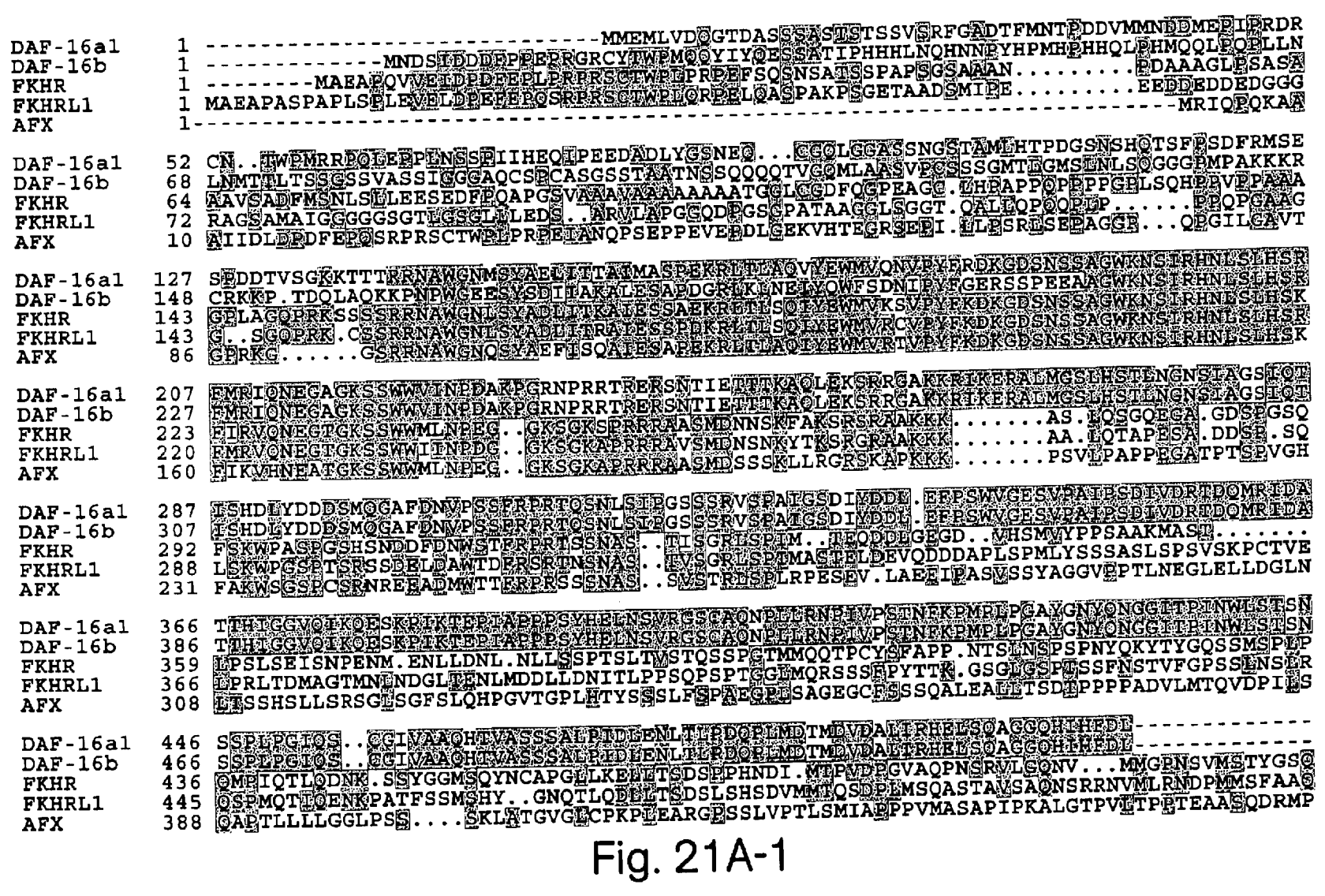
Figure 21B:
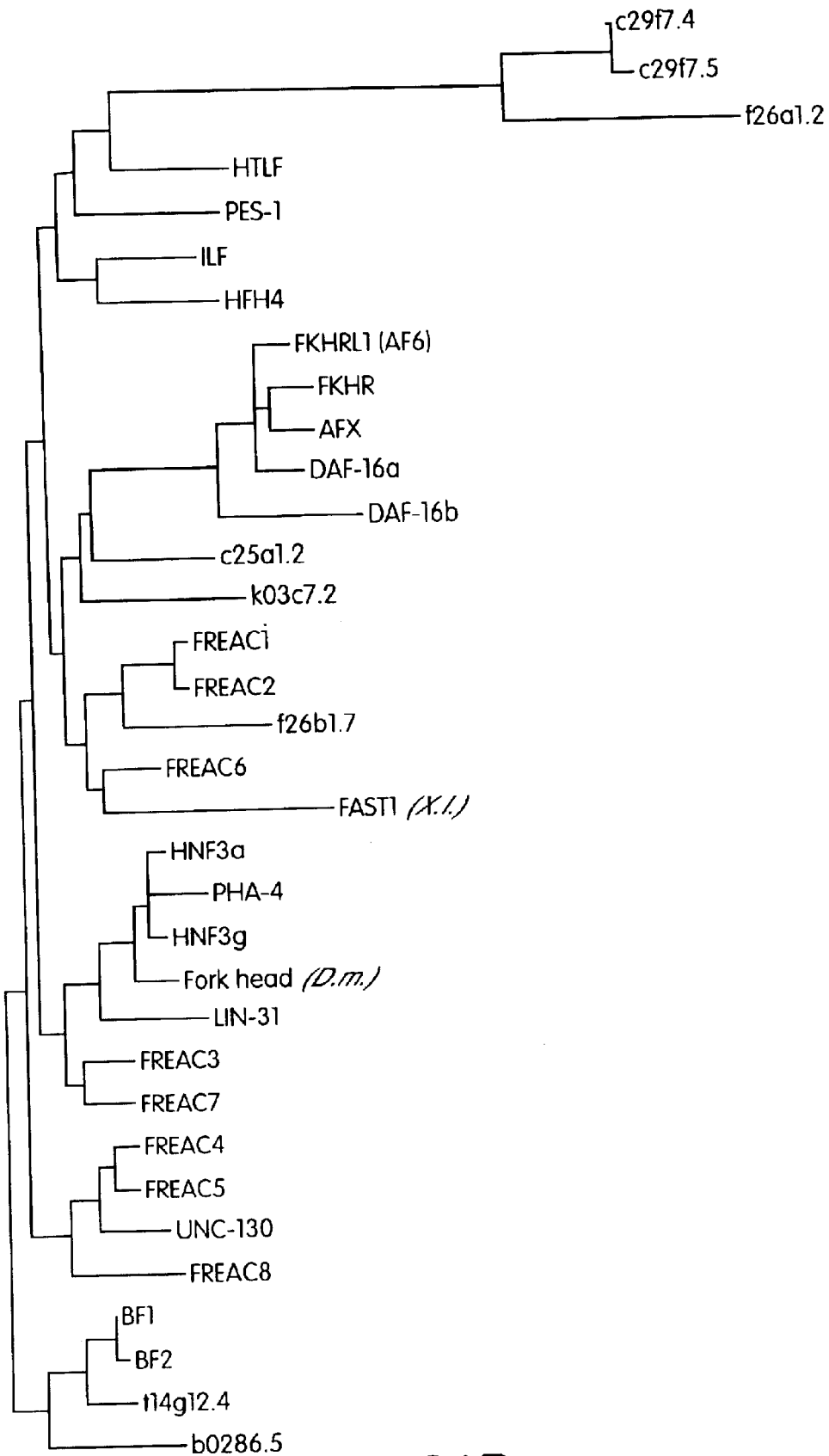
FIG. 21B is an illustration showing a forkhead family tree, illustrating that DAF-16 is much more closely related to FKHR, FKHRL1, and AFX than any other forkhead protein.

Sequence analysis has revealed that DAF-16 is a member of the forkhead (FH) transcription factor family (FIGS. 21A–21B). This strong amino acid homology indicates that DAF-16 is a transcription factor. Our genetic analysis indicates that DAF-16 activity is regulated by the DAF-2/AGE-1 insulin signaling pathway. Precedent from another receptor kinase signaling pathway endorses this model: the *C. elegans* LIN-31 forkhead protein has been shown to be regulated by a tyrosine kinase signaling cascade from the LET-23 EGF receptor homolog (Kim, *Genes Dev.* 7: 933–947, 1993). Consistent with a model that DAF-16 acts downstream of insulin signaling, forkhead transcription factors have also been implicated in metabolic regulation: another FH family member is mammalian HNF-3, an endoderm-specific transcription factor that acts at the same metabolic control protein promoters as HNF-1 and HNF-4, both of which are mutant in maturity onset diabetes of the young (MODY) (Yamagata et al., *Nature* 384: 455–458, 1996; Yamagata et al., *Nature* 384: 458–460, 1996).

The identification of DAF-16 as a forkhead transcription factor also explains much of the complex daf genetics of *C. elegans*. The convergence of DAF-7 TGF-β-like signaling and DAF-2 insulin-like signaling is also explained by our discovery that DAF-16 is a FH protein and DAF-3 is a Smad protein: Precedent for an interaction between Smad and forkhead proteins has been found in *Xenopus*. Response to the TGF-β superfamily relative activin in early frog development is mediated by an interaction between the distant relative of DAF-16 called FAST-1, and the Smad protein, Smad2 (*Nature* 383: 600–608, 1996). These proteins bind to an enhancer element that is very similar to the myosin II promoter to which DAF-3 binds (see below). Thus our molecular and genetic data indicate that the DAF Smad proteins and DAF-16 FH protein interact on metabolic control promoters.

Figure 22:
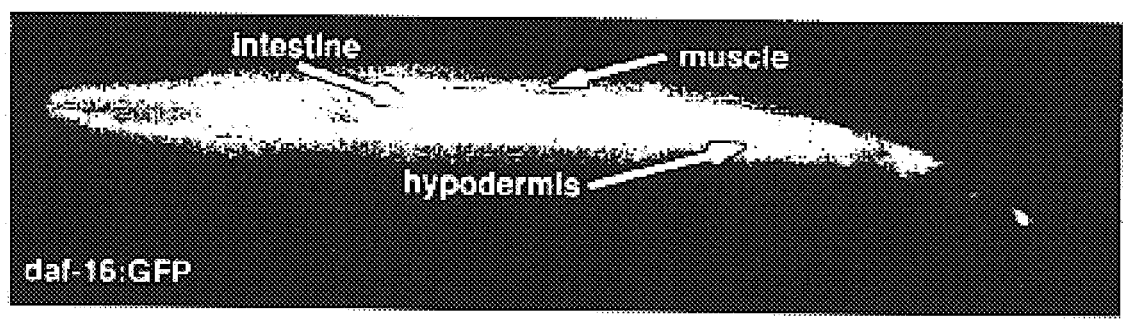
FIG. 22 is a photograph showing that daf-16 is expressed in target tissues, like daf-3. This supports the model that DAF-3 and DAF-16 are capable of interacting.

Interestingly, analogously to daf-16 bypass of the need for DAF-2 insulin receptor signaling in daf-16 mutant animals, lin-31 mutations suppress the need for LET-23 EGF signaling in *C. elegans* vulval development. These findings indicate that the DAF-2 receptor, a downstream signaling molecule (AGE-1), and a transcription factor target DAF-16 are involved in insulin-like signaling in *C. elegans* development. Without being bound by any particular theory, we hypothesize that *C. elegans* insulin signaling via DAF-2 and AGE-1 activate DAF-16 transcriptional activity, so that in a daf-2 or age-1 mutant, or in dauer pheromone, DAF-16 acts as a repressor protein causing a metabolic shift to fat metabolism. Our analysis of daf-16 expression shows that, like DAF-3, it is expressed in target tissues (FIG. 22). Our evidence indicates that Smad protein transcription factors (e.g., DAF 3, DAF8, DAF14) and DAF-16 act on a common set of promoters as combinatorial transcriptional regulators. Thus, it is at these metabolic genes that DAF-7 and TGF-β-like and DAF-2 insulin-like signals converge to control metabolism. In addition, our evidence indicates that in the presence of DAF-2 signaling (mimicking high insulin), DAF-16 acts as an activator of transcription, causing a shift in metabolism toward glucose utilization for cell growth. The molecular analysis described herein suggests that lack of daf-16 gene activity completely bypasses the need for insulin signaling in metabolic control by releasing metabolic control from DAF-16 repression. These data suggest that if a human DAF-16 homolog acts downstream of insulin signaling in humans, drugs could be developed that inhibit its activity to bypass the need for insulin signaling. Identification of a such a drug should provide a means for treating both Type I and Type II diabetes.

As shown in FIGS. 21A–21B, the human FKHR, FKHRL1, and AFX genes, identified as oncogene breakpoints but not as insulin signaling genes, are much more closely related to DAF-16 than the next closest relative in either Genbank or in the 94% complete *C. elegans* genome sequence. These data indicate that FKHR, FKHRL1, and AFX are excellent candidates for subserving the same function as *C. elegans* DAF-16: transduction of insulin signals and convergence with DAF-7-like Smad signals.

Evidence for the *C. elegans* AKT Kinase as the Probable Output of DAF-2/AGE-1 Signaling We screened genetically for mutations that bypass the need for age-1 signaling. This was done by mutagenizing a strain carrying an age-1(mg44) null mutation (this mutation was heterozygous to allow the strain to grow). After two generations, animals that could survive without age-1 gene activity were selected by their lack of arrest at the dauer stage. We identified daf-16 mutations, as expected. However, we also identified two new gain of function mutations, sup(mg142) and sup(mg144).

sup(mg144) suppresses three different age-1 alleles, indicating that this mutation bypasses the need for AGE-1 production of PIP3. For example, sup(mg144) suppresses the dauer arrest of age-1(mg44), (m333), (mg109) such that fertile adults are formed. sup(mg144) does not suppress the lack of insulin signaling in the daf-2 mutant: daf-2(e1370); sup(mg144) form dauers at 25 degrees. This suggests that not all of the DAF-2 signaling output is via AGE-1. However, in the absence of both DAF-2 and AGE-1 signaling, sup(mg144) weakly suppresses, allowing some fertile adults to bypass arrest at the dauer stage. daf-2 (e1370); sqt-1 age-1(mg44); sup(mg144) form 8% fertile adults, 12% sterile adults, and 80% dauers at 25 degrees.

Interestingly, sup(mg144) is a dominant suppressor of age-1 mutations. sqt-1 age-1(mg44); sup(mg144)/+ form 100% fertile adults. The sup(mg144) parental genotype does not affect this outcome. This data indicates that sup(mg144) is a dominant activating or dominant inactivating mutation.

Figure 24:
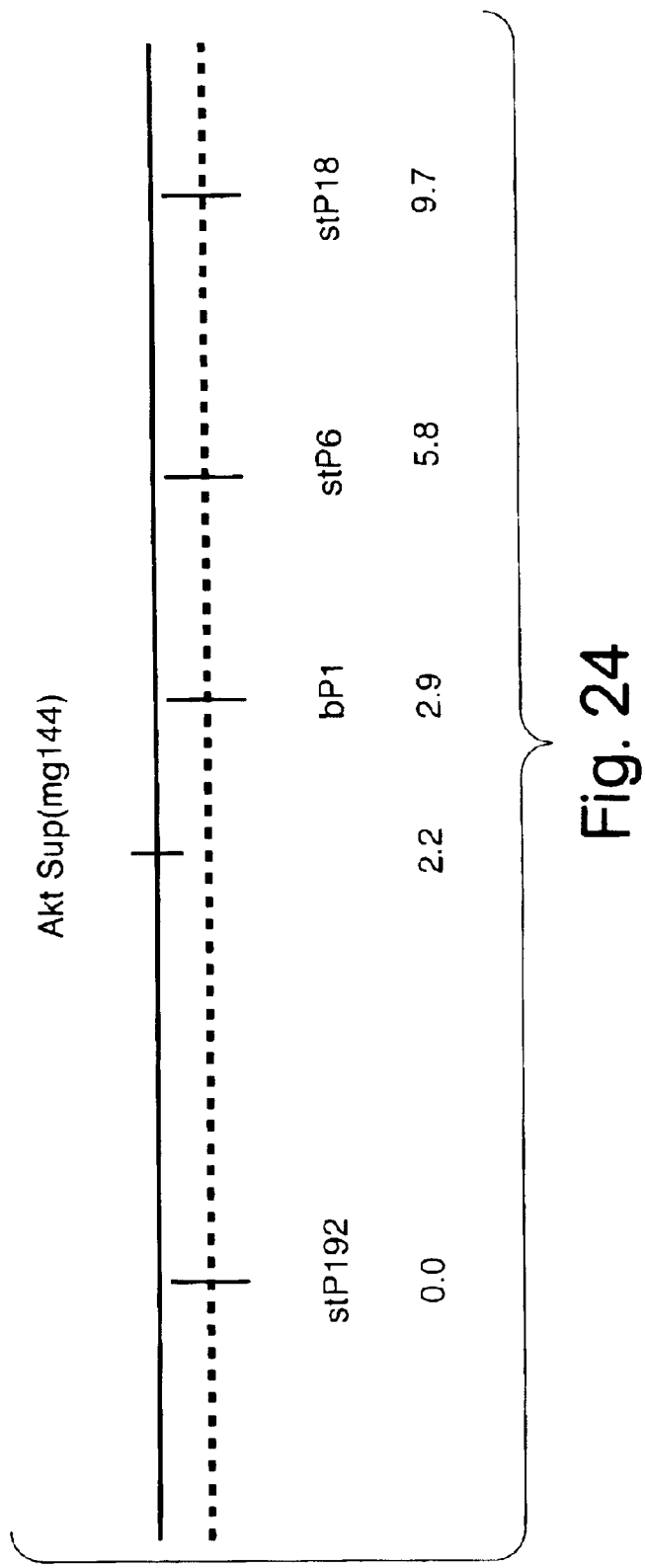
FIG. 24 is an illustration showing the genetic mapping of sup(mg144) to the AKT genetic region.

Genetic mapping indicates that sup(mg144) may identify an activating mutation in the *C. elegans* AKT homologue (FIG. 25). By placing sup(mg144) in trans to a multiply marked chromosome (using PCR based RFLPs), we found that sup(mg144) maps to a 2 map unit genetic interval that includes *C. elegans* AKT (FIG. 24).

In particular, 2/39 sup(mg144) homozygous animals isolated from a sup(mg144)/polymorphic Bergerac chromosome parent recombined between sup(mg144)mg144 and stP6 (these animals also carried stP18). In this experiment mg144 was a heterozygote with RW7000 for three generations, thus placing sup(mg144) approximately 2.2 mu to the left of stP6.

In addition, 1/39 sup(mg144) homozygous animals isolated from a sup(mg144)/polymorphic Bergerac chromosome parent recombined between sup(mg144) and bP1. In this experiment mg144 was a heterozygote with RW7000 for two generations. Accordingly, this number is approximately 1/80 or 1.2 mu from bP1.

Figure 26A:
FIG. 26A is a photograph showing the expression of AKT:GFP in daf-2 dauers.
Figure 26B:
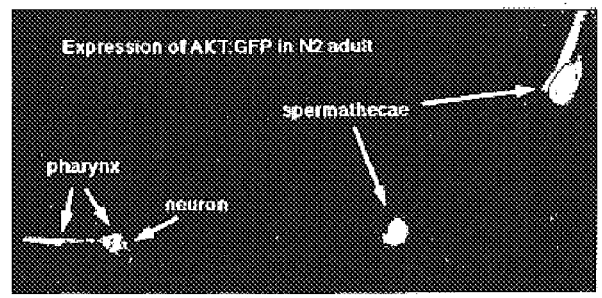
FIG. 26B is a photograph showing the expression of AKT:GFP in an N2 adult worm.

We generated a GFP fusion to AKT and showed that this gene is expressed at high levels in dauer larvae but at much lower levels and in fewer cells in wild type animals. (FIGS. 26A–26B) Thus AKT represents a dauer regulated gene that may respond to DAF-16 and DAF-3 transcriptional control. Multiple probable binding sites, related to the DAF-3 binding site in myoII have been identified.

Sup(mg142) Identifes Another Likely Output of Age-1 Signaling mg142 suppresses three different age-1 alleles (age-1 (mg44), age-1(m333), and age-1(mg109) at 20 degrees. age-1(mg44); sup(mg142) form fertile adults at 15 and 20 degrees. At 25 degrees, they form 33% fertile adults and 67% sterile adults.

sqt-1 age-1(mg44); mg142/+ form 14% fertile adults and 86% sterile adults when the parent was homozygous for mg142. sqt-1 age-1(mg44); mg142/+ form 67% fertile adults and 33% sterile adults when the parent was heterozygous for mg142. daf-2(e1370); mg142 form sterile adults at 25 degrees; daf-2(e1370); sqt-1 age-1(mg44); mg142 form sterile adults and dauers at 25 degrees. Preliminary mapping places mg142 approximately 1.6 mu to the left of unc-1 on LGX.

Novel *C. elegans* Insulin-like Hormones are Probable DAF-2 Ligands

Mutations in daf-2 not only cause a metabolic shift, but also affect longevity of *C. elegans*. The nearly complete *C. elegans* genome sequence allowed a definitive search for insulin superfamily members to be performed, and, in this search, we detected multiple insulin-related proteins in the *C. elegans* genome database. When insulin, IGF-I, or IGF-II were compared to the translated worm genome sequence, this large set of insulin superfamily members was not detected. However, when the search was carried out with the conserved signature residues shown below that are the hallmark of the insulin superfamily (SEQ ID NOS: 115, 116), as now defined, we detected a number of novel insulin molecules.

Conserved Insulin Motifs

1   L C G X X L V E A L X X V C G X R G F F Y T P K T R - R K R G I V E Q C C X X X C X X X Q L  E X Y C N  50 (SEQ ID NO: 115); and 1   a a n q r L C G R H L A D A L Y F V C G N R G F f y s p - k g G I V E E C C H N P C T L Y Q L E  N Y C n  51 (an insulin superfamily consensus from the Blocks database at www-.blocks.fhcrc.org; SEQ ID NO: 116).

The insulin superfamily signature residues were assembled using a set of vertebrate insulins and IGF-I and II proteins as well as silk moth bombyxin (a distant insulin relative) and a Limulus insulin superfamily member. The use of superfamily signature amino acid positions to detect distant relatives in databases is a more definitive approach to ascertaining gene superfamily members than simple searches with single family members.

Using these motifs, eight novel *C. elegans* insulin superfamily members were identified (SEQ ID NOS: 117–124), the coding sequences of which are shown in FIG. 28. In this Figure, the family members are named from the cosmid genomic DNA sequences from which they were detected. All of these insulins have A and B peptide homology to the insulin superfamily, and some of them have conserved dibasic processing sites that would mediate processing of the intervening unconserved C peptide. These genes are widely distributed on the *C. elegans* genome, although some are clustered (for example, ZK75.1, ZK75.2, ZK75.3, and ZK84.6). More distant insulin relatives may exist, but these are likely to engage receptors other than DAF-2.

Figure 29:
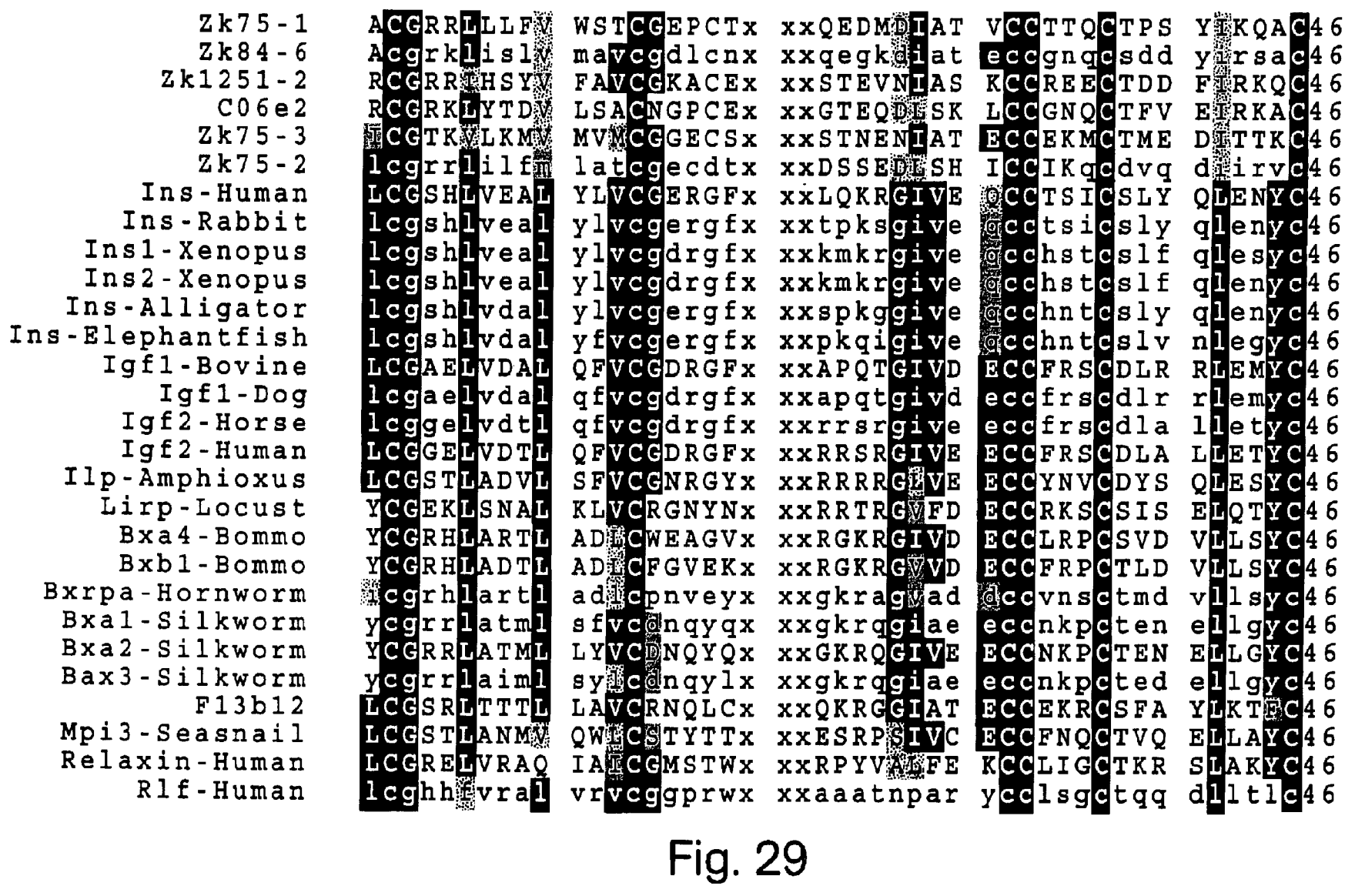
Figure 30:
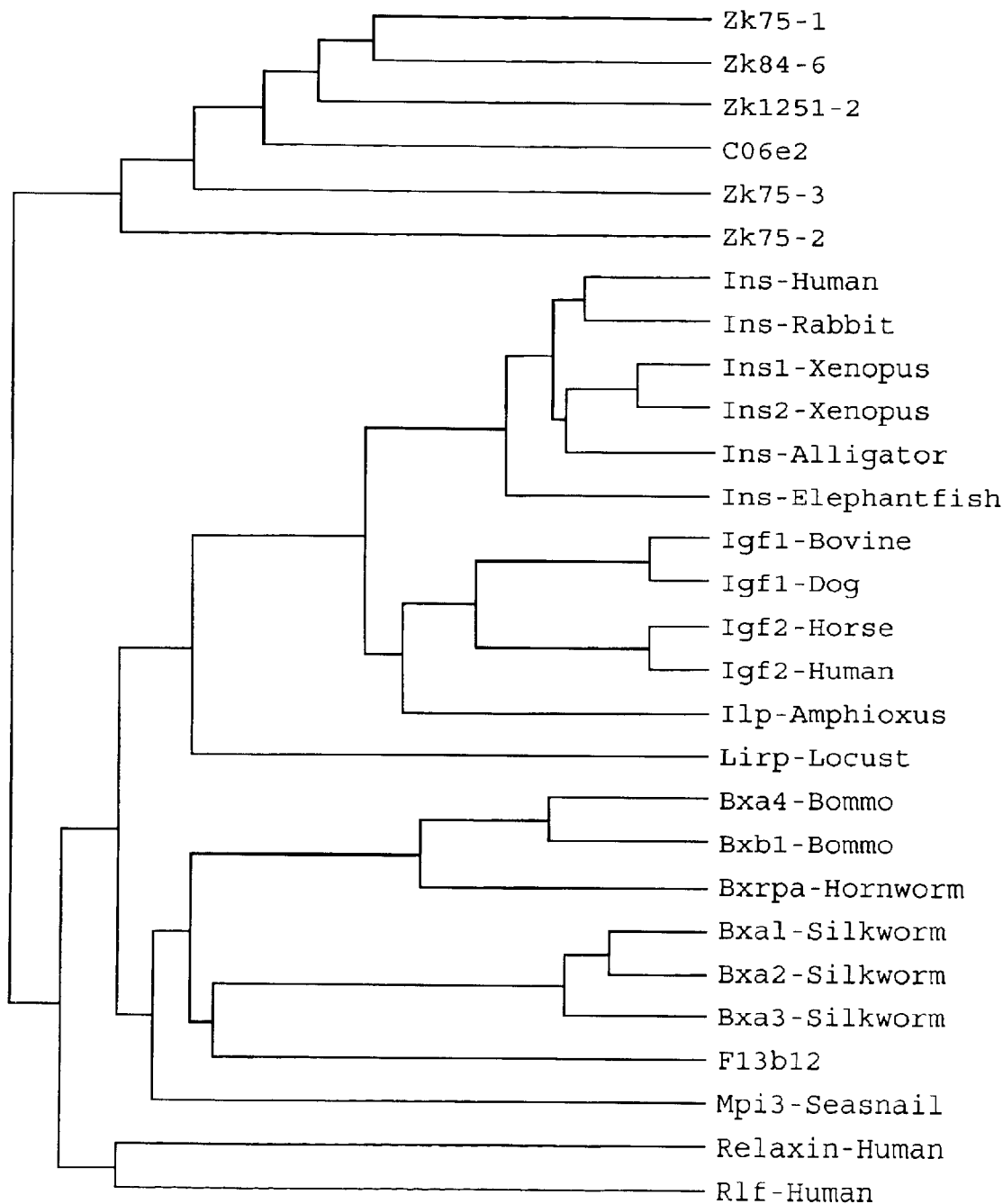
FIG. 30 is a graph illustrating a PILEUP analysis of insulin superfamily members.

Of the isolated insulin superfamily members, F13B12 was most closely related to human insulin and IGF-I,II. This was especially obvious from a PILEUP analysis in which a phylogenetic tree of protein superfamily members was constructed (FIGS. 29 and 30). The insulin product of F13B12 clustered more closely to the mammalian insulin and IGF-I,II proteins than to other distant relatives like relaxin. Relaxin defined the most distantly related insulin superfamily member in the analysis, and it appeared to engage a tyrosine kinase receptor distinct from the insulin receptor.

These insulin-like hormones are expected to subserve the longevity, dauer arrest, and/or metabolic effects of DAF-2 signaling. For example, each of these insulin superfamily members are expected to engage the DAF-2 receptor, leading to a result in which a mutation in daf-2 "sums" the functions of these eight or more insulin-like signals.

An analysis of the F13B12 insulin-like hormone is consistent with this view (Tables II–VI). First, as shown below, increasing the dose of the F13B12 insulin-like hormone potently modulates dauer arrest, both in animals carrying weak daf-2 or weak daf-7 mutations, and in animals carrying defects in synaptic components likely to mediate insulin release in *C. elegans* (unc-64).

TABLE II

High copy F13B12(ins) enhances the Daf-c phenotype of daf-2(e1365) at 20° C.

| | Phenotype of progeny (%) | | | | | |
|---|---|---|---|---|---|---|
| | transgenic | | | non-transgenic | | |
| Parental Genotype | non-dauer | dauer | N | non-dauer | dauer | N |
| F13B12 transgenic: | | | | | | |
| daf-2(e1365); mgex309 | 89.0 | 11.0 | 163 | 2.3 | 97.7 | 213 |
| daf-2(e1365); mgex310 | 90.5 | 9.5 | 220 | 2.6 | 97.4 | 115 |
| Control transgenic: | | | | | | |
| daf-2(e1365); mgex315 | 1.8 | 98.2 | 283 | 0.5 | 99.5 | 184 |

TABLE III

High copy F13B12(ins) maternally suppresses the Daf-c phenotype of daf-7(e1372) at 25° C.

| | Phenotype of progeny (%) | | | | | |
|---|---|---|---|---|---|---|
| | transgenic | | | non-transgenic (but parent was) | | |
| Parental Genotype | non-dauer | dauer | N | non-dauer | dauer | N |
| F13B12 transgenic: | | | | | | |
| daf-7(e1372); mgex299 | 31.4 | 68.6 | 236 | 2.9 | 97.1 | 172 |
| daf-7(e1372); mgex301 | 16.8 | 83.2 | 250 | 0 | 100 | 122 |
| Control transgenic: | | | | | | |
| daf-7(e1372); mgex312 | 100 | 0 | 78 | 100 | 0 | 60 |

TABLE IV

High copy F13B12(ins) maternally suppresses the Daf-c phenotype of daf-7(e1372) at 15° C.

| | Phenotype of progeny (%) | | | | | |
|---|---|---|---|---|---|---|
| | transgenic | | | non-transgenic (but parent was) | | |
| Parental Genotype | non-dauer | dauer | N | non-dauer | dauer | N |
| F13B12 transgenic: | | | | | | |
| daf-7(e1372); mgex299 | 1.4 | 98.6 | 73 | 0.3 | 99.7 | 343 |
| daf-7(e1372); mgex301 | 0.5 | 99.5 | 194 | 0 | 100 | 278 |
| Control transgenic: | | | | | | |
| daf-7(e1372); mgex312 | 26.4 | 73.6 | 91 | 25.6 | 74.4 | 39 |

TABLE V

High copy F13B12(ins) promotes recovery of unc-64(e246) dauers at 27° C.

| | Phenotype of progeny (%) | | | | | | |
|---|---|---|---|---|---|---|---|
| | Day 2 Transgenic | | | | Day 3 Non-transgenic | | |
| Parental Genotype | Dauer | Non-dauer | Dauer | Non-dauer | Dauer | Non-dauer | N |
| F13B12(ins) transgenic: | | | | | | | |
| unc-64(e246); mgex299 | 91.0 | 9.0 | 10.4 | 56.6 | 23.6 | 9.4 | 106 |
| unc-64(e246); mgex301 | 75.3 | 24.7 | 22.9 | 51.1 | 18.7 | 7.3 | 96 |
| Control transgenic: unc-64(e246); mgex312 | 88.9 | 11.1 | 54.3 | 10.6 | 29.8 | 5.3 | 208 |

TABLE VI

High copy F13B12(ins) enhances the Daf-c phenotype of unc-64(e246) at 15° C.

| | Phenotype of progeny (%) | | | | | |
|---|---|---|---|---|---|---|
| | transgenic | | | non-transgenic | | |
| Parental Genotype | dauer | non-dauer | N | dauer | non-dauer | N |
| F13B12 transgenic: | | | | | | |
| unc-64(e246); mgex299 | 23.2 | 76.8 | 185 | 0 | 100 | 170 |
| unc-64(e246); mgex301 | 36.0 | 64.0 | 75 | 0 | 100 | 77 |
| Control transgenic: unc-64(e246); mgex312 | 0 | 100 | 177 | 0 | 100 | 134 |

A genetic analysis has shown that high F13B12 insulin-like hormone signaling can suppress dauer arrest induced by daf-7 mutations or decreases in synaptic signaling, but can enhance dauer arrest caused by decreases in daf-2 signaling. Thus, the F13B12 insulin-like hormone may act synergistically with DAF-7 signals, like the DAF-2 receptor, but may interfere with the secretion or activity of another DAF-2 ligand. These genetic data strongly implicate the F13B12 insulin-like hormone in DAF-2 signaling.

In addition, the expression pattern of a promoter fusion of the F13B12 insulin-like hormone to GFP is also consistent with the genetic results. In these experiments, GFP was expressed in several head neurons, including ASJ and ASH, a pair of pharyngeal neurons, with processes that looked most like NSM, and three tail neurons. The full-length GFP looked similar but very faint. Worms expressing the full-length GFP lived longer than wild type. Interestingly, the NSM neuron had dense core vesicles by EM analysis, which is also true of beta cells of the pancreas. Pancreatic beta cells are also neuronal in character; they use synaptic components for insulin vesicle release, are synaptically connected to the autonomic nervous system, and are electrically active. Sulfonyl ureas, which are used to increase insulin release, act by regulating the activity of K channels in beta cells, much the way K channels regulate excitability in other neurons. Finally, the NSM neuron is a part of the C. elegans enteric nervous system, just like the pancreas in mammals. Accordingly, the expression and functional analysis of the F13B12 insulin-like hormone is highly supportive of its role in insulin-like control of worm metabolism and aging.

Although the F13B12 insulin-like hormone is the closest C. elegans homologue to insulin, it is likely that many or all of these insulin superfamily members engage the DAF-2 receptor to regulate their activity. For example, they are more closely related to insulin than to the ligands of the other growth factor receptors present in the worm genome. These distinct insulin superfamily ligands could regulate DAF-2 at distinct times or places, or act antagonistically or synergistically to the F13B12 insulin-like hormone. Some of these insulin-like hormones may regulate metabolism, like insulin, whereas others may regulate dauer arrest or longevity. Thus, the daf-2 mutant phenotype that results from loss of the receptor for these many hormones may be a composite loss of many hormonal signals. Consistent with such a model, neuronal expression of the DAF-2 receptor in a daf-2 null mutant has been found to complement the dauer arrest phenotype of a daf-2 mutant but not the metabolic or aging defects. Accordingly, one DAF-2 ligand may be expressed in or near the brain to control dauer arrest, but other ligands may impinge on DAF-2, for example, in non-neuronal cells, to control metabolism and aging.

By this view, loss of only one of the insulin-like hormones may cause only a subset of the daf-2 mutant phenotype, for example, only increased longevity or only metabolic dysregulation. These C. elegans insulin superfamily members may, for example, subserve the longevity or senescence function of DAF-2 receptor signaling, and an increase in such a hormone activity late in life may actually mediate the increase in DAF-2 activity that causes senescence. Conversely, if any of these insulin-like proteins have antagonistic effects on DAF-2, any decline in their activity late in life could mediate senescence. Application of only one hormone by injection or germ line therapy could therefore be used to target, for example, aging without any effects on metabolism.

In addition, since the F13B12 insulin-like hormone is a detectable worm homologue of insulin, it is possible that the other 7 worm insulins also have human homologues that are more closely related to their nematode counterparts than they are to each other. In fact the divergence of the F13B12 insulin-like hormone from insulin and IGF-I and IGF-II gives a measure of how much divergence may be expected for the mammalian homologues of the other insulin superfamily members. The F13B12 insulin-like hormone is slightly more closely related to IGF-II than insulin or IGF-I, but these three genes are probably duplicated and diverged homologues of a F13B12 homologue in the common ancestor of C. elegans and Homo sapiens. In fact, it is a current rule of thumb that many gene families in mammals have 4 times as many members as in C. elegans. For example, there are 4 Hox clusters in mammals and only one in C. elegans.

Similarly, there are 3 known DAF-2 receptor homologues and DAF-16 transcription factor homologues in mammals (it is likely that the fourth mammalian member of these gene families will become known when the full mammalian genome sequence is finished). Thus, it is reasonable to expect that, for every insulin like protein in *C. elegans*, there may be four in mammals, or a total of 24 for the family of 8 shown above. In addition, since the F13B12 insulin-like hormone is expressed in only a few neurons, it is possible that the other insulin superfamily members are similarly expressed in a small set of neurons, and that the human homologues may be expressed in only rare regulatory cell types.

The insulin-like hormones described herein, as well as their human homologues, provide valuable candidate regulators of senescence. For example, if human senescence is triggered by a decline in an insulin-like longevity hormone, in analogy to how puberty is triggered by a timed change in sexual maturation hormones, it may prove possible to regulate the aging process in the same way that sexual maturation can be regulated by hormone treatment. In addition, the *C. elegans* aging hormones may reveal which human genes have such a function. Because daf-2 mutations cause longevity increases in a manner analogous to caloric restriction in mammals, it is possible that caloric restriction in mammals regulates the level of an insulin-like hormone that in turn engages the insulin or IGF-I, II receptors. Such a hormone may not have been detected if its level is very low or if it signals over a short range. However, once the human genome sequence is complete, the detection of human homologues to the *C. elegans* superfamily members listed above will become a trivial matter of database searching. In this way, the determination of the function of the worm homologue function in longevity or growth arrest or metabolism control will supply valuable functional information about the activity of human homologues.

The effect of the *C. elegans* insulin-like proteins on longevity, metabolism, or growth arrest may be readily determined by a combination of high copy studies, as shown above for the F13B12 insulin-like hormone, as well as by using RNA inhibition and knockout strategies to inhibit the activities of these genes. The *C. elegans* strains are then tested for interactions with daf pathway mutants, for example, as shown for the F13B12 insulin-like hormone above, and for longevity effects by standard techniques.

The human proteins that regulate longevity may be detected by a combination of database searches and genetic complementation of worm RNAi or gene knockout mutants (for example, as described herein), as well as by high copy effects of human genes on worm longevity and metabolic control.

Because these human proteins are hormones, they may be used to directly regulate human longevity, for example, by injection into the bloodstream. Depending on the particular hormone and its effects, the hormones themselves may cause increased longevity, or they may be modified to generate dominant interfering hormones (for example, by engineering chimeras between the insulin superfamily members). The function of these proteins upon injection into the bloodstream may be predicted from their function in *C. elegans*, for example, as ascertained by transgenic analysis. Because of their effects on longevity, the human homologues of these *C. elegans* insulin-like endocrine signals have important applications in preventing or retarding the aging process.

*C. elegans* Akt/PKB Transduces Insulin Receptor-like Signals from AGE-1 Phosphoinositide-3-OH Kinase to the DAF-16 Transcription Factor An insulin receptor-like signaling pathway regulates *C. elegans* metabolism, development, and longevity (Kimura et al., *Science* 277:942–946, 1997). In response to a secreted pheromone, wild type animals arrest development at the dauer stage with a concomitant switch to fat storage metabolism in the intestine and hypodermis, increased lifespan, and remodelling of many tissues (Kimura et al., *Science* 277:942–946, 1997; Riddle and Albert, in *C. elegans* II, eds. Riddle, D. L., Blumenthal, T., Meyer, B. J. & Priess, J. R., Cold Spring Harbor Laboratory Press, Cold Spring Harbor, N.Y., pp. 739–768, 1997). Mutations in the insulin/IGF-I receptor homolog daf-2 (Kimura et al., *Science* 277:942–946, 1997) or in the phosphoinositide-3-OH kinase (PI3K) homolog age-1 (Morris et al., *Nature* 382:536–539, 1996) cause constitutive arrest at the dauer stage; genetic analysis is consistent with AGE-1 functioning downstream of DAF-2 (Gottlieb and Ruvkun, *Genetics* 137:107–120, 1994; Larsen et al., *Genetics* 139:1567–1583, 1995). Mutations in the Fork head transcription factor DAF-16 completely suppress the dauer arrest, metabolic shift, and longevity phenotypes of daf-2 and age-1 mutants (Gottlieb and Ruvkun, *Genetics* 137:107–120, 1994; Larsen et al., *Genetics* 139:1567–1583, 1995; Kenyon et al., *Nature* 366:461–464, 1993; Ogg et al., *Nature* 389:994–999, 1997; Lin et al., *Science* 278:1319–1322, 1997), indicating that DAF-16 is a negatively regulated downstream target of *C. elegans* insulin receptor signaling. Molecules that couple the DAF-2 insulin receptor protein and AGE-1 PI3K to the DAF-16 transcription factor have not been identified by previous extensive genetic screens. While biochemical studies have suggested that the mammalian Akt/PKB (also known as RAC) serine/threonine kinase may transduce signals from PI3Ks associated with receptor tyrosine kinases (Franke et al., *Cell* 81:727–736, 1995; Burgering and Coffer, *Nature* 376:599–602, 1995; Cross et al., *Nature* 378:785–589, 1995), such as the insulin receptor to downstream effectors, this has not been demonstrated by genetic analysis of signaling pathways in whole organisms. We established the action of *C. elegans* Akt/PKB in the DAF-2 insulin receptor-like signaling pathway by the genetic identification of an activating Akt/PKB mutation and by genetic analysis of Akt/PKB inactivation and overexpression.

An activating mutation (mg144) in akt-1, one of two *C. elegans* Akt/PKB homologs, was identified in a genetic screen for mutations that suppress the dauer arrest phenotype of the age-1(mg44) null mutant (Morris et al., *Nature* 382:536–539, 1996). This screen was designed to isolate reduction of function mutations in molecules negatively regulated by PI3K signaling, or gain of function mutations in molecules positively regulated by PI3K signaling. Among 10 independent suppressor mutations isolated in a screen of 3800 haploid genomes, in addition to the activating akt-1 mutation, we also isolated multiple alleles of a previously known negatively regulated target, daf-16 (Gottlieb and Ruvkun, *Genetics* 137:107–120, 1994; Larsen et al., *Genetics* 139:1567–1583, 1995) and one other suppressor that maps to the daf-16 interval between lin-11 and unc-75, suggesting that the screen revealed genes that act in this insulin-like signaling pathway. Another dominant mutation, mg142, that suppresses multiple age-1 alleles and six mutations that vary in their ability to suppress multiple age-1 alleles were also isolated in the screen.

The mg144 mutation suppresses the three age-1 alleles tested, including two classes of nonsense alleles and one missense substitution (Ala845Thr) in a conserved region of PI3K (Morris et al., *Nature* 382:536–539, 1996). mg144 is completely dominant for suppression of the dauer constitutive phenotype of age-1(mg44) (75.1% of the progeny of age-1(mg44); mg144/+ animals developed as non-dauers, and 24.9% arrested at the dauer stage, N=774). On its own, mg144 does not have any obvious phentoypes; it moves normally, has a normal vulva and brood size, and makes dauers on starved plates and on plates treated with pheromone. Thus mg144 does not activate the AGE-1 PI3K signaling pathway to the point that normal dauer arrest is affected but does activate the pathway sufficiently to alleviate the requirement for AGE-1 PI3K outputs.

Using suppression of the dauer constitutive phenotype of age-1(mg44), mg144 was mapped to a region on chromosome V within 1.3 mu of the polymorphic STS marker bP1 (FIG. 31). From the *C. elegans* genome sequence in this 1.3 mu region, we identified a *C. elegans* Akt/PKB homolog which we named akt-1 (FIG. 31). Because an activating mutation in Akt/PKB is a good candidate to be a genetically dominant suppressor of an age-1 PI3K null mutant, we determined the akt-1 DNA sequence in the mg144 strain by PCR amplification and direct sequencing. The akt-1 gene in the mg144 mutant strain was shown to bear an Ala183Thr substitution (FIG. 34). akt-1 is differentially spliced within the conserved kinase domain to generate the akt-1a and akt-1b isoforms with distinct kinase domain subregions IV, V, and VI (92% identical, 238/258 amino acids over the entire kinase domain; 69% identical, 44/64 amino acids in the differentially spliced region). akt-1a is 58% identical to human Akt/PKBa (FIG. 33 and 34). akt-1 has a pleckstrin homology domain, kinase domain, and the two phosphorylation sites necessary for Akt/PKB activation (Alessi et al., *EMBO J*. 15:6541–6551, 1996) which are the hallmarks of the Akt/PKB family (FIG. 34). The next most closely related non-Akt/PKB mammalian kinase is rat PKCβ1 which is 38% identical to akt-1a. The akt-1(mg144) mutation is present in both splice forms of akt-1 and is located in a region of the protein that links the N-terminal pleckstrin homology domain to the C-terminal kinase domain. This mutation is in a region that is not conserved between *C. elegans* and mammalian Akt/PKB. This mutation may reveal a negative regulatory region on akt-1 because the mg144 allele is an activating mutation (see below).

To confirm that the mg144 suppression of age-1 that is genetically linked to akt-1 was due to a mutation in akt-1, we used a reverse genetic assay termed RNA interference (RNAi) (Fire et al., *Nature* 391:806–811, 1998; Rocheleau et al., *Cell* 90:707–716, 1997; Zhang et al., *Nature* 390:477–484, 1997) to decrease akt-1 gene activity in an age-1(mg44); akt-1(mg144) strain. If a mutation in akt-1 was responsible for the suppression of age-1 observed in this strain, RNAi of akt-1 in this strain should revert the suppression phenotype and result in a dauer constitutive phenotype. This experiment was conceptually similar to the classic genetic arguments that show that a cis-acting loss of function mutation can revert a gain of function mutation in the same gene. Inhibition of akt-1 activity in an age-1 (mg44); akt-1(mg144) strain reverted the akt-1(mg144) suppression phenotype, indicating that the mg144 activating mutation was a lesion in the akt-1 locus.

We identified another Akt/PKB homolog in the nearly complete *C. elegans* genome sequence (Wilson et al., *Nature* 368:32–38, 1994) which we named akt-2 (FIG. 32). akt-1 and akt-2 are more closely related to each other (66% identity between akt-1a and akt-2 overall) than to any other Akt/PKB homolog (FIG. 33). akt-2 is 55% identical to human Akt/PKBa overall and 35% identical to rat PKCβ1 overall. Interestingly, akt-2 only has the Thr308 phosphorylation site that is necessary for Akt/PKB activation by PDK1 (Alessi et al., *Current Biology* 7:261–269, 1997; Stokoe et al., *Science* 277:567–570, 1997) but not the Ser473 phosphorlyation site (Alessi et al., *EMBO J*. 15:6541–6551, 1996) (FIG. 34) and yet clearly functions in the insulin-like signaling pathway (see below).

Reduction of both akt-1 and akt-2 activities revealed that they transduce insulin-like signals from the AGE-1 PI3K to the DAF-16 forkhead transcription factor. Inhibition of either akt-1 or akt-2 activity by RNAi did not cause dauer arrest. However, simultaneous inhibition of both akt-1 and akt-2 activities caused nearly 100% arrest at the dauer stage. We concluded that Akt/PKB signaling from either akt-1 or akt-2 is sufficient for reproductive development. This result indicates that akt-1 and akt-2 can function redundantly for dauer formation in *C. elegans* and raises the possibility that various mammalian Akt/PKB isoforms could function redundantly as well. Significantly, the constitutive dauer arrest induced by inhibition of both akt-1 and akt-2 is fully suppressed by a null mutation in daf-16 (Ogg et al., *Nature* 389:994–999, 1997) but is not suppressed by a null mutation in the Smad homolog daf-3 (Patterson et al., *Genes & Development* 11:2679–2690, 1997) which confirms its placement in the DAF-2/AGE-1/DAF-16 signaling pathway. Because a null mutation in daf-16 alleviates the need for *C. elegans* Akt/PKB signaling, the primary function of AKT-1 and AKT-2 is to antagonize DAF-16. Interestingly, DAF-16 contains four consensus sites for phosphorylation by Akt/PKB (Alessi et al., *FEBS Letters* 399:333–338, 1996) and three of these sites are conserved in the human DAF-16 homologs AFX, FKHR, and FKHRL1. AKT-1 and AKT-2 may exert their negative regulatory effect by directly phosphorylating DAF-16. Shown below are comparisons of AFX, FKHR, and DAF-16, indicating the conservation between the consensus phosphorylation sites. The AKT sites indicated are located downstream and upstream, respectively, of the Forkhead domain (SEQ ID NOS: 161–169).

Score=151 (68.4 bits), Expect=1.9e–140, Sum P(8)=1.9e–140 Identities=28/54 (51%), Positives=38/54 (70%)

```
SEQ ID NO:161  AFX:     226 SPVGHFAKWSGSPCSRNREEADMWTTFRPRSSSNASSVSTRLSPLRPESEVLAE 279
SEQ ID NO:162                SP   F+KW  SP S +  ++ D W+TFRPR+SSNAS++S RLSP+   E +L E
SEQ ID NO:163  FKHR:    287 SPGSQFSKWPASPGSHSNDDFDNWSTFRPRTSSNASTISGRLSPIMTEQDDLGE 340
SEQ ID NO:164  DAF-16 a              SFRPRTQSNLSIPGSSS
```

Score=132 (59.8 bits), Expect=1.9e–140, Sum P(8)=1.9e–140 Identities=22/42 (52%), Positives=28/42 (66%)

```
SEQ ID NO:165  AFX:     7 KAAAIIDLDPDFEPQSRPRSCTWPLPRPEIANQPSEPPEVEP 48
SEQ ID NO:166              +A ++++DPDFEP RPRSCTWPLPRPE +   S       P
SEQ ID NO:167  FKHR:    3 EAPQVVEIDPDFEPLPRPRSCTWPLPRPEFSQSNSATSSPAP 44
SEQ ID NO:168  DAF-16   TFMNTPDDVMMNDDMEPIPRDRCNTWPMRRPQLEPPLNSSP 177
SEQ ID NO:169             T  ++P+ V ++ D EP+PR R  TWP+ RP++  + ++++
```

We have shown that human AKT will phosphorylate *C. elegans* DAF-16 and that this phosphorylation is dependent on these sites. Upon mutation of the serine or threonine in these sites to alanine, in vitro phosphorylation of DAF-16 (or fragments of DAF-16) is abolished. It is expected that the lack of akt input to DAF-16 in these mutant nematodes will result in dauer arrest, just like animals lacking akt-1/akt-2 gene activity.

The above genetic results show that Akt/PKB is the major output of PI3K signaling and implicate a transcription factor downstream target for the Akt/PKB kinase. Because mutations in daf-16 suppress akt-1 and akt-2 reduction of function, it is likely that DAF-16 represents a major signaling output of Akt/PKB in *C. elegans* insulin-like signaling. Akt/PKB has been implicated in mammalian insulin receptor signaling that localizes glucose transporters to the plasma membrane (Kohn et al., *J. Biol. Chem.* 271:31372–31378, 1996) and has been shown to regulate glycogen synthesis via direct phosphorylation of GSK-3 (Cross et al., *Nature* 378:785–589, 1995), two events which are not transcriptionally regulated. While there also may be such Akt/PKB outputs in *C. elegans*, the DAF-16 Fork head transcription factor represents the major output of DAF-2/AGE-1/AKT-1/AKT-2 insulin receptor-like signaling (Ogg et al., *Nature* 389:994–999, 1997). Similarly Akt/PKB action in the insulin/IGF-I anti-apoptotic pathway (Dudek et al., *Science* 275:661–665, 1997; Kauffmann-Zeh et al., *Nature* 385:544–548, 1997; Kulik et al., *Mol. Cell Biol.* 17:1595–1606, 1997 24–26) may also converge on transcription factors related to DAF-16.

The normal requirement of age-1 activity for reproductive development is also bypassed by increased gene dosage of wild type akt-1. Transgenic age-1(mg44) animals carrying a 7.3 kb akt-1(+) genomic region can grow reproductively rather than arrest at the dauer stage. Greater than 75% of age-1(mg44) animals that contain the akt-1(+) transgene at high copy bypass dauer arrest while non-transgenic age-1 (mg44) animals never bypass dauer arrest. This rescue is dependent on a conserved lysine residue implicated in mammalian AKT/PKB kinase activity (Franke et al., *Cell* 81:727, 1995). In a similar experiment with age-1(mg44) animals carrying the same genomic region amplified from akt-1(mg144) at high copy, the transgenic animals bypassed dauer arrest at a similar frequency. The age-1(mg44) animals carrying the akt-1(mg144) transgene at low copy bypass dauer arrest more frequently than the age-1(mg44) animals carrying the akt-1(+) transgene at low copy (approximately 85% of age-1(mg44) animals carrying akt-1(mg144) transgene bypass dauer compared to 38% of age-1(mg44) animals carrying the akt-1(+) transgene). These results indicate that the same 7.3 kb genomic region amplified from the akt-1(mg144) strain is a more potent suppressor of age-1 (mg44) than the akt-1(+) transgene. These data map mg144 to the 7.3 kb region of akt-1 that includes the Ala183Thr substitution in AKT-1. However, while multiple independent akt-1(mg144) transgenes are more potent suppressors of age-1(mg44) than akt-1(+) transgenes, which suggests that more akt-1 gene activity is generated by akt-1(mg144), there is significant variation in the penetrance of suppression observed with different transgenes. In addition, even though akt-1(+) transgenes confer suppression of age-1(mg44) that is not observed with chromosomal akt-1(+), the penetrance of suppression of age-1(mg44) by either akt-1(+) or akt-1 (mg144) transgenes is less than from akt-1(mg144)/+ heterozygotes or akt-1(mg144) homozygotes. This may be due to mosaicism of akt-1 gene expression from transgenic arrays or a saturation of akt-1 gene function by high gene dosage. These data also suggest that the mutation may act by increasing AKT-1 abundance or stability, thus conferring the ability to grow in the absence of age-1 signaling.

Null mutations in age-1 cause dauer arrest as does inactivation of akt-1 and akt-2 by RNAi. This indicates that akt-1(+), akt-2(+), and age-1(+) are required for reproductive development. Because the dominant allele akt-1 (mg144) also promotes reproductive growth by virtue of its ability to suppress the dauer constitutive phenotype of age-1 null mutants, it functions similarly to akt-1(+) and akt-2(+). Thus akt-1(mg144) is an activating mutation, as opposed to a loss of function or dominant negative mutation in akt-1. In addition, the fact that both akt-1(mg144) and providing additional copies of the akt-1(+) gene suppress an age-1 null mutant is consistent with akt-1(mg144) being an activating mutation.

Because akt-1 and akt-2 function redundantly to repress dauer formation we asked whether overexpression of akt-2 (+) could also bypass the normal requirement of AGE-1 PI3K signaling. age-1(mg44) animals carrying the akt-2(+) transgene arrested as dauers while age-1(mg44) animals carrying the akt-1(+) transgene bypassed dauer. Thus, either because of differences in the AKT-2 protein or differences in protein expression, high gene dosage of akt-2 is not able to bypass the usual requirement for AGE-1 PI3K signaling.

akt-1(mg144) suppresses the dauer constitutive phenotype of three age-1 alleles. Because age-1(mg44) is a null mutant, these data strongly suggest that akt-1 acts downstream of age-1 and demonstrates that the biochemical ordering of PI3K upstream of Akt/PKB kinase is also true in an intact organism. AGE-1 is the only PI3K homolog in *C. elegans* of the type regulated by tyrosine kinase receptors. Significantly, our results demonstrate that *C. elegans* Akt/PKB gene activity is not strictly dependent on upstream age-1 activity if Akt/PKB activity is increased because akt-1(mg144) as well as akt-1(+) overexpression suppress null mutations in AGE-1 PI3K. This is comparable to the suppression by daf-16(m27), a reduction of function allele (Lin et al., *Science* 278:1319–1322, 1997), and daf-16 null alleles (Ogg et al., *Nature* 389:994–999, 1997).

A mutation in daf-2 is suppressed more poorly by akt-1 (mg144) than by a reduction of function mutation in daf-16. The age-1 alleles suppressed by akt-1(mg144) are null (Morris et al., *Nature* 382:536–539, 1996) whereas daf-2 (e1370) is a temperature sensitive mutation in the kinase domain (Kimura et al., *Science* 277:942–946, 1997). This daf-2 allele is completely suppressed by many daf-16 alleles, including null alleles (Gottlieb and Ruvkun, *Genetics* 137:107–120, 1994; Larsen et al., *Genetics*

139:1567–1583, 1995; Ogg et al., *Nature* 389:994–999, 1997). This result, in comparison to the robust suppression of age-1 mutations by akt-1(mg144), suggests that akt-1 is a major output of AGE-1 signaling and one of multiple outputs of DAF-2 signaling. In addition, because akt-1 (mg144) can bypass the need for AGE-1 PI3K signaling but not for DAF-2 insulin receptor-like signaling, akt-1(mg144) defines a bifurcation in the signaling pathway downstream of daf-2. It is likely that age-1 and akt-1 constitute one major signaling pathway from DAF-2 and that other, as yet unidentified genes, constitute one or more parallel pathways. These pathways converge downstream of AGE-1 and at or upstream of the DAF-16 Fork head transcription factor and negatively regulate its activity, since loss of function mutations in daf-16 completely suppress both daf-2 and age-1 mutations (Gottlieb and Ruvkun, *Genetics* 137:107–120, 1994). Because a decline in AGE-1 PI3K or AKT-1/AKT-2 signaling induces dauer arrest in the presence of signaling from this parallel pathway, both are necessary for reproductive development. The genetic evidence for multiple DAF-2 insulin receptor-like outputs demonstrate that biochemical studies showing that parallel PI3K, ras, SHP2, and other signaling outputs are activated by the insulin receptor in mammals (Kahn, *Diabetes* 43:1066–1084, 1994) are relevant to insulin receptor-like signaling in intact organisms.

In addition, a mutation in daf-2 is suppressed more poorly by akt-1(mg144) than by a reduction of function mutation in daf-16. The age-1 alleles suppressed by akt-1(mg144) are null (Morris et al. (1996) Nature 382:536–539) whereas daf-2(e1370) is a temperature sensitive mutation in the kinase domain (Kimura et al. (1997) Science 277:942–946). This daf-2 allele is completely suppressed by many daf-16 alleles, including null alleles (Gottlieb and Ruvkun (1994) Genetics 137:107–120; Larsen et al. (1995) Genetics 139:1567–1583; Ogg et al. (1997) Nature 389:994–999). This result, in comparison to the robust suppression of age-1 mutations by akt-1(mg144), suggests that AKT-1 is a major output of AGE-1 signaling and one of multiple outputs of DAF-2 signaling.

Overexpression of either akt-1(+) or akt-1(mg144) can bypass the need for DAF-2 signaling while overexpression of akt-2(+) or akt-1(KD) does not alleviate the need for DAF-2 signaling. However, akt-1(+) and akt-1(mg144) transgenes are more efficient suppressors of the dauer constitutive phenotype of age-1(mg44) than of daf-2(e1370). This supports the model that AKT-1 is a primary output of AGE-1 signaling but not DAF-2 signaling.

Reduction of zygotic age-1 activity increases *C. elegans* lifespan greater than two-fold (Morris et al., *Nature* 382:536–539, 1996; Larsen et al., *Genetics* 139:1567–1583, 1995; Klass, *Mech. Ageing Dev.* 22:279–286, 1983). Mutations in daf-16 suppress this lifespan increase (Larsen et al., *Genetics* 139:1567–1583, 1995; Dorman et al., *Genetics* 141:1399–1406, 1995). akt-1(mg144) does not suppress the age-1(mg44) induced increase in lifespan (for the following strains, mean lifespans, maximum lifespan are given: N2 12 days, 16 days, N=28; sqt-1(sc13) age-1(mg44) 18 days, 36 days, N=20; sqt-1(sc13) age-1(mg44); akt-1(mg144) 22 days, 38 days, N=36; daf-16(m27); sqt-1(sc13) age-1(mg44) 14 days, 16 days, N=32). Thus akt-1(mg144) bypasses the need for AGE-1 signaling in reproductive development but does not activate normal aging pathways. It is possible that akt-1(mg144) does not subserve all the functions of the wild type akt-1 or akt-2. akt-2 or other as yet unidentified downstream effectors of age-1 may be the pertinent signaling molecules for lifespan regulation.

The expression patterns of both akt-1 and akt-2 were examined in transgenic animals containing a translational fusion of each genomic locus to Green Fluorescent Protein (GFP) (Chalfie et al., *Science* 263:802–805, 1994). The GFP fusion proteins contain the entire genomic coding region from either akt-1 or akt-2, including 5' upstream regulatory sequence, fused in frame at the C-terminus to GFP. The AKT-1/GFP construct is sufficient to suppress the dauer constitutive phenotype of age-1(mg44) while the AKT-2/GFP construct is not. This result is not unexpected because increased gene dosage of akt-2(+) does not suppress age-1 (mg44) while increased gene dosage of akt-1(+) does. AKT-1/GFP expression is first observed in late embryos and is maintained throughout the life of the animal. In post-embryonic animals, AKT-1/GFP is expressed in the majority of head neurons including sensory neurons. Expression is also observed in motor neurons of the ventral and dorsal nerve cord, neuronal commissures and processes throughout the body, and the tail neurons. The fusion protein is localized throughout the cell body and axonal and dendritic processes of neurons but is usually excluded from the nucleus. Additional tissues which consistently express AKT-1/GFP include neurons and muscle cells of the pharynx, the rectal gland cells, and the spermatheca. AKT-1/GFP expression was observed more variably in a variety of cell types including hypodermis, intestine, muscle, some of the P cell descendants that form the vulva, and in the excretory canal.

Consistent with redundant roles of akt-1 and akt-2, an AKT-2/GFP full length protein fusion gene is expressed at the same times as AKT-1/GFP and in the same tissues that express AKT-1/GFP, although AKT-2/GFP seems to be less abundant. In dauers induced by starvation on crowded plates, AKT-1/GFP and AKT-2/GFP expression does not differ dramatically from their expression during reproductive growth. These expression patterns are consistent with AKT-1 and AKT-2 functioning either in secretory neurons to regulate dauer arrest and metabolic shift or in the target tissues that are remodeled during dauer formation such as the pharynx, hypodermis, and intestine.

The activating mutation akt-1(mg144), as well as overexpression of akt-1(+), bypasses the normal requirement for AGE-1 PI3K signaling in the DAF-2 insulin receptor-like signal transduction pathway. These results demonstrate that *C. elegans* Akt/PKB gene activity is not strictly dependent on upstream age-1 activity if Akt/PKB activity is increased. In the almost complete *C. elegans* genome sequence, AGE-1 is the only PI3K homolog of the type known to generate 3-phosphoinositides. If AGE-1 is the only protein able to generate 3-phosphoinositides in *C. elegans*, these results suggest that, while normal AKT-1 signaling is dependent on 3-phosphoinositides, AKT-1 can become activated in their absence if gene dosage is increased or the mg144 mutation is introduced.

Importantly, either activated akt-1 or higher akt-1(+) gene dosage does not efficiently suppress mutations in the DAF-2 insulin receptor suggesting that age-1 and akt-1 constitute one major signaling pathway from DAF-2 and that other, as yet unidentified genes, constitute one or more parallel pathways. These pathways most likely converge on the DAF-16 Fork head transcription factor and negatively regulate its activity, since loss of function mutations in daf-16 completely suppress both daf-2 and age-1 mutations (Gottlieb and Ruvkun (1994) Genetics 137:107–120; Larsen et al. (1995) Genetics 139:1567–1583), as well as inactivation of akt-1 and akt-2 signaling.

While AKT-1 and AKT-2 appear to function redundantly in transduction of DAF-2/AGE-1 signals, increased akt-1 gene dosage is a much more potent suppressor of age-1 null mutations than increased akt-2 gene dosage. A major distinction between AKT-1 and AKT-2 is that AKT-1 bears two distinct phosphorylation sites (corresponding to Thr308 and Ser473 in human Akt/PKBa) that are necessary for activation of Akt/PKB by upstream growth factor inputs (Alessi et al. (1996) EMBO J. 15:6541–6551; Alessi et al. (1996) FEBS Letters 399:333–338) while AKT-2 only has the Thr308 phosphorylation site. In mammals, Akt/PKB is phosphorylated at Thr308 by PDK1 and at Ser473 by the as yet unpurified PDK2 (Alessi et al. (1997) Current Biology 7:261–269; Stokoe et al. (1997) Science 277:567–570). Thus AKT-1 may couple to a PDK2-like kinase whereas AKT-2 cannot do so. AKT-1 and AKT-2 may also differ in other kinase inputs or in their substrates. Interestingly, at lower temperatures, the akt-2(+) transgene can supply sufficient Akt/PKB activity to weakly suppress the dauer arrest caused by age-1(mg44). Temperature is a major modulator of dauer arrest (Riddle and Albert (1997) Genetic and Environmental Regulation of Dauer Larva Development. In *C. elegans* II (ed. D. L. Riddle, T. Blumenthal, B. J. Meyer and J. R. Priess), pp. 739–768, Cold Spring Harbor Laboratory Press, Cold Spring Harbor, N.Y.). The penetrance of dauer arrest in most dauer constitutive mutants is increased at high temperatures (Riddle and Albert (1997) Genetic and Environmental Regulation of Dauer Larva Development. In *C. elegans* II (ed. D. L. Riddle, T. Blumenthal, B. J. Meyer and J. R. Priess), pp. 739–768, Cold Spring Harbor Laboratory Press, Cold Spring Harbor, N.Y.), suggesting that some signals in the pathway are enhanced at low temperature. Thus at low temperatures perhaps PDK1 signaling to AKT-1 and AKT-2 or signaling in pathways parallel to AGE-1/AKT-1/AKT-2 are enhanced, allowing increased akt-2(+) gene dosage to weakly bypass the normal requirement for AGE-1 PI3K signaling.

Insulin-like and TGF-β neuroendocrine signals regulate whether animals arrest at the dauer stage or grow to reproductive adults (Kimura et al. (1997) Science 277:942–946; Riddle and Albert (1997) Genetic and Environmental Regulation of Dauer Larva Development. In *C. elegans* II (ed. D. L. Riddle, T. Blumenthal, B. J. Meyer and J. R. Priess), pp. 739–768, Cold Spring Harbor Laboratory Press, Cold Spring Harbor, N.Y.). The TGF-β-like molecule DAF-7 is a probable neuroendocrine signal: it is expressed in the sensory neuron ASI that represses dauer arrest (Bargmann and Horvitz (1991) Science 251:1243–1246) and its expression is regulated by dauer-inducing pheromone (Ren et al. (1996) Science 274:1389–1392; Schackwitz et al. (1996) Neuron 17:719–728). While the insulin-like ligand for the DAF-2 insulin-like receptor has not yet been identified, it may also be produced by secretory neurons and regulated by pheromone. Precedent from biochemical analysis predicts that DAF-2, AGE-1, AKT-1/AKT-2, and DAF-16 function in the same cells. It is not yet clear whether the DAF-2 signaling pathway acts in the target tissues that are remodeled in dauer larvae such as the pharynx, hypodermis, and intestine, or in other signaling cells that in turn control target tissues. The broad expression pattern of akt-1 and akt-2 includes the nervous system, pharynx, and hypodermis. This expression pattern is consistent with a role for these genes either in sensory neurons that signal to repress dauer arrest or in the target tissues that receive the dauer repressing signal. The expression patterns of daf-2 and age-1 have not been reported; daf-16 is widely expressed (Ogg et al. (1997) Nature 389:994–999) as are daf-3 and daf-4, two genes that comprise the DAF-7 TGF-β signal reception pathway (Patterson et al. (1997) Genes and Development 11:2679–2690). Mosaic or tissue-specific expression analysis will be required to demonstrate in which cell types the DAF-2 insulin-like and DAF-1/DAF-4 TGF-β signal transduction pathways act.

The role of AKT-1 and AKT-2 in regulating the metabolic shift and developmental arrest associated with dauer formation suggests the following model. Under normal growth conditions, an insulin-like molecule binds to the DAF-2 insulin receptor kinase inducing autophosphorylation and recruitment of AGE-1 PI3K. As discussed herein, PI3K signals via Akt/PKB. Precedent from biochemical experiments in other systems (Franke et al., *Cell* 81:727–736, 1995; Franke et al., *Science* 275:665–668, 1997; Klippel et al., *Mol. Cell Biol.* 17:338–344, 1997) suggests that AGE-1 activation produces phospholipids that bind to and activate AKT-1 and AKT-2 by inducing a conformational change in the protein that makes it accessible to phosphorylation events which are necessary for activation (Alessi et al., *Current Biology* 7:261–269, 1997; Stokoe et al., *Science* 277:567–570, 1997). A parallel pathway or pathways from the DAF-2 insulin receptor-like protein is also activated. The AKT-1 and AKT-2 kinases, as well as molecules from the parallel pathway, negatively regulate DAF-16 activity, possibly via phosphorylation. Phosphorylated DAF-16 could be inactive, function to activate genes required for reproductive growth and metabolism, or repress genes required for dauer arrest and energy storage. Other signaling molecules that are activated by DAF-2 must also converge downstream of AGE-1 (for example, on DAF-16 or AKT-1/AKT-2) for proper regulation of metabolism and lifespan: the dauer arrest induced by loss of AGE-1 PI3K or AKT-1/AKT-1 activity implies that the loss of only one of these inputs to DAF-16 is sufficient to cause dauer arrest. Under dauer inducing conditions, DAF-2, AGE-1, AKT-1/AKT-2, and other signaling pathways from DAF-2 are inactive and therefore DAF-16 is active, presumably because it is underphosphorylated. Active DAF-16 either represses genes required for reproductive growth and metabolism or activates genes necessary for dauer arrest and energy storage.

The DAF-16 Fork head protein has been suggested to interact with the DAF-3, DAF-8, or DAF-14 Smad proteins to integrate converging TGF-β like neuroendocrine signals with insulin-like signals (Ogg et al., *Nature* 389:994–999, 1997; Patterson et al., *Genes & Development* 11:2679–2690, 1997). DAF-16 may form a complex with the DAF-3 Smad protein under dauer inducing conditions to regulate these downstream genes (Ogg et al., *Nature* 389:994–999, 1997), while AKT-1 phosphorylation of DAF-16 may inhibit the formation of a Smad/Fork head complex during reproductive development.

Akt/PKB has been implicated in mammalian insulin receptor signaling that localizes glucose transporters to the plasma membrane (Kohn et al. (1996) J. Biol. Chem. 271:31372–31378) and has been shown to regulate glycogen synthesis via direct phosphorylation of GSK3 (Cross et al. (1995) Nature 378:785–789); two events that are not transcriptionally regulated. While there also may be such Akt/PKB outputs in *C. elegans*, the DAF-16 Fork head transcription factor represents the major output of DAF-2/AGE-1/AKT-1/AKT-2 insulin receptor-like signaling (Ogg et al. (1997) Nature 389:994–999). Similarly Akt/PKB action in the insulin/IGF-I anti-apoptotic pathway (Dudek et al. (1997) Science 275:661–665; Kauffmann-Zeh et al. (1997) Nature 385:544–548; Kulik et al. (1997) Mol. Cell Biol. 17:1595–1606) may also converge on transcription factors related to DAF-16.

The present model, based on genetic evidence that Akt/PKB couples insulin receptor-like signaling to transcriptional output via the DAF-16 Fork head transcription factor in *C. elegans*, predicts that Akt/PKB will have transcriptional outputs in insulin-like signaling across phylogeny. It was previously suggested that the human homologs of the DAF-16 transcription factor (AEX, FKHR, FKIHRL1 and AF6q21) may be the pertinent downsteam effectors of insulin signaling in humans (Ogg et al., *Nature* 389:994–999, 1997). Two of the consensus Akt/PKB sites conserved in DAF-16 and its human homologs are located outside of the Fork head DNA binding domain, and two sites are located in the highly basic W2 region of the Fork head domain that has been shown to mediate DNA phosphate backbone contacts (Clark et al. (1993) Nature 364:412–420). Insulin stimulated Akt/PKB phosphorylation of the W2 sites may affect DNA binding whereas the other conserved sites may affect transactivation. A recent report shows that Akt/PKB mediates insulin dependent repression of the insulin-like growth factor binding protein-1 (IGFBP-1) gene in HepG2 cells via a conserved insulin response sequence (CAAAAC/TAA) (SEQ ID NO:318) (Cichy et al., *J. Biol. Chem.* 273:6482–6487, 1998). Interestingly, we have determined that DAF-16 binds to this same insulin response sequence in vitro. We propose that Akt/PKB mediates its transcriptional effects on insulin responsive genes such as IGFBP-1 via the human homologs of DAF-16: AFX, FKHR, FKHRL1, or AF6q21.

In addition, genetic analysis suggests that drugs that activate AKT or PDK can bypass the need for AGE-1 PI3K signaling, and mapping of mutations to particular regions of AKT-1 and PDK-1 points out targets for activation of these enzymes. Thus, drugs that activate these kinases are expected to partially relieve defects in insulin signaling, for example, associated with type II diabetes. The genetic analysis described herein also suggests that another unknown output of DAF-2 insulin like signaling exists. That output may be identified using AKT gain of function mutations to activate the AGE-1 PI3K pathway and screening for mutations that allow daf-2 receptor mutations to grow reproductively. Alternatively, the genes in this parallel pathway may be identified by screening age-1;daf-18 mutants for arrest at the dauer stage.

PDK Genetics

From the same genetic screen that generated the akt-1 (mg144gf) allele, we identified another age-1 suppressor, mg142. This mutation also bypasses the need for upstream age-1 signaling and is genetically dominant. Genetic mapping placed the mutation in the region where a *C. elegans* homologue maps. The genomic sequence of pdk-1, starting 60 bp upstream of the start codon and ending 60 bp downstream of the stop codon is shown in FIG. 35 (SEQ ID NO: 158). FIGS. 36 and 37 show the two *C. elegans* pdk-1 spliced forms, pdk-1 a (FIG. 36; SEQ ID NO: 159) and pdk-1b (FIG. 37; SEQ ID NO: 160). The pdk-1(mg142) gain of function mutation is Ala303Val (splice 1). This protein is 58% identical to mammalian PDK in the plecstrin homology domain and 39% identical in the kinase domain as shown below (SEQ ID NOS: 170–199).

Score=252 (88.7 bits), Expect=2.2e−60, Sum P(6) =2.2e−60
Identities=47/80 (58%), Positives=60/80 (75%). Frame=+3

```
            Score = 252 (88.7 bits), Expect = 2.2e-60, Sum P(6) 2.2e-60
            Identities = 47/80 (58%), Positives = 60/80 (75%), Frame = +3

SEQ ID NO:170 Query:   439 LEKQAGGNPWHQFVENNLILKMGPVDKRKGLFARRRQLLLTEGPHLYYVDPVNKVLKGEI 498
SEQ ID NO:171              LE+Q   NP+H  F   N+LILK  G ++K++GLFARRR   LLTEGPHL  Y+D   N VLKGE+
SEQ ID NO:172 Sbjct: 1818 LEEQRVKNPFHIFTNNSLILKQGYLEKKRQIJFARRRMFLLTEGPHLLYIDVPNLVLKQEV 1997

SEQ ID NO:170 Query:   499 PWSQELRPEAKMFKTFFVHT 518
SEQ ID NO:171              PW+  ++E KN TFF+HT
SEQ ID NO:172 Sbjct: 1998 PWTPCMQVELKNSGTFFIHT 2057

Score = 201 (70.8 bits), Expect = 2.2e-60, Sum P(6) = 2.2e-60
            Identities = 48/123 (39%) , Positives = 72/123 (58%), Frame = +1

SEQ ID NO:173 Query:   263 SDLWALGCIIYQLVAGLPPFRAGNEYLIFQKIIKLEYDFPEKFFPKARDLVEKLLVLDAT 322
SEQ ID NO:174              +D+W LGCI++Q +AG PPFRA N+Y +  ++I +L++ FPE F   +A +++ K+LV
SEQ ID NO:175 Sbjct:   802 TDIWGLGCILFQCLAGQPPFRAVNQYHLLKRIQELDFSFPEGFPEEASEIIAKILV-G*H 978

SEQ ID NO:173 Query:   323 KRLGCE----EMEGYGP--------LKAHPFFESVTWENLHQQTPPKLTAYLPANSEDDE 370
SEQ ID NO:174              +L E     ++     P         L AH FFE+V W N+    PP L AY+PA   +E
SEQ ID NO:175 Sbjct:   979 ETLKTEYVIFNLQVRDPSTRITSQELMAHKFFENVDWVNIANIKPPVLHAYIPATFGEPE 1158

SEQ ID NO:173 Query:   371 DCYGN 375
SEQ ID NO:174              Y N
SEQ ID NO:175 Sbjct: 1159 -YYSN 1170

Score = 180 (63.4 bits), Expect = 2.2e-60, Sum P(6) = 2.2e-60
            Identities = 31/72 (43%), Positives = 52/72 (72%) , Frame = +2

SEQ ID NO:176 Query:   157 FGLSYAKNOELLKYIRKIGSFDETcTRFYTAEIVSALEYLHGKGIIHRDLKPENILIMED 216
SEQ ID NO:177              F +   +NG+L + + GSFD   ++F+ +EI++ L++LH    I+HRD+KP+N+L+ +D
SEQ ID NO:178 Sbjct:   287 FVIGLVENGDLGESLCHFGSFDMLTSKFFASEILTGLQFLHDNKIVHRDMKPDNVLIQKD 466

SEQ ID NO:176 Query:   217 MHIQITDFGTAK 228
SEQ ID NO:177              HI  ITDFG+A+
SEQ ID NO:178 Sbjct:   467 GHILITDFGSAQ 502

Score = 83 (29.2 bits), Expect = 2.2e-60, Sum P(6) = 2.2e-60
            Identities = 15/53 (28%), Positives = 32/53 (60%), Frame = +2
```

-continued

```
SEQ ID NO:179 Query:  108 YAIKILEKPHIIKENKVPYVTREFDVMSRLD-----HPFFVKLYFTFQDDEKL 155
SEQ ID NO:180             +A+K+L+K ++ + K+  + RE+++++ L      HPF  +LY   F D  ++
SEQ ID NO:181 Sbjct:    8 FAVKVLQKSYLNRHQKMDAIIREKNILTYLSQECGGHPFVTQLYTHFHDQARI 166

Score = 81 (28.5 bits), Expect = 2.2e-60, Sum P(6) = 2.2e-60
         Identities = 15/29 (51%), Positives = 19/29 (65%), Frame = +2

SEQ ID NO:182 Query:  519 PNRTYYLMDPSGNAHKWCRKIQEVWRQRY 547
SEQ ID NO:183             PNR YYL D    A +WC+ I +V R+RY
SEQ ID NO:184 Sbjct: 2129 PNRVYYLFDLEKKADEWCKAINDV-RKRY 2212

Score = 78 (27.5 bits), Expect = 2.2e-60, Sum P(6) = 2.2e-60
         Identities = 15/25 (60%), Positives = 18/25 (72%) , Frame = +3

SEQ ID NO:185 Query:  232 PESKQARANSFVGTAQYVSPELLTE 256
SEQ ID NO:186             PE  AR   +FVGTA YVSPE+L +
SEQ ID NO:187 Sbjct:  660 PEENTARRTTFVGTALYVSPEMLAD 734
```

Overall, *C. elegans* pdk-1 Exhibits the Following Homology to Human PDK- 1
Score=118 (54.4 bits), Expect=1.4e–104, Sum P(5)=1.4e–104 Identities=21/62 (33%), Positives=41/62 (66%)

Mapping of the mg142 mutation to this open reading frame establishes the function of this protein. It is much more closely related to PDK than to any other known kinase. PDK is a mammalian kinase that phosphorylates an essential

```
         Score = 118 (54.4 bits), Expect = 1.4e-104, Sum P(5) = 1.4e-104
         Identities = 21/62 (33%), Positives = 41/62 (66%)

SEQ ID NO:188 Query:  63 KRTSNDFMFLQSMGEGAYSQVFRCREVATDANFAVKVLQKSYLNRHQKMDAIIREKNILT 122
SEQ ID NO:189            K+    DF F ++GEG++S V   RE+AT   +A+K+L+K ++ +  K+  +RE+++++
SEQ ID NO:190 Sbjct: 76 KKRPEDFKFGKILGEGSFSTVVLARELATSREYAIKILEKRHIIKENKVPYVTRERDVMS 135

SEQ ID NO:188 Query: 123 YL 124
SEQ ID NO:189            L
SEQ ID NO:190 Sbjct: 136 RL 137

Score = 230 (106.0 bits), Expect = 1.4e-104, Sum P(5) = 1.4e-104
         Identities = 39/90 (43%), Positives = 63/90 (70%)

SEQ ID NO:191 Query: 131 HPFVTQLYTHFHDQARIYFVIGLVENCDLGESLCHFGSFDMLTSKFFASEILTGLQFLHD 190
SEQ ID NO:192            HPF  +LY   F D  ++YF +   +NG+L ++    GSFD    ++F+ +EI++ L ++LH
SEQ ID NO:193 Sbjct: 139 HPFFVKLYFTFQDDEKLYFGLSYAKNGELLKYIRKIGSFDETCTRFYTAEIVSALEYLHG 198

SEQ ID NO:191 Query: 191 NKIVHRDMKPDNVLIQKDGHILITDFGSAQ 220
SEQ ID NO:192               I+HRD+KP+N+L+ +D HI ITDFG+A+
SEQ ID NO:193 Sbjct: 199 KGIIHRDLKPENILLNEDMHIQITDFGTAK 228

Score = 238 (109.7 bits), Expect = 1.4e-104, Sum P(5) = 1.4e-104
         Identities = 43/98 (43%), Positives = 67/98 (68%)

SEQ ID NO:194 Query: 259 EENTARRTTFVGTALYVSPEMLADGDVGPQTDIQGLGCILFQCLAGQPPFRAVNQYHLLK 318
SEQ ID NO:195            E   AR   +FVGTA  YVSPE+L +        +D+W LGCI++Q +AG PPFBA N+Y + +
SEQ ID NO:196 Sbjct: 233 ESKQARANSFVGTAQYVSPELLTEKSACKSSDLWALGCIIYQLVAGLPPFRAGNEYLIFQ 292

SEQ ID NO:194 Query: 319 RIQELDFSFPEGFPEEASEIIAKILVRDPSTRITSQEL 356
SEQ ID NO:195            +I +L++FPE F  +A +++ K+LV D + R+  +E+
SEQ ID NO:196 Sbjct: 293 KIIKLEYDFPEKFFPKARDLVEKLLVLDATKRLGCEEM 330

Score = 85 (39.2 bits), Expect = 1.4e-104, Sum F(5) = 1.4e-104
         Identities = 17/35 (48%), Positives = 21/35 (60%)

SEQ ID NO:197 Query: 356 LMAHKFFENVDWVNIANIKPPVLHAYIPATFGEPE 390
SEQ ID NO:198            L AH FFE+V W N+PP L AY+PA   +E
SEQ ID NO:199 Sbjct: 336 LKAHPFFESVTWENLHQQTPPKLTAYLPANSEDDE 370

Score = 324 (149.3 bits), Expect = 1.4e-104, Sum F(5) = 1.4e-104
         Identities = 59/104 (56%), Positives = 75/104 (72%)

SEQ ID NO:200 Query: 458 LEEQRVKNPFHIFTNNSLILKQGYLEKKRGLFARRRMFLLTEGPHLLYIDVPNLVLKGEV 517
SEQ ID NO:201            LE+Q   NP+H F  N+LILK G ++K++GLFARRR   LLTEGPHL Y+D  N VLKGE+
SEQ ID NO:202 Sbjct: 439 LEKQAGGNPWHQFVENNLILKMPGPVDKRKGLFARRRQLLLTEGPHLYYVDPVNKVLKGEI 498

SEQ ID NO:200 Query: 518 PWTPCMQVELKNSGTFFIHTPNRVYYLFDLEKKADEWCKAINDV 561
SEQ ID NO:201            PW+   ++  E KN   TFF+HTPNR YYL D    A +WC+ I +V
SEQ ID NO:202 Sbjct: 499 PWSQELRPEAKNFKTFFVHTFNRTYYLMDPSGNARKWCRKIQEV 542
``` serine residue on AKT, contributing to its activation. The region of akt-1 phosphorylated by PDK-1 is shown below (SEQ ID NO: 203–207 and 305).

homologues of AKT-1, AKT-2, and PDK-1 may activate these kinases, bypassing the need for upstream insulin input and ameliorating the glucose intolerance.

```
SEQ ID NO:203 human AFT 276 KLENLMLDKDGHIKITDFGLCKEGIKDGATMKTFCGTPEYTLAPEV 320
SEQ ID NO:204               KLENL+LDKDGHIKI DFGLCKE I G    TFCGTPEYLAFEV
SEQ ID NO:205 Ce akt-133509 KLENLLLDKDGHTKIADFGLCKEEISFGDKTSTFCGTPEYLAPEV 33643

SEQ ID NO:206 Ceakt2 326 LCKEEIKYGDKTSTPCGTPEYLAPEVIEDIDYDRSVDWWGVGVVMYEMMCGRLPFSAKENGK
SEQ ID NO:207            LCKE I G    TFCGTPEYLAEV+ED DYR+VDWWG+GVVMYEMMCGRLPF  +++ +
SEQ ID NO:305 moAKT: 298 LCKEGISDGATMKTPCGTPEYLAPEVLEDNDYGRAVDWWGLGVVMYEMMCGRLPFYNQDHER
```

The phosphorylated serine is conserved in akt-1 and akt-2. Thus, PDK is an excellent candidate gene for the mg142 mutation. The genetic region bearing pdk-1 was amplified from the mg142 strain, and an amino acid substitution in a conserved region of the PDK kinase domain was detected. While a gain of function mutation in pdk would be consistent with the biochemical work that shows that PDK acts upstream of AKT to activate it, this genetic work suggests that, if PDK can be activated (for example, by the mg142 mutation), no PIP3 signaling from the AGE-1 PI3K is necessary, since mg142 suppresses an age-1 null allele. To establish that this substitution causes the suppression of age-1 induced dauer arrest, a strategy analogous to that used to analyze the akt-1(mg144gf) mutation may be utilized.

Because we have implicated PDK in the *C. elegans* insulin signaling pathway, human PDK1 becomes a candidate gene for variation in diabetes. Mutations in human PDK1 may underlie the genetic variation that causes diabetes in some families. Similarly, drugs that activate PDK, like the mg142 mutation that activates *C. elegans* pdk-1, may bypass the need for upstream signaling in some diabetics with such upstream defects. The region of human PDK1 that is homologous to the *C. elegans* pdk-1 at alanine 303 provides a good candidate for screening for drugs that bind and activate signaling. Similarly, the region of human AKT between the kinase domain and the PH domain, where the *C. elegans* akt-1 gain of function mutation maps is a good candidate for the design of drugs that activate AKT. Exemplary screens identify daf-2 receptor mutations that are capable of reproductive growth or age-1;daf-18 mutants that arrest at dauer stage. Such activated AKT in *C. elegans* bypasses the need for upstream signaling from the AGE-1 PI3K and may similarly treat diabetics with defects in insulin signaling between insulin and AKT.

In addition, another mutation, pdk-1(lof), has been identified as a Gly to Arg substitution at position 295. This mutation causes dauer arrest in an otherwise wild-type background. This and the mg142 mutation are located near the psuedosubstrate binding region of PDK-1, based on the crystal structure of PKA. It is likely that the G to R mutation disallows recognition of the substrate AKT-1 and AKT-2, whereas the A to V gain of function mutation may disallow recognition of a psuedosubstrate site on PDK but allow recognition of the substrate, AKT-1 and AKT-2.

Our gain of function mutations in PDK-1 and AKT-1 point to negative regulatory domains of these proteins. For example, the region flanking the akt-1(mg144) mutation in the nonconserved domain of akt-1 may mediate blocking of the kinase activity, so that when this region is mutant, the kinase is more active. Similarly the region flanking the pdk-1(mg142) mutations in the conserved kinase domain may promiscously activate pdk-1. This region is conserved in human pdk-1 and may expose the kinase domain to the substrates, AKT-1 and AKT-2, constitutively. Chemicals that target the homologous or analogous domains in the human Function of the Insulin-Like Pathway in Neurons In addition to the above results, we have also found that the dauer arrest and aging effects of defects in age-1 signaling can be complemented by expression of this gene in the nervous system only. We used the nervous system-specific promoter unc-14 to drive expression of an age-1 cDNA. The age-1 fusion genes were placed in an age-1 null mutant, mg44, which arrests at the dauer stage 100% of the time and shifts to fat storage metabolism if no maternal or zygotic age-1 is supplied. Expression of age-1 in just the nervous system in this mutant completely complemented the dauer arrest and long lifespan phenotypes and partially complemented the metabolic fat storage defect. The expression of age-1 from a ubiquitous promter, dpy-30, rescued all of the defects of an age-1 mg44 null mutant. In parallel experiments, two different nervous system promoters, unc-14 and unc-119, were used to drive expression of daf-2 cDNA in daf-2 mutant animals. However, neuronal expression of DAF-2 did not rescue the aging or metabolic phenotypes of the daf-2 mutants. Given the multiple insulin-like ligands for DAF-2, these results may indicate that there is differential splicing of this receptor so that the cDNA introduced in these experiments supplied only one functional isoform. On the other hand, age-1 rescues all phenotypes when expressed ubiquitously, arguing against a differential splicing mechanism.

These data indicate that the insulin signaling pathway can regulate dauer arrest from the nervous system and may also regulate aging from the nervous system. The data also show that this pathway may function as well in target tissues to regulate metabolism. It is likely that the same situation may be true of mammalian insulin like signaling: the effects of insulin on aging may be in the nervous system whereas their well known effects on muscle and adipocyte metabolism may be akin to the DAF-2/AGE-1 regulation of metabolism from non-neuronal foci of action.

Diapause and Longevity

Weak daf-2 and age-1 mutants that do not arrest at the dauer stage nevertheless live much longer than wild-type (Larsen et al., *Genetics* 139: 1567–1583, 1995; Kenyon et al., *Nature* 366: 461–464, 1993; Dorman et al., *Genetics* 141: 1399–1406, 1995). This connection between longevity and diapause control may not be unique to *C. elegans*. Diapause arrest is an essential feature of many vertebrate and invertebrate life cycles, especially in regions with seasonal temperature and humidity extremes (Tauber et al., *Seasonal Adaptation of Insects*, Oxford University Press, New York, N.Y., 1986). Animals in diapause arrest slow their metabolism and their rates of aging, and can survive for periods for much longer than their reproductive lifespan (Tauber et al., supra, 1986).

Because insulin-like DAF-2/AGE-1 signaling mediates *C. elegans* diapause longevity control, the mammalian insulin signaling pathway may also control longevity homologously. In fact, the increase in longevity associated with decreased DAF-2 signaling is analogous to mammalian longevity increases associated with caloric restriction (Finch, *Longevity, Senescence and the Genome*, The University of Chicago Press, Chicago, 1990). It is possible that caloric restriction causes a decline in insulin signaling to induce a partial diapause state, like that induced in weak daf-2 and age-1 mutants. The induction of diapause-like states may affect post-reproductive longevity (Finch, supra), as in *C. elegans*. Alternatively, it is the changes in the mode and tempo of metabolism itself rather than diapause per se that causes increased longevity. Another long-lived *C. elegans* mutant, clk-1, may also regulate lifespan via such metabolic effects (Ewbank et al., *Science* 275: 980–983, 1997). This association of metabolic rate with longevity is also consistent with the correlation of free radical generation to aging (Finch, supra).

Daf-18 Suppresses the Metabolic and Dauer Phenotypes of Age-1 and Daf-2

In addition to the genes described above, we have also discovered that daf-18 functions in the insulin signaling cascade as follows. age-1 null mutant progeny of heterozygote mothers are maternally rescued for arrest at the dauer diapause stage (Gottlieb and Ruvkun (1994) Genetics 137:107–120), but not for accumulation of fat (FIG. 38D) or increased longevity (Gottlieb and Ruvkun (1994) Genetics 137:107–120). The progeny of these fat and long lived age-1 homozygous animals, which receive no maternal or zygotic AGE-1 PI3K activity, arrest development as dauer larvae (Morris et al. (1996) Nature 382:536–539) (Tables VII and VIII).

TABLE VII

Suppression of daf-18 by inhibition of akt-1 and akt-2 gene activity

| | | Phenotype of Progeny at 25° C.(%) | | | |
|---|---|---|---|---|---|
| Strain | dsRNA injected | L4 and Adult | Dauer | Other | N |
| Wild type (Bristol N2) | uninjected | 99.8 | 0 | 0.2 | 1040 |
| Wild type (Bristol N2) | akt-1 & akt-2 | 13.7 | 85.9 | 0.3 | 2199 |
| daf-18(e1375) | uninjected | 99.1 | 0 | 0.9 | 1213 |
| daf-18(e1375) | akt-1 & akt-2 | 23.2 | 76.6 | 0.2 | 1455 |
| daf-16(mgDf50) | uninjected | 99.9 | 0 | 0.1 | 1266 |
| daf-16(mgDf50) | akt-1 & akt-2 | 97.5 | 0 | 2.5 | 1970 |
| age-1(mg44) | uninjected | 0 | 99.5 | 0.4 | 228 |
| age-1(mg44) | akt-1 & akt-2 | 0 | 94.2 | 5.8 | 277 |
| age-1(mg44); daf-18(e1375) | uninjected | 99.3 | 0.7 | 0 | 274 |
| age-1(mg44); daf-18(e1375) | akt-1 & akt-2 | 14.4 | 85.0 | 0.7 | 592 |
| daf-16(mgDf50); age-1(mg44) | uninjected | 100 | 0 | 0 | 465 |
| daf-16(mgDf50); age-1(mg44) | akt-1 & akt-2 | 96.2 | 0 | 3.8 | 1098 |
| daf-2(e1370) | uninjected | 0 | 99.1 | 0.9 | 109 |
| daf-2(e1370) | akt-1 & akt-2 | 0 | 100 | 0 | 176 |
| daf-2(e1370); daf 18(e1375) | uninjected | 2.2 | 97.8 | 0 | 225 |
| daf-2(e1370); daf 18(e1375) | akt-1 & akt-2 | 0 | 99.9 | 0.1 | 682 |
| daf-16(mgDf50); daf-2(e1370) | uninjected | 100 | 0 | 0 | 487 |
| daf-16(mgDf50); daf-2(e1370) | akt-1 & akt-2 | 99.1 | 0 | 0.9 | 780 |

'Other' includes animals that could not be classified as dauer or non-dauer because the animal died as an embryo or young larva.
N, total number of animals scored.

TABLE VIII

Suppression of age-1 and daf-2 by inhibition of daf-18 gene activity

| | | Phenotype of Progeny at 23° C.(%) | | | |
|---|---|---|---|---|---|
| Strain | dsRNA injected | L4 and Adult | Dauer | Other | N |
| Wild type (Bristol N2) | uninjected | 100 | 0 | 0 | 763 |
| Wild type (Bristol N2) | daf-18 | 99.4 | 0 | 0.6 | 1305 |
| age-1(m333) | uninjected | 0 | 100 | 0 | 434 |
| age-1(m333) | daf-18 | 94.2 | 5.6 | 0.3 | 771 |
| age-1(mg109) | uninjected | 0 | 99.4 | 0.6 | 172 |
| age-1(mg109) | daf-18 | 94.7 | 0.3 | 5.0 | 341 |
| age-1(mg44) | uninjected | 0 | 97.9 | 2.1 | 389 |
| age-1(mg44) | daf-18 | 90.7 | 7.1 | 2.1 | 701 |
| age-1(mg44); daf-18(e1375) | uninjected | 99.8 | 0 | 0.2 | 569 |
| daf-2(e1370) | uninjected | 0 | 100 | 0 | 606 |
| daf-2(e1370) | daf-18 | 57.7 | 39.8 | 2.5 | 1266 |
| daf-2(e1370); daf-18(e1375) | uninjected | 6.3 | 93.7 | 0 | 317 |

'Other' includes animals that could not be classified as dauer or non-dauer because the animal died as an embryo or young larva.
N, total number of animals scored.

Dauer larvae accumulate large amounts of fat (FIG. 38E) and live much longer than reproductively growing animals (Klass and Hirsh (1976) Nature 260:523–525). The dauer arrest (Gottlieb and Ruvkun (1994) Genetics 137:107–120; Larsen et al. (1995) Genetics 139:1567–1583; Tables VII and VIII), fat accumulation (FIG. 38F) and longevity phenotypes (Larsen et al. (1995) Genetics 139:1567–1583) of age-1 null mutations are suppressed by daf-18(e1375). daf-18(e1375) gene activity does not appear to interfere with normal age-1 signaling and growth because daf-18(e1375) mutant animals in a wild type age-1 background accumulate wild type amounts of fat (FIG. 38B).

Although daf-18(e1375) behaves as a semi-dominant suppressor of age-1, it phenocopies inactivation of daf-18(+) gene activity by RNA interference (RNAi) (see below). This suggests that daf-18(e1375) is a loss-of-function allele that is either haploinsufficient or dominantly antimorphic. The bypass of the normal requirement for AGE-1 PI3K signaling by daf-18(e1375) suggests that either lack of AGE-1 activity causes increased daf-18 activity or that decreased daf-18 activity increases PIP3 signals in an AGE-1-independent manner.

Although daf-18(e1375) readily suppresses age-1 mutations for the metabolic, dauer, and longevity phenotypes, daf-18(e1375) is a less effective suppressor of daf-2 insulin receptor-like mutations (Dorman et al. (1995) Genetics 141:1399–1406; Larsen et al. (1995) Genetics 139:1567–1583 and Tables VII and VIII). This is similar to the gain-of-function akt-1(mg144) which can suppress age-1 null mutants, but not daf-2 mutants (Paradis and Ruvkun (1998) Genes Dev. 12:2488–2498). Like the increase in akt-1 gene activity induced by akt-1(mg144), the decrease in daf-18 gene activity caused by daf-18(e1375) can bypass the normal requirement for AGE-1 PI3K signaling, but not for DAF-2 insulin receptor-like signaling (Tables VII and VIII). As in the case of biochemically studied receptor tyrosine kinases, the DAF-2 receptor may have multiple parallel outputs, with AGE-1, AKT-1/AKT-2, and DAF-18 acting in one of these pathways. Signals from DAF-2 converge at the DAF-16 Fork head transcription factor, because null mutations in daf-16 suppress all known phenotypes of daf-2 and age-1 null mutations (Ogg et al. (1997) Nature 389:994–999; Tables VII and VIII).

Daf-18 Functions Upstream of Akt-1 and Akt-2

In contrast to the action of DAF-2 and AGE-1, AKT-1 and AKT-2 act downstream of DAF-18. akt-1 and akt-2 function redundantly in the regulation of dauer arrest. Inhibition of both gene activities in wild type animals by RNAi causes constitutive dauer arrest, whereas inhibition of either akt-1 or akt-2 alone does not (Paradis and Ruvkun (1998) Genes Dev. 12:2488–2498). Inhibition of akt-1 and akt-2 by RNAi causes dauer arrest in either daf-18 or wild type animals (77% and 86%, respectively, Table VII). In contrast, 0% of daf-16(mgDf50) animals arrest as dauers when akt-1 and akt-2 are inhibited (Paradis and Ruvkun (1998) Genes Dev. 12:2488–2498 and Table VII). Thus mutations in daf-18 do not bypass the normal requirement for akt-1 and akt-2 activity. These data suggest that daf-18 functions upstream or parallel to akt-1 and akt-2.

The suppression of age-1 null mutations by daf-18(e1375) is also dependent upon akt-1 and akt-2. No progeny of age-1(mg44) null mutant homozygous animals develop to become fertile adults (99% dauer larvae, Table VII). In contrast, few age-1(mg44); daf-18(e1375) animals arrest as dauers (0.7% dauer larvae, Table VII), instead of developing into reproductive adults. However, when akt-1 and akt-2 are inhibited by RNAi in age-1(mg44); daf-18(e1375), most progeny arrest at the dauer stage (85% dauers, Table VII). The weaker suppression of daf-2 by daf-18 is also dependent upon akt-1 and akt-2 (Table VII). These data suggest that the ability of daf-18 to suppress defects in insulin-like signaling is dependent upon akt-1 and/or akt-2, showing that daf-18 acts downstream of AGE-1 PI3K, but upstream of AKT-1 and AKT-2 in this signaling cascade.

Daf-18 Encodes a Homologue of Mammalian PTEN (MMAC1/TEP1)

Daf-18 maps to a genetic region (Larsen et al. (1995) Genetics 139:1567–1583) which bears the probable C. elegans homologue (T07A9.6) of the tumor suppressor gene PTEN (Li and Sun (1997) Cancer Res. 57:2124–2129; Li et al. (1997) Science 275:1943–1947; and Steck et al. (1997) Nat. Genet. 15:356–362). Consistent with the role of PTEN as a daf-18 homologue is the fact that PTEN has lipid phosphatase activity that dephosphorylates position 3 on the inositol ring of $PIP_3$ in vitro and decreases the levels of the lipid products of PI3K in response to insulin signaling in human 293 cells (Maehama and Dixon (1998) J. Biol. Chem. 273:13375–13378). Accordingly, a decrease in PTEN activity would be predicted to enhance PI3K signaling, consistent with daf-18 activity. Genetic mapping, the detection of the daf-18(e1375) mutation in this PTEN homologue, and the similar phenotype to daf-18(e1375) caused by RNAi of this PTEN homologue all demonstrate that daf-18 corresponds to this gene.

The sequence of a full length daf-18 cDNA predicts a protein of 962 amino acids (FIGS. 40A and 40B). Homology between DAF-18 and human PTEN (U93051; Li et al. (1997) Science 275:1943–1947) is highest within the phosphatase domain (38% identical, 94/250 aa) which is located at the amino-terminal end of both proteins (FIGS. 39A and 39B). Amino acids surrounding the probable active site $Cys-(X)_5-Arg$ sequence are 90% identical (18/20 aa) between DAF-18 and PTEN (FIG. 39B). This suggests that the substrate specificity of DAF-18 and PTEN may be similar.

Using the canonical daf-18 PTEN cDNA sequences and genomic sequence from the C. elegans Genome Sequencing Consortium, the coding region and intron/exon boundaries of daf-18 were sequenced in daf-18(e1375) and compared to the sequence of wild type. A 30 base pair insertion mutation was detected in daf-18(e1375) (FIG. 39A). This insertion mutation occurs within exon 4 and is predicted to insert 6 amino acids to the coding sequence before introducing a stop codon. The insertion is composed of a thirteen base pair repeat and two smaller repeat segments. The mutation is predicted to leave the phosphatase domain intact, but to truncate the carboxy-terminal half of the protein. Since the mutation maps to an unconserved domain and because inhibition of daf-18 by RNAi is more severe than daf-18 (e1375) (see below), it is unlikely that daf-18(e1375) is a null mutant.

Although many of the oncogenic human PTEN mutations map to the phosphatase domain, several have been identified in the carboxy-terminal half of the protein (see the Human Gene Mutation Database and references therein; Krawczak and Cooper (1997) Trends Genet. 13:121–2). These carboxy-terminal mutations are analogous to daf-18(e1375). Since some oncogenic mutations in PTEN and the daf-18 (e1375) allele are localized to the carboxyl-terminal end, these regions, though unconserved between C. elegans and mammals, may be critical for phosphatase localization or function.

Daf-18(e1375) is the only identified daf-18 allele, despite the extensive genetic screens that have been done for genes in the daf pathway. Additional daf-18 alleles have not been isolated in screens for suppressors of daf-2 (in contrast to the scores of daf-16 alleles), which may be due to the weak suppression of daf-2 by daf-18(e1375) (Tables VII and VIII). Because of the strong suppression of age-1 null mutants by daf-18(e1375), more alleles would be expected from screens for age-1 suppressor mutations.

The daf-18(e1375) allele causes other phenotypes besides suppression of the age-1 null mutant. 8% of daf-18(e1375) animals (n=831) die as adults with a burst vulva compared to 0% of wild type (Bristol N2) adults (n=920) grown at 23° C. This suggests that daf-18 may function in other signal transduction pathways. Consistent with this, a daf-18 promoter::green fluorescent protein fusion is expressed in many tissues throughout the animal.

Inactivation of Daf-8 by RNAi Suppresses Age-1 and Daf-2

Inactivation of the C. elegans PTEN homologue T07A9.6 by RNAi confirms the assignment of daf-18 to the gene and the assignment of daf-18 to a function downstream of age-1 PI3K and upstream of akt-1 and akt-2. The inactivation of daf-18 by RNAi potently suppresses null mutations in age-1 and more weakly suppresses a daf-2 insulin receptor-like mutant. Whereas the homozygous progeny of three different age-1 mutant alleles, including two null alleles, arrest at the dauer stage virtually 100% of the time (Dorman et al. (1995) Genetics 141:1399–1406; Larsen et al. (1995) Genetics 139:1567–1583 and Table VIII), inhibition of daf-18 by RNAi suppresses the dauer constitutive phenotype of age-1(m333), age-1(mg109) and age-1(mg44) (only 6%, 1% and 8% dauers, respectively) (Table VIII). This is comparable to the suppression of age-1(mg44) by daf-18(e1375) (0% dauers, Table VIII).

Inhibition of daf-18 PTEN by RNAi partially suppresses a loss-of-function allele of the daf-2 insulin receptor-like gene. This suppression is most easily observed under conditions where daf-2 gene activity is decreased, but probably not missing. daf-2(e1370) is a temperature sensitive allele with a mutation in the kinase domain (Kimura et al. (1997) Science 277:942–946). At a low temperature (15° C.), daf-2(e1370) animals do not form dauers, but more restrictive temperatures (25° C. or 23° C.) cause 100% arrest at the dauer stage (Tables VII and VIII). The arrest of daf-2(e1370) at 23° C. is weakly suppressed by daf-18(e1375) (94% dauers), but inhibition of daf-18(+) by RNAi suppresses daf-2(e1370) much more potently (40% dauers) (Table VIII). At 25° C., daf-18(e1375) is a weaker daf-2 suppressor, suggesting that DAF-2 insulin receptor-like outputs, parallel to the AGE-1 PI3K, DAF-18 PTEN, and AKT-1/2 pathways, are more essential at this higher temperature. In contrast, the daf-16(mgDf50) null mutation completely suppresses daf-2 (e1370) at all temperatures (0% dauers, Tables VII and VIII). This suggests that divergent signals from DAF-2 (AGE-1/ DAF-18/AKT-1/2 and another putative pathway) converge upon DAF-16.

These results suggest that daf-18(e1375) is a partial loss-of-function mutation and that inhibition of daf-18 by RNAi causes a larger decrease in daf-18 gene activity. Similar to daf-18(e1375), the inhibition of daf-18 gene activity in wild type causes some animals to burst at the vulva, but no other obvious phenotypes. The inhibition of daf-18 gene activity by RNAi, however, does not necessarily reveal the phenotype induced by the complete loss of daf-18 gene activity.

Assignment of Daf-18 to the DAF-2 Signaling Pathway

Our assignment of the daf-18 molecular function to a homologue of the PTEN lipid phosphatase fits into our genetic analysis of its action in the DAF-2 insulin receptor-like signaling pathway. The genetic pathway analysis shows that DAF-18 is likely to act between the AGE-1 PI3K and AKT-1/AKT-2. Because PTEN has been shown to dephosphorylate position 3 of the inositol ring of PIP3, DAF-18 may modulate DAF-2 signals by decreasing the PIP3 output of AGE-1 PI3K. DAF-18 may normally decrease the level of PIP3 signals, perhaps insulating signals emanating from the DAF-2/AGE-1 signaling complex from other PIP3 signals in the cell, or resolving insulin-like signaling episodes by restoring lipid levels to pre-insulin status. Perhaps the long carboxyl-terminal tail region of DAF-18 PTEN mediates its localization to insulin signaling complexes, insulating them from other signaling complexes, or vice versa. Loss of DAF-18 would be expected to enhance PIP3 signaling to the Akt kinases by allowing the second messenger to promiscuously signal between receptor complexes.

It is not clear from the genetic analysis whether DAF-18/ PTEN activity is regulated during insulin-like or other signaling. For example, there may be phosphorylation input to activate or inactivate DAF-18 activity. One attractive possibility is that DAF-18 becomes activated by Akt or PDK1 as a component in the recovery from an episode of insulin signaling. It may be significant that PTEN lipid phosphatase activity in vitro is low (Maehama and Dixon (1998) J. Biol. Chem. 273:13375–13378), perhaps due to a missing modification by the insulin signaling cascade.

DAF-18 may also be regulated by a TGF-β signaling pathway. In C. elegans a TGF-β signaling pathway converges with the DAF-2 insulin receptor-like signaling pathway (Ogg et al. (1997) Nature 389:994–999) and PTEN expression has been reported to be downregulated by TGF-β signaling in cell culture (Li and Sun (1997) Cancer Res. 57:2124–2129). The C. elegans DAF-7 TGF-β and insulin-like signaling pathways are also synergistic, whereby declines in the TGF-β signals enhance the mutant phenotypes caused by declines in insulin-like signals (Ogg et al. (1997) Nature 389:994–999). If DAF-18 PTEN expression is similarly responsive to DAF-7 TGF-β inputs, its activity may mediate cross talk between these pathways in metabolic control.

The molecular assignment of DAF-18 to the PTEN lipid phosphatase rationalizes daf-18 genetic activities in C. elegans metabolic control and longevity. Reduction of daf-18 gene activity causes a decrease in fat storage in an age-1 mutant, perhaps because the ensuing activation of AKT-1 and AKT-2 mimics that induced by insulin-like signaling, causing a shift from fat storage metabolism to reproductive, perhaps sugar-based, metabolism. The daf-18(e1375) mutation also strongly suppresses the longevity increase caused by the weak age-1(hx546) PI3K mutation or the weak daf-2(e1370) insulin receptor-like mutation at a semipermissive temperature (Dorman et al., (1995) Genetics 141:1399–1406; Larsen et al. (1995) Genetics 139:1567–1583), whereas daf-18(e1375) only weakly suppresses the longevity increase caused by null age-1 mutations or daf-2(e1370) at the non-permissive temperature (Dorman et al., (1995) Genetics 141:1399–1406; Larsen et al. (1995) Genetics 139:1567–1583). These data show that even though the increase in $PIP_3$ levels caused by a decrease in daf-18 gene activity can bypass the need for AGE-1 signaling in dauer arrest, the resulting level of $PIP_3$ is not sufficient to induce normal aging. These results are congruent with aging and dauer arrest phenotypes of an age-1 allelic series: the highest levels of age-1(i.e., $PIP_3$) are necessary for normal longevity, whereas animals with decreased but non-zero levels of $PIP_3$ age more slowly, but do not arrest at the dauer stage. And only when both zygotic and maternal AGE-1 is missing do $PIP_3$ levels decline to the point that animals arrest at the dauer stage (Gottlieb and Ruvkun (1994) Genetics 137:107–120; and Riddle (1988) The Dauer Larva. In The Nematode Caenorhabditis elegans, W. B. Wood, ed. (Cold Spring Harbor, N.Y.: Cold Spring Harbor Laboratory), pp. 393–412). We have not yet determined whether the regulation of metabolism is the cause of the longevity phenotype (or vice versa) or represents a co-regulated output of the DAF-2 insulin receptor-like pathway.

This genetic behavior is similar to that of activated AKT-1, which can suppress the dauer arrest caused by complete lack of AGE-1 PI3K signaling, but not the longevity increase (Paradis and Ruvkun (1998) Genes Dev. 12:2488–2498). The suppression of the age-1 null mutant metabolic phenotypes by daf-18, but not by the akt-1 gain-of-function mutation, suggests that an increase in $PI(3,4)P_2$ and $PIP_3$ levels is a closer mimic to wild type than activated AKT-1, perhaps because both AKT-1 and AKT-2 are activated by increased lipid signaling in a daf-18 mutant. It may also be significant that declines in daf-18 activity and the presumed concomitant increase in $PI(3,4)P_2$ and $PIP_3$ levels in wild type has a negligible effect on longevity (Dorman et al., (1995) Genetics 141:1399–1406; Larsen et al. (1995) Genetics 139:1567–1583). Presumably, once $PIP_3$ levels are above a threshold, increasing their levels does not influence lifespan.

Our molecular model suggests that DAF-2, AGE-1, DAF-18, AKT-1, AKT-2, and DAF-16 act in the same cells. It has not addressed whether these genes in fact act in the same cells nor have we discerned whether this pathway acts in key endocrine signaling cells or in target tissues. daf-18, akt-1, and daf-16 are all expressed in neurons and throughout much of the animal (Ogg et al. (1997) Nature 389:994–999; Paradis and Ruvkun (1998) Genes Dev. 12:2488–2498), consistent with their function either in signaling cells or target tissues.

Inhibition of daf-18 can suppress age-1 mutations (m333 and mg44) that are predicted to truncate AGE-1 before the kinase domain and therefore generate no $PIP_3$ at all (Morris et al. (1996) Nature 382:536–539); Table VIII). The ability of daf-18 inhibition to suppress age-1 null mutations, and our demonstration that daf-18 suppression depends on the Akt kinases, suggests that there must be another source of PI(3,4)P$_2$ or PIP$_3$. This alternative source of lipids is not normally redundant with those generated by DAF-2/AGE-1 signaling because age-1 mutations have metabolism, reproductive growth, and lifespan phenotypes. In the absence of daf-18, lipids may accumulate to levels sufficient to activate the Akt kinases.

In addition to AGE-1, there are two other PI3K genes in the C. elegans genome. AGE-1 is the only member of the "Type I" class that includes the 110–130 kilodalton catalytic/ 50–85 or 101 kilodalton adaptor heterodimers (Vanhaesebroeck et al. (1997) TIBS 22:267–272). Members of this class of PI3Ks are activated by growth factors and heterotrimeric GTP-binding protein-coupled receptors and phosphorylate phosphatidylinositol, PI(4)P, and PI(4,5)P$_2$ to generate PI(3)P, PIP(3,4)P$_2$ and PIP$_3$ in vitro. PIP$_3$ may be dephosphorylated at the 5-position to yield the actual PI(3, 4)P$_2$ signal (Damen et al. (1996) Proc. Natl. Acad. Sci. U.S.A. 93:1689–93; Ono et al. (1996) Nature 383:263–6). The "type II" class is represented in C. elegans by F39B1.1. Members of this class are defined by amino terminal extensions and a C2 domain at their carboxy termini (Newton (1995) Curr. Biol. 5:973–6; Vanhaesebroeck et al. (1997) TIBS 22:267–272). C2 domains were originally described as Ca$^{2+}$-dependent phospholipid binding motifs, but they have been found to bind lipid in a Ca$^{2+}$-independent manner and may also mediate protein-protein interactions. Type II PI3Ks preferentially phosphorylate phosphatidylinositol and PI(4) P, over PI(4,5)P$_2$, to generate PI(3)P and PI(3,4)P$_2$. "Type III" PI3Ks are related to yeast protein VPS34 (Vanhaesebroeck et al. (1997) TIBS 22:267–272). These proteins have regulatory subunits and phosphorylate phosphatidylinositol, exclusively. Rather than being activated by cellular agonists, type III PI3Ks are thought to participate in vesicle sorting (De Camilli et al. (1996) Science 271:1533–9). The C. elegans gene, B0025.1, is most closely related to this family.

Since AGE-1 is the only known C. elegans type I PI3K, the type II PI3K, F39B1.1, may be the alternative source of 3-phosphorylated phosphoinositides which can activate Akt. DAF-18 may normally insulate DAF-2/AGE-1 signaling from other PI(3,4)P2 or PIP$_3$ second messenger signals in the cell. But when DAF-18 activity is inhibited, cross talk from this other PI3K may promiscuously activate the Akt kinases which are normally dependent on AGE-1 PI3K generated PIP3.

Our placement of DAF-18/PTEN downstream from AGE-1 PI3K and upstream from AKT-1 and AKT-2 suggests that mammalian PTEN may also regulate Akt activity by modulating PI3K signals. In fact, recent experiments with PTEN knockout mutant mice have shown that PTEN acts upstream of Akt in mammalian growth factor signaling pathways (Stambolic et al. (1998) Cell 95:29–39). More specifically, the action of DAF-18 PTEN in the C. elegans insulin signaling metabolic and longevity control pathway suggests that mammalian PTEN may modulate insulin control of metabolism and lifespan. Reduction in PTEN activity would be expected to potentiate insulin and/or insulin-like growth factor signaling, but an increase of PTEN activity would be expected to cause insulin resistance downstream of the insulin receptor, the type observed in late onset diabetes. Thus PTEN on chromosome 10 is a candiate gene for human autosomal dominant type II diabetes as well as for human longevity control.

Methods

The experiments described above were carried out using the following materials and methods.

Strains

Alleles used were as follows: LGI daf-16(mgDf50); LG II sqt-1(sc13) age-1(mg44)/mnC1, unc-4(e120) age-1(m333)/mnC1, unc-4(e120) age-1(mg109)/mnC1; LGIII daf-2 (e1370).

Sudan Black Staining

Larvae and young adults maintained in well fed conditions were washed in M9 buffer (Brenner (1974) Genetics 77:71–94) for 30 minutes, fixed in M9 with 1% paraformaldehyde, and subjected to three freeze thaws. Animals were then washed and dehydrated through washes with 25%, 50% and 70% ethanol. Staining was performed overnight in a 50% saturated solution of Sudan Black B in 70% EtOH. Stained animals were visualized with a Zeiss Axioplan microscope.

RNA Interference (RNAi) and Dauer Arrest Assays akt-1 and akt-2 RNAi was performed as described (Paradis and Ruvkun (1998) Genes Dev. 12:2488–2498). daf-18 RNAi was performed in a similar manner. The full length daf-18 cDNA was amplified by PCR from yk400b8 (Y. Kohara) using primers CM024 and CM025 (Paradis and Ruvkun (1998) Genes Dev. 12:2488–2498). RNA was transcribed using MEGAscript T3 and T7 kit (Ambion) and then single stranded RNA was combined prior to injection. L4 hermaphrodites or young adults were injected into the gut with approximately 5 $\mu$g/$\mu$l double stranded RNA and then were allowed to recover overnight at the experimental temperature. To assay dauer arrest, single injected animals or uninjected L4 hermaphrodites or young adults were moved to new plates and again on the next two subsequent days. All progeny laid after the recovery period were scored two days after being laid as dead eggs, dauer larvae, L4 larvae, adults or animals with aberrant development. "Dauers" included dauers and partial dauers as defined (Paradis and Ruvkun (1998) Genes Dev. 12:2488–2498). For the experiments with age-1 mutants, age-1 homozygous mutant progeny of age-1 heterozygous mothers were injected.

Sequencing

Genomic DNAs from daf-18(e1375) and wild type (Bristol N2) were PCR amplified and directly sequenced. A putative full length clone, yk400b8 (gift from Y. Kohara), was fully sequenced. The sequence of this clone and additional clones partially sequenced by Y. Kohara (yk423e3, yk400b8, yk419d6, yk282b4, yk226d6, yk219b10, yk200a11, yk181h9, yk49a4, and yk43e5) have a differ exon/intron structure than was predicted for T07A9.6 by Genefinder.

Drugs that Regulate DAF-18 PTEN Lipid Phosphatase in the Treatment of Diabetes, Obesity, and Aging Since DAF-18/PTEN is a lipid phosphatase, chemical modulation of its activity may be readily identified using any standard in vitro lipid phosphatase assay (see, for example, Maehama and Dixon, J. Biol. Chem. 273:13375, 1998). Chemicals identified by this initial screen may then be tested in a C. elegans assay as described herein. These tests are best done using the human homologue of DAF-18, the oncogene PTEN, both in vitro and transformed into a C. elegans strain lacking daf-18 gene activity (also as described herein). In particular, chemicals that activate human PTEN in vitro may be tested on C. elegans daf-18 mutants expressing human PTEN from the daf-18 promoter, assaying for dauer arrest, metabolic switch from fat storage, and/or increased longevity, either in an otherwise wild type background or in an age-1 or daf-2 mutant background. If desired, chemicals that perturb longevity or metabolism of such humanized *C. elegans* could also be tested on mice.

These chemicals would be expected to affect glucose and fat levels and treat type II diabetes and obesity. In particular, chemicals that activate DAF-18 would be expected in increase longevity. In addition, even though such chemicals could affect the cell cycle, since PTEN is a recessive oncogene, skin creams that activate PTEN would be expected to have youth enhancing activities. Conversely, chemicals that inhibit DAF-18 activity would be expected to treat type II diabetes and obesity, consistent with the fact that decreases in DAF-18 gene activity completely bypass the need for age-1 PI3 kinase signaling and partially bypass the need for daf-2 insulin receptor-like signaling. Thus, drugs that inhibit human PTEN activity in vitro are preferably tested on *C. elegans* for the ability to bypass the need for age-1 PI3K signaling in an animal carrying human PTEN expressed from the daf-18 promoter. In one particular example, any drug that inhibited human PTEN activity would allow an age-1(0); daf-18(0) mutant strain carrying human PTEN expressed from the daf-18 promoter to grow reproductively, rather than arresting in a manner characteristic of the parent strain. Thus, drugs shown to inhibit human PTEN in vitro could be tested on worms of the age1(0); daf-18(0); daf-18 promoter/PTEN genotype for ability to allow reproductive growth. If desired, such drugs could then be tested for diabetic therapeutic efficacy in mouse or rat models of obesity onset diabetes (as described herein). Drugs identified by this screen would treat some type II diabetic patients as well as some obese patients with defects in the PI3K outputs of the insulin receptor pathway.

Glucose Regulation by the *C. elegans* Insulin Like Signaling Pathway:

Confirmation of its Applicability to Human Diabetes

We have constructed a full length protein fusion of GFP to a highly expressed glucose transporter orthologue in the worm genome: H17B01. The H17B01.1 (GLUT) GEP fusion was amplified with primer CAW59 (ccactatggccgagatttcc) (SEQ ID NO: 319) and CAW60 (ccagtgaaaagttcttctcctttcttcctcttctcgaattcgga) (SEQ ID NO: 320). CAW 59 is the promoter primer and corresponds to nucleotides 31101–31120 in cosmid H17B01 and 39249–39268 in YAC Y51H7.contig253. Primer CAW60 is the GFP-fusion primer. The first 23 nucleotides are GFP and the last 21 are GLUT bottom strand (i.e., cttcctcttctcgaattcggc) (SEQ ID NO:321) corresponding to 48128–48108 in Y51H7.contig253 and 5015–5035 in C13F7 (the cosmid that joins H17B01). The protein sequence is as follows (SEQ ID NO: 208):

MGVNDHDVSVPLQEVQSRTVEGKLTKCLAFSAFVITLASFQFGYHIGCVN

APGGLITEWIIGSHKDLFDKELSRENADLAWSVAVSVFAVGGMIGGLSSG

WLADKVGRRGALFYNNLLALAAAALMGLAKSVGAYPMVILGRLIIGLNCG

FSSALVPMFLTEISPNNLRGMLGSLHQLLVTIAILVSQIFGLPHLLGTGD

RWPLIFAFTVVPAVLQLALLMLCPESPKYTMAVRGQRNEAESALKKLRDT

EDVSTEIEAMQEEATAAGVQEKPKMGDMFKGALLWPMSIAIMMMLAQQLS

GINVAMFYSTVIFRGAGLTGNEPFYATIGMGAVNVIMTLISVWLVDHPKF

GRRSLLLAGLTGMFVSTLLLVGALTIQNSGGDKWASYSAIGFVLLFVISF

ATGPGAIPWFFVSEIFDSSARGNANSIAVMVNWAANLLVGLTFLPINNLM

QQYSFFIFSGFLAFFIFYTWKFVPETKGKSIEQIQAEFEKRK

The predicted coiled-coil domain is from 237–258 (SEQ ID NO: 209):

RNEAESALKKLRDTEDVSTEIE

This transporter contains a coiled coil domain in common with the glut4 insulin responsive mammalian glucose transporter and the glut1 mammalian thrombin responsive glucose transporter of platelets. This coiled coil domain may mediate the tethering of these subfamily of glucose transporters adjacent to the plasma membrane so that these transporters can be fused upon triggering signals, for example, from insulin.

We have verified that the localization of the H17B01 glucose transporter is responsive to daf-2 insulin like signaling. In particular, the transporter is suspended in vesicles in a daf-2 mutant but is placed in the cell membrane in wild type animals with normal insulin like signaling. The insulin responsive fusion of these transporters with the cell membrane is most easily observed in the nervous system of *C. elegans*. This discovery endorses the glucoregulatory role of DAF-2 insulin like signaling in *C. elegans*, further confirming the orthology with mammalian insulin regulation of glucose transport. It also points out a possible regulatory role for glucose transport in the nervous system. It is possible that the regulation of sugar metabolism by insulin in the brain may be more important in humans than has previously been appreciated. The study of human insulin responses have been focused on peripheral tissues, but it is entirely possible that the central responses to insulin are key in the disease progression.

We have also shown that the glucose transporter genes of *C. elegans* are transcriptionally responsive to insulin signaling. The promoter of this gene is a good candidate for finding DAF-16 binding sites and DAF-3 binding sites. In mammals, glucose transporters are transcriptionally regulated by insulin signaling, suggesting that the connection between DAF-16 and the glucose transporter may be general to the DAF-16 homologues, AFX, FKHR, and FKHRL1 and mammalian glucose transporters such as Glut4 whose transcription is regulated by insulin. Indeed we find that the expression of the glucose transporter GFP fusion is down-regulated in starved wild type animals but is not so down-regulated in daf-16 mutant animals, suggesting that it is daf-16 activity that represses the expression of this gene.

Synergistic Control of Metabolism and Diapause by Insulin and TGF-β Signaling Pathways In addition to DAF-2 signaling, the DAF-7 TGF-β neuroendocrine signal is also necessary for reproductive development of *C. elegans* (Ren et al., *Science* 274: 1389–1391, 1996; Schackwitz et al., *Neuron* 17: 719–728, 1996). The signals in these two pathways are not redundant: animals missing either daf-2 signaling or daf-7 signaling (FIG. 3) shift their metabolism and arrest at the dauer stage (Table IX). In addition the phenotypes caused by mutations in either pathway are strongly synergistic, suggesting that the two pathways are integrated. Synchronised eggs were grown and counted as described above. daf-1(m40) and daf-2 (e1370) form 100% dauer at 25° C. Numbers shown in Table IX indicate percentage dauer formation and number of animals counted (in parenthesis). Data presented is the sum of three independent trials.

TABLE IX

Synergy of daf-1 and daf-2

| | % dauer formation | |
|---|---|---|
| | 15° C. | 20° C. |
| daf-1(m40) | 0.0(532) | 1.9(909) |
| daf-2(e1370) | 0.0(798) | 3.8(503) |
| daf-1(m40); daf-2(e1370) | 19.4(747) | 100(718) |

This data indicates that DAF-7 TGF-β signals and DAF-2 ligand insulin-like signals are integrated. In support of this model, weak mutations in the daf-2 insulin signaling pathway and in the daf-7 TGF-β signaling pathway are highly synergistic (Table IX). Genetic epistasis analysis indicates that the DAF-7 and DAF-2 pathways are parallel rather than sequential (Vowels and Thomas, *Genetics* 130: 105–123, 1992; Gottlieb and Ruvkun, *Genetics* 137: 107–120, 1994). That is, daf-16 mutations strongly suppress daf-2 mutations but not daf-7, daf-1, or daf-4 mutations, whereas daf-3 mutations strongly suppress daf-7, daf-1, and daf-4 mutations, but not daf-2 mutations. Analogous synergism between activin and FGF tyrosine kinase pathways in Xenopus mesoderm induction has been noted (Green et al., *Cell* 71: 731–739, 1992).

A dauer-inducing pheromone regulates the production of DAF-7 by the ASI sensory neuron (Ren et al., *Science* 274: 1389–1391, 1996; Schackwitz et al., *Neuron* 17: 719–728, 1996). Because animals carrying daf-7 nonsense or truncation mutations are responsive to pheromone (Golden and Riddle, *Proc. Natl. Acad. Sci. U.S.A.* 81: 819–823, 1984), we further suggest that the production of the insulin-like ligand for DAF-2 is also regulated by pheromone. It is not yet clear whether these DAF-7 and DAF-2 signals converge in target tissues or in other regulatory (i.e., hormonal) cells; however the expression of the DAF-7 receptor pathway genes in essentially all target tissues (infra) suggests that integration occurs there.

DAF-7 and Diabetes

Figure 17:
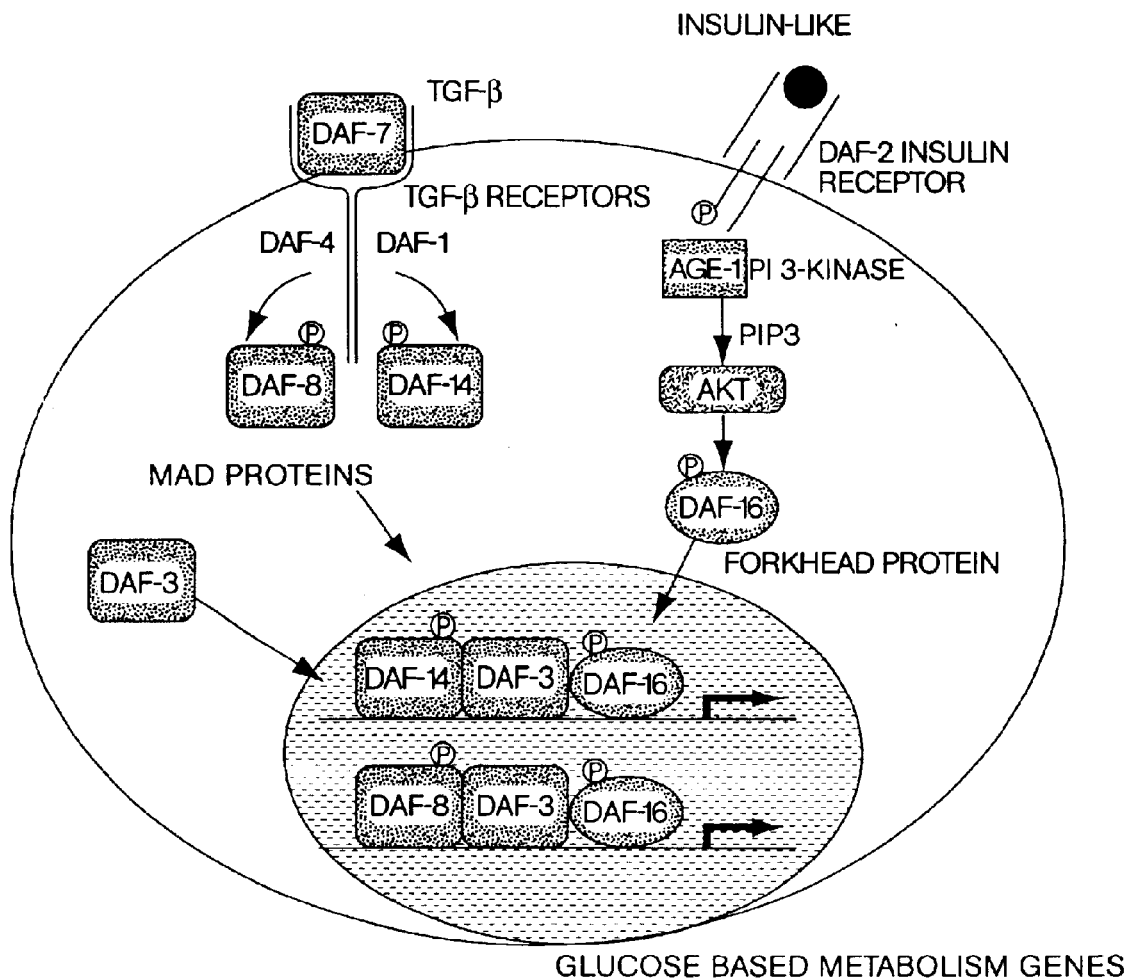
FIG. 17 is a schematic diagram illustrating that convergent TGF-β and insulin signaling activates glucose-based metabolic genes.
Figure 18:
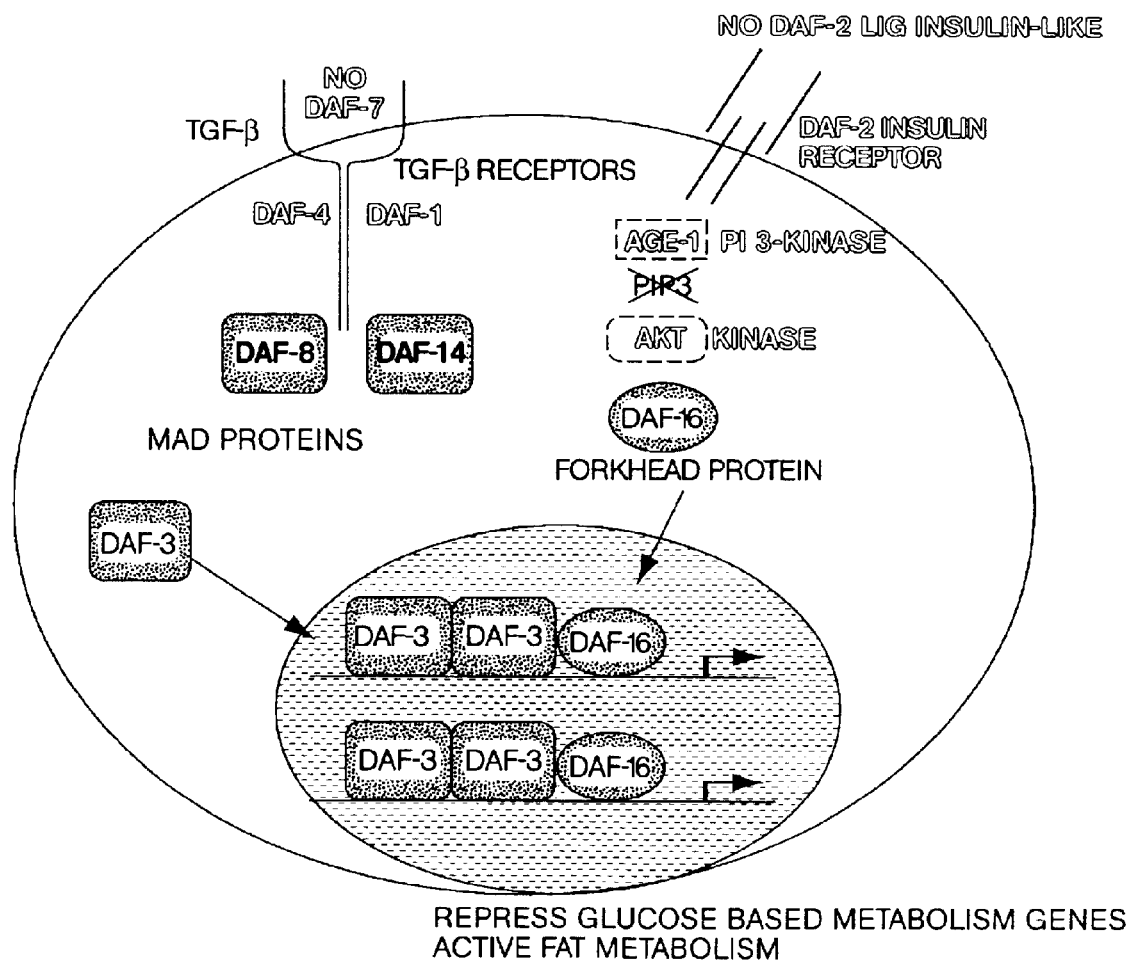
FIG. 18 is a schematic diagram illustrating a switch to fat-based metabolism in the absence of DAF-7 and DAF-2 signals (in pheromone).

Based on the data herein, we propose that in humans as in *C. elegans*, both a DAF-7-like neuroendocrine signal and insulin are necessary for metabolic control by insulin. According to this model, the failure of target tissues to respond to insulin signals in Type II diabetic patients could be due to defects either in the insulin or TGF-β-like control pathways. Pedigree analysis has shown a strong genetic component in Type II diabetes (Kahn et al., *Annu. Rev. Med.* 47: 509–531,1996). In addition, obesity is also a major risk factor in Type II diabetes (Kahn et al., *Annu. Rev. Med.* 47: 509–531,1996). Genetic or obesity-induced (Hotamisligil et al., *Science* 259: 87–91, 1993; Lonnqvist et al., *Nat Med* 1: 950–953, 1995) declines in a DAF-7-like signaling pathway could underlie the lack of response to insulin in Type II diabetes, just as in *C. elegans* daf-7 mutants cause metabolic defects very similar to daf-2 mutants. The discovery that the DAF-7 and DAF-2 pathways converge indicates that DAF-7 hormonal signals are defective in diabetic conditions (for example, Type II diabetes), and that administration of human DAF-7 is useful for ameliorating the glucose intolerance, ketoacidosis, and atherosclerosis associated with diabetes. This is shown schematically in FIGS. 17, 18, and 23.

Figure 4:
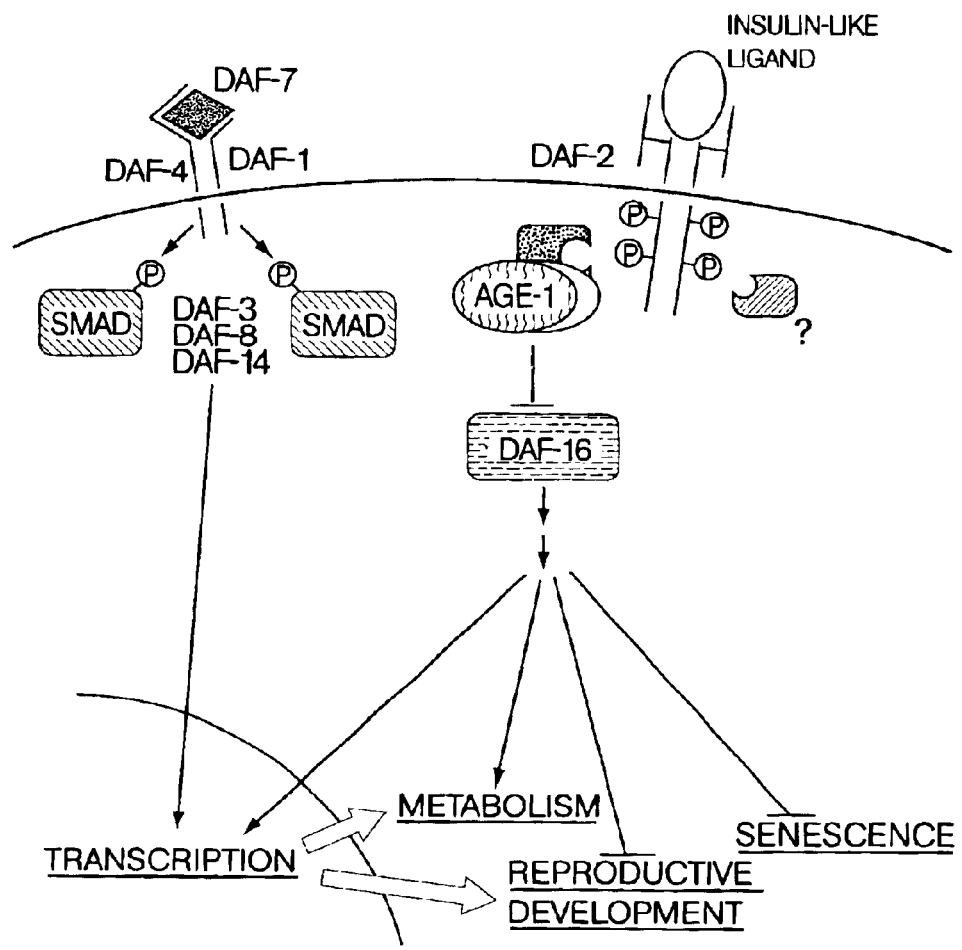

Whereas the DAF-7 TGF-β like and DAF-2 insulin-like signaling pathways converge to control diapause and metabolism, only the DAF-2/AGE-1 pathway has been implicated in reproductive adult stage longevity control in the absence of dauer formation (Larsen et al., *Genetics* 139: 1567–1583, 1995; Kenyon et al., *Nature* 366: 461–464, 1993; Dorman et al., *Genetics* 141: 1399–1406, 1995; and Morris et al., *Nature* 382: 536–539, 1996). Both pathways control the longevity increase associated with dauer arrest, since dauer larvae live much longer than reproductive *C. elegans* (Riddle, In: *Caenorhabditis elegans* II, D. Riddle, T. Blumenthal, B. Meyer, J. Priess, ed., Cold Spring Harbor Laboratory, Cold Spring Harbor, N.Y., 1997, pp. 739–768; Kenyon, op cit. pp., 791–813: Chayen and Bitensky, *Practical Histochemistry*, Chichester; N.Y.: Wiley, 1991. The distinction between DAF-7 and DAF-2 regulation of longevity could also reflect a more profound regulation of metabolism by the DAF-2 pathway than the DAF-7 pathway (FIG. 4). For example, based on precedents from TGF-β signaling in other systems and analysis of this pathway in *C. elegans*, all of the known signaling output of the DAF-7 TGF-β pathway are via downstream Smad transcriptional regulation (infra). Insulin signaling, and by extension, DAF-2 signaling, is more ramified: outputs from this receptor regulate sugar transport, metabolic enzyme activities, translation of mRNAs encoding these and other enzymes, as well as transcription (White and Kahn, *J. Biol. Chem.* 269: 1–4, 1994). We suggest that it is the regulatory output distinct to the DAF-2 pathway that controls longevity. Alternatively, TGF-β and insulin-like signals may converge only during the L1 stage, when diapause is regulated, and that after this stage, only DAF-2 signaling is necessary for normal metabolic control.

The involvement of insulin and TGF-β signaling in *C. elegans* diapause control suggests that the homologous human pathways may similarly mediate response to famine. Just as environmental extremes can select for variation in the genetic pathways that regulate *C. elegans* dauer formation, famines and droughts in human history may have selected for analogous variants in the human homolog of the daf genes. In fact, heterozygous mice carrying either the db or ob recessive diabetes genes, survive fasting about 20% longer than wild type controls (Coleman, *Science* 203: 663–665, 1979). The high frequency of Type II diabetes in many human populations may be the legacy of such selections.

The DAF-3 Smad Protein Anatagonizes DAF-7 TGF-β Receptor Signaling in the *C. elegans* Dauer Regulatory Pathway In response to environmental signals *C. elegans* arrests development at the anatomically and metabolically distinctive third-larval dauer stage (Riddle In: *C. elegans* N, D. L. Riddle, T. Blumenthal, B. J. Meyer, J. R. Priess, eds., Cold Spring Harbor Press, 1997, pp. 739–768). Pheromone signal is transduced by chemosensory neurons (Bargmann and Horvitz, *Science* 251:1243, 1991) which couple to a TGF-β signaling pathway (Ren et al., *Science* 274:1389, 1996; Schackwitz et al., *Neuron* 17:719, 1989), as well as an insulin-related signaling pathway (as discussed, infra) to trigger changes in the development of the many tissues remodeled in dauer larvae (Riddle, supra). Mutations in daf-7 (a TGF-β homolog (Estevez et al., *Nature* 365:644, 1993)), daf-4 (a type II TGF-β receptor (Estevez et al., *Nature* 365:644, 1993)), daf-1 (a type I TGF-β receptor), daf-8, and daf-14 (Smad homolog) cause constitutive arrest at the dauer stage even in the absence of pheromone. These genes constitute a neuroendocrine signaling pathway that is active during non-dauer development: the DAF-7 TGF-β signal is produced by the sensory neuron ASI during non-dauer development, whereas daf-7 expression in this neuron is inhibited during dauer-inducing conditions (Ren, supra).

daf-7 and its receptors and Smad proteins are antagonists to daf-3. The dauer constitute phenotypes of mutations in the daf-7 signal transduction pathway genes (including putative null mutations) are fully suppressed by mutations in daf-3. These genetic data indicate that in the absence of daf-7 signaling, daf-3 acts to induce dauer arrest.

Figure 5A:
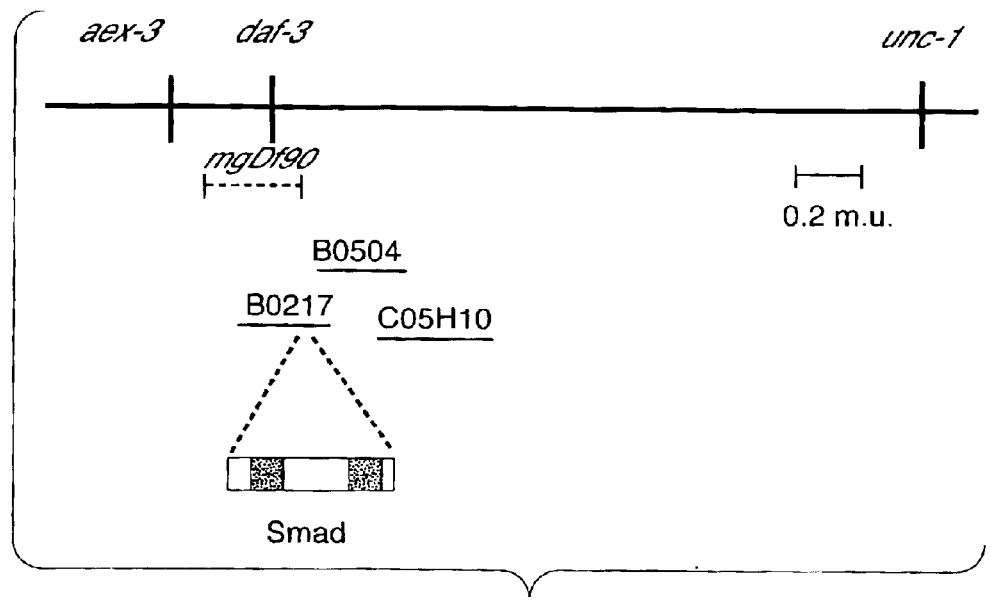
Figure 5B:
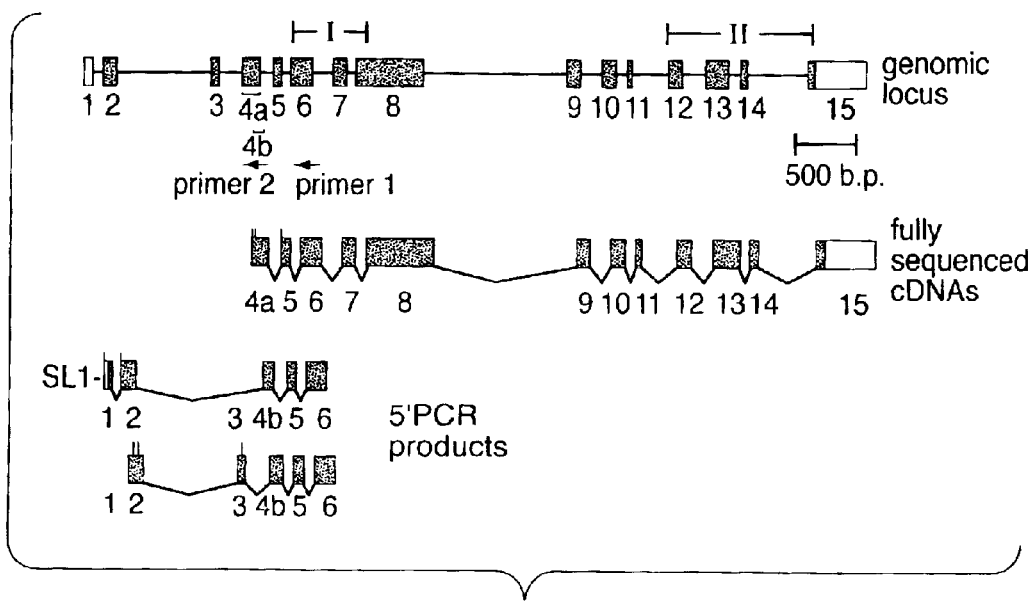

To discern the molecular basis of the DAF-3 function in this pathway, we determined the sequence and expression pattern of daf-3. Cosmids in the daf-3 genetic region were assayed for gene activity by transformation. Cosmid B0217 partially complemented a daf-3 mutation, while other cosmids from the region did not (FIG. 5A). A subclone of B0217 containing only the Smad homolog, but no other coding regions also rescued daf-3. Our detection of mutations in the Smad homolog (see below) confirmed its assignment to daf-3. Analysis of daf-3 cDNAs revealed that the gene was transcribed from fifteen exons and was alternatively spliced upstream of the region conserved in Smad proteins. (FIG. 5B) The biological activity of these alternatively spliced isoforms is unknown. The nucleotide (SEQ ID NOS: 39, 52, and 53) and amino acid sequences (SEQ ID NOS: 40, 41, and 42) of DAF-3 are shown in FIGS. 11 and 12, respectively.

Thus far, the *C. elegans* DAF-3 Smad protein is most closely related in sequence to DPC4, which is a putative cofactor for Smad1, Smad2, and Smad3 (Zhang et al., *Nature*, 383:168, 1996; Lagna et al., *Nature*, 383:832, 1996; Savage et al., *Proc.Natl.Acad.Sci*., 93:790, 1996; Hahn et al., *Science*, 271:350 (1996). Smads have two conserved domains (Wrana et al., *Trends Genet*., 12:493, 1996). DAF-3 has these two domains; compared to its closest known relative DPC-4, daf-3 has 55% amino acid identity in domain I and 30% in domain II (FIG. 5C). However, DPC-4 is not the mammalian DAF-3 homologue: *C. elegans* Sma-4, for example, is more closely related to DPC-4 than DAF-3.

We identified three mutations in daf-3, all of which were isolated as suppressors of daf-7(e1372). mgDf90 is a homozygous viable deletion of 15–90 kb that removes the entire Smad gene (FIG. 5A). mgDf90 was identified as a spontaneous mutation that suppressed daf-7 in the strain of GR1300 (daf-7 (e1372) 111; mut-6(st 702) unc-22 (St192) IV). Thus, suppression of the daf-7 dauer constitutive phenotype of daf-3 is daf-3 null phenotype, demonstrating that wild-type DAF-3 acts antagonistically to signaling from the DAF-7 TGF-β pathway signaling. daf-3(mg125) and daf-3 (mg132) are missense mutations that alter conserved residues in domains 1 and 2 respectively (FIG. 5C). Most of the mutations detected in other Smads localize to a 45 amino acid segment of domain II (Wrana et al., *Trends in Genet*. 12:493, 1996). Clustering of mutations is observed even in DPC4, for which homozygous null mutations have been identified (Hahn et al., *Science* 271:350, 1996), so the clustering is unlikely to be due to selection for non-null mutations. This hotspot region was sequenced in nine daf-3 alleles, and no mutations were detected. This difference in mutation location may be a simple statistical anomaly, or may indicate functional differences between DAF-3 and other Smad proteins, consistent with the fact that DAF-3 is antagonized, rather than activated, by an upstream TGF-β molecule.

Figure 7:
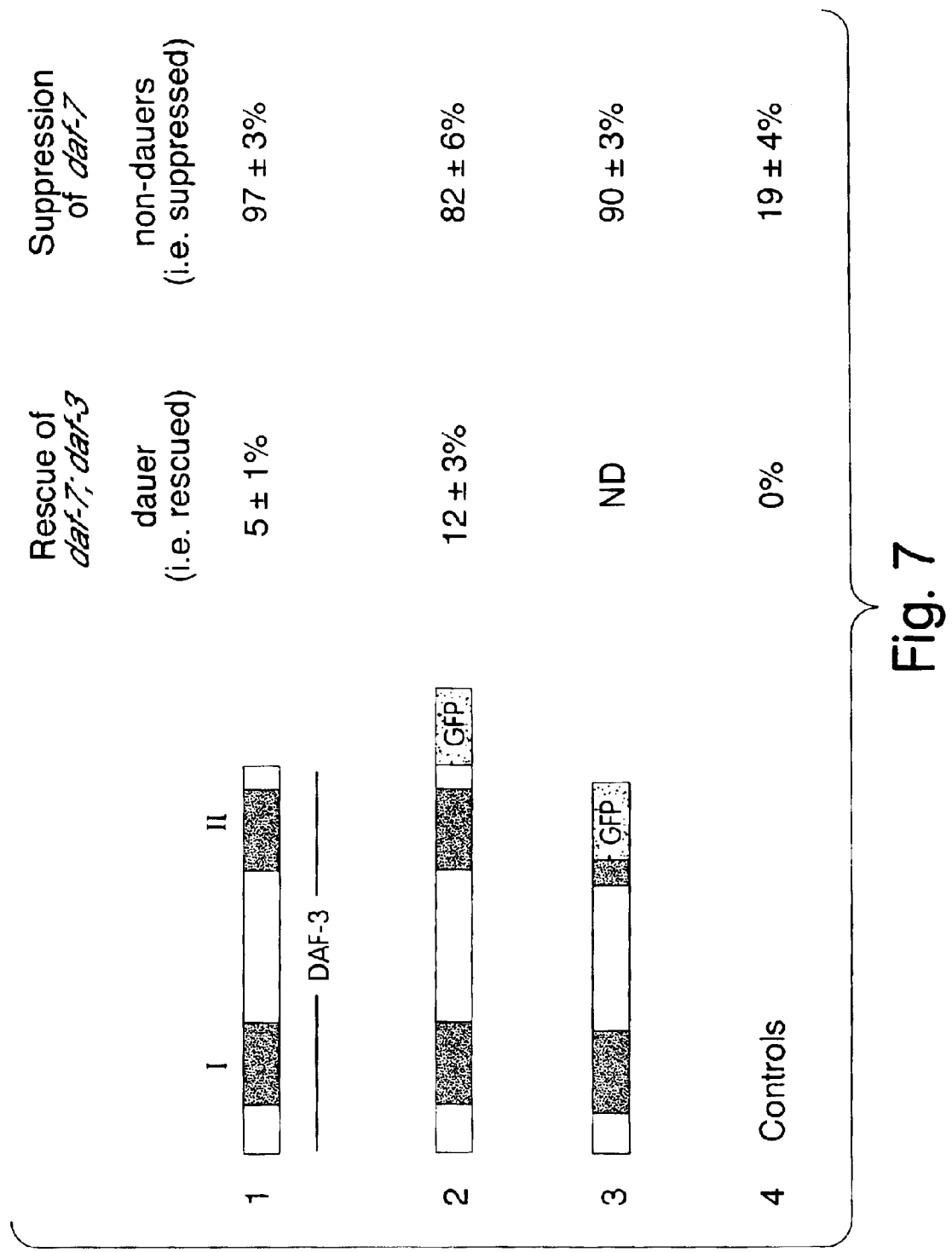

To determine where DAF-3 may function in control of dauer formation, we examined the expression pattern of a functional daf-3/Green Fluorescent Protein (GFP) fusion gene. This was accomplished by replacing a AvrII/SacI fragment from pGP8 with a PCR product in which several restriction sites were inserted after the last codon of daf-3 before the stop codon. A GFP/unc-54 3' end PCR product from pPD95.81 was cloned into the 3' restriction sites to produce pGP19. This DAF-3/GFP fusion partially rescues a daf-3 mutant (FIG. 7). GFP fluorescence therefore indicates the functional location of DAF-3. DAF-7 signaling from the ASI neuron begins during the L1 stage, and neuron ablations and dauer-formation assays in various environmental conditions indicate that the signal for dauer formation is also received during the first two larval stages (Ren et al., *Science* 274:1389, 1996, Schackwitz et al., *Neuron* 17:719, 1996; Bargmann and Horvitz, *Science* 251:1243, 1991; Golden and Riddle, *Developmental Biology* 102:368, 1984; Swanson and Riddle, *Developmental Biology* 84:27, 1981). Therefore, we most extensively examined L1 larvae.

Figure 6A:
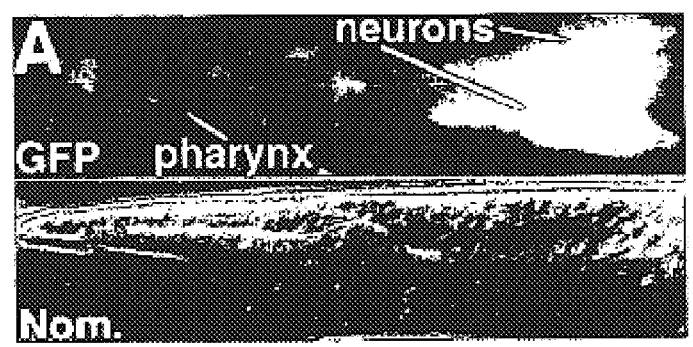
Figure 6B:
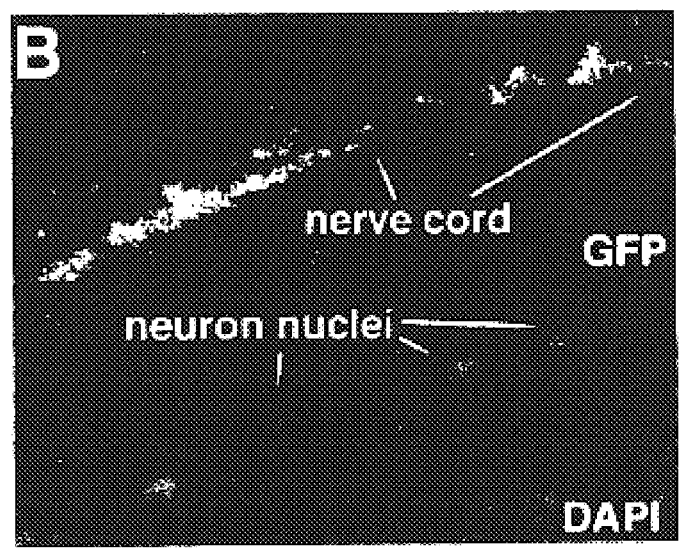
Figure 6C:
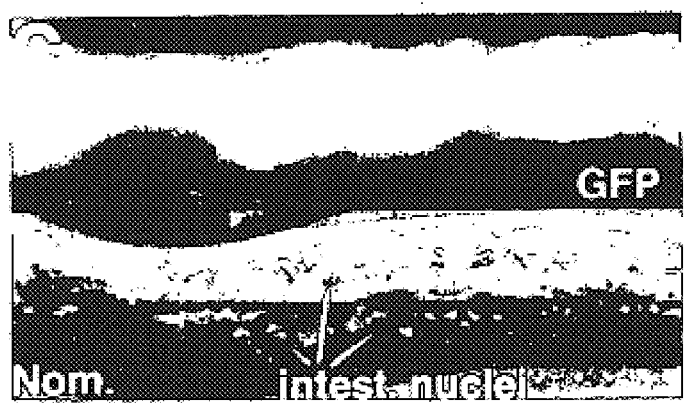
Figure 6D:
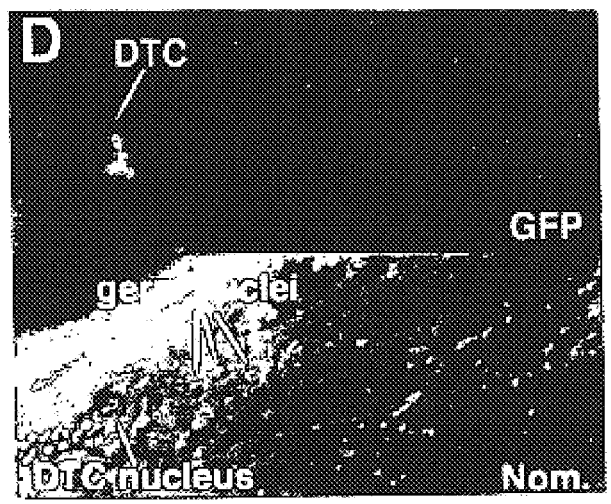
Figure 6E:
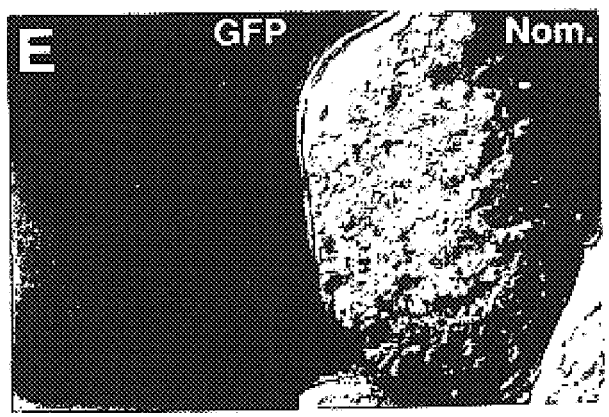
Figure 6F:
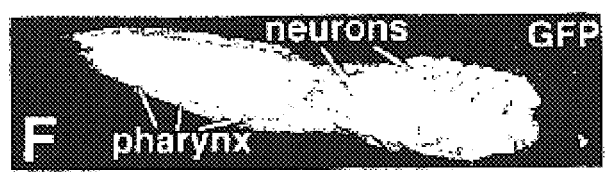
Figure 6G:

Almost every transgenic animal showed strong daf-3/GFP expression in head neurons (FIG. 6A), the ventral nerve cord (both cell bodies and processes, see FIG. 6B), the intestinal cells (FIG. 6C), especially the membrane adjacent to the intestinal lumen, the tail hypodermis, and tail neurons. For all GFP scoring, animals were grown at 25–26° C. For scoring of DAF-3/GFP in wild-type and in dauer constitutive mutant backgrounds, three or more lines were scored in each case. A large number of animals were surveyed to determine the expression pattern, and at least 30 animals were scored head-to-tail, and expression was tallied for each tissue. About half of the transgenic animals have weak expression in V blast cells, P blast cells, hyp7 hypodermal cells, and the pharynx. The weak expression impedes cell identification, but the main body of the pharynx is filled, implying expression in pharyngeal muscle (FIG. 6A). Expression is rarely detected in dorsal body wall muscle. The expression pattern in older larvae and adults is similar to that of L1 animals. In addition, DAF-3/GFP is expressed in the distal tip cells and in their precursors, Z1.a and Z4.p, throughout development (FIG. 6D, FIG. 8). DAF-3/GFP is also strongly expressed in unidentified vulval cells. In wild-type embryos of 200–400 cells, DAF-3/GFP is expressed uniformly thoughout the embryo (FIG. 6E). Under the conditions of the experiment, which promote reproductive growth, the subcellular localization of the DAF-3/GFP protein is mainly cytoplasmic (FIGS. 6B–E, and see below).

Because DAF-3 activity may be regulated by the DAF-1 and DAF-4 TGF-β receptors, we examined the expression of a DAF-4/GFP fusion in wild-type (FIGS. 6A–6G). This construct complements a daf-4 mutant. A 10 kb SalI fragment from cosmid CO5D2 contains 3 kb of sequence upstream of the daf-4 transcriptional start, and all of the daf-4 coding region except codons for the last fourteen residues of daf-4. This fragment was subcloned into the SalI site of the GFP plasmid TU#61 (Chalfie et al., *Science* 263: 802–805, 1994). This plasmid was injected into the daf-4 (m72) strain to test the fusion for DAF-4 activity. More than 95% of the transgenic animals were rescued for the dauer-constitutive and small phenotypes of daf-4(m 72), indicating that the fusion has robust DAF-4 activity. The pattern of DAF-4/GFP expression is similar to that of daf-3/GFP, except that DAF-4/GFP is localized to membranes, consistent with its role as a receptor. DAF-4/GFP is expressed more strongly in the pharynx (FIGS. 6F–G), and more weakly in the ventral nerve cord cell bodies and the body hypodermis. Expression of DAF-4/GFP in wild-type animals is detected later than DAF-3/GFP. DAF-4/GFP is first detectable at late embryogenesis when the embryo resembles an L1 larva. The DAF-4/GFP construct contains an older version of GFP than in DAF-3/GFP; in the older version, the chromophore takes longer to mature. To verify that the difference in embryonic expression of DAF-4/GFP and DAF-3/GFP is not an artefact of the slower maturation time in the daf-4 strain, we used anti-GFP antibodies to assay GFP. These antibodies should recognize the two forms of GFP equally well. We found that the antibodies recapitulated the results with direct GFP fluorescence: DAF-3/GFP is expressed in early embryos; DAF-4/GFP is not. DAF-4/GFP is also not expressed in membrane surrounding the intestinal lumen, unlike DAF-3/GFP.

The combination of the DAF-3 and DAF-4 expression patterns suggests that these genes act in target tissues to transduce pheromone-regulated DAF-7 neuroendocrine signals. The early expression of DAF-3 in embryos is also consistent with a model that DAF-3 acts during embryonic development, for example, to mediate the development of neuronal pathways that emit neuroendocrine signals that antagonize DAF-7 TGF-β signaling during the L1 stage. However our data indicates that DAF-3 functions in transducing environmental signals during the L1 and L2 stages. This is supported by the following observations. (1) DAF-7 TGF-β signal from ASI neurons occurs during the L1 and L2 stages and is repressed by dauer-inducing environmental conditions. (2) Expression of the DAF-4 type II receptor begins in very late embryogenesis. (3) Expression patterns of DAF-3 and DAF-4 are coincident in most of the tissues remodeled during dauer morphogenesis. For example, the cuticle secreted by the hypodermis is modified, the pharynx is slimmed, and the lumen of the intestine is less convoluted. In addition, somatic gonad development is arrested in dauers, and the distal tip cell, in which DAF-3 is expressed, is an important regulator of that development (Kimble, *Developmental Biology* 87:286, 1981). In addition, the intestine and hypodermis of dauer larvae contain large fat stores indicative of a metabolic shift to fat storage. The expression of both the DAF-4 TGF-β family receptor kinase and the DAF-3 Smad protein in these target tissues is consistent with a model that the DAF-7 neuroendocrine signal from the ASI neuron is received directly by these tissues during non dauer development. In addition, the observation that DAF-4 and DAF-3 are expressed in many of the same cells is consistent with a model that DAF-4 signaling to downstream Smads (DAF-8 and DAF-14 are likely candidates) directly regulates DAF-3 gene activity. The TGF-β regulated nuclear localization and transcriptional activation of some Smad proteins suggests that DAF-3 might induce the dauer-specific changes by activating transcription in target tissues of genes required for dauer formation or repressing transcription of genes necessary for nondauer growth.

Smad1 and Smad2 relocalize to become predominantly nuclear when the upstream TGF-β signaling pathways are activated (Baker and Harland, *Genes and Development* 10: 1880, 1996; Hoodless et al., *Cell* 85:489, 1996; Liu et al., *Nature* 381:620, 1996; Macias-Silva et al., *Cell* 87:1215, 1996). In wild-type, DAF-3/GFP is primarily, although not exclusively, cytoplasmic. DAF-3/GFP subcellular distribution was examined in head neurons in the vicinity of ASI (the cell that produces the DAF-7 signal), as well as in intestinal cells. DAF-3/GFP was predominantly cytoplasmic in all animals. However, in all animals, dim GFP fluorescence was observed in the nucleus of some of the cells with bright fluorescence, and in approximately twenty-five percent of the animals, equivalent DAF-3/GFP levels in the nucleus and cytoplasm has observed in one or more cells.

Because DAF-3 is antagonized by the other members of the DAF-7 TGF-β pathway, we expect that DAF-3 is active (and perhaps localized to the nucleus) when these genes are inactive. We therefore observed the subcellular localization of the full-length DAF-3/GFP fusion protein in the head neurons, tail neurons, and intestine of dauer-constitutive mutant L1 worms, when DAF-3 gene activity is predicted to be highest. In DAF-1(m402), daf-4(m72), daf-7(m62), daf-8(sa233), and daf-14(m77) mutants, DAF-3/GFP was predominantly cytoplasmic, although, as in wild-type, cells were seen with some GFP in the nucleus. In three daf-4(m72) mutant lines, DAF-3/GFP was localized to the nucleus more than in wild-type lines. When these strains were crossed to wild-type, the increased nuclear localization was seen in both the daf-4 and wild-type segregants. Thus the increased nuclear GFP was a property of the array, rather than of daf-4. Even in the neurons nearest to ASI, where the DAF-7 signal should be strongest, no change in DAF-3/GFP subcellular localization was detected. The DAF-3/GFP fusion protein is predominantly cytoplasmic in L1 and L2 stages of larvae induced to form dauers by environmental conditions or by mutations in the insulin receptor pathway gene daf-2, rather than by mutations in the DAF-7 signaling pathway mutants (data not shown). The tissue-specific expression pattern of DAF-3/GFP was unaltered in these mutant backgrounds (data not shown).

The finding that DAF-3/GFP subcellular localization is not strongly responsive to DAF-7 signaling defects or to dauer-inducing environmental conditions does not rule out a role for DAF-3 in the nucleus in dauer formation. Even though we detect no change in DAF-3/GFP subcellular localization, we do detect some DAF-3/GFP in nuclei, and a minor change in nuclear localization or a change in activity due to phosphorylation state may couple DAF-3 to DAF-7 signaling. In fact, the subcellular localization of *Drosophila* MAD protein is not detectably altered in wild-type when receptor signaling to MAD occurs; relocalization is seen only if the DPP ligand is drastically overexpressed. It is unlikely that a set of undiscovered TGF-β receptors regulates DAF-3. The *C. elegans* genome sequence is 90% complete, and there is only one candidate TGF-β receptor gene other than daf-1 and daf-4. If this receptor were a positive regulator of DAF-3, mutants would be expected to, like daf-3 mutants, suppress daf-7 mutants. This receptor acts in a signaling pathway distinct from DAF-3, and it is not a suppressor of daf-7.

Figure 8A:
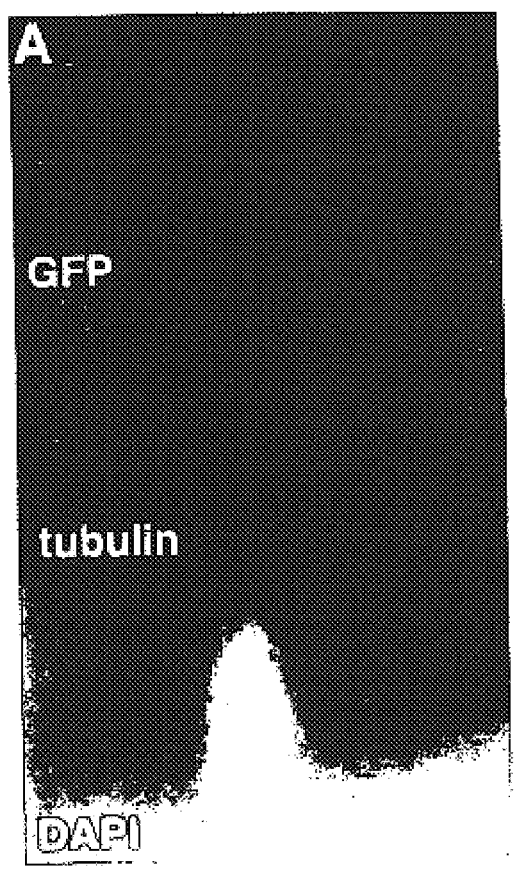
Figure 8B:
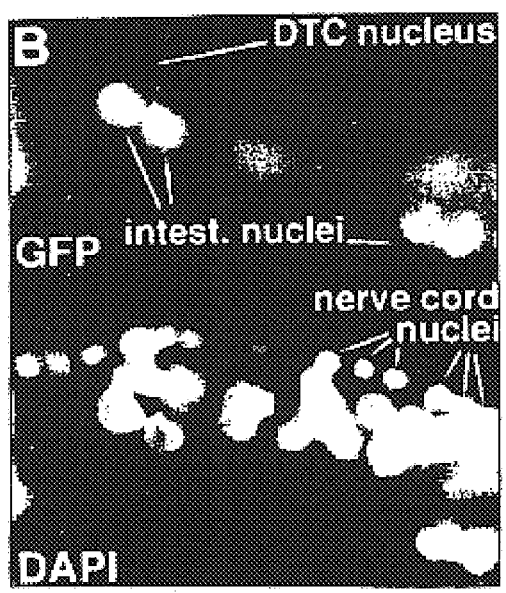

The implication from Smad homology that DAF-3 is active in the nucleus is supported by two additional observations. First, DAF-3/GFP is associated with chromosomes in intestinal cells during mitosis. These cells divide at the end of the L1 stage, and antibody staining with anti-GFP antibodies and anti-α-tubulin antibodies reveals that DAF-3/GFP is found associated with DNA between the spindles during mitosis (FIG. 8A). We see DAF-3 GFP co-localized with DAPI from prophase to late anaphase. DAF-3/GFP was associated with nuclei in prophase by the following criteria. The spindles were present on either side of the nucleus, but the nucleus has not completely broken down. In particular, an indistinct nucleolus was present. DAF-3/GFP continues to co-localize with DAPI until the chromosomes have separated to the normal distance by which nuclei are separated in the intestine, implying continued association until telophase. At this point in mitosis, DAF-3/GFP fades and becomes undectectable before the nuclei reform the nuclear envelope and nucleolus. Thus, DAF-3 can, indirectly or directly, bind DNA, consistent with the hypothesis that it is a transcriptional activator that acts in the nucleus. DAF-3 is not predicted from its mutant phenotype to have a role in mitosis. It is possible that the brighter GFP on mitotic chromosomes is due to increased access to DNA due to the breakdown of the nuclear envelope. The second indication of DAF-3 function in the nucleus is our examination of a truncated DAF-3/GFP fusion that is missing most of conserved domain II. The truncated construct pGP7 consists of 8 kb of daf-3 fused to GFP. An 8 kb EcoR1 fragment from B0217 was cloned into the EcoR1 site of pBluescript SK(−). A PvuI/SalI fragment of this subclone was ligated to a PvuI/SalI fragment from the GFP vector pPD95.81. The resulting plasmid contains ~2.5 kb of sequence upstream of the 5'-most exon of daf-3 and coding region through the first 58 amino acid residues of domain II. The remaining 175 amino acids of daf-3 and the 3' noncoding region are replaced with GFP and the unc-54 3' end. Three transgenic lines were isolated, and all had a similar phenotype. This fusion protein interferes with dauer induction; like a daf-3 loss-of-function mutant, it suppresses mutations in daf-7 (FIG. 7). This truncated protein is predominantly nuclear, suggesting that it represses dauer formation by acting in the nucleus (FIG. 8B). This result implies that wild-type DAF-3 also has a function in the nucleus. The full-length DAF-3/GFP construct also suppresses mutations in daf-7, as does a full-length DAF-3 construct without GFP (FIG. 7). This suppression indicates that overexpression of DAF-3 in the cytoplasm has dominant-negative activity, perhaps due to interference with DAF-3 interactions with receptors or cofactors such as other Smads.

The constitutive nuclear localization of truncated DAF-3/GFP fusion gene missing part of domain II suggests that control of Smad localization is complex. A Smad2 construct containing only the conserved domain II of the protein is constitutively nuclear, leading to the suggestion that the C-terminus is an effector domain, and the N-terminus tethers the protein in the cytoplasm (Baker and Harland, *Genes and Development* 10:1880, 1996; Hoodless et al., *Cell* 85:489, 1996; Liu et al., *Nature* 381:620, 1996; and Macias-Silva et al., *Cell* 87:1215, 1996). Our construct, in which the N-terminus is intact, is nuclear. Perhaps both domains provide tethering in the cytoplasm, and any disruption leads to nuclear entry. Alternatively, entry may be differently regulated for DAF-3 and Smad2. Significantly, Smad2, like Smad1 and Smad3 has an SSXS motif at the C terminus (Zhang et al., *Nature* 383:168, 1996; Lagna et al., *Nature* 383:832, 1996; Savage et al., PNAS 93:790; Baker and Harland, *Genes and Development* 10:1880, 1996; Hoodless et al., *Cell* 85:489, 1996; Liu et al., *Nature* 381:620, 1996; Macias-Silva et al., *Cell* 87:1215, 1996; and Graf et al., *Cell* 85:479, 1996); this motif is a substrate for phosphorylation and required for nuclear localization of Smad2 (Baker and Harland, *Genes and Development* 10:1880, 1996; Hoodless et al., *Cell* 85:489, 1996; Liu et al., *Nature* 381:620, 1996; and Macias-Silva et al., *Cell* 87:1215, 1996). DAF-3 has a single serine in the C terminal region, and DPC4 has no serines at this location.

Figure 9A:
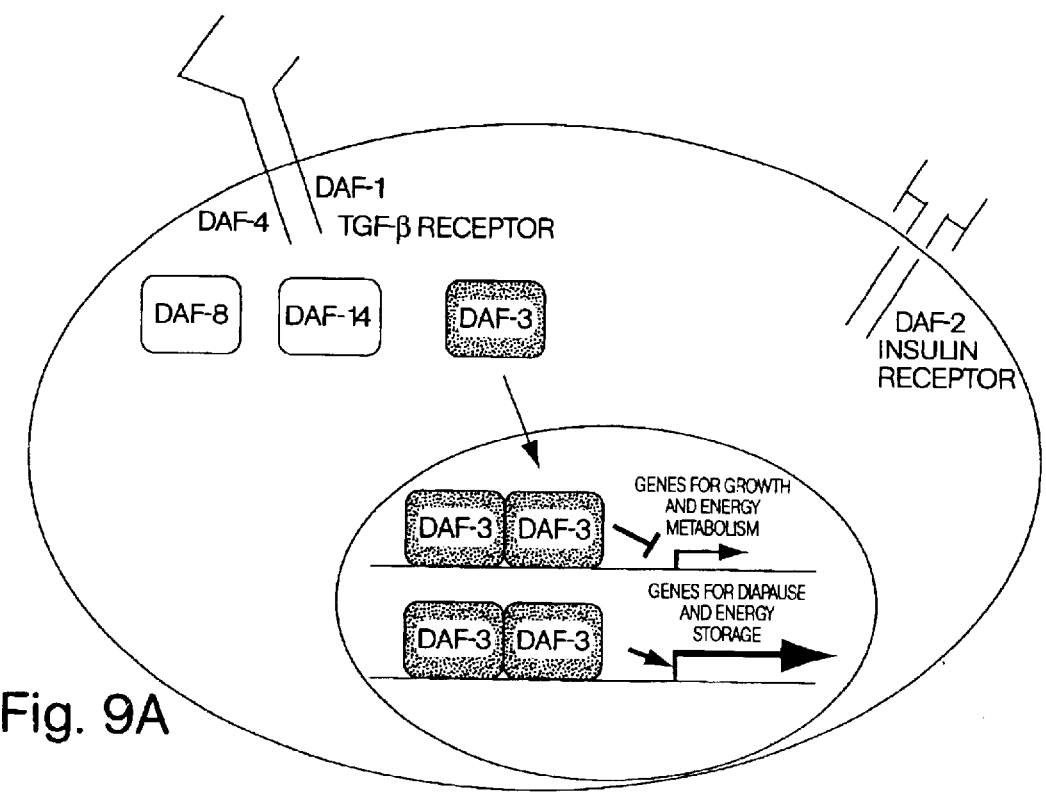
Figure 9B:
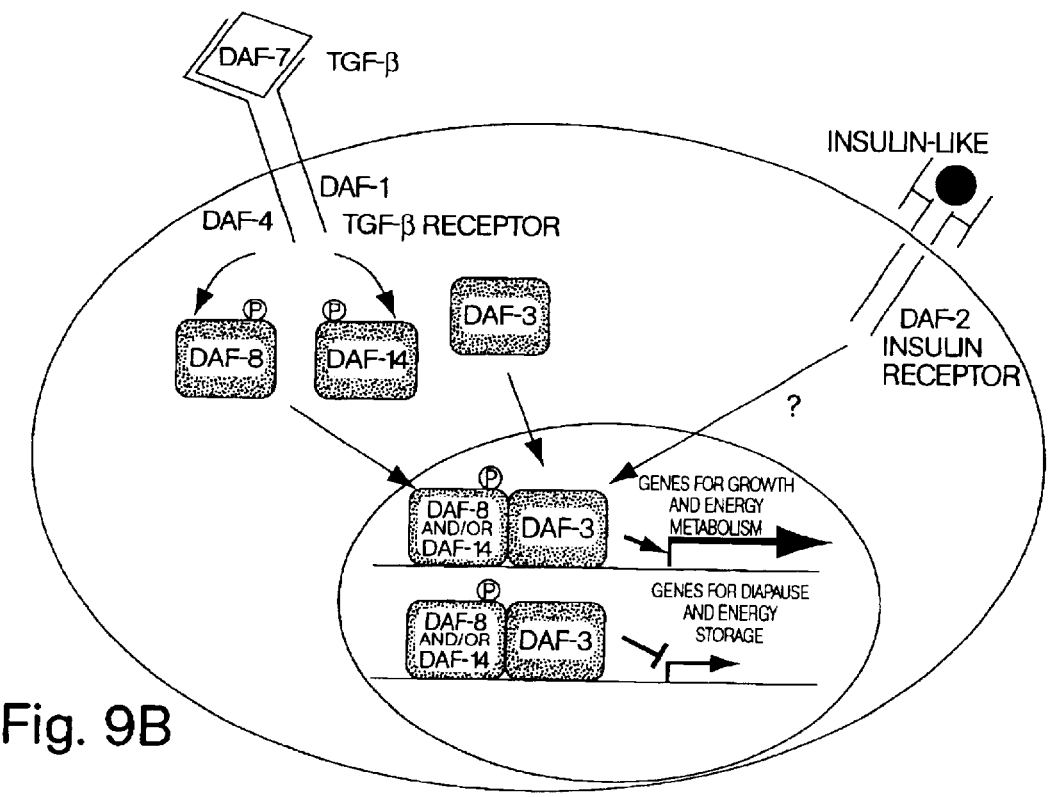
Figure 10:
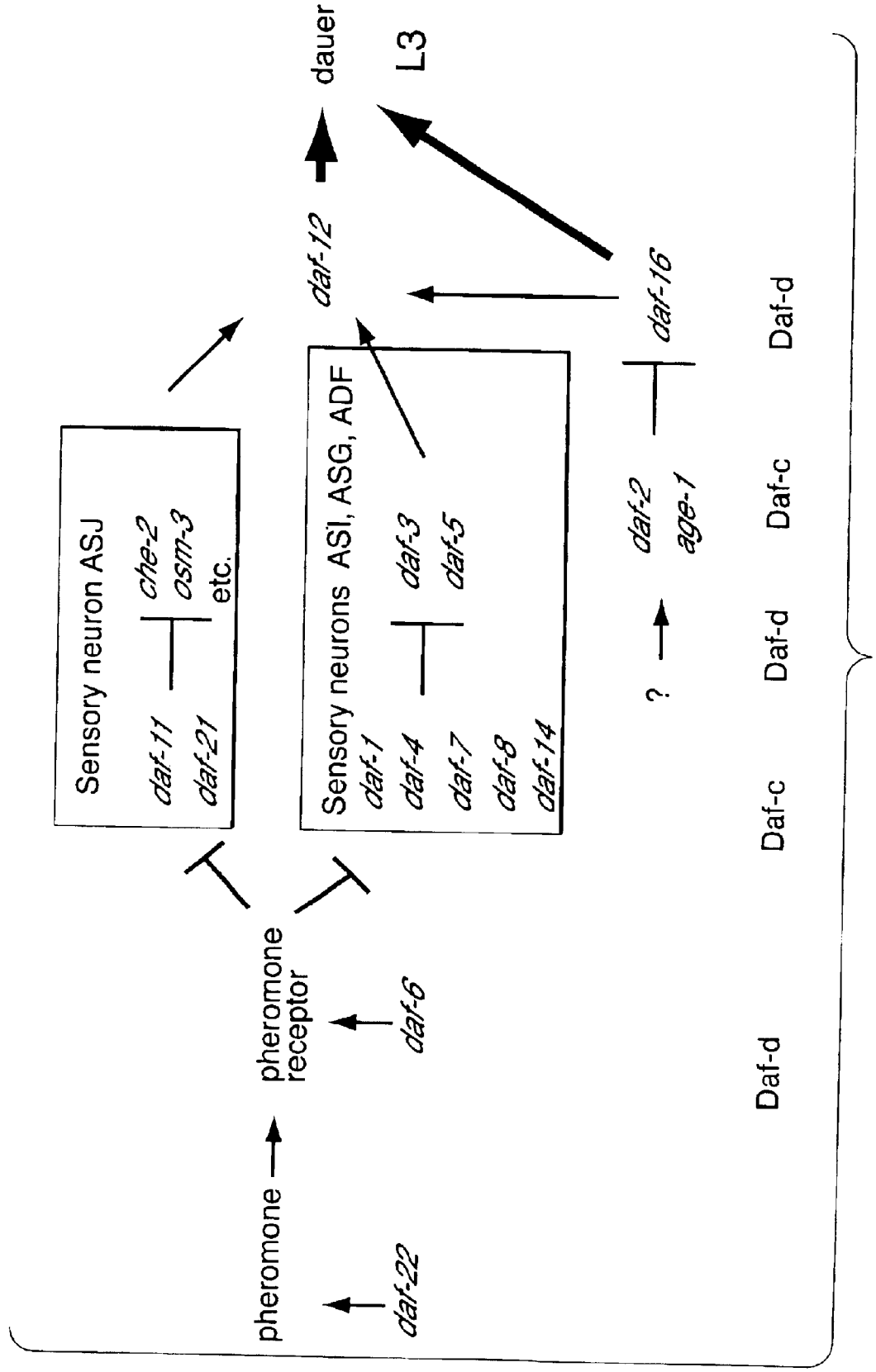
FIG. 10 is a schematic illustration showing the genetic pathway that regulates C. elegans dauer formation.

We propose a model for the TGF-β pathway in dauer formation (FIGS. 9A-B). The DAF-7 TGF-β ligand, which is produced by the ASI sensory neuron in conditions that induce reproductive organ (Ren et al., *Science* 274:1389, 1996; Schakwitz et al., *Neuron* 17:719, 1996), binds to the DAF-1/DAF-4 receptor kinases on target tissues. These receptor kinases then phosphorylate the Smads DAF-8 and/or DAF-14, analogous to the phosphorylation and activation of Smad1, Smad2, and Smad3 (Zhang et al., *Nature* 383:168, 1996; Lagna et al., *Nature* 383:832, 1996; Savage et al., PNAS 93:790, 1996). We propose that DAF-3 functions like its closest homolog, DPC4, which dimerizes with phosphorylated Smad1 and Smad2, even under conditions that do not lead to detectable DPC4 phosphorylation (Zhang et al., *Nature* 383:168, 1996; Lagna et al., *Nature* 383:832, 1996; and Savage et al., PNAS 93:790). We suggest that DAF-3 forms dauer-inducing homodimers in the absence of DAF-7 signaling (FIGS. 9A–B) that are disrupted when DAF-3 heterodimerizes with a phosphorylated DAF-8 and/or DAF-14 (FIG. 9B). Because daf-8 and daf-14 are only partially redundant (Riddle et al., *Nature* 290:668, 1981; Vowels and Thomas, *Genetics* 130:105, 1992; and Thomas et al., *Genetics* 134:1105, 1993), each is likely to perform a unique function in dauer formation. Thus, DAF-3/DAF-8 dimers are proposed to have different activity from DAF-3/DAF-14. Perhaps each activates a subset of genes required for dauer formation. The formation of DAF-8/DAF-3 and/or DAF-14/DAF-3 heterodimers antagonizes dauer induction by the DAF-3/DAF-3 homodimer. A daf-8(sa233); daf-14(m77); daf-3(mgDf90) triple mutant can form some dauers in dauer-inducing conditions (data not shown); we suggest that activity of the Daf-2 pathway may induce dauer in this mutant background.

The dauer genetic pathway represents a neuroendocrine pathway for control of a diapause arrest and its associated shifts in metabolism and rates of senescence (Ren et al., *Science* 274:1389, 1996; Schackwitz et al., *Neuron* 17:719, 1996; and Georgi et al., *Cell* 61:635, 1990). Similarly, activins, members of the TGF-β family, were originally identified based on their neuroendocrine regulatory activity, for example, in regulation of gonadotropin signaling (Vale et al., in *Peptide Growth Factors and Their Receptors*, Sporn and Roberts, Eds., Springer-Verlag, Heidelberg, 1990). The DAF-7 signal is not the only signal that is necessary for reproductive development. Because mutations in the DAF-7 TGF-β pathway and in the DAF-2 insulin-like signaling pathway cause the same dauer arrest phenotypes, we propose that both the DAF-7 TGF-β signals and the DAF-2 insulin-like signals are necessary for reproductive development. The involvement of an insulin-like signaling pathway in diapause with its associated metabolic shifts is consistent with metabolic regulation by insulin in vertebrates. Genetic experiments indicate that these pathways act in parallel (Riddle et al., *Nature* 290:668, 1981; Vowels and Thomas, *Genetics* 130:105, 1992; and Thomas et al., *Genetics* 134:1105, 1993). In particular, daf-3 mutants efficiently suppress daf-7 mutants, but not daf-2 mutants, and daf-16 mutants efficiently suppress daf-2 mutants, but poorly suppress daf-7 mutants. It is not yet clear whether these two signaling pathways coverage on target tissues or in other regulatory (e.g., hormone secreting) cells. However, the expression of the DAF-7 receptor pathway genes and the DAF-16 gene in essentially all target tissues suggests that the TGF-β and insulin pathways act there, and therefore that integration must occur there. Thus, we suggest in FIGS. 9A and 9B that the DAF-2 pathway converges on DAF-3/DAF-8DAF-1 Smad signaling to regulate metabolic gene expression in target tissues.

The integration of insulin-like and TGF-β signals in metabolic control has important implications for the molecular basis of diabetes. For example, these converging pathways for dauer control suggest that in human metabolic control both a DAF-7-like signal and insulin may be necessary for full metabolic control. Thus, declines in signaling from the human homolog of DAF-7 could underlie the insulin resistance associated with Type II diabetes. In fact the dauer pheromone has been reported to be a fatty acid and to cause down-regulation of DAF-7 expression (Ren et al., supra). Thus pheromone regulation of metabolism may be related to mammalian obesity induced diabetes, and a human mutation in DAF-7 or its receptors is expected to contribute to a diabetic condition, just like mutations in the insulin receptor. In addition if obesity or age or both cause human DAF-7 to decline, e.g., under high leptin conditions, such a result would explain late onset/obesity related diabetes.

Converging Transcriptional Outputs of the Insulin and DAF-7 Endocrine Signals

Further support for the view that insulin-like and DAF-7 neuroendocrine signals regulate common transcriptional targets via the DAF-16 Forkhead protein and the DAF-8, DAF-14, and DAF-3 Smad proteins, respectively, comes from the following experiments. First, we have shown that the a 30 base element in the myosin 2 promoter, previously shown to bind to DAF-3 and be responsive to DAF-7 signaling, is also responsive to DAF-2 insulin like signaling (Okkema, Development, 1994, 120(8):2175–86). This element has the following sequence (SEQ ID NO: 210): TCTCGTTGTTTGCCGTCGGATGTCTGCC. The bolded nucleotide positions are conserved in the Xenopus activin response element. Specifically, a GFP fusion of this element (multimerized 6x) expresses 24 units of fluorescence in wild type, but less than 4 units in a daf-4 TGF-β signaling mutant or in a daf-2 insulin-like signaling mutant. This repression of expression by lack of neuroendocrine input is relieved by mutations in daf-3 in the case of the daf-4 mutant and daf-6 in the case of the daf-2 mutant. The daf-4; daf-3 double mutant expresses 12 units of GFP fluorescence and the daf-2; daf-16 double mutant expresses 18 units of GFP fluorescence. These data strongly support the model that DAF-16 and DAF-3 bind to the same element in the myosin promoter. This is biologically relevant since the pharynx is smaller in dauer arrested animals, consistent with lower pharyngeal myosin expression in animals with defective DAF-7 or DAF-2 signaling.

Serotinergic Input to the Dauer Pathway

We have further shown that mutants completely lacking in serotonin have defects in metabolic control. Specifically we have knocked out the serotonin synthesis gene, tryptophan hydroxylase, cod-5, by directed mutagenesis. Cod-5 is the aromatic amino acid hydroxylase that synthesises serotonin from the precursor L tryptophan (FIG. 42). It is the rate determining step in the synthesis of serotonin, and we have shown that it is only transcribed in the serotinergic neurons of C. elegans.

Our deletion mutant deletes most of the cod-5 gene and causes a frameshift in the remaining coding region (FIG. 43). This mutant makes no serotonin as measured with antiserotonin antibody staining. The promoter of cod-5 fused to GFP displays all of the serotinergic neurons of C. elegans, NSM, HSN, ADF, RIH (but not VC4 and VC5 which probably uptake 5HT from surrounding serotinergic neurons).

The cod-5 null mutant has a number of behavioral abnormalities, including egg laying defects, fertility declines, thermal regulation defects, and hyperactive movement, but most dramatic is that up to half of the mutant animals arrest at the dauer stage and accumulate large amounts of fat. This is quite similar to the regulation of feeding, appetite, and metabolism by serotonin in vertebrates. The behavior of cod-5 mutants also shows the hallmarks of defects in DAF-7 signaling: the cod-5 mutant animals tend to cluster at the edge of a lawn of bacteria, as if they are attracted to each other and repelled by the bacteria. This type of behavior is also seen in an NPY receptor mutant, bor-1. It is possible that DAF-7 normally regulates the secretion of the NPY like ligand of bor-1, and 5HT regulates DAF-7. This would explain the dauer arrest and bordering behavior of cod-5 mutants, that it acts high in the pathway of DAF-7.

5HT production is normally under feeding and temperature control: wild type C. elegans makes almost undetectable levels of 5HT when starved and makes lower amounts at low temperature. We believe that 5HT receptors are expressed on particular regulatory neurons that also express or respond to the DAF-7 or DAF-2 signals, either as ligands or receptors. 5HT regulation of metabolism may occur via the DAF-7 pathway or the DAF-2 pathway, for example, by regulating expression of DAF-7, expression or secretion of the DAF-2 ligands, or signaling from the receptors. Moreover, given that cod-5 mutations induce the same behavioral changes (that is, crowding at the edge of food) as daf-7 mutants (in distinction from daf-11 or daf-2 pathway mutants), we believe that there is 5HT input to the daf-7 pathway.

Our discovery of 5HT input to C. elegans metabolic control is important because it may reveal the mechanism by which drugs like dexfenfluramine and fluoxetine control weight in humans (Weiser et al., J Clin Pharmacol, 1997, 37(6):453–73). For example, if 5HT input to worm metabolic control is via the DAF-7 signaling system, the mechanism of action of serotinergic signals in metabolic control in mammals may be via serotonin modulation of expression or secretion of the mammalian DAF-7 homologue.

In addition, the cod-5 promoter-GFP fusion is valuable for its ability to display serotinergic neurons, for example, for screens of mutants that fail to generate serotinergic neurons or screens for mutants that generate ectopic serotinergic neurons. Such a promoter fusion, for example, facilitates the identification of the neural pathway for the generation of 5HT neurons. In fact, the transcription factor unc-86 has already been identified as part of that pathway. Unc-86 mutants cause a lack of serotonin synthesis, due to loss of cod-5 expression in all serotinergic neurons except ADF, and we have shown that the accumulation of serotonin in the NSM in an unc-86 mutant is due to reuptake of 5HT, presumably from the ADF site of serotonin synthesis. Prozac, a reuptake inhibitor, causes 5HT accumulation in the NSM to disappear in unc-86 mutants.

Cloning Mammalian DAF Sequences

Based on our isolation of novel nematode DAF cDNAs, the isolation of mammalian DAF nucleic acid sequences, including human DAF sequences, is made possible using the sequences described herein and standard techniques. In particular, using all or a portion of a nematode DAF sequence, one may readily design oligonucleotide probes, including degenerate oligonucleotide probes (i.e., a mixture of all possible coding sequences for a given amino acid sequence). These oligonucleotides may be based upon the sequence of either strand of the DNA.

Exemplary probes or primers for isolating mammalian DAF sequences preferably correspond to conserved blocks of amino acids, for example, conserved DAF motifs. Exemplary motifs are as follows:

DAF-2 (tyrosine kinase domain) (SEQ ID NO:33)
1242 KFHEWAAQICDGMAYLESLKFCHRDLAARNCMINRDETVKIGDFGM
ARDLFYHDYYKPSGKRMMPVRWMSPESLKDGKFDSKSDVWSFGVVLYE
MVTLGAQPYIGLSNDEVLNYIGMARKVIKKPEC 1368

DAF-2 (ligand binding domain) (SEQ ID NO:34)
242 NTTCQKSCAYDRLLPTKEIGPGCDANGDRCHDQCVGGCERVNDATA
CHACKNVYHKGKCIEKCDAHLYLLLQRRCVTREQCLQLNPVLSNKTVPIK
ATAGLCSDKCPDGYQINPDDHRECRKCVGKCEIVC 372

DAF-2 (67 amino acid motif) (SEQ ID NO:79)
1158 AIKINVDDPASTENLNYLMEANIMKNFKTNFIVQLYGVISTVQPAMV
VMEMMDLGNLRDYLRSKRED 1224

DAF-2 (54 amino acid motif) (SEQ ID NO:80)
1362 VIKKPECCENYWYKVMKMCWRYSPRDRPTFLQLVHLLAAEASPEFR
DLSFVLTD 1415

DAF-2 (69 amino acid motif) (SEQ ID NO:81)
404 KQDSGMASELKDIFANIHTITGYLLVRQSSPFISLNMFRNLRRIEAKSL
FRNLYAITVFENPNLKKLFD 472

DAF-2 (52 amino acid motif) (SEQ ID NO:82)
98 FPHLREITGTLLVFETEGLVDLRKIFPNLRVIGGRSLIQHYALIIYRN
PDLE 149

DAF-2 (46 amino acid motif) (SEQ ID NO:83)
149 EIGLDKLSVIRNGGVRIIDNRKLCYTKTIDWKHLITSSINDVVVDN 194

DAF-2 (36 amino acid motif) (SEQ ID NO:84)
1112 YNADDWELRQDDVVLGQQCGEGSFGKVYLGTGNNVV 1147

DAF-3 (Smad Domain I) (SEQ ID NO:35)
240 FDQKACESLVKKLKDKKNDLQNLIDVVLSKGTKYTGCITIPRTLDGR
LQVHGRKGFPHVVYGKLWRFNEMTKNETRHVDHCKHAFEMKSDMVC
VNPYHYEIVI 342

DAF-3 (Smad Domain II) (SEQ ID NO:36)
690 NRYSLGLEPNPIREPVAFKVRKAIVDGIRFSYKKDGSVWLQNRMKYPV
FVTSGYLDEQSGGLKKDKVHKVYGCASIKTF 768

DAF-3 (24 amino acid motif) (SEQ ID NO:85)
819 DSLAKYCCVRVSFCKGFGEAYPER 842

DAF-16 (forkhead DNA binding domain) (SEQ ID NO:37)
727 KKTTTRRNAWGNMSYAELITTAIMASPEKRLTLAQVYEWMVQNVPY
FRDKGDSNSSAGWKNSIRHNLSLHSRFMRIQNEGAGKSSWWVINPDAKPG
MNPRRTRERS 1044

DAF-16 (103 amino acid motif) (SEQ ID NO:54)
242 KKTTTRRNAWGNMSYAELITTAIMASPEKRLTLAQVYEWMVQNVPY
FRDKGDSNSSAGWKNSIRHNLSLHSRFMRIQNEGAGKSSWWVINPDAKPG
MNPRRTR 344

DAF-16 (41 amino acid motif) (SEQ ID NO:55)
137 TFMNTPDDVMMNDDMEPIPRDRCNTWPMRRPQLEPPLNSSP 177

DAF-16 (109 amino acid motif) (SEQ ID NO: 56)
236 DDTVSGKKTTTRRNAWGNMSYAELITTAIMASPEKRLTLAQVYEWM
VQNVPYFRDKGDSNSSAGWKNSIRHNLSLHSRFMRIQNEGAGKSSWWVI
NPDAKPGMNPRRTR 344

DAF-16 (98 amino acid motif) (SEQ ID NO:58)
372 KPNPWGEESYSDIIAKALESAPDGRLKLNEIYQWFSDNIPYFGERSSPE
EAAGWKNSIRHNLSLHSRFMRIQNEGAGKSSWWVINPDAKPGMNP
RRTR 469

Using such motifs, mammalian DAF-2, DAF-3, and DAF-16 genes may be isolated from sequence databases (for example, by the use of standard programs such as Pileup). Alternatively, such sequences may be used to design degenerate oligonucleotide probes to probe large genomic or cDNA libraries directly. General methods for designing and preparing such probes are provided, for example, in Ausubel et al., *Current Protocols in Molecular Biology*, 1996, Wiley & Sons, New York, N.Y.; and *Guide to Molecular Cloning Techniques*, 1987, S. L. Berger and A. R. Kimmel, eds., Academic Press, New York. These oligonucleotides are useful for DAF gene isolation, either through their use as probes for hybridizing to DAF complementary sequences or as primers for various polymerase chain reaction (PCR) cloning strategies. If a PCR approach is utilized, the primers are optionally designed to allow cloning of the amplified product into a suitable vector. PCR is particularly useful for screening cDNA libraries from rare tissue types.

Hybridization techniques and procedures are well known to those skilled in the art and are described, for example, in Ausubel et al., supra, and *Guide to Molecular Cloning Techniques*, supra. If desired, a combination of different oligonucleotide probes may be used for the screening of the recombinant DNA library. The oligonucleotides are, for example, labelled with $^{32}$P using methods known in the art, and the detectably-labelled oligonucleotides are used to probe filter replicas from a recombinant DNA library. Recombinant DNA libraries (for example, human cDNA libraries, such as hypothalamus- or pancreas-derived cDNA libraries, particularly for DAF-2 and DAF-7 cDNAs) may be prepared according to methods well known in the art, for example, as described in Ausubel et al., supra, or may be obtained from commercial sources.

For detection or isolation of closely related DAF sequences, high stringency hybridization conditions may be employed; such conditions include hybridization at about 42° C. and about 50% formamide; a first wash at about 65° C., about 2×SSC, and 1% SDS; followed by a second wash at about 65° C. and about 0.1% SDS, 1×SSC. Lower stringency conditions for detecting DAF genes having less sequence identity to the nematode DAF genes described herein include, for example, hybridization at about 42° C. in the absence of formamide; a first wash at about 42° C., about 6×SSC, and about 1% SDS; and a second wash at about 50° C., about 6×SSC, and about 1% SDS.

As discussed above, DAF-specific oligonucleotides may also be used as primers in PCR cloning strategies. Such PCR methods are well known in the art and are described, for example, in *PCR Technology*, H. A. Erlich, ed., Stockton Press, London, 1989; *PCR Protocols: A Guide to Methods and Applications*, M. A. Innis, D. H. Gelfand, J. J. Sninsky, and T. J. White, eds., Academic Press, Inc., New York, 1990; and Ausubel et al., supra. Again, sequences corresponding to conserved regions in a DAF sequence (for example, those regions described above) are preferred for use in isolating mammalian DAF sequences. Such probes may be used to screen cDNA as well as genomic DNA libraries.

Sequences obtained are then examined (for example, using the Pileup program) to identify those sequences having the highest amino acid sequence identity to the *C. elegans* sequence, particularly in or between conserved DAF domains (for example, those domains described above). In one particular example, the human FKHR, FKHRL1, and AFX genes are $10^{33}$ more closely related to the DAF-16 forkhead domain than the next most closely related forkhead domain protein, making FKHR, FKHRL1, and AFX candidates for mammalian DAF-16 genes.

Following isolation of such candidate genes by sequence homology, the genes are then tested for their ability to functionally complement a daf mutation. This is most readily assayed by transformation of the sequence into a *C. elegans* strain having an appropriate mutant background. Exemplary *C. elegans* transformation techniques are described, for example, in Mello et al., *EMBO J.* 10: 3959–3970, 1991, and assays for DAF-2, DAF-3, and DAF-16 polypeptide function are described herein. To be considered useful in the invention, a mammalian sequence need not fully complement a *C. elegans* defect, but must provide a detectable level of functional complementation.

The DAF, AGE, or AKT gene homologue identified as above, may also complement or alter the metabolic phenotypes of a mammalian cell line.

For example, addition of DAF-7, TGF-β-like growth factor to an insulin responsive cell line (e.g., the 3T3-L1 cell line) may accentuate insulin responsiveness. Similarly genetic transformation of such a cell line with wild type or dominantly activated versions of a DAF, AGE, or AKT gene may alter metabolism. Such perturbations of metabolic control are stringent tests of candidate genes as DAF, AGE, or AKT homologues.

In addition, if that mammalian candidate homologue acts in a metabolic control pathway, and is expressed in similar metabolic control tissues (liver, adipose), it is likely to function homologously to DAF proteins from *C. elegans*. Addition of a wild type or activated DAF, AKT, or AGE protein (for example by VP16 activation of the DAF-3 or DAF-16 transcription factors) can confer on cell lines altered metabolic phenotypes. Thus supplying daf, age, or akt gene activity to such a cell line can alter its metabolism. This is one explemplary test of homologous DAF function in metabolic control.

DAF Polypeptide Expression

In general, DAF polypeptides according to the invention may be produced by transformation of a suitable host cell with all or part of DAF-encoding cDNA fragment (e.g., one of the cDNAs described herein or isolated as described above) in a suitable expression vehicle.

Those skilled in the field of molecular biology will understand that any of a wide variety of expression systems may be used to provide the recombinant protein. The precise host cell used is not critical to the invention. The DAF polypeptide may be produced in a prokaryotic host (e.g., *E. coli*) or in a eukaryotic host (e.g., *Saccharomyces cerevisiae*, insect cells, e.g., Sf9 or Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, Sf9 cells and the method of Ausubel et al., supra). Another baculovirus system makes use of the vector pBacPAK9 and is available from Clontech (Palo Alto, Calif.).

Alternatively, an DAF polypeptide is produced in a mammalian system, for example, by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the DAF protein is cloned into an expression vector which includes the dihydrofolate reductase (DHFR) gene. Integration of the plasmid and, therefore, the DAF protein-encoding gene into the host cell chromosome is selected for by inclusion of 0.01–300 μM methotrexate in the cell culture medium (as described in Ausubel et al., supra). This dominant selection may be accomplished in most cell types. Recombinant protein expression may be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

In yet other alternative approaches, the DAF polypeptide is produced in vivo or, preferably, in vitro using a T7 system (see, for example, Ausubel et al., supra, or other standard techniques).

Once the recombinant DAF protein is expressed, it is isolated, e.g., using affinity chromatography. In one example, an anti-DAF protein antibody (e.g., produced as described herein) may be attached to a column and used to isolate the DAF protein. Lysis and fractionation of DAF protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short DAF polypeptide fragments, may also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification may also be used to produce and isolate useful DAF fragments or analogs (described herein).

Anti-DAF Antibodies

Using any of the DAF polypeptides described herein or isolated as described above, anti-DAF antibodies may be produced by any standard technique. In one particular example, a DAF cDNA or cDNA fragment encoding a conserved DAF domain is fused to GST, and the fusion protein produced in *E. coli* by standard techniques. The fusion protein is then purified on a glutathione column, also by standard techniques, and is used to immunize rabbits. The antisera obtained is then itself purified on a GST-DAF affinity column, for example, by the method of Finney and Ruvkun (*Cell* 63:895–905, 1990), and is shown to specifically identify GST-DAF, for example, by Western blotting.

Polypeptides for antibody production may be produced by recombinant or peptide synthetic techniques (see, e.g., *Solid Phase Peptide Synthesis*, supra; Ausubel et al., supra).

For polyclonal antisera, the peptides may, if desired, be coupled to a carrier protein, such as KLH as described in Ausubel et al, supra. The KLH-peptide is mixed with Freund's adjuvant and injected into guinea pigs, rats, or preferably rabbits. Antibodies may be purified by any method of peptide antigen affinity chromatography.

Alternatively, monoclonal antibodies may be prepared using a DAF polypeptide (or immunogenic fragment or analog) and standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific DAF recognition by Western blot or immunoprecipitation analysis (by the methods described in Ausubel et al., supra). Antibodies which specifically recognize a DAF polypeptide described herein are considered to be useful in the invention. Anti-DAF antibodies, as isolated above, may be used, e.g., in an immunoassay to measure or monitor the level of DAF polypeptide produced by a mammal or to screen for compounds which modulate DAF polypeptide production (for example, in the screens described herein). In one particular example, antibodies to human DAF-7 polypeptide are useful for screening blood samples from patients to determine whether they possess decreased DAF-7 polypeptide levels. Such antibodies may be used in any immunological assay, for example, an ELISA assay, and a decrease in DAF-7 is taken as an indication of a diabetic condition, for example, obesity onset Type II diabetes. In another particular example, anti-DAF antibodies are useful for carrying out pedigree analysis. For example, blood samples from individuals may be screened with anti-DAF-7 antibodies to detect those members of a family with a predisposition to a diabetic condition. Anti-DAF antibodies may also be used to identify cells that express a DAF gene.

DAF-7 Therapy for Obesity-Onset Type II Diabetes

Our data indicates that DAF-7 represents an endocrine hormone for metabolic control that acts synergistically with insulin. Declines in DAF-7 may be induced by obesity, just as the dauer pheromone, a fatty acid, causes declines in *C. elegans* DAF-7 production.

Figure 23:
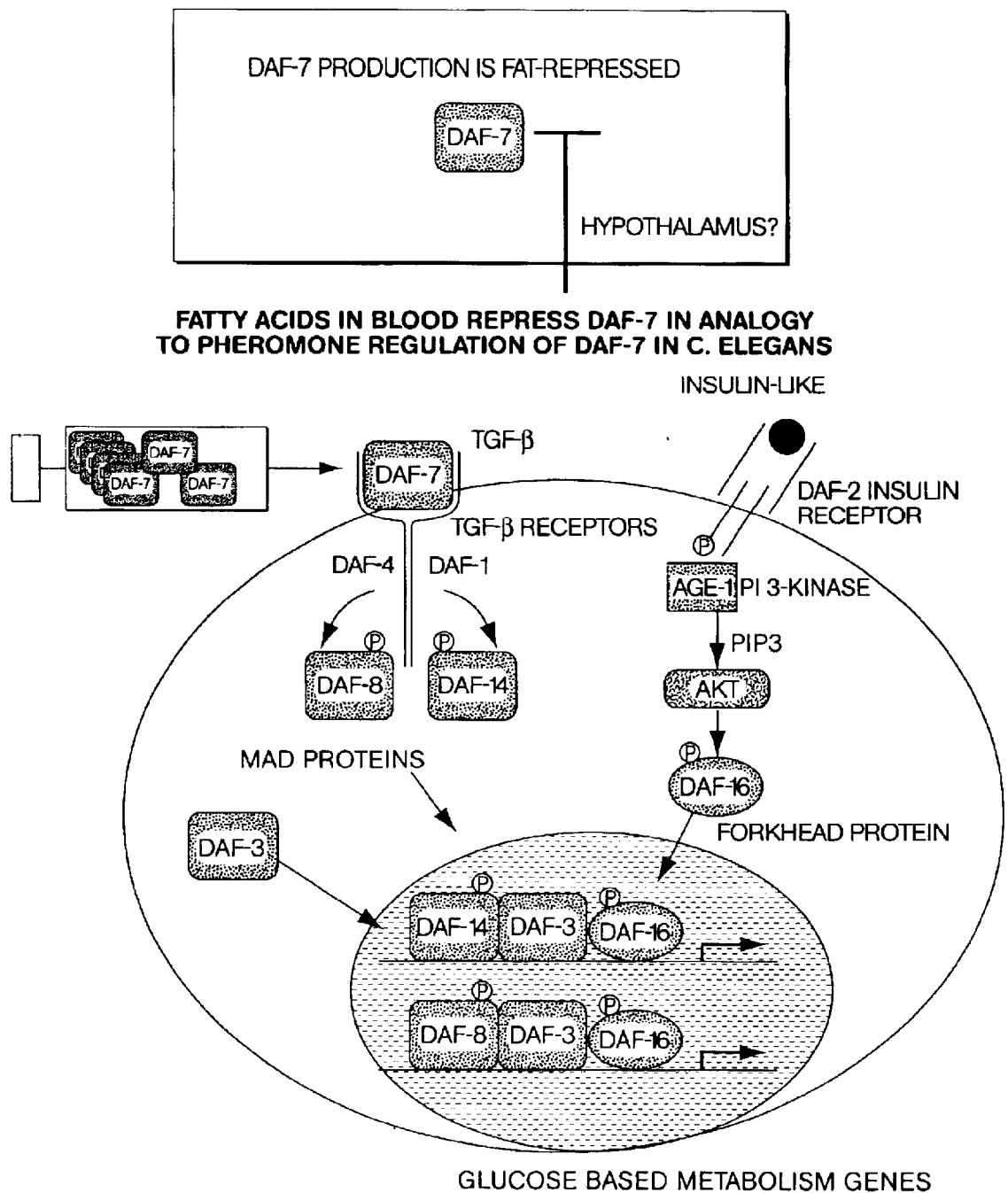
FIG. 23 is an illustration showing a model for treatment of obesity-induced diabetes with DAF-7 protein.

Accordingly, obesity onset Type II diabetes, glucose intolerance, and the associated atherosclerosis may be treated if DAF-7 hormone is injected intramuscularly or intravenously (FIG. 23).

In addition, antibodies to human DAF-7 should detect declines in DAF-7 in pre-diabetic, glucose-intolerant, or obesity induced diabetes. Such antibodies will detect DAF-7 levels in blood, just as insulin levels are detected in metabolic disease.

DAF-7 therapeutic potential and dosage can be developed in mouse models of obesity onset diabetes, for example, the db and ob mouse.

DAF-7 may be injected either intravenously or intramuscularly, in analogy to insulin therapy.

The decision of which classes of diabetics to treat with DAF-7 will come from a combination of blood tests for DAF-7 levels and genetic testing to determine which daf, age, or akt mutations a particular diabetic or pre-diabetic patient carries.

Screening Systems for Identifying Therapeutics

Based on our experimental results, we have developed a number of screening procedures for identifying therapeutic compounds (e.g., anti-diabetic and anti-obesity pharmaceuticals or both) which can be used in human patients. In particular examples, compounds that down regulate daf-3 or daf-16 or their human homologs are considered useful in the invention. Similarly, compounds that up regulate or activate daf-1, daf-2, daf-4, daf-7, daf-8, daf-11 daf-14, age-1, or akt (or each of their corresponding human homologs) are also considered useful as drugs for the treatment of impaired glucose tolerance conditions, such as diabetes and obesity. In general, the screening methods of the invention involve screening any number of compounds for therapeutically active agents by employing any number of in vitro or in vivo experimental systems. Exemplary methods useful for the identification of such compounds are detailed below.

The methods of the invention simplify the evaluation, identification, and development of active agents for the treatment and prevention of impaired glucose tolerance conditions, such as diabetes and obesity. In general, the screening methods provide a facile means for selecting natural product extracts or compounds of interest from a large population which are further evaluated and condensed to a few active and selective materials. Constituents of this pool are then purified and evaluated in the methods of the invention to determine their anti-diabetic or anti-obesity activities or both.

Below we describe screening methods for evaluating the efficacy of a compound as anti-diabetic or anti-obesity agents or both. These examples are intended to illustrate, not limit, the scope of the claimed invention.

Test Extracts and Compounds

In general, novel drugs for the treatment of impaired glucose tolerance conditions are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-diabetic and anti-obesity activities should be employed whenever possible.

When a crude extract is found to have anti-diabetic or anti-obesity activities or both, further fractionation of the positive lead extract is necessary to isolate chemical constituents responsible for the observed effect. Thus, the goal of the extraction, fractionation, and purification process is the careful characterization and identification of a chemical entity within the crude extract having anti-diabetic or anti-obesity activities. The same in vivo and in vitro assays described herein for the detection of activities in mixtures of compounds can be used to purify the active component and to test derivatives thereof. Methods of fractionation and purification of such heterogenous extracts are known in the art. If desired, compounds shown to be useful agents for the treatment of pathogenicity are chemically modified according to methods known in the art. Compounds identified as being of therapeutic value are subsequently analyzed using any standard animal model of diabetes or obesity known in the art.

There now follow examples of high-throughput systems useful for evaluating the efficacy of a molecule or compound in treating (or preventing) an impaired glucose tolerance condition.

Nematode Release of Dauer Arrest Bioassays

To enable mass screening of large quantities of natural products, extracts, or test compounds in an efficient and systematic fashion, *C. elegans* mutant dauer larvae (e.g., *C. elegans* containing mutations described herein, such as *C. elegans* daf-2 mutant dauer larvae) are cultured in wells of a microtiter plate, facilitating the semiautomation of manipulations and full automation of data collection. In one particular example, the assay for dauer release involves a measurement of culture turbidity. Specifically, dauer larvae are treated with candidate compounds and allowed to incubate. If dauer release occurs, the animals grow and reproduce, and consume their light-scattering bacterial food source, decreasing the turbidity of the microtiter well culture. Thus, dauer release is measured by the extent of the decrease in culture turbidity. This type of assay allows millions of microtiter samples to be simultaneously screened.

As discussed above, compounds that down regulate DAF-3 or DAF-16 activities or up regulate DAF-1, DAF-2, DAF-4, DAF-7, DAF-8, DAF-11, DAF-14, AGE-1, or AKT activities are considered useful in the invention. Such compounds are identified by their effect on dauer formation in *C. elegans* strains carrying mutations in these genes (as described above).

In particular examples, nematodes bearing mutations in the DAF-2 polypeptide arrest as dauer larvae, never producing progeny. All of the metabolic and growth arrest phenotypes caused by lack of daf-2 are suppressed by mutations in daf-16. Mutations in the PI 3-kinase, AGE-1, have the same phenotype as lack of daf-2, and such mutations are also suppressed by daf-16 mutations. Biochemical analysis of insulin signaling in mammals supports the view that AGE-1 transduces signals from the DAF-2 receptor by generating a PIP3 signal. Because daf-16 mutations suppress lack of daf-2, or age-1 gene activity, it is believed that PIP3 down regulates or modifies daf-16 gene activity. The biochemical overlap between DAF-2/AGE-1 and insulin receptors/PI 3-kinase indicates that the human homolog of the *C. elegans* daf-16 gene acts in the insulin pathway as well. Thus, the *C. elegans* insulin signaling pathway yields the surprising result that the animals can live without insulin signaling, provided they are mutant in daf-16. This analysis therefore indicates that a compound that inhibits DAF-16 activity would reverse the effects of diabetic lesions, e.g., in the production or secretion of insulin or in the reception of insulin signals by target tissues. Such drugs would be expected to be efficacious in the treatment of insulin deficiencies due to pancreatic β cell destruction in Type I diabetes, as well as some Type II diabetes due to defects in insulin signaling.

Figure 19:
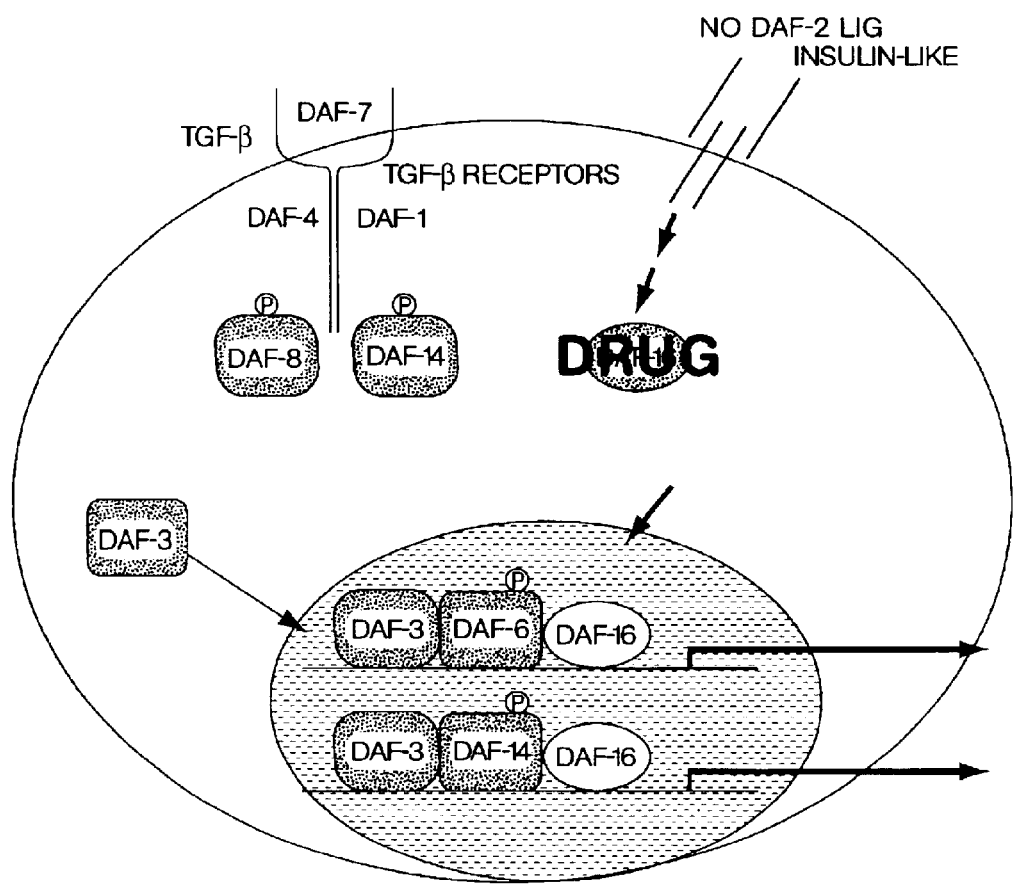
FIG. 19 is a schematic diagram illustrating inhibition of the DAF-16 pathway by drugs to ameliorate lack of insulin signaling.

To evaluate the ability of a test compound or an extract to decrease daf-16 gene activity, mutant daf-2 (e1370); daf-16 (mgDf50) animals carrying an integrated human DAF-16 gene are incubated in microtiter dishes in the presence of a test compound. This human DAF-16 gene supplies all of the DAF-16 activity in the *C. elegans* strain and thus allows daf-2-induced dauer arrest unless its activity is decreased by the candidate test compound. If desired, various concentrations of the test compound or extract can be inoculated to assess the dosage effect. Control wells are incubated in the absence of a test compound or extract. Plates are then incubated at 25° C. After an appropriate period of time, e.g., 2 to 5 days, wells are examined for progeny. The presence of progeny is taken as an indication that the test compound or extract is effective at inhibiting daf-3 or daf-16 activity, and therefore is considered useful in the invention. Any compound that inhibits DAF-16 gene activity (or activates upstream signaling in the absence of receptor function) will allow reproduction. This is shown schematically in FIG. 19.

Figure 20:
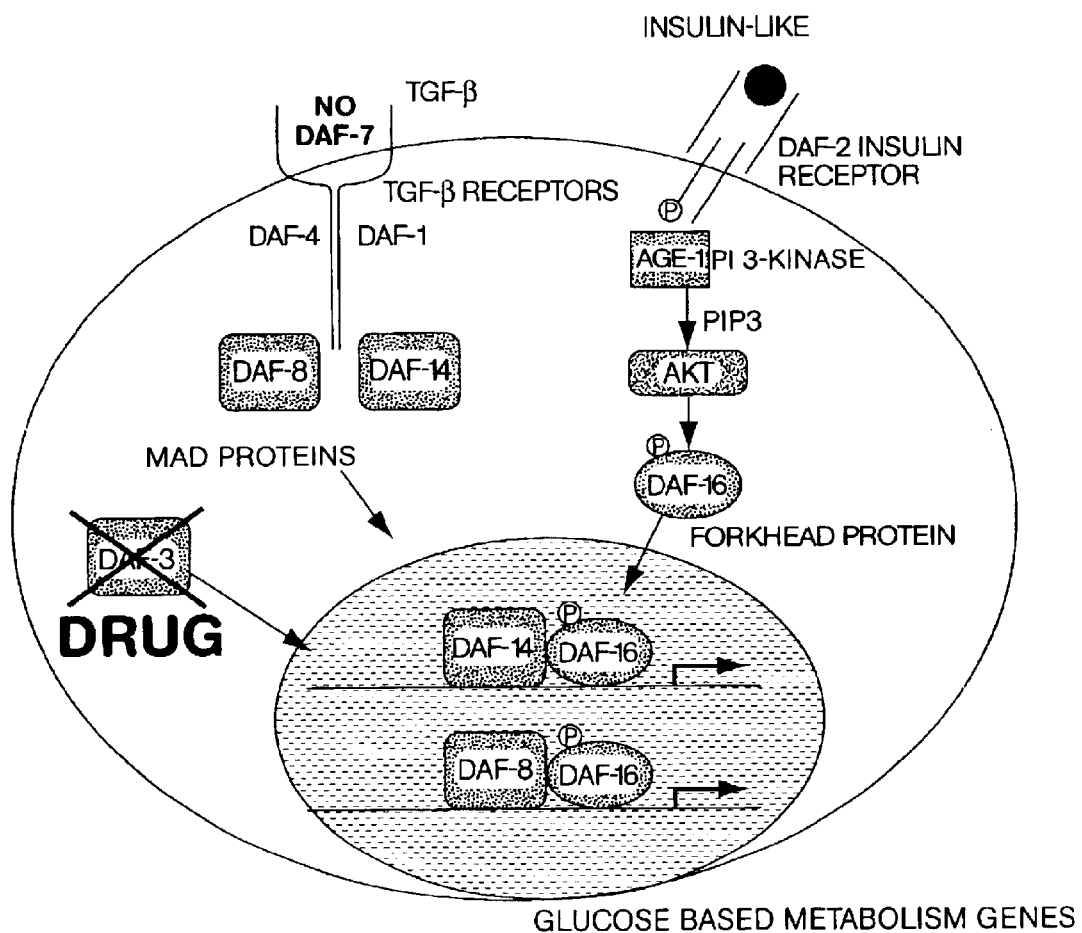
FIG. 20 is a schematic diagram illustrating inhibition of DAF-3 by drugs to ameliorate a lack of DAF-7 signaling (for example in obesity-induced diabetes).

Alternatively, a diabetic condition may arise from defects in the DAF-7 TGF-β signaling pathway. Since a decrease in DAF-3 activity bypasses the need for DAF-7 activity in *C. elegans* metabolic control, drugs that down regulate DAF-3 activity are useful for ameliorating the metabolic defects associated with diabetes. To screen for such drugs, daf-7 (e1372); daf-3 (mg90) nematodes expressing human DAF-3 are exposed to chemicals as described above. In this strain, human DAF-3 supplies all DAF-3 activity, causing daf-7 induced dauer arrest unless its activity is inhibited (FIG. 20). Compounds capable of inhibiting this activity are considered useful therapeutics in the invention.

Finally, in a less complex screen for drugs that inhibit *C. elegans* daf-3 or daf-16, daf-7 or daf-2 mutants are directly screened for compounds that decrease *C. elegans* daf-3 or daf-16 gene activity.

In addition, *C. elegans* worms carrying other daf mutations may be utilized in an assay to obtain additional information on the mode of action of the test compound in the insulin or TGF-β signaling pathways. For example, a drug having PIP3 agonist activity would be expected to allow age-1 and daf-2 mutants (but not akt or daf-7 mutants) to not arrest at the dauer stage. Similarly, drugs that inhibit daf-3 are expected to suppress daf-7 mutants but not daf-2 or age-1 mutants.

Exemplary Dauer Recovery Screen

Using screens such as those described above, muscarinic agonists have been shown to specifically promote dauer recovery in pheromone-induced dauers as well as particular classes of dauer constitutive mutants. Strikingly, the muscarinic agonists could not induce recovery of daf-2 induced dauers, which have defective insulin-like signaling. This muscarinic pathway was also shown to regulate *A. caninum* recovery from dauer arrest. In mammals, such muscarinic agonists promote insulin release both in vivo and in vitro (Ahren et al., (1986) Diabetologia 29:827–836; and Miller (1981) Endocr. Rev. 2:471–494). We suggest that insulin-like secretory cells in the nematodes are regulated by cholinergic inputs in a metabolic control pathway that is homologous to the mammalian autonomic input to pancreatic beta cell activity. Drugs that activate cholinergic as well as other mammalian insulin release pathways may prove useful in the control of parasitic nematode life cycles. These experiments were carried out as follows.

Strains and Growth Conditions

All strains were maintained and handled as described in Brenner (1974) Genetics 77:71–94; and Sulston and Hodgkin (1988) Methods (Cold Spring Harbor Laboratory, Cold Spring Harbor. Animals were grown on standard NG agar plates. In this study, the mutations in *C. elegans* used were LGI: daf-8(e1393); LGII: daf-22(m130); LGIII: daf-7 (e1372), daf-2(e1370), daf-4(m63); and LGIV: daf-1(m40), daf-14(m77), daf-10(e1387); LGX: daf-12(m20). *Ancylostoma caninum* were maintained as described previously (Hawdon and Schad (1993) Exper. Parasitol. 77:489–491).

Dauer Arrest Assay

Minimal media plates were used for the drug assays: 3.0 g NaCl, 20 g agarose (Sigma-Type II #A6877) and 970 ml of water. The autoclaved solution was cooled to 50–55° C. before 25 ml of 1M $KPO_4$ (pH 6.0), 1.0 ml 1M $CaCl_2$, 1.0 ml of 1M $MgSO_4$, and 1 ml of 5 mg/ml cholesterol were added. In some assays, *Escherichia coli* (DH5α) bacteria arrested with streptomycin was added to each plate.

Animals were grown at 15° C. for several generations and then were placed in a bleach solution to isolate eggs. 100–200 eggs were added to each 10 ml drug plate with food. In several assays, eggs were placed in 5–6 ml of S medium (Wood (1988) (Cold Spring Harbor Laboratory Press, Cold Spring Harbor, N.Y.)) in a 15 ml polypropylene tube on a rotary platform at 25° C. overnight for 12–16 hours without food. This yields a synchronous preparation of L1 animals. The synchronized L1s were placed onto the drug plates at 20° C. Two, four, and eight days later, plates were examined for the presence of arrested dauers and reproductive non-dauers. When the non-dauers had reached the gravid adult hermaphrodite stage and were beginning to lay eggs, each plate was examined visually for the presence of dauers and non-dauers. Following this, animals from each plate were rinsed off the plate into a plastic dish containing 1% SDS (dauers are the only larval stage resistant to this treatment). After 30 minutes, dishes were examined under the dissecting microscope for the presence of dauers and non-dauers.

Dauer Recovery Assay

We found that the most effective assay for dauer recovery was to place dauer stage animals onto drug plates at 25° C. without the addition of food. In some experiments, 100–200 eggs or synchronized L1s were put onto the drug plates. For all experiments described herein, about 10,000 L1s were placed in 10 ml of S Medium containing 1–2 ml of a 0.4% (w/v) solution of *Escherichia coli* DH5α bacteria in M9 solution (Wood (1988) (Cold Spring Harbor Laboratory Press, Cold Spring Harbor, N.Y.)) arrested with streptomycin, in a 25 ml flask on a rotating heated water bath at 25° C. For wild-type N2 dauers, 600 µl of the 0.4% bacterial solution and pheromone was also added to flask as described in Gottlieb and Ruvkun (1994) Genetics 137:107120. The pheromone preparation is a solution prepared as follows. Animals were grown in a large flask for several generations, and then spun down. The supernatant was boiled down to a brownish powder and then ethanol extracted. After 72 hours of liquid growth, animals were centrifuged and the supernatant removed. Animals were then resuspended in a 15 ml tube with a pre-heated 25° C. solution of 1% SDS and tubes were placed on a rocker at 25° C. for 30 minutes. Animals were centrifuged and the SDS removed. Animals were washed with either M9 or S medium (Wood (1988) (Cold Spring Harbor Laboratory Press, Cold Spring Harbor, N.Y.)) 4–6 times. After a final spin, 100–200 dauers were placed onto the drug plates without food. 24 and 48 hours later, plates were scored for the number of dauers and non-dauer adults.

For each strain tested, a control plate without any drug, with and without food was also tested. With no drug, there was 40% recovery in N2 dauers. The high value for the control plate in N2 may have been due to experimental procedure. The background recovery rate for N2 was much higher than the background recovery rate for the dauer constitutive mutants where there was very little, if any, background recovery. The assay was performed at 25° C., which means that the daf-c mutants are still under full dauer inducing conditions. However, for N2, no exogenous pheromone was added to the drug plate and therefore, even though the plates were kept at a high temperature and had no food, dauer-maintaining conditions may not have been as severe as for the daf-c mutants.

Drug Assay in *A. caninum*

Hookworm infective L3 animals were collected from 1–4 wk old coproculture by the Baermann technique, and decontaminated with 1% HCL in BU buffer (50 mM Na2PO4/22 mM KH2PO4/70 mM NaCl, pH 6.8) (Hawdon and Schad (1991) in Developmental Adaptations in Nematodes., ed. C. A. Toft, A. A. a. L. B. (Oxford University Press, Oxford), pp. 274–298; and Hawdon and Schad (1991) J. Helm. Soc. Wash. 58:140–142) for 30 minutes at 22° C. Approximately 250 L3 animals were incubated in individual wells of a 96-well tissue culture plate containing 0.1 ml RPMI1640 tissue culture medium, supplemented with 0.25 mM HEPES pH 7.2, 100 U/ml penicillin, 100 µg/ml streptomycin, 100

μg/ml gentamycin, and 2.5 μg/ml amphotericin B. The L3 animals were activated to resume development and feeding by including 10% (v/v) canine serum and 25 mM S-methylglutathione (GSM; Hawdon et al. (1995) Exper. Parasitol. 80:205–211). Non-activated L3 animals were incubated in RPMI alone (i.e., without the stimulus). Stock solutions of the drugs were made in RPMI, and included in the incubation at the indicated concentrations. The agonists were tested for activation by incubation with the L3 animals in the absence of the normal stimulus (i.e., serum+GSM), whereas atropine was tested in the presence of the normal stimulus, as well as with the agonists. The L3 animals were incubated at 37° C. 5% $CO_2$ for 24 hours. The percentage of feeding L3 animals was determined by incubating the L3 animals with 2.5 mg/ml FITC-BSA for 2–3 hours, followed by counting the number of L3 animals that had ingested the labeled BSA by microscopic examination under epifluorescent illumination (Hawdon and Schad (1990) J. Parasit. 76:394–398). Each treatment was done in triplicate, and each experiment was repeated at least once.

Neurotransmitter Regulation of Diapause

Dauer arrest is modulated by sensory inputs (Golden and Riddle (1984) Developmental Biology 102:368–378). Arrest at the dauer stage is controlled by parallel TGF-β and insulin-like signaling pathways (Riddle (1988) in The Nematode *Caenorhabditis elegans*, ed. Wood, W. B. (Cold Spring Harbor Laboratory Press, Cold Spring Harbor, N.Y.), pp. 393–412; Riddle and Albert (1997) in *C. elegans* II, eds. Riddle, D. L., Blumenthal, T., Meyer, B. J. & Priess, J. R. (Cold Spring Harbor Laboratory Press), pp. 739–768; Thomas (1993) Bioessays 15:791–797; Riddle et al. (1981) Nature 290:668–671; Vowels and Thomas (1992) Genetics 130:105–123; Thomas et al. (1993) Genetics 134:1105–1117; Gottlieb and Ruvkun (1994) Genetics 137:107120; Georgi et al. (1990) Cell 61:635–645; Estevez et al. (1993) Nature 365:644–649; Ren et al. (1996) Science 274:1389–1391; Kimura et al. (1997) Science 277:942–946; and Morris et al. (1996) Nature 382:536–539.41). Animals arrest at the dauer stage when they are lacking signaling from either of these two pathways (Georgi et al. (1990) Cell 61:635–645; Estevez et al. (1993) Nature 365:644–649; Ren et al. (1996) Science 274:1389–1391; Kimura et al. (1997) Science 277:942–946; and Morris et al. (1996) Nature 382:536–539.41). Animals will arrest development at the dauer stage when high levels of pheromone result in the absence of both the DAF-7/TGF-β ligand which is secreted from the ASI sensory neuron as well as an as yet unidentified secretory cell that releases the insulin-like ligand. Lack of the TGF-β ligand results in an upregulation of the DAF-3 Smad protein, while lack of the insulin-like ligand causes an upregulation of the DAF-16 forkhead transcription factor. Therefore, for dauer arrest, two separate signaling pathways are involved. Recovery from the dauer arrest when pheromone levels decline is thought to involve up-regulation of these TGF-β and insulin-like signals.

To detect possible neural inputs to this neuroendocrine system, we tested drugs that affect a variety of neurotransmitter signaling pathways, including agonists, antagonists, and reuptake inhibitors, for effects on either dauer arrest or dauer recovery. We have shown that muscarinic agonists (oxotremorine, arecoline, pilocarpine and muscarine) promoted dauer recovery. None of the drugs tested promoted dauer arrest under replete conditions.

Cholinergic Input to Dauer Recovery

We tested drugs that affected the following mammalian neuronal pathways: adrenergic/noradrenergic, serotonergic, cholinergic, glutaminergic, dopaminergic, gabaergic and opiod for effects on *C. elegans* dauer induction and dauer recovery. In each category both agonists and antagonists were examined. Most drugs tested did not affect dauer recovery and the animals remained arrested at the dauer stage. However, multiple unrelated muscarinic agonists could promote dauer recovery. Four muscarinic agonists, oxotremorine, pilocarpine, arecoline, and carbachol (Avery et al. (1993) Genetics 134:455–464), promoted recovery of dauers induced by mutation as well as pheromone. The dose response curves in FIGS. 44A–44C show the muscarinic agonists induced about 50% recovery of dauers induced by defective TGF-β signaling in the daf-7(e1372) mutant, with a defect in the TGF-β ligand. Similar results were seen with other mutants in the TGF-β signaling pathway, daf-1(m40) in the type I TGF-β receptor and daf-4(m63) in the type II TGF-β receptor. For example, 30% of daf-1(m40) dauers recover in oxotremorine, whereas plates with no drug had less than 5% recovery. Similarly, 50% of daf-4(m63) dauers recover in oxotremorine, while plates with no drug had less than 1% recovery.

The infective "dauer" L3 of the hookworm *A. caninum* can be stimulated to resume feeding and development in vitro by incubation with canine serum and S-methylglutathione (GSM), but not by tissue culture medium alone (Sulston and Hodgkin (1988) Methods (Cold Spring Harbor Laboratory, Cold Spring Harbor)). However, when *A. caninum* L3 were incubated with either oxotremorine or arecoline in the tissue culture medium, 60–80% of the animals recovered, as indicated by the resumption of feeding. Therefore, muscarinic agonists mimicked the recovery induced by serum and GSM.

FIGS. 44A–44C show the dose response curves of two of the muscarinic agonists tested: oxotremorine and arecoline. In each figure we show the dose response for wild-type induced dauers, daf-7(e1372), daf-2(e1370) and *A. caninum* dauers. Pilocarpine (data not shown) and oxotremorine (FIG. 44A) induced maximum recovery of daf-7(e1372) dauers at 5 mM concentration, while wild-type pheromone-induced dauers reached maximum recovery at 1 mM. *A. caninum* L3 dauers also reached maximum recovery at 5 mM oxotremorine (FIG. 44A), but failed to recover when incubated with pilocarpine. The maximal response for arecoline was 10 fold lower than for the other agonists in both *C. elegans* and *A. caninum* (FIG. 44B). Concentrations of 1 mM to 5 mM of a drug are routinely used in drug assays in *C. elegans* (Hart et al. (1995) Nature 378:82–85.21; Horvitz et al. (1982) Science 216:1012–1014; Lewis et al. (1980) Genetics 95:905–928; Lewis et al. (1980) Neuroscience 5:967–989; Maricq et al. (1995) Nature 378:78–81; McIntire et al. (1993) Nature 364:334–337; McIntire et al. (1993) Nature 364:337–341; Schinkmann and L1 (1992) J. Comp. Neurol. 316:251–260.51; and Avery et al. (1993) Genetics 134:455–464). The unusually high doses may be due to a cuticle permeability barrier.

While the muscarinic agonists were potent inducers of recovery in daf-7 induced and pheromone-induced dauers, they did not induce recovery of a daf-2 mutant with defects in the *C. elegans* homologue of the mammalian insulin receptor gene (FIG. 44A–44C). Thus the muscarinic recovery pathway depends on insulin-like signaling. Atropine specifically inhibits dauer recovery To determine the specificity of the muscarinic response, we added both oxotremorine, the agonist, and atropine, a muscarinic antagonist, to plates varying the concentration of antagonist to obtain a dose response shown in FIG. 44C. In 1 mM oxotremorine, 40% of the daf-7(e1372) dauers recovered. However, in combination with 1 mM atropine, 1 mM oxotremorine only induced 5% recovery; at 5 mM atropine, the 1 mM oxotremorine response was completely abolished. For wild-type N2 dauers, the results were almost identical (FIG. 44C). This suggested that the drug-induced recovery was a specific muscarinic response, since in mammals atropine is only a muscarinic antagonist and did not interfere with nicotinic receptors (Lefkowitz et al. (1996) in Goodman and Gilman's The Pharmacological Basis of Therapeutics, eds. Hardman, J. G. & Limbird, L. E., McGraw Hill, pp. 105–139; and Brown and Taylor (1996) in Goodman and Gilman's The Pharmacological Basis of Therapeutics, eds. Hardman, J. G. & Limbrid, L. E., McGraw Hill, pp. 141–160).

Atropine (0.5 mM) inhibited recovery of A. caninum L3 incubated with serum and GSM by 99.5%. Moreover, A. caninum L3 incubated with 0.5 mM arecoline and 1.0 mM atropine failed to recover (FIG. 44C). These data indicate that recovery from arrest in hookworm L3 is also mediated by a muscarinic signal.

Atropine inhibits C. elegans dauer recovery induced by food signals. When killed bacteria are added to pheromone-induced dauers at 25° C., 99% of the animals recovered (FIG. 45A). Without bacteria, no dauers recovered in the same time period (FIG. 45A). However, only 21% of the dauer larvae recovered in bacterial food plus atropine (FIG. 45A). Similarly, atropine (0.5 mM) inhibited recovery of A. caninum L3 incubated with serum and GSM by 99.5%.

Temperature is a potent inducer of dauer recovery in animals bearing mutations in the TGF-β or insulin-like signaling pathways. For example, null mutations in daf-7 are temperature sensitive, and recovery of both daf-7 and daf-2-induced dauer larvae was stimulated by shift to 15° C. (FIG. 45A). Temperature downshift in the absence of food did not induce dauer recovery in either daf-7 or daf-2 mutants (FIG. 45A) nor did bacterial food at 25° C. allow non dauer development. However, temperature downshift and addition of food induced more than 75% recovery of both mutants. This recovery in both daf-7 and daf-2 mutants was inhibited by atropine (FIGS. 45A–45B).

We tested whether it was necessary to have functioning sensory neurons to mediate the muscarinic induced response. daf-10 mutants have abnormal mechanocilia and irregular contours in the amphid sensilla. A daf-7(e1372); daf-10(e1387) double mutant gave a maximum response of 13% recovery with 1 mM oxotremorine. This suggests that the amphid neurons are necessary to meditate the muscarinic response. Alternatively, it is possible that the amphid defects do not allow the drug to enter the worm, if the drug indeed does penetrate the worm through these neurons.

We also examined whether exogenous application of neurotransmitters could mimic the dauer pheromone to induce dauer arrest. We tested these drugs for induction of dauer arrest in wild-type and daf-22 mutants. daf-22 is a mutant that does not secrete pheromone, but will arrest at the dauer stage when exposed to exogenous pheromone (Golden and Riddle (1985) Molecular and General Genetics 198:534–536). None of the drugs tested caused dauer entry under favorable growth conditions. The drugs were active in the plate because several of the drugs caused either paralysis, death, or egg-laying defects.

Dauer Recovery by Muscarinic Agonists

Arrest at the dauer stage is a nematode survival strategy that is a specific example of the related and phyletically general diapause arrest. In C. elegans, dauer arrest occurs under harsh environmental conditions whereas in the hookworm, A. caninum, a parasitic nematode, diapause is a non-conditional stage in the life cycle (Riddle and Bird (1985) J. Nematol. 17:165–168; and Schmidt and Roberts (1985) Foundations of Parasitology (Times Mirros/Mosby College Publishing)). Dauer recovery is regulated by levels of pheromone, food, and temperature in C. elegans, whereas in A. caninum unknown host factors induce dauer recovery upon infection (Golden and Riddle (1984) Developmental Biology 102:368–378).

We have shown that muscarinic agonists cause dauer recovery in both C. elegans and A. caninum, and that this recovery is specifically inhibited by the muscarinic antagonist atropine. The endogenous neurotransmitter at muscarinic receptors is acetylcholine, which in vertebrates functions at cholinergic synapses in both the peripheral and central nervous system (Brown and Taylor (1996) in Goodman and Gilman's The Pharmacological Basis of Therapeutics, eds. Hardman, J. G. & Limbird, L. E., McGraw Hill, pp. 141–160). Acetylcholine has a wide variety of functions in vertebrate signaling including sympathetic and parasympathetic ganglion cells as well as the adrenal medulla, synapses within the central nervous system, and motor end plates on skeletal muscle innervated by somatic motoneurons (Brown and Taylor (1996) in Goodman and Gilman's The Pharmacological Basis of Therapeutics, eds. Hardman, J. G. & Limbird, L. E., McGraw Hill, pp. 141–160). Muscarinic receptors are found in muscle, the autonomic ganglia, the central nervous system and secretory glands. These receptors couple to G proteins and signal on longer time scales than nicotinic receptors. Signaling can be either excitatory or inhibitory (Lefkowitz et al. (1996) in Goodman and Gilman's The Pharmacological Basis of Therapeutics, eds. Hardman, J. G. & Limbird, L. E., McGraw Hill, pp. 105–139). Both muscarinic and nicotinic receptors have been found in invertebrates such as Drosophila and C. elegans as well as vertebrates (Lewis et al. (1980) Genetics 95:905–928; Dudai and Ben-Barak (1977) FEBS Lett. 81:134–136; Haim et al. (1979) J. Neurochem. 32:543–522; and Culotti and Klein (1983) J. Neurosci. 3:359–368).

The nicotinic receptor has been the primary focus of the studies on cholinergic signaling in the worm. The drug levamisole, a nicotinic agonist, is toxic to animals, causing muscle hypercontraction (Lewis et al. (1980) Genetics 95:905–928; and Lewis et al. (1980) Neuroscience 5:967–989). Mutants that are resistant to this drug have revealed components of a nicotinic signaling cascade (Lewis et al. (1980) Genetics 95:905–928; and Lewis et al. (1980) Neuroscience 5:967–989). Levamisole has no effect on dauer recovery, suggesting that the nicotinic receptor pathway does not regulate dauer arrest.

Fewer studies, however, have been done on muscarinic signaling in C. elegans. Binding studies on crude homogenates of C. elegans have shown that they contain muscarinic receptors that have the potential to bind to the muscarinic ligands, [3H] QNB (Yamamura & Snyder (1974) Proc. Natl. Acad. Sci. ?:1725–1729) and [3H] N-methylscopalamine (Burgermeister et al. (1978) Mol. Pharmacol. 14:240–256) with high affinity (Culotti and Klein (1983) J. Neurosci. 3:359–368). These receptors were found in both C. elegans adults and L1 and L2 larvae ((Culotti and Klein (1983) J. Neurosci. 3:359–368). Several potential muscarinic receptor homologues have been identified in the C. elegans genome sequence database (Sulston et al. (1992) Nature 356:37–41)

There are two different classes of muscarinic receptor agonists: choline esters and cholinomimetic allkaloids. Both arecoline and pilocarpine are naturally occurring drugs from the betel nut seed and the Pilocarpus leaf, respectively, while oxotremorine is a synthetic drug (Brown and Taylor (1996)

in Goodman and Gilman's The Pharmacological Basis of Therapeutics, eds. Hardman, J. G. & Limbird, L. E., McGraw Hill, pp. 141–160). Carbachol is a synthetic choline ester which mimics acetylcholine and acts at both muscarinic and nicotinic receptors in mammals (Brown and Taylor (1996) in Goodman and Gilman's The Pharmacological Basis of Therapeutics, eds. Hardman, J. G. & Limbird, L. E., McGraw Hill, pp. 141–160). Arecoline, pilocarpine, and oxotremorine are drugs that have the same sites of action and function as the choline esters (Brown and Taylor (1996) in Goodman and Gilman's The Pharmacological Basis of Therapeutics, eds. Hardman, J. G. & Limbird, L. E., McGraw Hill, pp. 141–160). Arecoline also acts on nicotinic receptors. Atropine specifically inhibits mammalian muscarinic responses (Brown and Taylor (1996) in Goodman and Gilman's The Pharmacological Basis of Therapeutics, eds. Hardman, J. G. & Limbird, L. E., McGraw Hill, pp. 141–160). Since all of the drug-induced dauer recovery was inhibited by atropine, we concluded that this response was mediated by muscarinic signaling.

Molecular analysis of the dauer mutants revealed that a TGF-β signaling pathway regulated dauer arrest (FIG. 46). Mutations in daf-7, which encodes a TGF-β ligand, caused animals to arrest at the dauer stage even under favorable growth conditions (Ren et al. (1996) Science 274:1389–1391). The same phenotype was observed in animals bearing a mutation in either of the two TGF-β receptors, daf-1 and daf-4 (Georgi et al. (1990) Cell 61:635–645; and Estevez et al. (1993) Nature 365:644–649; FIG. 46). Downstream of the receptors are members of the Smad signaling group including the genes daf-8, daf-14 and daf-3 (FIG. 46). Muscarinic agonists potently induced recovery of dauer larvae induced by mutations in this group of genes (FIGS. 44A–44C).

An insulin-like signaling pathway represented by daf-2 and age-1 functions in parallel to this TGF-β pathway (Riddle et al. (1981) Nature 290:668–671; Vowels and Thomas (1992) Genetics 130:105–123; Thomas et al. (1993) Genetics 134:1105–1117; Gottlieb and Ruvkun (1994) Genetics 137:107120; Kimura et al. (1997) Science 277:942–946; and Morris et al. (1996) Nature 382:536–539.41; FIG. 46). daf-2 is a member of the insulin receptor family (Kimura et al. (1997) Science 277:942–946) and age-1 encodes phosphatidylinositol (PI)-3-kinase (Morris et al. (1996) Nature 382:536–539.41) suggesting that the level of an insulin-like molecule is down-regulated during pheromone-induced dauer arrest. None of the drugs tested, including the muscarinic agonists and antagonists, could induce dauer recovery in daf-2 mutants (FIGS. 44A–44C). Thus the cholinergic input to dauer recovery depends on insulin-like signaling. We suggest that muscarinic agonists induce recovery of the TGF-β pathway mutant dauer larvae or pheromone-induced dauer larvae by stimulating signaling in the daf-2 insulin-like pathway. In this way, cholinergic stimulation can induce recovery in animals with defective TGF-β pathway genes but not in animals with defect insulin-like pathway genes.

In vertebrate insulin signaling, many studies link muscarinic and insulin signaling pathways. Both adrenergic and cholinergic fibers innervate secretory cells in the vertebrate islet of Langerhans (Ahren et al. (1986) Diabetologia 29:827–836; and Yamamura and Snyder (1974) Proc. Natl. Acad. Sci.1725–1729). Consistent with the suggestion that muscarinic inputs increase C. elegans insulin-like signaling, mammalian autonomic cholinergic fibers enhance insulin secretion. Pharmacological stimulation with acetylcholine or carbachol can induce insulin release both in vivo and in vitro. This induction is completely abolished by atropine, showing that it is mediated by activation of muscarinic receptors on the β cells (Ahren et al. (1986) Diabetologia 29:827–836; Boschero et al. (1995) Am. J. Physiol. 268:E336–E342; and Latifpour et al. (1992) J. Urol. 147:760–763). In mammalian systems, binding of acetylcholine to the β cell muscarinic receptor causes activation of sodium channels, which in turn leads to a change in membrane potential to induce insulin.

These data suggest the model shown in FIG. 46 for dauer recovery in C. elegans. When pheromone levels decrease and food levels increase, acetylcholine is secreted from an as yet unidentified neuron and binds to the muscarinic receptor on an insulin-like secreting neuron or other cell. This induces secretion of an insulin-like signal to in turn induce dauer recovery (FIG. 46). The lack of muscarinic induced dauer recovery in daf-2 mutants suggest that the insulin-like dauer recovery signal acts via the DAF-2 receptor homologue. From analogy with the vertebrate studies, we suggest that a muscarinic signal causes an increase in insulin release that would bind to the DAF-2 receptor and activate downstream genes which promote dauer recovery. We suggest that the insulin-like DAF-2 ligand is produced by neurons just as the DAF-7 TGF-β signal is produced by the ASI sensory/secretory neuron. Insulin secreting pancreatic β-cells have many neuronal features and are thought to be specialized "ganglia" related to the enteric nervous system of lower vertebrates. In addition, proteins related to insulin are produced by metabolism regulating neurons in Limulus. Distant relatives of insulin are found in the C. elegans genome database. We suggest that the secretory cells that express such an insulin-like gene will also express muscarinic receptors and be connected to food, pheromone, and temperature sensory neurons.

Temperature acts as a modulator for dauer recovery (Riddle and Albert (1997) in C. elegans II, eds. Riddle, D. L., Blumenthal, T., Meyer, B. J. & Priess, J. R., Cold Spring Harbor Laboratory Press, pp. 739–768, FIGS. 45A–B). The thermoregulatory circuit for temperature sensation and output of that information to motor and endocrine pathways has been identified (Hobert et al. (1997) Neuron 19:345–357). This pathway consists of the thermosensory neuron AFD coupled to the interneurons AIY and AIZ (Hobert et al. (1997) Neuron 19:345–357; and Henquin (1994) in Joslin's Diabetes Mellitus, eds. Kahn, C. R. & Weir, G. C., (Lea & Febiger, pp. 56–80)). Mutations in the gene ttx-3, which affect AIY function and is expressed exclusively in the AIY interneurons (Hobert et al. (1997) Neuron 19:345–357), decouple this thermoregulatory pathway from the dauer pathway: daf-7; ttx-3 double mutant animals form dauers that recover at high temperature, unlike daf-7 single mutants (Hobert et al. (1997) Neuron 19:345–357). However, daf-2; ttx-3 double mutant dauers do not recover at high temperature, like the daf-2 mutant alone. We suggest that thermosensory signals through the thermoregulatory AIY and AIZ interneurons couple via as yet unidentified insulin-like secretory neurons (FIG. 46). Given that rates of growth and metabolism are intimately connected to cultivation temperature in invertebrates, the coupling of thermosensation to metabolic control is reasonable. Such a coupling of thermosensory input to metabolic control by the daf-2 insulin-like signaling pathway is analogous to the hypothalamic modulation of autonomic input to the pancreatic beta cells.

The muscarinic signaling pathway also acts in recovery of hookworm infective L3 from their arrested "dauer" state. Recovery from dauer arrest in hookworm occurs in the definitive host in response to an undefined host-specific signal. We suggest that upregulation of an insulin-like molecule by a cholinergic pathway also causes dauer recovery upon entry into the host in *A. caninum*. Accordingly, such parasite insulin-like signals provide targets for antihelminthic drugs. For example, known muscarinic signaling drugs may constitute novel chemotherapeutic strategies to perturb the dauer maintainence process in invertebrate hosts as well as the recovery process in human hosts.

Other Screening Assays

Other drug screening assays may also be performed using either *C. elegans* worms or mammalian cell cultures. If desired, such assays may include the use of reporter gene constructs.

For example, evaluation of the effects of test compounds on dauer formation or reporter gene expression in mutant *C. elegans* strains expressing particular human homologs of the daf age, or akt genes (i.e., humanized *C. elegans*) represent useful screening methods. Expression of the human homologs in *C. elegans* is accomplished according to standard methods and, if desired, such genes may be operatively linked to a gene promoter obtained from *C. elegans*. Such promoters include, without limitation, the *C. elegans* daf-16, age-1, daf-3, daf-4, and akt gene promoters. For example, the 2.5 kb age-1 promoter can be generated and isolated by employing standard PCR methods using the following primers: 5'GGAAATATTTTAGGCCAGATGCG3' (SEQ IS NO: 49) and 5'CGGACAGTCCTGAATACACC3' (SEQ ID NO: 50).

Additionally, mammalian tissue culture cells expressing *C. elegans* daf age-1, or akt homologs may be used to evaluate the ability of a test compound or extract to modulate the insulin or TGF-β signaling pathways. Because the signaling pathways from the ligands, receptors, kinase cascades, and downstream transcription factors are conserved from man to worm, test compounds or extracts that inhibit or activate the worm signaling proteins should also inhibit or activate their respective human homolog. For example, our identification that DAF-16 is a transcription factor that acts downstream of insulin-like signaling in *C. elegans* indicates that human DAF-16 transcription reporter genes also can be used to identify drugs that inhibit any of the kinases in the signaling pathway downstream of insulin signaling. For example, the use of DAF-16 and DAF-3 protein binding sites in reporter gene constructs may be used to monitor insulin signaling. Candidate compounds mimicking insulin signaling (e.g., PIP3 agonists) are expected to increase reporter gene expression and are considered useful in the invention.

Reporter Gene Construct

In one particular example, the invention involves the use of a reporter gene that is expressed under the control of a *C. elegans* gene promoter, e.g., a promoter that includes the TCTCGTTGTTTGCCGTCGGATGTCTGCC (SEQ ID NO: 51) enhancer element, such as the *C. elegans* pharyngeal myosin promoter (Okkema and Fire, *Development* 120: 2175–2186, 1994). This enhancer element is known to respond to DAF-3 regulation (i.e., in daf-7 mutants, where daf-3 is active, the element confers high level expression to reporter genes; whereas in a daf-7; daf-3 mutant (for example, daf-7 (e1372); daf-3), the element confers low level expression to reporter genes). Other equivalent enhancer elements may also be used in the invention, e.g., the enhancer element which is bound by the *Xenopus* Smad1 and Fast1 forkhead proteins (*Nature* 383 600–608, 1996). The enhancer element is cloned upstream of any standard reporter gene, e.g., the luciferase or green fluorescent protein (GFP) reporter genes. In preferred embodiments, the GFP reporter gene is used in *C. elegans*. In other preferred embodiments, either the GFP or the luciferase reporter genes may be used in a mammalian cell based assay. The reporter gene construct is subsequently introduced into an appropriate host (e.g., *C. elegans* or a mammalian cell) according to any standard method known in the art. Analysis of reporter gene activity in the host organism or cell is determined according to any standard method, e.g., those methods described herein. Such reporter gene (and host cell systems) are useful for screening for drugs that modulate insulin or DAF-7 metabolic control signaling.

In addition, any number of other transcriptional fusions to fat based metabolic genes, such as fatty acid synthase, hormone sensitive lipase orthologue, and acetyl coa synthase, may also be constructed. These genes are expected to be up regulated when the animals shift to fat based metabolism and to be directly regulated by DAF-16 and DAF-3, and perhaps DAF-12.

Transcriptional fusions to GFP allow the screening of drugs or mutants for altered regulation of these genes and altered metabolism. Such drugs or gene targets are useful in the control of obesity and diabetes. For example, drugs that inactivate the expression of fat synthesis genes in *C. elegans* may be used to treat diabetes and obesity. Similarly, full length protein fusions of these genes to GFP reveal the subcellular localization of the proteins. Drugs or mutants that perturb the cell biology of these proteins also provide useful treatments and drug targets for obesity control as well as diabetes.

Shown below are conserved protein regions of *C. elegans* homologues of key metabolic enzymes SEQ ID NOs: 211–303). GFP fusions may be constructed using the 5' promoter regions located between these conserved protein domains and the next gene located 5' to these regions, as described above for the glucose transporter GFP fusion gene.

```
>R11A5
Length = 26,671
Plus Strand HSPs:

Score = 994 (461.5 bits), Expect = 0.0, Sum P(5) = 0.0
Identities = 176/223 (78%), Positives = 195/223 (87%), Frame = +1

SEQ ID NO:211 Query:   201 AKNNGEFVRCVHSVGQPKPVATKVINHWPCNPEKTIIAHRPAEREIWSFGSGYGGNSLLG 260
SEQ ID NO:212              A N +FVRC+HSVG P+PV   +VINHWPCNPE+ +IAHRP EREIWSFGSGYGGNSLLG
SEQ ID NO:213 Sbjct: 8682 ALGBQDFVRCIHSVGLPRPVKQRVINHWPCNPERVLIAHRPPEREIWSFGSGYGGNSLLG 18861

SEQ ID NO:211 Query:   261 KKCFALRIAMNIGYDEGWMAEHMLIMGVTSPKGEERFVAAAFPSACGKTNLAMLEPTIPG 320
SEQ ID NO:212              KKCFALRIA NI  DEGWMAEHMLIMGVT P G E F+AAAFPSACGKTNLAMLEPT+PG
SEQ ID NO:213 Sbjct: 18862 KKCFALRIASNIAKDEGWMAEHMLIMGVTRPCGREHFIAAAFPSACGKTNLAMLEPTLPG 19041
```

-continued

```
SEQ ID NO:211 Query:   321 WKVRVIGDDIAWMKFGADGRLYAINPEYGFFGVAPGTSHKTNPMAMASFQENTIFTNVAE 380
SEQ ID NO:212              WKVR +GDDIAWMKFG DGRLYAINPE GFFGVAPGTS+KTNPMA+A+FQ+N+IFTNVAE
SEQ ID NO:213 Sbjct: 19042 WKVRCVGDDIAWMKFGEDGRLYAINPEAGFFGVAPGTSNKTNPMAVATFQKNSIFTNVAE 19221

SEQ ID NO:211 Query:   381 TADGEYFWEGLEHEVKNPKVDMINWLGEPWHIGDESKAAHPNS 423
SEQ ID NO:212              TA+GEYFWEGLE E+ +  VD+  WLGE WHIG+  AAHPNS
SEQ ID NO:213 Sbjct: 19222 TANGEYFWEGLEDEIADKNVDITTWLGEKWHIGEPGVAAHPNS 19350

Score = 657 (305.1 bits), Expect = 0.0, Sum P(5) = 0.0
Identities = 120/173 (69%), Positives = 144/173 (83%), Frame = +1

SEQ ID NO:214 Query:    32 KGDFVSLPKHVQRFVAEKAELMKPSAIFICDGSQNEADELIARCVERGVLVPLKAYKNNY 91
SEQ ID NO:215              +GDF   LP VQRF+AEKAELM+P  IFICDGSQ+EADELI + +ERG+L  L+AY+NNY
SEQ ID NO:216 Sbjct: 18181 QGDFHLLPAKVQRFIAEKAELMRPRGIFICDGSQHEADELIDKLIERGMLSKLEAYENNY 18360

SEQ ID NO:214 Query:    92 LCRTDPRDVARVESKTWMITPEKYDSVCHTPEGVKPMMGQWMSPDEFGKELDDRFPGCMA 151
SEQ ID NO:215              +CRTDP+DVARVESKTWM+T  KYD+V HT EGV+P+MG W++P++  ELD RFPGCMA
SEQ ID NO:216 Sbjct: 18361 ICRTDPKDVARVESKTWMVTKNKYDTVTHTKEGVEPIMGHWLAPELATELDSRFPGCMA 18540

SEQ ID NO:214 Query:   152 GRTMYVIPYSMGPVGGPLSKIGIELTDSDYVVLCMRIMTRMGEPVLKALAKNN 204
SEQ ID NO:215              GR MYVIP+SMGPVGGPLSKIGI+LTDS+YVVL MRIMTR+  V  AL  +
SEQ ID NO:216 Sbjct: 18541 GRIMYVIPFSMGPVGGPLSKIGIQLTDSNYVVLSMRIMTRVNNDVWDALGNQD 18699

Score = 453 (210.3 bits), Expect = 0.0, Sum P(5) = 0.0
Identities = 77/107 (71%), Positives = 90/107 (84%), Frame = +1

SEQ ID NO:217 Query:   424 RFTAPAGQCPIIHPDWEKPEGVPIDAIIFGGRRPEGVPLVFESRSWVHGIFVGAACVKSEA 483
SEQ ID NO:218              RF APA  QCPIIHPDWE P+GVPI+AIIFGGRRP+GVPL++E+  SW HG+F G+C+KSEA
SEQ ID NO:219 Sbjct: 19396 RFAAPANQCPIIHPDWESPQGVPIEAIIFGGRRPQGVPLIYETNSWEHGVFTGSCLKSEA 19575

SEQ ID NO:217 Query:   484 TAAAEHTGKQVMHDPMAMRPFMGYNFGRYMRHWMKLGQPPHKVPKIF 530
SEQ ID NO:218              TAAAE TGK VMHDPMAMRPFMGYNFG+Y++HW+ L      KV  F
SEQ ID NO:219 Sbjct: 19576 TAAAEFTGKTVMHDPMAMRPFMGYNFGKYLQHWLDLKTDSRKVIDFF 19716

Score = 404 (187.6 bits), Expect = 0.0, Sum P(5) 0.0
Identities = 68/116 (58%), Positives = 89/116 (76%), Frame = +1

SEQ ID NO:220 Query:   526 VPKIFHVNWFRQSADHKFLWPGYGDNIRVIDWILRRCSGDATIAEETPIGFIPKKGTINL 585
SEQ ID NO:221              +PKI+HVNWFR+ +++KFLWPG+GDNIRVIDWI+RR  G+  I  ETPIG +P KG+INL
SEQ ID NO:222 Sbjct: 19750 MPKIYHVNWFRDSNNKFLWPGFGDNIRVIDWIIRRLDGEQEIGVETPIGTVPAKGSINL 19929

SEQ ID NO:220 Query:   586 EGLPNVNWDELMSIPKSYWLEDMVETKTFFENQVGSDLPPEIAKELEAQTERIKAL 641
SEQ ID NO:221              EGL  VNWDELMS+P  YW+D  E + F +QVG DLP  +  E++AQ +R++ L
SEQ ID NO:222 Sbjct: 19930 EGLGEVNWDELMSVPADYWKQDAQEIRKFLDEQVGEDLPEPVRAEMDAQEKRVQTL 20097

Score = 69 (32.0 bits), Expect = 0.0, Sum P(5) = 0.0
Identities = 15/36 (41%), Positives = 21/36 (58%), Frame = +1

SEQ ID NO:223 Query:     5 SLSHFKDDDFAVVSEVVTHKQNHIPVIKGDFVSLPK 40
SEQ ID NO:224              SL     +D F VV+EVV  +  H+P++K  F S K
SEQ ID NO:225 Sbjct: 14722 SLRQISEDAFYVVNEVVMKRLGHVPILKVIFESSEK 14829

Score = 39 (18.1 bits), Expect = 6.9e-244, Sum P(4) = 6.9e-244
Identities = 9/25 (36%), Positives = 11/25 (44%), Frame = +3

SEQ ID NO:226 Query:   148 GCMAGRTMYVIPYSMGPVGGPLSKI 172
SEQ ID NO:227              GC   R +  V P S    PL K+
SEQ ID NO:228 Sbjct:  8040 GCSGRRVLCVCPCSHSSSALPLQKV 8114

Score = 38 (17.6 bits), Expect = 4.0e-285, Sum P(5) = 4.0e-285
Identities = 7/16 (43%), Positives = 9/16 (56%), Frame = +1

SEQ ID NO:229 Query:   588 LPNVNWDELMSIPKSY 603
SEQ ID NO:230              L + NW  +S P SY
SEQ ID NO:231 Sbjct: 22654 LESFNWFSFVSCPDSY 22701

Score = 37 (17.2 bits), Expect = 2.0e-48, Sum P(3) = 2.0e-48
Identities = 6/14 (42%), Positives = 9/14 (64%), Frame = +1

SEQ ID NO:232 Query:   117 SVCHTPEGVKPMMG 130
SEQ ID NO:233              +V H P  ++P MG
SEQ ID NO:234 Sbjct: 19603 TVMHDPMAMRPFMG 19644
```

Acetyl Coa Carboxylase

```
>W09B6
Length = 32,900
Plus Strand HSPs:

Score = 562 (259.1 bits), Expect = 0.0, Sum P(14) = 0.0
Identities = 109/197 (55%), Positives = 138/197 (70%), Frame = +2

SEQ ID NO:235 Query:   1951 SGFFDYGSFSEIMQPWAQTVVJGRARLGGIPVGWAVETRTVELSVPADPANLDSEAKII 2010
SEQ ID NO:236                +G D   SF EI   WA+++V GRARL GIP+GVV+E R      VPADPA   S++
SEQ ID NO:237 Sbjct: 28280 TGTCDTMSFDEICGDWAKSIVAGRRLCGIPIGWSSEFRNFSTIVPADPAIDGSQVQNT 28459

SEQ ID NO:235 Query:   2011 QQAGQVWFPDSAFKTYQAIKDFNREGLPLMVFANWRGFSGGMKDMYDQVLKFGAYIVDGL 2070
SEQ ID NO:236                Q+AGQVW+PDSAFKT +AI D N+E LPLM+ A+ RGFSGG KDMYD VLKFGA IVD L
SEQ ID NO:237 Sbjct: 28460 QRAGQVWYPDSAFKTAEMNDLNKENLPLMIIASLRGFSGGQKDMYDMVLKFGAQIVDAL 28639

SEQ ID NO:235 Query:   2071 RECSQPVMWIPPQAELRGGSWVVIDPTTNPRHMEMYADRESRGSVLEPEGTVEIKFRKK 2130
SEQ ID NO:236                 ++PV+VYIP   ELRGG+W V+D   I P + + AD +SRG +LEP V IKFRK
SEQ ID NO:237 Sbjct: 28640 AVYNRPVTVYIPEAGELRGGAWAVLDSKIRPEFIHLVADEKSRGGTLEPNAWGIKFRKP 28819

SEQ ID NO:235 Query:   2131 DLVKTMRRVDPVYTRLA 2147
SEQ ID NO:236                +++M+R DP Y  +L+
SEQ ID NO:237 Sbjct: 28820 MMMEMMKRSDPTYSKLS 28870

Score = 357 (164.6 bits), Expect = 0.0, Sum P(14) = 0.0
Identities = 68/124 (54%), Positives = 89/124 (71%), Frame = +2

SEQ ID NO:238 Query:    303 VGYPVMIKASEGGGGKGIRKKVNNADDFPNLFRQVQAEVPGSPIFVNRLAKQSRHLEVQIL 362
SEQ ID NO:239                +G+P+MIKASEGGGGKGIRK    +DF ++F +V EV GSPIF+M+     +RH+EVQ+L
SEQ ID NO:240 Sbjct: 23264 IGFPLMIKASEGGGGKGIRKCTKVEDFKSMFEEVAQEVQGSPIFLMKCVDGARHIEVQLL 23443

SEQ ID NO:238 Query:    363 ADQY0NAISLFGRDCSVQRRHQKXXXXXXXXXXXXXXXVFEHMEQCAVKLAKMVGYVSAGTV 422
SEQ ID NO:239                AD+Y N IS++ RDCS+QRR QK           +  +M++ AV+LAK VGY SAGTV
SEQ ID NO:240 Sbjct: 23444 ADRYENVISVYTRDCSIQRRCQKIIEEAPAIIASSHIRKSMQEDAVRLAKYYGYESAGTV 23623

SEQ ID NO:238 Query:    423 EYLY 426
SEQ ID NO:239                HYLY
SEQ ID NO:240 Sbjct: 23624 EYLY 23635

Score = 345 (159.1 bits), Expect = 0.0, Sum P(14) = 0.0
Identities = 65/116 (56%), Positives 86/116 (74%), Frame = +2

SEQ ID NO:241 Query:   1787 KEEGLGAENLRGSGMIAGESSLAYDEIITISLVTCRAIGIGAYLVRLGQKTIQVENSHLI 1846
SEQ ID NO:242                K H +G ENL+GSG+IAGE++ AY E+ T   VT R++GIGAY RL F +Q + SHLI
SEQ ID NO:243 Sbjct: 27794 KNEKIGVENLQGSGLIAGETAAYAEVPTYCYVTGRSVGIGAYTARLAHRIVQHKQSHLI 27973

SEQ ID NO:241 Query:   1847 LTGAGALNKVLGFEVYTSNNQLGGIQINHNNGVTHCTVCDDFEGVFTVLHWLSYMP 1902
SEQ ID NO:242                LTG  ALN +LG++VYTSNNQLGG ++M  NGVTH  V +D EG+   V+ W+S++P
SEQ ID NO:243 Sbjct: 27974 LTGYEALNTLLGKKVYTSNNQLGGPEVMFRNGVTHAVVDNDLEGIAKVIRWMSFLP 28141

Score = 319 (147.1 bits), Expect = 0.0, Sum P(14) 0.0
Identities = 59/119 (49%), Positives = 80/119 (67%), Frame = +2

SEQ ID NO:244 Query:    503 HVIAARITSENPDEGFKPSSGTVQELNFFSNKNVWGYFSVAAAGGLHEFADSQFGHCFSW 562
SEQ ID NO:245                H  IAARIT ENPD+ F+PS+G V  E+NF S+++ W YFSV    +H+FADSQFGH F+
SEQ ID NO:246 Sbjct: 23870 HAIAAFITCENPDDSFRPSTGKVYEINFPSSQDAWAYFSVGFGSSVHQFADSQFGHIFTF 24049

SEQ ID NO:244 Query:    563 GENFEHAISNMVVALKELSIFGDFFTTVEYLIKLLETESFQLNFIDTGWLDRLIAEKVQ 621
SEQ ID NO:245                G +R EA++ M   LK++IR  F T V YL+L+       F N   +T WLD+ IA K++
SEQ ID NO:246 Sbjct: 24050 GTSRTEAMNTMCSTLKHMTIRSSFPTQVNYLVDLMHDADFINNAFNTQWLDKRIAMKIK 24226

Score = 303 (139.7 bits), Expect = 0.0, Sum P(14) = 0.0
Identities = 55/90 (61%), Positives = 70/90 (77%), Frame = +2

SEQ ID NO:247 Query:    178 PGGANNNYAWELILDIAKRIFVQAVWAGWGHASENPKLPELLLKNGIAFMGPFSQAMW 237
SEQ ID NO:248                P G N NN+ANV+ IL A +  V AVWAGWGHASENP LP L + IAF+GPP+AN+
SEQ ID NO:249 Sbjct: 22886 PSGTNKNNFAVDEILKHAIKYEVDAVWAGWGHASENPDLPRRLNDHNIAFIGPPASMF 23065

SEQ ID NO:247 Query:    238 ALGDKIASSIVAQTAGTPTLPWSGSGLRVD 267
SEQ ID NO:248                +LGDKIAS+I+AQT G+PT+ WSGSG+ ++
SEQ ID NO:249 Sbjct: 23066 SLGDKIASTITAQTVGVPTVAWSGSGITME 23155
```

Trehelase

```
>C23H3
Length = 39,721
Minus Strand HSPs:

Score = 227 (104.5 bits), Expect = 1.0e-95, Sum P(6) = 1.0e-95
Identities = 36/67 (53%), Positives = 51/67 (76%), Frame = -2

SEQ ID NO:250 Query:     2 VIKNLGYMVDNHGFVPNGGRVYYLTRSQPPLLTPMVYEYThSTGDLDFVMEILPTLDKEY 61
SEQ ID NO:251                +I N +++++ GFVPNGGRVYYL RSQPP   PMVYEYY++T  D+ V +++P ++KEY
SEQ ID NO:252 Sbjct:  9798 MTLNFAHIIETYGFVPNGGRVYYLRRSQPPFFAPMVYEYYLATQDIQLVADLIPVIEKEY 9619

SEQ ID NO:250 Query:    62 EFWIKNR 68
SEQ ID NO:251              FW + K
SEQ ID NO:252 Sbjct:  9618 TFWSERR 9598

Score = 182 (83.8 bits), Expect = 1.0e-95, Sum P(6) = 1.0e-95
Identities = 32/92 (34%), Positives = 55/92 (59%), Frame = -2

SEQ ID NO:253 Query:   146 MDSIRTWSIIPADLNAFMCANARILASLYEIAGDFKKVKVFEQRYTWAKREMRELHWNET 205
SEQ ID NO:254              ++I T +I+P DLNAF+C N  I+    Y++ G+   K    + R+T +     ++ +
SEQ ID NO:255 Sbjct:  9372    ISTIETTNIVPVDLNAFLCYNMNIMQLFYKLTGNPLKHLEWSSRFTNFREAFTKVFYVPA 9193

SEQ ID NO:253 Query:   206 DGIWYDYDIELKTHSNQYYVSNAVPLYAKCYD 237
SEQ ID NO:254                 WYDY++    TH+  ++SNAVPL+++CYD
SEQ ID NO:255 Sbjct:  9192 RKGWYDYNLRTLTHNTDFFASNAVPLFSQCYD 9097

Score = 178 (81.9 bits), Expect = 1.0e-95, Sum P(6) = 1.0e-95
Identities = 37/102 (36%), Positives = 55/102 (53%), Frame = -2

SEQ ID NO:256 Query:   246 VHDYLERQGLLKYTKGLPTSLANSSTQQWDKENAWPPMIHWIEGFRTTGDIKLMVAEK 305
SEQ ID NO:257              V++ ++  G     G+PTS+  + QQWD   N W PM HM+IEG R + ++ L + A
SEQ ID NO:258 Sbjct:  9069 VYNEMQNSGAFSIPGGIPTSMNEETNQQWDFPNGWSPMNHMIIEGTJRKSNNPILQQKAFT 8890

SEQ ID NO:256 Query:   306 MATSWLTGTYQSFIRTHASFEKYNVTPHTEETSCGGGGEYEV 347
SEQ ID NO:257              +A  WL    Q+F +   M+EKYNV    + +GG  E +V
SEQ ID NO:258 Sbjct:  8889 LAEKWLETNMQTFNVSDEMWEKYNVKEPLGKLATGGEYEVQV 8764

Score = 169 (77.8 bits), Expect = 1.0e-95, Sum P(6) = 1.0e-95
Identities = 29/58 (50%), Positives = 41/58 (70%), Frame = -2

SEQ ID NO:259 Query:    84 YQYKAKLKVPRFESYREDSELAEKLQTEAEKIQMWSEIASAAETGWDFSTRWFSQNGD 141
SEQ ID NO:260              +QY+ ++ PRFES+RED    AEH  T+   K Q + ++ SAAE+GWDFS+RWF  + D
SEQ ID NO:261 Sbjct:  9546 FQYRTEAETPRFESFREDVLSAEHFTTIWRKKQFFKDLGSAAESGWDFSSRWFKNHKD 9373

Score = 76 (35.0 bits), Expect = 1.0e-95, Sum P(6) =1.0e-95
Identities = 13/21 (61%), Positives = 15/21 (71%), Frame = -1

SEQ ID NO:262 Query:   348 QTGFGWTNGVILDLLDKYGDQ 368
SEQ ID NO:263              Q GFGWTNG  LDL+   Y D+
SEQ ID NO:264 Sbjct:  8722 QAGFGWTNGAALDIJIFTYSDR 8660

Score = 45 (20.7 bits), Expect = 1.0e-95, Sum F(S) =1.0e-95
Identities = 10/24 (41%), Positives = 15/24 (62%), Frame = -1

SEQ ID NO:265 Query:   371 SSSTASKFSFSLSNITFVVFILYI 394
SEQ ID NO:266              +SS++S  F  +S      VF+LYI
SEQ ID NO:267 Sbjct:  8545 TSSSSSTFGYSNILTIIITVFVLYI 8474

Score = 38 (17.5 bits), Expect = 2.6e-98, Sum P(7) = 2.6e-98
Identities = 7/7 (100%), Positives = 7/7 (100%), Frame = -2

SEQ ID NO:268 Query:   342 GGEYEVQ 348
SEQ ID NO:269              GGEYEVQ
SEQ ID NO:270 Sbjct:  8787 GGEYEVQ 8767

Score = 37 (17.0 bits), Expect = 1.6e-19, Sum P(4) = 1.6e-19
Identities = 8/18 (44%), Positives = 10/18 (55%), Frame = --2

SEQ ID NO:271 Query:    217 KTHSNQYYVSNAVPLYAK 234
SEQ ID NO:272               K ++   YYVS   P Y K
SEQ ID NO:273 Sbjct:  30345 KFTAHPYYVSRTPPRYHK 30292

>W0SE10
  Length = 31,273
  Minus Strand 14575:

Score = 224 (103.1 bits), Expect = 7.0e-90, Sum P(7) = 7.0e-90
Identities = 43/67 (64%), Positives = 49/67 (73%), Frame =-1
```

-continued

```
SEQ ID NO:274 Query:        2 VIKNLGYMVDNKGFVPNGGRVYYLTRSQPPLLTPMVYEYYMSTGDLDFVMEILPTLDKEY 61
SEQ ID NO:275                 +I+NL  MVD +GFVPNGGRVYYL RSQPP L  MVYE Y+T D  FV E+LPTL  KE
SEQ ID NO:276 Sbjct: 28957MIRNLASMVDKYGFVPNGGRVYYLQRSQPPFLAM4VYELYEATNDKAFVAELLPTLLKEL28778

SEQ ID NO:274 Query:   62 EFWIKNR 68
SEQ ID NO:275              FW + K
SEQ ID NO:276 Sbjct: 28777 NFWNEKR 28757

Score = 192 (88.4 bits), Expect = 7.0e-90, Sum P(7) = 7.0e-90
Identities = 31/84 (36%), Positives = 52/84 (61%), Frame = <3

SEQ ID NO:277 Query:   154 IIPADLNAFMCANA2ILASLYEIAGDFKKVFEQRYTWAKREMRELHWNETDGIWYDYD 213
SEQ ID NO:278               ++P DLN + C N   I + LYE  GD K  ++F  +   + ++ + +N TDG WYDY+
SEQ ID NO:279 Sbjct: 2842 7VLPVDLNGLLCWN14DTMEYLYEQIGDTKNSQIFRNKRADFRDVQNVFYNRTDGTWYDYN 28248

SEQ ID NO:277 Query:   214 IELKTHSNQYYVSNAVPLYAKCYD 237
SEQ ID NO:278               +  ++H+ ++Y S AVPL+CY+
SEQ ID NO:279 Sbjct: 28247 LRTQSHNPRFYTSTAVPLFTNCYN 28176

Score = 125 (57.5 bits), Expect = 7.0e-90, Sum P(7) = 7.0e-90
Identities = 20/48 (41%), Positives = 30/48 (62%), Frame = -2

SEQ ID NO:280 Query:   249 YLERQGLLKYTKGLPTSLAMSSTQQWDKENAWPPMIHMVIEGFRTTGD 296
SEQ ID NO:281               + ++ G+  Y  G+PTS++  S QQWD  N W P  HM+IEG R + +
SEQ ID NO:282 Sbjct: 28092 FFQIOVIGVFTYPGOIPTSMSQESDQQWDFPNGWSPNNHMIIEGLRKSAN 27949

Score = 90 (41.4 bits), Expect = 7.0e-90, Sum P(7) = 7.0e-90
Identities = 15/18 (83%), Positives = 18/18 (100%), Frame = --2

SEQ ID NO:283 Query:   120 EIASAAETGWDESTRWFS 137
SEQ ID NO:284              ++ASAAE+GWDFSTRWFS
SEQ ID NO:285 Sbjct: 28566 DLASAAESGWDFSTRWFS 28513

Score = 89 (41.0 bits), Expect = 7.0e-90, Sum P(7) = 7.0e-90
Identities = 18/40 (45%), Positives = 24/40 (60%), Frame = -1

SEQ ID NO:286 Query:    79 KQFPYYQYKAKLKVPRPESYREDSELAEHLQTEAEKIQMW 118
SEQ ID NO:287                K F  YQYK    VPRPESYR D++ +  L   A++ Q +
SEQ ID NO:288 Sbjct: 28732 KSFKVYQYKTASNVPRPESYRVDTQNSAKIJANGADQQQFY 28613

Score = 77 (35.4 bits), Expect = 7.0e-90, Sum P(7) = 7.0e-90
Identities = 14/21 (66%), Positives = 16/21 (76%), Frame = -3

SEQ ID NO:289 Query:       348 QTGFGWTNGVILDLLDKYGDQ 368
SEQ ID NO:290                    Q GFGW+NG ILDLL  Y D+
SEQ ID NO:291 Sbjct: 24395 QDGFGWSNGAILDLLLTYNDR 24333

Score = 51 (23.5 bits), Expect = 7.0e-90, Sum P(7) = 7.0e-90
Identities = 11/27 (40%), Positives = 16/27 (59%), Frame = -3

SEQ ID NO:292 Query:   365 YGDQFASSSTASKFSFSLSNITFVVFI 391
SEQ ID NO:293                Y    FASSS AS   FS +++ F ++
SEQ ID NO:294 Sbjct: 2846 YN*PFASSSDASSCPFSTNSVIFSILV 2766

Score = 41 (18.9 bits), Expect = 3.3e-93, Sum P(8) = 3.3e-93
Identities = 7/9 (77%), Positives = 8/9 (88%), Frame = -2

SEQ ID NO:295 Query:    340 GGGGEYEVQ 348
SEQ ID NO:296                G GGEY+VQ
SEQ ID NO:297 Sbjct: 24468 GSGGEYDVQ 24442

Score = 39 (18.0 bits), Expect = 2.0e-37, Sum P(5) 2.0e-37
Identities = 7/14 (50%), Positives = 8/14 (57%), Frame = 2

SEQ ID NO:298 Query:   221 NQYYVSNAVPLYAK 234
SEQ ID NO:299               N YY+   V LY K
SEQ ID NO:300 Sbjct: 4524 NHYYIIQMVSLYTK 4483

Score = 38 (17.5 bits), Expect = 4.0e-88, Sum P(7) = 4.0e-88
Identities = 11/30 (36%), Positives = 13/30 (43%), Frame = -1

SEQ ID NO:301 Query:   367 DQFASSSTASKFSFSLSNTTFVVFILYIFS 396
SEQ ID NO:302               DQF  S    SKFS    +F     +FS
SEQ ID NO:303 Sbjct: 7588 DQFVISFICSKFSSKNKKLYFCPSHFSLFS 7499
```

Gene fusions to GFP may also be constructed using, for example, the isocitrate dehydrogenase and isocitrate lyase genes to test for transition to the glyoxylate cycle for the generation of glucose from fatty acid metabolism during dauer arrest and recovery. Moreover, gene fusions to hexokinase and glucose metabolism genes may be used test for the switch to sugar based metabolism during reproductive development.

GFP fusions to these genes are expected to be transcriptionally regulated depending on whether the animal is in fat storage, fat breakdown, glycogen storage, or glycogen breakdown, trehalose storage, or trehalose breakdown metabolic states. Drugs that perturb the expression of these genes may regulate transcriptional regulatory proteins like DAF-3, DAF-12, and DAF-16 that may regulate batteries of such metabolic genes. The GFP reporter genes provide a screen for perturbations of these regulatory genes. In addition, GFP fusions to the full length proteins may also reveal subcellular localization, for example, of fat storage proteins to fat droplets and regulation of the localization of these proteins. Drugs that perturb the localization of these fusion proteins may also be potent regulators of fat metabolism and may be used to treat obesity and diabetes.

Daf12-GFP Fusions

Daf-12 expression has been examined using a full length, rescuing GFP fusion to daf-12. We have found that the gene is expressed in a small number of neurons in wild type animals, and many more in a daf-2, daf-7, or pheromone induced dauer. Thus, the daf-12 expression pattern is transcriptionally regulated by the daf pathway, perhaps by DAF-2 or DAF-16. We have also observed DAF-12/GFP expression in hypodermal cells at the L2 and later stages, showing that daf-12 is a stage specific gene activity in this tissue. This is consistent with the heterochronic effects of weak daf-12 mutations.

This daf-12-GFP fusion also allowed us to view the dynamic regulation of daf-12 gene action during insulin and TGF-β regulated dauer or reproductive development. daf-12 encodes a nuclear hormone receptor most closely related to the mammalian vitamin D and thyroid hormone receptors. We believe that the ligand for DAF-12 is likely to be regulated by insulin like or TGF-β daf gene signaling. That ligand may be produced by the *C. elegans* equivalent to the thyroid gland, which may be related to the subesophageal glands of insects. For example, neurons in the retrovesicular ganglion of *C. elegans* may produce the daf-12 ligand under DAF-16 and DAF-3 control. The mapping of exactly which neurons the daf-2 and age-1 gene products function to regulate dauer arrest will identify the neuron. To identify the genes regulated by the DAF-16 and DAF-3 transcription factors, a yeast one hybrid experiment may be used (as described herein). GFP fusion to the genes so revealed should show that they are expressed in the key DAF-12 ligand producing neuron and are responsive to daf-3 and daf-16 mutations.

C. elegans

In one working example, the above-described reporter gene construct is introduced into wild-type *C. elegans* according to standard methods known in the art. If the enhancer element is operational, then it is expected that reporter gene expression is turned on. Alternatively, in daf mutants (e.g., daf-7 or daf-2 mutants, where insulin signaling is defective) carrying the above-described reporter gene construct, reporter gene activity is turned off.

Using this on/off distinction, test compounds or extracts are evaluated for the ability to disrupt the signaling pathways described herein. In one working example, daf-2 mutant worms carrying the reporter gene construct are used to assay the expression of the reporter gene. The majority of worms expressing the reporter gene will arrest at the dauer stage because of the daf-2 phenotype. If however the test compound or extract inhibits DAF-16 activity, then the worms will exhibit a daf-2; daf-16 phenotype (i.e., do not arrest), developing to produce eggs. Such eggs are selected using a bleach treatment and reporter gene expression in the test compound or extract is assayed according to standard methods, e.g., worms are examined with an automated fluorometer to reveal the presence of reporter gene expression, e.g., GFP. Candidate compounds that suppress the daf-2 phenotype or turn on reporter gene expression, i.e., activate signals in the absence of DAF-2 receptor (e.g., PIP3 mimetics) or inactivate DAF-16, are considered useful in the invention.

Analogous screens may also be performed using daf-7 mutants as a means to identify drugs that inactivate other daf-genes, such as DAF-3, or compounds that activate the DAF-1/DAF-4 receptors. Such screens may be coupled to reporter screens, for example, using GFP reporter genes whose expression is under DAF-3 transcriptional control (e.g., the myoII element). Drugs identified in such screens are useful as DAF-7 mimetics. Because DAF-7 expression may be down regulated in obesity, such drugs are useful in the treatment of obesity induced Type II Diabetes In yet another working example, *C. elegans* DAF-3 and DAF-16 genes can be replaced with a human homolog, (e.g., FKHR or FKHRL1 for DAF-16), and screens similar to those described above performed in the nematode system. Because drugs may act upstream of the transcription factors, it is useful to replace DAF-1, DAF-4, DAF-8, DAF-14, DAF-2, DAF-3, DAF-16, or AGE-1 with the appropriate human homolog, and to screen the humanized *C. elegans* animals. Such screens are useful for identifying compounds having activities in humans.

Mammalian Cells

Mammalian insulin-responsive cell lines are also useful in the screening methods of the invention. Here reporter gene constructs (for example, those described above) are introduced into the cell line to evaluate the ability of a test compound or extract to modulate insulin and TGF-β signaling pathways using a second construct expressing a *C. elegans* daf, age, or akt gene or their corresponding human homologs. Exemplary cell lines include, but are not limited to, mouse 3T3, L6, and L1 cells (MacDougald et al., *Ann. Rev. Biochem.* 64: 345–373, 1995) Introduction of the constructs into such cell lines is carried out according to standard methods well known in the art.

To test a compound or extract, it is added to the cell line, and reporter gene expression is monitored. Compounds that induce reporter gene expression in the absense of insulin or DAF-7 signaling are considered useful in the invention. Such compounds may also turn the cells into adipocytes, as insulin does.

Compounds identified in mammalian cells may be tested in other screening assays described herein, and, in general, test compounds may be assayed in multiple screens to confirm involvement in insulin or DAF-7 signaling.

Metabolic control by DAF-7 protein may be tested using any known cell line, e.g., those described herein.

In Vitro Screening Methods

A variety of methods are also available for identifying useful compounds in in vitro assays. In one particular example, test compounds are screened for the ability to activate the phosphorylation of Smad proteins, DAF-8, DAF-14, or DAF-3, by DAF-1 or DAF-4 in vitro. In these assays, DAF-8, DAF-14, or DAF-3 is preferably tagged with a heterologous protein domain, for example, the myc epitope tag domain(s) by the method of Ausubel et al., and are incubated with the C-terminal kinase domain of DAF-1 or DAF-4. Phosphorylation of the Smad proteins is preferably detected by immunoprecipitation using antibodies specific to the tag, followed by scintillation counting. Test compounds may be screened in high throughout microtiter plate assays. A test compound that effectively stimulates the phosphorylation of DAF-8, DAF-14, or DAF-3 is considered useful in the invention. Using these same general assays, compounds that activate the phosphorylation of DAF-16 by AKT or GSK-3 may also be identified.

In another working example, test compounds are screened for the ability to inhibit the in vitro association of DAF-16 and the Smad proteins DAF-3, or to preferentially activate the association of DAF-16 with DAF-8 or DAF-14, or to inhibit the association of DAF-3 and DAF-16 with DNA in vitro. These assays are carried out by any standard biochemical methods that test protein-protein binding or protein-DNA binding. In one particular example, to test for interactions between proteins, each protein is tagged with a different heterologous protein domain (as described above). Immunoprecipitations are carried out using an antibody to one tag, and an ELISA assay is carried out on the immunoprecipitation complex to test for the presence of the second tag. In addition, if interaction capability is enhanced by a DAF or AKT kinase, this protein is also preferably included in the reaction mixture. Similarly, to test for interactions of these proteins with DNA, antibodies to the tag are utilized in immunoprecipitations, and the presence of the DNA detected by the presence of the DNA label in the immunoprecipitation complex. A test compound that effectively inhibits the association between these proteins or between DAF-3 and DAF-16 with DNA or both is considered useful in the invention.

In still another working example, test derivatives of PIP3 are screened for the ability to increase in vitro AKT activity. This is accomplished, in general, by combining a labeled PIP3 and an AKT polypeptide in the presence and absence of the test compound under conditions that allow PIP3:AKT to bind in vitro. Compounds are then identified that interfere with the formation of the PIP3:AKT complex. Test compounds that pass this first screen may then be tested for increased AKT activation in vitro using GSK3 targets, or may be tested in nematodes or mammalian cells (as described above). An increase in AKT kinase activity is taken as an indication of a compound useful for ameliorating or delaying an impaired glucose tolerance condition.

In yet another working example, DAF-3 or DAF-16 may be expressed in a yeast one-hybrid assay for transcriptional activation. Methods for such assays are described in Brent and Ptashne (*Cell* 43:729–736, 1985). A test compound that blocks the ability of DAF-3 or DAF-16 or both to activate (or repress) transcription in this system is considered useful in the invention.

In a final working example, compounds may be screened for their ability to inhibit an interaction between any of DAF-3, DAF-8, and DAF-14, or between DAF-3 and DAF-16. These in vivo assays may be carried out by any "two-hybrid" or "interaction trap" method (for example, by using the methods described by Vijaychander et al (*Biotechniques* 20: 564–568)).

Screens for Isolating Longevity Therapeutics

The worm insulin signaling pathway has been implicated in longevity control of *C. elegans*. Drugs which perturb this pathway could affect lifespan. Specifically, inhibition of the pathway would be expected to extend lifespan. Drugs that inactivate the DAF-2 ligands, the AGE-1 PI3 kinase, or decrease PIP3 signals in any way, for example, by increasing DAF-18/PTEN activity, decreasing PDK or AKT activity, or decreasing the phosphorylation of DAF-16, are expected to increase longevity. Such drugs may be used topically on the skin to increase longevity in this organ. It is significant that AGE-1 generates a second messenger, PIP3, that directly regulates AKT and perhaps PDK activity. Antagonists to PIP3 are expected to extend lifespan, but any drug that mimics the activity state of the pathway during aging is expected to increase longevity. For example, drugs causing low activity of the following proteins: DAF-2 agonist, DAF-2 receptor, AGE-1, PDK, and AKT, would increase longevity. Drugs causing high activity of PTEN or DAF-16 (high meaning unphosphorylated) would increase longevity.

The insulin-like signaling genes that function in metabolic regulation and molting control also function to control aging in the animal. We have shown that declines in daf-2 insulin receptor-like age-1 PI-3 kinase, PDK-1, and akt-1/2 signaling cause dauer arrest and a corresponding increase in lifespan and a change in metabolism towards fat storage. Thus, drugs that perturb the gene activities in this pathway are expected to regulate longevity as well as metabolism. Specifically, chemicals that decrease the activity of the human homologues of the DAF-2 insulin/IGF-I receptor homologue, decrease the activity of the human homologue of the AGE-1/PI3 kinase, decrease the activity of human homologues of AKT-1 and AKT-2, decrease the activity of the human homologue of PDK-1, or inhibit the phosphorylation of the human homologues of DAF-16 by the human homologues of AKT-1 and AKT-2 increase longevity. Chemicals that increase the activity of DAF-18 PTEN also increase longevity, since decreases in DAF-18 activity decrease longevity.

Similarly, the AGE-1 and AKT-1/2 proteins are enzymes with in vitro activities. An AGE-1 assay preferably involves phophorylation of a phosphatidyl inositol target on the 3 position. The AKT-1 or AKT-2 kinase assay involves phosphorylation of DAF-16 as well as the human DAF-16 homologues, FKHR, FKHRL1, and AFX targets. Chemical screens for drugs that inhibit in vitro activities of the human homologues of these *C. elegans* kinases are first preferably performed in vitro. Chemicals that perturb this function are then tested on *C. elegans* mutants carrying the human gene as the only functional copy of the gene. If desired, positive drugs could then be tested on mice for those that increase longevity.

Screens for Identifying Pesticide and Nematicide Compounds

Our discovery that converging insulin-like and DAF-7 TGF-β like neuroendocrine signals regulate diapause arrest in *C. elegans* is also important for the development of novel nematicides and pesticides. For example, the finding that insulin like signaling regulates metabolism in animals as phylogenetically distant as nematodes and mammals suggests that this pathway was present in the common ancestor of worms and mammals over 600,000,000 years ago. Diapause, the suspension of development by environmental signals, is phyletically general. In view of the results described herein, insulin may regulate diapause/developmental arrest in many animals, including insects and other nematodes. In fact, human insulin induces recovery of diapausing corn borers, and a cholinergic neuronal input to dauer arrest has been shown herein to exist in both *C. elegans* and the mammalian parasitic nematode *Ancylos-*

*toma caninum*. These observations indicate that daf pathway results from *C. elegans* can be generalized to distant nematode relatives as well as other invertebrates, most importantly, insects. Since diapause is a non feeding state, novel insecticides and nematicides may be developed which induce diapause if the insulin like pathway can be inactivated in insects or nematodes. Specifically, drugs that induce downregulation of the insect or parasitic nematode homologues of DAF-2, AGE-1, PDK-1, AKT-1, or AKT-2, or upregulation of DAF-18 or DAF-16 would induce non feeding diapause. Such an agent would be expected to protect crops from destruction by feeding and infection. In addition, agents that induce activity of DAF-2, AGE-1, PDK-1, AKT-1, or AKT-2, or downregulation of DAF-18 or DAF-16 would be expected to induce recovery from diapause. Since diapause is an overwintering stress resistant state, and is generally the infective stage of plant and animal parasitic nematodes, such agents would improve pest infestations by perturbing the overwintering or infective process.

Modulatory Compounds

Our experimental results facilitate the isolation of compounds useful in the treatment of impaired glucose tolerance diseases that are antagonists or agonists of the insulin or TGF-β signaling pathways identified in *C. elegans* and described above. Exemplary methods for the isolation of such compounds now follow.

Antagonists

As discussed above, useful therapeutic compounds include those which down regulate the expression or activity of DAF-3, DAF-16, or DAF-18 (PTEN). To isolate such compounds, DAF-3, DAF-16, or DAF-18 (PTEN) expression is measured following the addition of candidate antagonist molecules to a culture medium of DAF-3, DAF-16, or DAF-18 (PTEN) expressing cells. Alternatively, the candidate antagonists may be directly administered to animals (for example, nematodes or mice) and used to screen for their effects on DAF-3, DAF-16, or DAF-18 (PTEN) expression.

DAF-3, DAF-16, or DAF-18 (PTEN) expression is measured, for example, by standard Northern blot analysis (Ausubel et al., supra) using a DAF-3, DAF-16, or DAF-18 (PTEN) nucleic acid sequence (or fragment thereof) as a hybridization probe. The level of DAF-3, DAF-16, or DAF-18 (PTEN) expression in the presence of the candidate molecule is compared to the level measured for the same cells, in the same culture medium, or in a parallel set of test animals, but in the absence of the candidate molecule. Preferred modulators for anti-diabetic or anti-obesity purposes are those which cause a decrease in DAF-3, DAF-16, or DAF-18 (PTEN) expression.

Alternatively, the effect of candidate modulators on expression or activity may be measured at the level of DAF-3, DAF-16, or DAF-18 (PTEN) protein production using the same general approach in combination with standard immunological detection techniques, such as Western blotting or immunoprecipitation with a DAF-3, DAF-16, or DAF-18 (PTEN) specific antibody (for example, the DAF-3 or DAF-16 antibodies described herein). Again, useful anti-diabetic or anti-obesity therapeutic modulators are identified as those which produce a decrease in DAF-3, DAF-16, or DAF-18 (PTEN) polypeptide production. Antagonists may also affect DAF-3, DAF-16, or DAF-18 (PTEN) activity without any effect on expression level. For example, the identification of kinase cascades upstream of DAF-3 and DAF-16 (as described herein) suggest that the phosphorylation state of these polypeptides is correlated with activity. Phosphorylation state may be monitored by standard Western blotting using antibodies specific for phosphorylated amino acids. In addition, because DAF-3 and DAF-16 are transcription factors, reporter genes bearing operably linked DAF-3 or DAF-16 binding sites (for example, the myoII enhancer element) may be used to directly monitor the effects of antagonists on DAF-3 or DAF-16 gene activity.

Candidate modulators may be purified (or substantially purified) molecules or may be one component of a mixture of compounds (e.g., an extract or supernatant obtained from cells). In a mixed compound assay, DAF-3, DAF-16, or DAF-18 (PTEN) expression is tested against progressively smaller subsets of the candidate compound pool (e.g., produced by standard purification techniques, e.g., HPLC or FPLC; Ausubel et al., supra) until a single compound or minimal compound mixture is demonstrated to modulate DAF-3, DAF-16, or DAF-18 (PTEN) expression.

Candidate DAF-3, DAF-16, or DAF-18 (PTEN) antagonists include peptide as well as non-peptide molecules (e.g., peptide or non-peptide molecules found, e.g., in a cell extract, mammalian serum, or growth medium on which mammalian cells have been cultured).

Antagonists found to be effective at the level of cellular DAF-3, DAF-16, or DAF-18 (PTEN) expression or activity may be confirmed as useful in animal models (for example, nematodes or mice). For example, the compound may ameliorate the glucose intolerance and diabetic symptoms of mouse models for Type II diabetes (e.g., a db mouse model), mouse models for Type I diabetes, or models of streptozocin-induced β cell destruction.

A molecule which promotes a decrease in DAF-3, DAF-16, or DAF-18 (PTEN) expression or DAF-3, DAF-16, or DAF-18 (PTEN) activity is considered particularly useful in the invention; such a molecule may be used, for example, as a therapeutic to decrease the level or activity of native, cellular DAF-3, DAF-16, or DAF-18 (PTEN) and thereby treat a glucose intolerance condition in an animal (for example, a human).

If desired, treatment with an antagonist of the invention may be combined with any other anti-diabetic or anti-obesity therapies.

Agonists

Also as discussed above, useful therapeutic compounds are those which up regulate the expression or activity of DAF-1, DAF-2, DAF-4, DAF-7, DAF-8, DAF-11, DAF-14, AGE-1, AKT, COD-5, or PDK-1. To isolate such compounds, expression of these genes is measured following the addition of candidate agonist molecules to a culture medium of DAF-1, DAF-2, DAF-4, DAF-7, DAF-8, DAF-11, DAF-14, AGE-1, AKT, COD-5, or PDK-1 expressing cells. Alternatively, the candidate agonists may be directly administered to animals (for example, nematodes or mice) and used to screen for effects on DAF-1, DAF-2, DAF-4, DAF-7, DAF-8, DAF-1, DAF-14, AGE-1, AKT, COD-5, or PDK-1 expression.

DAF-1, DAF-2, DAF-4, DAF-7, DAF-8, DAF-11, DAF-14, AGE-1, AKT, COD-5, or PDK-1 expression is measured, for example, by standard Northern blot analysis (Ausubel et al., supra) using all or a portion of one of these genes as a hybridization probe. The level of DAF-1, DAF-2, DAF-4, DAF-7, DAF-8, DAF-11, DAF-14, AGE-1, AKT, COD-5, or PDK-1 expression in the presence of the candidate molecule is compared to the level measured for the same cells, in the same culture medium, or in a parallel set of test animals, but in the absence of the candidate molecule. Preferred modulators for anti-diabetic or anti-obesity purposes are those which cause an increase in DAF-1, DAF-2, DAF-4, DAF-7, DAF-8, DAF-11, DAF-14, AGE-1, AKT, COD-5, or PDK-1 expression.

Alternatively, the effect of candidate modulators on expression may be measured at the level of DAF-1, DAF-2, DAF-4, DAF-7, DAF-8, DAF-11, DAF-14, AGE-1, AKT, COD-5 or PDK-1 protein production using the same general approach in combination with standard immunological detection techniques, such as Western blotting or immunoprecipitation with an appropriate antibody. Again, the phosphorylation state of these polypeptides is indicative of DAF activity and may be measured on Western blots. Useful anti-diabetic or anti-obesity modulators are identified as those which produce an increase in DAF-1, DAF-2, DAF-4, DAF-7, DAF-8, DAF-11, DAF-14, AGE-1, AKT, COD-5, or PDK-1 polypeptide production.

Candidate modulators may be purified (or substantially purified) molecules or may be one component of a mixture of compounds (e.g., an extract or supernatant obtained from cells). In a mixed compound assay, DAF-1, DAF-2, DAF-4, DAF-7, DAF-8, DAF-11, DAF-14, AGE-1, AKT, COD-5, or PDK-1 expression is tested against progressively smaller subsets of the candidate compound pool (e.g., produced by standard purification techniques, e.g., HPLC or FPLC; Ausubel et al., supra) until a single compound or minimal compound mixture is demonstrated to modulate DAF-1, DAF-2, DAF-4, DAF-7, DAF-8, DAF-11, DAF-14, AGE-1, AKT, COD-5, or PDK-1 expression.

Alternatively, or in addition, candidate compounds may be screened for those which agonize native or recombinant DAF-1, DAF-2, DAF-4, DAF-7, DAF-8, DAF-11, DAF-14, AGE-1, AKT, COD-5, or PDK-1 activities. In one particular example, DAF-1 and DAF-4 phosphorylation of DAF-8 and DAF-14, or AKT phosphorylation of DAF-16, may be activated by agonists.

Candidate DAF-1, DAF-2, DAF-4, DAF-7, DAF-8, DAF-11, DAF-14, AGE-1, AKT, COD-5, or PDK-1 agonists include peptide as well as non-peptide molecules (e.g., peptide or non-peptide molecules found, e.g., in a cell extract, mammalian serum, or growth medium on which mammalian cells have been cultured).

Agonists found to be effective at the level of cellular DAF-1, DAF-2, DAF-4, DAF-7, DAF-8, DAF-11, DAF-14, AGE-1, AKT, COD-5, or PDK-1 expression or activity may be confirmed as useful in animal models (for example, nematodes or mice).

A molecule which promotes an increase in DAF-1, DAF-2, DAF-4, DAF-7, DAF-8, DAF-11, DAF-14, AGE-1, AKT, COD-5, or PDK-1 expression or activities is considered particularly useful in the invention; such a molecule may be used, for example, as a therapeutic to increase the level or activity of these native, cellular genes and thereby treat a glucose intolerance condition.

If desired, treatment with an DAF-1, DAF-2, DAF-4, DAF-7, DAF-8, DAF-11, DAF-14, AGE-1, AKT, COD-5, or PDK-1 agonist may be combined with any other anti-diabetic or anti-obesity therapies.

Animal Model Systems

Compounds identified as having activity in any of the above-described assays are subsequently screened in any number of available diabetic or obesity animal model systems, including, but not limited to ob (Coleman, *Dibetologia* 14: 141–148, 1978; Chua et al., *Science* 271: 994–996, 1996; Vaisse et al., *Nature Genet.* 14:95–100, 1996), db (Chen et al., *Cell* 84: 491–495, 1996), agouti mice, or fatty rats (Takaga et al. *Biochem. Biophys. Res. Comm.* 225: 75–83, 1996). Test compounds are administered to these animals according to standard methods. Additionally, test compounds may be tested in mice bearing knockout mutations in the insulin receptor, IGF-1 receptor (e.g., Liu et al., *Cell* 75:59–72, 1993), IR-related receptor, DAF-7 homolog, or any of the daf(FKHR, FKHRL1, AFX) genes described herein. Compounds can also be tested using any standard mouse or rat model of Type I diabetes, e.g., a streptozin ablated pancreas model.

In one particular example, the invention involves the administration of DAF-7 or its homolog as a method for treating diabetes or obesity. Evaluation of the effectiveness of such a compound is accomplished using any standard animal model, for example, the animal diabetic model systems described above. Because these mouse diabetic models are also associated with obesity, they provide preferred models for human obesity associated Type II diabetes as well. Such diabetic or obese mice are administered *C. elegans* or human DAF-7 according to standard methods well known in the art. Treated and untreated controls are then monitored for the ability of the compound to ameliorate the symptoms of the disease, e.g., by monitoring blood glucose, ketoacidosis, and atherosclerosis. Normalization of blood glucose and insulin levels is taken as an indication that the compound is effective at treating a glucose intolerance condition.

Therapy

Compounds of the invention, including but not limited to, DAF-7 and its homologs, and any antagonist or agonist therapeutic agent identified using any of the methods disclosed herein, may be administered with a pharmaceutically-acceptable diluent, carrier, or excipient, in unit dosage form. Conventional pharmaceutical practice may be employed to provide suitable formulations or compositions to administer such compositions to patients. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for antagonists or agonists of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

DAF polypeptides are administered at any appropriate concentration, for example, for DAF-7, at a concentration of around 10 nM.

Pedigree Analysis and Genetic Testing

The discovery described herein that DAF polypeptides are involved in glucose metabolism enables assays for genetic testing to identify those individuals with predispositions toward the development of glucose intolerance conditions, such as diabetes or obesity, by determining the presence of a mutation found in a human gene having identity to any of the C. elegans daf-1, daf-2, daf-3, daf-4, daf-7, daf-8, daf-11, daf-14, daf-16, age-1, akt, daf-18 (PTEN), or pdk-1 genes. In one embodiment, the development of this testing method requires that the individual be a member of a family that has multiple affected and unaffected members carrying one mutation from the list of above-listed genes. Those skilled in the art will understand that a diabetic or obesity phenotype may be produced by daf, age, or akt mutations found on different chromosomes, and that low resolution genetic mapping of the diabetic condition in single family pedigrees will be sufficient to favor some daf, age, or akt genes over others as causing the glucose intolerance condition in a particular pedigree. In one particular example, mutations associated with glucose intolerance may be found in different genes in, for example, the DAF-7 signaling pathway in each pedigree. In addition, because mutations in a common pathway can show complex genetic interactions, multiple DAF mutations may segregate in single pedigress. These mutations can behave recessively in some genetic backgrounds and dominantly in others.

Those skilled in the art further understand that, to determine disease linkage with a chromosomal marker, it may be necessary to evaluate the association of inheritance patterns of several different chromosomal markers (for example, from the collection of highly polymorphic mapped DNA allelic variants) in the genomic DNAs of family members and of the clinically affected individuals. Methods commonly used in determining segregation patterns of human genetic diseases are well known in the art. In addition, methods are known in the art for determining whether individuals in a family are useful for providing information to determine co-segregation of an allele with a glucose intolerance trait.

Here, fragments of genomic DNA (e.g., RFLP fragments) are prepared from each of the available members of the family, and each distinctive DNA allelic variant of the polymorphic chromosome marker within the family is evaluated to determine which polymorphisms (i.e., chromosomal region) is linked with the glucose intolerance phenotype within a particular family. It is preferred that the parents of the marker individual be heterozyous for a DNA allelic variant so that the segregation pattern of the DNA allelic variant linked with the diabetic or obese phenotype in the marker can be recognized. The inheritance of the diabetic phenotype can be judged to be dominant or recessive, depending on the pattern of inheritance. Most diabetes is dominantly inherited, and therefore inbred pedigrees are generally not necessary in the etiology of the diabetic condition.

With respect to Type II diabetes, the highest rate of this kind of diabetes in the world is found in American Indians of the Pima tribe. Such families are useful for mapping one particular cause of diabetes, but, in general, diabetes is caused by mutations in a variety of genes, including daf genes. Thus, by testing for low resolution linkage to a candidate daf, age, or akt mutation, and then by sequencing the particular linked daf gene in affected and unaffected individuals, a particular daf mutation can be associated with a particular diabetic pedigree.

Human DAF homologues are mapped to chromosome regions using standard methods. For example, the probable DAF-16 homologues FKHR and FKHRL1 are located on chromosomes 13 and 11, respectively, and AFX is located on the X chromosome. In particular, candidate loci for human DAF homologues are as follows: P85=5q13, P110alpha= 3q26.3, PTEN=10q23.3, Akt-1=14q32.3, Akt-2=19q13.1, FKHRL1=11q23, FKHR=13q14.1, Afx=xq13.1, and Daf-7 (GDF-8)=2q32.1 (the position at which NIDDM1 has been mapped).

Any daf, akt, or age genes mapping to the approximate chromosomal regions associated with diabetes or glucose intolerance are sequenced from affected and unaffected individuals. Preferably, at least two genes per pedigree of 5-20 affected (and unaffected controls) are sequenced. The daf genomic regions are PCR amplified and compared between affected and unaffected DNA samples. Mutations detected in affected individuals are expected to (but need not) map to conserved domains of the DAF genes. Because it is known that not all carriers of known diabetes-inducing mutations show metabolic defects, we expect that some non-diabetic non-glucose intolerant family members will carry the same daf mutation as affected family members. For this reason, a correlation of affected family members with a daf mutation is more important than a correlation of nonaffected with no mutation. Those skilled in the art will know that phenotypic classification of affected and unaffected individuals can greatly enhance the power of this genetic analysis (Nature Genet. 11: 241–247, 1995). In addition, other mutations in the same daf gene are expected in some but not all diabetic pedigrees. For dominant diabetic inheritance, the affected individuals carry a daf, age, or akt mutation as well as a normal allele. For recessive diabetic inheritance, individuals carry two daf mutations that may be identical or two independent mutations in the same gene. In addition, some diabetic individuals may carry mutations in more than one daf, age, or akt gene (so called non-allelic non-complementation).

It is routine in the art of genetic counseling to determine risk factors given the presence of a closely linked molecular genetic marker in the genomic DNA of the individual and when combined with the additional understanding provided by the pedigree of the individual in the family. For example, a risk factor may be calculated for an individual in an age, akt, or daf chromosome family in a manner similar to those described for assessing the risk of other commonly known genetic diseases that are known to run in families, e.g., Huntington's disease and cystic fibrosis.

Once mutations in daf, akt, or age genes are associated with diabetes in a pedigree analysis, diagnostic PCR sequencing of these daf genes can be used to diagnose glucose intolerant, prediabetic, diabetic, obesity, and atherosclerotic conditions. Preferably, the daf, akt, or age gene regions are PCR amplified from patients and mutations detected in the daf genes using standard DNA sequencing or oligonucleotide hybridization techniques. The use of such gene sequences or specific antibody probes to the products of these sequences provide valuable diagnostics, particularly in view of the likelihood there exist two classes of type II diabetics: those with defects in the TGF-β signaling genes, and those with defects in insulin signaling genes. Such genetic tests will influence whether drugs that affect DAF-7 TGF-β or DAF-2 insulin like signals are prescribed.

To carry out the above analysis (as well as the other screening, diagnostic, and therapeutic methods described herein), mammalian homologs corresponding to the C. elegans daf-1, age-1, daf-4, daf-8, and daf-7 genes are isolated as described above for daf-2, daf-3, and daf-16. Again, standard hybridization or PCR cloning strategies are employed, preferably utilizing conserved DAF, AGE, or AKT motifs for probe design followed by comparison of less conserved sequences flanking these motifs. Exemplary motifs for these genes are as follows:

DAF-1(139 amino acid motif) (SEQ ID NO: 13)
274 TSGSGMGPTTLHKLTIGGQIRLTGRVGSGRFGNVSRGDYRGEAVAVK
VFNALDEPAFHKETEIFETRMLRHPNVLRYIGSDRVDTGFVTELWLVTEYH
PSGSLHDFLLENTVNIETYYNLMRSTASGLAFLHNQIGGSK 412

DAF-1(62 amino acid motif) (SEQ ID NO: 14)
450 EDAASDIIANENYKCGTVRYLAPEILNSTMQFTVFESYQCADVYSFSL
VMWETLCRCEDGDV 511

DAF-1(31 amino acid motif) (SEQ ID NO: 15)
416 KPAMAHRDIKSKNIMVKNDLTCAIGDLGLSL 466

DAF-1(72 amino acid motif) (SEQ ID NO: 16)
520 IPYIEWTDRDPQDAQMFDVVCTRRLRPTENPLWKDHPEMKHIMEIIKT
CWNGNPSAFETS YICRKRMDERQQ 591

AGE-1(150 amino acid motif) (SEQ ID NO: 17)
991 YFESVDRFLYSCVGYSVATYIMGIKDRHSDNLMLTEDGKYVHIDFGHI
LGHGKTKLGIQRDRQPFILTEHFMTVIRSGKSVDGNSHELQKFKTLCVEAY
EVMWNNRDLFVSLFTLMLGMELPELSTKADLDHLKKTLFCNGESKEEAR
KF 1140

AGE-1(113 amino acid motif) (SEQ ID NO: 18)
826 SPLDPVYKLGEMIIDKAIVLGSAKRPLMLHWKNKNPKSDLHLPFCAMI
FKNGDDLRQDMLVLQVLEVMDNIWKAANIDCCLNPYAVLPMGEMIGIIE
VVPNCKTIFEIQVGTG 938

AGE-1(106 amino acid motif) (SEQ ID NO: 19)
642 LAFVWTDRENFSELYVMLEKWKPPSVAAALTLLGKRCTDRVIRKFAV
EKLNEQLSPVTFHLFILPLIQALKYEPRAQSEVGMMLLTRALCDYRIGHRLF
WLLRAEI 747

AGE-1(60 amino acid motif) (SEQ ID NO: 38)
91 EIKLSDFKHQLFELIAPMKWGTYSVKPQDYVFRQLNNFGEIEVIFND
DQPLSKLELHGTF 150

AKT(121 amino acid motif) (SEQ ID NO: 60)
33685 QVLDDHDYGRCVDWWGVGVVMYEMMCGRLPFYSKDHNKLF
ELIMAGDLRFPSKLSQEARTLLTGLLVKDPTQRLGGGPEDALEICRADFFR
TVDWEATYRKEIEPPYKPNVQSETDTSYFD 34047

AKT(66 amino acid motif) (SEQ ID NO: 61)
32314 TMEDFDFLKVLGKGTFGKVILCKEKRTQKLYAIKILKKDVIIARE
EVAHTLTENRVLQRCKHPFLT 32511

AKT(45 amino acid motif) (SEQ ID NO: 62)
33509 KLENLLLDKDGHIKIADFGLCKEEISFGDKTSTFCGTPEYL
APEV 33643

AKT(57 amino acid motif) (SEQ ID NO: 63)
32667 YFQELKYSFQEQHYLCFVMQFANGGELFTHVRKCGTFSEPRARFY
GAEIVLALGYLH 32837

AKT(59 amino acid motif) (SEQ ID NO: 64)
31846 STFAIFYFQTMLFEKPRNPMFMVRCLQWTTVIERTFYAESAEVRQ
RWIHAIESISKKYK 32022

AKT(33 amino acid motif) (SEQ ID NO: 65)
33156 LQELKYSFQTNDRLCFVMEFAIGGDLYYHLNRE 33254

AKT(21 amino acid motif) (SEQ ID NO: 66)
30836 VVIEGWLHKKGEHIRNWRPRF 30898

AKT(26 amino acid motif) (SEQ ID NO: 67)
33276 FSEPRARFYGSEIVLALGYLHANSIV 33353

DAF-4(139 amino acid motif) (SEQ ID NO: 20)
380 EYWIVTEFHERLSLYELLKNNVISITSANRIIMSMIDGLQFLHDDRPYFF
GHPKKPIIHRDIKSKNILVKSDMTTCIADFGLARIYSYDIEQSDLLGQVGTK
RYMSPEMLEGATEFTPTAFKAMDVYSMGLVMWEVISR 518

DAF-4(61 amino acid motif) (SEQ ID NO: 21)
537 IGFDPTIGRMRNYVVSKKERPQWRDEIIKHEYMSLLKKVTEEMWDPE
ACARITAGCAFARV 597

DAF-4(20 amino acid motif) (SEQ ID NO: 22)
305 PITDFQLISKGRFGKVFKAQ 324

DAF-8(163 amino acid motif) (SEQ ID NO: 23)
382 TDSETRSRFSLGWYNNPNRSPQTAEVRGLIGKGVRFYLLAGEVYVENL -continued CNIPVFVQSIGANMKNGFQLNTVSKLPPTGTMKVFDMRLFSKQLRTAAEK
TYQDVYCLSRMCTVRVSFCKGWGEHYRRSTVLRSPVWFQAHLNNPMHW
VDSVLTCMGAPPRICSS 544

DAF-8(44 amino acid motif) (SEQ ID NO: 24)
91 RAFRFPVIRYESQVKSILTCRHAFNSHSRNVCLNPYHYRWVELP 134

DAF-8(38 amino acid motif) (SEQ ID NO: 25)
341 VEYEESPSWLKLIYYEEGTMIGEKADVEGHHCLIDGFT 378

DAF-14(39 amino acid motif) (SEQ ID NO: 68)
9709 IRVSFCKGFGETYSRLKVVNLPCWIEIILHEPADEYDTV 9825

DAF-14(45 amino acid motif) (SEQ ID NO: 69)
9409 SRNSKSSQIRNTVGAGIQLAYENGELWLTVLTDQIVFVQCPFLNQ
9543

DAF-14(29 amino acid motif) (SEQ ID NO: 70)
9160 NEMLDPEPKYPKIEEKPWCTIFYYELTVRV 9246

DAF-14(29 amino acid motif) (SEQ ID NO: 71)
9307 QLGKAFEAKVPTITIDGATGASDECRMSL 9393

DAF-12(105 amino acid motif) (SEQ ID NO: 72)
103 SPDDGLLDSSEESRRRQKTCRVCGDHATGYNFNVITCESCKAFFRR
NALRPKEFKCPYSEDCEINSVSRRFCQKCRLRKCFTVGMKKEWILNEEQLR
RRKNSRLN 207

DAF-12(89 amino acid motif) (SEQ ID NO: 73)
109 LDSSEESRRRQKTCRVCGDHATGYNFNVITCESCKAFFRRNALRPKE
FKCPYSEDCEINSVSRRFCQKCRLRKCFTVGMKKEWILNEEQ 197

DAF-12(73 amino acid motif) (SEQ ID NO: 74)
551 DIMNIMDVTMRRFVKVAKGVPAFREVSQEGKFSLLKGGMIEMLTV
RGVTRYDASTNSFKTPTIKGQNVSVNVD 623

DAF-11(112 amino acid motif) (SEQ ID NO: 75)
708 SGSLVDLMIKNLTAYTQGLNETVKNRTAELEKEQEKGDQLLMELL
PKSVANDLKNGIAVDPKVYENATILYSDIVGFTSLCSQSQPMEVVTLLSGM
YQRFDLIISQQGGYKV 819

DAF-11(107 amino acid motif) (SEQ ID NO: 76)
825 METIGDAYCVAAGLPVVMEKDHVKSICMIALLQRDCLHHFEIPHR
PGTFLNCRWGFNSGPVFAGVIGQKAPRYACFGEAVILASKMESSGVEDRIQ
MTLASQQLLEE 931

DAF-11(43 amino acid motif) (SEQ ID NO: 77)
520 DILKGLEYIHASAIDFHGNLTLHNCMLDSHWIVKLSGFGVNRL 562

DAF-11(15 amino acid motif) (SEQ ID NO: 78)
618 DMYSFGVILHEIILK 632

DAF-7(60 amino acid motif) (SEQ ID NO: 26)
290 NLAETGHSKIMRAAHKVSNPEIGYCCHPTEYDYIKLIYVNRDGRVSIA
NVNGMIAKKCGC 349

DAF-7(20 amino acid motif) (SEQ ID NO: 27)
265 DWIVAPPRYNAYMCRGDCHY 284

DAF-7(43 amino acid motif) (SEQ ID NO: 28)
240 VCNAEAQSKGCCLYDLEIEFEKIGWDWIVAPPRYNAYMCRGDC 282

DAF-7(70 amino acid motif) (SEQ ID NO: 29)
281 DCHYNAHHFNLAETGHSKIMRAAHKVSNPEIGYCCHPTEYDYIKLIYV
NRDGRVSIANVN GMIAKKCGCS 350

DAF-7(35 amino acid motif) (SEQ ID NO: 30)
250 CCLYDLEIEFEKIGWDWIVAPPRYNAYMCRGDCHY 284

DAF-7(13 amino acid motif) (SEQ ID NO: 86)
GWDWIVAPPRYNA

DAF-7 (9 amino acid motif) (SEQ ID NO: 304)
GWDXXIAPK

In one particular example, mammalian DAF-7 may be identified using the sub-domain amino acids 314–323. Exemplary degenerate oligonucleotides designed to PCR amplify this domain or hybridize (for example, as described in Burglin et al., (Nature 341:239–243, 1989) are as follows:

aa 263 oligo: GGNTGGGAYTRNRTNRTNGCNCC (23-mer, 16,000-fold degeneracy) (SEQ ID NO: 31)

aa 314 oligo: TGYTGYNNNCCNACNGAR (18-mer, 8000-fold degeneracy) (SEQ ID NO: 32).

The DNA sequence between the oligonucleotide probes is determined, and those sequences having the highest degree of homology are selected. Once isolated, these sequences are then tested in a C. elegans daf-7 mutant or mouse model as described above for the ability to functionally complement the mutation or ameliorate the glucose intolerance phenotype.

To date, the closest homologues of C. elegans appear to be members of the vertebrate GDF-8 and GDF-11 gene family, with a representative homologue shown in FIGS. 47A and 47B. These human proteins, whose composition and function in muscle size determination have been described (McPherron A C, Lee S J, Proc Natl Acad Sci U.S.A. 1997 Nov. 11, 1994(23):12457–61), may also function in metabolic control in conjunction with insulin. Alterntaively, there may be more than one DAF-7 orthologue, or a closer relative to DAF-7 in mammalian databases that subserves the metabolic role, whereas GDF-8,11 serve related roles in muscle control. The DAF-7 gene does not appear in worm EST databases, most likely because it is expressed in a single neuron, a very low expression level. Even though the mammalian EST databases are about 10 fold larger than the C. elegans EST base, if human DAF-7 is expressed in a small set of neurons, it is not surprising that it has not yet been seen in the EST database. Nonetheless, human DAF-7 may be instantly recognized using the motif, GWDXXIAPK as a means to search updated sequence databases or by standard techniques as described herein.

Other Embodiments

In other embodiments, the invention includes any protein which possesses the requisite level of amino acid sequence identity (as defined herein) to DAF-2, DAF-3, or a DAF-16 sequence; such homologs include other substantially pure naturally-occurring mammalian DAF polypeptides (for example, human DAF polypeptides) as well as allelic variants; natural mutants; induced mutants; proteins encoded by DNA that hybridizes to the DAF DNA sequence or degenerate conserved domains of DAF proteins (e.g., those described herein) under high stringency conditions; and proteins specifically bound by antisera directed to a DAF-2, DAF-3, or DAF-16 polypeptide.

The invention further includes analogs of any naturally-occurring DAF-2, DAF-3, or DAF-16 polypeptides. Analogs can differ from the naturally-occurring protein by amino acid sequence differences which do not destroy function, by post-translational modifications, or by both. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring DAF polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, Molecular Cloning: A Laboratory Manual (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes DAF-2, DAF-3, and DAF-16 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of such DAF polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

For certain purposes, all or a portion of the DAF-2, DAF-3, or DAF-16 polypeptide sequence may be fused to another protein (for example, by recombinant means). In one example, the DAF polypeptide may be fused to the green fluorescent protein, GFP (Chalfie et al., Science 263:802–805, 1994). Such a fusion protein is useful, for example, for monitoring the expression level of the DAF polypeptide in vivo (for example, by fluorescence microscopy) following treatment with candidate or known DAF agonists or antagonists.

The methods of the invention may be used to diagnose or treat any condition related to glucose intolerance or obesity in any mammal, for example, humans, domestic pets, or livestock. Where a non-human mammal is diagnosed or treated, the DAF polypeptide, nucleic acid, or antibody employed is preferably specific for that species.

All publications and patent applications mentioned in this specification are herein incorporated by reference to the same extent as if each independent publication or patent application was specifically and individually indicated to be incorporated by reference.

Other embodiments are within the following claims.

What is claimed is:

1. A method for identifying a compound that modulates DAF-18 expression or activity, comprising:
   (a) providing a *C. elegans*, isolated *C. elegans* cell, or isolated mammalian cell expressing a daf-18 gene that encodes a polypeptide having 95% amino acid sequence identity to SEQ ID NO:310; and has lipid phosphatase activity
   (b) contacting said *C. elegans*, isolated *C. elegans* cell, or isolated mammalian cell with a candidate compound to determine the effect of said candidate compound on said daf-18 expression or activity, an alteration in said daf-18 expression or activity following contact of said *C. elegans*, isolated *C. elegans* cell, or isolated mammalian cell with said candidate compound identifying said candidate compound as a modulatory compound.

2. A method for identifying a compound that modulates PTEN expression or activity, comprising:
   (a) providing a *C. elegans* or isolated *C. elegans* cell comprising a mutation in its endogenous daf-8 gene;
   (b) expressing in said *C. elegans* or isolated *C. elegans* cell a PTEN gene that encodes a polypeptide having 95% amino acid sequence identity to SEQ ID NO:309; and has lipid phosphatase activity and
   (c) contacting said *C. elegans* or isolated *C. elegans* cell with a candidate compound to determine the effect of said candidate compound on said PTEN expression or activity, an alteration in said PTEN expression or activity following contact with said candidate compound identifying said candidate compound as a modulatory compound.

3. The method of claim 1 or 2, wherein said compound increases said daf-18 or said PTEN expression or activity and is therefore a candidate compound for increasing longevity of a cell or organism.

4. The method of claim 1 or 2, wherein said compound decreases said daf-18 or said PTEN expression or activity and is therefore a candidate compound for treating an impaired glucose tolerance condition or obesity.

5. The method of claim 1 or 2, wherein said method is carried out in a transgenic *C. elegans*.

6. A method for identifying a compound that is a candidate compound for ameliorating or delaying an impaired glucose tolerance condition or obesity, comprising contacting a biological sample with a candidate compound and assaying said sample for DAF-18-mediated lipid phosphatase activity, wherein said DAF-18 has at least 95% amino acid sequence identity to SEQ ID NO:310, a decrease in said activity indicating a candidate compound for ameliorating or delaying an impaired glucose tolerance condition or obesity.

7. A method for identifying a compound that is a candidate compound for increasing longevity of a cell or organism, comprising contacting a biological sample with a candidate compound and assaying said sample for DAF-1 8-mediated lipid phosphatase activity, wherein said DAF-18 has at least 95% amino acid sequence identity to SEQ ID NO:310, an increase in said activity indicating a candidate compound for increasing longevity of a cell or organism.

8. A method for identifying a compound that is a candidate compound for ameliorating or delaying an impaired glucose tolerance condition or obesity, comprising contacting a biological sample with a candidate compound and assaying said sample for PTEN-mediated lipid phosphatase activity, wherein said PTEN has at least 95% amino acid sequence identity to SEQ ID NO:309, a decrease in said activity indicating a candidate compound for ameliorating or delaying an impaired glucose tolerance condition or obesity.

9. A method for identifying a compound that is a candidate compound for increasing longevity of a cell or organism, comprising contacting a biological sample with a candidate compound and assaying said sample for PTEN-mediated lipid phosphatase activity, wherein said PTEN has at least 95% amino acid sequence identity to SEQ ID NO:309, an increase in said activity indicating a candidate compound for increasing longevity of a cell or organism.

10. The method of claim 6 or 8, wherein said method further comprises assaying said compound in a *C. elegans* or isolated *C. elegans* cell which comprises a mutation in its endogenous daf-18 gene and which expresses a PTEN gene which has at least 95% amino acid sequence identity to SEQ ID NO:309, a decrease in said PTEN activity indicating a candidate compound for treating an impaired glucose tolerance condition or obesity.

11. The method of claim 7 or 9, wherein said method further comprises assaying said compound in a *C. elegans* or isolated *C. elegans* cell which comprises a mutation in its endogenous daf-18 gene and which expresses a PTEN gene which has at least 95% amino acid sequence identity to SEQ ID NO:309, an increase in said PTEN activity indicating a candidate compound for increasing longevity of a cell or organism.

12. A transgenic *C. elegans* whose cells contain a transgene encoding a PTEN polypeptide, said PTEN polypeptide having at least 95% amino acid sequence identity to SEQ ID NO:309 and has lipid phosphatase activity.

13. The transgenic *C. elegans* of claim 12, wherein said *C. elegans* carries a mutation in its endogenous daf-18 gene.

14. The method of claim 5, further comprising the step of testing said identified compound in a diabetic or obesity mouse model system.

15. The method of claim 1, wherein said daf-18 gene encodes a polypeptide having 100% amino acid sequence identity to SEQ ID NO:310.

16. The method of claim 2, wherein said PTEN gene encodes a polypeptide having 100% amino acid sequence identity to SEQ ID NO:309.

17. The method of claim 3, wherein said daf-18 gene encodes a polypeptide having 100% amino acid sequence identity to SEQ ID NO:310 or said PTEN gene encodes a polypeptide having 100% amino acid sequence identity to SEQ ID NO:309.

18. The method of claim 4, wherein said daf-18 gene encodes a polypeptide having 100% amino acid sequence identity to SEQ ID NO:310 or said PTEN gene encodes a polypeptide having 100% amino acid sequence identity to SEQ ID NO:309.

19. The method of claim 6 or 7, wherein said DAF-18 has 100% amino acid sequence identity to SEQ ID NO:310.

20. The method of claim 8 or 9, wherein said PTEN has 100% amino acid sequence identity to SEQ ID NO:309.

21. The transgenic *C. elegans* of claim 12, wherein said PTEN polypeptide has 100% amino acid sequence identity to SEQ ID NO:309.

* * * * *

UNITED STATES PATENT AND TRADEMARK OFFICE
CERTIFICATE OF CORRECTION

PATENT NO. : 6,861,256 B2  
APPLICATION NO. : 09/205658  
DATED : March 1, 2005  
INVENTOR(S) : Ruvkun et al.

Page 1 of 1

It is certified that error appears in the above-identified patent and that said Letters Patent is hereby corrected as shown below:

<u>Title page,</u>
Item [*] Notice, delete "by 351 days" and insert -- by 197 days --.

Signed and Sealed this

Twentieth Day of June, 2006

JON W. DUDAS  
*Director of the United States Patent and Trademark Office*